US011873532B2

(12) United States Patent
Davicioni et al.

(10) Patent No.: US 11,873,532 B2
(45) Date of Patent: Jan. 16, 2024

(54) SUBTYPING PROSTATE CANCER TO PREDICT RESPONSE TO HORMONE THERAPY

(71) Applicants: Veracyte SD, Inc., San Diego, CA (US); The Regents of the University of Michigan, Ann Arbor, MI (US)

(72) Inventors: Elai Davicioni, La Jolla, CA (US); Nicholas Erho, Vancouver (CA); Shuang G. Zhao, Ann Arbor, MI (US); S. Laura Chang, Ann Arbor, MI (US); Felix Y. Feng, Ann Arbor, MI (US)

(73) Assignees: Decipher Biosciences, Inc., San Diego, CA (US); 2. The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/492,055

(22) PCT Filed: Mar. 9, 2018

(86) PCT No.: PCT/US2018/021826

§ 371 (c)(1),
(2) Date: Sep. 6, 2019

(87) PCT Pub. No.: WO2018/165600

PCT Pub. Date: Sep. 13, 2018

(65) Prior Publication Data

US 2021/0130902 A1 May 6, 2021

Related U.S. Application Data

(60) Provisional application No. 62/469,174, filed on Mar. 9, 2017.

(51) Int. Cl.
*C12Q 1/68* (2018.01)
*C12Q 1/6886* (2018.01)
*G16B 5/00* (2019.01)
*G06N 3/00* (2023.01)

(52) U.S. Cl.
CPC ............. *C12Q 1/6886* (2013.01); *G06N 3/00* (2013.01); *G16B 5/00* (2019.02); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 3,645,691 | A | 2/1972 | Guenter et al. |
| 3,687,808 | A | 8/1972 | Thomas, Jr. et al. |
| 4,323,546 | A | 4/1982 | Crockfor et al. |
| 4,683,195 | A | 7/1987 | Mullis et al. |
| 4,683,202 | A | 7/1987 | Mullis et al. |
| 4,800,159 | A | 1/1989 | Mullis et al. |
| 4,965,188 | A | 10/1990 | Mullis et al. |
| 5,130,238 | A | 7/1992 | Malek et al. |
| 5,143,854 | A | 9/1992 | Pinung et al. |
| 5,225,326 | A | 7/1993 | Bresser et al. |
| 5,270,184 | A | 12/1993 | Walker et al. |
| 5,283,174 | A | 2/1994 | Arnold et al. |
| 5,288,514 | A | 2/1994 | Ellman |
| 5,384,261 | A | 1/1995 | Winkle et al. |
| 5,399,491 | A | 3/1995 | Kacian et al. |
| 5,455,166 | A | 10/1995 | Walker |
| 5,480,784 | A | 1/1996 | Kacian et al. |
| 5,494,810 | A | 2/1996 | Barany et al. |
| 5,538,848 | A | 7/1996 | Livak et al. |
| 5,545,524 | A | 8/1996 | Trent et al. |
| 5,677,195 | A | 10/1997 | Winkler et al. |
| 5,705,365 | A | 1/1998 | Ryder et al. |
| 5,710,029 | A | 1/1998 | Ryder et al. |
| 5,711,029 | A | 1/1998 | Ryder et al. |
| 5,744,305 | A | 4/1998 | Fodor et al. |
| 5,814,447 | A | 9/1998 | Ishiguro et al. |

(Continued)

FOREIGN PATENT DOCUMENTS

| | | |
|---|---|---|
| EP | 0 684 315 | 11/1995 |
| EP | 1 409 727 | 11/2005 |

(Continued)

OTHER PUBLICATIONS

US 5,962,233 A, 10/1999, Livak et al. (withdrawn)

(Continued)

*Primary Examiner* — Juliet C Switzer

(74) *Attorney, Agent, or Firm* — Knobbe, Martens, Olson & Bear, LLP

(57) ABSTRACT

The present invention relates to methods, systems and kits for the diagnosis, prognosis and the determination of progression of cancer in a subject. The invention also provides biomarkers that define subgroups of prostate cancer, clinically useful classifiers for distinguishing prostate cancer subtypes, bioinformatic methods for determining clinically useful classifiers, and methods of use of each of the foregoing. The methods, systems and kits can provide expression-based analysis of biomarkers for purposes of subtyping prostate cancer in a subject. Further disclosed herein, in certain instances, are probe sets for use in subtyping prostate cancer in a subject. Classifiers for subtyping a prostate cancer are provided. Methods of treating cancer based on molecular subtyping are also provided.

10 Claims, 18 Drawing Sheets

Specification includes a Sequence Listing.

(56) References Cited

U.S. PATENT DOCUMENTS

| | | | |
|---|---|---|---|
| 5,824,518 | A | 10/1998 | Kacian et al. |
| 5,830,711 | A | 11/1998 | Barany et al. |
| 5,846,717 | A | 12/1998 | Brow et al. |
| 5,854,033 | A | 12/1998 | Lizardi |
| 5,854,206 | A | 12/1998 | Twardzik et al. |
| 5,888,779 | A | 3/1999 | Kacian et al. |
| 5,925,517 | A | 7/1999 | Tyagi et al. |
| 5,928,862 | A | 7/1999 | Morrison |
| 5,965,360 | A | 10/1999 | Zain et al. |
| 5,985,557 | A | 11/1999 | Prudent et al. |
| 5,989,815 | A | 11/1999 | Skolnick et al. |
| 5,994,069 | A | 11/1999 | Hall et al. |
| 6,001,567 | A | 12/1999 | Brow et al. |
| 6,022,692 | A | 2/2000 | Coulie et al. |
| 6,027,887 | A | 2/2000 | Zavada et al. |
| 6,034,218 | A | 3/2000 | Reed et al. |
| 6,090,543 | A | 7/2000 | Prudent et al. |
| 6,121,489 | A | 9/2000 | Dorner et al. |
| 6,136,182 | A | 10/2000 | Dolan et al. |
| 6,150,097 | A | 11/2000 | Tyagi et al. |
| 6,198,107 | B1 | 3/2001 | Seville |
| 6,218,523 | B1 | 4/2001 | French |
| 6,225,051 | B1 | 5/2001 | Sugiyama et al. |
| 6,251,639 | B1 | 6/2001 | Kurn |
| 6,262,245 | B1 | 7/2001 | Xu et al. |
| 6,268,142 | B1 | 7/2001 | Duff et al. |
| 6,303,305 | B1 | 10/2001 | Wittwer et al. |
| 6,410,278 | B1 | 6/2002 | Notomi et al. |
| 6,436,642 | B1 | 8/2002 | Gould-Rothberg et al. |
| 6,541,205 | B1 | 4/2003 | Yokoyama et al. |
| 6,573,043 | B1 | 6/2003 | Cohen et al. |
| 6,630,358 | B1 | 10/2003 | Wagner et al. |
| 6,723,506 | B2 | 4/2004 | Fletcher et al. |
| 6,828,429 | B1 | 12/2004 | Srivastava et al. |
| 7,008,765 | B1 | 3/2006 | Bussemakers et al. |
| 7,186,514 | B2 | 3/2007 | Zavada et al. |
| 7,211,390 | B2 | 5/2007 | Rothberg et al. |
| 7,244,559 | B2 | 7/2007 | Rothberg et al. |
| 7,264,929 | B2 | 9/2007 | Rothberg et al. |
| 7,280,922 | B2 | 10/2007 | Mei et al. |
| 7,300,788 | B2 | 11/2007 | Matsuzaki et al. |
| 7,319,011 | B2 | 1/2008 | Riggins et al. |
| 7,323,305 | B2 | 1/2008 | Leamon et al. |
| 7,335,762 | B2 | 2/2008 | Rothberg et al. |
| 7,358,061 | B2 | 4/2008 | Yamamoto et al. |
| 7,361,488 | B2 | 4/2008 | Fan et al. |
| 7,378,233 | B2 | 5/2008 | Sidransky et al. |
| 7,407,755 | B2 | 8/2008 | Lubinski et al. |
| 7,541,169 | B2 | 6/2009 | Freimuth et al. |
| 7,598,052 | B2 | 10/2009 | Giordanos et al. |
| 7,662,553 | B2 | 2/2010 | Lenz et al. |
| 7,767,391 | B2 | 8/2010 | Scott et al. |
| 7,901,881 | B2 | 3/2011 | Libutti et al. |
| 7,901,888 | B2 | 3/2011 | Kebebew |
| 7,914,988 | B1 | 3/2011 | Chudin et al. |
| 7,927,826 | B2 | 4/2011 | Riggins et al. |
| 8,008,009 | B2 | 8/2011 | Choquet-Kastylevsky et al. |
| 8,202,692 | B2 | 6/2012 | Giordano et al. |
| 8,273,539 | B2 | 9/2012 | Klee et al. |
| 8,293,880 | B2 | 10/2012 | Cote et al. |
| 8,299,233 | B2 | 10/2012 | Andre et al. |
| 8,338,109 | B2 | 12/2012 | Vasmatzis et al. |
| 8,354,228 | B2 | 1/2013 | Ron |
| 8,465,914 | B2 | 6/2013 | Brown et al. |
| 8,541,170 | B2 | 9/2013 | Kennedy et al. |
| 8,568,971 | B2 | 10/2013 | Brown et al. |
| 8,669,057 | B2 | 3/2014 | Kennedy et al. |
| 8,802,599 | B2 | 8/2014 | Aharonov et al. |
| 8,828,656 | B2 | 9/2014 | Bullerdiek et al. |
| 8,877,445 | B2 | 11/2014 | Shackney |
| 8,945,829 | B2 | 2/2015 | Keutgen et al. |
| 9,040,286 | B2 | 5/2015 | Zon et al. |
| 9,074,258 | B2 | 7/2015 | Davicion et al. |
| 9,096,906 | B2 | 8/2015 | Aharonov et al. |
| 9,157,123 | B2 | 10/2015 | Xing |
| 9,175,352 | B2 | 11/2015 | Keutgen et al. |
| 9,206,481 | B2 | 12/2015 | Srivastava et al. |
| 9,206,482 | B2 | 12/2015 | Davicioni et al. |
| 9,234,244 | B2 | 1/2016 | Zeiger et al. |
| 9,435,812 | B2 | 9/2016 | Pestano et al. |
| 9,495,515 | B1 | 11/2016 | Giulia et al. |
| 9,534,249 | B2 | 1/2017 | Vasmatzis et al. |
| 9,587,279 | B2 | 3/2017 | Fahey, III et al. |
| 9,617,604 | B2 | 4/2017 | Davicion et al. |
| 9,631,239 | B2 * | 4/2017 | Perou .................... G16B 25/00 |
| 9,708,667 | B2 | 7/2017 | Yanai et al. |
| 9,714,452 | B2 | 7/2017 | Davicioni et al. |
| 9,856,537 | B2 | 1/2018 | Kennedy et al. |
| 9,994,907 | B2 | 6/2018 | Davicioni et al. |
| 10,114,924 | B2 | 10/2018 | Kennedy et al. |
| 10,407,731 | B2 | 9/2019 | Klee et al. |
| 10,407,735 | B2 | 9/2019 | Chinnaiyan et al. |
| 10,422,009 | B2 | 9/2019 | Davicioni et al. |
| 10,494,677 | B2 | 12/2019 | Vasmatzis et al. |
| 10,513,737 | B2 | 12/2019 | Davicioni et al. |
| 10,865,452 | B2 | 12/2020 | Davicioni |
| 2001/0051344 | A1 | 12/2001 | Shalon et al. |
| 2002/0076735 | A1 | 6/2002 | Williams et al. |
| 2002/0090633 | A1 | 7/2002 | Becker et al. |
| 2002/0119463 | A1 | 8/2002 | Fads |
| 2002/0168638 | A1 | 11/2002 | Schlegel et al. |
| 2002/0169137 | A1 | 11/2002 | Reiner et al. |
| 2002/0182586 | A1 | 12/2002 | Morris et al. |
| 2003/0119168 | A1 | 6/2003 | Madison et al. |
| 2003/0152980 | A1 | 8/2003 | Golub et al. |
| 2003/0175736 | A1 | 9/2003 | Chinnaiyan et al. |
| 2003/0185830 | A1 | 10/2003 | Xu et al. |
| 2003/0186248 | A1 | 10/2003 | Erlander et al. |
| 2003/0190602 | A1 | 10/2003 | Pressman et al. |
| 2003/0194734 | A1 | 10/2003 | Jatkoe |
| 2003/0224399 | A1 | 12/2003 | Reed et al. |
| 2003/0235820 | A1 | 12/2003 | Mack et al. |
| 2004/0009481 | A1 | 1/2004 | Schlegel et al. |
| 2004/0018493 | A1 | 1/2004 | Anastasio et al. |
| 2004/0019466 | A1 | 1/2004 | Minor et al. |
| 2004/0029114 | A1 | 2/2004 | Mack et al. |
| 2004/0058378 | A1 | 3/2004 | Kong et al. |
| 2004/0259086 | A1 | 12/2004 | Schlegel et al. |
| 2005/0042222 | A1 | 2/2005 | Yamamoto et al. |
| 2005/0042638 | A1 | 2/2005 | Arnold et al. |
| 2005/0048533 | A1 | 3/2005 | Sidransky et al. |
| 2005/0064455 | A1 | 3/2005 | Baker et al. |
| 2005/0118625 | A1 | 6/2005 | Mounts |
| 2005/0137805 | A1 | 6/2005 | Lewin et al. |
| 2005/0202442 | A1 | 9/2005 | Morris et al. |
| 2005/0227917 | A1 | 10/2005 | Williams et al. |
| 2005/0240357 | A1 | 10/2005 | Minor |
| 2005/0250125 | A1 | 11/2005 | Novakoff |
| 2005/0260646 | A1 | 11/2005 | Baker et al. |
| 2005/0266443 | A1 | 12/2005 | Croce et al. |
| 2005/0266459 | A1 | 12/2005 | Poulsen |
| 2006/0019256 | A1 | 1/2006 | Clarke et al. |
| 2006/0019615 | A1 | 1/2006 | Ditmer |
| 2006/0035244 | A1 | 2/2006 | Riggins et al. |
| 2006/0046253 | A1 | 3/2006 | Nakao |
| 2006/0046265 | A1 | 3/2006 | Becker et al. |
| 2006/0083744 | A1 | 4/2006 | Chen et al. |
| 2006/0088851 | A1 | 4/2006 | Erlander et al. |
| 2006/0094061 | A1 | 5/2006 | Brys et al. |
| 2006/0105360 | A1 | 5/2006 | Croce et al. |
| 2006/0127907 | A1 | 6/2006 | Matsubara et al. |
| 2006/0134663 | A1 | 6/2006 | Harkin et al. |
| 2006/0204989 | A1 | 9/2006 | Kopreski |
| 2006/0211017 | A1 | 9/2006 | Chinnaiyan et al. |
| 2007/0010469 | A1 | 1/2007 | Chan |
| 2007/0020657 | A1 | 1/2007 | Grebe et al. |
| 2007/0031873 | A1 | 2/2007 | Wang et al. |
| 2007/0037165 | A1 | 2/2007 | Venter et al. |
| 2007/0037186 | A1 | 2/2007 | Jiang et al. |
| 2007/0048738 | A1 | 3/2007 | Donkena et al. |
| 2007/0065827 | A1 | 3/2007 | Pauloski et al. |
| 2007/0065833 | A1 | 3/2007 | Gupta |
| 2007/0083334 | A1 | 4/2007 | Mintz et al. |
| 2007/0099197 | A1 | 5/2007 | Afar et al. |

(56) References Cited

U.S. PATENT DOCUMENTS

2007/0099209 A1 5/2007 Clarke et al.
2007/0105133 A1 5/2007 Clarke et al.
2007/0148667 A1 6/2007 Williams et al.
2007/0148687 A1 6/2007 Bedingham et al.
2007/0161004 A1 7/2007 Brown et al.
2007/0172841 A1 7/2007 Wang
2007/0172844 A1 7/2007 Lancaster et al.
2007/0212702 A1 9/2007 Tomlins et al.
2007/0220621 A1 9/2007 Clarke et al.
2007/0238119 A1 10/2007 Yu et al.
2007/0259352 A1 11/2007 Bentwich et al.
2007/0275915 A1 11/2007 Hallenbeck et al.
2008/0009001 A1 1/2008 Bettuzzi et al.
2008/0028302 A1 1/2008 Meschkat
2008/0044824 A1 2/2008 Giordano et al.
2008/0076674 A1 3/2008 Litman et al.
2008/0124344 A1 5/2008 Combs et al.
2008/0131892 A1 6/2008 Becker et al.
2008/0145841 A1 6/2008 Libutti et al.
2008/0254470 A1 10/2008 Berlkin
2008/0269157 A1 10/2008 Srivastava et al.
2008/0274457 A1 11/2008 Eng et al.
2008/0281568 A1 11/2008 Kao et al.
2009/0020433 A1 1/2009 Cohen et al.
2009/0036415 A1 2/2009 Rubin et al.
2009/0062144 A1 3/2009 Guo
2009/0075921 A1 3/2009 Ikegawa
2009/0149333 A1 6/2009 Knudsen et al.
2009/0191535 A1 7/2009 Connelly et al.
2009/0204333 A1 8/2009 Friend et al.
2009/0239221 A1 9/2009 Chinnaiyan et al.
2009/0280490 A1 11/2009 Baker et al.
2009/0298082 A1 12/2009 Klee et al.
2010/0055704 A1 3/2010 Giordano et al.
2010/0075384 A1 3/2010 Kong et al.
2010/0099093 A1 4/2010 Weaver et al.
2010/0131286 A1 5/2010 Houlgatte et al.
2010/0131432 A1 5/2010 Kennedy et al.
2010/0137164 A1 6/2010 Rubin et al.
2010/0178653 A1 7/2010 Aharonov et al.
2010/0021538 A1 8/2010 Iljin et al.
2010/0215638 A1 8/2010 Iljin et al.
2010/0257617 A1 10/2010 Ami et al.
2010/0279327 A1 11/2010 Ossovskaya
2010/0285979 A1 11/2010 Zeiger et al.
2011/0009286 A1 1/2011 Andre et al.
2011/0045462 A1 2/2011 Fu et al.
2011/0092375 A1 4/2011 Zamore et al.
2011/0136683 A1 6/2011 Davicioni
2011/0152110 A1 6/2011 Vierlinger et al.
2011/0166838 A1* 7/2011 Gehrmann ............. G16B 20/20
703/2
2011/0178163 A1 7/2011 Chowdhury
2011/0212855 A1 9/2011 Rafnar et al.
2011/0229894 A1 9/2011 Levy et al.
2011/0230372 A1 9/2011 Willman et al.
2011/0236903 A1 9/2011 McClelland
2011/0287946 A1 11/2011 Gudmundsson et al.
2011/0294123 A1 12/2011 Nakamura et al.
2011/0312520 A1 12/2011 Kennedy et al.
2012/0015839 A1 1/2012 Chinnaiyan
2012/0015843 A1 1/2012 Von et al.
2012/0041274 A1 2/2012 Stone et al.
2012/0108453 A1 5/2012 Smit et al.
2012/0115743 A1 5/2012 Davicioni et al.
2012/0122698 A1 5/2012 Stacey et al.
2012/0122718 A1 5/2012 Reisman
2012/0157334 A1 6/2012 Beaudenon-Huibregtse et al.
2012/0172243 A1 7/2012 Davicioni et al.
2012/0214165 A1 8/2012 Walfish et al.
2012/0220474 A1 8/2012 Kennedy et al.
2012/0304318 A1 11/2012 Ohnuma et al.
2013/0004974 A1 1/2013 Klee et al.
2013/0023434 A1 1/2013 Van
2013/0142728 A1 6/2013 Beaudenon-Huibregtse et al.
2013/0150257 A1 6/2013 Abdueva et al.
2013/0172203 A1 7/2013 Yeatman et al.
2013/0184999 A1 7/2013 Ding
2013/0196866 A1 8/2013 Pestano et al.
2013/0225662 A1 8/2013 Kennedy et al.
2013/0231258 A1 9/2013 Wilde et al.
2013/0273543 A1 10/2013 Gudmundsson et al.
2013/0302808 A1 11/2013 Vasmatzis
2013/0302810 A1 11/2013 Latham et al.
2013/0303826 A1 11/2013 Jurisica et al.
2014/0030714 A1 1/2014 Paschke et al.
2014/0066323 A1 3/2014 Buerki et al.
2014/0080731 A1 3/2014 Davicioni et al.
2014/0087961 A1 3/2014 Sulem et al.
2014/0099261 A1 4/2014 Keutgen et al.
2014/0121126 A1 5/2014 Bivona et al.
2014/0143188 A1 5/2014 Mackey et al.
2014/0228237 A1 8/2014 Kennedy et al.
2014/0243240 A1 8/2014 Soldin et al.
2014/0302042 A1 10/2014 Chin et al.
2014/0303002 A1 10/2014 Shak et al.
2014/0303034 A1 10/2014 Gascoyne et al.
2014/0315199 A1 10/2014 Rhodes et al.
2014/0315739 A1 10/2014 Aharonov et al.
2014/0349856 A1 11/2014 Schnabel et al.
2014/0349864 A1 11/2014 Kennedy et al.
2014/0371096 A1 12/2014 Umbright et al.
2015/0038376 A1 2/2015 Tian et al.
2015/0099665 A1 4/2015 Rosenfeld et al.
2015/0141470 A1 5/2015 Garraway et al.
2015/0253331 A1 9/2015 Zijlstra
2015/0275306 A1 10/2015 Bernards et al.
2015/0292030 A1 10/2015 McConkey
2015/0299808 A1 10/2015 Gonzalez et al.
2015/0307947 A1 10/2015 Basu et al.
2015/0329915 A1 11/2015 Davicioni et al.
2015/0368724 A1 12/2015 Aharonov et al.
2016/0024586 A1 1/2016 Delfour et al.
2016/0032395 A1 2/2016 Davicioni et al.
2016/0032400 A1 2/2016 Gomis et al.
2016/0068915 A1 3/2016 Kennedy et al.
2016/0076108 A1 3/2016 Davicioni et al.
2016/0115546 A1 4/2016 Rosenfeld et al.
2016/0120832 A1 5/2016 Rabinowitz et al.
2016/0251729 A1 9/2016 Chinnaiyan
2016/0312294 A1* 10/2016 Walker ................. A61K 31/337
2016/0312305 A1 10/2016 Kennedy et al.
2016/0312306 A1 10/2016 Kennedy et al.
2016/0312307 A1 10/2016 Kennedy et al.
2016/0312308 A1 10/2016 Kennedy et al.
2017/0016076 A1 1/2017 Barnett-Itzhaki et al.
2017/0145513 A1 5/2017 Kennedy et al.
2017/0166980 A1 6/2017 Fahey, III et al.
2017/0218455 A1* 8/2017 Steelman ............. C12Q 1/6844
2017/0329894 A1 11/2017 Kennedy et al.
2018/0016642 A1 1/2018 Kennedy et al.
2018/0216197 A1 1/2018 Davicioni et al.
2018/0030540 A1 2/2018 Davicioni et al.
2018/0068058 A1 3/2018 Abdueva et al.
2018/0112275 A1 4/2018 Davicioni et al.
2018/0122508 A1 5/2018 Wilde et al.
2018/0127832 A1 5/2018 Kennedy et al.
2018/0282817 A1* 10/2018 You ...................... A61K 31/337
2018/0291459 A1 10/2018 Al-Deen Ashab et al.
2019/0017123 A1 1/2019 Davicioni et al.
2019/0204322 A1 7/2019 Alshalalfa et al.
2019/0218621 A1 7/2019 Davicioni
2020/0165682 A1 5/2020 Chinnaiyan et al.
2020/0181710 A1* 6/2020 Steelman ........... C12N 15/1096
2020/0191773 A1 6/2020 Kitano et al.
2020/0224276 A1 7/2020 Chinnaiyan et al.
2021/0317531 A1 10/2021 Da Vicioni
2022/0177974 A1 6/2022 Davicioni
2022/0213557 A1 7/2022 De Jong

(56) References Cited

U.S. PATENT DOCUMENTS

| | | | |
|---|---|---|---|
| 2023/0115828 | A1 | 4/2023 | De Jong |
| 2023/0151429 | A1 | 5/2023 | Davicioni |

FOREIGN PATENT DOCUMENTS

| | | |
|---|---|---|
| EP | 1 777 523 | 4/2007 |
| EP | 2 366 800 | 9/2011 |
| WO | WO 90/015070 | 12/1990 |
| WO | WO 92/010092 | 6/1992 |
| WO | WO 93/009668 | 5/1993 |
| WO | WO 93/022684 | 11/1993 |
| WO | WO 98/045420 | 10/1998 |
| WO | WO 01/060860 | 8/2001 |
| WO | WO 01/066753 | 9/2001 |
| WO | WO 02/000929 | 1/2002 |
| WO | WO 02/083921 | 10/2002 |
| WO | WO 03/012067 | 2/2003 |
| WO | WO 04/037972 | 5/2004 |
| WO | WO 05/040396 | 5/2005 |
| WO | WO 05/085471 | 9/2005 |
| WO | WO 05/100608 | 10/2005 |
| WO | WO 06/047484 | 5/2006 |
| WO | WO 06/091776 | 8/2006 |
| WO | WO 06/110264 | 10/2006 |
| WO | WO 06/127537 | 11/2006 |
| WO | WO 06/135596 | 12/2006 |
| WO | WO 07/056049 | 5/2007 |
| WO | WO 07/070621 | 6/2007 |
| WO | WO 07/081720 | 7/2007 |
| WO | WO 07/081740 | 7/2007 |
| WO | WO 08/023087 | 2/2008 |
| WO | WO 08/046911 | 4/2008 |
| WO | WO 08/086478 | 7/2008 |
| WO | WO 08/112283 | 9/2008 |
| WO | WO 09/009432 | 1/2009 |
| WO | WO 09/020521 | 2/2009 |
| WO | WO 09/020905 | 2/2009 |
| WO | WO 09/029266 | 3/2009 |
| WO | WO 09/045115 | 4/2009 |
| WO | WO 09/074968 | 6/2009 |
| WO | WO 09/108860 | 9/2009 |
| WO | WO 09/143603 | 12/2009 |
| WO | WO 10/018601 | 2/2010 |
| WO | WO 10/056374 | 5/2010 |
| WO | WO 10/073248 | 7/2010 |
| WO | WO 10/099598 | 9/2010 |
| WO | WO 10/123626 | 10/2010 |
| WO | WO 10/124372 | 11/2010 |
| WO | WO 11/150453 | 12/2011 |
| WO | WO 12/031008 | 3/2012 |
| WO | WO 12/068383 | 5/2012 |
| WO | WO 12/135008 | 10/2012 |
| WO | WO 13/006495 | 1/2013 |
| WO | WO 13/088457 | 6/2013 |
| WO | WO 13/116472 | 8/2013 |
| WO | WO 13/116742 | 8/2013 |
| WO | WO 14/028884 | 2/2014 |
| WO | WO 14/043803 | 3/2014 |
| WO | WO 14/085666 | 5/2014 |
| WO | WO 14/138101 | 9/2014 |
| WO | WO 14/151764 | 9/2014 |
| WO | WO 15/024942 | 2/2015 |
| WO | WO 15/071876 | 5/2015 |
| WO | WO 15/073949 | 5/2015 |
| WO | WO 16/141127 | 9/2016 |
| WO | WO 17/059549 | 4/2017 |
| WO | WO 17/062505 | 4/2017 |
| WO | WO 18/161081 | 9/2018 |
| WO | WO 18/165600 | 9/2018 |
| WO | WO 19/023517 | 1/2019 |
| WO | WO 19/133697 | 7/2019 |

OTHER PUBLICATIONS

Livingston et al. PDF, *Homo sapiens* CDC20 Cell Division Cycle 20 Homolog (CDC20) Gene, Complete eds. NCBI PDB accession DQ473545.1, Submitted Apr. 4, 2006; retrieved from internet < https://www.ncbi.nlm.nih.gov/nuccore/92918938/> on Feb. 19, 2021). (Year: 2006).*

Kelly et al. Agreement in Risk Prediction Between the 21-Gene Recurrence Score Assay (Oncotype DX ) and the PAM50 Breast Cancer Intrinsic Classifier™ in Early-Stage Estrogen Receptor-Positive Breast Cancer. The Oncologist; 2012;17:492-498. (Year: 2012).*

Prat et al. PAM50 assay and the three-gene model for identifying the major and clinically relevant molecular subtypes of breast cancer. Breast Cancer Res Treat; 2012; 135:301-306. (Year: 2012).*

Guo et al. DeepCC: a novel deep learning-based framework for cancer molecular subtype classification. Oncogenesis; 2019; 8 :44: p. 1-12. (Year: 2019).*

Parker et al. American Society of Clinical Oncology; 2009; 27; 8: 1160-1167. Appendix Figure A3., retrieved from internet, retrieved on Aug. 26, 2021. (Year: 2009).*

Damrauer et al. Intrinsic subtypes of high-grade bladder cancer reflect the hallmarks of breast cancer biology. PNAS; 2014; 111; 8: 3110-3115. (Year: 2014).*

Feng et al. Luminal and basal subtyping of prostate cancer. Journal of Clinical Oncology; Feb. 2017; vol. 35(6) Supplement; p. 3; Prostate Cancer-Localized Disease: 2017 Genitourinary Cancers Symposium, Feb. 16-18, 2017, Oral Abstract Session add Poster Session: p. 1-2. (Year: 2017).*

Zhang et al. Nature Communication; 2016; DOI: 10.1038/ncomms10798: p. 1-15; and supplemental data 1 (supplementary information at http://www.nature.com/naturecommunications). (Year: 2016).*

Parker et al. American Society of Clinical Oncology; 2009; 27; 8: 1160-1167. (Year: 2009).*

Abdueva et al., "Quantitative Expression Profiting in Formalin-Fixed Paraffin-Embedded Samples by Affymetrix Microarrays," Journal of Molecular Diagnostics (Jul. 2010) vol. 12, No. 4, pp. 409-417.

Adamo and Ladomery, "The Oncogene ERG: A Key Factor in Prostate Cancer," *Oncogene*(2016), 35:403-414.

Affymetrix GeneChip Human Genome U133 Array Set HG-U133A, Geo, Mar. 11, 2002, retrieved on Mar. 11, 2002.

Affymetrix: Data Sheet, "GeneChip® Exon Array System for Human, Mouse, and Rat," Internet Citation, [Online] Jan. 25, 2012 [Retrieved from the Internet] Intp://www.biainformatics.atickland.aciaz/workshops/1O_March_2011 1Exon_EOST_Datasheet.pdf, 8 pages.

Agell et al., "A 12-Gene Expression Signature Is Associated with Aggressive Histological in Prostate Cancer: SEC14L1 and TCEB1 Genes Are Potential Markers of Progression," Am J Pathol (2012) vol. 181 (5), pp. 1585-1594.

Alberts et al., "Vesicular traffic in the secretory and endocytic pathways," Molecular Biology of the Cell (1994) 3rd Ed., p. 465.

Aldred et al., "Papillary and follicular thyroid carcinomas show distinctly different microarray expression profiles and can be distinguished by a minimum of five genes," J Clin Oncol. (2004) 22(17):3531-9.

Amling et al.: "Long-term hazard of progression after radical prostatectomy for clinically EB localized prostate cancer continued risk of biochemical failure after 5 years," J Urol. (2000) 164:101-105.

Amundadottir et al., "A common variant associated with prostate cancer in European and African populations," Nat Genet. (2006) 38:652-658.

Amundson et al., "Integrating global gene expression and radiation survival parameters across the 60 cell lines of the National Cancer Institute Anticancer Drug Screen," Cancer Research (2008) 68(2):415-424.

Anonymous, UCSC Genome Browser on Human Mar. 2006, NCBI36/hg18) Assembly, Mar. 2006, XP055587638, Retrieved from the Internet: URL:https://genome-euro.ucsc.edu/cgi-bin/hgTracks?db=hg18&lastVirtModeType=default&lastVirtModeExtraState=&virtModeType=default&virtMode=0&nonVirtPosition=&position=

(56) References Cited

OTHER PUBLICATIONS chr5%3A 14025126%2D14062770&hgsid=232148223_IYly9VS0Lh0jhldEBQ3nViBrQuB5 [retrieved on May 10, 2019].
Ausubel, et al. Current Protocols in Molecular Biology. Wiley & Sons, New York (1995) Table of Contents.
Baetke et al., "Molecular Pathways Involved in Prostate Carcinogenesis: Insights from Public Microarray Datasets," PLoS One (2012) 7(11):e49831, 1-11.
Baggerly et al., "Deriving Chemosensitivity from Cell Lines: Forensic Bioinformatics and Reproducible Research in High-Throughput Biology," The Annals of Applied Sciences (2009) vol. 3, No. 4, pp. 1309-1334.
Ballman et al., "Faster cyclic loess: normalizing RNA arrays via linear models," Bioinformatics, 2004, 20 :2778-2786.
Bannert et al., "Retroelements and the human genome: new perspectives on an old relation." PNAS (Oct. 5, 2004) vol. 101, Suppl. 2, pp. 14572-14579.
Barlow et al., "Analysis of Case-Cohort Designs," J Clin Epidemiol (1999) vol. 52 (12), 1165-1172.
Bauer et al., "Identification of Markers of Taxane Sensitivity Using Proteomic and Genomic Analyses of Breast Tumor from Patients Receiving Neoadjuvant Paclitaxel and Radiation," Clin. Cancer Res. (2010) 16(2):681-690, American Association for Cancer Research.
Becht et al., Oct. 20, 2016, Estimating the popluation abundance of tissue-infiltraign immune and stromal cell populations using gene expression, Gemone Biology, 52(Suppl 2):218.
Benner et al., "Evolution, language and analogy in functional genomics," Trends in Genetics, (Jul. 2001) vol. 17, pp. 414-418.
Bergstralh et al., "Software for optimal matching in observation al studies," Epidemiology (1996) 7(3):331-332.
Best et al., "Molecular differentiation of high- and moderate-grade human prostate cancer by cDNA microarray analysis", Diagn Mol Pathol. (2003) 12(2):63-70.
Bibikova et al., "Expression signatures that correlated with Gleason score and relapse in prostate cancer," Genomics (2007) 89(6):666-672.
Bibikova et al., "Gene expression profiles in formalin-fixed, paraffin-embedded tissues obtained with a novel assay for microarray analysis," Clin Chem., 2004, 50:2384-2386.
Bibikova et al., "Quantitative gene expression profiling in formalin-fixed, paraffin-embedded tissues using universal bead arrays," Am J Pathol. (2004) 165:1799-1807.
Birney et al., "Identification and analysis of functional elements in 1% of the human genome by the Encode pilot project." Nature Jun. 14, 2007; 447(7146):799-816.
Bismar et al., "ERG Protein Expression Reflects Hormonal Treatment Response and is Associated with Gleason Score and Prostate Cancer Specific Mortality," *Eur. J. Cancer* (2012), 48:538-546,Elsevier Ltd.
Biton et al., Nov. 20, 2014, Independent component analysis uncovers the landscape of the bladder tumor transcriptome and reveals insights into luminal and basal subtypes, Cell Reports, 9(4):1235-1245.
Blute et al., "Use of Gleason score, prostate specific antigen, seminal vesicle and margin status to predict biochemical failure after radical prostatectomy," J Urol (2001) 165: 119-125.
Boorjian et al., "Long-term risk of clinical progression after biochemical recurrence following radical prostatectomy: the impact of time from surgery to recurrence." Eur Urol. (Jun. 2011) 59(6):893-9.
Boormans et al., "Identification of TDRD1 as a direct target gene of ERG in primary prostate cancer," Int J Cancer (2013) vol. 133 (2), pp. 335-345.
Bostwick et al., "Prognostic factors in prostate cancer: College of American Pathologists consensus statement," Arch Pathol Lab Med (2000) 124(7):995-1000.
Bott et al., "Prostate cancer management: (2) an update on locally advanced and metastatic disease", Postgrad Med J, Dec. 3, 2003, 79(937), 643-645.
Brase et al., "TMPRSS2-ERG—specific transcriptional modulation is associated with prostate cancer biomarkers and TGF-β signaling," BMC Cancer (2011) 11(507):1-8.
Breiman, "Random Forests," Machine Learning (2001) 45:5-32.
Brouha et al., "Hot L1s account for the bulk of retrotransposition in the human population." PNAS USA (Apr. 29, 2003) 100(9):5280-5.
Bueno et al., "A diagnostic test for prostate cancer from gene expression profiling data," J Urol, Feb. 2004; 171(2 Pt 1):903-6.
Bull et al., "Identification of potential diagnostic markers of prostate cancer and prostatic intraepithelial neoplasia using cDNA microarray," British J Cancer (Jun. 1, 2001) 84(11):1512-1519.
Bussemakers et al., "DD3: a new prostate-specific gene, highly overexpressed in prostate cancer." Cancer Res. (Dec. 1, 1999) 59(23):5975-9.
Carninci et al., "The transcriptional landscape of the mammalian genome," Science (Sep. 2, 2005) 09(5740):1559-63.
Cerutti et al. "Diagnosis of suspicious thyroid nodules using four protein biomarkers," Clin Cancer Res. (2006) 12(11 Pt 1):3311-8.
Chalitchagorn et al., "Distinctive pattern of LINE-1 methylation level in normal tissues and the association with carcinogenesis." Oncogene (Nov. 18, 2004) 23(54):8841-6.
Che et al.: "Prognostic Value of Abnormal p53 Expression in Locally Advanced Prostate Cancer Treated With Androgen Deprivation and Radiotherapy: A Study Based on RTOG 9202"; International Journal of Radiation: Oncology Biology Physics (Nov. 15, 2007) vol. 69, No. 4, pp. 1117-1123.
Chen et al., "Deregulation of a Hox Protein Regulatory Network Spanning Prostate Cancer Initiation and Progression," Clin Cancer Res (Jun. 2012) 18(16):4291-4302.
Chen et al., "Hepsin and maspin are inversely expressed in laser capture microdissectioned prostate cancer," J Urol. (Apr. 2003) 169(4):1316-1319.
Chen et al., "Significance of noninvasive diagnosis of prostate cancer with cytologic examination of prostatic fluid," J Nippon Med Sch. (Jun. 2006) 73(3):129-135.
Chen et al.: "Molecular determinants of resistance to antiandrogen therapy"; Nature Medicine, Nature Publishing Group, New York, NY (Jan. 1, 2004) vol. 10, No. 1, pp. 33-39.
Cheng et al. "Cell Proliferation in Prostate Cancer Patients with Lymph Node Metastasis", Clin Cancer Res (Oct. 1999) 5(10): 2820-2823.
Cheung et al., "Natural variation in human gene expression assessed in lymphoblastoid cells," Nature Genetics (2003) vol. 33, pp. 422-425.
CHEVILLE et at., "Gene Panel Model Predictive of Outcome in Men at High-Risk of Systemic Progression and Death From Prostate Cancer After Radical Retropubic Prostatectomy," Journal Of Clinical Oncology (Aug. 20, 2008) vol. 26 , No. 24.
Chifman et al., "Conservation of immune gene signatures in solid tumors and prognostic implications," BMC Cancer (2016) 16:911, pp. 1-17. Doi 10.1186/S12885-016-2948-Z.
Cho et al., "Hypermethylation of CpG island loci and hypomethylation of LINE-1 and Alu repeats in prostate adenocarcinoma and their relationship to clinicopathological features", J Pathol (Feb. 2007) 211(3):269-77.
Choi et al., Feb. 2014, Identification of distinct basal and luminal subtypes of muscle-invasive bladder cancer with different sensitivities to frontline chemotherapy, Cancer Cell, 25(2):152-165.
Choi et al., Jun. 24, 2014, Intrinsic basal and luminal subtypes of muscle-invasive bladder cancer, Nature Reviews Urology, 11(7):400-410.
Chow et al., "LINE-1 activity in facultative heterochromatin formation during X chromosome inactivation," Cell (Jun. 11, 2010) 141(6):956-69.
Cibas, et al. "The Bethesda System for Reporting Thyroid Cytopathology," Am J Clin Pathol. (Nov. 2009) 132(5):658-65. doi: 10.1309/AJCPPHLWMI3JV4LA.
Clancy et al., "Profiling networks of distinct immune-cells in tumors," BMC Bioinformatics (2016) 17:263, pp. 1-15. DOI 10.1186/s12859-016-1141-3.
Clark-Langone et al. "Biomarker discovery for colon cancer using a 761 gene RT-PCR assay 2007," BMC Genomics (2007) 8:279 pp. 1-18.

(56) References Cited

OTHER PUBLICATIONS

Cologne et al., "Optimal Case-Control Matching in Practice," Epidemiology Resources Inc. (1995) 6(3):271-275.
Cooper et al., "Mechanisms of Disease: biomarkers and molecular targets from microarray gene expression studies in prostate cancer ," Nat Clin Pract Urol. (2007) Dee:4(12):677-87.
Cooperberg et al., "The CAPRA-S score: A straightforward tool for improved prediction of outcomes after radical prostatectomy," Cancer (2011) vol. 117 (22), pp. 5039-5046.
Cordaux et al., "The impact of retrotransposons on human genome evolution." Nat Rev Genet. (Oct. 2009) 10(10):691-703.
Cordon-Cardo et al., "Improved prediction of prostate cancer recurrence through systems pathology," The Journal of Clinical Investigation (Jul. 2007) vol. 117, No. 7, pp. 1876-1883.
Couzin-Frankel, Jennifer, "As Questions Grow, Duke Halts Trials, Launches Investigation," Science (Aug. 6, 2010) vol. 329, pp. 614-615.
Cuzik et al., "Prognostic value of an RNA expression signature derived from cell cycle proliferation genes in patients with prostate cancer: a retrospective study," thelancet.com/oncology (Mar. 2011) vol. 12, pp. 245-255.
Dahlman et al., "Effect of androgen deprivation therapy on the expression of prostate cancer biomarkers MSMB and MSMB-binding protein CRISP3," Prostate Cancer and Prostatic Diseases (2010) 13:369-375.
Dalela et a., Jun. 20, 2017, Genomic classifier augments the role of pathological features in identifying optimal candidates for adjuvant radiation therapy in patients with prostate cancer: development and internal validation of a multivariable prognostic model, Journal of Clinical Oncology, 35(18):1982-1990.
Dalela et al., "Contemporary Role of the Decipher Test in Prostate Cancer Management: Current Practice and Future Perspectives," Rev. Urol. (2016), 18(1):1-9, MedReviews®, LLC.
Dalsgaard Sorensen et al.: "Discovery of prostate cancer biomarkers by microarray gene expression profiling"; Expert Review of Molecular Diagnostics, vol. 10, No. 1, Jan. 1, 2010, pp. 49-64.
D'Amico et al., "Cancer-specific mortality after surgery or radiation for patients with clinically localized prostate cancer managed during the prostate-specific antigen era," J Clin Oncol. (2003) 21:2163-2172.
D'Amico et al., "Determinants of prostate cancer-specific survival after radiation therapy for patients with clinically localized prostate cancer," J Clin Oncol. (2002) 20:4567-4573.
Damrauer et al., Feb. 25, 2014, Intrinsic subtypes of high-grade bladder cancer reflect the hallmarks of breast cancer biology, Proc Natl Acad Sci USA, 111(8):3110-3115.
Dawood, Shaheenah, "Novel Biomarkers of Metastatic Cancer," Expert Rev. Mo/. Diagn. (2010) 10(5):581-590, Expert Reviews Ltd.
Day et al., "Estimating enrichment of repetitive elements from high-throughput sequence data." Genome Biol. (2010) 11 (6):R69.
De Klein et al., "A cellular oncogene is translocated to the Philadelphia chromosome in chronic myelocytic leukaemia." Nature (Dec. 23, 1982) 300(5894):765-7.
De Marzo et al., "Pathological and molecular mechanisms of prostate carcinogenesis: implications for diagnosis, detection, prevention, and treatment," J Cell Biochem. (Feb. 15, 2004) 91(3):459-477.
Dechassa et al., "Architecture of the SWI/SNF-nucleosome complex," Mol Cell Biol. (Oct. 2008) vol. 28, No. 19, pp. 6010-6021.
Demichelis et al., "TMPRSS2:ERG gene fusion associated with lethal prostate cancer in a watchful waiting cohort," Oncogene (2007) 26:4596-4599.
Den et al., Mar. 10, 2015, Genomic classifier identifies men with adverse pathology after racial prostatectomy who benefit from adjuvant radiation therapy, Journal of Clinical Oncology, 33(8):944-951.
Dhanasekaran et al., "Delineation of prognostic biomarkers in prostate cancer," Nature (2001) 412:822-826.
Dhani et al., 2011, Phase II study of cytarabine in men with docetaxel-refractory, castration-resistnt prostate cancer with evaluation of TMPRSS2-ERG and SPINK1 as serum biomarkers, BJUI, 110:840- 845.
Dougherty, "The fundamental role of pattern recognition for gene-expression/microarray data in bioinformatics," Pattern recognition (2005) 38:2226-2228.
Eder et al., "Genes differentially expressed in prostate cancer," BJU Int. (May 2004) 93(8): 1151-1155.
Edwards et al., "Expression analysis onto microarrays of randomly selected cDNA clones highlights HOXB13 as a marker of human prostate cancer," Br J Cancer. (Jan. 31, 2005) 92(2):376-381.
Edwards et al.: "MicroRNAs and Ultraconserved Genes as Diagnostic Markers and Therapeutic Targets in Cancer and Cardiovascular Diseases", Journal of Cardiovascular Translational Research (May 5, 2010) vol. 3, No. 3, pp. 271-279.
Englisch, et al., "Chemically Modified Oligonucleotides as Probes and Inhibitors," Angew. Chem. Int. Ed. Eng. (1991) 30:613-629.
Epstein et al., "Prognostic factors and reporting of prostate carcinoma in radical AU prostatectomy and pelvic lymphadenectomy specimens," Scand. J. Urol. Nephrol. Suppl. (2005) 216:34-63.
Erho et al., "Discovery and Validation of a Prostate Cancer Genomic Classifier that Predicts Early Metastasis Following Radical Prostatectomy," PLoS One (2013) 8(6):e66855, 1-12.
Ernst et al., "Decrease and gain of gene expression are equally discriminatory markers for prostate carcinoma: a gene expression analysis on total and microdissected prostate tissue," Am J Pathol. (Jun. 2002) 160(6):2169-2180.
Etzioni et al. "The case for early detection", Nature Reviews | Cancer (Apr. 2003) vol. 3, pp. 1-10.
Fan et al., "Concordance among gene- expression-based predictors for breast cancer," N Engl J Med. (2006) 355:560-569.
Feng et al., "Luminal and basal subtyping of prostate cancer," *J Clin Oncol* (Feb. 20, 2017) 35(6).
Feroze-Merzoug et al., "Molecular profiling in prostate cancer," Cancer Metastasis Rev. 1 (2001) 20(3-4):165-71.
Fine et al., "A Proportional Hazards Model for the Subdistribution of a Competing Risk," Journal of the American Statistical Association (1999) vol. 94 (446), pp. 496-509.
Finley et al., "Advancing the molecular diagnosis of thyroid nodules: defining benign lesions by molecular profiling," Thyroid (2005) 15(6):562-8.
Finley et al., "Discrimination of benign and malignant thyroid nodules by molecular profiling," Ann Surg. (2004) 240(3):425-36; discussion 436-7.
Fodor et al., "Light-directed, spatially addressable parallel chemical synthesis," Science (Feb. 15, 1991) 251(4995):767-773.
Foley et al., "Molecular pathology of prostate cancer: the key to identifying new biomarkers of disease," Endocrine-Related Cancer (2004) 11:477-488.
Fontaine, et al., "Increasing the number of thyroid lesions classes in microarray analysis improves the relevance of diagnostic markers," PLoS One (Oct. 29, 2009) 4(10):e7632. doi: 10.1371/journal.pone.0007632.
Fryknas et al., "Molecular markers for discrimination of benign and malignant follicular thyroid tumors," Tumour Biol. (2006) 27(4):211-20.
Fu et al., "Regulation of apoptosis by a prostate-specific and prostate cancer-associated noncoding gene, PCGEM1." DNA Cell Biol. (Mar. 2006) 25(3): 135-41.
Fujarewicz et al., "A multi-gene approach to differentiate papillary thyroid carcinoma from benign lesions: gene selection using support vector machines with bootstrapping," Endocr Relat Cancer (Sep. 2007) 14(3):809-26.
Gait. Chapter 16: Oligoribonucleotides. Antisense Research and Applications, Crooke and Lebleu Eds., CRC Press (1993) pp. 289-302.
Galamb et al., "Diagnostic mRNA Expression Patterns of Inflamed, Benign, and Malignant Colorectal Biopsy Specimen and their Correlation with Peripheral Blood Results," Cancer Epidemiology, Biomarkers & Prevention (Oct. 2008) 17(10):2835-2845.

(56) References Cited

OTHER PUBLICATIONS

Galavotti et al., Apr. 2012, The autophagy-associated factors DRAM1 and p62 regulate cell migration and invasion in glioblastoma stem cells, Oncogene, 32:699-712.
Gao et al., "VISTA is an inhibitory immune checkpoint that is increased after ipilimumab therapy in patients with prostate cancer," Nat Med. (May 2017) 23(5):551-555.
Garber et al., "Diversity of gene expression in adenocarcinoma of the lung," PNAS (Nov. 20, 2001) vol. 98, No. 24, pp. 13784-13789.
Genevieve de Saint Basile et al., "Severe Combined Immunodeficiency Caused By Deficiency In Either The li Or the E Subunit Of CD3," Journal of Clinical Investigation (2004) vol. 114, No. 10. p. 1512-1517.
Gentles et al., Jul. 20, 2015, The prognostic landscape of genes and infiltrating immune cells across human cancers, Nature Medicine, 21(8):938-945.
Gibb et al., "The functional role of long non-coding RNA in human carcinomas", Molecular Cancer, Biomed Central, London, GB (Apr. 13, 2011) vol. 10, No. 1, p. 38.
Giordano et al., "Organ-Specific Molecular Classification of Primary Lung, Colon, and Ovarian Adenocarcinomas Using Gene Expression Profiles," Am J Pathol (2001) 159(4):1231-1238.
Gleason: "Histologic grading and clinical staging of prostatic carcinoma", Urologic pathology: the prostate, (Tannenbaum, ed.) (1977) Lea & Febiger, Philadelphia, PA, pp. 171-197.
Gleason: "Histologic grading of prostate cancer: a perspective"; Hum. Pathol. (1992) 23(3):273-279.
Gleave et al., "Randomized comparative study of 3 versus 8-month neoadjuvant hormonal therapy before radical prostatectomy : biochemical and pathological effects," J Urol. (2001) 166:500-507.
Glinsky et al., "Gene expression profiling predicts clinical outcome of prostate cancer," J Clin Investigation (2004) 113(6):913-923.
Glinsky et al., "Microarray analysis identifies a death-from-cancer signature predicting therapy i failure in patients with multiple types of cancer," J Clin Invest. (2005) 115: 1503-1521.
Gonzalgo et al.: "Molecular pathways to prostate cancer"; J Urol. (2003) 170(6 Pt 1):2444-2452.
Gore et al., Aug. 1, 2017, Decipher test impacts decision making among patients considering adjuvant and salvage treatment after radical prostatectomy: interim results from the multicenter prospective Pro-Impact study, Cancer, pp. 2850-2959.
Grambsch et al., "Proportional Hazards Tests and Diagnostics Based on Weighted Residuals," Biometrika (2013) vol. 81 (3), pp. 515-526.
Greenbaum et al.: "Comparing protein abundance and mRNA expression levels on a genomic scale"; Genome Biology (2003) 4(9):117.1-117.8.
Griffith et al., "Meta-analysis and meta-review of thyroid cancer gene expression profiling studies identifies important diagnostic biomarkers," J Clin Oncol. (2006) 24(31):5043-51.
Griffith, et al. Biomarker panel diagnosis of thyroid cancer: a critical review. Expert Rev Anticancer Ther. (Sep. 2008) 8(9):1399-413. doi: 10.1586/14737140.8.9.1399.
Gupta et al., "Long non-coding RNA HOTAIR reprograms chromatin state to promote cancer metastasis," Nature (Apr. 15, 2010) 464(7291): 1071-6.
Guttman et al., "Ab initio reconstruction of transcriptomes of pluripotent and lineage committed cells reveals gene structures of thousands of lincRNAs," Nat Biotechnol. (May 2010) 28(5):503-10.
Guttman et al., "Chromatin signature reveals over a thousand highly conserved large non-coding RNAs in mammals", Nature (Mar. 12, 2009) 458(7235):223-7.
Ha et al., Nov. 12, 2009, Comparison of affymetrix gene array with the exon array shows potential application for detection of transcript isoform variation, BMC Genomics, 19(1):519.
Haiman et al.: "Multiple regions within 8q24 independently affect risk for prostate cancer"; Nat Genet. (2007) 39:638-644.
Hamada et al., "Diagnostic usefulness of PCR profiling of the differentially expressed marker genes in thyroid papillary carcinomas," Cancer Lett. (Jun. 28, 2005) 224(2):289-301. Epub Nov. 18, 2004.
He et al., "The antisense transcriptomes of human cells", Science (Dec. 19, 2008) 322(5909): 1855-7.
Heagerty et al., "Time-Dependent ROC Curves for Censored Survival Data and a Diagnostic Marker," Biometrics (2000) vol. 56 (2), pp. 337-344.
Heemers, H. V. et al.: "Identification of a Clinically Relevant Androgen-Dependent Gene Signature in Prostate Cancer"; Cancer Research, vol. 71, No. 5 (2011) pp. 1978-1988.
Heidenreich et al., "EAU Guidelines on Prostate Cancer. Part 1: Screening, Diagnosis, and Treatment of Clinically Localised Disease," European Urology (2011) vol. 59, pp. 61-71.
Henrotin et al.: "Type II collagen peptides for measuring cartilage degradation," Biorheology (2004) 41 (3 -4): Abstract.
Henshall et al., "Survival Analysis of Genome-Wide Gene Expression Profiles of Prostate cancers Identifies New Prognostic Targets of Disease Relapse," Cancer Research (Jul. 15, 2003) 63, 14196-4203.
Holzbeierlein et al., "Gene expression analysis of human prostate carcinoma during hormonal therapy identifies androgen-responsive genes and mechanisms of therapy resistance," Am. J . Pathol. (Jan. 2004) 164(1):217-227.
Hornberger et al., "A Multigene Prognostic Assay for Selection of Adjuvant Chemotherapy in Patients with T3, Stage II Colon Cancer: Impact on Quality-Adjusted Life Expectancy and Costs," Value In Health 15 (2012) pp. 1014-1021.
Huarte et al., "Large non-coding RNAs: missing links in cancer?" Human Molecular Genetics (Oct. 15, 2010) 19(2): R152-R161.
Hughes et al., "Molecular pathology of prostate cancer," J Clin Pathol. (Jul. 2005) 58(7):673-684.
Hughes et al., "Topoisomerase II—a expression increases with increasing Gleason score and with hormone insensitivity in prostate carcinoma," J Clin Pathol. (Jul. 2006) 59(7): 721-724.
Humphrey et al.: "Histologic grade, DNA ploidy, and intraglandular tumor extent as indicators of tumor progression of clinical Stage B prostatic carcinoma"; Am J Surg Pathol (1991) 15(12):1165-1170.
Ida et al., "Topoisomerase II alpha protein expression Is predictive of outcome in Gleason score 7 prostate cancer patients treated surgically and is dependent on ERG status." Mod Pathol. (Feb. 2010) Abstract 1895, 23 : 424A-425A.
Ito et al., "Linkage of elevated ets-2 expression to hepatocarcinogenesis," Anticancer Research (2002) 22(4):2385-2389.
Jemal et al.: "Cancer statistics," CA Cancer J Clin. (2005) 55:10-30.
Jenkins et al., "Prognostic significance of ailetic imbalance of chromosome arms 71, 8p, 16q, and 18q in stage T3NOMO prostate cancer," Genes, Chromosomes & Cancer (1998) 21:131-143.
Jhavar et al., "Integration of ERG gene mapping and gene-expression profiling identifies distinct categories of human prostate cancer," BJUI (2008) vol. 103 (9), pp. 1256-1269.
Jhavar et al., "Technical Advance: Detection of TMPRSS2-ERG Translocations in Human Prostate Cancer by Expression Profiling Using GeneChip Human Exon 1.0 ST Arrays," J Mol. Diag (Jan. 2008) vol. 10, No. 1, pp. 50-57.
Jones et al., "Frequent mutations of chromatin remodeling gene ARID1A in ovarian clear cell carcinoma" Science (Oct. 8, 2010) 330(6001):228-31.
Kanehisa, "Use of statistical criteria for screening potential homologies in nucleic acid sequences," Nucleic Acids Res. (Jan. 11, 1984) 12(1 Pt 1):203-13.
Karan et al., "Current status of the molecular genetics of human prostatic adenocarcinomas," Int J Cancer, 2003, 103(3):285-293.
Karayi et al., "Molecular biology of prostate cancer," Prostate Cancer Prostatic Dis. (2004) 7(1):6-20.
Karnes et al., "Radical prostatectomy for high-risk prostate cancer," Jpn. J. Clin. Oneal. (Oct. 19, 2009) 40 (1): 3-9, Epub.
Karnes et al., "The ability of biomarkers to predict systemic progression in men with high-risk prostate cancer treated surgically is dependent on ERG status," Cancer Res. (Nov. 9, 2010) 70(22):8994-9002, Epub.

(56) References Cited

OTHER PUBLICATIONS

Kasraeian, et al. , "A comparison of fine-needle aspiration, core biopsy, and surgical biopsy in the diagnosis of extremity soft tissue masses," Clin Orthop Relat Res. (Nov. 2010) 468(11):2992-3002.
Kawamorita et al., "Radical prostatectomy for high-risk prostate cancer: Biochemical outcome," International Journal of Urology (2009) 16:733-738.
Kebebew et al., "Diagnostic and extent of disease multigene assay for malignant thyroid neoplasms," Cancer (2006) 106(12):2592-7.
Kestin, "Potential survival advantage with early androgen deprivation for biochemical failure after external beam radiotherapy: the importance of accurately defining biochemical disease status," Int J Rad Oncol Biol Phys. (2004) 60:453-62.
Khor et al.: "Bcl-2 and Bax Expression Predict Prostate Cancer Outcome in Men Treated with Androgen Deprivation and Radiotherapy on Radiation Therapy Oncology Group Protocol 92-02"; Clinical Cancer Research (Jun. 15, 2007) vol. 13, No. 12, pp. 3585-3590.
Kiessling, et al., "D-TMPP: A novel androgen-regulated gene preferentially expressed in prostate and prostate cancer that is the first characterized member of an eukaryotic gene family," The Prostate (2005) 64:387-400.
Kikuchi et al., "Expression profiles of non-small cell lung cancers on cDNA microarrays: identification of genes for prediction of lymph-node metastasis and sensitivity to anti-cancer drugs," Oncogene (2003) 22, pp. 2192-2205.
Kishi et al., "Expression of the surviving gene in prostate cancer: correlation with clinicopathological characteristics, proliferative activity and apoptosis," J Urol. (May 2004) 171(5): 1855-1860.
Klee et al., "Candidate Serum Biomarkers for Prostate Adenocarcinoma identified by mRNA Differences in Prostate Tissue and Verified with Protein Measurements in Tissue and Blood," Clinical Chemistry (2012) 58(3):599-609.
Knowles et al., Dec. 23, 2014, Molecular biology of bladder cancer: new insights into pathogenesis and clinical diversity, Nature Reviews Cancer, 15(1):25-41.
Kosari et al., "Identification of biomarkers for prostate cancer," Clin. Cancer Res. (2008) 1734-1743.
Koshkin et al., "LNA (locked nucleic acids): An RNA mimic forming exceedingly stable LNA," LNA duplexes. J Am Chem Soc (1998) 120:13252-13253.
Koshkin et al., "LNA (locked nucleic acids): synthesis of the adenine, cytosine, guanine 5-methylcytosine, thymine and uracil bicyclonucleoside monomers, oligomerisation, and unprecedented nucleic acid recognition," Tetrahedron (1998) 54(14):3607-3630.
Kroschwitz The Concise Encyclopedia Of Polymer Science And Engineering (1990) (pp. 858-859).
Kube et al., "Optimization of laser capture microdissection and RNA amplification for gene expression profiling of prostate cancer," BMC Mol. Biol. (2007) 8:25.
Kumar, et al., "The first analogues of LNA (locked nucleic acids): phosphorothioate-LNA and 2'-thio-LNA," Bioorg Med Chem Lett. (Aug. 18, 1998) 8(16):2219-22.
Kumar-Sinha et al., "Molecular markers to identify patients al risk for recurrence after primary treatment for prostate cancer," Urology, 62 Suppl 1:19-35, Dec. 29, 2003.
Kunarso et al., "Transposable elements have rewired the core regulatory network of human embryonic stem cells," Nat Genet (Jul. 2010) 42(7):631-4.
Landers et al.: "Use of multiple biomarkers for a molecular diagnosis of prostate cancer"; Int. J. Cancer (May 10, 2005) 114 pp. 950-956.
Lapointe et al., "Gene expression profiling identifies clinically relevant subtypes of prostate cancer," PNAS USA (2004) 101:811-816.
Latulippe et al., "Comprehensive Gene Expression Analysis of Prostate Cancer Reveals Distinct Transcriptional Programs Associated with Metastatic Disease," Cancer Res. (2002) 62:4499-4506.
Lawton et al., "Updated results of the phase III Radiation Therapy Oncology Group (RTOG) trial 85-31 evaluating the potential benefit of androgen suppression following standard radiation therapy for unfavorable prognosis carcinoma of the prostate," Int J Rad Oncol Biol Phys. (2001) 49:937-946.
Leyten et al., "Identification of a Candidate Gene Panel for the Early Diagnosis of Prostate Cancer," Clinical Cancer Research (2015) 21(13):3061-3070.
Lin et al., "Cox Regression with Incomplete Covariate Measurements," Journal of the American Statistical Association (1993) vol. 88 (424), pp. 1341-1349.
Lin et al., "Nuclear receptor-induced chromosomal proximity and DNA breaks underlie specific translocations in cancer," Cell (Dec. 11, 2009) 139(6):1069-83.
Liong et al., "Blood-Based Biomarkers of Aggressive Prostate Cancer," PLoS One (Sep. 2012) vol. 7, Issue 7, e45802, pp. 1-7.
Liu et al., 2014, Synergistic killing of lung cancer cells by cisplatin and radiation via autophagy and apoptosis, Oncology Letters, 7:1903-1910.
Livingston et al., "Homo sapiens CDC20 Cell Division Cycle 20 Homolog (CDC20)," Gene (Apr. 24, 2006).
Lockstone, "Exon array data analysis using Affymetrix power tools and R statistical software," Briefings in bioinformatics (2011) vol. 12 (6), pp. 634-644.
Lunardi et al., "A co-clinical approach identified mechanisms and potential therapies for androgen deprivation resistance in prostate cancer," Nature Genetics (Jul. 2013) vol. 45, No. 7, pp. 747-757.
Luo et al., "Gene expression analysis of prostate cancers," Molecular Carcinogenesis (Jan. 2002) 33(1):25-35.
Luo et al., "Human Prostate Cancer and Benign Prostatic Hyperplasia : Molecular Dissection by Gene Expression Profiling," Cancer Res. (2001) 61:4683-4688.
Magee et al., "Expression Profiling Reveals Hepsin Overexpression in Prostate Cancer," Cancer Res. (2001) 61:5692-5696.
Martens-Uzunova, E. S. et al.: "Diagnostic and prognostic signatures from the small non-coding RNA transcriptome in prostate cancer", Oncogene (Jul. 18, 2011) vol. 31, No. 8, pp. 978-991.
Martin, "A New Access to 2'-O-Alkylated Ribonucleosides and Properties of 2'-O-Alkylated Oligoribonucleotides," Helv. Chim. Acta. (1995) 78:486-504. (in German with English abstract).
Mazzanti, et al., "Using gene expression profiling to differentiate benign versus malignant thyroid tumors," Cancer Res. (Apr. 15, 2004) 64(8):2898-903.
McCall et al., "Frozen robust multiarray analysis (fRMA)", Biostatistics (2010) vol. 11 (2), 242-253.
McConkey et al., Apr. 2015, Therapeutic opportunities in the intrinsic subtypes of muscle-invasive bladder cancer, Hematology/Oncology Clinics of North America, 29(2):377-394.
McConkey et al., May 2016, A prognostic gene expression signature in the molecular classification of chemotherapy-naïve urothelial cancer is predictive of clinical outcomes from neoadjuvant chemotherapy: a phase 2 trial of dose-dense methotrexate, vinblastine, doxorubicin, and cisplatin with bevacizumab in urothelial cancer, European Urology, 69(5):855-862.
Mendiratta et al., "Genomic signatures associated with the development, progression, rand outcome of prostate cancer," Molecular diagnosis & therapy (2007) 11(6):345-54.
Mercer, DW, "Use of multiple markers to enhance clinical utility", Immunol Ser. (1990) 53: 39-54.
Mineva et al., "Differential expression of alphaB-crystallin and Hsp27-1 in anaplastic thyroid carcinomas because of tumor-specific alphaB-crystallin gene (CRYAB) silencing," Cell Stress Chaperones (Autumn 2005) 10(3):171-84.
Mitelman, "Recurrent chromosome aberrations in cancer," Mutation Research (2000) 462: 247-253.
Montironi et al., "Carcinoma of the prostate: inherited susceptibility, somatic gene defects and androgen receptors," Virchows Arch. (Jun. 2004) 444(6):503-508.
Moul et al., "Early versus delayed hormonal therapy for prostate specific antigen only recurrence of prostate cancer after radical prostatectomy," J Urol. (2004) 171:1141-1147.
Moul, "Prostate specific antigen only progression of prostate cancer," J Urol. (2000) 163:1632-42.

(56) References Cited

OTHER PUBLICATIONS

Mühlenbruch et al., "Multiple imputation was a valid approach to estimate absolute risk from a prediction model based on case-cohort data," Journal of Clinical Epidemiology (2017) 84:130-141.
Nakagawa et al., "A Tissue Biomarker Panel Predicting Systemic Progression after PSA Recurrence Post-Definitive Prostate Cancer Therapy," PLos One (2008) 3(5):e2318, 14 pages.
Nelson, "Predicting prostate cancer behavior using transcript profiles," J Urol. (Nov. 2004) 172(5 Pt 2):S28-32; discussion S33.
Newson, Roger, "Confidence intervals for rank statistics: Somers' D and extensions," The Stata Journal (Sep. 2006) 6(3):309-334.
Nielsen et al., "Sequence-selective recognition of DNA by strand displacement with a thymine-substituted polyamide," Science (1991) 254: 1497-1500.
Noordzij et al. "The prognostic value of CD44 isoforms in prostate cancer patients treated by radical prostatectomy", Clin Cancer Res (May 1997) 3(5): 805-815.
Norman, James, "Thyroid Nodule Ultrasound", Endocrine website (Updated Oct. 13, 2010) http://www.endocrineweb.com/noduleus.html.
Ohl et al., "Gene expression studies in prostate cancer tissue: which reference gene should be selected for normalization?," J. Mol. Med . (2005) 83(12):1014-1024.
Ong et al., "Expression Profiling Identifies a Novel-Methylacyl-CoA Racemase Exon with Fumarate Hydratase Homology," Cancer Research (Jun. 15, 2003) 63:3296-3301.
Oosumi et al., "Mariner transposons in humans", Nature (Dec. 14, 1995) 378 (6558): 672.
Ozen et al., Sep. 24, 2007, Widespread deregulation of microRNA expression in human prostate cancer, Oncogene, 27:1788-1793.
Parker et al., "High expression levels of surviving protein independently predict a poor outcome for patients who undergo surgery for clear cell renal cell carcinoma," Cancer (2006) 107:37-45.
Pascal et al., "Correlation of mRNA and protein levels: Cell type-specific gene expression of cluster designation antigens in the prostate," BMC Genomics (2008) 9:246 (13 pages).
Patel et al., "Preoperative PSA velocity is an independent prognostic factor for relapse after radical prostatectomy," J Clin Oncol. (2005) 23:6157-6162.
Paulo et al., "Molecular Subtyping of Primary Prostate Cancer Reveals Specific and Shared Target Genes of Different ETS Rearrangements," *Neoplasia* (Jul. 2012) 14(7):600-611.
Penney et al., "mRNA Expression Signature of Gleason Grade Predicts Lethal Prostate Cancer," J Clin Oncol (Jun. 10, 2011) vol. 29, No. 17, pp. 2391-2396 and Appendix.
Pereira et al., "Coagulation factor V and VIIIN ratio as predictors of outcome in paracetamol induced fulminant hepatic failure: relation to other prognostic indicators," Gut (1992) 33:98-102.
Perez et al., "Long, abundantly expressed non-coding transcripts are altered in cancer," Human Molecular Genetics (2008) vol. 17, No. 5, pp. 642-655. Published online Nov. 15, 207.
Pienta et al. "The current state of preclinical prostate cancer animal models"; Prostate (2008) 69: 629-639.
Pilepich et al., "Phase III radiation therapy oncology group (RTOG) trial 86-10 of androgen deprivation adjuvant to definitive radiotherapy in locally advanced carcinoma of the prostate," Int. J. Radiation Oncology Biol. Phys. (2001) vol. 50, No. 5, pp. 1243-1252.
Pinover et al., "Validation of a treatment policy for patients with prostate specific antigen failure after three-dimensional conformal prostate radiation therapy," Cancer (Feb. 15, 2003) vol. 97, No. 4, pp. 1127-1133.
Pittoni et al., "The Dark Side of Mast Cell-Targeted Therapy in Prostate Cancer," Cancer Res. (2012) 72(4):831-835.
Porkka et al., "RAD21 and KIAA0196 at 8q24 are amplified and overexpressed in prostate cancer," Genes Chromosomes Cancer (2007) 39:1-10.
Porkka et al.: Molecular mechanisms of prostate cancer'; Eur Urol. (2004) 45(6):683-691.
Pound et al., "Natural history of progression after PSA elevation following radical prostatectomy," JAMA (1999) 281:1591-1597.
Prasad et al., "Identification of genes differentially expressed in benign versus malignant thyroid tumors," Clin Cancer Res. (2008) 14(11):3327-37.
Prensner et al., "Transcriptome Sequencing Identifies PCAT-1, a Novel lincRNA Implicated in Prostate Cancer Progression," (2012) 29 (8): 742-749.
Probe Set Listing for the Affymetrix Human Genome U133 Plus 2.0 array (Accessed from https://www.affymetrix.com/analysis/index.affx on Jul. 1, 2015) (Year: 2015).
Puskas, et al., "Gene profiling identifies genes specific for well-differentiated epithelial thyroid tumors," Cell Mol Biol (Noisy-le-grand) (Sep. 5, 2005) 51(2):177-86.
Rabbits, "Chromosomal translocations in human cancer", Nature (Nov. 10, 1994) 372: 143-149.
Reddy et al., "Clinical utility of microarray-derived genetic signatures in predicting outcomes in prostate cancer," Clinical Genitourinary Cancer (2006) 5(3):187-189.
Reis et al., "Antisense intronic non-coding RNA levels correlate to the degree of tumor differentiation in prostate cancer," Oncogene (2004) 23(39):6684-6692.
Rhodes et al., "Large-scale meta-analysis of cancer microarray data identifies common transcriptional profiles of neoplastic transformation and progression," Proc Nat Acad Sci USA (2004) 101:9309-9314.
Rhodes et al., "Multiplex biomarker approach for determining risk of prostate specific antigen-defined recurrence of prostate cancer," J Nat Cancer Inst. (May 7, 2003) vol. 95, No. 9, pp. 661-668.
Rhodes et al., "ONCOMINE: A Cancer Microarray Database and Integrated Data-Mining Platform," Neoplasia (2004) 6:1-6.
Rinn et al., "Functional demarcation of active and silent chromatin domains in human HOX loci by noncoding RNAs," Cell (Jun. 29, 2007) 129(7):1311-23.
Roberts et al., "The SWI/SNF complex-chromatin and cancer." Nat Rev Cancer (Feb. 2004) 4(2):133-42.
Robertson et al., "DNA in radical prostatectomy specimens. Prognostic value of tumor ploidy," Acta Oncologica (1991) 30(2):205-207.
Robertson et al., "Reconstructing the ancient mariners of humans." Nat Genet. (Apr. 1996) 12(4):360-1.
Robinson et al., "A dynamic programming approach for the alignment of signal peaks in multiple gas chromatography-mass spectrometry experiments," BMC Bioinformatics (2007) 8.1:419.
Robinson, et al., "A comparison of Affymetrix gene expression arrays," BMC Bioinformatics (Nov. 15, 2007) 8:449.
Romanuik et al., "LNCaP Atlas: Gene expression associated with in vivo progression to castration-recurrent prostate cancer," GMB Medical Genomics (2010) 3:43, pp. 1-19.
Ross et al., "Tissue-based Genomics Augments Post-prostatectomy Risk Stratification in a Natural History Cohort of Intermediate- and High-Risk Men," European Urology 69 (2016) pp. 157-165.
Rotblat et al., "A Possible Role for Long Non-Coding RNA in Modulating Signaling Pathways," Med. Hvnotheses (2011) 77:962-965, Elsevier.
Rotunno et al., "A Gene Expression Signature from Peripheral Whole Blood for Stage I Lung Adenocarcinoma," Cancer Prevention Research (Jul. 8, 2011) 4(10) 1599-1607.
Rowley, "A new Consistent Chromosomal Abnormal ity in Chronic Myelogenous Leukaemia Identified by Quinacrine fluorescence and Giemsa Staining," Nature (Jun. 1, 1973) 243:290-293.
Rowley, "Chromosome translocations: dangerous liaisons revisited," Nature Reviews: Cancer (Dec. 2001) 1):245-250.
Rubin et al., "Molecular genetics of human prostate cancer," Modern Pathol. (2004) 17(3):380-388.
Saito-Hisaminato et al., "Genome-Wide Profiling of Gene Expression in 29 Normal Human Tissues with a cDNA Microarray," DNA Research (2002) vol. 9, pp. 35-45.
Saligan et al., "Supervised Classification by Filter Methods and Recursive Feature Elimination Predicts Rick of Radiotherapy-Related Fatigue in Patients with Prostate Cancer," Cancer Informatics (2014) 13: 141-152.

(56) References Cited

OTHER PUBLICATIONS

Sandler et al., "Overall survival after prostate-specific-antigen-detected recurrence following conformal radiation therapy," Int J Rad Oncol Biol Phys. (2000) 48:629-633.
Sanghvi, "Heterocyclic base modifications in nucleic acids and their applications in antisense oligonucleotides in Antisense Research and Applications," Crooke, S. T. and Lebleu, B., ed., CRC Press. (1993) Ch 15 274-285.
Saramaki et al., "Amplification of EIF3S3 gene is associated with advanced stage in prostate cancer," Am J Pathol. (2001) 159:2089-2094.
Sato et al., "Clinical significance of alterations of chromosome 8 in high-grade, advanced, nonmetastatic prostate carcinoma," J Natl Cancer Inst. (1999) 91:1574-1580.
Savinainen et al., "Expression and copy number analysis of TRPS 1, EIF3S3 and MYC genes in breast and prostate cancer," Br J Cancer (2004) 90: 1041-1046.
Savinainen et al., "Over expression of EIF3S3 promotes cancer cell growth," The Prostate (2006) 66: 1144-1150.
Schlomm et al., "Molecular staging of prostate cancer in the year 2007," World .J. Urol. (Mar. 2007) 25(1):19-30.
Schmidt et al., "Lack of interferon consensus sequence binding protein (ICSBP) transcripts in human myeloid leukemias," Blood (1998) 91:22-29.
Schumacher et al., "A Common 8q24 Variant in Prostate and Breast Cancer from a Large Nested Case-Control Study," Cancer Res. (2007) 67:2951-2956.
Seiler et al., Oct. 2017, Impact of molecular subtypes in muscle-invasive bladder cancer on predicting response and survival after neoadjuvant chemotherapy, European Urology, 72(4):544-554.
Severi et al., "The Common Variant rs1447295 on Chromosome 8q24 and Prostate Cancer Risk: Results from an Australian Population-based Case-Control Study", Cancer Epidemiology, Biomarkers & Prevention (2007) 16:610-611.
Shariat et al., "An updated catalog of prostate cancer predictive tools," Cancer (2008) 113(11):3062-6.
Shariat et al., "Surviving expression is associated with features of biologically aggressive prostate carcinoma," Cancer (2004) 100(4): 751-757.
Shen et al., "The SWI/SNF ATPase Brm is a gatekeeper of proliferative control in prostate cancer," Cancer Res. (Dec. 15, 2008) 68(24):10154-62.
Shibru et al., "Does the 3-gene diagnostic assay accurately distinguish benign from malignant thyroid neoplasms?" Cancer (Sep. 1, 2008) 113(5):930-5. doi: 10.1002/cncr.23703.
Shipley et al., "Radiation therapy for clinically localized prostate cancer: a multi-institutional pooled analysis," JAMA (1999) 281:1598-1604.
Simmons et al., "Natural history of biochemical recurrence after radical prostatectomy: risk assessment for secondary therapy," Eur Urol. (May 2007) 51(5):1175-84.
Singh et al., "Gene expression correlates of clinical prostate cancer behavior," Cancer Cell (Mar. 2002) vol. 1, pp. 1203-1209.
Singh et al., "LNA (locked nucleic acids): synthesis and high-affinity nucleic acid recognition," Chem Commun (1998) 4:455-456.
Singh et al., "Synthesis of 2'-amino-LNA: A novel conformationally restricted high-affinity oligonucleotide analogues with a handle," J Org Chem (1998) 63:10035-10039.
Slotkin et al., "Transposable elements and the epigenetic regulation of the genome." Nat Rev Genet. (Apr. 2007) 8(4):272-85.
Smit et al., "High-Resolution ERG-Expression Profiling on GeneChip Exon 1.0 ST Arrays in Primary and Castration-Resistant Prostate Cancer," *BJU International* (2013), 111(5):836-842, BJU International.
Solo et al., "Prevalence of prostate cancer (PC) clinical states (CS) in the United States: Estimates using a dynamic progression model," ASCO Annual Meeting, Journal of Clinical Oncology (May 20, 2011) vol. 29, No. 15, Abstract 4637.
Srikantan et al., "PCGEM1, a prostate-specific gene, is overexpressed in prostate cancer," PNAS (Oct. 24, 2000) 97(22): 12216-12221.
Stamey et al., "Molecular genetic profiling of Gleason grade 415 prostate cancers compared to benign prostatic hyperplasia," J Urol. (2001) 166(6):2171-2177.
Stanbrough et al., "Increased Expression of Genes Converting Adrenal Androgens to Testosterone in Androgen-Independent Prostate Cancer," Cancer Res (Mar. 1, 2006) 66(5):2815-2825.
Stavenhagen et al., "An ancient provirus has imposed androgen regulation on the adjacent mouse sex-limited protein Jene." Cell (Oct. 21, 1988) 55(2):247-54.
Stephenson et al., "Integration of gene expression profiling and clinical variables to predict prostate carcinoma recurrence after radical prostatectomy," Cancer (Jul. 15, 2005) 104(2):290-298.
Stephenson et al., "Postoperative Nomogram Predicting the 10-Year Probability of Prostate Cancer Recurrence After Radical Prostatectomy," J Clin Oncol (2008) vol. 23 (28), pp. 7005-7012.
Subramanian et al., "Gene set enrichment analysis: A knowledge-based approach for interpreting genome-wide expression profiles," PNAS USA (2005) 102:15545-15550.
Sun et al., "Aberrant expression of SWI/SNF catalytic subunits BRG1/BRM is associated with tumor development and increased invasiveness in prostate cancers," Prostate (Feb. 1, 2007) 67(2):203-13.
Taft et al., "Non-coding RNAs: regulators of disease," J Pathol. (Jan. 2010) 220(2):126-39.
Takayama et al., "TACC2 Is an Androgen-Responsive Cell Cycle Regulator Promoting Androgen-Mediated and Castration-Resistant Growth of Prostate Cancer," Mol Endocrinol (May 2012) 26(5):748-761.
Talantov et al., "Gene Based Prediction of Clinically Localized Prostate Cancer Progression After Radical Prostatectomy," The Journal Of Urology (Oct. 2010) vol. 184, 1521-1528.
Taylor et al., "Integrative genomic profiling of human prostate cancer," Cancer Cell (Jul. 13, 2010) vol. 18 (1), pp. 11-22.
Thompson et al., "Adjuvant and Salvage Radiotherapy After Prostatectomy: AUA/ASTRO Guideline," J Urol. (2013) 190(2):441-449.
Thompson et al., "Is the GPSM scoring algorithm for patients with prostate cancer valid in the contemporary era?" J Urol. (Aug. 2007) vol. 178 (2), 459-463.
Thorsen et al., "Alternative Splicing in Colon, Bladder, and Prostate Cancer Identified by Exon Array Analysis," Molecular & Cellular Proteomics (Mar. 18, 2008) vol. 7, No. 7, pp. 1214-1224.
Tockman et al., "Considerations in bringing a cancer biomarker to clinical application," Cancer Research (1992) 52:2711-2718.
Tollefson et al., "Stratification of Patient Risk Based on Prostate-Specific Antigen Doubling Time After Radical Retropubic Prostatectomy," Mayo Clin Proc. (2007) 82:422-427.
Tomlins et al., "Distinct classes of chromosomal rearrangements create oncogenic ETS gene fusions in prostate cancer," Nature (Aug. 2, 2007) 448(7153):595-9.
Tomlins et al., "Integrative molecular concept modeling of prostate cancer progression," Nat Genet. (2007) 39:41-51.
Tomlins et al., "Recurrent Fusion of TMPRSS2 and ETS Transcription Factor Genes in Prostate Cancer," Science (2005) 310(5748):644-648.
Tomlins et al., "TMPRSS2:ETV4 Gene Fusions Define a Third Molecular Subtype of Prostate Cancer," Cancer Res. (2006) 66:3396-3400.
Tricoli et al., "Detection of prostate cancer and predicting progression: current and future diagnostic markers," Clinical Cancer Research (Jun. 15, 2004) 10:3943-3953.
True et al., "A molecular correlate to the Gleason grading system for prostate adenocarcinoma," PNAS (Jul. 18, 2006) vol. 103, No. 29, pp. 10991-10996.
Tsuchiya et al., "Clinical significance in situ hybridization analysis in pathologic of alterations of chromosome 8 detected by fluorescence organ-confined prostate cancer," Genes Chromosomes Cancer (2002) 34:363-371.
Tsuchiya et al., "Mapping and gene expression profile of the minimally overrepresented 8q24 region in prostate cancer," Am J Pathol. (May 2002) 160(5):1799-1806.

(56) References Cited

OTHER PUBLICATIONS

Vanaja et al., "PDLIM4 Repression by Hypermethylation as a Potential Biomarker for Prostate Cancer," Clin. Cancer Res. (2006) 12(4):1128-1136.
Vanaja et al., "Transcriptional Silencing of Zinc Finger Protein 185 Identified Profiling Is Associated with Prostate Cancer Progression," Cancer Research (Jul. 15, 2003) 63:3877-3882.
Varambally et al., "Integrative Genomic and Proteomic Analysis of Prostate Cancer Reveals Signatures of Metastatic Progression," Cancer Cell (Nov. 2005) 8(5):393-406.
Varela et al., "Exome sequencing identifies frequent mutation of the SWI/SNF complex gene PBRM1 in renal carcinoma," Nature (Jan. 27, 2011) 469(7331):539-42.
Varricchi et al., "Are Mast Cells MASTers in Cancer?" Front Immunol. ePub (Apr. 12, 2017) 8:424.
Versteege et al., "Truncating mutations of hSNF5/INI1 in aggressive paediatric cancer." Nature (Jul. 9, 1998) 394 6689):203-6.
Vickers et al., "Extensions to decision curve analysis, a novel method for evaluating diagnostic tests, prediction models and molecular markers," BMC Medical Informatics and Decision Making, (2008) 8(53):1-17.
Visakorpi, "The molecular genetics of prostate cancer," Urology (2003) 62(5 Suppl 1):3-10.
Wang et al., "RNA-Seq: a revolutionary tool for transcriptomics," Nature Reviews/Genetics (Jan. 2009) vol. 10, pp. 57-63.
Wang et al., "Two common chromosome 8q24 variants are associated with increased risk for prostate cancer," Cancer Res. (2007) 67:2944-2950.
Warrick et al., 2016, FOXA1, GATA3 and PPARγ cooperate to drive luminal subtype in bladder cancer: a molecular analysis of established human cell lines, Scientific Reports, 6:38531, DOI: 10.1038, 15 pp.
Watson et al., "Future opportunities for the diagnosis and treatment of prostate cancer," Prostate Cancer Prostatic Dis. (2004) 7:S8-S13.
Weber et al., "The prognostic value of expression of HIF1[alpha], EGFR and VEGF-A, in localized prostate cancer for intermediate- and high-risk patients treated with radiation therapy with or without androgen deprivation therapy," Radiation Oncology (Apr. 30, 2012) vol. 7, No. 66, 8 pages.
Welsh et al., "Analysis of Gene Expression Identifies Candidate Markers and Pharmacological Targets in Prostate Cancer," Cancer Res. (Aug. 15, 2001) 61:5974-5978.
Wiegand et al., "ARID1A mutations in endometriosis-associated ovarian carcinomas," N Engl J Med. (Oct. 14, 2010) 363 (16):1532-43.
Willman et al., "Immunohistochemical staining for DNA topoisomerase II-alpha in benign, premalignant, and malignant lesions of the prostate," Prostate (Mar. 1, 2000) 42(4):280-286.
Winkler et al.: "Stage D1 prostatic adenocarcinoma: significance of nuclear DNA ploidy patterns studied by flow cytometry," Mayo Clin Proc. (1988) 63(2): 103-112.
Wyatt et al., "Heterogeneity in the inter-tumor transcriptome of high risk prostate cancer," *Genome Biology* (Aug. 26, 2014) vol. 15, No. 8, pp. 2-14.
Xiong et al., Dec. 2017, Low CCL17 expression associated with unfavorable postoperative prognosis of patients with clear cell renal cll carcinoma, BMC Cancer, 17(1):117.
Yap et al., "Molecular interplay of the noncoding RNA ANRIL and methylated histone H3 lysine 27 by polycomb CBX7 n transcriptional silencing of INK4a," Mol Cell. (Jun. 11, 2010) 38(5):662-74.
Yates et al., "X:Map: annotation and visualization of genome structure for Affymetrix exon array analysis," Nucleic Acids Res. (2008) vol. 36:D780-D786.
Yeager et al., "Genome-wide association study of prostate cancer identifies a second risk locus at 8q24," Nat Genet (2007) 39:645-649.
Yegnasubramanian et al., "DNA hypomethylation arises later in prostate cancer progression than CpG island hypermethylation and contributes to metastatic tumor heterogeneity," Cancer Res. (Nov. 1, 2008) 68(21): pp. 8954-8967.
Yeliin et al., "Widespread occurrence of antisense transcription in the human genome," Nat Biotechnol. (2003) 21(4):379-86.
You et al., Jun. 14, 2016, Integrated classification of prostate cancer reveals a novel luminal subtype with poor outcome, Cancer Research 76(17):4948-4958.
Yu et al., "An integrated network of androgen receptor, polycomb, and TMPRSS2-ERG gene fusions in prostate cancer progression," Cancer Cell. (May 18, 2010) 17(5):443-54.
Yu et al., "Gene expression alterations in prostate cancer predicting tumor aggression and preceding development of malignancy," J Clin Oncol. (Jul. 15, 2004) 22(14):2790-2799.
Yukinawa et al., "A multi-class predictor based on a probabilistic model: application to gene expression profiling-based diagnosis of thyroid tumors," BMC Genomics (Jul. 27, 2006) 7:190.
Zanetta et al., "Flow-cytometric analysis of deoxyribonucleic acid content in advanced ovarian carcinoma: its importance in long-term survival," Am J Obstet Gynecol (1996) 175(5): 1217-1225.
Zelefsky et al., "High dose radiation delivered by intensity modulated conformal radiotherapy improves the outcome of localized prostate cancer," The Journal of Urology (Sep. 2001) 166(3):876-881.
Zelefsky et al., "Neoadjuvant hormonal therapy improves the therapeutic ratio in patients with bulky prostatic cancer treated with three-dimensional conformal radiation therapy," Int J Radiat Oncol Biol Phys. (1994) 29:755-761.
Zhao et al., "Development and validation of a 24-gene predictor of response to postoperative radiotherapy in prostate cancer: a matched, retrospective analysis," Lancet Oncol (2016) 17, pp. 1612-1620.
GenBank Accession No. AA462934 dated Jun. 10, 1997, 2 pages.
GenBank Accession No. AA920095 dated Apr. 20, 1998, 2 pages.
GenBank Accession No. AB028840 dated Jan. 12, 2000, 2 pages.
GenBank Accession No. AB030836 dated Oct. 23, 1999, 2 pages.
GenBank Accession No. AB036741 dated Dec. 22, 2000, 3 pages.
GenBank Accession No. AF077349 dated Dec. 14, 2000, 2 pages.
GenBank Accession No. AF077351 dated Dec. 20, 2000, 3 pages.
GenBank Accession No. AF115517 dated Nov. 23, 2005, 4 pages.
GenBank Accession No. AI413910 dated Feb. 9, 1999, 2 pages.
GenBank Accession No. AI414999 dated Feb. 9, 1999, 2 pages.
GenBank Accession No. AI425960 dated Mar. 9, 1999, 2 pages.
GenBank Accession No. AI851940 dated Jul. 15, 1999, 2 pages.
GenBank Accession No. AK018022 dated Sep. 19, 2008, 4 pages.
GenBank Accession No. AK019341 dated Sep. 19, 2008, 3 pages.
GenBank Accession No. AK019342 dated Sep. 19, 2008, 3 pages.
GenBank Accession No. AK034387 dated Sep. 19, 2008, 4 pages.
GenBank Accession No. AK038229 dated Sep. 19, 2008, 4 pages.
GenBank Accession No. AK038434 dated Sep. 19, 2008, 4 pages.
GenBank Accession No. AK041534 dated Sep. 19, 2008, 4 pages.
GenBank Accession No. AK042683 dated Sep. 19, 2008, 4 pages.
GenBank Accession No. AK136096 dated Sep. 19, 2008, 4 pages.
GenBank Accession No. AK136101 dated Sep. 19, 2008, 4 pages.
GenBank Accession No. AK142768 dated Sep. 19, 2008, 3 pages.
GenBank Accession No. AL591433 dated Jan. 15, 2009, 56 pages.
GenBank Accession No. BC004702 dated Jul. 15, 2006, 3 pages.
GenBank Accession No. BC055737 dated Jul. 15, 2006, 2 pages.
GenBank Accession No. BC086799 dated Sep. 21, 2006, 3 pages.
GenBank Accession No. BF449664 dated Dec. 1, 2000, 1 page.
GenBank Accession No. BG063957 dated Jan. 26, 2001, 2 pages.
GenBank Accession No. BG077309 dated Dec. 17, 2003, 2 pages.
GenBank Accession No. BM114282 dated Jan. 30, 2002, 2 pages.
GenBank Accession No. BY023910 dated Dec. 6, 2002, 2 pages.
GenBank Accession No. CN724527 dated May 18, 2004, 2 pages.
GenBank Accession No. NM_000130 dated Oct. 18, 2009, 6 pages.
GenBank Accession No. NM_000493 dated Mar. 15, 2009, 4 pages.
GenBank Accession No. NM_000598, GI No. 62243067 , dated Jun. 6, 2010, 5 pages.
GenBank Accession No. NM_000688, GI No. 40316942, dated Apr. 11, 2010, 5 pages.
GenBank Accession No. NM_001013398; GI No. 62243247, dated Jun. 6, 2010, 5 pages.
GenBank Accession No. NM_001034 dated Oct. 5, 2009, 5 pages.
GenBank Accession No. NM_001039573, GI No. 221316683, dated Mar. 4, 2010, 5 pages.
GenBank Accession No. NM_001049 dated Jun. 21, 2009, 4 pages.

(56) References Cited

OTHER PUBLICATIONS

GenBank Accession No. NM_001067 dated Oct. 18, 2009, 5 pages.
GenBank Accession No. NM_001098533, GI No. 237858579, dated May 7, 2010, 5 pages.
GenBank Accession No. NM_001130851; GI No. 195927024, dated Mar. 5, 2010, 4 pages.
GenBank Accession No. NM_001136154 dated Jan. 8, 2012, 6 pages.
GenBank Accession No. NM_001136155 dated Jan. 8, 2012, 6 pages.
GenBank Accession No. NM_001143998, GI No. 221316675, dated Mar. 4, 2010, 5 pages.
GenBank Accession No. NM_001143999, GI No. 221316679, dated Mar. 5, 2010, 5 pages.
GenBank Accession No. NM_001144001, GI No. 221316686, dated Mar. 4, 2010, 5 pages.
GenBank Accession No. NM_001160367, GI No. 237858581, dated May 7, 2010, 5 pages.
GenBank Accession No. NM_001786 dated Nov. 1, 2009, 4 pages.
GenBank Accession No. NM_001844 dated Sep. 28, 2009, 7 pages.
GenBank Accession No. NM_003003, GI No. 221316681, dated Mar. 4, 2010, 5 pages.
GenBank Accession No. NM_003014; GI No. 170784837, dated Mar. 13, 2010, 5 pages.
GenBank Accession No. NM_003184; GI No. 115527086, dated Mar. 4, 2010, 7 pages.
GenBank Accession No. NM_003873.3 dated Oct. 18, 2009, 4 pages.
GenBank Accession No. NM_004336; GI No. 211938448, dated Mar. 14, 2010, 6 pages.
GenBank Accession No. NM_004449 dated Jan. 8, 2012, 6 pages.
GenBank Accession No. NM_005025.2 dated Jul. 12, 2009, 4 pages.
GenBank Accession No. NM_005192, GI No. 195927023, dated Mar. 4, 2010, 4 pages.
GenBank Accession No. NM_005651.1 dated Oct. 27, 2009, 3 pages.
GenBank Accession No. NM_006265, GI No. 208879448, dated Apr. 11, 2010, 6 pages.
GenBank Accession No. NM_006558 dated 812109, 3 pages.
GenBank Accession No. NM_006727 dated Oct. 18, 2009, 3 pages.
GenBank Accession No. NM_006819; GI No. 110225356, dated 517/2010, 5 pages.
GenBank Accession No. NM_012152; GI No. 183396778, dated Apr. 5, 2010, 5 pages.
GenBank Accession No. NM_014846; GI No. 120952850, dated Mar. 4, 2010, 6 pages.
GenBank Accession No. NM_016623; GI No. 42734437, dated Mar. 29, 2009, 4 pages.
GenBank Accession No. NM_018930 dated Feb. 10, 2008, _pages.
GenBank Accession No. NM_031966 GI No. 34304372, dated Jun. 6, 2010, 5 pages.
GenBank Accession No. NM_032334; GI No. 223468686, dated Mar. 5, 2010, 3 pages.
GenBank Accession No. NM_052987, GI No. 237858574, dated 517/2010, 5 pages.
GenBank Accession No. NM_052988, GI No. 237858573, dated 517/2010, 5 pages.
GenBank Accession No. NM_080546; GI No. 112363101, dated 517/2010, 6 pages.
GenBank Accession No. NM_080607 dated Sep. 3, 2009, 2 pages.
GenBank Accession No. NM_133445 dated Sep. 20, 2009, 5 pages.
GenBank Accession No. NM_138455; GI No. 34147546, dated May 7, 2010, 3 pages.
GenBank Accession No. NM_182918 dated Jan. 8, 2012, 6 pages.
GenBank Accession No. NM_199166, GI No. 40316938, dated Apr. 11, 2010, 5 pages.
GenBank Accession No. NP_001058 dated Dec. 25, 2011, 9 pages.
GenBank Accession No. W34764 dated May 13, 1996, 2 pages.
Supplemental Table 1 of U.S. Appl. No. 61/057,698, filed May 30, 2008, 13 pages.
Supplemental Table 2 of U.S. Appl. No. 61/057,698, filed May 30, 2008, 15 pages.
Supplemental Table 3 of U.S. Appl. No. 61/057,698, filed May 30, 2008, 21 pages.
Supplemental Table 4 of U.S. Appl. No. 61/057,698, filed May 30, 12008, 1 page.
Supplemental Table 5 of U.S. Appl. No. 61/057,698, filed May 30, 12008, 2 pages.
Supplemental Table 6 of U.S. Appl. No. 61/057,698, filed May 30, 2008, 1 page.
International Search Report and Written Opinion dated Jul. 9, 2018 for PCT/US18/21826.
Alkateeb et al., Mar. 13, 2019, Transcriptomics signature from next-generation sequencing data reveals new transcriptomic biomarkers related to prostate cancer, Cancer Informatics, 18:1-12.
Altintas et al., Jun. 2013 Differentially expressed androgen-regulated genes in androgen-sensitive tissues reveal potential biomarkers of early prostate cancer, PLOS One, 8(6):e66278.
Ateeq et al., Mar. 2, 2011, Therapeutic targeting of SPINK1-positive prostate cancer, Sci Transl Med, 3(72):1-18.
Bhaskar et al., Oct. 1, 2003, E-selective up-regulation allows for targeted drug delivery in prostate cancer, Cancer Research 63:6387-6394.
Droz et al., Aug. 2014, Management of prostate cancer in older patients: updated recommendations of a working group of the International Society of Geriatric Oncology, The Lancet, 15:e404-e414.
Fischer et al., Sep. 2, 2019, A radiogenomic approach for decoding molecular mechanisms underlying tumor progression prostate cancer, Cancers, 11(9), 18 pp.
Forker et al. 2015, Biomarkers of Tumour Radiosensitivity and Predicting Benefit from Radiotherapy, 27: 561-569.
Iljin et al., Nov. 1, 2006, TMPRSS2 fusions with oncogenic ETS factors in prostate cancer involve unbalanced genomic rearrangements and are associated with HDAC1 and epigenetic reprogramming, Cancer Res., 66(21):10242-10246.
Inamura, Apr. 2018, Bladder Cancer: new insights into its molecular pathology, Cancers (Basel), 10(4):100.
Kronick, 2004, Creation of the whole human genome microarray, Expert Review of Proteomics, 1:19-28.
Michiels et al. 2005, Prediction of cancer outcome with microarrays: a multiple random validation strategy, Lancet, 365:488-492.
Nevins et al., Aug. 2007, Mining gene expression profiles: expression signatures as cancer phenotypes, Genetics, 8:601-609.
Setlur et al., 2008, Estrogen-dependent signaling in a molecularly distinct subclass of aggressive prostate cancer, Journal of the National Cancer Institute, 100:815-813.
Sparano et al., 2015, Prospective Validation of a 21-Gene Expression Assay in Breast Cancer New Eng. J. Med. 373:20 2005-2014.
Vainio, 2011, High-throughput screening for novel prostate cancer drug targets, dissertation, Turun Yliopisot, University of Turku, Finland, 74 pp.
Zhang et al. Apr. 2019, 21-Gene Recurrence Score Assay Could Not Predict Benefit of Post-mastectomy Radiotherapy in T1-2 N1 mic ER-Pos ve HER2 Negative Breast Cancer, Frontiers in Oncology, 9(270): 8 pp.
Affymetrix, Human Exon 1.0 ST Array—Support Materials, https://www.affymetrix.com/support/technical/byproduct.affx?product=huexon-st, Jan. 1, 2006 (Jan. 1, 2006).
Fridman et al., Jul. 25, 2017, The immune contexture in cancer prognosis and treatment, Nature Reviews Clinical Oncology, 14:717-734.
Halvorson et al., 2018, Interpreting GLM results: making sense of some odd ratios: a tutorial and improvements to present practices in reporting and visualizing quantities of interest for binary and count outcome models, National Research Service Award, NIH, pp. 1-39.
Litwin et al., Jun. 27, 2017, The diagnosis and treatment of prostate cancer: a review, JAMA, 317(24):2532-2542.
McArdle et al., 2004, The relationship between T-lymphocyte subset infiltration and survival in patients with prostate cancer, British Journal of Cancer, 91:541-543.

(56) References Cited

OTHER PUBLICATIONS

Newman et al., May 2015, Robust enumeration of cell subsets form tissue expression profiles, Nature Methods, 12(5):453-457 with online methods.

* cited by examiner

C Androgen

Retrospective Cohorts

SUBTYPING PROSTATE CANCER TO PREDICT RESPONSE TO HORMONE THERAPY

CROSS-REFERENCE TO RELATED APPLICATIONS

This application claims benefit of priority under 35 U.S.C. § 119(e) of U.S. Ser. No. 62/469,174, filed Mar. 9, 2017, the entire contents of which is incorporated herein by reference in its entirety.

INCORPORATION OF SEQUENCE LISTING

The material in the accompanying sequence listing is hereby incorporated by reference into this application. The accompanying sequence listing text file, name GBX1280_1WO_Sequence_Listing.txt, was created on Mar. 9, 2018, and is 289 kb. The file can be assessed using Microsoft Word on a computer that uses Windows OS.

FIELD OF THE INVENTION

The present invention relates to methods, systems and kits for the diagnosis, prognosis and the determination of cancer progression of prostate cancer in a subject. The invention also provides biomarkers that define subgroups of prostate cancer, clinically useful classifiers for distinguishing prostate cancer subtypes, bioinformatic methods for determining clinically useful classifiers, and methods of use of each of the foregoing. The methods, systems and kits can provide expression-based analysis of biomarkers for purposes of subtyping prostate cancer in a subject. Further disclosed herein, in certain instances, are probe sets for use in subtyping prostate cancer in a subject. Classifiers for subtyping a prostate cancer are provided. Methods of treating cancer based on molecular subtyping are also provided. The methods and classifiers of the present invention are also useful for predicting response to hormonal therapy (e.g., androgen deprivation therapy).

BACKGROUND OF THE INVENTION

Cancer is the uncontrolled growth of abnormal cells anywhere in a body. The abnormal cells are termed cancer cells, malignant cells, or tumor cells. Many cancers and the abnormal cells that compose the cancer tissue are further identified by the name of the tissue that the abnormal cells originated from (for example, prostate cancer). Cancer cells can proliferate uncontrollably and form a mass of cancer cells. Cancer cells can break away from this original mass of cells, travel through the blood and lymph systems, and lodge in other organs where they can again repeat the uncontrolled growth cycle. This process of cancer cells leaving an area and growing in another body area is often termed metastatic spread or metastatic disease. For example, if prostate cancer cells spread to a bone (or anywhere else), it can mean that the individual has metastatic prostate cancer.

Standard clinical parameters such as tumor size, grade, lymph node involvement and tumor-node-metastasis (TNM) staging (American Joint Committee on Cancer http://www.cancerstaging.org) may correlate with outcome and serve to stratify patients with respect to (neo)adjuvant chemotherapy, immunotherapy, antibody therapy and/or radiotherapy regimens. Incorporation of molecular markers in clinical practice may define tumor subtypes that are more likely to respond to targeted therapy. However, stage-matched tumors grouped by histological or molecular subtypes may respond differently to the same treatment regimen. Additional key genetic and epigenetic alterations may exist with important etiological contributions. A more detailed understanding of the molecular mechanisms and regulatory pathways at work in cancer cells and the tumor microenvironment (TME) could dramatically improve the design of novel anti-tumor drugs and inform the selection of optimal therapeutic strategies. The development and implementation of diagnostic, prognostic and therapeutic biomarkers to characterize the biology of each tumor may assist clinicians in making important decisions with regard to individual patient care and treatment. Thus, provided herein are methods, systems and kits for the diagnosis, prognosis and the determination of cancer progression of cancer in a subject. The invention also provides biomarkers that define subgroups of prostate cancer, clinically useful classifiers for distinguishing prostate cancer subtypes, bioinformatic methods for determining clinically useful classifiers, and methods of use of each of the foregoing. The methods, systems and kits can provide expression-based analysis of biomarkers for purposes of subtyping prostate cancer in a subject. Further disclosed herein, in certain instances, are probe sets for use in subtyping prostate cancer in a subject. Classifiers for subtyping a prostate cancer are provided. Methods of treating cancer based on molecular subtyping are also provided. The classifiers of the present invention are useful for identifying prostate cancer patients that will respond to hormone therapy (e.g., androgen deprivation therapy).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention relates to methods, systems and kits for the diagnosis, prognosis and the determination of cancer progression of cancer in a subject. The invention also provides biomarkers that define subgroups of prostate cancer, clinically useful classifiers for distinguishing prostate cancer subtypes, bioinformatic methods for determining clinically useful classifiers, and methods of use of each of the foregoing. The methods, systems and kits can provide expression-based analysis of biomarkers for purposes of subtyping prostate cancer in a subject. Further disclosed herein, in certain instances, are probe sets for use in subtyping prostate cancer in a subject. Classifiers for subtyping a prostate cancer are provided. Methods of treating cancer based on molecular subtyping are also provided.

In one embodiment, the present invention provides a method comprising: providing a biological sample from a prostate cancer subject; detecting the presence or expression level of at least one or more targets selected from Table 8, Table 9 or SEQ ID NOs: 1-1029; and subtyping the prostate cancer in the subject according to a genomic subtyping classifier based on the presence or expression levels of the plurality of targets wherein said subtyping comprises assigning the prostate cancer to one of three subtypes selected from the group consisting of a luminal A subtype, a luminal B subtype, and a basal subtype. In some embodiments, the method further comprises administering androgen deprivation therapy to the subject if the subtyping indicates that the subject has the luminal B subtype and administering an anti-cancer treatment other than the androgen deprivation therapy to the subject if the subtyping indicates that the subject has the luminal A subtype or the basal subtype, wherein the anti-cancer treatment other than androgen deprivation therapy is selected from the group consisting of surgery, chemotherapy, radiation therapy, immunotherapy, biological therapy, neoadjuvant chemotherapy, and photodynamic therapy.

In one embodiment, the present invention provides a method comprising: a) providing a biological sample from a subject having prostate cancer; b) detecting the presence or expression level in the biological sample for a plurality of targets selected from Table 8, Table 9 or SEQ ID NOs: 1-1029 and c) subtyping the prostate cancer in the subject according to a genomic subtyping classifier based on the presence or expression levels of the plurality of targets, wherein said subtyping comprises assigning the prostate cancer to one of three subtypes selected from the group consisting of a luminal A subtype, a luminal B subtype, and a basal subtype.

In one embodiment, the present invention provides a method comprising: a) providing a biological sample from a subject having prostate cancer; b) detecting the presence or expression level in the biological sample for a plurality of targets selected from the group consisting of CDC20; KIF2C; PHGDH; NUF2; CENPF; EXO1; UBE2T; RRM2; MLPH; GPR160; CCNB1; CXXC5; PTTG1; FGFR4; FOXC1; ESR1; ANLN; BLVRA; EGFR; ACTR3B; NAT1; MYC; SFRP1; MELK; BAG1; CEP55; MKI67; TMEM45B; PGR; MDM2; KRT5; FOXA1; ORC6; CDH3; ERBB2; GRB7; CDC6; MAPT; BIRC5; KRT14; KRT17; TYMS; NDC80; SLC39A6; BCL2; CCNE1; MIA; MYBL2; UBE2C; MMP11; TDRD1; CACNA1D; NCALD; HLA-DMB; KCNH8; PDE3B; PLA2G7; CSGALNACT1; PART1; HES1; F3; GPR110; SH3RF; PDE8B; SEPT9; CRISP3; AMD1; KCNG3; PLA1A; MYO6; FRK; SH3YL1; ACER3; C8orf4; GHR; ITPR1; KHDRBS3; NPY; GUCY1A3; ARHGDIB; LAMC2; VWA2; ZNF432; MORN1; CYorf15B; AMPD3; QDPR; HDAC1; KIF16B; GJB1; ITPR3; ZNF615; ANKRD6; APOD; STEAP4; RGS17; MAP7; C22orf36; NKAIN1; CHN2; LRRFIP1; SERGEF; ATP8A2; NDRG1; CDC42SE1; LUZP2; HNF1B; TFAP2A; ANKRD34B; SLC12A2; PRAC; SLC5A4; ACSL3; CD24P4; DNASE2B; SLC22A3; ODC1; SMOC2; UGDH; DSC2; WNK2; RAB3B; FAM198B; KCNC2; SNAP91; FAM65B; AMACR; ZNF385B; CDK19; ARHGAP18; IL5RA; SLC16A1; CNTLN; FKBP10; SLC45A2; CLIP1; HEXB; NEFH; ODZ1; SS18L2; HPGD; FAM3B; MIPEP; NCAPD3; INPP4B; ANPEP; TFF3; IL31RA; EHHADH; RP11-45B20.2; CCDC141; RLN1; ABHD2; SCIN; ALOX15B; MON1B; MME; BANK1; LEPREL1; VGLL3; NPR3; OR4K7P; OR4K6P; POTEB2; RP11; TTN; FAP5; GPR116; RP11.403; and FABP5P7; and c) subtyping the prostate cancer in the subject according to a genomic subtyping classifier based on the presence or expression levels of the plurality of targets, wherein said subtyping comprises assigning the prostate cancer to one of three subtypes selected from the group consisting of a luminal A subtype, a luminal B subtype, and a basal subtype.

In one embodiment, the present invention provides a method comprising: a) providing a biological sample from a subject having prostate cancer and b) detecting the presence or expression level in the biological sample for a plurality of targets selected from Table 8, Table 9 or SEQ ID NOs: 1-1029. In some embodiments, the method further comprises subtyping the prostate cancer in the subject according to a genomic subtyping classifier based on the presence or expression levels of the plurality of targets, wherein said subtyping comprises assigning the prostate cancer to one of three subtypes selected from the group consisting of a luminal A subtype, a luminal B subtype, and a basal subtype.

In some embodiments, the method further comprises administering androgen deprivation therapy to the subject if the subtyping indicates that the subject has the luminal B subtype and administering an anti-cancer treatment other than the androgen deprivation therapy to the subject if the subtyping indicates that the subject has the luminal A subtype or the basal subtype, wherein the anti-cancer treatment other than androgen deprivation therapy is selected from the group consisting of surgery, chemotherapy, radiation therapy, immunotherapy, biological therapy, neoadjuvant chemotherapy, and photodynamic therapy.

In some embodiments, the present invention provides a method comprising: providing a biological sample from a prostate cancer subject; detecting the presence or expression level of at least one or more targets selected from Table 8, Table 9 or SEQ ID NOs: 1-1029; and administering a treatment to the subject, wherein the treatment is selected from the group consisting of surgery, chemotherapy, radiation therapy, immunotherapy/biological therapy, hormonal therapy, and photodynamic therapy. In some embodiments, the treatment is androgen deprivation therapy. In some embodiments, the present invention provides a method of subtyping prostate cancer in a subject, comprising: providing a biological sample comprising prostate cancer cells from the subject, and determining the level of expression or amplification of at least one or more targets selected from Table 8, Table 9 or SEQ ID NOs: 1-1029 using at least one reagent that specifically binds to said targets; wherein the alteration of said expression level provides an indication of the prostate cancer subtype. In some embodiments, the alteration in the expression level of said target is reduced expression of said target. In other embodiments, the alteration in the expression level of said target is increased expression of said target. In yet other embodiments, the level of expression of said target is determined by using a method selected from the group consisting of in situ hybridization, a PCR-based method, an array-based method, an immunohistochemical method, an RNA assay method and an immunoassay method. In other embodiments, the reagent is selected from the group consisting of a nucleic acid probe, one or more nucleic acid primers, and an antibody. In still other embodiments, the target comprises a nucleic acid sequence.

In some embodiments, the present invention also provides a method of diagnosing, prognosing, assessing the risk of recurrence or predicting benefit from therapy in a subject with prostate cancer, comprising: providing a biological sample comprising prostate cancer cells from the subject; assaying an expression level in the biological sample from the subject for a plurality of targets using at least one reagent that specifically binds to said targets, wherein the plurality of targets comprises one or more targets selected from Table 8, Table 9 or SEQ ID NOs: 1-1029; and diagnosing, prognosing, assessing the risk of recurrence or predicting benefit from therapy in the subject based on the expression levels of the plurality of targets. In some embodiments, the expression level of the target is reduced expression of the target. In other embodiments, the expression level of said target is increased expression of said target. In yet other embodiments, the level of expression of said target is determined by using a method selected from the group consisting of in situ hybridization, a PCR-based method, an array-based method, an immunohistochemical method, an RNA assay method and an immunoassay method. In other embodiments, the reagent is selected from the group consisting of a nucleic acid probe, one or more nucleic acid primers, and an antibody. In other embodiments, the target comprises a nucleic acid sequence.

In some embodiments, the present invention provides a system for analyzing a cancer, comprising, a probe set comprising a plurality of target sequences, wherein the plurality of target sequences hybridizes to one or more targets selected from Table 8, Table 9 or SEQ ID NOs: 1-1029; or the plurality of target sequences comprises one or more targets selected from Table 8, Table 9 or SEQ ID NOs: 1-1029; and a computer model or algorithm for analyzing an expression level and/or expression profile of the target hybridized to the probe in a sample from a subject suffering from prostate cancer. In some embodiments, the method further comprises a label that specifically binds to the target, the probe, or a combination thereof.

In some embodiments, the present invention provides a method comprising: (a) providing a biological sample from a subject with prostate cancer; (b) detecting the presence or expression level in the biological sample for a plurality of targets, wherein the plurality of targets comprises one or more targets selected from Table 8, Table 9 or SEQ ID NOs: 1-1029; (c) subtyping the prostate cancer in the subject based on the presence or expression levels of the plurality of targets; and (d) administering a treatment to the subject, wherein the treatment is selected from the group consisting of surgery, chemotherapy, radiation therapy, immunotherapy/biological therapy, hormonal therapy, and photodynamic therapy. In some embodiments, the present invention provides a method of treating a subject with prostate cancer, comprising: providing a biological sample comprising prostate cancer cells from the subject; determining the level of expression or amplification of at least one or more targets selected from Table 8, Table 9 or SEQ ID NOs: 1-1029 using at least one reagent that specifically binds to said targets; subtyping the prostate cancer based on the level of expression or amplification of the at least one or more targets; and prescribing a treatment regimen based on the prostate cancer subtype. In some embodiments, the prostate cancer subtype is selected from the group consisting of luminal A, luminal B, and basal.

In some embodiments, the present invention provides a kit for analyzing a prostate cancer, comprising, a probe set comprising a plurality of target sequences, wherein the plurality of target sequences comprises at least one target sequence listed in Table 8, Table 9 or SEQ ID NOs: 1-1029; and a computer model or algorithm for analyzing an expression level and/or expression profile of the target sequences in a sample. In some embodiments, the method further comprises a computer model or algorithm for correlating the expression level or expression profile with disease state or outcome. In other embodiments, the method further comprises a computer model or algorithm for designating a treatment modality for the individual. In yet other embodiments, the method further comprises a computer model or algorithm for normalizing expression level or expression profile of the target sequences. In some embodiments, the method further comprises sequencing the plurality of targets. In some embodiments, the method further comprises hybridizing the plurality of targets to a solid support. In some embodiments, the solid support is a bead or array. In some embodiments, assaying the expression level of a plurality of targets may comprise the use of a probe set. In some embodiments, assaying the expression level may comprise the use of a classifier. The classifier may comprise a probe selection region (PSR). In some embodiments, the classifier may comprise the use of an algorithm. The algorithm may comprise a machine learning algorithm. In some embodiments, assaying the expression level may also comprise sequencing the plurality of targets.

Further disclosed herein methods for molecular subtyping of prostate cancer, wherein the subtypes have an AUC value of at least about 0.40 to predict patient outcomes. In some embodiments, patient outcomes are selected from the group consisting of biochemical recurrence (BCR), metastasis (MET) and prostate cancer death (PCSM) after radical prostatectomy. The AUC of the subtype may be at least about 0.40, 0.45, 0.50, 0.55, 0.60, 0.61, 0.62, 0.63, 0.64, 0.65, 0.66, 0.67, 0.68, 0.69, 0.70 or more.

Further disclosed herein is a method for subtyping a prostate cancer, comprising determining the level of expression or amplification of at least one or more targets of the present invention, wherein the significance of the expression level of the one or more targets is based on one or more metrics selected from the group comprising T-test, P-value, KS (Kolmogorov Smirnov) P-value, accuracy, accuracy P-value, positive predictive value (PPV), negative predictive value (NPV), sensitivity, specificity, AUC, AUC P-value (Auc.pvalue), Wilcoxon Test P-value, Median Fold Difference (MFD), Kaplan Meier (KM) curves, survival AUC (survAUC), Kaplan Meier P-value (KM P-value), Univariable Analysis Odds Ratio P-value (uvaORPval), multivariable analysis Odds Ratio P-value (mvaORPval), Univariable Analysis Hazard Ratio P-value (uvaHRPval) and Multivariable Analysis Hazard Ratio P-value (mvaHRPval). The significance of the expression level of the one or more targets may be based on two or more metrics selected from the group comprising AUC, AUC P-value (Auc.pvalue), Wilcoxon Test P-value, Median Fold Difference (MFD), Kaplan Meier (KM) curves, survival AUC (survAUC), Univariable Analysis Odds Ratio P-value (uvaORPval), multivariable analysis Odds Ratio P-value (mvaORPval), Kaplan Meier P-value (KM P-value), Univariable Analysis Hazard Ratio P-value (uvaHRPval) and Multivariable Analysis Hazard Ratio P-value (mvaHRPval). The molecular subtypes of the present invention are useful for predicting clinical characteristics of subjects with prostate cancer. In some embodiments, the clinical characteristics are selected from the group consisting of seminal vesical invasion (SVI), lymph node invasion (LNI), prostate-specific antigen (PSA), and gleason score (GS).

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

FIGS. 4A-4C set forth data showing predicted response in ADT. A matched cohort was obtained from the MCI and MCII cohorts which matched 1:2 ADT treated and untreated patients based on Gleason, PSA, LNI, ECE, SVI, and SMS resulting in 315 total patients (A). Kaplan-Meier curves are shown for the luminal B and non-luminal B patients, which group the luminal A and basal patients (B). A bar plot (C) is shown comparing the 10-year metastasis rates for treated and untreated patients in the luminal B and non-luminal B patients, with the interaction term Wald p=0.006.

DETAILED DESCRIPTION OF THE INVENTION

Figure 1A:
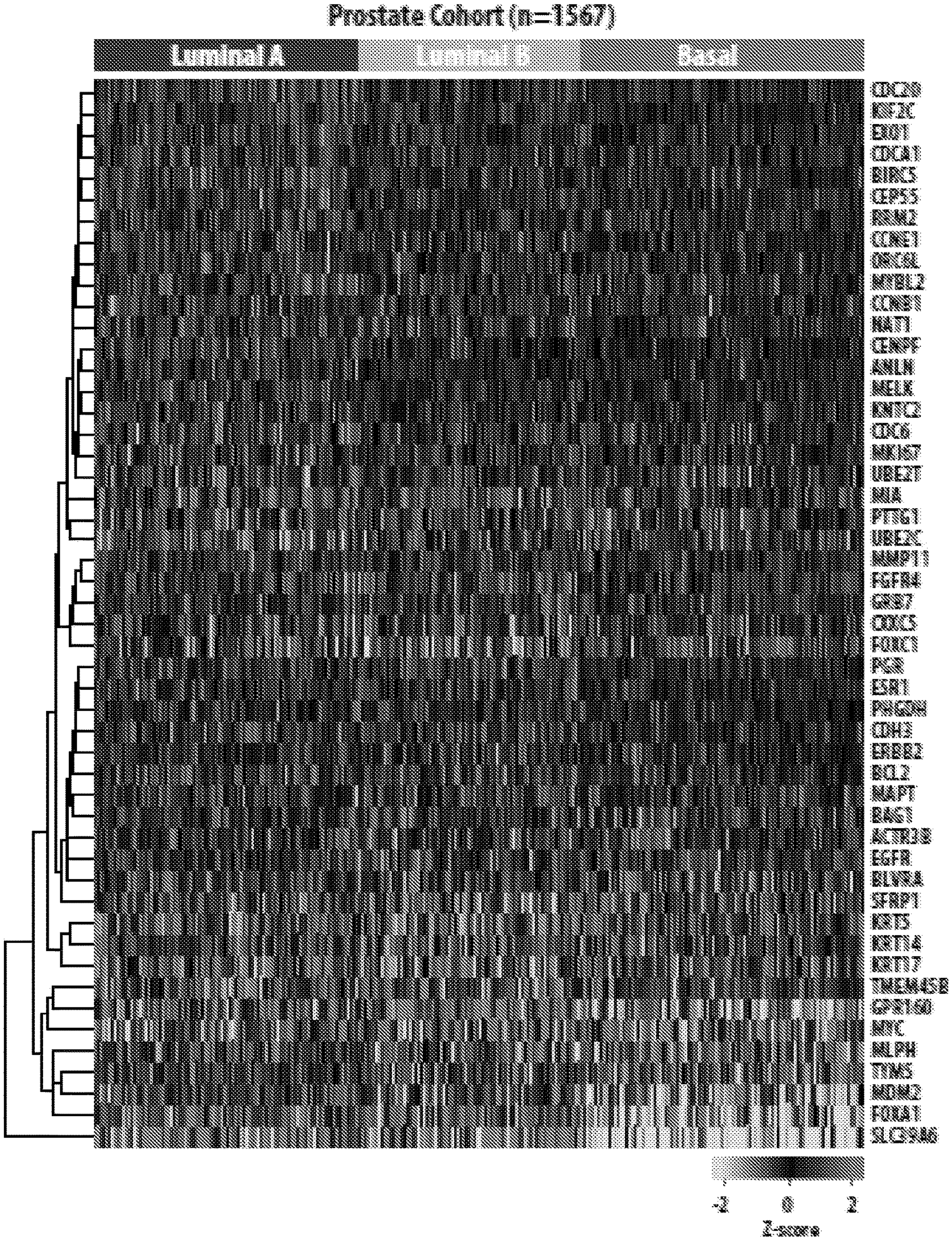
FIGS. 1A-1B set forth data showing PAM50 clustering and clinical outcomes in prostate cancer. (A) The PAM50 genes cluster prostate cancer samples into three subtypes, luminal A (dark blue), luminal B (light blue) and basal (red), in the pooled prostate cancer cohorts (MCI, II, CC, TJU, JHU, DVA) using hierarchical clustering of the genes. Each column represents a patient sample and each row represents a gene. (B) Kaplan-Meier curves showing that the PAM50 clusters risk stratify bRFS (biochemical recurrence-free survival), DMFS (distant metastasis-free survival), PCSS (prostate cancer specific survival), and OS (overall survival).

The present invention discloses systems and methods for diagnosing, predicting, and/or monitoring the status or outcome of a prostate cancer in a subject using expression-based analysis of a plurality of targets. Generally, the method comprises (a) optionally providing a sample from a subject; (b) assaying the expression level for a plurality of targets in the sample; and (c) diagnosing, predicting and/or monitoring the status or outcome of a prostate cancer based on the expression level of the plurality of targets.

Assaying the expression level for a plurality of targets in the sample may comprise applying the sample to a microarray. In some instances, assaying the expression level may comprise the use of an algorithm. The algorithm may be used to produce a classifier. Alternatively, the classifier may comprise a probe selection region. In some instances, assaying the expression level for a plurality of targets comprises detecting and/or quantifying the plurality of targets. In some embodiments, assaying the expression level for a plurality of targets comprises sequencing the plurality of targets. In some embodiments, assaying the expression level for a plurality of targets comprises amplifying the plurality of targets. In some embodiments, assaying the expression level for a plurality of targets comprises quantifying the plurality of targets. In some embodiments, assaying the expression level for a plurality of targets comprises conducting a multiplexed reaction on the plurality of targets.

In some instances, the plurality of targets comprises one or more targets selected from Table 8, Table 9 or SEQ ID NOs: 1-1029. In some instances, the plurality of targets comprises at least about 2, at least about 3, at least about 4, at least about 5, at least about 6, at least about 7, at least about 8, at least about 9, at least about 10, at least about 20, at least about 30, at least about 40, or at least about 50 targets selected from Table 8, Table 9 or SEQ ID NOs: 1-1029.

Further disclosed herein are methods for subtyping prostate cancer. Generally, the method comprises: (a) providing a sample comprising prostate cancer cells from a subject; (b) assaying the expression level for a plurality of targets in the sample; and (c) subtyping the cancer based on the expression level of the plurality of targets. In some instances, the plurality of targets comprises one or more targets selected from Table 8, Table 9 or SEQ ID NOs: 1-1029. In some instances, the plurality of targets comprises at least about 2, at least about 3, at least about 4, at least about 5, at least about 6, at least about 7, at least about 8, at least about 9, at least about 10, at least about 20, at least about 30, at least about 40, or at least about 50 targets selected from Table 8, Table 9 or SEQ ID NOs: 1-1029.

In some instances, subtyping the prostate cancer comprises determining whether the cancer would respond to an anti-cancer therapy. Alternatively, subtyping the prostate cancer comprises identifying the cancer as non-responsive to an anti-cancer therapy. Optionally, subtyping the prostate cancer comprises identifying the cancer as responsive to an anti-cancer therapy.

Before the present invention is described in further detail, it is to be understood that this invention is not limited to the particular methodology, compositions, articles or machines described, as such methods, compositions, articles or machines can, of course, vary. It is also to be understood that the terminology used herein is for the purpose of describing particular embodiments only, and is not intended to limit the scope of the present invention.

Targets

The methods disclosed herein often comprise assaying the expression level of a plurality of targets. The plurality of targets may comprise coding targets and/or non-coding targets of a protein-coding gene or a non protein-coding gene. A protein-coding gene structure may comprise an exon and an intron. The exon may further comprise a coding sequence (CDS) and an untranslated region (UTR). The protein-coding gene may be transcribed to produce a pre-mRNA and the pre-mRNA may be processed to produce a mature mRNA. The mature mRNA may be translated to produce a protein.

A non protein-coding gene structure may comprise an exon and intron. Usually, the exon region of a non protein-coding gene primarily contains a UTR. The non protein-coding gene may be transcribed to produce a pre-mRNA and the pre-mRNA may be processed to produce a non-coding RNA (ncRNA).

A coding target may comprise a coding sequence of an exon. A non-coding target may comprise a UTR sequence of an exon, intron sequence, intergenic sequence, promoter sequence, non-coding transcript, CDS antisense, intronic antisense, UTR antisense, or non-coding transcript antisense. A non-coding transcript may comprise a non-coding RNA (ncRNA).

In some instances, the plurality of targets may be differentially expressed. In some instances, a plurality of probe selection regions (PSRs) is differentially expressed.

In some instances, the plurality of targets comprises one or more targets selected from at least about 10, at least about 20, at least about 30, at least about 40, or at least about 50 targets selected from Table 8, Table 9 or SEQ ID NOs: 1-1029. In some instances, the plurality of targets comprises at least about 2, at least about 3, at least about 4, at least about 5, at least about 6, at least about 7, at least about 8, at least about 9, at least about 10, at least about 20, at least about 30, at least about 40, or at least about 50 targets selected from Table 8, Table 9 or SEQ ID NOs: 1-1029.

In some instances, the plurality of targets comprises a coding target, non-coding target, or any combination thereof. In some instances, the coding target comprises an exonic sequence. In other instances, the non-coding target comprises a non-exonic or exonic sequence. Alternatively, a non-coding target comprises a UTR sequence, an intronic sequence, antisense, or a non-coding RNA transcript. In some instances, a non-coding target comprises sequences which partially overlap with a UTR sequence or an intronic sequence. A non-coding target also includes non-exonic and/or exonic transcripts. Exonic sequences may comprise regions on a protein-coding gene, such as an exon, UTR, or a portion thereof. Non-exonic sequences may comprise regions on a protein-coding, non protein-coding gene, or a portion thereof. For example, non-exonic sequences may comprise intronic regions, promoter regions, intergenic regions, a non-coding transcript, an exon anti-sense region, an intronic anti-sense region, UTR anti-sense region, non-coding transcript anti-sense region, or a portion thereof. In other instances, the plurality of targets comprises a non-coding RNA transcript.

The plurality of targets may comprise one or more targets selected from a classifier disclosed herein. The classifier may be generated from one or more models or algorithms The one or more models or algorithms may be Naïve Bayes (NB), recursive Partitioning (Rpart), random forest (RF), support vector machine (SVM), k-nearest neighbor (KNN), high dimensional discriminate analysis (HDDA), or a combination thereof. The classifier may have an AUC of equal to or greater than 0.60. The classifier may have an AUC of equal to or greater than 0.61. The classifier may have an AUC of equal to or greater than 0.62. The classifier may have an AUC of equal to or greater than 0.63. The classifier may have an AUC of equal to or greater than 0.64. The classifier may have an AUC of equal to or greater than 0.65. The classifier may have an AUC of equal to or greater than 0.66. The classifier may have an AUC of equal to or greater than 0.67. The classifier may have an AUC of equal to or greater than 0.68. The classifier may have an AUC of equal to or greater than 0.69. The classifier may have an AUC of equal to or greater than 0.70. The classifier may have an AUC of equal to or greater than 0.75. The classifier may have an AUC of equal to or greater than 0.77. The classifier may have an AUC of equal to or greater than 0.78. The classifier may have an AUC of equal to or greater than 0.79. The classifier may have an AUC of equal to or greater than 0.80. The AUC may be clinically significant based on its 95% confidence interval (CI). The accuracy of the classifier may be at least about 70%. The accuracy of the classifier may be at least about 73%. The accuracy of the classifier may be at least about 75%. The accuracy of the classifier may be at least about 77%. The accuracy of the classifier may be at least about 80%. The accuracy of the classifier may be at least about 83%. The accuracy of the classifier may be at least about 84%. The accuracy of the classifier may be at least about 86%. The accuracy of the classifier may be at least about 88%. The accuracy of the classifier may be at least about 90%. The p-value of the classifier may be less than or equal to 0.05. The p-value of the classifier may be less than or equal to 0.04. The p-value of the classifier may be less than or equal to 0.03. The p-value of the classifier may be less than or equal to 0.02. The p-value of the classifier may be less than or equal to 0.01. The p-value of the classifier may be less than or equal to 0.008. The p-value of the classifier may be less than or equal to 0.006. The p-value of the classifier may be less than or equal to 0.004. The p-value of the classifier may be less than or equal to 0.002. The p-value of the classifier may be less than or equal to 0.001.

The plurality of targets may comprise one or more targets selected from a Random Forest (RF) classifier. The plurality of targets may comprise two or more targets selected from a Random Forest (RF) classifier. The plurality of targets may comprise three or more targets selected from a Random Forest (RF) classifier. The plurality of targets may comprise 2, 3, 4, 5, 6, 7, 8, 9, 10, 11, 12, 13, 14, 15, 20, 25, 30, 40, 50 or more targets selected from a Random Forest (RF) classifier. The RF classifier may be an RF2, and RF3, or an RF4 classifier. The RF classifier may be an RF50 classifier (e.g., a Random Forest classifier with 50 targets).

A RF classifier of the present invention may comprise two or more targets comprising two or more targets selected from Table 8, Table 9 or SEQ ID NOs: 1-1029.

The plurality of targets may comprise one or more targets selected from an SVM classifier. The plurality of targets may comprise 2, 3, 4, 5, 6, 7, 8, 9, 10, 11, 12, 13, 14, 15, 20, 25, 30, 40, 50 or more targets selected from an SVM classifier. The plurality of targets may comprise 12, 13, 14, 15, 17, 20, 22, 25, 27, 30, 40, 50 or more targets selected from an SVM classifier. The plurality of targets may comprise 32, 35, 37, 40, 43, 45, 47, 50 or more targets selected from an SVM classifier. The SVM classifier may be an SVM2 classifier.

A SVM classifier of the present invention may comprise two or more targets comprising two or more targets selected from Table 8, Table 9 or SEQ ID NOs: 1-1029.

The plurality of targets may comprise one or more targets selected from a KNN classifier. The plurality of targets may comprise 2, 3, 4, 5, 6, 7, 8, 9, 10 or more targets selected from a KNN classifier. The plurality of targets may comprise 12, 13, 14, 15, 17, 20, 22, 25, 27, 30 or more targets selected from a KNN classifier. The plurality of targets may comprise 32, 35, 37, 40, 43, 45, 47, 50 or more targets selected from a KNN classifier.

The KNN classifier may be a KNN50 classifier. A KNN classifier of the present invention may comprise fifty or more targets comprising fifty or more targets selected from Table 8, Table 9 or SEQ ID NOs: 1-1029.

The plurality of targets may comprise one or more targets selected from a Naïve Bayes (NB) classifier. The plurality of targets may comprise 2, 3, 4, 5, 6, 7, 8, 9, 10 or more targets selected from an NB classifier. The plurality of targets may comprise 12, 13, 14, 15, 17, 20, 22, 25, 27, 30 or more targets selected from an NB classifier. The plurality of targets may comprise 32, 35, 37, 40, 43, 45, 47, 50 or more targets selected from a NB classifier.

The NB classifier may be a NB2 classifier. An NB classifier of the present invention may comprise two or more targets comprising two or more targets selected from Table 8, Table 9 or SEQ ID NOs: 1-1029.

The plurality of targets may comprise one or more targets selected from a recursive Partitioning (Rpart) classifier. The plurality of targets may comprise 2, 3, 4, 5, 6, 7, 8, 9, 10 or more targets selected from an Rpart classifier. The plurality of targets may comprise 12, 13, 14, 15, 17, 20, 22, 25, 27, 30 or more targets selected from an Rpart classifier. The plurality of targets may comprise 32, 35, 37, 40, 43, 45, 47, 50 or more targets selected from an Rpart classifier.

The Rpart classifier may be an Rpart2 classifier. An Rpart classifier of the present invention may comprise two or more targets comprising two or more targets selected from Table 8, Table 9 or SEQ ID NOs: 1-1029.

The plurality of targets may comprise one or more targets selected from a high dimensional discriminate analysis (HDDA) classifier. The plurality of targets may comprise two or more targets selected from a high dimensional discriminate analysis (HDDA) classifier. The plurality of targets may comprise three or more targets selected from a high dimensional discriminate analysis (HDDA) classifier. The plurality of targets may comprise 5, 6, 7, 8, 9, 10, 11, 12, 13, 14, 15, 20, 30, 40, 50 or more targets selected from a high dimensional discriminate analysis (HDDA) classifier.

The plurality of targets may comprise one or more targets selected from CDC20, KIF2C, PHGDH, NUF2, CENPF, EXO1, UBE2T, RRM2, MLPH, GPR160, CCNB1, CXXC5, PTTG1, FGFR4, FOXC1, ESR1, ANLN, BLVRA, EGFR, ACTR3B, NAT1, MYC, SFRP1, MELK, BAG1, CEP55, MKI67, TMEM45B, PGR, MDM2, KRT5, FOXA1, ORC6, CDH3, ERBB2, GRB7, CDC6, MAPT, BIRC5, KRT14, KRT17, TYMS, NDC80, SLC39A6, BCL2, CCNE1, MIA, MYBL2, UBE2C, and MMP11; CDC20; CDC20 and KIF2C; CDC20 and PHGDH; CDC20 and NUF2; CDC20 and CENPF; CDC20 and EXO1; CDC20 and UBE2T; CDC20 and RRM2; CDC20 and MLPH; CDC20 and GPR160; CDC20 and CCNB1; CDC20 and CXXC5; CDC20 and PTTG1; CDC20 and FGFR4; CDC20 and FOXC1; CDC20 and ESR1; CDC20 and ANLN; CDC20 and BLVRA; CDC20 and EGFR; CDC20 and ACTR3B; CDC20 and NAT1; CDC20 and MYC; CDC20 and SFRP1; CDC20 and MELK; CDC20 and BAG1; CDC20 and CEP55; CDC20 and MKI67; CDC20 and TMEM45B; CDC20 and PGR; CDC20 and MDM2; CDC20 and KRT5; CDC20 and FOXA1; CDC20 and ORC6; CDC20 and CDH3; CDC20 and ERBB2; CDC20 and GRB7; CDC20 and CDC6; CDC20 and MAPT; CDC20 and BIRC5; CDC20 and KRT14; CDC20 and KRT17; CDC20 and TYMS; CDC20 and NDC80; CDC20 and SLC39A6; CDC20 and BCL2; CDC20 and CCNE1; CDC20 and MIA; CDC20 and MYBL2; CDC20 and UBE2C; CDC20 and MMP11; CDC20, KIF2C and PHGDH; CDC20, KIF2C and NUF2; CDC20, KIF2C and CENPF; CDC20, KIF2C and EXO1; CDC20, KIF2C and UBE2T; CDC20, KIF2C and RRM2; CDC20, KIF2C and MLPH; CDC20, KIF2C and GPR160; CDC20, KIF2C and CCNB1; CDC20, KIF2C and CXXC5; CDC20, KIF2C and PTTG1; CDC20, KIF2C and FGFR4; CDC20, KIF2C and FOXC1; CDC20, KIF2C and ESR1; CDC20, KIF2C and ANLN; CDC20, KIF2C and BLVRA; CDC20, KIF2C and EGFR; CDC20, KIF2C and ACTR3B; CDC20, KIF2C and NAT1; CDC20, KIF2C and MYC; CDC20, KIF2C and SFRP1; CDC20, KIF2C and MELK; CDC20, KIF2C and BAG1; CDC20, KIF2C and CEP55; CDC20, KIF2C and MKI67; CDC20, KIF2C and TMEM45B; CDC20, KIF2C and PGR; CDC20, KIF2C and MDM2; CDC20, KIF2C and KRT5; CDC20, KIF2C and FOXA1; CDC20, KIF2C and ORC6; CDC20, KIF2C and CDH3; CDC20, KIF2C and ERBB2; CDC20, KIF2C and GRB7; CDC20, KIF2C and CDC6; CDC20, KIF2C and MAPT; CDC20, KIF2C and BIRC5; CDC20, KIF2C and KRT14; CDC20, KIF2C and KRT17; CDC20, KIF2C and TYMS; CDC20, KIF2C and NDC80; CDC20, KIF2C and SLC39A6; CDC20, KIF2C and BCL2; CDC20, KIF2C and CCNE1; CDC20, KIF2C and MIA; CDC20, KIF2C and MYBL2; CDC20, KIF2C and UBE2C; CDC20, KIF2C and MMP11; CDC20, KIF2C, PHGDH and NUF2; CDC20, KIF2C, PHGDH and CENPF; CDC20, KIF2C, PHGDH and EXO1; CDC20, KIF2C, PHGDH and UBE2T; CDC20, KIF2C, PHGDH and RRM2; CDC20, KIF2C, PHGDH and MLPH; CDC20, KIF2C, PHGDH and GPR160; CDC20, KIF2C, PHGDH and CCNB1; CDC20, KIF2C, PHGDH and CXXC5; CDC20, KIF2C, PHGDH and PTTG1; CDC20, KIF2C, PHGDH and FGFR4; CDC20, KIF2C, PHGDH and FOXC1; CDC20, KIF2C, PHGDH and ESR1; CDC20, KIF2C, PHGDH and ANLN; CDC20, KIF2C, PHGDH and BLVRA; CDC20, KIF2C, PHGDH and EGFR; CDC20, KIF2C, PHGDH and ACTR3B; CDC20, KIF2C, PHGDH and NAT1; CDC20, KIF2C, PHGDH and MYC; CDC20, KIF2C, PHGDH and SFRP1; CDC20, KIF2C, PHGDH and MELK; CDC20, KIF2C, PHGDH and BAG1; CDC20, KIF2C, PHGDH and CEP55; CDC20, KIF2C, PHGDH and MKI67; CDC20, KIF2C, PHGDH and TMEM45B; CDC20, KIF2C, PHGDH and PGR; CDC20, KIF2C, PHGDH and MDM2; CDC20, KIF2C, PHGDH and KRT5; CDC20, KIF2C, PHGDH and FOXA1; CDC20, KIF2C, PHGDH and ORC6; CDC20, KIF2C, PHGDH and CDH3; CDC20, KIF2C, PHGDH and ERBB2; CDC20, KIF2C, PHGDH and GRB7; CDC20, KIF2C, PHGDH and CDC6; CDC20, KIF2C, PHGDH and MAPT; CDC20, KIF2C, PHGDH and BIRC5; CDC20, KIF2C, PHGDH and KRT14; CDC20, KIF2C, PHGDH and KRT17; CDC20, KIF2C, PHGDH and TYMS; CDC20, KIF2C, PHGDH and NDC80; CDC20, KIF2C, PHGDH and SLC39A6; CDC20, KIF2C, PHGDH and BCL2; CDC20, KIF2C, PHGDH and CCNE1; CDC20, KIF2C, PHGDH and MIA; CDC20, KIF2C, PHGDH and MYBL2; CDC20, KIF2C, PHGDH and UBE2C; CDC20, KIF2C, PHGDH and MMP11; KIF2C; KIF2C and PHGDH; KIF2C and NUF2; KIF2C and CENPF; KIF2C and EXO1; KIF2C and UBE2T; KIF2C and RRM2; KIF2C and MLPH; KIF2C and GPR160; KIF2C and CCNB1; KIF2C and CXXC5; KIF2C and PTTG1; KIF2C and FGFR4; KIF2C and FOXC1; KIF2C and ESR1; KIF2C and ANLN; KIF2C and BLVRA; KIF2C and EGFR; KIF2C and ACTR3B; KIF2C and NAT1; KIF2C and MYC; KIF2C and SFRP1; KIF2C and MELK; KIF2C and BAG1; KIF2C and CEP55; KIF2C and MKI67; KIF2C and TMEM45B; KIF2C and PGR; KIF2C and MDM2; KIF2C and KRT5; KIF2C and FOXA1; KIF2C and ORC6; KIF2C and CDH3; KIF2C and ERBB2; KIF2C and GRB7; KIF2C and CDC6; KIF2C and MAPT; KIF2C and BIRC5; KIF2C and KRT14; KIF2C and KRT17; KIF2C and TYMS; KIF2C and NDC80; KIF2C and SLC39A6; KIF2C and BCL2; KIF2C and CCNE1; KIF2C and MIA; KIF2C and MYBL2; KIF2C and UBE2C; KIF2C and MMP11; KIF2C, PHGDH and NUF2; KIF2C, PHGDH and CENPF; KIF2C, PHGDH and EXO1; KIF2C, PHGDH and UBE2T; KIF2C, PHGDH and RRM2; KIF2C, PHGDH and MLPH; KIF2C, PHGDH and GPR160; KIF2C, PHGDH and CCNB1; KIF2C, PHGDH and CXXC5; KIF2C, PHGDH and PTTG1; KIF2C, PHGDH and FGFR4; KIF2C, PHGDH and FOXC1; KIF2C, PHGDH and ESR1; KIF2C, PHGDH and ANLN; KIF2C, PHGDH and BLVRA; KIF2C, PHGDH and EGFR; KIF2C, PHGDH and ACTR3B; KIF2C, PHGDH and NAT1; KIF2C, PHGDH and MYC; KIF2C, PHGDH and SFRP1; KIF2C, PHGDH and MELK; KIF2C, PHGDH and BAG1; KIF2C, PHGDH and CEP55; KIF2C, PHGDH and MKI67; KIF2C, PHGDH and TMEM45B; KIF2C, PHGDH and PGR; KIF2C, PHGDH and MDM2; KIF2C, PHGDH and KRT5; KIF2C, PHGDH and FOXA1; KIF2C, PHGDH and ORC6; KIF2C, PHGDH and CDH3; KIF2C, PHGDH and ERBB2; KIF2C, PHGDH and GRB7; KIF2C, PHGDH and CDC6; KIF2C, PHGDH and MAPT; KIF2C, PHGDH and BIRC5; KIF2C, PHGDH and KRT14; KIF2C, PHGDH and KRT17; KIF2C, PHGDH and TYMS; KIF2C, PHGDH and NDC80; KIF2C, PHGDH and SLC39A6; KIF2C, PHGDH and BCL2; KIF2C, PHGDH and CCNE1; KIF2C, PHGDH and MIA; KIF2C, PHGDH and MYBL2; KIF2C, PHGDH and UBE2C; KIF2C, PHGDH and MMP11; KIF2C, PHGDH, NUF2 and CENPF; KIF2C, PHGDH, NUF2 and EXO1; KIF2C, PHGDH, NUF2 and UBE2T; KIF2C, PHGDH, NUF2 and RRM2; KIF2C, PHGDH, NUF2 and MLPH; KIF2C, PHGDH, NUF2 and GPR160; KIF2C, PHGDH, NUF2 and CCNB1; KIF2C, PHGDH, NUF2 and CXXC5; KIF2C, PHGDH, NUF2 and PTTG1; KIF2C, PHGDH, NUF2 and FGFR4; KIF2C, PHGDH, NUF2 and FOXC1; KIF2C, PHGDH, NUF2 and ESR1; KIF2C, PHGDH, NUF2 and ANLN; KIF2C, PHGDH, NUF2 and BLVRA; KIF2C, PHGDH, NUF2 and EGFR; KIF2C, PHGDH, NUF2 and ACTR3B; KIF2C, PHGDH, NUF2 and NAT1; KIF2C, PHGDH, NUF2 and MYC; KIF2C, PHGDH, NUF2 and SFRP1; KIF2C, PHGDH, NUF2 and MELK; KIF2C, PHGDH, NUF2 and BAG1; KIF2C, PHGDH, NUF2 and CEP55; KIF2C, PHGDH, NUF2 and MKI67; KIF2C, PHGDH, NUF2 and TMEM45B; KIF2C, PHGDH, NUF2 and PGR; KIF2C, PHGDH, NUF2 and MDM2; KIF2C, PHGDH, NUF2 and KRT5; KIF2C, PHGDH, NUF2 and FOXA1; KIF2C, PHGDH, NUF2 and ORC6; KIF2C, PHGDH, NUF2 and CDH3; KIF2C, PHGDH, NUF2 and ERBB2; KIF2C, PHGDH, NUF2 and GRB7; KIF2C, PHGDH, NUF2 and CDC6; KIF2C, PHGDH, NUF2 and MAPT; KIF2C, PHGDH, NUF2 and BIRC5; KIF2C, PHGDH, NUF2 and KRT14; KIF2C, PHGDH, NUF2 and KRT17; KIF2C, PHGDH, NUF2 and TYMS; KIF2C, PHGDH, NUF2 and NDC80; KIF2C, PHGDH, NUF2 and SLC39A6; KIF2C, PHGDH, NUF2 and BCL2; KIF2C, PHGDH, NUF2 and CCNE1; KIF2C, PHGDH, NUF2 and MIA; KIF2C, PHGDH, NUF2 and MYBL2; KIF2C, PHGDH, NUF2 and UBE2C; KIF2C, PHGDH, NUF2 and MMP11; PHGDH; PHGDH and NUF2; PHGDH and CENPF; PHGDH and EXO1; PHGDH and UBE2T; PHGDH and RRM2; PHGDH and MLPH; PHGDH and GPR160; PHGDH and CCNB1; PHGDH and CXXC5; PHGDH and PTTG1; PHGDH and FGFR4; PHGDH and FOXC1; PHGDH and ESR1; PHGDH and ANLN; PHGDH and BLVRA; PHGDH and EGFR; PHGDH and ACTR3B; PHGDH and NAT1; PHGDH and MYC; PHGDH and SFRP1; PHGDH and MELK; PHGDH and BAG1; PHGDH and CEP55; PHGDH and MKI67; PHGDH and TMEM45B; PHGDH and PGR; PHGDH and MDM2; PHGDH and KRT5; PHGDH and FOXA1; PHGDH and ORC6; PHGDH and CDH3; PHGDH and ERBB2; PHGDH and GRB7; PHGDH and CDC6; PHGDH and MAPT; PHGDH and BIRC5; PHGDH and KRT14; PHGDH and KRT17; PHGDH and TYMS; PHGDH and NDC80; PHGDH and SLC39A6; PHGDH and BCL2; PHGDH and CCNE1; PHGDH and MIA; PHGDH and MYBL2; PHGDH and UBE2C; PHGDH and MMP11; PHGDH, NUF2 and CENPF; PHGDH, NUF2 and EXO1; PHGDH, NUF2 and UBE2T; PHGDH, NUF2 and RRM2; PHGDH, NUF2 and MLPH; PHGDH, NUF2 and GPR160; PHGDH, NUF2 and CCNB1; PHGDH, NUF2 and CXXC5; PHGDH, NUF2 and PTTG1; PHGDH, NUF2 and FGFR4; PHGDH, NUF2 and FOXC 1; PHGDH, NUF2 and ESR1; PHGDH, NUF2 and ANLN; PHGDH, NUF2 and BLVRA; PHGDH, NUF2 and EGFR; PHGDH, NUF2 and ACTR3B; PHGDH, NUF2 and NAT1; PHGDH, NUF2 and MYC; PHGDH, NUF2 and SFRP1; PHGDH, NUF2 and MELK; PHGDH, NUF2 and BAG1; PHGDH, NUF2 and CEP55; PHGDH, NUF2 and MKI67; PHGDH, NUF2 and TMEM45B; PHGDH, NUF2 and PGR; PHGDH, NUF2 and MDM2; PHGDH, NUF2 and KRT5; PHGDH, NUF2 and FOXA1; PHGDH, NUF2 and ORC6; PHGDH, NUF2 and CDH3; PHGDH, NUF2 and ERBB2; PHGDH, NUF2 and GRB7; PHGDH, NUF2 and CDC6; PHGDH, NUF2 and MAPT; PHGDH, NUF2 and BIRC5; PHGDH, NUF2 and KRT14; PHGDH, NUF2 and KRT17; PHGDH, NUF2 and TYMS; PHGDH, NUF2 and NDC80; PHGDH, NUF2 and SLC39A6; PHGDH, NUF2 and BCL2; PHGDH, NUF2 and CCNE1; PHGDH, NUF2 and MIA; PHGDH, NUF2 and MYBL2; PHGDH, NUF2 and UBE2C; PHGDH, NUF2 and MMP11; PHGDH, NUF2, CENPF and EXO1; PHGDH, NUF2, CENPF and UBE2T; PHGDH, NUF2, CENPF and RRM2; PHGDH, NUF2, CENPF and MLPH; PHGDH, NUF2, CENPF and GPR160; PHGDH, NUF2, CENPF and CCNB1; PHGDH, NUF2, CENPF and CXXC5; PHGDH, NUF2, CENPF and PTTG1; PHGDH, NUF2, CENPF and FGFR4; PHGDH, NUF2, CENPF and FOXC1; PHGDH, NUF2, CENPF and ESR1; PHGDH, NUF2, CENPF and ANLN; PHGDH, NUF2, CENPF and BLVRA; PHGDH, NUF2, CENPF and EGFR; PHGDH, NUF2, CENPF and ACTR3B; PHGDH, NUF2, CENPF and NAT1; PHGDH, NUF2, CENPF and MYC; PHGDH, NUF2, CENPF and SFRP1; PHGDH, NUF2, CENPF and MELK; PHGDH, NUF2, CENPF and BAG1; PHGDH, NUF2, CENPF and CEP55; PHGDH, NUF2, CENPF and MKI67; PHGDH, NUF2, CENPF and TMEM45B; PHGDH, NUF2, CENPF and PGR; PHGDH, NUF2, CENPF and MDM2; PHGDH, NUF2, CENPF and KRT5; PHGDH, NUF2, CENPF and FOXA1; PHGDH, NUF2, CENPF and ORC6; PHGDH, NUF2, CENPF and CDH3; PHGDH, NUF2, CENPF and ERBB2; PHGDH, NUF2, CENPF and GRB7; PHGDH, NUF2, CENPF and CDC6; PHGDH, NUF2, CENPF and MAPT; PHGDH, NUF2, CENPF and BIRC5; PHGDH, NUF2, CENPF and KRT14; PHGDH, NUF2, CENPF and KRT17; PHGDH, NUF2, CENPF and TYMS; PHGDH, NUF2, CENPF and NDC80; PHGDH, NUF2, CENPF and SLC39A6; PHGDH, NUF2, CENPF and BCL2; PHGDH, NUF2, CENPF and CCNE1; PHGDH, NUF2, CENPF and MIA; PHGDH, NUF2, CENPF and MYBL2; PHGDH, NUF2, CENPF and UBE2C; PHGDH, NUF2, CENPF and MMP11; NUF2; NUF2 and CENPF; NUF2 and EXO1; NUF2 and UBE2T; NUF2 and RRM2; NUF2 and MLPH; NUF2 and GPR160; NUF2 and CCNB1; NUF2 and CXXC5; NUF2 and PTTG1; NUF2 and FGFR4; NUF2 and FOXC1; NUF2 and ESR1; NUF2 and ANLN; NUF2 and BLVRA; NUF2 and EGFR; NUF2 and ACTR3B; NUF2 and NAT1; NUF2 and MYC; NUF2 and SFRP1; NUF2 and MELK; NUF2 and BAG1; NUF2 and CEP55; NUF2 and MKI67; NUF2 and TMEM45B; NUF2 and PGR; NUF2 and MDM2; NUF2 and KRT5; NUF2 and FOXA1; NUF2 and ORC6; NUF2 and CDH3; NUF2 and ERBB2; NUF2 and GRB7; NUF2 and CDC6; NUF2 and MAPT; NUF2 and BIRC5; NUF2 and KRT14; NUF2 and KRT17; NUF2 and TYMS; NUF2 and NDC80; NUF2 and SLC39A6; NUF2 and BCL2; NUF2 and CCNE1; NUF2 and MIA; NUF2 and MYBL2; NUF2 and UBE2C; NUF2 and MMP11; NUF2, CENPF and EXO1; NUF2, CENPF and UBE2T; NUF2, CENPF and RRM2; NUF2, CENPF and MLPH; NUF2, CENPF and GPR160; NUF2, CENPF and CCNB1; NUF2, CENPF and CXXC5; NUF2, CENPF and PTTG1; NUF2, CENPF and FGFR4; NUF2, CENPF and FOXC1; NUF2, CENPF and ESR1; NUF2, CENPF and ANLN; NUF2, CENPF and BLVRA; NUF2, CENPF and EGFR; NUF2, CENPF and ACTR3B; NUF2, CENPF and NAT1; NUF2, CENPF and MYC; NUF2, CENPF and SFRP1; NUF2, CENPF and MELK; NUF2, CENPF and BAG1; NUF2, CENPF and CEP55; NUF2, CENPF and MKI67; NUF2, CENPF and TMEM45B; NUF2, CENPF and PGR; NUF2, CENPF and MDM2; NUF2, CENPF and KRT5; NUF2, CENPF and FOXA1; NUF2, CENPF and ORC6; NUF2, CENPF and CDH3; NUF2, CENPF and ERBB2; NUF2, CENPF and GRB7; NUF2, CENPF and CDC6; NUF2, CENPF and MAPT; NUF2, CENPF and BIRC5; NUF2, CENPF and KRT14; NUF2, CENPF and KRT17; NUF2, CENPF and TYMS; NUF2, CENPF and NDC80; NUF2, CENPF and SLC39A6; NUF2, CENPF and BCL2; NUF2, CENPF and CCNE1; NUF2, CENPF and MIA; NUF2, CENPF and MYBL2; NUF2, CENPF and UBE2C; NUF2, CENPF and MMP11; NUF2, CENPF, EXO1 and UBE2T; NUF2, CENPF, EXO1 and RRM2; NUF2, CENPF, EXO1 and MLPH; NUF2, CENPF, EXO1 and GPR160; NUF2, CENPF, EXO1 and CCNB1; NUF2, CENPF, EXO1 and CXXC5; NUF2, CENPF, EXO1 and PTTG1; NUF2, CENPF, EXO1 and FGFR4; NUF2, CENPF, EXO1 and FOXC1; NUF2, CENPF, EXO1 and ESR1; NUF2, CENPF, EXO1 and ANLN; NUF2, CENPF, EXO1 and BLVRA; NUF2, CENPF, EXO1 and EGFR; NUF2, CENPF, EXO1 and ACTR3B; NUF2, CENPF, EXO1 and NAT1; NUF2, CENPF, EXO1 and MYC; NUF2, CENPF, EXO1 and SFRP1; NUF2, CENPF, EXO1 and MELK; NUF2, CENPF, EXO1 and BAG1; NUF2, CENPF, EXO1 and CEP55; NUF2, CENPF, EXO1 and MKI67; NUF2, CENPF, EXO1 and TMEM45B; NUF2, CENPF, EXO1 and PGR; NUF2, CENPF, EXO1 and MDM2; NUF2, CENPF, EXO1 and KRT5; NUF2, CENPF, EXO1 and FOXA1; NUF2, CENPF, EXO1 and ORC6; NUF2, CENPF, EXO1 and CDH3; NUF2, CENPF, EXO1 and ERBB2; NUF2, CENPF, EXO1 and GRB7; NUF2, CENPF, EXO1 and CDC6; NUF2, CENPF, EXO1 and MAPT; NUF2, CENPF, EXO1 and BIRC5; NUF2, CENPF, EXO1 and KRT14; NUF2, CENPF, EXO1 and KRT17; NUF2, CENPF, EXO1 and TYMS; NUF2, CENPF, EXO1 and NDC80; NUF2, CENPF, EXO1 and SLC39A6; NUF2, CENPF, EXO1 and BCL2; NUF2, CENPF, EXO1 and CCNE1; NUF2, CENPF, EXO1 and MIA; NUF2, CENPF, EXO1 and MYBL2; NUF2, CENPF, EXO1 and UBE2C; NUF2, CENPF, EXO1 and MMP11; CENPF; CENPF and EXO1; CENPF and UBE2T; CENPF and RRM2; CENPF and MLPH; CENPF and GPR160; CENPF and CCNB1; CENPF and CXXC5; CENPF and PTTG1; CENPF and FGFR4; CENPF and FOXC1; CENPF and ESR1; CENPF and ANLN; CENPF and BLVRA; CENPF and EGFR; CENPF and ACTR3B; CENPF and NAT1; CENPF and MYC; CENPF and SFRP1; CENPF and MELK; CENPF and BAG1; CENPF and CEP55; CENPF and MKI67; CENPF and TMEM45B; CENPF and PGR; CENPF and MDM2; CENPF and KRT5; CENPF and FOXA1; CENPF and ORC6; CENPF and CDH3; CENPF and ERBB2; CENPF and GRB7; CENPF and CDC6; CENPF and MAPT; CENPF and BIRC5; CENPF and KRT14; CENPF and KRT17; CENPF and TYMS; CENPF and NDC80; CENPF and SLC39A6; CENPF and BCL2; CENPF and CCNE1; CENPF and MIA; CENPF and MYBL2; CENPF and UBE2C; CENPF and MMP11; CENPF, EXO1 and UBE2T; CENPF, EXO1 and RRM2; CENPF, EXO1 and MLPH; CENPF, EXO1 and GPR160; CENPF, EXO1 and CCNB1; CENPF, EXO1 and CXXC5; CENPF, EXO1 and PTTG1; CENPF, EXO1 and FGFR4; CENPF, EXO1 and FOXC1; CENPF, EXO1 and ESR1; CENPF, EXO1 and ANLN; CENPF, EXO1 and BLVRA; CENPF, EXO1 and EGFR; CENPF, EXO1 and ACTR3B; CENPF, EXO1 and NAT1; CENPF, EXO1 and MYC; CENPF, EXO1 and SFRP1; CENPF, EXO1 and MELK; CENPF, EXO1 and BAG1; CENPF, EXO1 and CEP55; CENPF, EXO1 and MKI67; CENPF, EXO1 and TMEM45B; CENPF, EXO1 and PGR; CENPF, EXO1 and MDM2; CENPF, EXO1 and KRT5; CENPF, EXO1 and FOXA1; CENPF, EXO1 and ORC6; CENPF, EXO1 and CDH3; CENPF, EXO1 and ERBB2; CENPF, EXO1 and GRB7; CENPF, EXO1 and CDC6; CENPF, EXO1 and MAPT; CENPF, EXO1 and BIRC5; CENPF, EXO1 and KRT14; CENPF, EXO1 and KRT17; CENPF, EXO1 and TYMS; CENPF, EXO1 and NDC80; CENPF, EXO1 and SLC39A6; CENPF, EXO1 and BCL2; CENPF, EXO1 and CCNE1; CENPF, EXO1 and MIA; CENPF, EXO1 and MYBL2; CENPF, EXO1 and UBE2C; CENPF, EXO1 and MMP11; CENPF, EXO1, UBE2T and RRM2; CENPF, EXO1, UBE2T and MLPH; CENPF, EXO1, UBE2T and GPR160; CENPF, EXO1, UBE2T and CCNB1; CENPF, EXO1, UBE2T and CXXC5; CENPF, EXO1, UBE2T and PTTG1; CENPF, EXO1, UBE2T and FGFR4; CENPF, EXO1, UBE2T and FOXC1; CENPF, EXO1, UBE2T and ESR1; CENPF, EXO1, UBE2T and ANLN; CENPF, EXO1, UBE2T and BLVRA; CENPF, EXO1, UBE2T and EGFR; CENPF, EXO1, UBE2T and ACTR3B; CENPF, EXO1, UBE2T and NAT1; CENPF, EXO1, UBE2T and MYC; CENPF, EXO1, UBE2T and SFRP1; CENPF, EXO1, UBE2T and MELK; CENPF, EXO1, UBE2T and BAG1; CENPF, EXO1, UBE2T and CEP55; CENPF, EXO1, UBE2T and MKI67; CENPF, EXO1, UBE2T and TMEM45B; CENPF, EXO1, UBE2T and PGR; CENPF, EXO1, UBE2T and MDM2; CENPF, EXO1, UBE2T and KRT5; CENPF, EXO1, UBE2T and FOXA1; CENPF, EXO1, UBE2T and ORC6; CENPF, EXO1, UBE2T and CDH3; CENPF, EXO1, UBE2T and ERBB2; CENPF, EXO1, UBE2T and GRB7; CENPF, EXO1, UBE2T and CDC6; CENPF, EXO1, UBE2T and MAPT; CENPF, EXO1, UBE2T and BIRC5; CENPF, EXO1, UBE2T and KRT14; CENPF, EXO1, UBE2T and KRT17; CENPF, EXO1, UBE2T and TYMS; CENPF, EXO1, UBE2T and NDC80; CENPF, EXO1, UBE2T and SLC39A6; CENPF, EXO1, UBE2T and BCL2; CENPF, EXO1, UBE2T and CCNE1; CENPF, EXO1, UBE2T and MIA; CENPF, EXO1, UBE2T and MYBL2; CENPF, EXO1, UBE2T and UBE2C; CENPF, EXO1, UBE2T and MMP11; EXO1; EXO1 and UBE2T; EXO1 and RRM2; EXO1 and MLPH; EXO1 and GPR160; EXO1 and CCNB1; EXO1 and CXXC5; EXO1 and PTTG1; EXO1 and FGFR4; EXO1 and FOXC1; EXO1 and ESR1; EXO1 and ANLN; EXO1 and BLVRA; EXO1 and EGFR;

EXO1 and ACTR3B; EXO1 and NAT1; EXO1 and MYC; EXO1 and SFRP1; EXO1 and MELK; EXO1 and BAG1; EXO1 and CEP55; EXO1 and MKI67; EXO1 and TMEM45B; EXO1 and PGR; EXO1 and MDM2; EXO1 and KRT5; EXO1 and FOXA1; EXO1 and ORC6; EXO1 and CDH3; EXO1 and ERBB2; EXO1 and GRB7; EXO1 and CDC6; EXO1 and MAPT; EXO1 and BIRC5; EXO1 and KRT14; EXO1 and KRT17; EXO1 and TYMS; EXO1 and NDC80; EXO1 and SLC39A6; EXO1 and BCL2; EXO1 and CCNE1; EXO1 and MIA; EXO1 and MYBL2; EXO1 and UBE2C; EXO1 and MMP11; EXO1, UBE2T and RRM2; EXO1, UBE2T and MLPH; EXO1, UBE2T and GPR160; EXO1, UBE2T and CCNB1; EXO1, UBE2T and CXXC5; EXO1, UBE2T and PTTG1; EXO1, UBE2T and FGFR4; EXO1, UBE2T and FOXC1; EXO1, UBE2T and ESR1; EXO1, UBE2T and ANLN; EXO1, UBE2T and BLVRA; EXO1, UBE2T and EGFR; EXO1, UBE2T and ACTR3B; EXO1, UBE2T and NAT1; EXO1, UBE2T and MYC; EXO1, UBE2T and SFRP1; EXO1, UBE2T and MELK; EXO1, UBE2T and BAG1; EXO1, UBE2T and CEP55; EXO1, UBE2T and MKI67; EXO1, UBE2T and TMEM45B; EXO1, UBE2T and PGR; EXO1, UBE2T and MDM2; EXO1, UBE2T and KRT5; EXO1, UBE2T and FOXA1; EXO1, UBE2T and ORC6; EXO1, UBE2T and CDH3; EXO1, UBE2T and ERBB2; EXO1, UBE2T and GRB7; EXO1, UBE2T and CDC6; EXO1, UBE2T and MAPT; EXO1, UBE2T and BIRC5; EXO1, UBE2T and KRT14; EXO1, UBE2T and KRT17; EXO1, UBE2T and TYMS; EXO1, UBE2T and NDC80; EXO1, UBE2T and SLC39A6; EXO1, UBE2T and BCL2; EXO1, UBE2T and CCNE1; EXO1, UBE2T and MIA; EXO1, UBE2T and MYBL2; EXO1, UBE2T and UBE2C; EXO1, UBE2T and MMP11; EXO1, UBE2T, RRM2 and MLPH; EXO1, UBE2T, RRM2 and GPR160; EXO1, UBE2T, RRM2 and CCNB1; EXO1, UBE2T, RRM2 and CXXC5; EXO1, UBE2T, RRM2 and PTTG1; EXO1, UBE2T, RRM2 and FGFR4; EXO1, UBE2T, RRM2 and FOXC1; EXO1, UBE2T, RRM2 and ESR1; EXO1, UBE2T, RRM2 and ANLN; EXO1, UBE2T, RRM2 and BLVRA; EXO1, UBE2T, RRM2 and EGFR; EXO1, UBE2T, RRM2 and ACTR3B; EXO1, UBE2T, RRM2 and NAT1; EXO1, UBE2T, RRM2 and MYC; EXO1, UBE2T, RRM2 and SFRP1; EXO1, UBE2T, RRM2 and MELK; EXO1, UBE2T, RRM2 and BAG1; EXO1, UBE2T, RRM2 and CEP55; EXO1, UBE2T, RRM2 and MKI67; EXO1, UBE2T, RRM2 and TMEM45B; EXO1, UBE2T, RRM2 and PGR; EXO1, UBE2T, RRM2 and MDM2; EXO1, UBE2T, RRM2 and KRT5; EXO1, UBE2T, RRM2 and FOXA1; EXO1, UBE2T, RRM2 and ORC6; EXO1, UBE2T, RRM2 and CDH3; EXO1, UBE2T, RRM2 and ERBB2; EXO1, UBE2T, RRM2 and GRB7; EXO1, UBE2T, RRM2 and CDC6; EXO1, UBE2T, RRM2 and MAPT; EXO1, UBE2T, RRM2 and BIRC5; EXO1, UBE2T, RRM2 and KRT14; EXO1, UBE2T, RRM2 and KRT17; EXO1, UBE2T, RRM2 and TYMS; EXO1, UBE2T, RRM2 and NDC80; EXO1, UBE2T, RRM2 and SLC39A6; EXO1, UBE2T, RRM2 and BCL2; EXO1, UBE2T, RRM2 and CCNE1; EXO1, UBE2T, RRM2 and MIA; EXO1, UBE2T, RRM2 and MYBL2; EXO1, UBE2T, RRM2 and UBE2C; EXO1, UBE2T, RRM2 and MMP11; UBE2T; UBE2T and RRM2; UBE2T and MLPH; UBE2T and GPR160; UBE2T and CCNB1; UBE2T and CXXC5; UBE2T and PTTG1; UBE2T and FGFR4; UBE2T and FOXC1; UBE2T and ESR1; UBE2T and ANLN; UBE2T and BLVRA; UBE2T and EGFR; UBE2T and ACTR3B; UBE2T and NAT1; UBE2T and MYC; UBE2T and SFRP1; UBE2T and MELK; UBE2T and BAG1; UBE2T and CEP55; UBE2T and MKI67; UBE2T and TMEM45B; UBE2T and PGR; UBE2T and MDM2; UBE2T and KRT5; UBE2T and FOXA1; UBE2T and ORC6; UBE2T and CDH3; UBE2T and ERBB2; UBE2T and GRB7; UBE2T and CDC6; UBE2T and MAPT; UBE2T and BIRC5; UBE2T and KRT14; UBE2T and KRT17; UBE2T and TYMS; UBE2T and NDC80; UBE2T and SLC39A6; UBE2T and BCL2; UBE2T and CCNE1; UBE2T and MIA; UBE2T and MYBL2; UBE2T and UBE2C; UBE2T and MMP11; RRM2; RRM2 and MLPH; RRM2 and GPR160; RRM2 and CCNB1; RRM2 and CXXC5; RRM2 and PTTG1; RRM2 and FGFR4; RRM2 and FOXC1; RRM2 and ESR1; RRM2 and ANLN; RRM2 and BLVRA; RRM2 and EGFR; RRM2 and ACTR3B; RRM2 and NAT1; RRM2 and MYC; RRM2 and SFRP1; RRM2 and MELK; RRM2 and BAG1; RRM2 and CEP55; RRM2 and MKI67; RRM2 and TMEM45B; RRM2 and PGR; RRM2 and MDM2; RRM2 and KRT5; RRM2 and FOXA1; RRM2 and ORC6; RRM2 and CDH3; RRM2 and ERBB2; RRM2 and GRB7; RRM2 and CDC6; RRM2 and MAPT; RRM2 and BIRC5; RRM2 and KRT14; RRM2 and KRT17; RRM2 and TYMS; RRM2 and NDC80; RRM2 and SLC39A6; RRM2 and BCL2; RRM2 and CCNE1; RRM2 and MIA; RRM2 and MYBL2; RRM2 and UBE2C; RRM2 and MMP11; MLPH; MLPH and GPR160; MLPH and CCNB1; MLPH and CXXC5; MLPH and PTTG1; MLPH and FGFR4; MLPH and FOXC1; MLPH and ESR1; MLPH and ANLN; MLPH and BLVRA; MLPH and EGFR; MLPH and ACTR3B; MLPH and NAT1; MLPH and MYC; MLPH and SFRP1; MLPH and MELK; MLPH and BAG1; MLPH and CEP55; MLPH and MKI67; MLPH and TMEM45B; MLPH and PGR; MLPH and MDM2; MLPH and KRT5; MLPH and FOXA1; MLPH and ORC6; MLPH and CDH3; MLPH and ERBB2; MLPH and GRB7; MLPH and CDC6; MLPH and MAPT; MLPH and BIRC5; MLPH and KRT14; MLPH and KRT17; MLPH and TYMS; MLPH and NDC80; MLPH and SLC39A6; MLPH and BCL2; MLPH and CCNE1; MLPH and MIA; MLPH and MYBL2; MLPH and UBE2C; MLPH and MMP11; GPR160; GPR160 and CCNB1; GPR160 and CXXC5; GPR160 and PTTG1; GPR160 and FGFR4; GPR160 and FOXC1; GPR160 and ESR1; GPR160 and ANLN; GPR160 and BLVRA; GPR160 and EGFR; GPR160 and ACTR3B; GPR160 and NAT1; GPR160 and MYC; GPR160 and SFRP1; GPR160 and MELK; GPR160 and BAG1; GPR160 and CEP55; GPR160 and MKI67; GPR160 and TMEM45B; GPR160 and PGR; GPR160 and MDM2; GPR160 and KRT5; GPR160 and FOXA1; GPR160 and ORC6; GPR160 and CDH3; GPR160 and ERBB2; GPR160 and GRB7; GPR160 and CDC6; GPR160 and MAPT; GPR160 and BIRC5; GPR160 and KRT14; GPR160 and KRT17; GPR160 and TYMS; GPR160 and NDC80; GPR160 and SLC39A6; GPR160 and BCL2; GPR160 and CCNE1; GPR160 and MIA; GPR160 and MYBL2; GPR160 and UBE2C; GPR160 and MMP11; CCNB1; CCNB1 and CXXC5; CCNB1 and PTTG1; CCNB1 and FGFR4; CCNB1 and FOXC1; CCNB1 and ESR1; CCNB1 and ANLN; CCNB1 and BLVRA; CCNB1 and EGFR; CCNB1 and ACTR3B; CCNB1 and NAT1; CCNB1 and MYC; CCNB1 and SFRP1; CCNB1 and MELK; CCNB1 and BAG1; CCNB1 and CEP55; CCNB1 and MKI67; CCNB1 and TMEM45B; CCNB1 and PGR; CCNB1 and MDM2; CCNB1 and KRT5; CCNB1 and FOXA1; CCNB1 and ORC6; CCNB1 and CDH3; CCNB1 and ERBB2; CCNB1 and GRB7; CCNB1 and CDC6; CCNB1 and MAPT; CCNB1 and BIRC5; CCNB1 and KRT14; CCNB1 and KRT17; CCNB1 and TYMS; CCNB1 and NDC80; CCNB1 and SLC39A6; CCNB1 and BCL2; CCNB1 and CCNE1; CCNB1 and MIA; CCNB1 and MYBL2; CCNB1 and UBE2C; CCNB1 and MMP11; CXXC5; CXXC5 and PTTG1; CXXC5 and FGFR4; CXXC5 and FOXC1; CXXC5 and ESR1; CXXC5 and ANLN; CXXC5 and BLVRA; CXXC5 and EGFR; CXXC5 and ACTR3B; CXXC5 and NAT1; CXXC5 and MYC; CXXC5 and SFRP1; CXXC5 and MELK; CXXC5 and BAG1; CXXC5 and CEP55; CXXC5 and MKI67; CXXC5 and TMEM45B; CXXC5 and PGR; CXXC5 and MDM2; CXXC5 and KRT5; CXXC5 and FOXA1; CXXC5 and ORC6; CXXC5 and CDH3; CXXC5 and ERBB2; CXXC5 and GRB7; CXXC5 and CDC6; CXXC5 and MAPT; CXXC5 and BIRC5; CXXC5 and KRT14; CXXC5 and KRT17; CXXC5 and TYMS; CXXC5 and NDC80; CXXC5 and SLC39A6; CXXC5 and BCL2; CXXC5 and CCNE1; CXXC5 and MIA; CXXC5 and MYBL2; CXXC5 and UBE2C; CXXC5 and MMP11; PTTG1; PTTG1 and FGFR4; PTTG1 and FOXC1; PTTG1 and ESR1; PTTG1 and ANLN; PTTG1 and BLVRA; PTTG1 and EGFR; PTTG1 and ACTR3B; PTTG1 and NAT1; PTTG1 and MYC; PTTG1 and SFRP1; PTTG1 and MELK; PTTG1 and BAG1; PTTG1 and CEP55; PTTG1 and MKI67; PTTG1 and TMEM45B; PTTG1 and PGR; PTTG1 and MDM2; PTTG1 and KRT5; PTTG1 and FOXA1; PTTG1 and ORC6; PTTG1 and CDH3; PTTG1 and ERBB2; PTTG1 and GRB7; PTTG1 and CDC6; PTTG1 and MAPT; PTTG1 and BIRC5; PTTG1 and KRT14; PTTG1 and KRT17; PTTG1 and TYMS; PTTG1 and NDC80; PTTG1 and SLC39A6; PTTG1 and BCL2; PTTG1 and CCNE1; PTTG1 and MIA; PTTG1 and MYBL2; PTTG1 and UBE2C; PTTG1 and MMP11; FGFR4; FGFR4 and FOXC1; FGFR4 and ESR1; FGFR4 and ANLN; FGFR4 and BLVRA; FGFR4 and EGFR; FGFR4 and ACTR3B; FGFR4 and NAT1; FGFR4 and MYC; FGFR4 and SFRP1; FGFR4 and MELK; FGFR4 and BAG1; FGFR4 and CEP55; FGFR4 and MKI67; FGFR4 and TMEM45B; FGFR4 and PGR; FGFR4 and MDM2; FGFR4 and KRT5; FGFR4 and FOXA1; FGFR4 and ORC6; FGFR4 and CDH3; FGFR4 and ERBB2; FGFR4 and GRB7; FGFR4 and CDC6; FGFR4 and MAPT; FGFR4 and BIRC5; FGFR4 and KRT14; FGFR4 and KRT17; FGFR4 and TYMS; FGFR4 and NDC80; FGFR4 and SLC39A6; FGFR4 and BCL2; FGFR4 and CCNE1; FGFR4 and MIA; FGFR4 and MYBL2; FGFR4 and UBE2C; FGFR4 and MMP11; FOXC1; FOXC1 and ESR1; FOXC1 and ANLN; FOXC1 and BLVRA; FOXC1 and EGFR; FOXC1 and ACTR3B; FOXC1 and NAT1; FOXC1 and MYC; FOXC1 and SFRP1; FOXC1 and MELK; FOXC1 and BAG1; FOXC1 and CEP55; FOXC1 and MKI67; FOXC1 and TMEM45B; FOXC1 and PGR; FOXC1 and MDM2; FOXC1 and KRT5; FOXC1 and FOXA1; FOXC1 and ORC6; FOXC1 and CDH3; FOXC1 and ERBB2; FOXC1 and GRB7; FOXC1 and CDC6; FOXC1 and MAPT; FOXC1 and BIRC5; FOXC1 and KRT14; FOXC1 and KRT17; FOXC1 and TYMS; FOXC1 and NDC80; FOXC1 and SLC39A6; FOXC1 and BCL2; FOXC1 and CCNE1; FOXC1 and MIA; FOXC1 and MYBL2; FOXC1 and UBE2C; FOXC1 and MMP11; ESR1; ESR1 and ANLN; ESR1 and BLVRA; ESR1 and EGFR; ESR1 and ACTR3B; ESR1 and NAT1; ESR1 and MYC; ESR1 and SFRP1; ESR1 and MELK; ESR1 and BAG1; ESR1 and CEP55; ESR1 and MKI67; ESR1 and TMEM45B; ESR1 and PGR; ESR1 and MDM2; ESR1 and KRT5; ESR1 and FOXA1; ESR1 and ORC6; ESR1 and CDH3; ESR1 and ERBB2; ESR1 and GRB7; ESR1 and CDC6; ESR1 and MAPT; ESR1 and BIRC5; ESR1 and KRT14; ESR1 and KRT17; ESR1 and TYMS; ESR1 and NDC80; ESR1 and SLC39A6; ESR1 and BCL2; ESR1 and CCNE1; ESR1 and MIA; ESR1 and MYBL2; ESR1 and UBE2C; ESR1 and MMP11; ANLN; ANLN and BLVRA; ANLN and EGFR; ANLN and ACTR3B; ANLN and NAT1; ANLN and MYC; ANLN and SFRP1; ANLN and MELK; ANLN and BAG1; ANLN and CEP55; ANLN and MKI67; ANLN and TMEM45B; ANLN and PGR; ANLN and MDM2; ANLN and KRT5; ANLN and FOXA1; ANLN and ORC6; ANLN and CDH3; ANLN and ERBB2; ANLN and GRB7; ANLN and CDC6; ANLN and MAPT; ANLN and BIRC5; ANLN and KRT14; ANLN and KRT17; ANLN and TYMS; ANLN and NDC80; ANLN and SLC39A6; ANLN and BCL2; ANLN and CCNE1; ANLN and MIA; ANLN and MYBL2; ANLN and UBE2C; ANLN and MMP11; BLVRA; BLVRA and EGFR; BLVRA and ACTR3B; BLVRA and NAT1; BLVRA and MYC; BLVRA and SFRP1; BLVRA and MELK; BLVRA and BAG1; BLVRA and CEP55; BLVRA and MKI67; BLVRA and TMEM45B; BLVRA and PGR; BLVRA and MDM2; BLVRA and KRT5; BLVRA and FOXA1; BLVRA and ORC6; BLVRA and CDH3; BLVRA and ERBB2; BLVRA and GRB7; BLVRA and CDC6; BLVRA and MAPT; BLVRA and BIRC5; BLVRA and KRT14; BLVRA and KRT17; BLVRA and TYMS; BLVRA and NDC80; BLVRA and SLC39A6; BLVRA and BCL2; BLVRA and CCNE1; BLVRA and MIA; BLVRA and MYBL2; BLVRA and UBE2C; BLVRA and MMP11; EGFR; EGFR and ACTR3B; EGFR and NAT1; EGFR and MYC; EGFR and SFRP1; EGFR and MELK; EGFR and BAG1; EGFR and CEP55; EGFR and MKI67; EGFR and TMEM45B; EGFR and PGR; EGFR and MDM2; EGFR and KRT5; EGFR and FOXA1; EGFR and ORC6; EGFR and CDH3; EGFR and ERBB2; EGFR and GRB7; EGFR and CDC6; EGFR and MAPT; EGFR and BIRC5; EGFR and KRT14; EGFR and KRT17; EGFR and TYMS; EGFR and NDC80; EGFR and SLC39A6; EGFR and BCL2; EGFR and CCNE1; EGFR and MIA; EGFR and MYBL2; EGFR and UBE2C; EGFR and MMP11; ACTR3B; ACTR3B and NAT1; ACTR3B and MYC; ACTR3B and SFRP1; ACTR3B and MELK; ACTR3B and BAG1; ACTR3B and CEP55; ACTR3B and MKI67; ACTR3B and TMEM45B; ACTR3B and PGR; ACTR3B and MDM2; ACTR3B and KRT5; ACTR3B and FOXA1; ACTR3B and ORC6; ACTR3B and CDH3; ACTR3B and ERBB2; ACTR3B and GRB7; ACTR3B and CDC6; ACTR3B and MAPT; ACTR3B and BIRC5; ACTR3B and KRT14; ACTR3B and KRT17; ACTR3B and TYMS; ACTR3B and NDC80; ACTR3B and SLC39A6; ACTR3B and BCL2; ACTR3B and CCNE1; ACTR3B and MIA; ACTR3B and MYBL2; ACTR3B and UBE2C; ACTR3B and MMP11; NAT1; NAT1 and MYC; NAT1 and SFRP1; NAT1 and MELK; NAT1 and BAG1; NAT1 and CEP55; NAT1 and MKI67; NAT1 and TMEM45B; NAT1 and PGR; NAT1 and MDM2; NAT1 and KRT5; NAT1 and FOXA1; NAT1 and ORC6; NAT1 and CDH3; NAT1 and ERBB2; NAT1 and GRB7; NAT1 and CDC6; NAT1 and MAPT; NAT1 and BIRC5; NAT1 and KRT14; NAT1 and KRT17; NAT1 and TYMS; NAT1 and NDC80; NAT1 and SLC39A6; NAT1 and BCL2; NAT1 and CCNE1; NAT1 and MIA; NAT1 and MYBL2; NAT1 and UBE2C; NAT1 and MMP11; MYC; MYC and SFRP1; MYC and MELK; MYC and BAG1; MYC and CEP55; MYC and MKI67; MYC and TMEM45B; MYC and PGR; MYC and MDM2; MYC and KRT5; MYC and FOXA1; MYC and ORC6; MYC and CDH3; MYC and ERBB2; MYC and GRB7; MYC and CDC6; MYC and MAPT; MYC and BIRC5; MYC and KRT14; MYC and KRT17; MYC and TYMS; MYC and NDC80; MYC and SLC39A6; MYC and BCL2; MYC and CCNE1; MYC and MIA; MYC and MYBL2; MYC and UBE2C; MYC and MMP11; SFRP1; SFRP1 and MELK;

SFRP1 and BAG1; SFRP1 and CEP55; SFRP1 and MKI67; SFRP1 and TMEM45B; SFRP1 and PGR; SFRP1 and MDM2; SFRP1 and KRT5; SFRP1 and FOXA1; SFRP1 and ORC6; SFRP1 and CDH3; SFRP1 and ERBB2; SFRP1 and GRB7; SFRP1 and CDC6; SFRP1 and MAPT; SFRP1 and BIRC5; SFRP1 and KRT14; SFRP1 and KRT17; SFRP1 and TYMS; SFRP1 and NDC80; SFRP1 and SLC39A6; SFRP1 and BCL2; SFRP1 and CCNE1; SFRP1 and MIA; SFRP1 and MYBL2; SFRP1 and UBE2C; SFRP1 and MMP11; MELK; MELK and BAG1; MELK and CEP55; MELK and MKI67; MELK and TMEM45B; MELK and PGR; MELK and MDM2; MELK and KRT5; MELK and FOXA1; MELK and ORC6; MELK and CDH3; MELK and ERBB2; MELK and GRB7; MELK and CDC6; MELK and MAPT; MELK and BIRC5; MELK and KRT14; MELK and KRT17; MELK and TYMS; MELK and NDC80; MELK and SLC39A6; MELK and BCL2; MELK and CCNE1; MELK and MIA; MELK and MYBL2; MELK and UBE2C; MELK and MMP11; BAG1; BAG1 and CEP55; BAG1 and MKI67; BAG1 and TMEM45B; BAG1 and PGR; BAG1 and MDM2; BAG1 and KRT5; BAG1 and FOXA1; BAG1 and ORC6; BAG1 and CDH3; BAG1 and ERBB2; BAG1 and GRB7; BAG1 and CDC6; BAG1 and MAPT; BAG1 and BIRC5; BAG1 and KRT14; BAG1 and KRT17; BAG1 and TYMS; BAG1 and NDC80; BAG1 and SLC39A6; BAG1 and BCL2; BAG1 and CCNE1; BAG1 and MIA; BAG1 and MYBL2; BAG1 and UBE2C; BAG1 and MMP11; CEP55; CEP55 and MKI67; CEP55 and TMEM45B; CEP55 and PGR; CEP55 and MDM2; CEP55 and KRT5; CEP55 and FOXA1; CEP55 and ORC6; CEP55 and CDH3; CEP55 and ERBB2; CEP55 and GRB7; CEP55 and CDC6; CEP55 and MAPT; CEP55 and BIRC5; CEP55 and KRT14; CEP55 and KRT17; CEP55 and TYMS; CEP55 and NDC80; CEP55 and SLC39A6; CEP55 and BCL2; CEP55 and CCNE1; CEP55 and MIA; CEP55 and MYBL2; CEP55 and UBE2C; CEP55 and MMP11; MKI67; MKI67 and TMEM45B; MKI67 and PGR; MKI67 and MDM2; MKI67 and KRT5; MKI67 and FOXA1; MKI67 and ORC6; MKI67 and CDH3; MKI67 and ERBB2; MKI67 and GRB7; MKI67 and CDC6; MKI67 and MAPT; MKI67 and BIRC5; MKI67 and KRT14; MKI67 and KRT17; MKI67 and TYMS; MKI67 and NDC80; MKI67 and SLC39A6; MKI67 and BCL2; MKI67 and CCNE1; MKI67 and MIA; MKI67 and MYBL2; MKI67 and UBE2C; MKI67 and MMP11; TMEM45B; TMEM45B and PGR; TMEM45B and MDM2; TMEM45B and KRT5; TMEM45B and FOXA1; TMEM45B and ORC6; TMEM45B and CDH3; TMEM45B and ERBB2; TMEM45B and GRB7; TMEM45B and CDC6; TMEM45B and MAPT; TMEM45B and BIRC5; TMEM45B and KRT14; TMEM45B and KRT17; TMEM45B and TYMS; TMEM45B and NDC80; TMEM45B and SLC39A6; TMEM45B and BCL2; TMEM45B and CCNE1; TMEM45B and MIA; TMEM45B and MYBL2; TMEM45B and UBE2C; TMEM45B and MMP11; PGR; PGR and MDM2; PGR and KRT5; PGR and FOXA1; PGR and ORC6; PGR and CDH3; PGR and ERBB2; PGR and GRB7; PGR and CDC6; PGR and MAPT; PGR and BIRC5; PGR and KRT14; PGR and KRT17; PGR and TYMS; PGR and NDC80; PGR and SLC39A6; PGR and BCL2; PGR and CCNE1; PGR and MIA; PGR and MYBL2; PGR and UBE2C; PGR and MMP11; MDM2; MDM2 and KRT5; MDM2 and FOXA1; MDM2 and ORC6; MDM2 and CDH3; MDM2 and ERBB2; MDM2 and GRB7; MDM2 and CDC6; MDM2 and MAPT; MDM2 and BIRC5; MDM2 and KRT14; MDM2 and KRT17; MDM2 and TYMS; MDM2 and NDC80; MDM2 and SLC39A6; MDM2 and BCL2; MDM2 and CCNE1; MDM2 and MIA; MDM2 and MYBL2; MDM2 and UBE2C; MDM2 and MMP11; KRT5; KRT5 and FOXA1; KRT5 and ORC6; KRT5 and CDH3; KRT5 and ERBB2; KRT5 and GRB7; KRT5 and CDC6; KRT5 and MAPT; KRT5 and BIRC5; KRT5 and KRT14; KRT5 and KRT17; KRT5 and TYMS; KRT5 and NDC80; KRT5 and SLC39A6; KRT5 and BCL2; KRT5 and CCNE1; KRT5 and MIA; KRT5 and MYBL2; KRT5 and UBE2C; KRT5 and MMP11; FOXA1; FOXA1 and ORC6; FOXA1 and CDH3; FOXA1 and ERBB2; FOXA1 and GRB7; FOXA1 and CDC6; FOXA1 and MAPT; FOXA1 and BIRC5; FOXA1 and KRT14; FOXA1 and KRT17; FOXA1 and TYMS; FOXA1 and NDC80; FOXA1 and SLC39A6; FOXA1 and BCL2; FOXA1 and CCNE1; FOXA1 and MIA; FOXA1 and MYBL2; FOXA1 and UBE2C; FOXA1 and MMP11; ORC6; ORC6 and CDH3; ORC6 and ERBB2; ORC6 and GRB7; ORC6 and CDC6; ORC6 and MAPT; ORC6 and BIRC5; ORC6 and KRT14; ORC6 and KRT17; ORC6 and TYMS; ORC6 and NDC80; ORC6 and SLC39A6; ORC6 and BCL2; ORC6 and CCNE1; ORC6 and MIA; ORC6 and MYBL2; ORC6 and UBE2C; ORC6 and MMP11; CDH3; CDH3 and ERBB2; CDH3 and GRB7; CDH3 and CDC6; CDH3 and MAPT; CDH3 and BIRC5; CDH3 and KRT14; CDH3 and KRT17; CDH3 and TYMS; CDH3 and NDC80; CDH3 and SLC39A6; CDH3 and BCL2; CDH3 and CCNE1; CDH3 and MIA; CDH3 and MYBL2; CDH3 and UBE2C; CDH3 and MMP11; ERBB2; ERBB2 and GRB7; ERBB2 and CDC6; ERBB2 and MAPT; ERBB2 and BIRC5; ERBB2 and KRT14; ERBB2 and KRT17; ERBB2 and TYMS; ERBB2 and NDC80; ERBB2 and SLC39A6; ERBB2 and BCL2; ERBB2 and CCNE1; ERBB2 and MIA; ERBB2 and MYBL2; ERBB2 and UBE2C; ERBB2 and MMP11; GRB7; GRB7 and CDC6; GRB7 and MAPT; GRB7 and BIRC5; GRB7 and KRT14; GRB7 and KRT17; GRB7 and TYMS; GRB7 and NDC80; GRB7 and SLC39A6; GRB7 and BCL2; GRB7 and CCNE1; GRB7 and MIA; GRB7 and MYBL2; GRB7 and UBE2C; GRB7 and MMP11; CDC6; CDC6 and MAPT; CDC6 and BIRC5; CDC6 and KRT14; CDC6 and KRT17; CDC6 and TYMS; CDC6 and NDC80; CDC6 and SLC39A6; CDC6 and BCL2; CDC6 and CCNE1; CDC6 and MIA; CDC6 and MYBL2; CDC6 and UBE2C; CDC6 and MMP11; MAPT; MAPT and BIRC5; MAPT and KRT14; MAPT and KRT17; MAPT and TYMS; MAPT and NDC80; MAPT and SLC39A6; MAPT and BCL2; MAPT and CCNE1; MAPT and MIA; MAPT and MYBL2; MAPT and UBE2C; MAPT and MMP11; BIRC5; BIRC5 and KRT14; BIRC5 and KRT17; BIRC5 and TYMS; BIRC5 and NDC80; BIRC5 and SLC39A6; BIRC5 and BCL2; BIRC5 and CCNE1; BIRC5 and MIA; BIRC5 and MYBL2; BIRC5 and UBE2C; BIRC5 and MMP11; KRT14; KRT14 and KRT17; KRT14 and TYMS; KRT14 and NDC80; KRT14 and SLC39A6; KRT14 and BCL2; KRT14 and CCNE1; KRT14 and MIA; KRT14 and MYBL2; KRT14 and UBE2C; KRT14 and MMP11; KRT17; KRT17 and TYMS; KRT17 and NDC80; KRT17 and SLC39A6; KRT17 and BCL2; KRT17 and CCNE1; KRT17 and MIA; KRT17 and MYBL2; KRT17 and UBE2C; KRT17 and MMP11; TYMS; TYMS and NDC80; TYMS and SLC39A6; TYMS and BCL2; TYMS and CCNE1; TYMS and MIA; TYMS and MYBL2; TYMS and UBE2C; TYMS and MMP11; NDC80; NDC80 and SLC39A6; NDC80 and BCL2; NDC80 and CCNE1; NDC80 and MIA; NDC80 and MYBL2; NDC80 and UBE2C; NDC80 and MMP11; SLC39A6; SLC39A6 and BCL2; SLC39A6 and CCNE1; SLC39A6 and MIA; SLC39A6 and MYBL2; SLC39A6 and UBE2C; SLC39A6 and MMP11; BCL2; BCL2 and CCNE1; BCL2 and MIA;

BCL2 and MYBL2; BCL2 and UBE2C; BCL2 and MMP11; CCNE1; CCNE1 and MIA; CCNE1 and MYBL2; CCNE1 and UBE2C; CCNE1 and MMP11; MIA; MIA and MYBL2; MIA and UBE2C; MIA and MMP11; MYBL2; MYBL2 and UBE2C; MYBL2 and MMP11; UBE2C; UBE2C and MMP11; MMP11; TDRD1, CACNA1D, NCALD, HLA-DMB, KCNH8, PDE3B, PLA2G7, CSGALNACT1, PART1, HES1, F3, GPR110, SH3RF, PDE8B, and SEPT9; TDRD1; TDRD1 and CACNA1D; TDRD1 and NCALD; TDRD1 and HLA-DMB; TDRD1 and KCNH8; TDRD1 and PDE3B; TDRD1 and PLA2G7; TDRD1 and CSGALNACT1; TDRD1 and PART1; TDRD1 and HES1; TDRD1 and F3; TDRD1 and GPR110; TDRD1 and SH3RF; TDRD1 and PDE8B; TDRD1 and SEPT9; CACNA1D; CACNA1D and NCALD; CACNA1D and HLA-DMB; CACNA1D and KCNH8; CACNA1D and PDE3B; CACNA1D and PLA2G7; CACNA1D and CSGALNACT1; CACNA1D and PART1; CACNA1D and HES1; CACNA1D and F3; CACNA1D and GPR110; CACNA1D and SH3RF; CACNA1D and PDE8B; CACNA1D and SEPT9; NCALD; NCALD and HLA-DMB; NCALD and KCNH8; NCALD and PDE3B; NCALD and PLA2G7; NCALD and CSGALNACT1; NCALD and PART1; NCALD and HES1; NCALD and F3; NCALD and GPR110; NCALD and SH3RF; NCALD and PDE8B; NCALD and SEPT9; HLA-DMB; HLA-DMB and KCNH8; HLA-DMB and PDE3B; HLA-DMB and PLA2G7; HLA-DMB and CSGALNACT1; HLA-DMB and PART1; HLA-DMB and HES1; HLA-DMB and F3; HLA-DMB and GPR110; HLA-DMB and SH3RF; HLA-DMB and PDE8B; HLA-DMB and SEPT9; KCNH8; KCNH8 and PDE3B; KCNH8 and PLA2G7; KCNH8 and CSGALNACT1; KCNH8 and PART1; KCNH8 and HES1; KCNH8 and F3; KCNH8 and GPR110; KCNH8 and SH3RF; KCNH8 and PDE8B; KCNH8 and SEPT9; PDE3B; PDE3B and PLA2G7; PDE3B and CSGALNACT1; PDE3B and PART1; PDE3B and HES1; PDE3B and F3; PDE3B and GPR110; PDE3B and SH3RF; PDE3B and PDE8B; PDE3B and SEPT9; PLA2G7; PLA2G7 and CSGALNACT1; PLA2G7 and PART1; PLA2G7 and HES1; PLA2G7 and F3; PLA2G7 and GPR110; PLA2G7 and SH3RF; PLA2G7 and PDE8B; PLA2G7 and SEPT9; CSGALNACT1; CSGALNACT1 and PART1; CSGALNACT1 and HES1; CSGALNACT1 and F3; CSGALNACT1 and GPR110; CSGALNACT1 and SH3RF; CSGALNACT1 and PDE8B; CSGALNACT1 and SEPT9; PART1; PART1 and HES1; PART1 and F3; PART1 and GPR110; PART1 and SH3RF; PART1 and PDE8B; PART1 and SEPT9; HES1; HES1 and F3; HES1 and GPR110; HES1 and SH3RF; HES1 and PDE8B; HES1 and SEPT9; F3; F3 and GPR110; F3 and SH3RF; F3 and PDE8B; F3 and SEPT9; GPR110; GPR110 and SH3RF; GPR110 and PDE8B; GPR110 and SEPT9; SH3RF; SH3RF and PDE8B; SH3RF and SEPT9; PDE8B; PDE8B and SEPT9; SEPT9; CRISP3, AMD1, KCNG3, PLA1A, MYO6, FRK, GPR110, SH3YL1, ACER3, C8orf4, GHR, ITPR1, KHDRBS3, NPY, and GUCY1A3; CRISP3; CRISP3 and AMD1; CRISP3 and KCNG3; CRISP3 and PLA1A; CRISP3 and MYO6; CRISP3 and FRK; CRISP3 and GPR110; CRISP3 and SH3YL1; CRISP3 and ACER3; CRISP3 and C8orf4; CRISP3 and GHR; CRISP3 and ITPR1; CRISP3 and KHDRBS3; CRISP3 and NPY; CRISP3 and GUCY1A3; AMD1; AMD1 and KCNG3; AMD1 and PLA1A; AMD1 and MYO6; AMD1 and FRK; AMD1 and GPR110; AMD1 and SH3YL1; AMD1 and ACER3; AMD1 and C8orf4; AMD1 and GHR; AMD1 and ITPR1; AMD1 and KHDRBS3; AMD1 and NPY; AMD1 and GUCY1A3; KCNG3; KCNG3 and PLA1A; KCNG3 and MYO6; KCNG3 and FRK; KCNG3 and GPR110; KCNG3 and SH3YL1; KCNG3 and ACER3; KCNG3 and C8orf4; KCNG3 and GHR; KCNG3 and ITPR1; KCNG3 and KHDRBS3; KCNG3 and NPY; KCNG3 and GUCY1A3; PLA1A; PLA1A and MYO6; PLA1A and FRK; PLA1A and GPR110; PLA1A and SH3YL1; PLA1A and ACER3; PLA1A and C8orf4; PLA1A and GHR; PLA1A and ITPR1; PLA1A and KHDRBS3; PLA1A and NPY; PLA1A and GUCY1A3; MYO6; MYO6 and FRK; MYO6 and GPR110; MYO6 and SH3YL1; MYO6 and ACER3; MYO6 and C8orf4; MYO6 and GHR; MYO6 and ITPR1; MYO6 and KHDRBS3; MYO6 and NPY; MYO6 and GUCY1A3; FRK; FRK and GPR110; FRK and SH3YL1; FRK and ACER3; FRK and C8orf4; FRK and GHR; FRK and ITPR1; FRK and KHDRBS3; FRK and NPY; FRK and GUCY1A3; GPR110 and SH3YL1; GPR110 and ACER3; GPR110 and C8orf4; GPR110 and GHR; GPR110 and ITPR1; GPR110 and KHDRBS3; GPR110 and NPY; GPR110 and GUCY1A3; SH3YL1; SH3YL1 and ACER3; SH3YL1 and C8orf4; SH3YL1 and GHR; SH3YL1 and ITPR1; SH3YL1 and KHDRBS3; SH3YL1 and NPY; SH3YL1 and GUCY1A3; ACER3; ACER3 and C8orf4; ACER3 and GHR; ACER3 and ITPR1; ACER3 and KHDRBS3; ACER3 and NPY; ACER3 and GUCY1A3; C8orf4; C8orf4 and GHR; C8orf4 and ITPR1; C8orf4 and KHDRBS3; C8orf4 and NPY; C8orf4 and GUCY1A3; GHR; GHR and ITPR1; GHR and KHDRBS3; GHR and NPY; GHR and GUCY1A3; ITPR1; ITPR1 and KHDRBS3; ITPR1 and NPY; ITPR1 and GUCY1A3; KHDRBS3; KHDRBS3 and NPY; KHDRBS3 and GUCY1A3; NPY; NPY and GUCY1A3; GUCY1A3; ARHGDIB, LAMC2, VWA2, ZNF432, MORN1, CYorf15B, AMPD3, QDPR, HDAC1, KIF16B, GJB1, ITPR3, ZNF615, ANKRD6, and APOD; ARHGDIB; ARHGDIB and LAMC2; ARHGDIB and VWA2; ARHGDIB and ZNF432; ARHGDIB and MORN1; ARHGDIB and CYorf15B; ARHGDIB and AMPD3; ARHGDIB and QDPR; ARHGDIB and HDAC1; ARHGDIB and KIF16B; ARHGDIB and GJB1; ARHGDIB and ITPR3; ARHGDIB and ZNF615; ARHGDIB and ANKRD6; ARHGDIB and APOD; LAMC2; LAMC2 and VWA2; LAMC2 and ZNF432; LAMC2 and MORN1; LAMC2 and CYorf15B; LAMC2 and AMPD3; LAMC2 and QDPR; LAMC2 and HDAC1; LAMC2 and KIF16B; LAMC2 and GJB1; LAMC2 and ITPR3; LAMC2 and ZNF615; LAMC2 and ANKRD6; LAMC2 and APOD; VWA2; VWA2 and ZNF432; VWA2 and MORN1; VWA2 and CYorf15B; VWA2 and AMPD3; VWA2 and QDPR; VWA2 and HDAC1; VWA2 and KIF16B; VWA2 and GJB1; VWA2 and ITPR3; VWA2 and ZNF615; VWA2 and ANKRD6; VWA2 and APOD; ZNF432; ZNF432 and MORN1; ZNF432 and CYorf15B; ZNF432 and AMPD3; ZNF432 and QDPR; ZNF432 and HDAC1; ZNF432 and KIF16B; ZNF432 and GJB1; ZNF432 and ITPR3; ZNF432 and ZNF615; ZNF432 and ANKRD6; ZNF432 and APOD; MORN1; MORN1 and CYorf15B; MORN1 and AMPD3; MORN1 and QDPR; MORN1 and HDAC1; MORN1 and KIF16B; MORN1 and GJB1; MORN1 and ITPR3; MORN1 and ZNF615; MORN1 and ANKRD6; MORN1 and APOD; CYorf15B; CYorf15B and AMPD3; CYorf15B and QDPR; CYorf15B and HDAC1; CYorf15B and KIF16B; CYorf15B and GJB1; CYorf15B and ITPR3; CYorf15B and ZNF615; CYorf15B and ANKRD6; CYorf15B and APOD; AMPD3; AMPD3 and QDPR; AMPD3 and HDAC1; AMPD3 and KIF16B; AMPD3 and GJB1; AMPD3 and ITPR3; AMPD3 and ZNF615; AMPD3 and ANKRD6; AMPD3 and APOD; QDPR; QDPR and HDAC1; QDPR and KIF16B; QDPR and GJB1; QDPR and ITPR3; QDPR and ZNF615; QDPR and ANKRD6; QDPR and APOD; HDAC1; HDAC1 and KIF16B; HDAC1 and GJB1; HDAC1 and ITPR3; HDAC1 and ZNF615; HDAC1 and ANKRD6; HDAC1 and APOD; KIF16B; KIF16B and GJB1; KIF16B and ITPR3; KIF16B and ZNF615; KIF16B and ANKRD6; KIF16B and APOD; GJB1; GJB1 and ITPR3; GJB1 and ZNF615; GJB1 and ANKRD6; GJB1 and APOD; ITPR3; ITPR3 and ZNF615; ITPR3 and ANKRD6; ITPR3 and APOD; ZNF615; ZNF615 and ANKRD6; ZNF615 and APOD; ANKRD6; ANKRD6 and APOD; APOD; STEAP4, RGS17, MAP7, C22orf36, NKAIN1, CHN2, LRRFIP1, SERGEF, ATP8A2, NDRG1, CDC42SE1, LUZP2, HNF1B, TFAP2A and ANKRD34B STEAP4; STEAP4 and RGS17; STEAP4 and MAP7; STEAP4 and C22orf36; STEAP4 and NKAIN1; STEAP4 and CHN2; STEAP4 and LRRFIP1; STEAP4 and SERGEF; STEAP4 and ATP8A2; STEAP4 and NDRG1; STEAP4 and CDC42SE1; STEAP4 and LUZP2; STEAP4 and HNF1B; STEAP4 and TFAP2A; STEAP4 and ANKRD34B; RGS17; RGS17 and MAP7; RGS17 and C22orf36; RGS17 and NKAIN1; RGS17 and CHN2; RGS17 and LRRFIP1; RGS17 and SERGEF; RGS17 and ATP8A2; RGS17 and NDRG1; RGS17 and CDC42SE1; RGS17 and LUZP2; RGS17 and HNF1B; RGS17 and TFAP2A; RGS17 and ANKRD34B; MAP7; MAP7 and C22orf36; MAP7 and NKAIN1; MAP7 and CHN2; MAP7 and LRRFIP1; MAP7 and SERGEF; MAP7 and ATP8A2; MAP7 and NDRG1; MAP7 and CDC42SE1; MAP7 and LUZP2; MAP7 and HNF1B; MAP7 and TFAP2A; MAP7 and ANKRD34B; C22orf36; C22orf36 and NKAIN1; C22orf36 and CHN2; C22orf36 and LRRFIP1; C22orf36 and SERGEF; C22orf36 and ATP8A2; C22orf36 and NDRG1; C22orf36 and CDC42SE1; C22orf36 and LUZP2; C22orf36 and HNF1B; C22orf36 and TFAP2A; C22orf36 and ANKRD34B; NKAIN1; NKAIN1 and CHN2; NKAIN1 and LRRFIP1; NKAIN1 and SERGEF; NKAIN1 and ATP8A2; NKAIN1 and NDRG1; NKAIN1 and CDC42SE1; NKAIN1 and LUZP2; NKAIN1 and HNF1B; NKAIN1 and TFAP2A; NKAIN1 and ANKRD34B; CHN2; CHN2 and LRRFIP1; CHN2 and SERGEF; CHN2 and ATP8A2; CHN2 and NDRG1; CHN2 and CDC42SE1; CHN2 and LUZP2; CHN2 and HNF1B; CHN2 and TFAP2A; CHN2 and ANKRD34B; LRRF1P1; LRRFIP1 and SERGEF; LRRFIP1 and ATP8A2; LRRF1P1 and NDRG1; LRRFIP1 and CDC42SE1; LRRFIP1 and LUZP2; LRRFIP1 and HNF1B; LRRFIP1 and TFAP2A; LRRFIP1 and ANKRD34B; SERGEF; SERGEF and ATP8A2; SERGEF and NDRG1; SERGEF and CDC42SE1; SERGEF and LUZP2; SERGEF and HNF1B; SERGEF and TFAP2A; SERGEF and ANKRD34B; ATP8A2; ATP8A2 and NDRG1; ATP8A2 and CDC42SE1; ATP8A2 and LUZP2; ATP8A2 and HNF1B; ATP8A2 and TFAP2A; ATP8A2 and ANKRD34B; NDRG1; NDRG1 and CDC42SE1; NDRG1 and LUZP2; NDRG1 and HNF1B; NDRG1 and TFAP2A; NDRG1 and ANKRD34B; CDC42SE1; CDC42SE1 and LUZP2; CDC42SE1 and HNF1B; CDC42SE1 and TFAP2A; CDC42SE1 and ANKRD34B; LUZP2; LUZP2 and HNF1B; LUZP2 and TFAP2A; LUZP2 and ANKRD34B; HNF1B; HNF1B and TFAP2A; HNF1B and ANKRD34B; TFAP2A; TFAP2A and ANKRD34B; ANKRD34B; SLC12A2, PRAC, SLC5A4, ACSL3, CD24P4, DNASE2B, SLC22A3, ODC1, SMOC2, UGDH, DSC2, WNK2, RAB3B, FAM198B, KCNC2 and SNAP91; SLC12A2; SLC12A2 and PRAC; SLC12A2 and SLC5A4; SLC12A2 and ACSL3; SLC12A2 and CD24P4; SLC12A2 and DNASE2B; SLC12A2 and SLC22A3; SLC12A2 and ODC1; SLC12A2 and SMOC2; SLC12A2 and UGDH; SLC12A2 and DSC2; SLC12A2 and WNK2; SLC12A2 and RAB3B; SLC12A2 and FAM198B; SLC12A2 and KCNC2; SLC12A2 and SNAP91; PRAC; PRAC and SLC5A4; PRAC and ACSL3; PRAC and CD24P4; PRAC and DNASE2B; PRAC and SLC22A3; PRAC and ODC1; PRAC and SMOC2; PRAC and UGDH; PRAC and DSC2; PRAC and WNK2; PRAC and RAB3B; PRAC and FAM198B; PRAC and KCNC2; PRAC and SNAP91; SLC5A4; SLC5A4 and ACSL3; SLC5A4 and CD24P4; SLC5A4 and DNASE2B; SLC5A4 and SLC22A3; SLC5A4 and ODC1; SLC5A4 and SMOC2; SLC5A4 and UGDH; SLC5A4 and DSC2; SLC5A4 and WNK2; SLC5A4 and RAB3B; SLC5A4 and FAM198B; SLC5A4 and KCNC2; SLC5A4 and SNAP91; ACSL3; ACSL3 and CD24P4; ACSL3 and DNASE2B; ACSL3 and SLC22A3; ACSL3 and ODC1; ACSL3 and SMOC2; ACSL3 and UGDH; ACSL3 and DSC2; ACSL3 and WNK2; ACSL3 and RAB3B; ACSL3 and FAM198B; ACSL3 and KCNC2; ACSL3 and SNAP91; CD24P4; CD24P4 and DNASE2B; CD24P4 and SLC22A3; CD24P4 and ODC1; CD24P4 and SMOC2; CD24P4 and UGDH; CD24P4 and DSC2; CD24P4 and WNK2; CD24P4 and RAB3B; CD24P4 and FAM198B; CD24P4 and KCNC2; CD24P4 and SNAP91; DNASE2B; DNASE2B and SLC22A3; DNASE2B and ODC1; DNASE2B and SMOC2; DNASE2B and UGDH; DNASE2B and DSC2; DNASE2B and WNK2; DNASE2B and RAB3B; DNASE2B and FAM198B; DNASE2B and KCNC2; DNASE2B and SNAP91; SLC22A3; SLC22A3 and ODC1; SLC22A3 and SMOC2; SLC22A3 and UGDH; SLC22A3 and DSC2; SLC22A3 and WNK2; SLC22A3 and RAB3B; SLC22A3 and FAM198B; SLC22A3 and KCNC2; SLC22A3 and SNAP91; ODC1; ODC1 and SMOC2; ODC1 and UGDH; ODC1 and DSC2; ODC1 and WNK2; ODC1 and RAB3B; ODC1 and FAM198B; ODC1 and KCNC2; ODC1 and SNAP91; SMOC2; SMOC2 and UGDH; SMOC2 and DSC2; SMOC2 and WNK2; SMOC2 and RAB3B; SMOC2 and FAM198B; SMOC2 and KCNC2; SMOC2 and SNAP91; UGDH; UGDH and DSC2; UGDH and WNK2; UGDH and RAB3B; UGDH and FAM198B; UGDH and KCNC2; UGDH and SNAP91; DSC2; DSC2 and WNK2; DSC2 and RAB3B; DSC2 and FAM198B; DSC2 and KCNC2; DSC2 and SNAP91; WNK2; WNK2 and RAB3B; WNK2 and FAM198B; WNK2 and KCNC2; WNK2 and SNAP91; RAB3B; RAB3B and FAM198B; RAB3B and KCNC2; RAB3B and SNAP91; FAM198B; FAM198B and KCNC2; FAM198B and SNAP91; KCNC2; KCNC2 and SNAP91; SNAP91; FAM65B, AMACR, ZNF385B, CDK19, ARHGAP18, IL5RA, SLC16A1, CNTLN, FKBP10, SLC45A2, CLIP1, HEXB, NEFH, ODZ1 and SS18L2; FAM65B; FAM65B and AMACR; FAM65B and ZNF385B; FAM65B and CDK19; FAM65B and ARHGAP18; FAM65B and IL5RA; FAM65B and SLC16A1; FAM65B and CNTLN; FAM65B and FKBP10; FAM65B and SLC45A2; FAM65B and CLIP1; FAM65B and HEXB; FAM65B and NEFH; FAM65B and ODZ1; FAM65B and SS18L2; AMACR; AMACR and ZNF385B; AMACR and CDK19; AMACR and ARHGAP18; AMACR and IL5RA; AMACR and SLC16A1; AMACR and CNTLN; AMACR and FKBP10; AMACR and SLC45A2; AMACR and CLIP1; AMACR and HEXB; AMACR and NEFH; AMACR and ODZ1; AMACR and SS18L2; ZNF385B; ZNF385B and CDK19; ZNF385B and ARHGAP18; ZNF385B and IL5RA; ZNF385B and SLC16A1; ZNF385B and CNTLN; ZNF385B and FKBP10; ZNF385B and SLC45A2; ZNF385B and CLIP1; ZNF385B and HEXB; ZNF385B and NEFH; ZNF385B and ODZ1; ZNF385B and SS18L2; CDK19; CDK19 and ARHGAP18; CDK19 and IL5RA; CDK19 and SLC16A1; CDK19 and CNTLN; CDK19 and FKBP10; CDK19 and SLC45A2; CDK19 and CLIP1; CDK19 and HEXB; CDK19 and NEFH; CDK19 and ODZ1; CDK19 and SS18L2; ARHGAP18; ARHGAP18 and IL5RA; ARHGAP18 and SLC16A1; ARHGAP18 and CNTLN; ARHGAP18 and FKBP10; ARHGAP18 and SLC45A2; ARHGAP18 and CLIP1; ARHGAP18 and HEXB; ARHGAP18 and NEFH; ARHGAP18 and ODZ1; ARHGAP18 and SS18L2; IL5RA; IL5RA and SLC16A1; IL5RA and CNTLN; IL5RA and FKBP10; IL5RA and SLC45A2; IL5RA and CLIP1; IL5RA and HEXB; IL5RA and NEFH; IL5RA and ODZ1; IL5RA and SS18L2; SLC16A1; SLC16A1 and CNTLN; SLC16A1 and FKBP10; SLC16A1 and SLC45A2; SLC16A1 and CLIP1; SLC16A1 and HEXB; SLC16A1 and NEFH; SLC16A1 and ODZ1; SLC16A1 and SS18L2; CNTLN; CNTLN and FKBP10; CNTLN and SLC45A2; CNTLN and CLIP1; CNTLN and HEXB; CNTLN and NEFH; CNTLN and ODZ1; CNTLN and SS18L2; FKBP10; FKBP10 and SLC45A2; FKBP10 and CLIP1; FKBP10 and HEXB; FKBP10 and NEFH; FKBP10 and ODZ1; FKBP10 and SS18L2; SLC45A2; SLC45A2 and CLIP1; SLC45A2 and HEXB; SLC45A2 and NEFH; SLC45A2 and ODZ1; SLC45A2 and SS18L2; CLIP1; CLIP1 and HEXB; CLIP1 and NEFH; CLIP1 and ODZ1; CLIP1 and SS18L2; HEXB; HEXB and NEFH; HEXB and ODZ1; HEXB and SS18L2; NEFH; NEFH and ODZ1; NEFH and SS18L2; ODZ1; ODZ1 and SS18L2; SS18L2; HPGD, FAM3B, MIPEP, NCAPD3, INPP4B, ANPEP, TFF3, IL31RA, EHHADH, RP11-45B20.2, CCDC141, RLN1, ABHD2 and SCIN; HPGD; HPGD and FAM3B; HPGD and MIPEP; HPGD and NCAPD3; HPGD and INPP4B; HPGD and ANPEP; HPGD and TFF3; HPGD and IL31RA; HPGD and EHHADH; HPGD and RP11-45B20.2; HPGD and CCDC141; HPGD and RLN1; HPGD and ABHD2; HPGD and SCIN; FAM3B; FAM3B and MIPEP; FAM3B and NCAPD3; FAM3B and INPP4B; FAM3B and ANPEP; FAM3B and TFF3; FAM3B and IL31RA; FAM3B and EHHADH; FAM3B and RP11-45B20.2; FAM3B and CCDC141; FAM3B and RLN1; FAM3B and ABHD2; FAM3B and SCIN; MIPEP; MIPEP and NCAPD3; MIPEP and INPP4B; MIPEP and ANPEP; MIPEP and TFF3; MIPEP and IL31RA; MIPEP and EHHADH; MIPEP and RP11-45B20.2; MIPEP and CCDC141; MIPEP and RLN1; MIPEP and ABHD2; MIPEP and SCIN; NCAPD3; NCAPD3 and INPP4B; NCAPD3 and ANPEP; NCAPD3 and TFF3; NCAPD3 and IL31RA; NCAPD3 and EHHADH; NCAPD3 and RP11-45B20.2; NCAPD3 and CCDC141; NCAPD3 and RLN1; NCAPD3 and ABHD2; NCAPD3 and SCIN; INPP4B; INPP4B and ANPEP; INPP4B and TFF3; INPP4B and IL31RA; INPP4B and EHHADH; INPP4B and RP11-45B20.2; INPP4B and CCDC141; INPP4B and RLN1; INPP4B and ABHD2; INPP4B and SCIN; ANPEP; ANPEP and TFF3; ANPEP and IL31RA; ANPEP and EHHADH; ANPEP and RP11-45B20.2; ANPEP and CCDC141; ANPEP and RLN1; ANPEP and ABHD2; ANPEP and SCIN; TFF3; TFF3 and IL31RA; TFF3 and EHHADH; TFF3 and RP11-45B20.2; TFF3 and CCDC141; TFF3 and RLN1; TFF3 and ABHD2; TFF3 and SCIN; IL31RA; IL31RA and EHHADH; IL31RA and RP11-45B20.2; IL31RA and CCDC141; IL31RA and RLN1; IL31RA and ABHD2; IL31RA and SCIN; EHHADH; EHHADH and RP11-45B20.2; EHHADH and CCDC141; EHHADH and RLN1; EHHADH and ABHD2; EHHADH and SCIN; RP11-45B20.2; RP11-45B20.2 and CCDC141; RP11-45B20.2 and RLN1; RP11-45B20.2 and ABHD2; RP11-45B20.2 and SCIN; CCDC141; CCDC141 and RLN1; CCDC141 and ABHD2; CCDC141 and SCIN; RLN1; RLN1 and ABHD2; RLN1 and SCIN; ABHD2; ABHD2 and SCIN; SCIN; TFF3, ALOX15B, and MON1B; TFF3 and ALOX15B; TFF3 and MON1B; ALOX15B; ALOX15B, and MON1B; MON1B; MME, BANK1, LEPREL1, VGLL3, NPR3, OR4K7P, OR4K6P, POTEB2, RP11, TTN, FAP5 and GPR116; MME; MME and BANK1; MME and LEPREL1; MME and VGLL3; MME and NPR3; MME and OR4K7P; MME and OR4K6P; MME and POTEB2; MME and RP11; MME and TTN; MME and FAP5; MME and GPR116; BANK1; BANK1 and LEPREL1; BANK1 and VGLL3; BANK1 and NPR3; BANK1 and OR4K7P; BANK1 and OR4K6P; BANK1 and POTEB2; BANK1 and RP11; BANK1 and TTN; BANK1 and FAP5; BANK1 and GPR116; LEPREL1; LEPREL1 and VGLL3; LEPREL1 and NPR3; LEPREL1 and OR4K7P; LEPREL1 and OR4K6P; LEPREL1 and POTEB2; LEPREL1 and RP11; LEPREL1 and TTN; LEPREL1 and FAP5; LEPREL1 and GPR116; VGLL3; VGLL3 and NPR3; VGLL3 and OR4K7P; VGLL3 and OR4K6P; VGLL3 and POTEB2; VGLL3 and RP11; VGLL3 and TTN; VGLL3 and FAP5; VGLL3 and GPR116; NPR3; NPR3 and OR4K7P; NPR3 and OR4K6P; NPR3 and POTEB2; NPR3 and RP11; NPR3 and TTN; NPR3 and FAP5; NPR3 and GPR116; OR4K7P; OR4K7P and OR4K6P; OR4K7P and POTEB2; OR4K7P and RP11; OR4K7P and TTN; OR4K7P and FAP5; OR4K7P and GPR116; OR4K6P; OR4K6P and POTEB2; OR4K6P and RP11; OR4K6P and TTN; OR4K6P and FAP5; OR4K6P and GPR116; POTEB2; POTEB2 and RP11; POTEB2 and TTN; POTEB2 and FAP5; POTEB2 and GPR116; RP11; RP11 and TTN; RP11 and FAP5; RP11 and GPR116; TTN; TTN and FAP5; TTN and GPR116; FAP5; FAP5 and GPR116; GPR116; MME, BANK1, LEPREL1, VGLL3, NPR3, OR4K6P, OR4K7P, POTEB2, RP11.403, TTN and FABP5P7; RP11.403; RP11.403 and TTN; RP11.403 and FABP5P7; TTN; TTN and FABP5P7; and FABP5P7. The plurality of targets may comprise 5, 6, 7, 8, 9, 10, 11, 12, 13, 14, 15, 20, 30, 40, 50 or more targets.

The plurality of targets may comprise CDC20; KIF2C; PHGDH; NUF2; CENPF; EXO1; UBE2T; RRM2; MLPH; GPR160; CCNB1; CXXC5; PTTG1; FGFR4; FOXC1; ESR1; ANLN; BLVRA; EGFR; ACTR3B; NAT1; MYC; SFRP1; MELK; BAG1; CEP55; MKI67; TMEM45B; PGR; MDM2; KRT5; FOXA1; ORC6; CDH3; ERBB2; GRB7; CDC6; MAPT; BIRC5; KRT14; KRT17; TYMS; NDC80; SLC39A6; BCL2; CCNE1; MIA; MYBL2; UBE2C; MMP11; TDRD1; CACNA1D; NCALD; HLA-DMB; KCNH8; PDE3B; PLA2G7; CSGALNACT1; PART1; HES1; F3; GPR110; SH3RF; PDE8B; SEPT9; CRISP3; AMD1; KCNG3; PLA1A; MYO6; FRK; SH3YL1; ACER3; C8orf4; GHR; ITPR1; KHDRBS3; NPY; GUCY1A3; ARHGDIB; LAMC2; VWA2; ZNF432; MORN1; CYorf15B; AMPD3; QDPR; HDAC1; KIF16B; GJB1; ITPR3; ZNF615; ANKRD6; APOD; STEAP4; RGS17; MAP7; C22orf36; NKAIN1; CHN2; LRRFIP1; SERGEF; ATP8A2; NDRG1; CDC42SE1; LUZP2; HNF1B; TFAP2A; ANKRD34B; SLC12A2; PRAC; SLC5A4; ACSL3; CD24P4; DNASE2B; SLC22A3; ODC1; SMOC2; UGDH; DSC2; WNK2; RAB3B; FAM198B; KCNC2; SNAP91; FAM65B; AMACR; ZNF385B; CDK19; ARHGAP18; IL5RA; SLC16A1; CNTLN; FKBP10; SLC45A2; CLIP1; HEXB; NEFH; ODZ1; SS18L2; HPGD; FAM3B; MIPEP; NCAPD3; INPP4B; ANPEP; TFF3; IL31RA; EHHADH; RP11-45B20.2; CCDC141; RLN1; ABHD2; SCIN; ALOX15B; MON1B; MME; BANK1; LEPREL1; VGLL3; NPR3; OR4K7P; OR4K6P; POTEB2; RP11; TTN; FAP5; GPR116; RP11.403; and FABP5P7.

Probes/Primers

The present invention provides for a probe set for diagnosing, monitoring and/or predicting a status or outcome of a prostate cancer in a subject comprising a plurality of probes, wherein (i) the probes in the set are capable of detecting an expression level of at least one target selected from; and (ii) the expression level determines the cancer status of the subject with at least about 40% specificity.

The probe set may comprise one or more polynucleotide probes. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a target sequence in the probe set. Computer programs can also be employed to select probe sequences that may not cross hybridize or may not hybridize non-specifically.

In some instances, microarray hybridization of RNA, extracted from prostate cancer tissue samples and amplified, may yield a dataset that is then summarized and normalized by the fRMA technique. After removal (or filtration) of cross-hybridizing PSRs, and PSRs containing less than 4 probes, the remaining PSRs can be used in further analysis. Following fRMA and filtration, the data can be decomposed into its principal components and an analysis of variance model is used to determine the extent to which a batch effect remains present in the first 10 principal components.

These remaining PSRs can then be subjected to filtration by a T-test between CR (clinical recurrence) and non-CR samples. Using a p-value cut-off of 0.01, the remaining features (e.g., PSRs) can be further refined. Feature selection can be performed by regularized logistic regression using the elastic-net penalty. The regularized regression may be bootstrapped over 1000 times using all training data; with each iteration of bootstrapping, features that have non-zero co-efficient following 3-fold cross validation can be tabulated. In some instances, features that were selected in at least 25% of the total runs were used for model building.

The polynucleotide probes of the present invention may range in length from about 15 nucleotides to the full length of the coding target or non-coding target. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides, about 15 nucleotides and about 250 nucleotides, about 15 nucleotides and about 200 nucleotides in length. In some embodiments, the probes are at least 15 nucleotides in length. In some embodiments, the probes are at least 15 nucleotides in length. In some embodiments, the probes are at least 20 nucleotides, at least 25 nucleotides, at least 50 nucleotides, at least 75 nucleotides, at least 100 nucleotides, at least 125 nucleotides, at least 150 nucleotides, at least 200 nucleotides, at least 225 nucleotides, at least 250 nucleotides, at least 275 nucleotides, at least 300 nucleotides, at least 325 nucleotides, at least 350 nucleotides, at least 375 nucleotides in length.

The polynucleotide probes of a probe set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly Such modified or substituted polynucleotide probes may provide desirable properties such as, for example, enhanced affinity for a target gene and increased stability. The probe set may comprise a coding target and/or a non-coding target. Preferably, the probe set comprises a combination of a coding target and non-coding target.

In some embodiments, the probe set comprise a plurality of target sequences that hybridize to at least about 5 coding targets and/or non-coding targets selected from Table 8, Table 9 or SEQ ID NOs: 1-1029. Alternatively, the probe set comprise a plurality of target sequences that hybridize to at least about 10 coding targets and/or non-coding targets selected from Table 8, Table 9 or SEQ ID NOs: 1-1029. In some embodiments, the probe set comprise a plurality of target sequences that hybridize to at least about 15 coding targets and/or non-coding targets selected from Table 8, Table 9 or SEQ ID NOs: 1-1029. In some embodiments, the probe set comprise a plurality of target sequences that hybridize to at least about 20 coding targets and/or non-coding targets selected from Table 8, Table 9 or SEQ ID NOs: 1-1029. In some embodiments, the probe set comprise a plurality of target sequences that hybridize to at least about 30 coding targets and/or non-coding targets selected from Table 8, Table 9 or SEQ ID NOs: 1-1029. In some embodiments, the probe set comprise a plurality of target sequences that hybridize to at least about 40 coding targets and/or non-coding targets selected from Table 8, Table 9 or SEQ ID NOs: 1-1029. In some embodiments, the probe set comprise a plurality of target sequences that hybridize to at least about 50 coding targets and/or non-coding targets selected from Table 8, Table 9 or SEQ ID NOs: 1-1029.

The system of the present invention further provides for primers and primer pairs capable of amplifying target sequences defined by the probe set, or fragments or subsequences or complements thereof. The nucleotide sequences of the probe set may be provided in computer-readable media for in silico applications and as a basis for the design of appropriate primers for amplification of one or more target sequences of the probe set.

Primers based on the nucleotide sequences of target sequences can be designed for use in amplification of the target sequences. For use in amplification reactions such as PCR, a pair of primers can be used. The exact composition of the primer sequences is not critical to the invention, but for most applications the primers may hybridize to specific sequences of the probe set under stringent conditions, particularly under conditions of high stringency, as known in the art. The pairs of primers are usually chosen so as to generate an amplification product of at least about 50 nucleotides, more usually at least about 100 nucleotides.

Algorithms for the selection of primer sequences are generally known, and are available in commercial software packages. These primers may be used in standard quantitative or qualitative PCR-based assays to assess transcript expression levels of RNAs defined by the probe set. Alternatively, these primers may be used in combination with probes, such as molecular beacons in amplifications using real-time PCR.

In one embodiment, the primers or primer pairs, when used in an amplification reaction, specifically amplify at least a portion of a nucleic acid sequence of a target selected from Table 8, Table 9 or SEQ ID NOs: 1-1029 (or subgroups thereof as set forth herein), an RNA form thereof, or a complement to either thereof.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

In some embodiments, polynucleotides of the invention comprise at least 20 consecutive bases of the nucleic acid sequence of a target selected from Table 8, Table 9 or SEQ ID NOs: 1-1029 or a complement thereto. The polynucleotides may comprise at least 21, 22, 23, 24, 25, 27, 30, 32, 35 or more consecutive bases of the nucleic acids sequence of a target selected from Table 8, Table 9 or SEQ ID NOs: 1-1029, as applicable.

The polynucleotides may be provided in a variety of formats, including as solids, in solution, or in an array. The polynucleotides may optionally comprise one or more labels, which may be chemically and/or enzymatically incorporated into the polynucleotide.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Diagnostic Samples

Diagnostic samples for use with the systems and in the methods of the present invention comprise nucleic acids suitable for providing RNAs expression information. In principle, the biological sample from which the expressed RNA is obtained and analyzed for target sequence expression can be any material suspected of comprising prostate cancer tissue or cells. The diagnostic sample can be a biological sample used directly in a method of the invention. Alternatively, the diagnostic sample can be a sample prepared from a biological sample.

In one embodiment, the sample or portion of the sample comprising or suspected of comprising cancer tissue or cells can be any source of biological material, including cells, tissue or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs. In some embodiments, the sample is from urine. Alternatively, the sample is from blood, plasma or serum. In some embodiments, the sample is from saliva.

The samples may be archival samples, having a known and documented medical outcome, or may be samples from current patients whose ultimate medical outcome is not yet known.

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Hely solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods.

One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFMFM, Cryo-Gef™, and OCT Compound (Electron Microscopy Sciences, Hatfield, PA). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

RNA Extraction

RNA can be extracted and purified from biological samples using any suitable technique. A number of techniques are known in the art, and several are commercially available (e.g., FormaPure nucleic acid extraction kit, Agencourt Biosciences, Beverly MA, High Pure FFPE RNA Micro Kit, Roche Applied Science, Indianapolis, IN). RNA can be extracted from frozen tissue sections using TRIzol (Invitrogen, Carlsbad, CA) and purified using RNeasy Protect kit (Qiagen, Valencia, CA). RNA can be further purified using DNAse I treatment (Ambion, Austin, TX) to eliminate any contaminating DNA. RNA concentrations can be made using a Nanodrop ND-1000 spectrophotometer (Nanodrop Technologies, Rockland, DE). RNA can be further purified to eliminate contaminants that interfere with cDNA synthesis by cold sodium acetate precipitation. RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, CA).

Kits

Kits for performing the desired method(s) are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. The primers or pairs of primers suitable for selectively amplifying the target sequences. The kit may comprise at least two, three, four or five primers or pairs of primers suitable for selectively amplifying one or more targets. The kit may comprise at least 5, 10, 15, 20, 30, 40, 50, 60, 70, 80, 90, 100 or more primers or pairs of primers suitable for selectively amplifying one or more targets.

In some embodiments, the primers or primer pairs of the kit, when used in an amplification reaction, specifically amplify a non-coding target, coding target, exonic, or non-exonic target described herein, a nucleic acid sequence corresponding to a target selected from Table 8, Table 9 or SEQ ID NOs: 1-1029, an RNA form thereof, or a complement to either thereof. The kit may include a plurality of such primers or primer pairs which can specifically amplify a corresponding plurality of different amplify a non-coding target, coding target, exonic, or non-exonic transcript described herein, a nucleic acid sequence corresponding to a target selected from Table 8, Table 9 or SEQ ID NOs: 1-1029, RNA forms thereof, or complements thereto. At least two, three, four or five primers or pairs of primers suitable for selectively amplifying the one or more targets can be provided in kit form. In some embodiments, the kit comprises from five to fifty primers or pairs of primers suitable for amplifying the one or more targets.

The reagents may independently be in liquid or solid form. The reagents may be provided in mixtures. Control samples and/or nucleic acids may optionally be provided in the kit. Control samples may include tissue and/or nucleic acids obtained from or representative of tumor samples from patients showing no evidence of disease, as well as tissue and/or nucleic acids obtained from or representative of tumor samples from patients that develop systemic cancer.

The nucleic acids may be provided in an array format, and thus an array or microarray may be included in the kit. The kit optionally may be certified by a government agency for use in prognosing the disease outcome of cancer patients and/or for designating a treatment modality.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a target sequence, and may optionally be labeled. A variety of amplification methods are suitable for use, including polymerase-based methods and ligation-based methods. Exemplary amplification techniques include the polymerase chain reaction method (PCR), the lipase chain reaction (LCR), ribozyme-based methods, self-sustained sequence replication (3SR), nucleic acid sequence-based amplification (NASBA), the use of Q Beta replicase, reverse transcription, nick translation, and the like.

Asymmetric amplification reactions may be used to preferentially amplify one strand representing the target sequence that is used for detection as the target polynucleotide. In some cases, the presence and/or amount of the amplification product itself may be used to determine the expression level of a given target sequence. In other instances, the amplification product may be used to hybridize to an array or other substrate comprising sensor polynucleotides which are used to detect and/or quantitate target sequence expression.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that can produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfic, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfic, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, CA), including the WT-Ovation™ System, WT-Ovation™ System v2, WT-Ovation™ Pico System, WT-Ovation™ FFPE Exon Module, WT-Ovation™ FFPE Exon Module RiboAmp and RiboAmp$^{Plus}$ RNA Amplification Kits (MDS Analytical Technologies (formerly Arcturus) (Mountain View, CA), Genisphere, Inc. (Hatfield, PA), including the RampUp Plus™ and SenseAmp™ RNA Amplification kits, alone or in combination. Amplified nucleic acids may be subjected to one or more purification reactions after amplification and labeling, for example using magnetic beads (e.g., RNAC1ean magnetic beads, Agencourt Biosciences).

Multiple RNA biomarkers can be analyzed using real-time quantitative multiplex RT-PCR platforms and other multiplexing technologies such as GenomeLab GeXP Genetic Analysis System (Beckman Coulter, Foster City, CA), SmartCycler® 9600 or GeneXpert® Systems (Cepheid, Sunnyvale, CA), ABI 7900 HT Fast Real Time PCR system (Applied Biosystems, Foster City, CA), LightCycler® 480 System (Roche Molecular Systems, Pleasanton, CA), xMAP 100 System (Luminex, Austin, TX) Solexa Genome Analysis System (Illumina, Hayward, CA), OpenArray Real Time qPCR (BioTrove, Woburn, MA) and BeadXpress System (Illumina, Hayward, CA).

Detection and/or Quantification of Target Sequences

Any method of detecting and/or quantitating the expression of the encoded target sequences can in principle be used in the invention. The expressed target sequences can be directly detected and/or quantitated, or may be copied and/or amplified to allow detection of amplified copies of the expressed target sequences or its complement.

Methods for detecting and/or quantifying a target can include Northern blotting, sequencing, array or microarray hybridization, by enzymatic cleavage of specific structures (e.g., an Invader® assay, Third Wave Technologies, e.g. as described in U.S. Pat. Nos. 5,846,717, 6,090,543; 6,001,567; 5,985,557; and 5,994,069) and amplification methods, e.g. RT-PCR, including in a TaqMan® assay (PE Biosystems, Foster City, CA, e.g. as described in U.S. Pat. Nos. 5,962,233 and 5,538,848), and may be quantitative or semi-quantitative, and may vary depending on the origin, amount and condition of the available biological sample. Combinations of these methods may also be used. For example, nucleic acids may be amplified, labeled and subjected to microarray analysis.

In some instances, target sequences may be detected by sequencing. Sequencing methods may comprise whole genome sequencing or exome sequencing. Sequencing methods such as Maxim-Gilbert, chain-termination, or high-throughput systems may also be used. Additional, suitable sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, and SOLiD sequencing.

Additional methods for detecting and/or quantifying a target include single-molecule sequencing (e.g., Helicos, PacBio), sequencing by synthesis (e.g., Illumina, Ion Torrent), sequencing by ligation (e.g., ABI SOLID), sequencing by hybridization (e.g., Complete Genomics), in situ hybridization, bead-array technologies (e.g., Luminex xMAP, Illumina BeadChips), branched DNA technology (e.g., Panomics, Genisphere). Sequencing methods may use fluorescent (e.g., Illumina) or electronic (e.g., Ion Torrent, Oxford Nanopore) methods of detecting nucleotides.

Reverse Transcription for ORT-PCR Analysis

Reverse transcription can be performed by any method known in the art. For example, reverse transcription may be performed using the Omniscript kit (Qiagen, Valencia, CA), Superscript III kit (Invitrogen, Carlsbad, CA), for RT-PCR. Target-specific priming can be performed in order to increase the sensitivity of detection of target sequences and generate target-specific cDNA.

TaqMan® Gene Expression Analysis

TaqMan® RT-PCR can be performed using Applied Biosystems Prism (ABI) 7900 HT instruments in a 5 1.11 volume with target sequence-specific cDNA equivalent to 1 ng total RNA.

Primers and probes concentrations for TaqMan analysis are added to amplify fluorescent amplicons using PCR cycling conditions such as 95° C. for 10 minutes for one cycle, 95° C. for 20 seconds, and 60° C. for 45 seconds for 40 cycles. A reference sample can be assayed to ensure reagent and process stability. Negative controls (e.g., no template) should be assayed to monitor any exogenous nucleic acid contamination.

Classification Arrays

The present invention contemplates that a probe set or probes derived therefrom may be provided in an array format. In the context of the present invention, an "array" is a spatially or logically organized collection of polynucleotide probes. An array comprising probes specific for a coding target, non-coding target, or a combination thereof may be used. Alternatively, an array comprising probes specific for two or more of transcripts of a target selected from Table 8, Table 9 or SEQ ID NOs: 1-1029 or a product derived thereof can be used. Desirably, an array may be specific for 5, 10, 15, 20, 25, 30, 40, 50 or more of transcripts of a target selected from Table 8, Table 9 or SEQ ID NOs: 1-1029. Expression of these sequences may be detected alone or in combination with other transcripts. In some embodiments, an array is used which comprises a wide range of sensor probes for prostate-specific expression products, along with appropriate control sequences. In some instances, the array may comprise the Human Exon 1.0 ST Array (HuEx 1.0 ST, Affymetrix, Inc., Santa Clara, CA).

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that may be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In one embodiment of the present invention, the Cancer Prognosticarray is a chip.

Data Analysis

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (e.g., an 'expression signature') and converted into a likelihood score. This likelihood score indicates the probability that a biological sample is from a patient who may exhibit no evidence of disease, who may exhibit systemic cancer, or who may exhibit biochemical recurrence. The likelihood score can be used to distinguish these disease states. The models and/or algorithms can be provided in machine readable format, and may be used to correlate expression levels or an expression profile with a disease state, and/or to designate a treatment modality for a patient or class of patients.

Assaying the expression level for a plurality of targets may comprise the use of an algorithm or classifier. Array data can be managed, classified, and analyzed using techniques known in the art. Assaying the expression level for a plurality of targets may comprise probe set modeling and data pre-processing. Probe set modeling and data pre-processing can be derived using the Robust Multi-Array (RMA) algorithm or variants GC-RMA, IRMA, Probe Logarithmic Intensity Error (PLIER) algorithm or variant iterPLIER. Variance or intensity filters can be applied to pre-process data using the RMA algorithm, for example by removing target sequences with a standard deviation of <10 or a mean intensity of <100 intensity units of a normalized data range, respectively.

Alternatively, assaying the expression level for a plurality of targets may comprise the use of a machine learning algorithm. The machine learning algorithm may comprise a supervised learning algorithm. Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, temporal difference learning, Q-learning and Learning Automata. Alternatively, the machine learning algorithm may comprise Data Pre-processing.

Preferably, the machine learning algorithms may include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naïve Bayes classifier, k-nearest neighbor, high-dimensional discriminant analysis, or Gaussian mixture models. In some instances, the machine learning algorithm comprises Random Forests.

Cancer

The systems, compositions and methods disclosed herein may be used to diagnosis, monitor and/or predict the status or outcome of a cancer. Generally, a cancer is characterized by the uncontrolled growth of abnormal cells anywhere in a body. The abnormal cells may be termed cancer cells, malignant cells, or tumor cells. Cancer is not confined to humans; animals and other living organisms can get cancer.

In some instances, the cancer may be malignant. Alternatively, the cancer may be benign. The cancer may be a recurrent and/or refractory cancer. Most cancers can be classified as a carcinoma, sarcoma, leukemia, lymphoma, myeloma, or a central nervous system cancer.

The cancer may be a sarcoma. Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Alternatively, the cancer may be a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penic cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. Preferably, the cancer is a prostate cancer. Alternatively, the cancer may be a thyroid cancer, bladder cancer, or pancreatic cancer.

In some instances, the cancer is a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The cancer may be a leukemia. The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic-leukemia.

In some instances, the cancer is a lymphoma. Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Cancer Staging

Diagnosing, predicting, or monitoring a status or outcome of a cancer may comprise determining the stage of the cancer. Generally, the stage of a cancer is a description (usually numbers I to IV with IV having more progression) of the extent the cancer has spread. The stage often takes into account the size of a tumor, how deeply it has penetrated, whether it has invaded adjacent organs, how many lymph nodes it has metastasized to (if any), and whether it has spread to distant organs. Staging of cancer can be used as a predictor of survival, and cancer treatment may be determined by staging. Determining the stage of the cancer may occur before, during, or after treatment. The stage of the cancer may also be determined at the time of diagnosis.

Cancer staging can be divided into a clinical stage and a pathologic stage. Cancer staging may comprise the TNM classification. Generally, the TNM Classification of Malignant Tumours (TNM) is a cancer staging system that describes the extent of cancer in a patient's body. T may describe the size of the tumor and whether it has invaded nearby tissue, N may describe regional lymph nodes that are involved, and M may describe distant metastasis (spread of cancer from one body part to another). In the TNM (Tumor, Node, Metastasis) system, clinical stage and pathologic stage are denoted by a small "c" or "p" before the stage (e.g., cT3N1M0 or pT2N0).

Often, clinical stage and pathologic stage may differ. Clinical stage may be based on all of the available information obtained before a surgery to remove the tumor. Thus, it may include information about the tumor obtained by physical examination, radiologic examination, and endoscopy. Pathologic stage can add additional information gained by examination of the tumor microscopically by a pathologist. Pathologic staging can allow direct examination of the tumor and its spread, contrasted with clinical staging which may be limited by the fact that the information is obtained by making indirect observations at a tumor which is still in the body. The TNM staging system can be used for most forms of cancer.

Alternatively, staging may comprise Ann Arbor staging. Generally, Ann Arbor staging is the staging system for lymphomas, both in Hodgkin's lymphoma (previously called Hodgkin's disease) and Non-Hodgkin lymphoma (abbreviated NHL). The stage may depend on both the place where the malignant tissue is located (as located with biopsy, CT scanning and increasingly positron emission tomography) and on systemic symptoms due to the lymphoma ("B symptoms": night sweats, weight loss of >10% or fevers). The principal stage may be determined by location of the tumor. Stage I may indicate that the cancer is located in a single region, usually one lymph node and the surrounding area. Stage I often may not have outward symptoms. Stage II can indicate that the cancer is located in two separate regions, an affected lymph node or organ and a second affected area, and that both affected areas are confined to one side of the diaphragm—that is, both are above the diaphragm, or both are below the diaphragm. Stage III often indicates that the cancer has spread to both sides of the diaphragm, including one organ or area near the lymph nodes or the spleen. Stage IV may indicate diffuse or disseminated involvement of one or more extralymphatic organs, including any involvement of the liver, bone marrow, or nodular involvement of the lungs.

Modifiers may also be appended to some stages. For example, the letters A, B, E, X, or S can be appended to some stages. Generally, A or B may indicate the absence of constitutional (B-type) symptoms is denoted by adding an "A" to the stage; the presence is denoted by adding a "B" to the stage. E can be used if the disease is "extranodal" (not in the lymph nodes) or has spread from lymph nodes to adjacent tissue. X is often used if the largest deposit is >10 cm large ("bulky disease"), or whether the mediastinum is wider than ⅓ of the chest on a chest X-ray. S may be used if the disease has spread to the spleen.

The nature of the staging may be expressed with CS or PS. CS may denote that the clinical stage as obtained by doctor's examinations and tests. PS may denote that the pathological stage as obtained by exploratory laparotomy (surgery performed through an abdominal incision) with splenectomy (surgical removal of the spleen).

Therapeutic Regimens

Diagnosing, predicting, or monitoring a status or outcome of a cancer may comprise treating a cancer or preventing a cancer progression. In addition, diagnosing, predicting, or monitoring a status or outcome of a cancer may comprise identifying or predicting responders to an anti-cancer therapy. In some instances, diagnosing, predicting, or monitoring may comprise determining a therapeutic regimen. Determining a therapeutic regimen may comprise administering an anti-cancer therapy. Alternatively, determining a therapeutic regimen may comprise modifying, recommending, continuing or discontinuing an anti-cancer regimen. In some instances, if the sample expression patterns are consistent with the expression pattern for a known disease or disease outcome, the expression patterns can be used to designate one or more treatment modalities (e.g., therapeutic regimens, anti-cancer regimen). An anti-cancer regimen may comprise one or more anti-cancer therapies. Examples of anti-cancer therapies include surgery, chemotherapy, radiation therapy, immunotherapy/biological therapy, photodynamic therapy.

Surgical oncology uses surgical methods to diagnose, stage, and treat cancer, and to relieve certain cancer-related symptoms. Surgery may be used to remove the tumor (e.g., excisions, resections, debulking surgery), reconstruct a part of the body (e.g., restorative surgery), and/or to relieve symptoms such as pain (e.g., palliative surgery). Surgery may also include cryosurgery. Cryosurgery (also called cryotherapy) may use extreme cold produced by liquid nitrogen (or argon gas) to destroy abnormal tissue. Cryosurgery can be used to treat external tumors, such as those on the skin. For external tumors, liquid nitrogen can be applied directly to the cancer cells with a cotton swab or spraying device. Cryosurgery may also be used to treat tumors inside the body (internal tumors and tumors in the bone). For internal tumors, liquid nitrogen or argon gas may be circulated through a hollow instrument called a cryoprobe, which is placed in contact with the tumor. An ultrasound or MRI may be used to guide the cryoprobe and monitor the freezing of the cells, thus limiting damage to nearby healthy tissue. A ball of ice crystals may form around the probe, freezing nearby cells. Sometimes more than one probe is used to deliver the liquid nitrogen to various parts of the tumor. The probes may be put into the tumor during surgery or through the skin (percutaneously). After cryosurgery, the frozen tissue thaws and may be naturally absorbed by the body (for internal tumors), or may dissolve and form a scab (for external tumors).

Chemotherapeutic agents may also be used for the treatment of cancer. Examples of chemotherapeutic agents include alkylating agents, anti-metabolites, plant alkaloids and terpenoids, vinca alkaloids, podophyllotoxin, taxanes, topoisomerase inhibitors, and cytotoxic antibiotics. Cisplatin, carboplatin, and oxaliplatin are examples of alkylating agents. Other alkylating agents include mechlorethamine, cyclophosphamide, chlorambucil, ifosfamide. Alkylating agents may impair cell function by forming covalent bonds with the amino, carboxyl, sulfhydryl, and phosphate groups in biologically important molecules. Alternatively, alkylating agents may chemically modify a cell's DNA.

Anti-metabolites are another example of chemotherapeutic agents. Anti-metabolites may masquerade as purines or pyrimidines and may prevent purines and pyrimidines from becoming incorporated in to DNA during the "S" phase (of the cell cycle), thereby stopping normal development and division. Antimetabolites may also affect RNA synthesis. Examples of metabolites include azathioprine and mercaptopurine.

Alkaloids may be derived from plants and block cell division may also be used for the treatment of cancer. Alkyloids may prevent microtubule function. Examples of alkaloids are vinca alkaloids and taxanes. Vinca alkaloids may bind to specific sites on tubulin and inhibit the assembly of tubulin into microtubules (M phase of the cell cycle). The vinca alkaloids may be derived from the Madagascar periwinkle, *Catharanthus roseus* (formerly known as *Vinca rosea*). Examples of vinca alkaloids include, but are not limited to, vincristine, vinblastine, vinorelbine, or vindesine. Taxanes are diterpenes produced by the plants of the genus *Taxus* (yews). Taxanes may be derived from natural sources or synthesized artificially. Taxanes include paclitaxel (Taxol) and docetaxel (Taxotere). Taxanes may disrupt microtubule function. Microtubules are essential to cell division, and taxanes may stabilize GDP-bound tubulin in the microtubule, thereby inhibiting the process of cell division. Thus, in essence, taxanes may be mitotic inhibitors. Taxanes may also be radiosensitizing and often contain numerous chiral centers.

Alternative chemotherapeutic agents include podophyllotoxin. Podophyllotoxin is a plant-derived compound that may help with digestion and may be used to produce cytostatic drugs such as etoposide and teniposide. They may prevent the cell from entering the G1 phase (the start of DNA replication) and the replication of DNA (the S phase).

Topoisomerases are essential enzymes that maintain the topology of DNA. Inhibition of type I or type II topoisomerases may interfere with both transcription and replication of DNA by upsetting proper DNA supercoiling. Some chemotherapeutic agents may inhibit topoisomerases. For example, some type I topoisomerase inhibitors include camptothecins: irinotecan and topotecan. Examples of type II inhibitors include amsacrine, etoposide, etoposide phosphate, and teniposide.

Another example of chemotherapeutic agents is cytotoxic antibiotics. Cytotoxic antibiotics are a group of antibiotics that are used for the treatment of cancer because they may interfere with DNA replication and/or protein synthesis. Cytotoxic antiobiotics include, but are not limited to, actinomycin, anthracyclines, doxorubicin, daunorubicin, valrubicin, idarubicin, epirubicin, bleomycin, plicamycin, and mitomycin.

In some instances, the anti-cancer treatment may comprise radiation therapy. Radiation can come from a machine outside the body (external-beam radiation therapy) or from radioactive material placed in the body near cancer cells (internal radiation therapy, more commonly called brachytherapy). Systemic radiation therapy uses a radioactive substance, given by mouth or into a vein that travels in the blood to tissues throughout the body.

External-beam radiation therapy may be delivered in the form of photon beams (either x-rays or gamma rays). A photon is the basic unit of light and other forms of electromagnetic radiation. An example of external-beam radiation therapy is called 3-dimensional conformal radiation therapy (3D-CRT). 3D-CRT may use computer software and advanced treatment machines to deliver radiation to very precisely shaped target areas. Many other methods of external-beam radiation therapy are currently being tested and used in cancer treatment. These methods include, but are not limited to, intensity-modulated radiation therapy (IMRT), image-guided radiation therapy (IGRT), Stereotactic radiosurgery (SRS), Stereotactic body radiation therapy (SBRT), and proton therapy.

Intensity-modulated radiation therapy (IMRT) is an example of external-beam radiation and may use hundreds of tiny radiation beam-shaping devices, called collimators, to deliver a single dose of radiation. The collimators can be stationary or can move during treatment, allowing the intensity of the radiation beams to change during treatment sessions. This kind of dose modulation allows different areas of a tumor or nearby tissues to receive different doses of radiation. IMRT is planned in reverse (called inverse treatment planning). In inverse treatment planning, the radiation doses to different areas of the tumor and surrounding tissue are planned in advance, and then a high-powered computer program calculates the required number of beams and angles of the radiation treatment. In contrast, during traditional (forward) treatment planning, the number and angles of the radiation beams are chosen in advance and computers calculate how much dose may be delivered from each of the planned beams. The goal of IMRT is to increase the radiation dose to the areas that need it and reduce radiation exposure to specific sensitive areas of surrounding normal tissue.

Another example of external-beam radiation is image-guided radiation therapy (IGRT). In IGRT, repeated imaging scans (CT, MRI, or PET) may be performed during treatment. These imaging scans may be processed by computers to identify changes in a tumor's size and location due to treatment and to allow the position of the patient or the planned radiation dose to be adjusted during treatment as needed. Repeated imaging can increase the accuracy of radiation treatment and may allow reductions in the planned volume of tissue to be treated, thereby decreasing the total radiation dose to normal tissue.

Tomotherapy is a type of image-guided IMRT. A tomotherapy machine is a hybrid between a CT imaging scanner and an external-beam radiation therapy machine. The part of the tomotherapy machine that delivers radiation for both imaging and treatment can rotate completely around the patient in the same manner as a normal CT scanner. Tomotherapy machines can capture CT images of the patient's tumor immediately before treatment sessions, to allow for very precise tumor targeting and sparing of normal tissue.

Stereotactic radiosurgery (SRS) can deliver one or more high doses of radiation to a small tumor. SRS uses extremely accurate image-guided tumor targeting and patient positioning. Therefore, a high dose of radiation can be given without excess damage to normal tissue. SRS can be used to treat small tumors with well-defined edges. It is most commonly used in the treatment of brain or spinal tumors and brain metastases from other cancer types. For the treatment of some brain metastases, patients may receive radiation therapy to the entire brain (called whole-brain radiation therapy) in addition to SRS. SRS requires the use of a head frame or other device to immobilize the patient during treatment to ensure that the high dose of radiation is delivered accurately.

Stereotactic body radiation therapy (SBRT) delivers radiation therapy in fewer sessions, using smaller radiation fields and higher doses than 3D-CRT in most cases. SBRT may treat tumors that lie outside the brain and spinal cord. Because these tumors are more likely to move with the normal motion of the body, and therefore cannot be targeted as accurately as tumors within the brain or spine, SBRT is usually given in more than one dose. SBRT can be used to treat small, isolated tumors, including cancers in the lung and liver. SBRT systems may be known by their brand names, such as the CyberKnife®.

In proton therapy, external-beam radiation therapy may be delivered by proton. Protons are a type of charged particle. Proton beams differ from photon beams mainly in the way they deposit energy in living tissue. Whereas photons deposit energy in small packets all along their path through tissue, protons deposit much of their energy at the end of their path (called the Bragg peak) and deposit less energy along the way. Use of protons may reduce the exposure of normal tissue to radiation, possibly allowing the delivery of higher doses of radiation to a tumor.

Other charged particle beams such as electron beams may be used to irradiate superficial tumors, such as skin cancer or tumors near the surface of the body, but they cannot travel very far through tissue.

Internal radiation therapy (brachytherapy) is radiation delivered from radiation sources (radioactive materials) placed inside or on the body. Several brachytherapy techniques are used in cancer treatment. Interstitial brachytherapy may use a radiation source placed within tumor tissue, such as within a prostate tumor. Intracavitary brachytherapy may use a source placed within a surgical cavity or a body cavity, such as the chest cavity, near a tumor. Episcleral brachytherapy, which may be used to treat melanoma inside the eye, may use a source that is attached to the eye. In brachytherapy, radioactive isotopes can be sealed in tiny pellets or "seeds." These seeds may be placed in patients using delivery devices, such as needles, catheters, or some other type of carrier. As the isotopes decay naturally, they give off radiation that may damage nearby cancer cells. Brachytherapy may be able to deliver higher doses of radiation to some cancers than external-beam radiation therapy while causing less damage to normal tissue.

Brachytherapy can be given as a low-dose-rate or a high-dose-rate treatment. In low-dose-rate treatment, cancer cells receive continuous low-dose radiation from the source over a period of several days. In high-dose-rate treatment, a robotic machine attached to delivery tubes placed inside the body may guide one or more radioactive sources into or near a tumor, and then removes the sources at the end of each treatment session. High-dose-rate treatment can be given in one or more treatment sessions. An example of a high-dose-rate treatment is the MammoSite® system. Bracytherapy may be used to treat patients with breast cancer who have undergone breast-conserving surgery.

The placement of brachytherapy sources can be temporary or permanent. For permanent brachytherapy, the sources may be surgically sealed within the body and left there, even after all of the radiation has been given off. In some instances, the remaining material (in which the radioactive isotopes were sealed) does not cause any discomfort or harm to the patient. Permanent brachytherapy is a type of low-dose-rate brachytherapy. For temporary brachytherapy, tubes (catheters) or other carriers are used to deliver the radiation sources, and both the carriers and the radiation sources are removed after treatment. Temporary brachytherapy can be either low-dose-rate or high-dose-rate treatment. Brachytherapy may be used alone or in addition to external-beam radiation therapy to provide a "boost" of radiation to a tumor while sparing surrounding normal tissue.

In systemic radiation therapy, a patient may swallow or receive an injection of a radioactive substance, such as radioactive iodine or a radioactive substance bound to a monoclonal antibody. Radioactive iodine (131I) is a type of systemic radiation therapy commonly used to help treat cancer, such as thyroid cancer. Thyroid cells naturally take up radioactive iodine. For systemic radiation therapy for some other types of cancer, a monoclonal antibody may help target the radioactive substance to the right place. The antibody joined to the radioactive substance travels through the blood, locating and killing tumor cells. For example, the drug ibritumomab tiuxetan (Zevalin®) may be used for the treatment of certain types of B-cell non-Hodgkin lymphoma (NHL). The antibody part of this drug recognizes and binds to a protein found on the surface of B lymphocytes. The combination drug regimen of tositumomab and iodine I 131 tositumomab (Bexxar®) may be used for the treatment of certain types of cancer, such as NHL. In this regimen, nonradioactive tositumomab antibodies may be given to patients first, followed by treatment with tositumomab antibodies that have 131I attached. Tositumomab may recognize and bind to the same protein on B lymphocytes as ibritumomab. The nonradioactive form of the antibody may help protect normal B lymphocytes from being damaged by radiation from 131I.

Some systemic radiation therapy drugs relieve pain from cancer that has spread to the bone (bone metastases). This is a type of palliative radiation therapy. The radioactive drugs samarium-153-lexidronam (Quadramet®) and strontium-89 chloride (Metastron®) are examples of radiopharmaceuticals may be used to treat pain from bone metastases.

Biological therapy (sometimes called immunotherapy, biotherapy, or biological response modifier (BRM) therapy) uses the body's immune system, either directly or indirectly, to fight cancer or to lessen the side effects that may be caused by some cancer treatments. Biological therapies include interferons, interleukins, colony-stimulating factors, monoclonal antibodies, vaccines, gene therapy, and nonspecific immunomodulating agents.

Interferons (IFNs) are types of cytokines that occur naturally in the body. Interferon alpha, interferon beta, and interferon gamma are examples of interferons that may be used in cancer treatment.

Like interferons, interleukins (ILs) are cytokines that occur naturally in the body and can be made in the laboratory. Many interleukins have been identified for the treatment of cancer. For example, interleukin-2 (IL-2 or aldesleukin), interleukin 7, and interleukin 12 have may be used as an anti-cancer treatment. IL-2 may stimulate the growth and activity of many immune cells, such as lymphocytes, that can destroy cancer cells. Interleukins may be used to treat a number of cancers, including leukemia, lymphoma, and brain, colorectal, ovarian, breast, kidney and prostate cancers.

Colony-stimulating factors (CSFs) (sometimes called hematopoietic growth factors) may also be used for the treatment of cancer. Some examples of CSFs include, but are not limited to, G-CSF (filgrastim) and GM-CSF (sargramostim). CSFs may promote the division of bone marrow stem cells and their development into white blood cells, platelets, and red blood cells. Bone marrow is critical to the body's immune system because it is the source of all blood cells. Because anticancer drugs can damage the body's ability to make white blood cells, red blood cells, and platelets, stimulation of the immune system by CSFs may benefit patients undergoing other anti-cancer treatment, thus CSFs may be combined with other anti-cancer therapies, such as chemotherapy. CSFs may be used to treat a large variety of cancers, including lymphoma, leukemia, multiple myeloma, melanoma, and cancers of the brain, lung, esophagus, breast, uterus, ovary, prostate, kidney, colon, and rectum.

Another type of biological therapy includes monoclonal antibodies (MOABs or MoABs). These antibodies may be produced by a single type of cell and may be specific for a particular antigen. To create MOABs, a human cancer cells may be injected into mice. In response, the mouse immune system can make antibodies against these cancer cells. The mouse plasma cells that produce antibodies may be isolated and fused with laboratory-grown cells to create "hybrid" cells called hybridomas. Hybridomas can indefinitely produce large quantities of these pure antibodies, or MOABs. MOABs may be used in cancer treatment in a number of ways. For instance, MOABs that react with specific types of cancer may enhance a patient's immune response to the cancer. MOABs can be programmed to act against cell growth factors, thus interfering with the growth of cancer cells.

MOABs may be linked to other anti-cancer therapies such as chemotherapeutics, radioisotopes (radioactive substances), other biological therapies, or other toxins. When the antibodies latch onto cancer cells, they deliver these anti-cancer therapies directly to the tumor, helping to destroy it. MOABs carrying radioisotopes may also prove useful in diagnosing certain cancers, such as colorectal, ovarian, and prostate.

Rituxan® (rituximab) and Herceptin® (trastuzumab) are examples of MOABs that may be used as a biological therapy. Rituxan may be used for the treatment of non-Hodgkin lymphoma. Herceptin can be used to treat metastatic breast cancer in patients with tumors that produce excess amounts of a protein called HER2. Alternatively, MOABs may be used to treat lymphoma, leukemia, melanoma, and cancers of the brain, breast, lung, kidney, colon, rectum, ovary, prostate, and other areas.

Cancer vaccines are another form of biological therapy. Cancer vaccines may be designed to encourage the patient's immune system to recognize cancer cells. Cancer vaccines may be designed to treat existing cancers (therapeutic vaccines) or to prevent the development of cancer (prophylactic vaccines). Therapeutic vaccines may be injected in a person after cancer is diagnosed. These vaccines may stop the growth of existing tumors, prevent cancer from recurring, or eliminate cancer cells not killed by prior treatments. Cancer vaccines given when the tumor is small may be able to eradicate the cancer. On the other hand, prophylactic vaccines are given to healthy individuals before cancer develops. These vaccines are designed to stimulate the immune system to attack viruses that can cause cancer. By targeting these cancer-causing viruses, development of certain cancers may be prevented. For example, cervarix and gardasil are vaccines to treat human papilloma virus and may prevent cervical cancer. Therapeutic vaccines may be used to treat melanoma, lymphoma, leukemia, and cancers of the brain, breast, lung, kidney, ovary, prostate, pancreas, colon, and rectum. Cancer vaccines can be used in combination with other anti-cancer therapies.

Gene therapy is another example of a biological therapy. Gene therapy may involve introducing genetic material into a persons cells to fight disease. Gene therapy methods may improve a patient's immune response to cancer. For example, a gene may be inserted into an immune cell to enhance its ability to recognize and attack cancer cells. In another approach, cancer cells may be injected with genes that cause the cancer cells to produce cytokines and stimulate the immune system.

In some instances, biological therapy includes nonspecific immunomodulating agents. Nonspecific immunomodulating agents are substances that stimulate or indirectly augment the immune system. Often, these agents target key immune system cells and may cause secondary responses such as increased production of cytokines and immunoglobulins. Two nonspecific immunomodulating agents used in cancer treatment are *bacillus* Calmette-Guerin (BCG) and levamisole. BCG may be used in the treatment of superficial bladder cancer following surgery. BCG may work by stimulating an inflammatory, and possibly an immune, response. A solution of BCG may be instilled in the bladder. Levamisole is sometimes used along with fluorouracil (5-FU) chemotherapy in the treatment of stage III (Dukes' C) colon cancer following surgery. Levamisole may act to restore depressed immune function.

Photodynamic therapy (PDT) is an anti-cancer treatment that may use a drug, called a photosensitizer or photosensitizing agent, and a particular type of light. When photosensitizers are exposed to a specific wavelength of light, they may produce a form of oxygen that kills nearby cells. A photosensitizer may be activated by light of a specific wavelength. This wavelength determines how far the light can travel into the body. Thus, photosensitizers and wavelengths of light may be used to treat different areas of the body with PDT.

In the first step of PDT for cancer treatment, a photosensitizing agent may be injected into the bloodstream. The agent may be absorbed by cells all over the body but may stay in cancer cells longer than it does in normal cells. Approximately 24 to 72 hours after injection, when most of the agent has left normal cells but remains in cancer cells, the tumor can be exposed to light. The photosensitizer in the tumor can absorb the light and produces an active form of oxygen that destroys nearby cancer cells. In addition to directly killing cancer cells, PDT may shrink or destroy tumors in two other ways. The photosensitizer can damage blood vessels in the tumor, thereby preventing the cancer from receiving necessary nutrients. PDT may also activate the immune system to attack the tumor cells.

The light used for PDT can come from a laser or other sources. Laser light can be directed through fiber optic cables (thin fibers that transmit light) to deliver light to areas inside the body. For example, a fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumors, such as skin cancer. PDT is usually performed as an outpatient procedure. PDT may also be repeated and may be used with other therapies, such as surgery, radiation, or chemotherapy.

Extracorporeal photopheresis (ECP) is a type of PDT in which a machine may be used to collect the patient's blood cells. The patient's blood cells may be treated outside the body with a photosensitizing agent, exposed to light, and then returned to the patient. ECP may be used to help lessen the severity of skin symptoms of cutaneous T-cell lymphoma that has not responded to other therapies. ECP may be used to treat other blood cancers, and may also help reduce rejection after transplants.

Additionally, photosensitizing agent, such as porfimer sodium or Photofrin®, may be used in PDT to treat or relieve the symptoms of esophageal cancer and non-small cell lung cancer. Porfimer sodium may relieve symptoms of esophageal cancer when the cancer obstructs the esophagus or when the cancer cannot be satisfactorily treated with laser therapy alone. Porfimer sodium may be used to treat non-small cell lung cancer in patients for whom the usual treatments are not appropriate, and to relieve symptoms in patients with non-small cell lung cancer that obstructs the airways. Porfimer sodium may also be used for the treatment of precancerous lesions in patients with Barrett esophagus, a condition that can lead to esophageal cancer.

Laser therapy may use high-intensity light to treat cancer and other illnesses. Lasers can be used to shrink or destroy tumors or precancerous growths. Lasers are most commonly used to treat superficial cancers (cancers on the surface of the body or the lining of internal organs) such as basal cell skin cancer and the very early stages of some cancers, such as cervical, penile, vaginal, vulvar, and non-small cell lung cancer.

Lasers may also be used to relieve certain symptoms of cancer, such as bleeding or obstruction. For example, lasers can be used to shrink or destroy a tumor that is blocking a patient's trachea (windpipe) or esophagus. Lasers also can be used to remove colon polyps or tumors that are blocking the colon or stomach.

Laser therapy is often given through a flexible endoscope (a thin, lighted tube used to look at tissues inside the body). The endoscope is fitted with optical fibers (thin fibers that transmit light). It is inserted through an opening in the body, such as the mouth, nose, anus, or vagina. Laser light is then precisely aimed to cut or destroy a tumor.

Laser-induced interstitial thermotherapy (LITT), or interstitial laser photocoagulation, also uses lasers to treat some cancers. LITT is similar to a cancer treatment called hyperthermia, which uses heat to shrink tumors by damaging or killing cancer cells. During LITT, an optical fiber is inserted into a tumor. Laser light at the tip of the fiber raises the temperature of the tumor cells and damages or destroys them. LITT is sometimes used to shrink tumors in the liver.

Laser therapy can be used alone, but most often it is combined with other treatments, such as surgery, chemotherapy, or radiation therapy. In addition, lasers can seal nerve endings to reduce pain after surgery and seal lymph vessels to reduce swelling and limit the spread of tumor cells.

Lasers used to treat cancer may include carbon dioxide (CO2) lasers, argon lasers, and neodymium:yttrium-aluminum-garnet (Nd:YAG) lasers. Each of these can shrink or destroy tumors and can be used with endoscopes. CO2 and argon lasers can cut the skin's surface without going into deeper layers. Thus, they can be used to remove superficial cancers, such as skin cancer. In contrast, the Nd:YAG laser is more commonly applied through an endoscope to treat internal organs, such as the uterus, esophagus, and colon. Nd:YAG laser light can also travel through optical fibers into specific areas of the body during LITT. Argon lasers are often used to activate the drugs used in PDT.

For patients with high test scores consistent with systemic disease outcome after prostatectomy, additional treatment modalities such as adjuvant chemotherapy (e.g., docetaxel, mitoxantrone and prednisone), systemic radiation therapy (e.g., samarium or strontium) and/or anti-androgen therapy (e.g., surgical castration, finasteride, dutasteride) can be designated. Such patients would likely be treated immediately with anti-androgen therapy alone or in combination with radiation therapy in order to eliminate presumed micrometastatic disease, which cannot be detected clinically but can be revealed by the target sequence expression signature. Such patients can also be more closely monitored for signs of disease progression. For patients with intermediate test scores consistent with biochemical recurrence only (BCR-only or elevated PSA that does not rapidly become manifested as systemic disease only localized adjuvant therapy (e.g., radiation therapy of the prostate bed) or short course of anti-androgen therapy would likely be administered. For patients with low scores or scores consistent with no evidence of disease (NED) adjuvant therapy would not likely be recommended by their physicians in order to avoid treatment-related side effects such as metabolic syndrome (e.g., hypertension, diabetes and/or weight gain), osteoporosis, proctitis, incontinence or impotence. Patients with samples consistent with NED could be designated for watchful waiting, or for no treatment. Patients with test scores that do not correlate with systemic disease but who have successive PSA increases could be designated for watchful waiting, increased monitoring, or lower dose or shorter duration anti-androgen therapy.

Target sequences can be grouped so that information obtained about the set of target sequences in the group can be used to make or assist in making a clinically relevant judgment such as a diagnosis, prognosis, or treatment choice.

A patient report is also provided comprising a representation of measured expression levels of a plurality of target sequences in a biological sample from the patient, wherein the representation comprises expression levels of target sequences corresponding to any one, two, three, four, five, six, eight, ten, twenty, thirty, forty, fifty or more of the target sequences corresponding to a target selected from Table 8, Table 9 or SEQ ID NOs: 1-1029, the subsets described herein, or a combination thereof. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known disease status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

Subtyping

The inventors of the present invention discovered that luminal and basal subtyping of prostate cancer is prognostic and predicts response to androgen deprivation therapy. Prostate cancer subtypes useful in the methods of the present invention include, for example, luminal A, luminal B, and basal subtypes. Molecular subtyping is a method of classifying prostate cancers into one of multiple genetically-distinct categories, or subtypes. Each subtype responds differently to different kinds of treatments, and some subtypes indicate a higher risk of recurrence. Subtypes of the present invention may be used to predict outcomes such as distant metastasis-free survival (DMFS), biochemical recurrence-free survival (bRFS), prostate cancer specific survival (PCSS), and overall survival (OS). As described herein, each subtype has a unique molecular and clinical fingerprint. The subtyping methods described herein may be used to predict prostate cancer response to androgen deprivation therapy.

Differential expression analysis one or more of the targets listed in Table 8, Table 9 or SEQ ID NOs: 1-1029 allow for the identification of the molecular subtype of a prostate cancer.

In some instances, the molecular subtyping methods of the present invention are used in combination with other biomarkers, like tumor grade and hormone levels, for analyzing the prostate cancer.

Clinical Associations and Patient Outcomes

Molecular subtypes of the present invention have distinct clinical associations. Clinical associations that correlate to molecular subtypes include, for example, preoperative serum PSA, Gleason score (GS), extraprostatic extension (EPE), surgical margin status (SM), lymph node involvement (LNI), and seminal vesicle invasion (SVI).

In some embodiments, molecular subtypes of the present invention are used to predict patient outcomes such as biochemical recurrence (BCR), metastasis (MET) and prostate cancer death (PCSM) after radical prostatectomy. In other embodiments, molecular subtypes of the present invention are used to predict patient outcomes such as distant metastasis-free survival (DMFS), biochemical recurrence-free survival (bRFS), prostate cancer specific survival (PCSS), and overall survival (OS).

Treatment Response Prediction

In some embodiments, the molecular subtypes of the present invention are useful for predicting response to Androgen Deprivation Therapy (ADT) following radical prostatectomy. Androgen deprivation therapy (ADT), also called androgen suppression therapy, is an antihormone therapy whose main use is in treating prostate cancer. Prostate cancer cells usually require androgen hormones, such as testosterone, to grow. ADT reduces the levels of androgen hormones, with drugs or surgery, to prevent the prostate cancer cells from growing. The pharmaceutical approaches include antiandrogens and chemical castration.

In other embodiments, the molecular subtypes of the present invention are useful for predicting response to Radiation Therapy (RT) following radical prostatectomy.

EXAMPLES

Example 1

A Genetic Classifier (PAM50) to Identify Subtypes in Prostate Cancer and Predict Response to Therapy A genetic signature (PAM50) to identify subtypes in prostate cancer tissue and predict response to therapy was developed as follows. Affymetrix Human Exon 1.0 ST microarray (Affymetrix, Santa Clara, CA) data from formalin-fixed paraffin-embedded radical prostatectomy samples were obtained from six published retrospective patient cohorts (n=1,567) and one prospective cohort (n=2,215) for a total of 3,782 samples. Retrospective cohorts were from the Mayo Clinic (MC I and II), Cleveland Clinic (CC), Johns Hopkins University (JHU), Thomas Jefferson University (TJU), and Durham VA (DVA). Data collection was approved and supervised by local institutional review boards (IRB). 2,215 de-identified, anonymized, and prospectively-collected patients from clinical use of the Decipher test were obtained from Decipher GRID™ (ClinicalTrials.gov ID: NCT02609269). Clinical outcomes were not available for Decipher GRID. Informed consent and IRB approval for Decipher GRID were obtained. Microarray processing was performed in a CLIA-certified clinical operations laboratory (GenomeDx Biosciences, Inc, San Diego, CA). Microarrays were normalized using Single Channel Array Normalization. (Piccolo et al. *Genomics.* 2012; 100(6):337-344)

PAM50 Clustering

PAM50 clustering was performed based on the original algorithm from Parker et al. *J Clin Oncol.* 2009; 27(8):1160-1167. Source code was downloaded from [https://genome.unc.edu/pubsup/breastGEO/] and used without modification. Gene expression data were median-centered in each cohort individually as required by the PAM50 algorithm. The normal-like subtype was excluded as the prostate cancer samples were macro-dissected limiting the amount of normal tissue present in our data. The HER2 subtype was also excluded given the lack of HER2 amplification in prostate cancer (Ullen et al. *Acta Oncol.* 2005; 44(5):490-495). Assignment of subtype in the prostate cancer samples was thus assigned by the greatest correlation with luminal A, luminal B, or basal.

Clinical Endpoints

All primary and secondary endpoints were preplanned The primary clinical endpoint was distant metastasis-free survival (DMFS), with secondary clinical endpoints of biochemical recurrence-free survival (BRFS), prostate cancer specific survival (PCSS), and overall survival (OS). All endpoints were defined from time of surgery until time of the event, death, or last follow-up.

Gene Set Enrichment Analysis

Functional and biological analyses of the PAM50 subtypes in prostate cancer were investigated using Gene Set Enrichment Analysis (GSEA). First, a T-test was performed on every gene comparing expression in the specified subtype vs. not in that subtype. The T-statistic was used to generate a pre-ranked list which was input into GSEA.

Matched Cohort Design and Predicting Response to ADT

To investigate if subtype could predict ADT response, a matched cohort with 2:1 matching for ADT untreated and treated patients was created from the MCI and MCII cohorts in order to select patients from a single institution with a mix of post-operatively treated and untreated patients. This resulted in a cohort of 315 patients, 210 of which did not receive any ADT, and 105 which received ADT treatment. The decision to perform 2:1 matching was to maximize sample size using patients only from the MC cohorts. We chose to only include patients from the MC cohorts for this analysis because patients in these cohorts received a mix of adjuvant and salvage ADT and RT, allowing us to account for the effects of both in our models. JHMI patients did not receive any post-operative treatment. CCF patients did not receive adjuvant treatment, and information about salvage ADT treatment was unavailable in the dataset. All TJU and DVA patients were treated with radiation. We defined androgen deprivation therapy (ADT) as treatment (with LHRH agonist alone or in combination with androgen receptor antagonists) after radical prostatectomy but before the primary endpoint of metastasis. Matching was performed based on Gleason, prostate specific antigen (PSA, ng/mL), positive surgical margins (SM), extracapsular extension (ECE), seminal vesicle invasion (SVI), lymph node invasion (LNI), as well as post-operative radiation therapy (RT). Data on the duration and dose of ADT were not available. Table 7 provides details of which patients in this matched cohort received adjuvant, salvage, or both ADT and/or RT. Nearly all lymph node positive patients from the MC cohorts received ADT, as well as some who received ADT for other reasons at the treating physicians' discretion.

TABLE 7

Number of patients receiving ADT and RT in the matched cohort (n = 315)

| | Adjuvant ADT Only | Salvage ADT Only | Both Adjuvant and Salvage ADT | No ADT |
|---|---|---|---|---|
| Adjuvant RT Only | 4 | 6 | 2 | 23 |
| Salvage RT Only | 3 | 14 | 2 | 41 |
| Both Adjuvant and Salvage RT | 1 | 0 | 0 | 0 |
| No RT | 18 | 53 | 2 | 146 |

Abbreviations:
ADT: Androgen deprivation therapy;
RT: Radiation therapy

Statistical Analysis

In the demographics tables, ANOVA and Chi-squared test were used to evaluate differences between continuous and categorical variables, respectively, between patient groups. Kaplan-Meier curves were generated by pooling clinical data from all available microarray cohorts. Gleason score was stratified into low (<7), intermediate (7), and high risk (8-10). PSA was stratified into low (<10 ng/mL), intermediate (10-20 ng/mL), and high risk (>20 ng/mL) in a similar manner SM, ECE, SVI, and LNI were considered binary variables and defined by the respective institutions. Cox regression was used for both univariable and multivariable analysis (UVA/MVA). Stratification by cohort was used when performing UVA/MVA analyses to account for baseline differences between cohorts. The interaction term for treatment and subtype in a Cox model was used to evaluate prediction of treatment response, and a significant interaction Wald test p-value indicated that a subtype could predict response to ADT. Statistical significance was set as a two-tailed p-value <0.05. All statistical analyses were performed in R 3.1.2.

Microarray Data Accession

Microarray data is available on Gene Expression Omnibus with accession numbers GSE46691, GSE62116, GSE72291, GSE62667, GSE79956, GSE79957, and GSE79915. Subtyping target sequences (SEQ ID NOs 1-1029) are shown in Table 8.

Results

Figure 5:
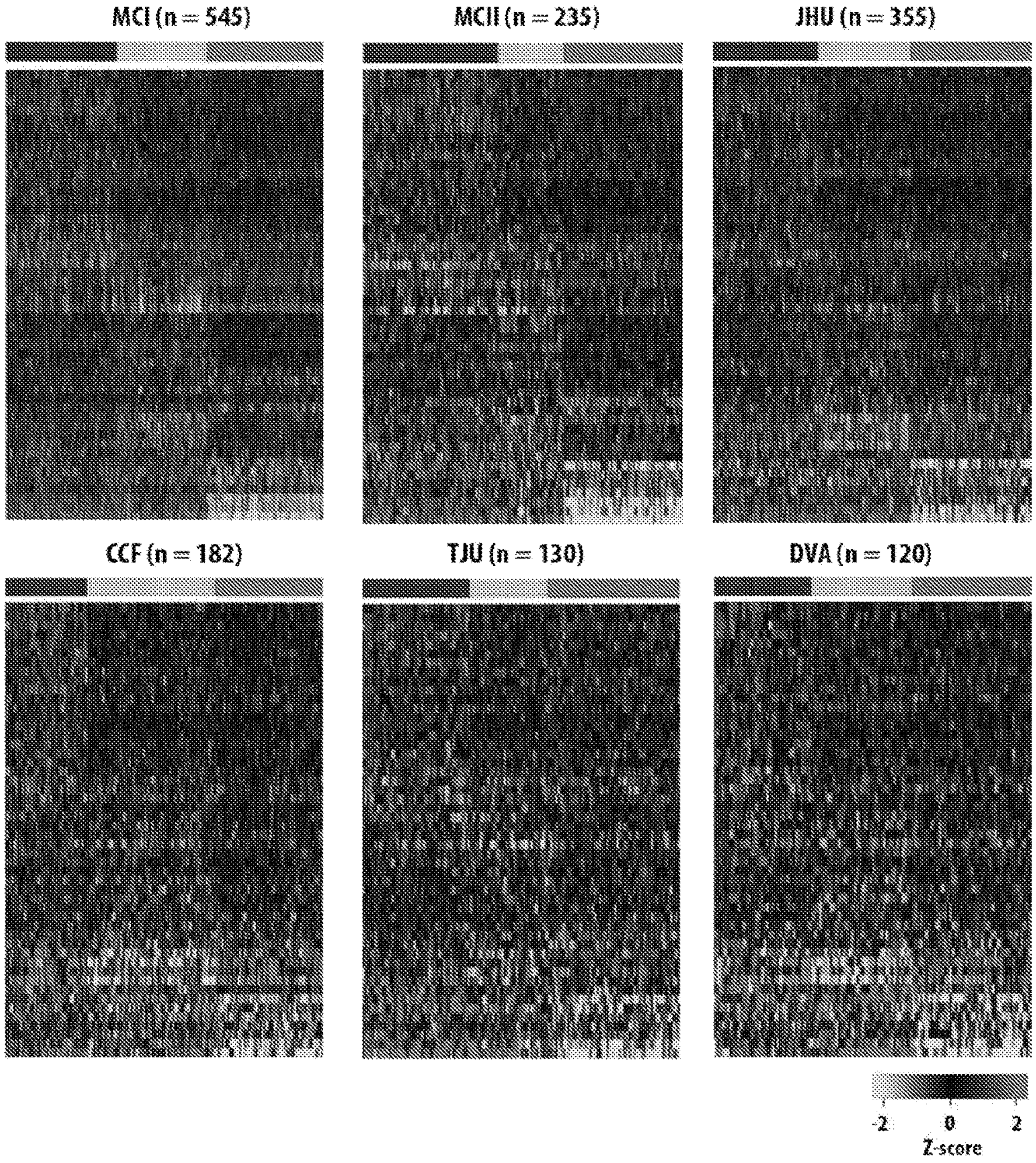
FIG. 5 sets forth data showing Heatmaps depicting the PAM50 subtypes (each column represents a sample, each row represents a gene, dark blue=Luminal A, light blue=Luminal B, red=Basal) with genes in the same order as shown in FIG. 1A.
Figure 6:
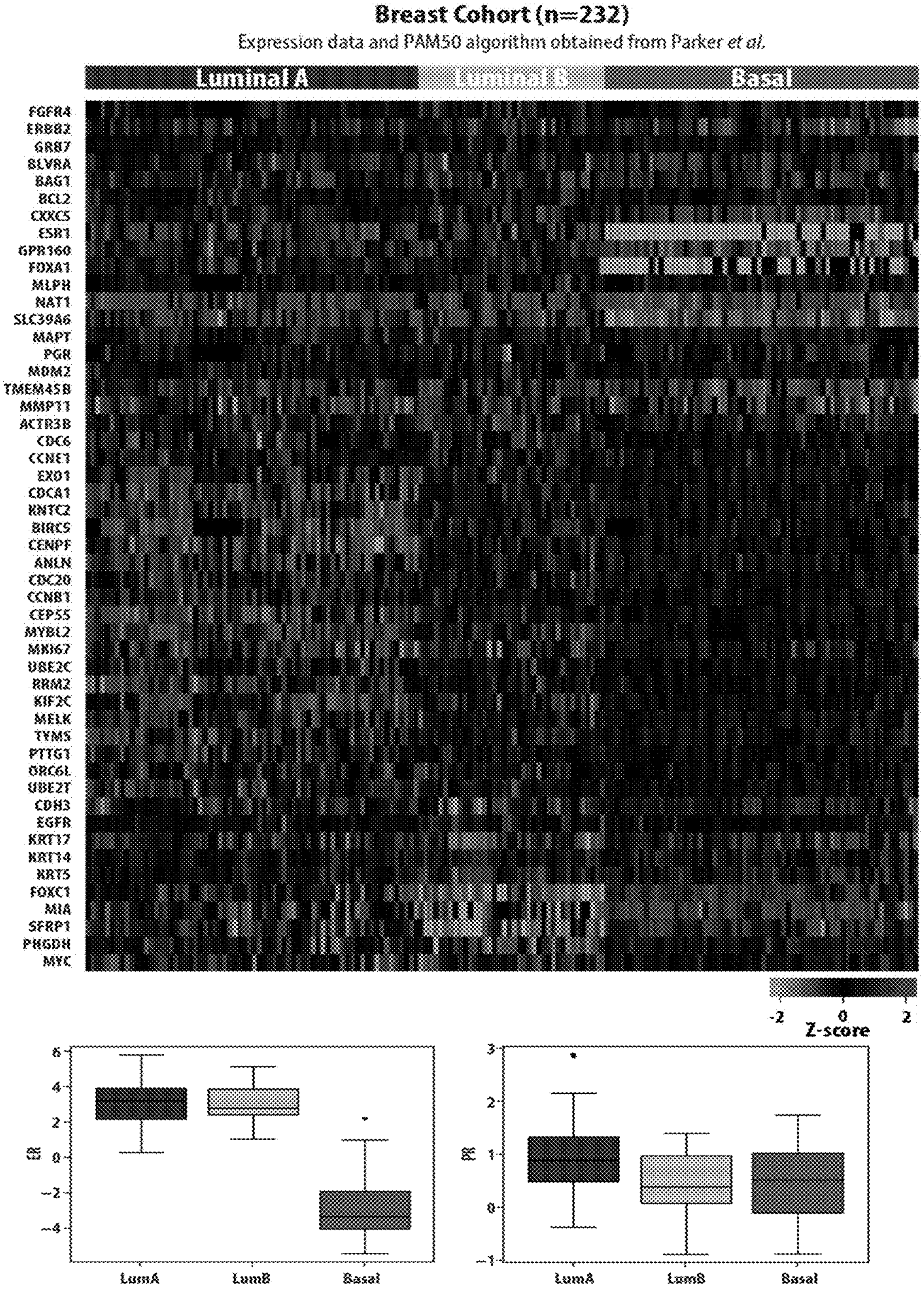
FIG. 6 sets forth data showing differences in genetic signatures for breast and prostate cancer for the markers of a genomic classifier of the present invention. A heatmap of the PAM50 clusters in the breast cohort from Parker et al. are shown for basal, luminal A, and luminal B. Boxplots demonstrate that in breast cancer, ER is higher in luminal versus basal, and that PR is highest in luminal A. A heatmap of the PAM50 clusters in prostate cancer is shown (MCI, II, CC, TJU, JHU, DVA) with the same order of genes as displayed for the breast cancer data. Boxplots show that ER does not demonstrate the same differences between luminal and basal as in breast, but PR does show lower expression in luminal B compared to luminal A as in breast cancer.
Figure 6:
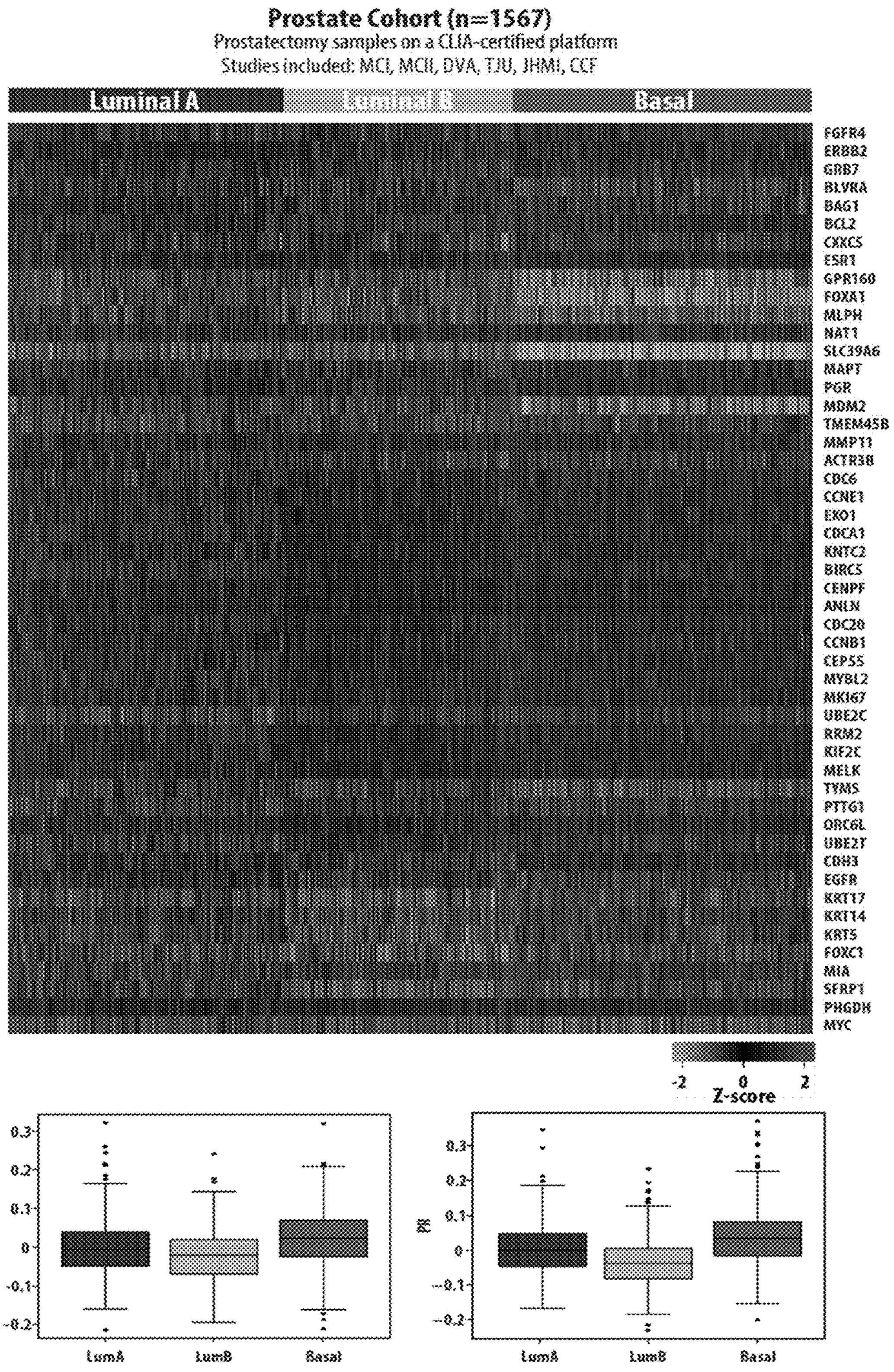

To subtype prostate cancers into luminal-like vs. basal-like subtypes, we applied the PAM50 classifier on 1,567 prostate cancer samples with a median clinical follow-up time of 10 years. 34.3% of samples are classified as luminal A, 28.5% as luminal B, and 37.1% as basal, with visually similar patterns of expression across all six independent cohorts (FIG. 1A, FIG. 5, Table 2). PAM50 expression patterns are also similar between breast and prostate cancer samples (FIG. 6). Notably, ER and PR, which are highest in luminal and luminal A breast cancer, respectively[8], do not demonstrate the same patterns in prostate cancer (FIG. 6).

Figure 1B:
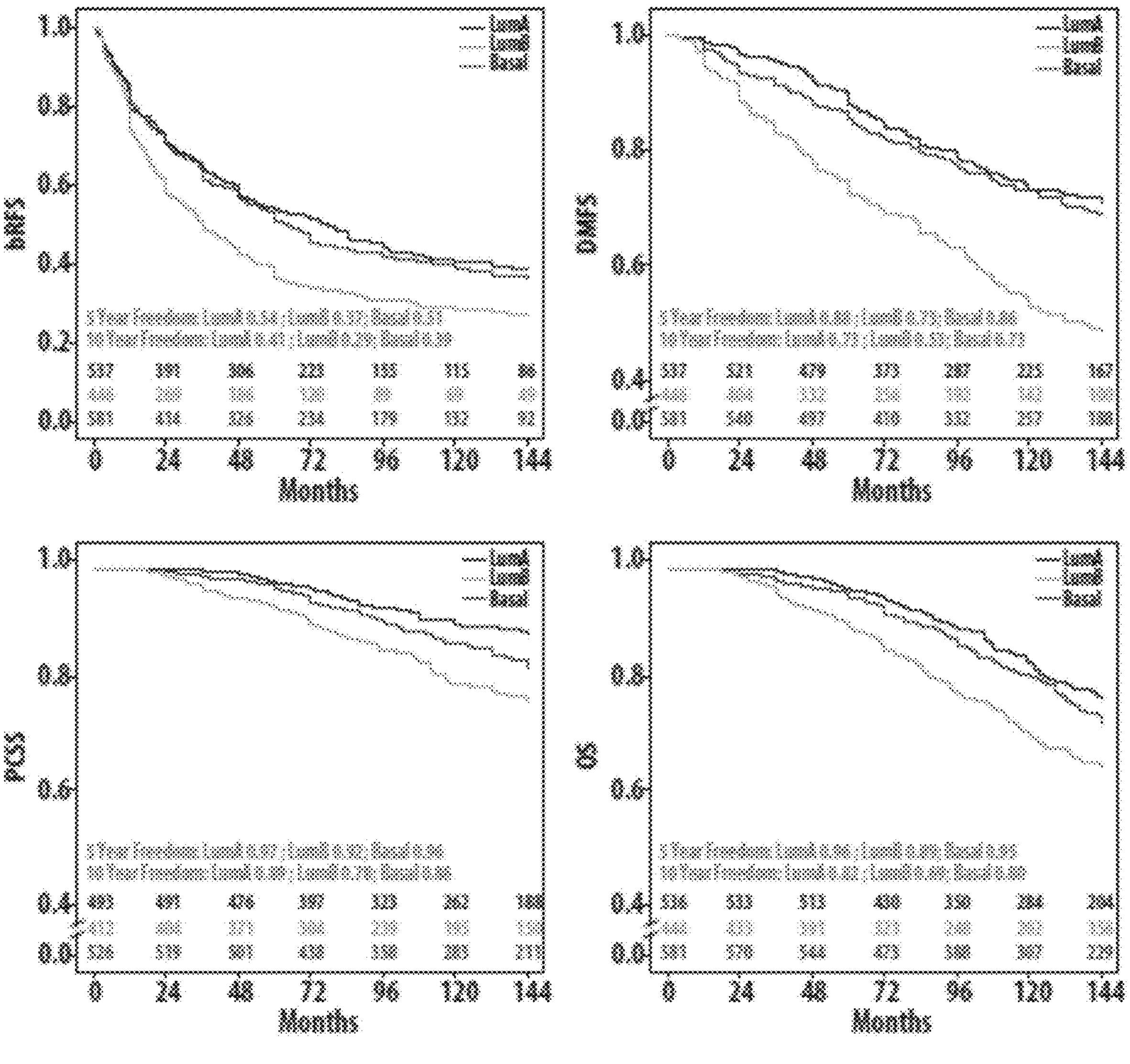

We next examined associations of luminal A, luminal B, and basal subtypes with clinical outcomes. Luminal B patients consistently have significantly worse outcomes for all endpoints compared to luminal A and basal subtypes (FIG. 1B). The 10-year actuarial rates for bRFS are 29% for luminal B compared to 41% and 39% for luminal A and basal, respectively; for DMFS, 53% for luminal B compared to 73% for both other subtypes; for PCSS, 78% for luminal B compared to 89% and 86% for luminal A and basal; and for OS, 69% for luminal B versus 82% and 80% for luminal A and basal.

On univariable Cox analysis (Table 1, Table 3), basal and luminal A have improved bRFS, DMFS, PCSS, and OS compared to luminal B (bRFS: basal (vs. luminal B) p<0.0001, HR=0.69 [0.59-0.81], luminal A p<0.0001, HR=0.66 [0.57-0.78]; DMFS: basal p<0.0001, HR=0.5 [0.4-0.61], luminal A p<0.0001, HR=0.42 [0.34-0.53]; PCSS: basal p=0.0003, HR=0.59 [0.44-0.79], luminal A p<0.0001, HR=0.38 [0.27-0.53]; OS basal p=0.0005, HR=0.69 [0.56-0.85], luminal A p<0.0001, HR=0.56 [0.45-0.7]). However, luminal A does not exhibit significantly different bRFS (p=0.61, HR=1.04 [0.89-1.22]) and DMFS (p=0.18, HR=1.17 [0.93-1.49]) versus basal. Luminal A does demonstrate worse PCSS (p=0.01, HR=1.54 [1.09-2.16]) and OS (p=0.05, HR=1.25 [1-1.55]) compared to basal, though this is difficult to interpret in the setting of non-significant differences in metastasis and biochemical recurrence. Consistent with our data demonstrating that luminal B patients have the worst clinical outcomes, luminal B patients also have the highest pre-operative PSA levels, Gleason score, and rates of ECE and LNI, followed by basal and then luminal A (Table 2). On multivariable analysis (Table 1, Table 3), adjusting for clinicopathologic variables (age, PSA, Gleason score, SM, ECE, SVI, and LNI), basal and luminal A have significantly better independent prognosis than luminal B for bRFS (basal vs. luminal B: p=0.01, HR=0.81 [0.69-0.96]; luminal A vs. luminal B: p=0.005, HR=0.79 [0.66-0.93]) and DMFS (basal vs. luminal B: p=0.0002, HR=0.66 [0.53-0.82]; luminal A vs. luminal B: p<0.0001, HR=0.55 [0.43-0.69]). Luminal A also has significantly improved outcomes compared to luminal B for PCSS (p<0.0001, HR=0.50 [0.35-0.71]) and OS (p=0.002, HR=0.69 [0.55-0.87]). To provide comparison to a composite clinical classifier, we similarly show that basal and luminal A have significantly better prognosis than luminal B for all endpoints on multivariable analysis adjusting for age, LNI, and the assessment by risk using the D'Amico classifier (D'Amico et al. *JAMA.* 1998; 280(11):969-974) (See Table 4).

TABLE 1

Univariable and Multivariable Analysis

| | | UVA | | MVA | |
|---|---|---|---|---|---|
| | | P-value | HR [95% CI] | P-value | HR [95% CI] |
| DMFS | Age (yrs) | 0.88 | 1 [0.99-1.02] | 0.15 | 0.99 [0.98-1] |
| | PSA 10-20 vs. <10 | 0.64 | 1.05 [0.85-1.31] | 0.29 | 0.89 [0.71-1.11] |
| | PSA >20 vs. <10 | 3.8E−03 | 1.42 [1.12-1.79] | 0.16 | 0.83 [0.64-1.08] |
| | Gleason 7 vs. <7 | 8.4E−05 | 4.57 [2.14-9.73] | 1.3E−03 | 3.49 [1.63-7.47] |
| | Gleason 8-10 vs. <7 | 4.0E−12 | 14.32 [6.75-30.37] | 2.4E−08 | 8.8 [4.1-18.88] |
| | SMS | 0.08 | 1.18 [0.98-1.42] | 0.74 | 1.03 [0.85-1.25] |
| | SVI | 0.0E+00 | 2.57 [2.14-3.08] | 3.5E−07 | 1.72 [1.39-2.11] |
| | ECE | 3.7E−12 | 2.04 [1.67-2.5] | 0.07 | 1.23 [0.99-1.54] |
| | LNI | 0.0E+00 | 2.56 [2.06-3.19] | 0.01 | 1.39 [1.09-1.78] |
| | Basal vs. LumB | 9.0E−11 | 0.5 [0.4-0.61] | 2.0E−04 | 0.66 [0.53-0.82] |
| | LumA vs. LumB | 9.1E−14 | 0.42 [0.34-0.53] | 5.4E−07 | 0.55 [0.43-0.69] |
| PCSS | Age (yrs) | 0.86 | 1 [0.98-1.02] | 0.24 | 0.99 [0.97-1.01] |
| | PSA 10-20 vs. <10 | 0.79 | 1.04 [0.76-1.42] | 0.16 | 0.8 [0.58-1.09] |
| | PSA >20 vs. <10 | 0.07 | 1.35 [0.97-1.86] | 0.01 | 0.62 [0.43-0.89] |
| | Gleason 7 vs. <7 | 0.02 | 3.35 [1.22-9.19] | 0.06 | 2.7 [0.98-7.46] |
| | Gleason 8-10 vs. <7 | 2.4E−07 | 13.76 [5.08-37.23] | 3.1E−05 | 8.6 [3.12-23.68] |
| | SMS | 9.3E−04 | 1.56 [1.2-2.02] | 0.11 | 1.25 [0.95-1.64] |
| | SVI | 0.0E+00 | 3.15 [2.43-4.08] | 2.0E−06 | 2.06 [1.53-2.78] |
| | ECE | 5.1E−08 | 2.22 [1.67-2.96] | 0.29 | 1.19 [0.87-1.63] |
| | LNI | 2.2E−15 | 3.19 [2.4-4.25] | 4.7E−03 | 1.6 [1.15-2.21] |
| | Basal vs. LumB | 3.4E−04 | 0.59 [0.44-0.79] | 0.21 | 0.83 [0.61-1.12] |
| | LumA vs. LumB | 1.8E−08 | 0.38 [0.27-0.53] | 8.1E−05 | 0.5 [0.35-0.71] |

Abbreviations:
PSA: prostate specific antigen,
SMS: positive surgical margin status,
ECE: extracapsular extension,
SVI: seminal vesicle invasion,
LNI: lymph node invasion,
DMFS: distant metastasis-free survival,
PCSS: prostate cancer-specific survival.

TABLE 2

Demographics for pooled retrospective cohort (n = 1,567)

| | | Basal (n = 582) | Luminal A (n = 538) | Luminal B (n = 447) | Total (n = 1567) | P-value |
|---|---|---|---|---|---|---|
| Age (years) | | 62.4 +/− 6.98 | 62.5 +/− 6.71 | 62.4 +/− 6.92 | 62.4 +/− 6.87 | 0.975 |
| | NA | 1 (0.002) | 1 (0.002) | 1 (0.002) | 3 (0.002) | |
| PSA | <10 | 351 (0.603) | 318 (0.591) | 238 (0.532) | 907 (0.579) | 0.002 |
| (ng/dL) | 10 to 20 | 131 (0.225) | 145 (0.27) | 113 (0.253) | 389 (0.248) | |
| | >20 | 87 (0.149) | 64 (0.119) | 92 (0.206) | 243 (0.155) | |
| | NA | 13 (0.022) | 11 (0.02) | 4 (0.009) | 28 (0.018) | |
| Gleason | <6 | 68 (0.117) | 53 (0.099) | 23 (0.051) | 144 (0.092) | <0.0001 |
| | 7 | 328 (0.564) | 335 (0.623) | 218 (0.488) | 884 (0.562) | |
| | 8 to 10 | 184 (0.316) | 149 (0.277) | 205 (0.459) | 538 (0.343) | |
| | NA | 2 (0.003) | 1 (0.002) | 1 (0.002) | 4 (0.003) | |
| SM | No | 297 (0.51) | 261 (0.485) | 214 (0.479) | 772 (0.493) | 0.554 |
| | Yes | 284 (0.488) | 276 (0.513) | 232 (0.519) | 792 (0.505) | |
| | NA | 1 (0.002) | 1 (0.002) | 1 (0.002) | 3 (0.002) | |
| SVI | No | 427 (0.734) | 388 (0.721) | 300 (0.671) | 1115 (0.712) | 0.077 |
| | Yes | 153 (0.263) | 148 (0.275) | 145 (0.324) | 446 (0.285) | |
| | NA | 2 (0.003) | 2 (0.004) | 2 (0.004) | 6 (0.004) | |
| ECE | No | 272 (0.467) | 259 (0.481) | 147 (0.329) | 678 (0.433) | <0.0001 |
| | Yes | 306 (0.526) | 278 (0.517) | 298 (0.667) | 882 (0.563) | |
| | NA | 4 (0.007) | 1 (0.002) | 2 (0.004) | 7 (0.004) | |
| LNI | No | 524 (0.9) | 486 (0.903) | 383 (0.857) | 1393 (0.889) | 0.032 |
| | Yes | 57 (0.098) | 50 (0.093) | 63 (0.141) | 170 (0.108) | |
| | NA | 1 (0.002) | 2 (0.004) | 1 (0.002) | 4 (0.003) | |

Abbreviations: PSA: prostate specific antigen, SM: positive surgical margins, SVI: seminal vesicle invasion, ECE: extracapsular extension, LNI: lymph node invasion.

TABLE 3

Univariable and multivariable analysis in pooled retrospective cohort (n = 1,567)

| | | UVA | | MVA | |
|---|---|---|---|---|---|
| | | P-value | HR [95% CI] | P-value | HR [95% CI] |
| bRFS | Age (yrs) | 0.36 | 1 [0.99-1.01] | 0.97 | 1 [0.99-1.01] |
| | PSA 10-20 vs. <10 | 0.13 | 1.13 [0.97-1.32] | 0.59 | 1.04 [0.89-1.22] |
| | PSA >20vs. <10 | 8.7E−06 | 1.49 [1.25-1.77] | 0.13 | 1.16 [0.96-1.4] |
| | Gleason 7 vs. <7 | 0.12 | 1.23 [0.95-1.61] | 0.89 | 1.02 [0.77-1.34] |
| | Gleason 8-10 vs. <7 | 3.0E−11 | 2.49 [1.9-3.27] | 3.9E−05 | 1.83 [1.37-2.43] |
| | SM | 1.2E−04 | 1.31 [1.14-1.5] | 0.03 | 1.17 [1.01-1.35] |
| | SVI | 0.0E+00 | 2.01 [1.75-2.31] | 4.5E−10 | 1.65 [1.41-1.93] |
| | ECE | 1.6E−09 | 1.51 [1.32-1.73] | 0.10 | 1.13 [0.98-1.31] |
| | LNI | 4.3E−05 | 1.49 [1.23-1.8] | 0.21 | 0.87 [0.71-1.08] |
| | Basal vs. LumB | 3.2E−06 | 0.69 [0.59-0.81] | 0.01 | 0.81 [0.69-0.96] |
| | LumA vs. LumB | 5.4E−07 | 0.66 [0.57-0.78] | 4.8E−03 | 0.79 [0.66-0.93] |
| OS | Age (yrs) | 7.6E−05 | 1.03 [1.01-1.04] | 0.01 | 1.02 [1-1.03] |
| | PSA 10-20 vs. <10 | 0.62 | 1.06 [0.85-1.31] | 0.20 | 0.87 [0.7-1.08] |
| | PSA >20vs. <10 | 0.01 | 1.35 [1.08-1.69] | 0.15 | 0.83 [0.65-1.07] |
| | Gleason 7 vs. <7 | 1.1E−03 | 1.98 [1.32-2.98] | 0.02 | 1.69 [1.11-2.59] |
| | Gleason 8-10 vs. <7 | 1.1E−14 | 5.01 [3.33-7.53] | 5.2E−09 | 3.65 [2.36-5.63] |
| | SM | 2.4E−03 | 1.32 [1.1-1.59] | 0.06 | 1.2 [1-1.45] |
| | SVI | 1.2E−13 | 1.96 [1.64-2.33] | 1.7E−04 | 1.49 [1.21-1.83] |
| | ECE | 1.2E−07 | 1.66 [1.38-2.01] | 0.34 | 1.11 [0.9-1.37] |
| | LNI | 6.0E−10 | 2.1 [1.66-2.65] | 0.03 | 1.33 [1.02-1.72] |

TABLE 3-continued

Univariable and multivariable analysis in pooled retrospective cohort (n = 1,567)

| | UVA | | MVA | |
|---|---|---|---|---|
| | P-value | HR [95% CI] | P-value | HR [95% CI] |
| Basal vs. LumB | 5.1E−04 | 0.69 [0.56-0.85] | 0.24 | 0.88 [0.71-1.09] |
| LumA vs. LumB | 2.8E−07 | 0.56 [0.45-0.7] | 1.9E−03 | 0.69 [0.55-0.87] |

Abbreviations:
PSA: prostate specific antigen,
SM: positive surgical margins,
SVI: seminal vesicle invasion,
ECE: extracapsular extension,
LNI: lymph node invasion,
bRFS: biochemical recurrence-free survival,
OS: overall survival.

TABLE 4

Univariable and multivariable analysis in pooled retrospective cohort (n = 1,567) to examine independence of subtypes from D'Amico Risk Classification

| | | UVA | | MVA | |
|---|---|---|---|---|---|
| | | P-value | HR 1195% CI | P-value | HR 1195% CI |
| bRFS | Age | 0.36 | 1 [0.99-1.01] | 0.30 | 1.01 [0.99-1.02] |
| | D'Amico | 3.49E−10 | 1.87 [1.54-2.27] | 5.71E−08 | 1.73 [1.42-2.1] |
| | LNI | 4.32E−05 | 1.49 [1.23-1.8] | 2.66E−15 | 3.46 [2.55-4.71] |
| | Basal vs. LumB | 3.23E−06 | 0.69 [0.59-0.81] | 0.01 | 0.78 [0.65-0.93] |
| | LumA vs. LumB | 5.44E−07 | 0.66 [0.57-0.78] | 1.40E−03 | 0.74 [0.61-0.89] |
| DMFS | Age | 0.88 | 1 [0.99-1.02] | 0.30 | 1.01 [0.99-1.03] |
| | D'Amico | 3.71E−10 | 2.86 [2.06-3.97] | 7.89E−08 | 2.48 [1.78-3.46] |
| | LNI | 0.00 | 2.56 [2.06-3.19] | 6.78E−10 | 3.21 [2.22-4.65] |
| | Basal vs. LumB | 8.95E−11 | 0.5 [0.4-0.61] | 2.19E−06 | 0.54 [0.42-0.7] |
| | LumA vs. LumB | 9.14E−14 | 0.42 [0.34-0.53] | 8.53E−08 | 0.49 [0.38-0.64] |
| PCSS | Age | 0.86 | 1 [0.98-1.02] | 0.31 | 1.01 [0.99-1.04] |
| | D'Amico | 7.47E−06 | 3 [1.86-4.86] | 6.06E−05 | 2.7 [1.66-4.4] |
| | LNI | 2.22E−15 | 3.19 [2.4-4.25] | 5.72E−04 | 2.71 [1.54-4.78] |
| | Basal vs. LumB | 3.40E−04 | 0.59 [0.44-0.79] | 0.06 | 0.71 [0.5-1.01] |
| | LumA vs. LumB | 1.84E−08 | 0.38 [0.27-0.53] | 7.95E−05 | 0.45 [0.3-0.67] |
| OS | Age | 7.62E−05 | 1.03 [1.01-1.04] | 1.09E−05 | 1.04 [1.02-1.06] |
| | D'Amico | 2.63E−06 | 1.98 [1.49-2.63] | 3.12E−05 | 1.85 [1.38-2.46] |
| | LNI | 6.02E−10 | 2.1 [1.66-2.65] | 2.28E−03 | 2.22 [1.33-3.71] |
| | Basal vs. LumB | 5.09E−04 | 0.69 [0.56-0.85] | 0.17 | 0.84 [0.66-1.08] |
| | LumA vs. LumB | 2.77E−07 | 0.56 [0.45-0.7] | 4.23E−05 | 0.57 [0.43-0.74] |

Abbreviations:
LNI: lymph node invasion.
Note:
D'Amico high-risk was compared to intermediate and low risk combined, as there were only 19 low risk patients.

Figure 2:
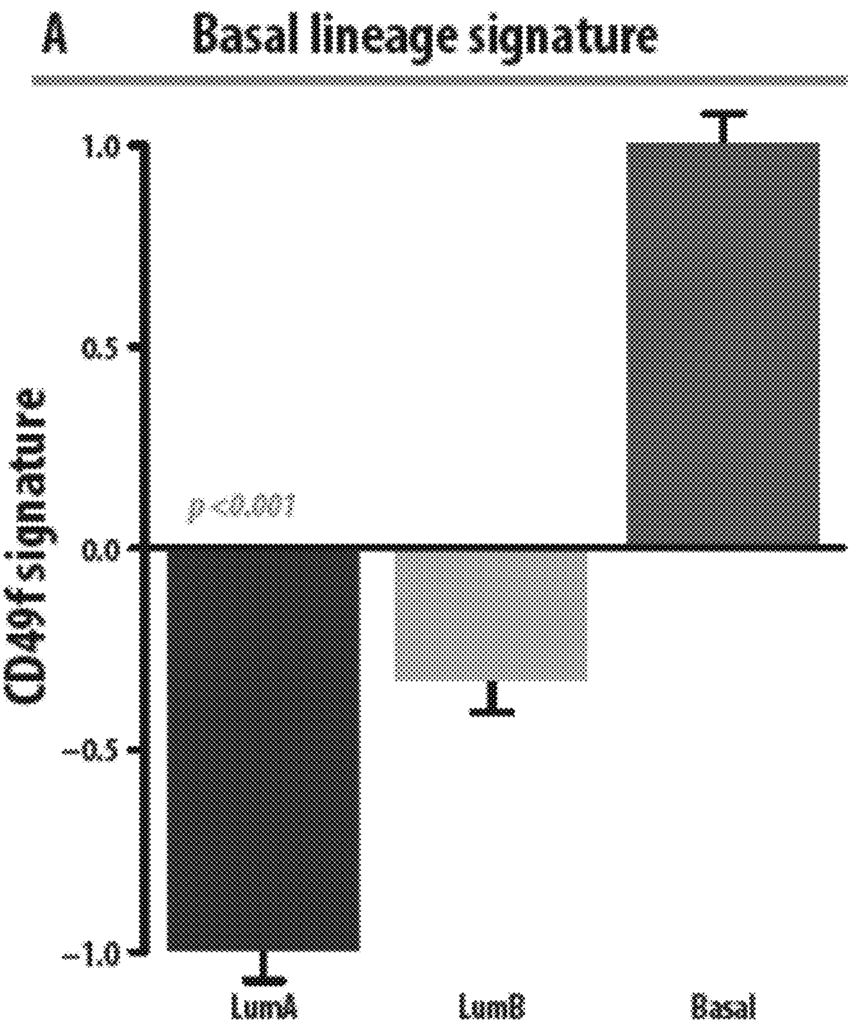
FIGS. 2A-2C set forth data showing basal and luminal subtypes are associated with basal and luminal lineage markers.
Figure 2:
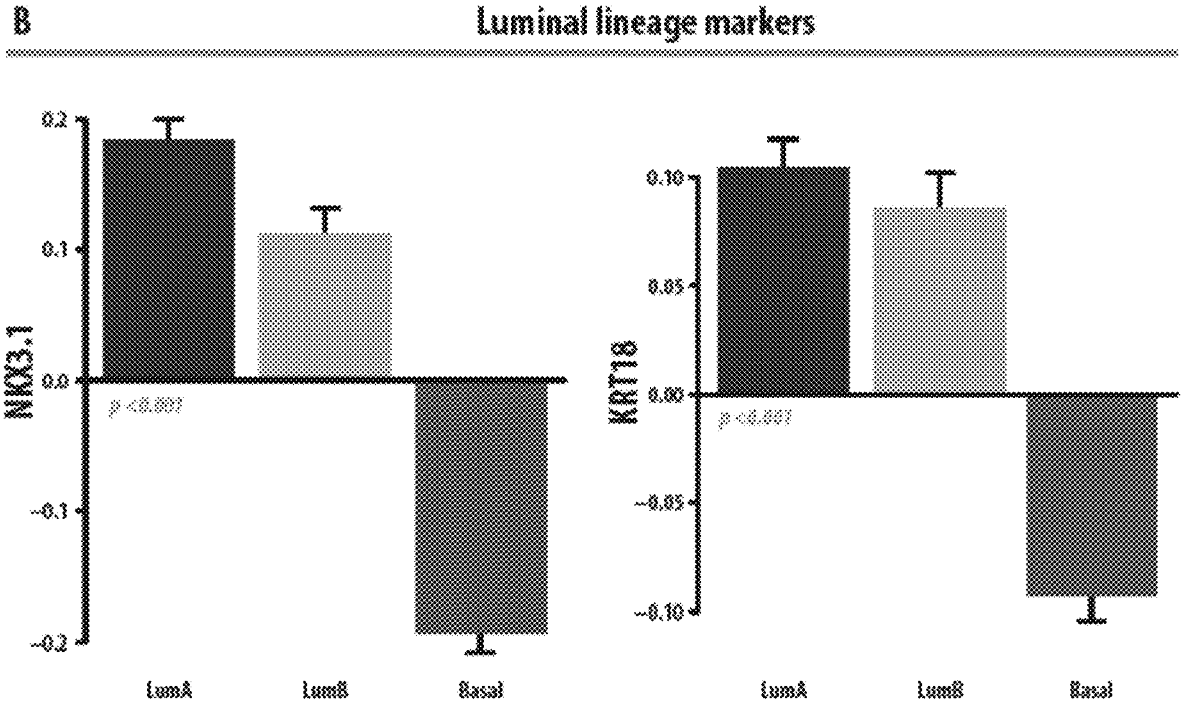
Figure 2:
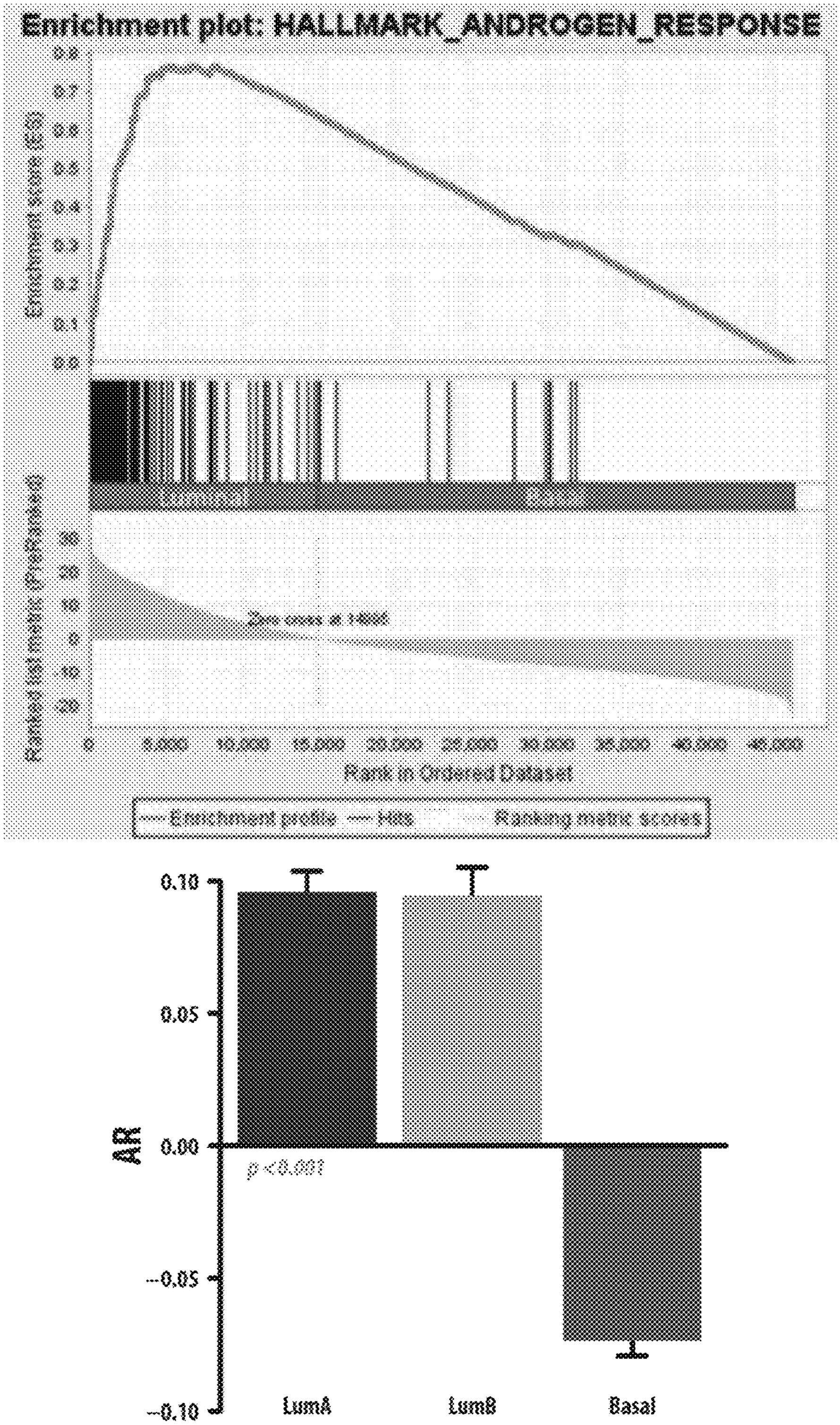
Figure 3A:
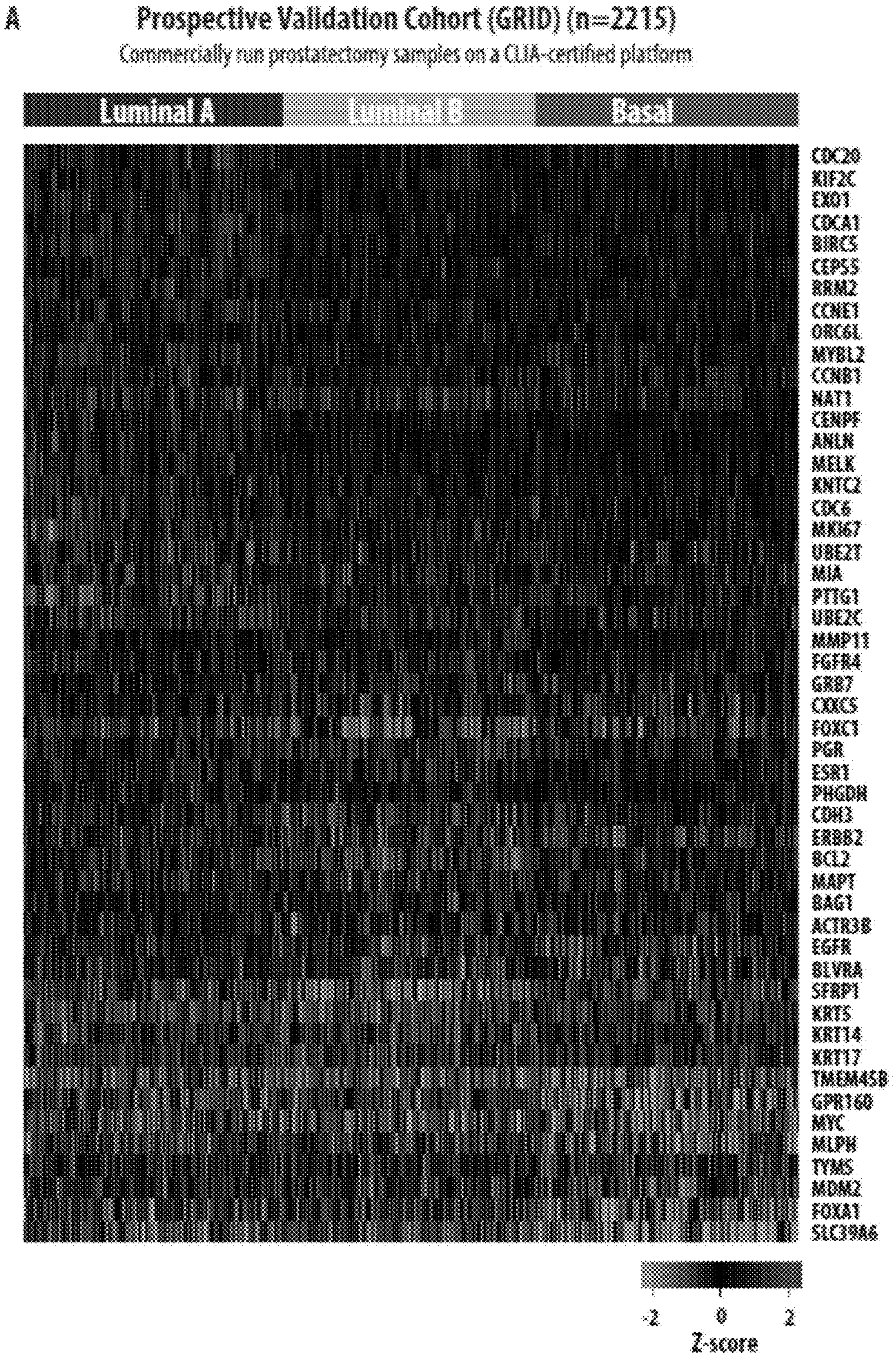
FIGS. 3A-3D set forth data showing Prospective validation in GRID. PAM50 clusters in a prospective validation cohort of 2215 prostate cancer samples run on a commercial clinical platform (A). AR expression increases in luminal samples (B), the basal lineage CD49f signature in the basal subtype (C), and NKX3-1 and KRT18 expression in the luminal subtypes (D). Bar-plots show the mean with standard error of median centered gene expression, and P-values are from ANOVA.
Figures 3B, 3C, 3D:
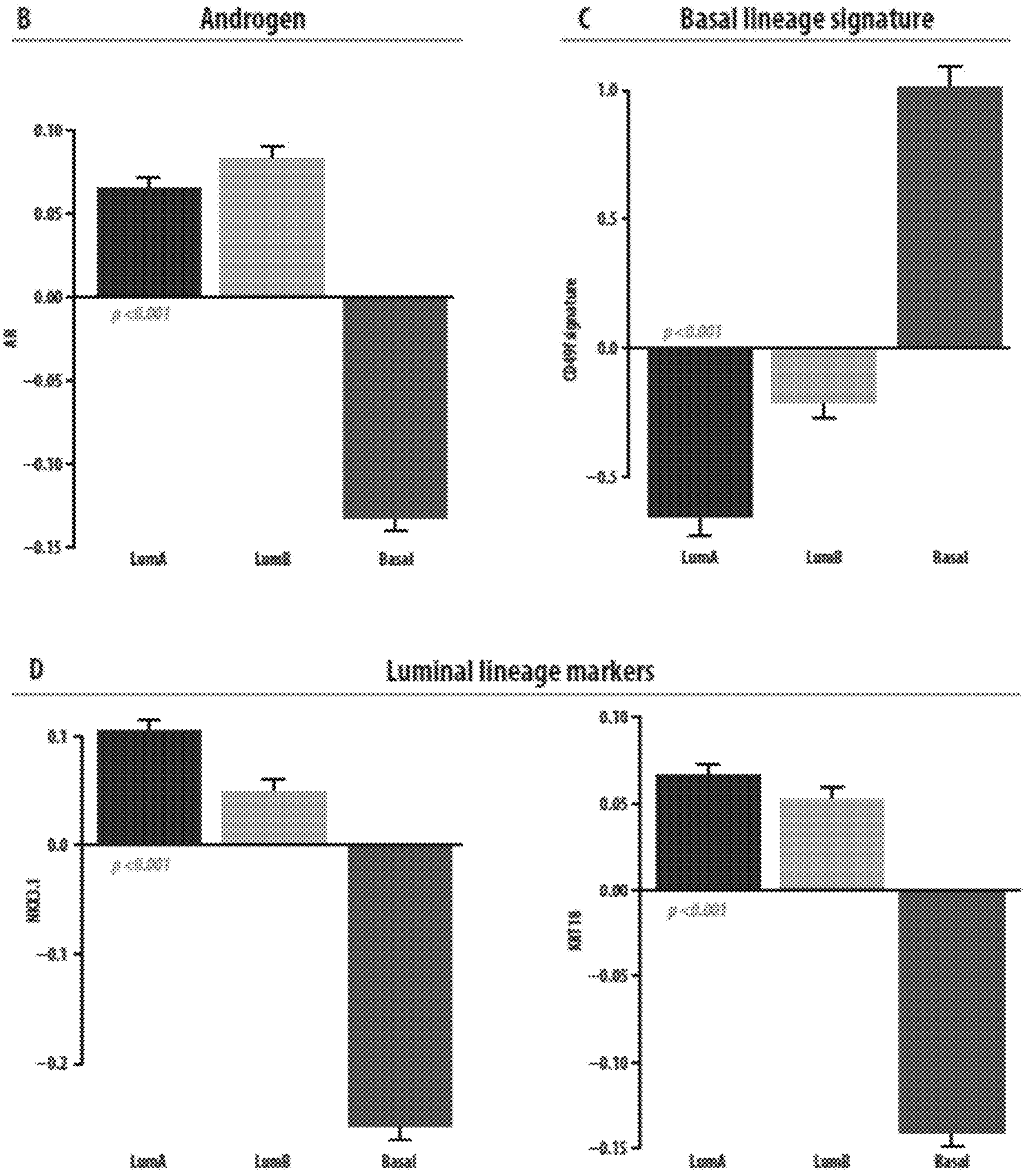

We then investigated the relationship between these subtypes and luminal and basal prostate cancer lineage markers. The basal lineage CD49f signature (Smith et al. *Proc Natl Acad Sci USA.* 2015; 112(47):E6544-6552) is increased in basal-like samples (ANOVA p<0.001, FIG. 2A). Concordantly, the luminal markers NKX3.1, KRT18, and AR are increased in luminal-like samples (ANOVA p<0.001, FIG. 2B-C). Consistent with our findings for AR, the androgen activity pathway is enriched in luminal compared to basal (ANOVA p<0.001, FIG. 2C). Examining the top GSEA hallmark concepts comparing luminal to basal (Supplementary Methods) reveals that the MYC pathway is the top enriched pathway in luminal-like samples, and genes down-regulated by KRAS are the top positive pathway in basal-like samples (negatively enriched in luminal samples). These results are concordant with MYC and KRAS expression, which are both increased in luminal-like samples (ANOVA p<0.001, FIG. 7). Upon observing that proliferation genes such as MKI67 are low in luminal A (FIG. 1A), we formally examined the subtypes using the PAM50 proliferation score (Parker et al. *J Clin Oncol.* 2009; 27(8): 1160-1167). Luminal A has a lower proliferation score than luminal B and basal (p<0.001, FIG. 8), which may explain the divergent clinical outcomes despite the biological similarities between luminal A and B.

Figure 7:
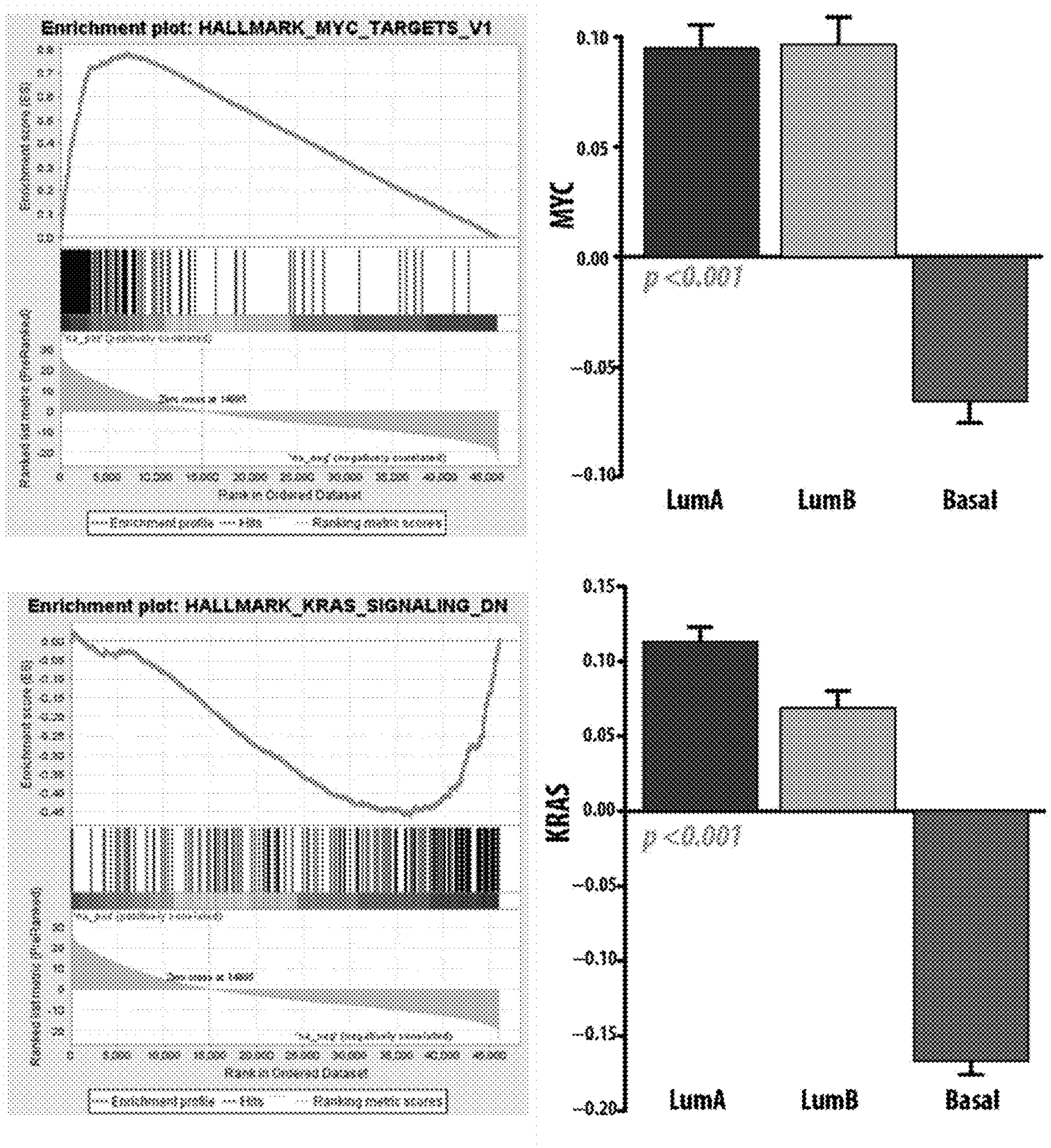
FIG. 7 sets forth data showing luminal subtypes are associated with MYC and KRAS.
Figure 7:
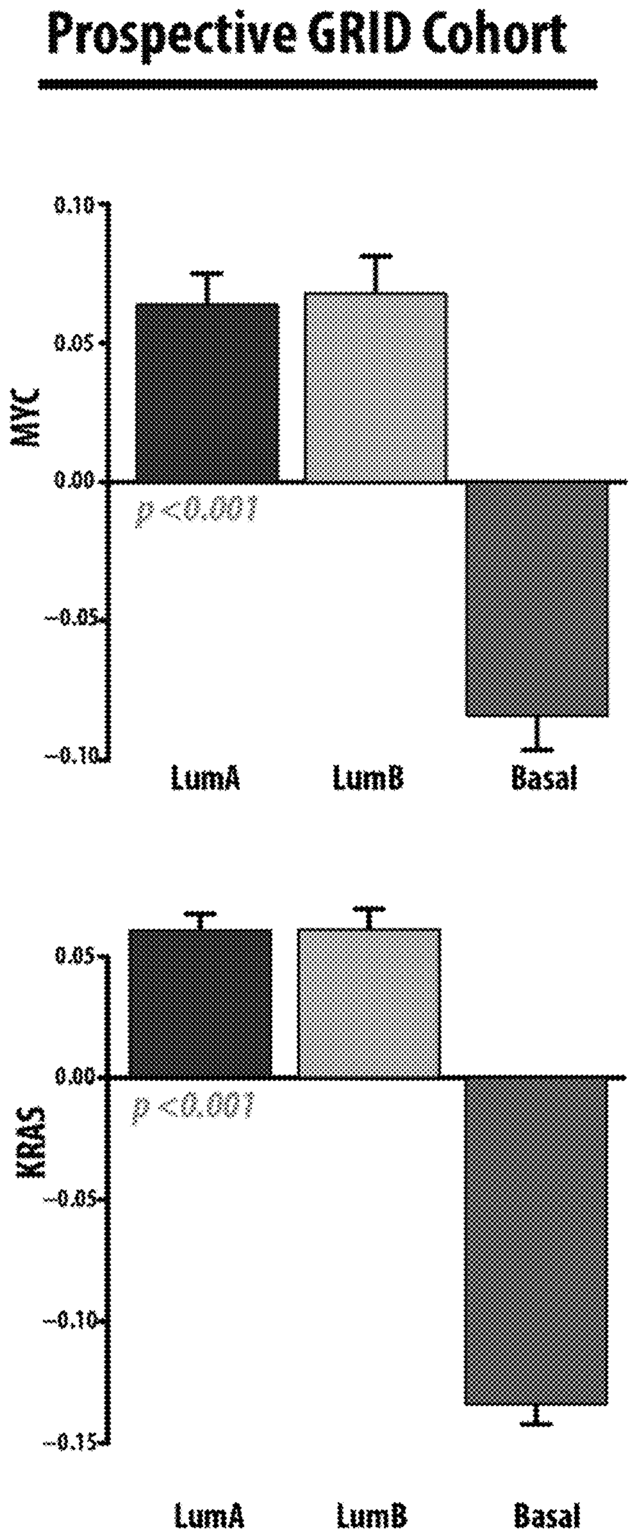
Figure 8:
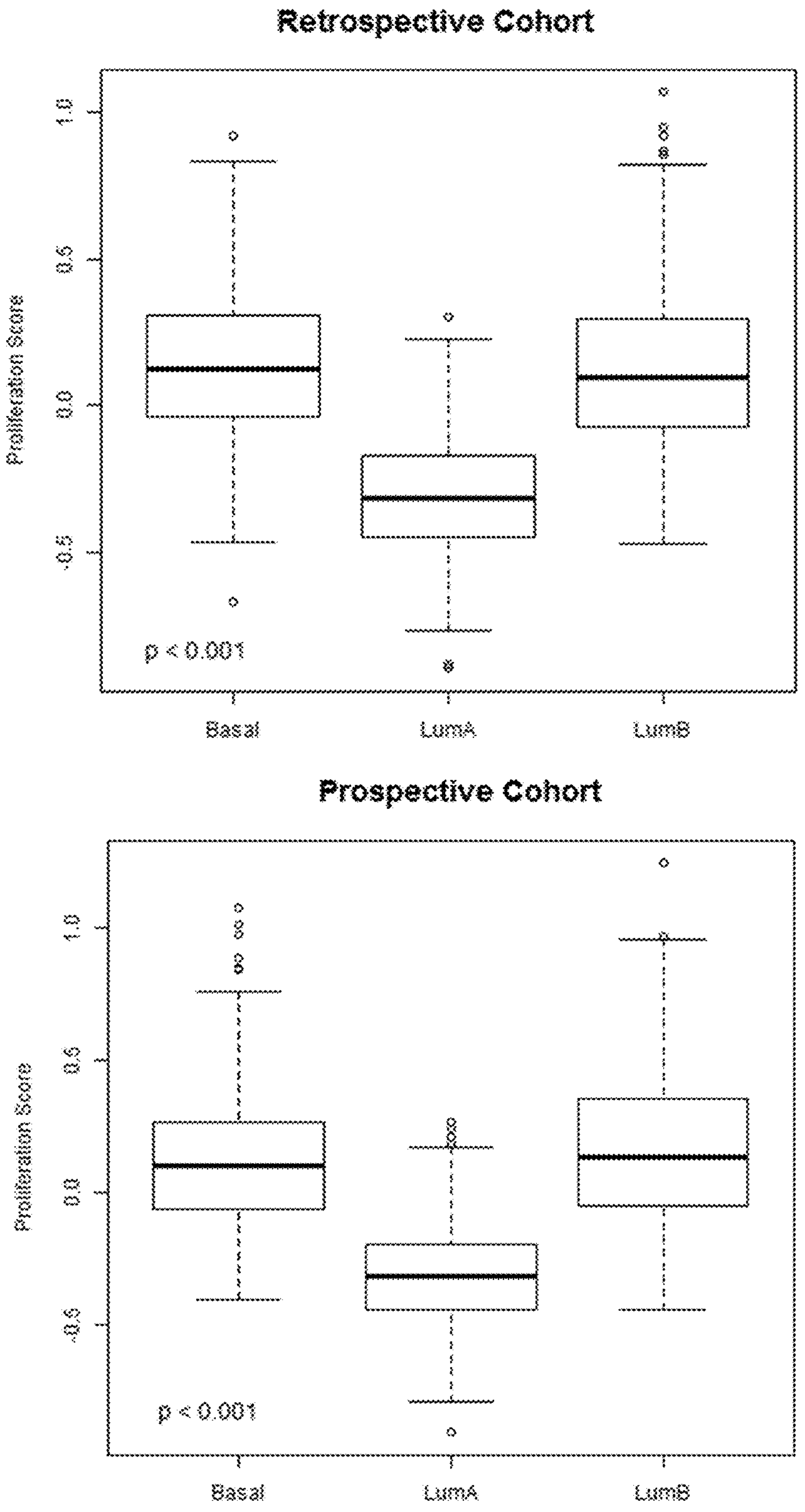
FIG. 8 sets forth data showing PAM50 proliferation score across subtypes. Box plots of the PAM50 proliferation score across the basal, luminal A and luminal B subtypes within the retrospective and prospective cohorts. ANOVA p-value<0.001 for both cohorts.

We next independently validated the associations of these subtypes with biologic and clinicopathologic factors in Decipher GRID™, a prospectively-collected cohort of 2,215 prostatectomy patient expression profiles. PAM50 gene expression patterns are similar to the pooled retrospective cohorts, and trends of AR/AR-signaling (higher in luminal), CD49f signature (higher in basal), and NKX3.1 and KRT19 (both higher in luminal) gene expression are conserved (FIGS. 3A-D). 33.3% of samples are classified as luminal A, 32.6% as luminal B, and 34.1% as basal. We also confirmed MYC and KRAS expression patterns, which are both increased in luminal samples (FIG. 7). Finally, while Decipher GRID does not have associated clinical outcomes, luminal B demonstrates the highest Gleason scores, as well as rates of SVI, ECE, and LNI, consistent with clinical outcomes and clinicopathologic data in our retrospective cohorts (Table 5).

TABLE 5

Demographics for GRID (n = 2,215)

| | | Basal (n = 755) | Luminal A (n = 737) | Luminal B (723) | Total (n = 2215) | P-value |
|---|---|---|---|---|---|---|
| Age (years) | | 64.1 +/- 7.09 | 64.4 +/- 6.64 | 64.9 +/- 6.61 | 64.4 +/- 6.79 | 0.109 |
| | NA | 67 (0.089) | 63 (0.085) | 59 (0.082) | 189 (0.085) | |
| PSA (ng/dL) | <10 | 382 (0.506) | 373 (0.506) | 360 (0.498) | 1115 (0.503) | 0.439 |
| | 10 to 20 | 72 (0.095) | 85 (0.115) | 90 (0.124) | 247 (0.112) | |
| | >20 | 33 (0.044) | 28 (0.038) | 36 (0.05) | 97 (0.044) | |
| | NA | 268 (0.355) | 251 (0.341) | 237 (0.328) | 756 (0.341) | |
| Gleason | <6 | 61 (0.081) | 53 (0.072) | 29 (0.04) | 143 (0.065) | <0.0001 |
| | 7 | 453 (0.6) | 489 (0.664) | 431 (0.596) | 1373 (0.62) | |
| | 8 to 10 | 174 (0.23) | 132 (0.179) | 204 (0.282) | 510 (0.23) | |
| | NA | 67 (0.089) | 63 (0.085) | 59 (0.082) | 189 (0.085) | |
| SM | No | 310 (0.411) | 295 (0.4) | 299 (0.414) | 904 (0.408) | 0.878 |
| | Yes | 375 (0.497) | 376 (0.51) | 365 (0.505) | 1116 (0.504) | |
| | NA | 70 (0.093) | 66 (0.09) | 59 (0.082) | 195 (0.088) | |
| SVI | No | 530 (0.702) | 554 (0.752) | 499 (0.69) | 1583 (0.715) | 0.003 |
| | Yes | 152 (0.201) | 116 (0.157) | 165 (0.228) | 433 (0.195) | |
| | NA | 73 (0.097) | 67 (0.091) | 59 (0.082) | 199 (0.09) | |
| ECE | No | 336 (0.445) | 325 (0.441) | 260 (0.36) | 921 (0.416) | <0.0001 |
| | Yes | 348 (0.461) | 345 (0.468) | 403 (0.557) | 1096 (0.495) | |
| | NA | 71 (0.094) | 67 (0.091) | 60 (0.083) | 198 (0.089) | |
| LNI | No | 646 (0.856) | 628 (0.852) | 624 (0.863) | 1898 (0.857) | 0.015 |
| | Yes | 8 (0.011) | 9 (0.012) | 21 (0.029) | 38 (0.017) | |
| | NA | 101 (0.134) | 100 (0.136) | 78 (0.108) | 279 (0.126) | |

Abbreviations: PSA: prostate specific antigen, SM: positive surgical margins, SVI: seminal vesicle invasion, ECE: extracapsular extension, LNI: lymph node invasion.

Figure 4A:
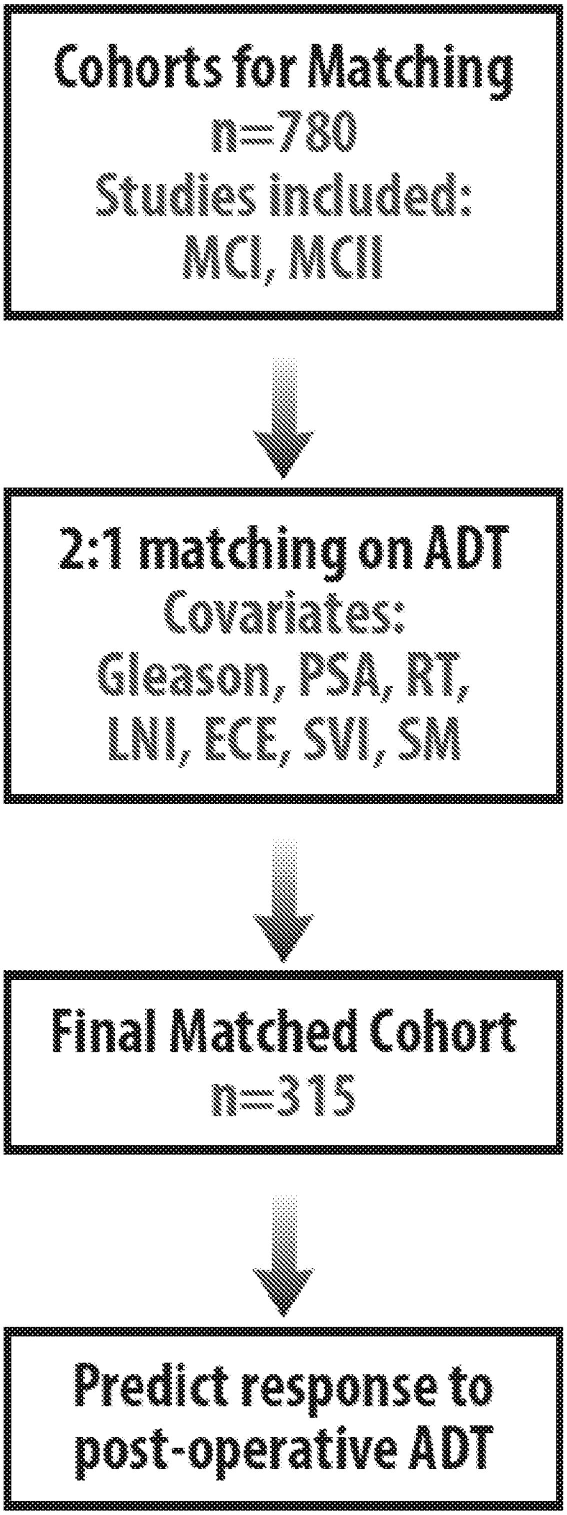
Figure 4B:
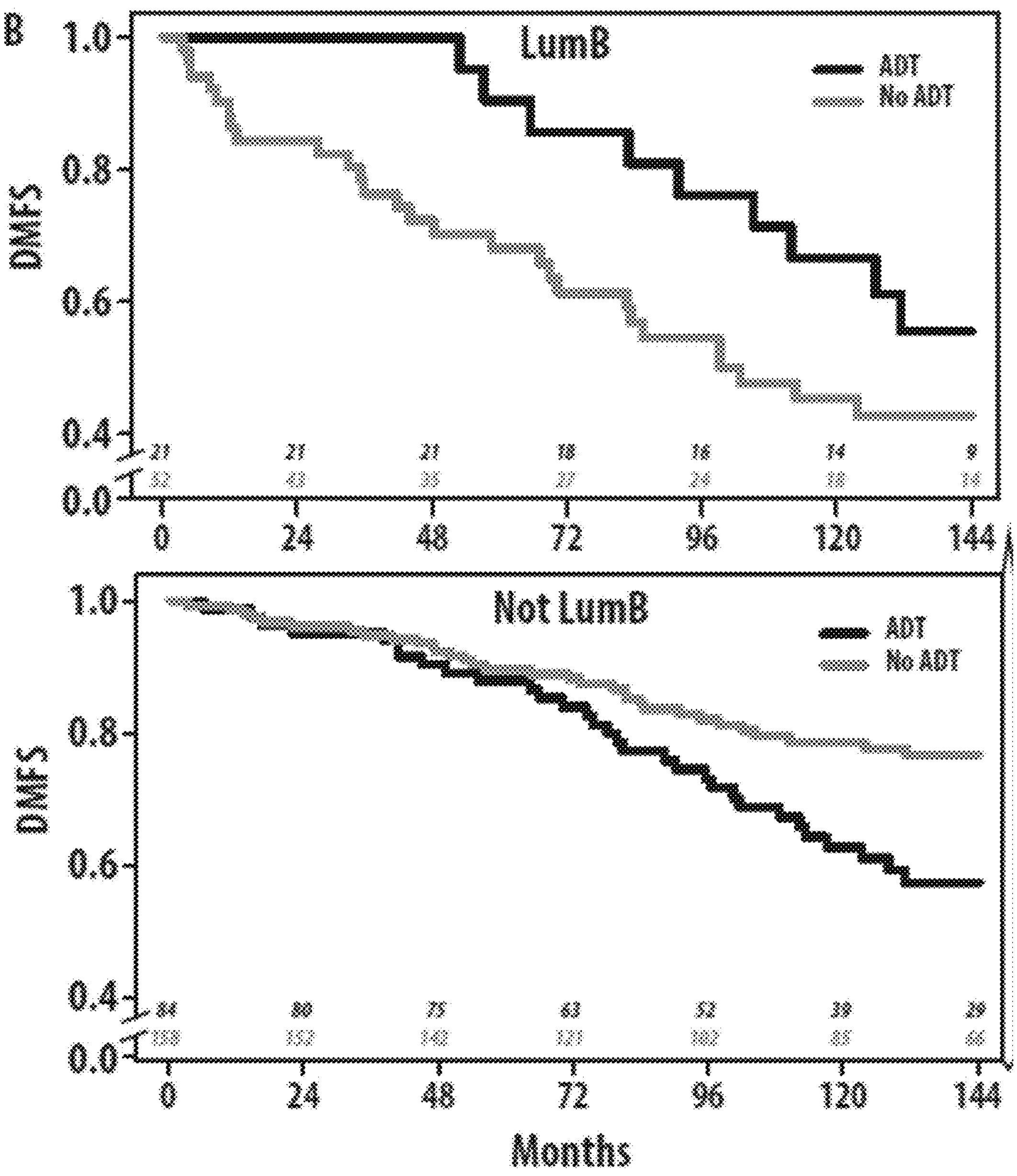
Figure 4B:
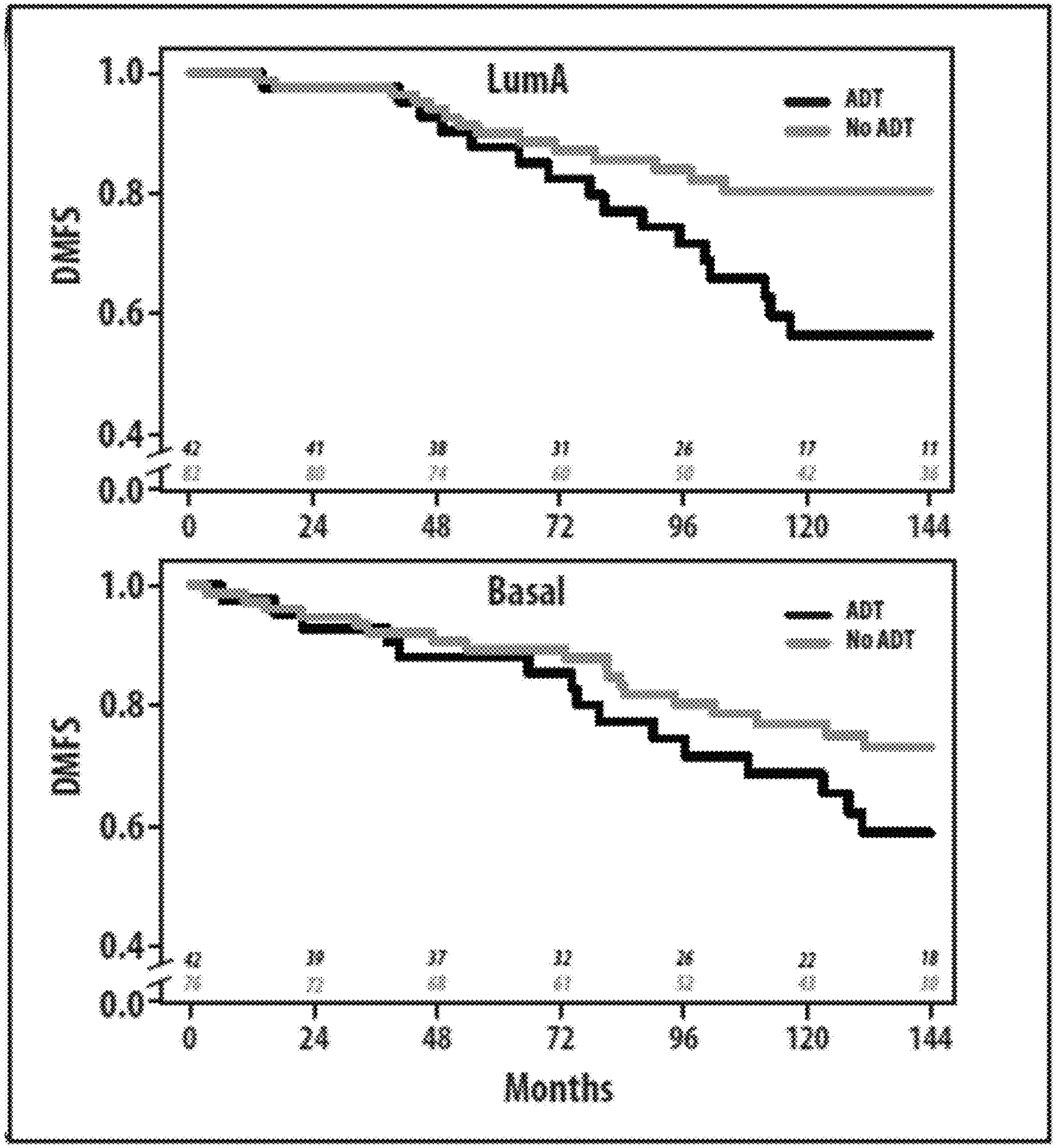
Figure 9:
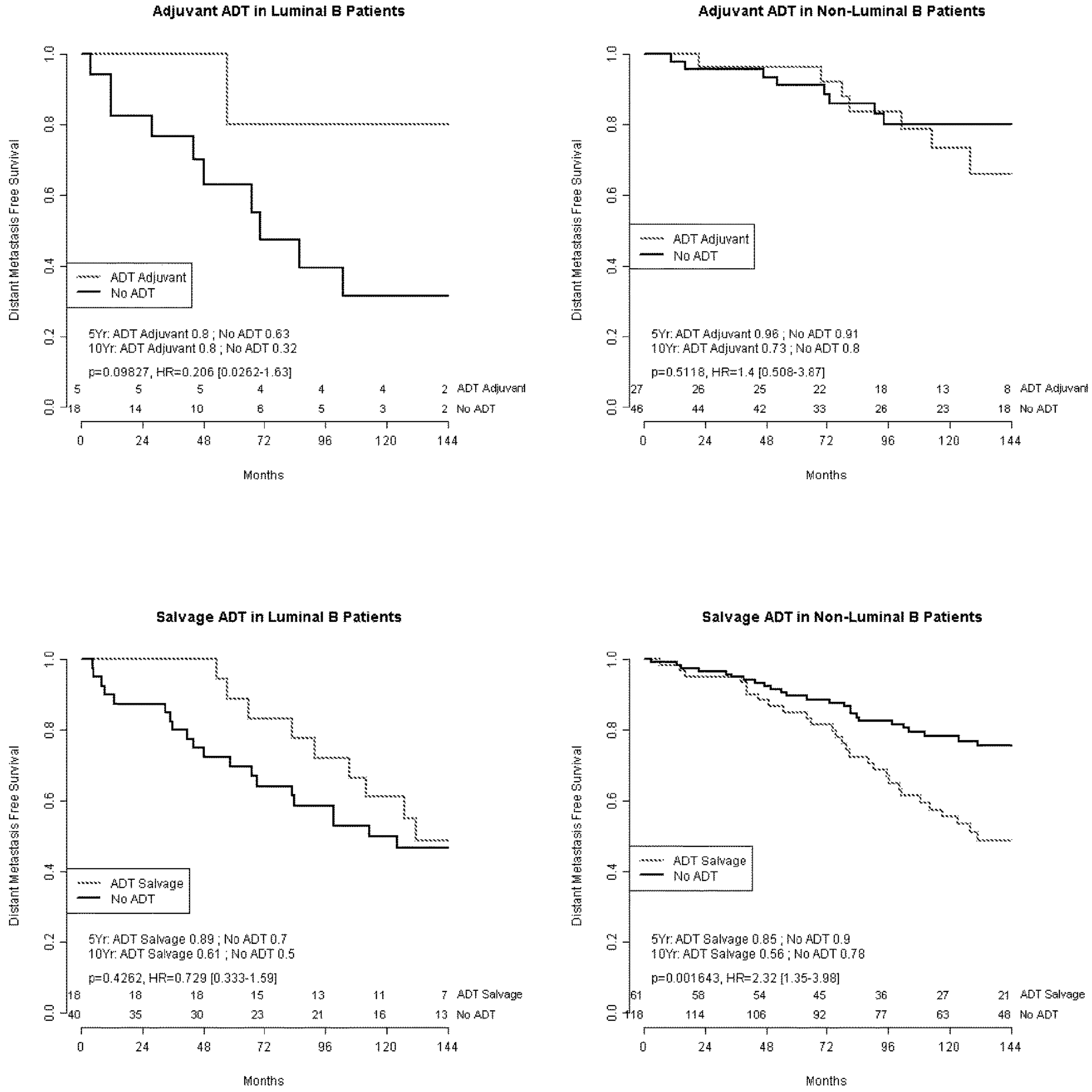
FIG. 9 sets forth data showing survival outcomes for the matched cohort, separating patients receiving adjuvant and salvage ADT. Kaplan-Meier curves are shown to visualize effect of adjuvant and salvage ADT separately within the Luminal B and non-Luminal B patients. Patients receiving adjuvant ADT and their matched no ADT samples. Patients receiving salvage ADT and their matched no ADT samples.
Figure 10:
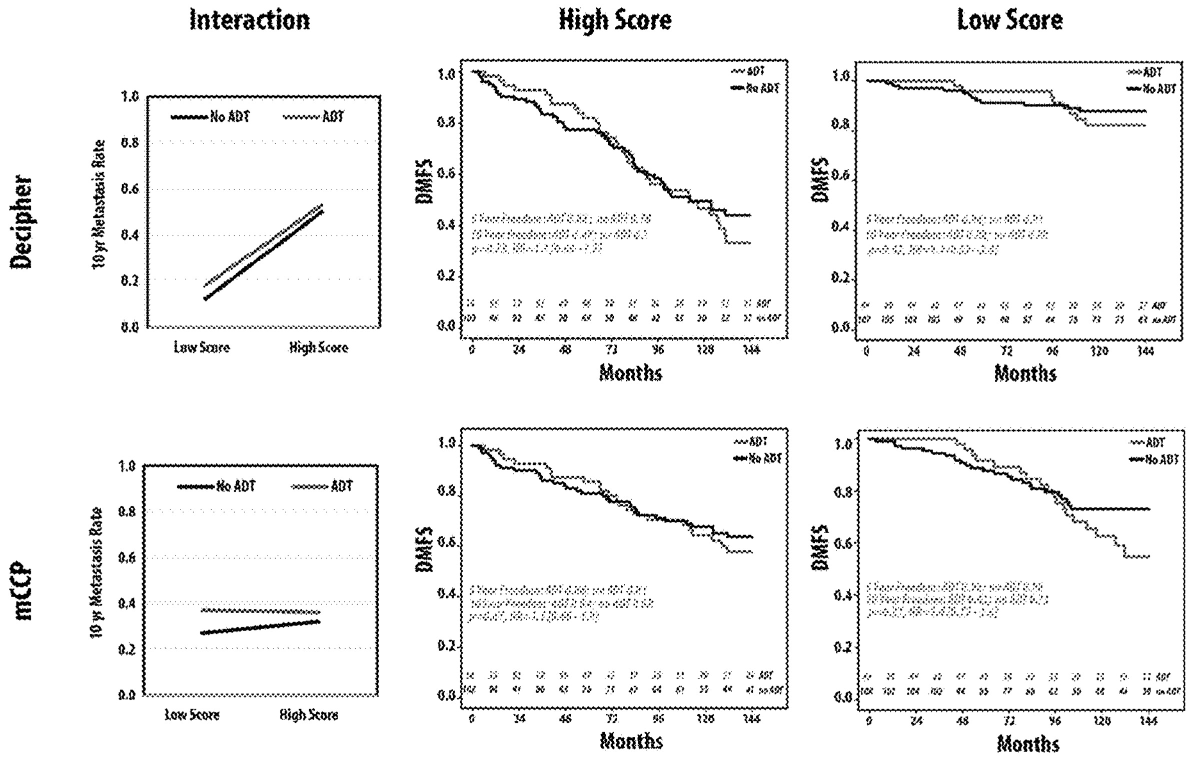
FIG. 10 sets forth data showing Decipher and mCCP are not predictive for response to post-operative ADT in a matched cohort.

The relationship between androgen signaling and luminal-like prostate cancer is of particular interest given the importance of ADT in treating prostate cancer. We investigated whether these subtypes could predict response to hormonal therapy in an exploratory subgroup analysis by first designing a post-prostatectomy ADT treated/untreated sub-cohort (n=315; ADT untreated n=210; ADT treated n=105) matched by clinicopathologic factors (Gleason, PSA, LNI, ECE, SVI, and SM), and post-operative RT (FIG. 4A and Tables 6 and 7). Matching was performed with a 2:1 ratio of patients (ADT untreated:ADT treated). The matched cohort had a median follow-up time of 13 years. In this analysis, we pool the luminal A and basal subtypes to compare to luminal B, as the luminal A and basal subtypes have similar outcomes for ADT and no ADT in the matched cohorts. In the luminal B subtype, which has the worst prognosis of the three subtypes and contains patients with increased expression of AR signaling genes, patients treated with ADT have improved DMFS compared to those that did not receive ADT (10-year metastasis rates of 33% vs. 55%, FIGS. 4B, 4C). However, in the non-luminal B patients, patients treated with ADT have worse DMFS compared to untreated patients (10-year metastasis rates of 37% vs. 21%, FIGS. 4B, 4C), with a similar trend in both luminal A and basal patients. Separating patients receiving adjuvant or salvage therapy in the matched cohort results in similar trends, although the p-values are insignificant due to the reduced numbers (FIG. 9). Finally, we used interaction analysis in a Cox model of these matched patients to demonstrate a statistically significant interaction term between ADT and the luminal B subtype (p=0.006). Luminal B represents a subgroup of prostate cancers with poor prognosis combined with biological differences in AR signaling that result in improved response to post-operative ADT.

TABLE 6

Demographics for matched cohort (n = 315)

| | | Basal (n = 118) | Luminal A (n = 124) | Luminal B (n = 73) | Total (n = 315) | P-value |
|---|---|---|---|---|---|---|
| Age (years) | | 64.4 +/- 6.64 | 64.2 +/- 7.04 | 64.8 +/- 6.65 | 64.4 +/- 6.79 | 0.860 |
| PSA (ng/dL) | <10 | 75 (0.636) | 80 (0.645) | 37 (0.507) | 192 (0.61) | 0.273 |
| | 10 to 20 | 19 (0.161) | 24 (0.194) | 17 (0.233) | 60 (0.19) | |
| | >20 | 24 (0.203) | 20 (0.161) | 19 (0.26) | 63 (0.2) | |
| Gleason | <6 | 13 (0.11) | 7 (0.056) | 1 (0.014) | 21 (0.067) | 0.002 |
| | 7 | 72 (0.61) | 91 (0.734) | 41 (0.562) | 204 (0.648) | |
| | 8 to 10 | 33 (0.28) | 26 (0.21) | 31 (0.425) | 90 (0.286) | |
| SM | No | 57 (0.483) | 49 (0.395) | 32 (0.438) | 138 (0.438) | 0.387 |
| | Yes | 61 (0.517) | 75 (0.605) | 41 (0.562) | 177 (0.562) | |
| SVI | No | 105 (0.89) | 100 (0.806) | 62 (0.849) | 267 (0.848) | 0.196 |
| | Yes | 13 (0.11) | 24 (0.194) | 11 (0.151) | 48 (0.152) | |

TABLE 6-continued

| Demographics for matched cohort (n = 315) | | | | | | |
|---|---|---|---|---|---|---|
| | | Basal (n = 118) | Luminal A (n = 124) | Luminal B (n = 73) | Total (n = 315) | P-value |
| ECE | No | 70 (0.593) | 79 (0.637) | 34 (0.466) | 183 (0.581) | 0.059 |
| | Yes | 48 (0.407) | 45 (0.363) | 39 (0.534) | 132 (0.419) | |
| LNI | No | 118 (1) | 124 (1) | 73 (1) | 315 (1) | NA |

Abbreviations: PSA: prostate specific antigen, SM: positive surgical margins, SVI: seminal vesicle invasion, ECE: extracapsular extension, LNI: lymph node invasion.

TABLE 7

| Number of patients receiving ADT and RT in the matched cohort (n = 315) | | | | |
|---|---|---|---|---|
| | Adjuvant ADT Only | Salvage ADT Only | Both Adjuvant and Salvage ADT | No ADT |
| Adjuvant RT Only | 4 | 6 | 2 | 23 |
| Salvage RT Only | 3 | 14 | 2 | 41 |
| Both Adjuvant and Salvage RT | 1 | 0 | 0 | 0 |
| No RT | 18 | 53 | 2 | 146 |

Abbreviations:
ADT: Androgen deprivation therapy;
RT: Radiation therapy

These results showed that a genomic classifier of the present invention could be utilized to identify three subtypes in prostate cancer subjects. These results suggested that the methods and markers of the present invention would be useful for diagnosing, prognosing, determining the progression of cancer, or predicting benefit from therapy in a subject having prostate cancer. These results further showed that the subtyping methods and genomic classifiers of the present invention are useful for predicting benefit from androgen deprivation therapy (ADT) and treating a subject with prostate cancer. The results showed that the subtyping methods of the present invention may be used to determine a treatment for a subject with prostate cancer.

TABLE 8

| Subtyping Target Sequences | | | |
|---|---|---|---|
| SEQ ID NO. | Gene | Affy Probeset ID | Sequence |
| 1 | CDC20 | 2333138 | GGGTGCTAGGCCGGAAGGGGCTGCAGCCGAGGGTGGC CCTGATTTTGTGGCCGGCCAGGAGCGAAGGGGTCCCTT TCTGTCCCCTGAGCACCGTCGCCTCCT |
| 2 | CDC20 | 2333139 | GCACCAACTGCAAGGACCCCTCCCCCTGCGGGC |
| 3 | CDC20 | 2333140 | TTCGCGTTCGAGAGTGACCTGCACTCGCTGCTTCAGCTG GATGCACCCATCCCCAATGCACCCCCTGCGCGCTGGCA GCGCAAAGCCAAGGAAGCCGCAGGCCCGGCCCCCTCAC CCATGCGGGCCGCCAACCGATCCCACAGCGC |
| 4 | CDC20 | 2333142 | GCAAATCCAGTTCCAAGGTTCAGACCACTCCTAGCAAA CCTGGCGGTGACCGCTATATCCCCCATCGCAGTGCTGCC CAGATGGAGGTGGCCAGCTTCCTCCTGAGCAAGGAGAA CCAGCCTGAAAACAGCCAGACGCCCACCA |
| 5 | CDC20 | 2333144 | GTAGAGGAAGCCAAGATCCTTCGGCTCAGTGGAAAACC ACAAAATGCGCCAGAGG |
| 6 | CDC20 | 2333145 | CGAAGTTCCTGGTTCCTGGAGGGAG |
| 7 | CDC20 | 2333146 | CCTCTTCCTATCTAAGATTGAGGGCAAG |
| 8 | CDC20 | 2333147 | CAGAACAGACTGAAAGTACTCTACAGCCAA |
| 9 | CDC20 | 2333148 | CCTGCCAGACCGTATCCTGGATGCGCCTGAAATCC |
| 10 | CDC20 | 2333149 | ACCTGAACCTTGTGGATTGGAGTTCTGGGAATGTACTG GCCGTGGCACTGGACAACAGTGTGTACCTGTGGAGTGC AAGCTCTGGTGACATCCTGCAGCTTTTGCAAATGGAGC AGCCTGGGGAATATATATCCTCTGTGGCCTG |
| 11 | CDC20 | 2333150 | CAGCAGCAGAAACGGCTTCGAAATATGACCAGTCACTC TGCCCGAGTGGGCTCCCTAAGCTGGAACAGCTATAT |

TABLE 8-continued

| Subtyping Target Sequences | | | |
|---|---|---|---|
| SEQ ID NO. | Gene | Affy Probeset ID | Sequence |
| 12 | CDC20 | 2333151 | CATCCACCACCATGATGTTCGGGTAGCAGAACACCATG TGGCCACACTGAGTGGCCACAGCCAGGAAGTGTGTGGG CTGCGCTGGGCCCCAGATGGACGACATTTGGCCAGTGG T |
| 13 | CDC20 | 2333152 | GTAATGATAACTTGGTCAATGTGTGGCCTAGTGCTCCTG GAGAGGGTGGCTGGGTTCCTCTGCAGACATTCACCCAG CATCAAGGGGCTGTCAA |
| 14 | CDC20 | 2333155 | GTGTCCCTGGCAGTCCAATGTCCTGGCAACA |
| 15 | CDC20 | 2333156 | GCCTGTCTGAGTGCCGTGGATGCCC |
| 16 | CDC20 | 2333158 | TTATTTGGAAGTACCCAACCATGGC |
| 17 | CDC20 | 2333159 | CACACATCCCGGGTCCTGAGTCTGACCATGAGCCCAGA TGGGGCCACAGTGGCATCCGCAGCAGCAGATGAGACCC TGAGGCTATGGCGCTGTTTTGAGTTGGACCC |
| 18 | CDC20 | 2333160 | AGACCAACCCATCACCTCAGTTGTTTTTTAT |
| 19 | KIF2C | 2334099 | TGCGGCGGTTTACGCGGCGTTAAGACTTCGTAGGGTTA GCGAAATTGAGGTTTCTTGGTATTGCGCGTTTCTCTT |
| 20 | KIF2C | 2334101 | GTCCCTAGGTCAAGGGGACTCGTGA |
| 21 | KIF2C | 2334103 | GTTTAATTCACAGTGCCAATGTAAGGACTGT |
| 22 | KIF2C | 2334105 | TCTTAGGGTTAGGTAGCAGCTGTCAGGAACTTGCCCCT GCCCATAAGATCCTAAAGGGCCCCCATTTGACTCTCAC CAGACAGTTAGAACTTGTTTCCTCCTCCGTGTCAGCCAT CAAGAGGTGCTTGGGGGGCTGTGCCCAGCAGGACCTCA CTGCCCAGCAGATCAGCAGGGGAGCCAAGTGGCCTAGA TCTGCTGTGGAGTACCCGACTGTTTGCCTGCCTGTCTGC CCTCCTCTTCACCTCATTCTCATCACTGACGTCTACCATT GGCTT |
| 23 | KIF2C | 2334106 | ATGATGTGGCTGCAATAAACCCAGAACTCTTACAGCTT CTTCCCTTACATCCGAAGGACAATCTGCCCTTGC |
| 24 | KIF2C | 2334107 | CAAAAACGGAGATCCGTCAACTCCAAAATTCC |
| 25 | KIF2C | 2334109 | GGACCTATTTCACCTTGTACAGAAACTTGGAGGTTTGCC CCTGACCACCCTCGAGATCGTGCAGCACTGACTGGCTA CTGCTCTCGGTTCTCCA |
| 26 | KIF2C | 2334111 | CTGCCCCCACTAGGCCTTCCTGCCCTGCAG |
| 27 | KIF2C | 2334112 | GGCTGAAATACCATTGAGGATGGTCAGCGAGGAGATGG AAGAGCAAGTCCATTCCATCCGAGGC |
| 28 | KIF2C | 2334113 | AGGCCCAGAACTCTGAAATGAGAATGAA |
| 29 | KIF2C | 2334114 | TATGACAGTAGTTTTCCAAACTGGGAATTTGCCCGAAT GATTAAAGAATTTCGGGCTACTTTGGAATGTCATCCACT TACTATGACTGATCC |
| 30 | KIF2C | 2334117 | GAGCACCCCCTGAAATACTCTCCTTC |
| 31 | KIF2C | 2334118 | ACATGAACCCAAGTTGAAAGTGGACTTAACAAAGTATC TGGAGAACCAAGCATTCTGCTTTGACTTTGCATTTGATG AAACAGCTTCG |
| 32 | KIF2C | 2334119 | AGGCCACTGGTACAGACAATCTTTGAAGGTGGA |
| 33 | KIF2C | 2334122 | CGGGACGTCTTCCTCCTGAAGAATCAACCCTGCTACCG GAAGTTGGGCCTGGAAGTCTATGTGACATTCTTCGAGA TCTACAATGGGA |
| 34 | KIF2C | 2334125 | AGGACGGCAAGCAACAGGTGCAAGTGGTGGGGCTGCA GGAGCATCTGGTTAACTCTGCTGATGATGTCATCAAGA TGATCGACATGGGCAGC |

TABLE 8-continued

| Subtyping Target Sequences | | | |
|---|---|---|---|
| SEQ ID NO. | Gene | Affy Probeset ID | Sequence |
| 35 | KIF2C | 2334126 | GCTCCCACGCGTGCTTCCAAATTATTCTTCGAGCTAAAG GGAGAATGCATGGCAAGTTCTCTTTGGTAGATCTGGCA GGGAATGAGCGAGGCGCGGACACTTCCAGTGCTGACCG GCAGACCCGCATGGAGGGCGCAGAAATCAACAAGAGT CTC |
| 36 | KIF2C | 2334130 | GCTGGGTGAGGGGCTTTTCCAGTCCA |
| 37 | KIF2C | 2334131 | GCAAGGTTGCCATTCCATCCCCTTGGAGCCTCAAGCCTC GAAGCCTGGGCGGTGCCACATTCCTC |
| 38 | KIF2C | 2334132 | AGTACCAAGGGGGTGCTGTGGGATCTGAGACCTCCTTG TTTCCT |
| 39 | KIF2C | 2334133 | GAAGAGATGGAAGCCTGCTCTAACGGGGCGCTGATTCC AG |
| 40 | KIF2C | 2334134 | CCAGATGTCCAGCTTTAACGAAGCCATGACTCAGA |
| 41 | KIF2C | 2334135 | AAGGACCAGACTGGCTTGAGCTCTCTGAGATGACCGAG CAGCCAGACTATGACCTGGAGACCTTTGTGAACAAAGC GGAATCTGCTCTGGCCCAGC |
| 42 | KIF2C | 2334136 | GTCATCAAGGCCTTGCGCCTGGCCATG |
| 43 | KIF2C | 2334137 | CGACTGCAAATAAAAATCTGTTTGGTTTG |
| 44 | KIF2C | 2334138 | GGGACAGGTTCTGGTAAATGCCAAGTATG |
| 45 | KIF2C | 2334139 | TTCCTCAGTTGTCGCCCTCACGAGAGGAAGGAGCTCTT AGTTACCCTTTTGTGTTGCCCTTCTTTCCATCAAGGGGA ATGTTCTCAGCATAGAGCTTTCTCCGCAGCATCCTGCCT GCGTGGACTGGCTGCTAATGGAGAGCTCCCTGGGGTTG TCCTGGCTCTGGGGAGAGAGACGGAGCCTTTAGTACAG CTATCTGCTGGCTCTAAACCTTCTACGCCTTTGGGCCGA GCACTGAATGTCTT |
| 46 | KIF2C | 2334140 | GTCTCCCTAGAGATCCTAGAGGATCCCTACTGTTTTC |
| 47 | PHGDH | 2354635 | AGGAGCCACATGCTCTCATCAAGCAGAAA |
| 48 | PHGDH | 2354639 | GTGCCCAACCAGTGAGGCCACGTTTCGAAAAGAAGAAA GAAACGACAAACTAAAATACATGACTGTGTAGATGAGG |
| 49 | PHGDH | 2354641 | GCTGGAGAATACTGCCCAGTTACTCTAGCGCGCCAGGC CGAACCGCAGCTTCTTGGCTTAGGTACTTCTACTCACAG CGGCCGA |
| 50 | PHGDH | 2354642 | ATGGCTTTTGCAAATCTGCGGAAAGTGCTCATCAGTGA CAGCCTGGACCCTTGCTGCCGGAAGATCT |
| 51 | PHGDH | 2354644 | GCAGCCTAAGCATCATTCCTCTTCTCTTCTTAGTGGAGA TAAAATTACCCACTGCTCTCCTTACATT |
| 52 | PHGDH | 2354645 | GTGTGGGCCCTTACCCTAGAAGCCAACTTCTCATGACCT TTCTCTATCTCCAGAATCCATGCAGTGGGAATGAAGGT AAAAGAAGGTTTTCATGGGATCCAGCTGAGAGCTCTAC GGGGAAAATGGATCTGAGGAGCCATGTGCTCCATCTCT TTTATTTTACAGGTAGAGACTAGGGGTATAGAGTGAGG TGAATTACCGCAGTGACCCACACATTGTTGGCAGACCT AGGATTAGAACTCTGTCTTCCTGGTTCCCAGCTTGGTGC TTTTGAAAGCATACTTGCTGCTTTCTTACCGGCCTGGTG TCTGCCACTTTGGGACAGAGTGTGGACTTGCTCACCTGC CCCATTTCTTAGGGATTCTCATTCTGTGTTTGAGCAAGA ATATTCTTATTCTGGAAAGAACCACATACCACAGGATT CTGGGTGAGCATAAGGAAGATTGTCTTGGGGATCTGAC TTAGCTCACGTATAGTGGCTATGATGAATTCAGTGTCTT ATTTTTTGCATATGTATATTTTTAGTCTAATATTGCCTGG GTGTCTGAGCAAGTCTAGATGAATTTAATTGCTCTCATT TTTCCCCTGCCCCTCTTCCTTTGGTCTCTCTTTTAGGAAA TGTTTTTCTTTCAACATTCGTTTCATTCATTATTTACTCA TTCGGCCAACCAACATTTATTGAGTGCCTTCCCTGTATC AGGGACAGGGGCTTACAAAGTAGAATTTGATCCCACCT CTGCCCTCAGTAGCTCAGTGTCTAATGGAGGTAGTGAT |

TABLE 8-continued

Subtyping Target Sequences

| SEQ ID NO. | Gene | Affy Probeset ID | Sequence |
|---|---|---|---|
| | | | GTTCATTAAGCGTCGCCAGATACTGTGCTAGGTGCTGTG CCTGTTCTCTCTCGCTTGTTCCTCACACACTTGAGAAGG CCGAAGCTGATTCATAGCTTGGAAGGCAGGGGCCTTGG ATTTGAACCCAGGCCTGACCAATGGCAGAACCTATCAG ATGTGTGGACAGATGACATTGCCTTTCTTTCTTTGGATA TATCAAAATCAGCCAGCAGGCAGGAACTCCCATTTT |
| 53 | PHGDH | 2354646 | TGTGTCTGATGGACATCCAGGCTGCAGG |
| 54 | PHGDH | 2354647 | ATGGTGCTGTCTAGAGAGATGAGCCAGGTGCCCAGAGC CCATGGGCCAATGCTGCCCTTTCTTGAGCATGCCAAAC AAAGCGGTTG |
| 55 | PHGDH | 2354648 | CAGTCTCCTCCACTCTAAGTAAAAATCAGCATGAGTCCT AGCCCACATTT |
| 56 | PHGDH | 2354649 | TGAGTATACCAAAGATATCTATGAACTGGCAGTCATCA GTGACTTCCTAAGGTTCCGGAAATGCATCTCTT |
| 57 | PHGDH | 2354650 | ATGTGCCTGCGGCTTTACGAGTTCTCACAGAATGACTTT C |
| 58 | PHGDH | 2354651 | ACTGTGAAGGCCTTATTGTTCGCTCTGCCACCAAGGTGA CCGCTGATGTCATCAACGCAGCTGAGAAACTCC |
| 59 | PHGDH | 2354652 | ATCTGGAGGCCGCAACAAGGAAGGGCATCTT |
| 60 | PHGDH | 2354653 | TGAGTGCGGAGACTGACCACACCTAGGGAGAAAAAAC TCACTTGAGAGAAAGCTGAGTCCATTGGAAGGGCTTCC AGGAGGATGCCTGGTCTAGGGCCTGCATGGTCAACACA |
| 61 | PHGDH | 2354657 | ATTACTTTTCCCATGGCGAGACCTGCTTTCCCTCCTGCT GGAGGAGGATCTGGGGGAATTTACCTCTGCTCTAACTC CTCCCTGCAGTTTCCATCTGAGCTCTCTGGTATTCACTG ATATTC |
| 62 | PHGDH | 2354660 | GCAGATTCCCCAGGCGACGGCTTCGATGAAGGACGGCA AATGGGA |
| 63 | PHGDH | 2354662 | GAGAGGTAGCTACCCGGATGCAGTCCTTTGGGA |
| 64 | PHGDH | 2354666 | TTCCTTCTCCGTGGCACCACTACACATCAATATTCCTGG CAATATTCTTCATCATGGAGACTTCGGCAGCGACTTCAA CCAGATGAAA |
| 65 | PHGDH | 2354667 | GAAACATGGCTTGGATCATTCCGTCTCCCACCTCAGCCC CTCCGGAGCTGCCTGGACCTCATCATTCCGGAGAGTCT AAGTGGC |
| 66 | PHGDH | 2354674 | CAGTCCCAGCATCATTGTGTGGTCATGAGAATTAATTA AGCTGATCATGGTACTTAGTATATGGTAAATAGTACTTA GTATGTGGAACATGGTACTTAGTGTATGGTAAATTAAC TGGAGAATTA |
| 67 | PHGDH | 2354675 | GGTATGACCCCATCATTTCCCCAGAGGTCTCGGCCTCCT TTGGTGTTCAGCA |
| 68 | PHGDH | 2354677 | CCTTTGCCCAGTGCAAGAAGGGGGTGCGTGTGGTGAAC TGTGCCCGTGGAGGGATCGTGGACGAAGGCGCCCTGCT CC |
| 69 | PHGDH | 2354682 | GCCTTGGTGGACCATGAGAATGTCATCAGCTGTCCCCA CCTGGGTGCCAGCACCAAGGAGGCTCAGAGCCGCTGTG GG |
| 70 | PHGDH | 2354687 | ATGGTTGACTTTACAAGTTATCTCAATAAAAGTGGCCA GATGCCTAACTCAGAA |
| 71 | PHGDH | 2354688 | TGGACTTCGCATGCGTTGATATTTGAAGCACGATCATCA AAACTTTGTGATAATTGATCGTAGTGTTTAGTAACAATG TAAACACTTAAAAAAATTCAAGATAGAAAATAAAAATG AAGGCAAGTTGGGACTGCCAGAGAAGACCCGTCACTCC TCATCCAAGTTATCTGCGACTCCCATATGTTTTGTGTCA AAGACTCACCTTTATTGTGCTGTCCAATCCCTTCCCCAG |

TABLE 8-continued

Subtyping Target Sequences

| SEQ ID NO. | Gene | Affy Probeset ID | Sequence |
|---|---|---|---|
| | | | TGCAGAAACAAGTCTCCCATGGAGGGGCTGGGGCAG ACACAGTTTGCTGAAAGGAGCAATTTTGAGTGGTTGTG GCATTCTGTGTCCATTTCTGGCTCCACAGCTTTCTTCATT TGTAGGAACAAGTCCTTGTCCTGTTGTTAGTGGCTGATG GAAGTTGTCACCCACCAGGCACCAAGGCAGGAGTGACC CTATACTGTCTTTC |
| 72 | PHGDH | 2354689 | CCAAGCCTTGGATTGGTCTGGCAGAAGCTCTGGGGACA CTGATGCGAGCCTGGGCTGGGT |
| 73 | PHGDH | 2354690 | AATGCTGGGAACTGCCTAAGCCCCGCAGTCATTGTCGG CCTCCTGAAAGAGGCTTCCAAGCAGGCGGATGTGAACT TGGTGAACGCTAAGCTGCTG |
| 74 | PHGDH | 2354695 | TGGGCTTGGTCCAAGGCACTACGCCTGTACTGCAGGGG CTCAATGGA |
| 75 | PHGDH | 2354698 | CAGGCGTGCGGCTGCTGTCCTACCAGACTTCACTGGTGT CAGATGGGGAGACCTGGCACGTCATGGGCATCTCCT |
| 76 | PHGDH | 2354699 | CCACTGTGATCAATAGGGAGAGAAAATCCACATTCTTG GGCTGAACGCGGGCCTCTGACACTGCTTACACT |
| 77 | NUF2 | 2364439 | TCCAGTAGGAGGCGGCAAGTTTGAAAAGTGATGACGGT TGACGTTTGCTGATTTTTGACTTTGCTTGTAGCTGCTCCC CGAACTCGCCGTCTTCCTGTCGGCGGCCGGCACTGT |
| 78 | NUF2 | 2364440 | TGAGCGCGAGAGGACGGAGGAAGGAAGCCTGCAGACA GACGCCTTCTCCATCCCAAGGCGCGGGCAGGTGCCGGG ACGCTGGGCCTGGCGGTGTTTTCGTCGTGCTCAGCGGTG GGAG |
| 79 | NUF2 | 2364441 | TCAAACTATGTAGTTGGAAAGTGTCTTCATCTCTCGTTA ATGAATAAATTGTAACTGAAATTGTACTTCGAAAGAAT GATAGAATTTGGATATTGGAGGAGGTTCCAAAAGGAAA TACTGGAAGTTTGGGAAAGTTAGGAGACTAACTTGGAG CAGAAATTTCATTCAATTATTAAAGGGTTTAGAAGCCT AGCAGAAAAATTTG |
| 80 | NUF2 | 2364442 | AATGTAGCTGAGATTGTGATTCATATTCGCAATAAGAT CTTAACAGGAGCTGATGGTAAAAACCTCACCAAGAATG ATCTTTATCCAAATC |
| 81 | NUF2 | 2364444 | CATGATCTACATGAGAGCCTTACAAATAGTATATGGAA TTCGACTGGAACATTTT |
| 82 | NUF2 | 2364445 | TGAACTCTGAAGTCATGTATCCACATTTAATGGAAGGC TTCTTACCATTCAGCAATTTAGTTACTCATCT |
| 83 | NUF2 | 2364449 | TTTAAGTGGCATTATCAACTTTATTCACTTC |
| 84 | NUF2 | 2364451 | TCCTCTGCGGACAAAATGCAACAGTTAAACGCCGCACA CCAGGAGGCATTAATGAAACTGG |
| 85 | NUF2 | 2364452 | TGAGGACAGGTATTTCATTTTAGCCTT |
| 86 | NUF2 | 2364453 | ATTCAGGAGCTACAACAATCACTAAA |
| 87 | NUF2 | 2364457 | AAAATGAAAGATACGGTCCAGAAGCTTAAA |
| 88 | NUF2 | 2364459 | ATCTATGGAGACTCAGTTGACTGCCTGCCTTCATGTCAG TTGGAAGTGCAGTTATATCAAAAGAAAATACAGGACCT TTCAGATAATAGGGAAAAATTAGCCAGTATCTTAAAGG AG |
| 89 | NUF2 | 2364460 | CGTTCAAAAGACTGATGATTGTGAAGAAGGAAAAACTT GCCACAGCACAATTCAAAATAAATAAGAAGCATGAAG ATGTTAAGCAATACAAACGCACAGTAATTG |
| 90 | NUF2 | 2364461 | AAAAAGAGGTGCTGTCTATGAACGAGTAACCACAATTA ATCAAGA |

TABLE 8-continued

Subtyping Target Sequences

| SEQ ID NO. | Gene | Affy Probeset ID | Sequence |
|---|---|---|---|
| 91 | NUF2 | 2364463 | AAAACTGCTTTGGAGAAATACCACGACGGTATTGAAAA GGCAGCAGAGGACTCCTATGCTAAGATAGATGAGAAG ACAGCTGAACTG |
| 92 | NUF2 | 2364464 | AAAAGTTGAAGCGAATGGAAGTATCAGAAGTACCAAA TAATGTTGGCTTCATCAGTTTTTATACACTCTCATAAGT AGTTAATAAGATGAATTTAATGTAGGCTTTTATTAATTT ATAATTAAAATAACTTGTGCAGCTATTCATGTC |
| 93 | CENPF | 2379864 | GCTGCGGGCAGTTTGAATTAGACTCTGGGCTC |
| 94 | CENPF | 2379865 | CGCGCCAGAACTGTACTCTCCGAGAGGTCGTTTTCC |
| 95 | CENPF | 2379867 | TGTCCCAGACCCTACTCGGTCACGGACTCACACTTTAGG GGATCATTTTCTTCCTCCGTAAAAGAATTGGAGATGACT A |
| 96 | CENPF | 2379878 | TTTACAAATGTTGGAGTAATAAAGAAGGCAGAAC |
| 97 | CENPF | 2379879 | GAAAGAAGGGCTGCCTACAAGAGCTCTTCAGAAAATTC AAGAGCTTGAAGGACAGCTTGACAAACTGAAGAAGGA AAAGCAGCAAAGGCAGTTTCAGCTTGACAGTCTCGAGG CTGCGCTGCAGAAGCAAAAA |
| 98 | CENPF | 2379880 | GAAGATTTCTCATGAACTTCAAGTCAAGGAGTCACAAG TGAATTTCCAGGAAGGACAACTGAATTCAGGCAAAAAA CA |
| 99 | CENPF | 2379881 | TATTTTGGGATGGTATTTATAGGGATGATATTTGTATGT ATTAATCAGATGCGTTTGTCTTTTCCTTTAACAATATAA TTATTATACTTTGCAATTTTTTTCCTGGTAGAATAAGT AATGATTCGGTCTCTGTACC |
| 100 | CENPF | 2379882 | GAAGCCAACAAGCTGCGCAGTCTGCAGATG |
| 101 | CENPF | 2379885 | AGACTCTTCCACAAGCCACCATGAATCACCGCGACATT GCCCGGCATCAGGCTTCATCATCTGT |
| 102 | CENPF | 2379886 | TAGGAGAGATTTCTCTGCATCTTACTTTTCTGGGGAACA AGAGGTGACTCCAAGTCGATCAACTTTGCAAATAGGGA AAAGAGATGCTAATAGCAGTTTCTTTGACAATTCTAGC AGTCCTCATCTTTTGGATCAATTAAAAGCGCAGAATC |
| 103 | CENPF | 2379888 | ACTGAAAAAATTGACGGAAGATTTGAGTTGTCAGCGAC AAAATGCAGAA |
| 104 | CENPF | 2379889 | GAGCTCTCCCGTCAACAGCGTTCTTTCCAAACACTGGAC CAGGAGTGCATCCAGATGAAGGCCAGACTCACCCAGGA GTTACAGCAAGCCAAGAATATGCACAACGTCCTGCAGG CTG |
| 105 | CENPF | 2379890 | AGAGTTTAAGCAAAAGTTGTGCAGAGCTGAACAGGCGT TCCAGGCGAGTCAGATCAAGGA |
| 106 | CENPF | 2379895 | AAAGGCCAGAGAAGTCTGCCACCTGGAGGCAGAACTC AAGAACATCAAACAGTGTTTAAATCAGAGCCAGAATTT TGCAGAAGA |
| 107 | CENPF | 2379896 | GCCTTGCTGAGTGCTTTAGAGTTAAAAAAGAAAGAATA TGAAGAATTGAAAGAAGAGAAAACTCTGTTTTCTTGTT GGAAAAGTGAAAACGAAAAACTTTTAACTCAGATGGA ATCAGAAAAGGAAAACTTGCAGAGTAAAATTAATCACT TGGAAACTTGTCTGAAGACACAGCAAATAAAAAGTCAT GAATACAACGAGAGAGTAAGAACGCTGGAGATGGACA GAGAAAACCTAAGTGTCGAGATCAGAAACCTTCACAAC GTGTTAGACAGTAAGTCAGTGGAGGTAGAGACCCAGAA ACTAGCTTATATGGAGCTACAGCAGAAAGCTGAGTTCT CAGATCAGAAACATCAGAAGGAAATAGAAAATATGTG TTTGAAGACTTCTCAGCTTACTGGGCAAGTTGAAGATCT AGAACACAAGCTTCAGTTACTGTCAAATGAAATAATGG ACAAAGACCGGTGTTACCAAGACTTGCATGCCGAATAT GAGAGCCTC |

TABLE 8-continued

Subtyping Target Sequences

| SEQ ID NO. | Gene | Affy Probeset ID | Sequence |
|---|---|---|---|
| 108 | CENPF | 2379897 | TTTGGCTTTTGATCAGCAGCCTGCCATGCATCATTCCTTTGCAAATATAATTGGAGAACAAGGAAGCATGCCTTCAGAGAGGAGTGAATGTCGTTTAGAAGCAGACCAAAGTCCGAAAAATTCTGCCATCCTACAAAATAGAGTTGATTCACTTGAATTTTCATTAGAGTCTCAAAAACAGATGAACTCAGACCTGCAAAAGCAGTGTGAAGAGTTGGTGCAAATCAAAGGAGAAATAGAAGAAAATCTCATGAAAGCAGAACAGATGCATCAAAGTTTTGTGGCTGAAACAAGTCAGCGCATTAGTAAGTTACAGGAAGACACTTCTGCTCACCAGAATGTTGTTGCTGAAACCTTAAGTGCCCTTGAGAACAAGGAAAAAGAGCTGCAACTTTTAAATGATAAGGTAGAAACTGAGCAGGCAGAGATTCAAGAATTAAAAAAGAGCAACCATCTACTTGAAGACTCTCTAAAGGAGCTACAACTTTTATCCGAAACCCTAAGCTTGGAGAAGAAAGAAATGAGTTCCATCATTTCTCTAAATAAAAGGGAAATTGAAGAGCTGACCCAAGAGAATGGGACTCTTAAGGAAATTAATGCATCCTTAAATCAAGAGAAGATGAACTTAATCCAGAAAAGTGAGAGTTTTGCAAACTATATAGATGAAAGGGAGAAAAGCATTTCAGAGTTATCTGATCAGTACAAGCAAGAAAAACTTATTTTACTACAAAGATGTGAAGAAACCGGAAATGCATATGAGGATCTTA |
| 109 | CENPF | 2379898 | ACTGTGAAATAGATGCGGAAGAAAAGTATATTTCAGGGCCTCATGAGTTGTCAACAAGTCAAAACGACAATGCACACCTTCAG |
| 110 | CENPF | 2379899 | TCTGCAAACAACAATGAACAAGCTGAATGAGCTAGAGAAAATATGTGAAATACTGCAGGCTGAAAAGTATGAACTCGTAACTGAGCTGAATGATTCAAGGTCAGAATGTATCACAGCAACTAGGAAAATGGCAGA |
| 111 | CENPF | 2379900 | TGGCTCCATTGGACGAGAGTAATTCCTACGAGCACTTGACATTGTCAGACAAAGAAGTTCAAATGCACTTTGCCGAATTGCAAGAGAAATTCTTATCTTTACAAAGTGAACACAAAATTTTACATGATCAGCACTGTCAGATGAGCTCTAAAATGTCAGAGCTGCAGACCTATGTTGACTCATTAAAGGCCGAAAATTTGGTCTTGTCAACGAATCTGAGAAACTTTCAAGGTGACTTGGTGAAGGAGATGCAGCTGGGCTTGGAGGAGGGGCTCGTTCCATCCCTGTCATCCTCTTGTGTGCCTGACAGCTCTAGTCTTA |
| 112 | CENPF | 2379901 | GCTGACAAGCGTGACTCTGGAGATGGAGTCCAAGTTGGCGGCAGAAAAGAAACAGACGGAACAACTGTCACTTGAGCTGGAAGTAGCACGACTCCAGCTACAAGGTCTGGACTTAAGTTCTCGGTCTTTGCTTGGCATCGACA |
| 113 | CENPF | 2379902 | AGATACCAATTATGAGCCTCCAGGGGAAGATAAAACCCAGGGCTCTTCAGAATGCATTTCTGAATTGTCATTTTCTGGTCCTAATGCTTTGGTACCTATGGATTTCCTGGGGAATCAGGAAGATATCCATAATCTTCAACTGCGGGTAAAAGAGACATCAAATGAGAATTTGAGATTACTTCATGTGATAGAGGACCGTGACAGAAAAGTTGAAAGTTTGCTAAATGAAATGAAAGAATTAGACTCAAAACTCCATTTACAGGAGGTACAACTAATGACCAAAATTGAAGCATGCATAGAATTGGAAAAAATAGTTGGGGAACTTAAGAAAGAAAACTCAGATTTAAGTGAAAAAATTGGAATATTTTTCTTGTGATCACCAGGAGTTACTCC |
| 114 | CENPF | 2379903 | ATTGAGCATGAAGCCCTCTACCTGGAGGCTGACTTAGAGGTAGTTCAAACAGAGAAGCTATGTTTAGAAAAAGACAATGAAAATAAGCAGAAGGTTATTGTCTGCCTTGAAGAAGAACTCTCAGTGGTCACAAGTGAGAGAAACCAGCTTCGTGGAGAATTAGATACTATGTCAAAAAAAACCACGGCACTGGATCAGTTGTCTGAAAAAATGAAGGAGAAAACACAAGAGCTTGAGTCTCATCAAAGTGAGTGTCTCCATTGCATTCAGGTGGCAGAGGCAGAGGTGAAGGAAAAGACGGAACTCCTTCAGACTTTGTCCTCTGATGTGAGTGAGCTGTTAAAAGACAAAACTCATCTCCAGGAAAAGCTGCAGAGTTTGGAAAAGGACTCACAGGCACTGTCTTTGACAAAATGTGAGCTGGAAAACCAAATTGCACAACTGAATAAAGAGAAAGAATTGCTTGTCAAGGAATCTGAAAGCCTGCAGGCCAGACTGAGTGAATCAGATTATGAAAAGCTGAATGTCTCCAAGGCCTTGGAGGCCGCACTGGTGGAGAAAGGTGAGTTCGCATTGAGGCTGAGCTCAACACAGGAGGAAGTGCATC |

TABLE 8-continued

| Subtyping Target Sequences | | | |
|---|---|---|---|
| SEQ ID NO. | Gene | Affy Probeset ID | Sequence |
| | | | AGCTGAGAAGAGGCATCGAGAAACTGAGAGTTCGCATT GAGGCCGATGAAAAGAAGCAGCTGCACATCGCAGAGA AACTGAAAGAACGCGAGCGGGAGAATGATTCACTTAA GGATAAAGTTGAGAACCTTGAAAGGGAATTGCAGATGT CAGAAGAAAACCAGGAGCTAGTGATTCTTGATGCC |
| 115 | CENPF | 2379904 | AGAGTCTAGACCCACCAATAGAGGAAGAGCATCAGCTG AGAAATAGCATTGAAAAGCTGAGAGCCCGCCTAGAAG CTGATGAAAAGAAGCAGCTCTGTGTCTTACAACAACTG AAGGAAAGTGAGCATCATGCAGATTTACTTAAGGGTAG AGTGGAGAACCTTGAAAGAGAGCTAGAGATAGCCAGG ACAAACCAAGAGCATGCAGCTCTTGAGGCAGAGAATTC CAAAGGAGAGGTAGAGACCCTAAAAGCAAAAATAGAA GGGATGACCCAAAGTCTGAGAGGTCTGGAATTA |
| 116 | CENPF | 2379905 | GCTCAATGAGAGAGTGGCAGCCCTGCATAATGACCAAG AAGCCTGTAAGGCCAAAGAGCAGAATCTTAGTAGTCAA GTAGAGTGTCTTGAACTTGAGAAGGCTCAGTTGCTACA AGGCCTTGATGAGGCCAAAAATAATTATATTGTTTTGC AATCTTCAGTGAATGGCCTCATTCAAGAAGTAGAAGAT GGCAAGCAGAAACTGGAGAAGAAGGATGAAGAAATCA GTAGACTGAAAAATCAAATTCAAGACCAAGAGCAGCTT GTCTCTAAACTGTCCCAGGTG |
| 117 | CENPF | 2379907 | AGAGAAAAATAGGCTAGCTGGAGAGTTGC |
| 118 | CENPF | 2379908 | ATAGTGAATTGAAGAAGAGCCTAGATTGCATGCACAAA GACCAGGTGGAAAAGGAAGGGAAAGTGAGAGAGGAAA TAGCTGAATATCAGCTACGGCTTCATGAAGCTG |
| 119 | CENPF | 2379909 | AATCCAGACATACCGAGAGAAATTGACTTCTAAAGAAG AATGTCTCAGTTCACAGAAGCTGGAGATAGACCTTTTA AAGTCTAGTAAAGAAGAGCTCAATAATTCATTGAAAGC TACTACTCA |
| 120 | CENPF | 2379910 | TCTTCCTTTGGAAATTCATGATGCCATATCAGATGGTTT TAGAATTCTGCACTTTAATAATGTAATGCATATGCCATA TATAATATCCCAGAGGGATCTGCTATAATATTGCATAAT CGAATTCATATTTCTGCAGCAAAATGTGTGGATACTCTC ACAAGGCAGGATAAATAGA |
| 121 | CENPF | 2379911 | TTTTTCCATATGCTTATAAAAAGAAATTCA |
| 122 | CENPF | 2379912 | ATGGACAATCTAAAATATGTAAATC |
| 123 | CENPF | 2379913 | GAAGTTGTTGATCAAATCCTGTAAACAGCTGGAAGAGG AAAAGGAGATACTGCAGAAAGAACTCTCTCAACTTCAA GCTGCACAGGAGAAGCA |
| 124 | CENPF | 2379914 | TCTAAACAAGATTCCCGAGGGTCTCCTTTGCTAGGTCCA GTTGTTCCAGGACCATCTCCAATCCCTTCTGTTACTGAA AAGAGGTTATCATCTGGCCAAAATAAAGCTTCAGGCAA GAGGCAAAGATCCAGTGGAATATGGGAGAATGGTAGA GGACCAACACCTGCTACCCCAGAGAGCTTTTCTAAAAA AAGCAAGAAAGCAGTCATGAGTGGTATTCACCCTG |
| 125 | CENPF | 2379915 | GACTAGCCCATATATCCTGCGAAGAACAACCATGGCAA CTCGGACCAGCCCCCGCCTGGCTGCACAGAAGTTAGCG CTATCCCCACTGAGTCTCGGCAAAGAAAATCTTGCAGA GTCCTCCAAACCAACAGCTGGTG |
| 126 | CENPF | 2379918 | CTCAGCGGAGCCCAGTAGATTCAGGCACCATCCTCCGA GAACCCACCACGAAATCCGTCCCAGTCAATAATCTTCC TGAGAGAAGTCCGACTGACAGCCCCAGAGAGGGCCTG AGGGTCAAGCGAGGCCGACTTGTCCCCAGCCCCAAAGC TGGACTGGAGTCCAACGGCAGTGAGAAC |
| 127 | CENPF | 2379919 | TTCTCTTTAGTCAGGGCATGCTTTATTAGTGAGGAGAAA ACAATTCCTTAGAAGTCTTAAATATATTGTACTCTTTAG ATCTCCCATGTGTAGGTATTGAAAAAGTTTGGAAGCAC TGATCACCTGTTAGCATTGCCATTCCTCTACTG |

TABLE 8-continued

Subtyping Target Sequences

| SEQ ID NO. | Gene | Affy Probeset ID | Sequence |
|---|---|---|---|
| 128 | CENPF | 2379920 | CTTCCTAGAGGTGTGCTATACCATGCGTCTGTCGTTGTG CTTTTTTCTGTTTTTAGACCAATTTTTTACAGTTCTTTGG TAAGCATTGTCGTATCTGGTGATGGATTAACATATAGCC |
| 129 | EXO1 | 2388223 | GGCCATCAGCGCCAGTGCCACTCGCGCCCTCAAG |
| 130 | EXO1 | 2388225 | TCGGAGCGGGTTTCTCCAACCGCAATCGGCTCCGCTCA AGGGGAGGA |
| 131 | EXO1 | 2388226 | AAACGTGTCGTCTGGAATGGGCTTGGGGGCCACGCCTG CACATCTCCGCGAGACAGAGGGATAAAGTGAAGATGGT GCTGTTATTGTTACCTCGAGTGCCACATGCGACCTCTGA GATATGTACACAGTCATTCTTACTATCGCACTCAGCCAT TCTTACTACGCTAAAGAAGAAATAATTATTCGAGGATA TTTGCCTGGCCC |
| 132 | EXO1 | 2388227 | TAGTGAATCCCAGTCACTGAGTGGAGTTGAGAGTCTAA GAACCTCTGAAATTTGAGAACTGCTGGACCAGAGCCTT TAGAGCTCTGATAAGGTGTC |
| 133 | EXO1 | 2388229 | TGGGGATACAGGGATTGCTACAATTTATCAAAGAAGCT TCAGAACCCATCCATGTGAGGAAGTATAAAGGGCAGGT AGTAGCTGTGGATACATATTGCTGGCTTCACAAAGGAG CTATTGCTTGTGCTGAAAAACTAGCCAAAGGTGAACCT ACTGATA |
| 134 | EXO1 | 2388230 | CTATCTCATGGGATCAAGCCTATTCTCGTATTTGATGGA TGTACTTTACCTTCTAAAA |
| 135 | EXO1 | 2388231 | AGACGACAAGCCAATCTTCTTAAGGGAAAGCAACTTCT TCGTGAGGGGAAAGTCTCGGAAGCTCGAGAGTGTTTCA CCCGGTC |
| 136 | EXO1 | 2388232 | CTCGTGGCTCCCTATGAAGCTGATGCGCAGTTGGCCTAT CTTAACAAAGCGGGAATTGTGCAAGCCATAATTACAGA GGACTCGGATCTCCTAGCTTTTGGCTGTA |
| 137 | EXO1 | 2388233 | TGAAATTGATCAAGCTCGGCTAGGAATGTGCAGACAGC TTGGGGATGTATTCACGGAAGAGAAGTTTCGTTACATG TGTATTCTTTCAGGTTGTGACTACCTGTCATCACTGCGT GGGATTGGA |
| 138 | EXO1 | 2388234 | TATCACGGTACCAGAGGATTACATCAACGGGTTTATTC GGGCCAACAATACCTTCCTCTATCAGCTAGTTTTTGATC CCATCAAAAGGAAACTTATTCCTCTGAACGCCTATGAA GATGATGTTGATCCTGAAACACTAAGCTACGCTGGG |
| 139 | EXO1 | 2388235 | TGATGATTCCATAGCTCTTCAAATAGCACTTGGAAATA AAGATATAAATACTTTTGAACAGATCGATGACTACAAT CCAGACACTGC |
| 140 | EXO1 | 2388238 | CATAGTTGGGATGACAAAACATGTCAAAAGTCAGCTAA TGTTAGCAGCATTTGGCATAGGAATTACTCTCCCAGACC AGAGTCGGGTACTGTTTCAGATGCCCCACAATTGAAGG AAAATCCAAGTACTGTGGGAGTGGAACGA |
| 141 | EXO1 | 2388239 | ACCTGTTGAGTCAGTATTCTCTTTCATTTACGAAGAAGA CCAAGAAAAATAGCTCTGAAGGCAATAAATCATTGAGC TTTTCTGAAGTGTTTGTGCCTGACCTGGTAAATGGACCT ACTAACAAAAAGAGTGTAAGCACTCCACCTAGGACGA |
| 142 | EXO1 | 2388240 | GTGGTGCAGTTGTGGTTCCAGGGACC |
| 143 | EXO1 | 2388242 | GCCTCTGGATGAAACTGCTGTCACAGATAAAGAGAACA ATCTGCATGAATCAGAGTATGGAGACCAAGAAGGCAA GAGACTGGTTGACACAGATGTAGCACGTAATTCAAGTG ATGACATTCCGAATAATCATATTCCAGGTGATCATATTC CAGACAAGGCAACAGTGTTTACAGATGAAGAGTCCTAC TCTTTTGAGAGCAGCAAATTTACAAGGACCATTTCACC ACCCACTTTGGGAACACTAAGAAGTTGTTTTAGTTGGTC TGGAGGTCTTGGAGATTTTTCAAGAACGCCGAGCCCCT CTCCAAGCACAGCATTGCAGCAGTTCCGAAGAAAGAGC GATTCCCCCACCTCTTTGCCTGAGAATAATATGTCTGAT |

TABLE 8-continued

Subtyping Target Sequences

| SEQ ID NO. | Gene | Affy Probeset ID | Sequence |
|---|---|---|---|
| | | | GTGTCGCAGTTAAAGAGCGAGGAGTCCAGTGACGATGA GTCTCATCCCTTACGAGAAGAGGCATGTTCTTCACAGTC CCAGGAA |
| 144 | EXO1 | 2388244 | TCTGATTGCAATATTAAGTTACTTGACAGTCAAAGTGAC CAGACCTCCAAGCTACGTTTATCTCATTTC |
| 145 | EXO1 | 2388246 | GGCTATATAAGTCCAGTTCTGCAGACTCTCTTTCTACAA CCAAGATCAAACCTCTAGGACCTGCCAGAGCCAGTGGG CTGAGCAAGAAGCCGGCAAGCATCCAGAAGAGAAAGC ATCATAATGCCGAGAACAAGCCGGGG |
| 146 | EXO1 | 2388248 | AGAGATAACATCCAACTAACTCCAGAAGCGGAAGAGG ATATATTTAACAAACCTGAATGTGGCCGTGTTCAAAGA GCAATATTCCA |
| 147 | EXO1 | 2388253 | TCTCGCTGTGTCACAATCTCAGCTCACT |
| 148 | EXO1 | 2388254 | TTCCTCCATCCTAGGCAGAAATAAAGTCCCAAATCTTTG TTTTTTAACGGGTCATAGAGGACCCATCATCACCCTTTA TTCATTCCTTGATCATCTCAGGCTAGAGAAGTCTAGGGA TACAGCT |
| 149 | UBE2T | 2451201 | TGTCCTGGTTCATCTTAGTTAATGTGTTCTTTGCCAAGG TGATCTAAGTTGCCTACCTTGAATTT |
| 150 | UBE2T | 2451202 | ACCAGAGGCTGGTGACTCCAGAGTACACAACTCAACAC AGAAAAGGAAGGCCAGTCAGCTAGTAGGCATAGAAAA |
| 151 | UBE2T | 2451205 | ATTTAAATATAATAAGCCAGCCTTCCTCAAGAAT |
| 152 | UBE2T | 2451206 | GCTCTAACCACTGCAAATCATGTTTTTCT |
| 153 | UBE2T | 2451207 | CTCTGCAACACATATCCTACCTTGTCTATACCGCTAACT CTC |
| 154 | UBE2T | 2451208 | CATCCCTCAACATCGCAACTGTGTTGACCTCTATTCAGC TGCTCATGTCAGAACCCAACCCTGATGACCCGCTCATG GCTGACATA |
| 155 | UBE2T | 2451210 | TGAACCTCCTCAGATCCGATTTCTCACTCCAATTTATCA TCCAAACATTGATTCTGCTGGAAGGATTTGTCTGGATGT TCTCAAATTGCC |
| 156 | UBE2T | 2451214 | TGGAGCCAACACACCTTATGAGAAAGGTGTTTTTAAGC TAGAAGTTATCATTCCTGAG |
| 157 | UBE2T | 2451215 | AGAGCTTCACGTCTGAAGAGAGAGCTGCACATGTTAGC CACAGAGCCACCCCCAGGCATCACATGTTGGCAAGATA AAGACCAAATGGATGACCTGCGAGCTC |
| 158 | UBE2T | 2451216 | GTGTGTGGTTCCTTCTACTTGGGGATC |
| 159 | RRM2 | 2469253 | TCCCGCGCTGCGCTTGAAAATCGCGCGCGGCCCCGCGG CCAGCCTGGGTAGGGGCAAGGCGCAGCCAATGGGAAG GGTCGGAGGCATGGCACAGCCAATGGGAAGGGCCGGG GCACCAAAGCCAATGGGAAGGGCCGGGAGCGCGCGGC GCGGGAGATTTAAAGGCTGCTGGAGTGAGGGGTCGCCC GTGCACCCTGTCCCAGCCGTCCTGTCCTGGCTGCTCGCT CTGCTTCGCTGCGCCTCCACT |
| 160 | RRM2 | 2469254 | AGCTGCAGCTCTCGCCGCTGAAGGGGC |
| 161 | RRM2 | 2469255 | GACCCGCGTCCTGGCCAGCAAGACCGCGAGGAGGATCT TCCAGG |
| 162 | RRM2 | 2469256 | TCTGCTGCGACCCACGGAGTGCGACGGGACAGCCACGT TTTCACATCGGGCCCCGTGAAATTGCCGCCAATGGAAA GGACTTGGTCCAGAAAAACGTTAGTTTCATATGGTTCG CCCGGTACTTA |
| 163 | RRM2 | 2469257 | GCTGCCCCCGGCGTGGAGGATGAGCCGCTGCTG |

TABLE 8-continued

Subtyping Target Sequences

| SEQ ID NO. | Gene | Affy Probeset ID | Sequence |
|---|---|---|---|
| 164 | RRM2 | 2469258 | CCCGCCGCTTTGTCATCTTCCCCATCGAGTACCATGATATCTGGCAGATGTATAAGAAGGCAGAGGCTTCCTTTTGGACCGCCGAG |
| 165 | RRM2 | 2469259 | ATCGGAGGACCCCAGAAGACCCCTGCAGGG |
| 166 | RRM2 | 2469260 | CCCGAGGAGAGATATTTTATATCCCA |
| 167 | RRM2 | 2469261 | TGACGATCTGAGGTCGAACTAGTTCGCTTTCCTCGTCTTGTATGTTTTTCCATGCTGAGTGCATCTGTGTGTGTAAGCTGGGTTTTATATTACATGGCATTTCCTGTTTTGTAACACTTTGCAGTTCTTTCTTATGGTATTTTCCCGACTCTAGAGAAGCTGAGACAATATTAAGTGGTAGCAATGTGATGACTCTTTGTGGCC |
| 168 | RRM2 | 2469263 | AGTCTTCTTATTGACACTTACATAAAAGATCCCAAAGAAAG |
| 169 | RRM2 | 2469266 | CCCTGCTGTACTGGACTATGTTTTACTGTCTGTAGACCCTGAAGCTCAATATGAACTACAGAATACCCAAACTTGTATTAATGTAAATCAAGTGTTGAGGTTTTTAAAAGAACACTGGAGGGAAAAACTGACCAGTAAAAATAAAACATTTCGGTGTGAGTTCTTCCTTTAGGAAGAGGATTGGCAAATACTTGAATTTGGCCTTTGTCCCAGAGCTCTTATCTAGCAGTTGGTAATCGGAGGTCTTTTACTGTAATGCTTCAATTGCTGATACCGTATGTG |
| 170 | RRM2 | 2469267 | AACGATGCCTTGTGTCAAGAAGAAGGCAGACTGGGCCTTGCGCTGGATTGGGGACAAAG |
| 171 | RRM2 | 2469269 | TCGATATTCTGGCTCAAGAAACGAGGAC |
| 172 | RRM2 | 2469270 | CAACTCGGGCATGCTCTTGTGTTCACTGACGGGGACCTGAGATGCTAGATGGCATATATCCACATTTA |
| 173 | RRM2 | 2469273 | ACACCTGGTACACAAACCATCGGAGGAG |
| 174 | RRM2 | 2469275 | GCTCATTGGGATGAATTGCACTCTAATGAAGCAATACATTGAGTTTGTGGCAGACAGACTTATGCTGGAACTGGGTTTTAG |
| 175 | RRM2 | 2469276 | AGTAGAGAACCCATTTGACTTTATGGAGAATATTTCACTGGAAGGAAAGACTAACTTCTTTGAGAAGAGAGTAGGCGAGTATCAGAGGATGGGAGTGATGTCAAGTCCAACAGAGAATTCTTTTACCTTGGATGC |
| 176 | RRM2 | 2469277 | TGAAGATGTGCCCTTACTTGGCTGATTTTTTTTTTTCCATCTCATAAGAAAAATCAGCTGAAGTGTTACCAACTAGCCACACCATGAATTGTCCGTAATGTTCATTAACAGCATCTTTAAAACTGTGTAGCTACCTCACAACCAGTCCTGTCTGTTTATAGTGCTGGTA |
| 177 | RRM2 | 2469278 | CTTTAGTGAGCTTAGCACAGCGGGATTAAACAGTCCTTTAACCAGCACAGCCAGTTAAAAGATGCAGCCTCACTGCTTCAACGCAGATT |
| 178 | RRM2 | 2469279 | AGTCAGTCCTGTGTATACCTAGATATTAGTCAGTTGGTGCCAGATAGAAGACAGGTTGTGTTTTTATCCTGTGGCTTGTGTAGTGTCCTGGGATTCTCTGCCCCCTCTGAGTAGAGTGTTGTGGGATAAAGGAATCTCTCAGGGCAAGGAGCTTCTTAAGTTAAATCACTAGAAATTTAGGGGTGATCTGGGCCTTCATATGTGTGAGAAGCCGTTTCATTTTATTTCTCACTGTATTTTCCTCAACGTCTGGTTGATGAGAAAAAATTCTTGAAGAGTTTTCATATGTGGGAGCTAAGGTAGTATTGTAAAATTTCAAGTCATCCTTAAACAAAATGATCCACCTAAGATCTTGCCCCTGTTAAGTGGTGAAATCAACTAGAGGTGGTTCCTACAAGTTGTTCATTCTAGTTTTGTTTGGTGTAAGTAGGTTGTGTGAGTTAATTCATTTATATTTACTATGTCTGTTAAATCAGAAATTTTTTATTATCTATGTTCTTCTAGATTTTACCTGTAGTTCATACTTCAGTCACCCAGTGTCTTATTCTGGCATTGTCTAAATCTGAGCATTGTCTAGGGGGATCTTAAACTTTAGTAGGAAACCATGAGCTGTTAATACAGTTTCCATTCAAATATTAATTTCAGAATGAAACATAATT |

TABLE 8-continued

| Subtyping Target Sequences | | | |
|---|---|---|---|
| SEQ ID NO. | Gene | Affy Probeset ID | Sequence |
| | | | TTTTTTTTTTTTTTTGAGATGGAGTCTCGCTCTGTTGCCC AGGCTGGAGTGCAGTGGCGCGATTTTGGCTCACTGTAA CCTCCATCTCCTGGGTTCAAGCAATTCTCCTGTCTCAGC CTCCCTAGTAGCTGGGACTGCAGGTATGTGCTACCACA CCTGGCTAATTTTTGTATTTTTAGTAGAGATGGAGTTTC ACCATATTGGTCAGGCTGGTCTTGAACTCCTGACCTCAG GTGATCCACCCACCTCGGCCTCCCAAAGTGCTGGGATT GCAGGCGTGATAAACAAATATTCTTAATAGGGCTACTT TGAATTAATCTGCCTTTATGTTTGGGAGAAGAAAGCTG AGACATTGCATGAAAGATGATGAGAGATAAATGTTGAT CTTTTGGCCCCATTTGTTAATTGTATTCAGTATTTGAAC GTCGTCCTGTTTATTGTTAGTTTTCTTCATCATTTATTGT ATAGACAATTTTTAAATCTCTGTAATATGATACATTTTC CTATCTTTTAAGTTATTGTTACCTAAAGTTAATCCAGAT TATATGGTCCTTATATGTGTACAACATTAAAATGAAAG GCTTTGTCTTGCATTGTGAGGTACAGGCGGAAGTTGGA ATCAGGTTTTAGGATTCTGTCTCTCATTAGCTGA |
| 179 | RRM2 | 2469280 | GTCTCAAAATTGAATAATGCACAAGTCTTAAGTGATTA AAATA |
| 180 | MLPH | 2534256 | TGAGCACCCAAAGGCCGGCCCTAGAGTCCAGGAGAAG AGCGCAGCGGCGCGGAGCTCCCAGGCGTTCCCCGCAGC GCGTCCTCGGTCCTGGAACCACCGCGCCGCGCGTCCTG GCTTCCACATCTGCCCCATTTGCCCGCGGATCTTGACTT TTTCTTGGCGGGCAAGGCC |
| 181 | MLPH | 2534257 | GAGAGCCAGGCGCTAACCAGCCGCTCTGCGCCCCGCGC CCTGCTTGCCCCCATTATCCAGCCTTGCCCCGGCGCCCT GACCTGACGCCCTGGCCTGACGCCCTGCTTCGTCGCCTC CTT |
| 182 | MLPH | 2534258 | TGCTGGACCAGGGACTGAGCGTCCCCCGGAGAGG |
| 183 | MLPH | 2534261 | TTGGAAGTTGTTCAACGAGATTTTGACCTCCGAAGG |
| 184 | MLPH | 2534266 | CAAACCTGGGGCGTTAGCTCAACTCTTGCCCCCCTGCTG AAGGAGACCAAAACAATGCTTGATCAGGAAACACCATC TGGCTTTGCCCCCAGGATTCTGTGACTGCCCTGGGGAG GGCGCAGTGACCTGCCAACCAAAATTGGTACAATTGTA AACAGCCACAGAAATGCTTAAATGCAATATCATTTCTA TGAAATTAACGTGTTTCCATTCCATTCCAGCCACCAAAA TTGCCCGTTTGAGCTCAGCCCTCAAAACAAAGATGCCT GTGTGGCTTTGCCCAACGTTGGGTCACTGTTTTCTGCAT A |
| 185 | MLPH | 2534267 | ATGCCCAATATATTTCTTGTTTCTGATATT |
| 186 | MLPH | 2534268 | CGTTGAAGGGCAAGATTAAGAAGGAAAGCTCC |
| 187 | MLPH | 2534269 | AAGAGGGAGCTGCTTTCCGACACTGCCCATCTGAACGA GACCCACTGCGCCCGCTGCCTGCAGCCCTACCAGCTGC TTGTGAATAGCAAAAGGCAGTGCCTGGAATGTGGCCTC TTCACCTGCAAAAGCTGTGGCCGCGTCCACCCGG |
| 188 | MLPH | 2534271 | AGTCGTGAAGATCGGCTCACTGGAGTGGTACTATGAGC ATGTGAAAGCCCGCTTCAAGAGGTTCGGAAGTGCCAAG GTCATCCGGTCCCT |
| 189 | MLPH | 2534272 | AGTGGAGAGTAAGAACGGCTTTTTGTTCCCAGGCATTTT AGGAATATTAA |
| 190 | MLPH | 2534278 | ATGGGTGGGTAGGTGAATACATGGATGGATGAGCCACT GATTGAGTGGGTGGATGGGTGGATGAATAGATGGGTGG AGGATAGATAGGTGGGTGTATGGGTGGGTGGATGGATT GATGCATGGATGGATGGGCTGCCCATTGAGTAGGTGGA TGAGTGGATAAATGGGTGGGTGGGTAGGTGAATAGATG AATAGATTGATAAATAGGGGGATGGGTGGATTGGTAGA TGGGTAGATGGAGGGATACATTGCTGTGTGGATAGGTG GGTGAA |
| 191 | MLPH | 2534279 | GGATGGGTGGATGGGCTGACAAATGGC |

TABLE 8-continued

| Subtyping Target Sequences | | | |
|---|---|---|---|
| SEQ ID NO. | Gene | Affy Probeset ID | Sequence |
| 192 | MLPH | 2534280 | CTGGGCCTGAACTGATATCTGAAGAGAGAAGTGGAGAC AGCGACCAGACAGATGAGGATGGAGAACCTGGCTCAG AGGCCCA |
| 193 | MLPH | 2534281 | AAAAAGCGCCTCCTCTCCGTCCACGACTTCGACTTCGA GGGAGACTCAGATGACTCCACTC |
| 194 | MLPH | 2534288 | TCTGGGTGCCACTCCCATCCGGAAGAGCAGCCGACCAG CATCTCACCTTCCAGACACGGCGCCCTGGCT |
| 195 | MLPH | 2534290 | GGTCGAATGTCATCAGGAATGAGCAGCTGCCCCT |
| 196 | MLPH | 2534291 | CCGATGTGGACACCTCTGATGAGGAAAGCATCCGGGCT CACGTGATGGCCTCCCACCATTCCAAGCGGA |
| 197 | MLPH | 2534294 | ATCTTTGAGCTGAATAAGCATATTTCAGCTGTGGAATGC CTGCTGACCTACCTGGAGAACACAGTTGTGCCTCCCTTG GC |
| 198 | MLPH | 2534296 | GTCATTCCCGATCTTTCCACCGAGGGCCTCTGTGATTTG GGGGCTTTGTCAGGAAAGTGGAGCCTCACGGAAAAGCA TACTGGCTAAAACACGCGGCTTCTTCATCGACTCAATCT AATCATCCCCTTGGTGTTCGTCTGTGAGACCCCAGGCAG CCAGCCCTGTCGATCTGTCTCAATAGGCTTC |
| 199 | MLPH | 2534299 | GTGCTGGAGTGCGCACGGAGGCCGATGTAG |
| 200 | MLPH | 2534300 | AGGAGGAGGCCCTGAGGAGGAAGCTGGAGGAGCTGAC CAGCAACGTCA |
| 201 | MLPH | 2534301 | CAGGAGACCTCGTCCGAGGAGGAGGAAGCCAAGGACG AAAAGGCAGAGCCCAACAGGGACAAATCAGTTGGGCC TCTC |
| 202 | MLPH | 2534302 | GGCACGGCTGCCCATCAAACCAACAGACAG |
| 203 | MLPH | 2534303 | CTGGGGACCCCGTCCAGTACAACAGGACCACAGATGAG GAGCTGTCAGAGCTGGAGGACAGAGTGGCAGTGACGG CCTCAGAAGTCCA |
| 204 | MLPH | 2534304 | ATTGAATCCAGGATTGCAGCCCTGAGGGCCGCAGGGCT CACGGTGAAGCCCTCGGGAAAGCC |
| 205 | MLPH | 2534305 | TCTTTATGAGGGGACTCTGAGCCTCTGCTCTGAGGATCT GAAACACACACACCCTGACAGTGTAAAATCCAAAAGG AGCCGCCTGAATCATGTTGCCTCATGTGGAAATCCTTAG TCCGCCGCCACGTG |
| 206 | MLPH | 2534311 | AAGACCACACACCAGTGCAGTGTGATGGGCCTTTCTGC TGCTTCATTAGTGTGAGGATTTCCAGGGCCACAGTGAG GAAGAATGTTAATGCCAGTGCCAGAGCAAAGGAGAAA GAAGTTGGCAAAACTGTTGATTTGCATGACAGCTGAAA TGTAAATACTTTTTAAAAAATATGTGATGTGGAAGCTTC TTAAAAGGGGATATGTCCATTTTTTTCTACCTTTTAAAT TTCTGAGGAGGCCAAGGCACTTGTTTGGGCTAAGTATG TGATTGATAAAGCACCATCCC |
| 207 | MLPH | 2534312 | ATGATGATTCTTTTGATCGGAAATCAGTGTACCGAGGCT CGCTGACACAGAGAAACCC |
| 208 | MLPH | 2534313 | AGGAGTGGCCCCAACCAATGTGATCAGTCGCAGGAGGC AACCAATCAGAGGCTGAAGGGAAGTTACAAAGTTACAC ATGAAGACTTGGCCGATGACCAG |
| 209 | MLPH | 2534314 | AAACCTGTGGTGGCCCACCAGTCCT |
| 210 | MLPH | 2534315 | ACAGAGCAGCCCTGCACTGTTTTCCCTCCACCACAGCC ATCCTGTCCCTCATTGGCTCTGTGCTTTCCACTATACAC |
| 211 | MLPH | 2534316 | CACCTGCAAGTGGACAGCGACATTCAGTCCTGCACTGC TCACCTGGGTTTACTGATGACTCCTGGCTGCCCCACCAT CCTCTCTGATCTGTGAGAAACAGCTAAGCTGCTGTGACT TCCCTTTAGGACAATGTTGTGTAAATCTTTGAAGGACAC |

TABLE 8-continued

| Subtyping Target Sequences | | | |
|---|---|---|---|
| SEQ ID NO. | Gene | Affy Probeset ID | Sequence |
| | | | ACCGAAGACCTTTATACTGTGATCTTTTACCCCTTTCAC TCTTGGCTTTCTTATGTTGCTTTCATGAATGGAATGGAA AAAAGATGACTCAGTTAAGGCACCAGCCATATGTGTAT TCTTGATGGTCTATATCGGGGTGTGAGCAGATGTTTGCG TATTTCTTGTGGGTGTGACTGGATATTAGACATCCGGAC AAGTGACTGAACTAATGATCTGCTGAATAATGAAGGAG GAATAGACACCCCAGTCCCCACCCTACGTGCACCCGCT CTGCAAGTTCCCATGTGATCTGTAGACCAGGGGAAATT ACACTGCGGTCAAGGGCAGAGCCTGCACATGACAGCAA GTGAGCATTTGATAGATGCTCAGATGCTAGTGCAGAGA GCCTGCTGGGAGACGAAGAGACAGCAGGCAGAGCTCC AGATGGGCAAGGAAGAGGCTTGGTTCTAGCCTGGCTCT GCCCCTCACTGCAGTGGATCCAGTGGGGCAGAGGACAG AGGGTCACAACCAATGAGGGATGTCTGCCAAGGATGGG GGTGCAGAGGCCACAGGAGTCAGCTTGCCACTCGCCCA TTGGTTACATAGATGATCTCTCAGACAGGCTGGGACTC AGAGTTATTTCCTAGTATCGGTGTGCCCCATCCAGTTTT AAGTGGAGCCCTCCAAGACTCTCCAGAGCTGCCTTTGA ACATCCTAACAGTAATCACATCTCACCCTCCCTGAGGTT CACTTTAGACAGGACCCAATGGCTGCACTGCCTTTGTCA GAGGGGGTGCTGAGAGGAGTGGCTTCTTTTAGAATCAA ACAGTAGAGACAAGAGTCAAGCCTTGTGTCTTCAAGCA TTGACCAAGTTAAGTGTTTCCTTCCCTCTCTCAATAAGA CACTTCCAGGAGCTTTCCAATCTCTCACTTAAAACTAAG GTTTGAATCTCAAAGTGTTGCTGGGAGGCTGATACTCCT GCAACTTCAGGAGACCTGTGAGCACACATTAGCAGCTG TTTC |
| 212 | GPR160 | 2651840 | CCAGGAGTGGAGCCCGGACGCCCGAGCCTTCCTGCTTC GGGATGGGGATTACCGCGGAGCCTTAGCAACTG |
| 213 | GPR160 | 2651841 | ATCCTGGCTGGCTCAAAATTCCCTCTAGATTACCTGCGA CCACCCCCAGGAACCCGGAGACTGAAACTCCT |
| 214 | GPR160 | 2651842 | CCTGCAGTCCGGAGACGAACGCACGGACCGGGCCTCCG GAGGCAGGTTCGGCTGGAAGGAACCGCTCTCGCTTCGT CCTACACTTGCGCAAATGTCTC |
| 215 | GPR160 | 2651850 | GCTTTGTGCAGTGGCCATTTCATAGCCAGTGAAGTTTAT CTGAGGCACTTGCTAATTGAAAACTTTTCTCAATACCCT GCCATGATGAAATATGGTTGGCACTGGCAATTTT |
| 216 | GPR160 | 2651851 | ATGTCCAAGTCCCGTGCGGCGGAGGCAGCAGCGGGGGT GACAGCGACGGCCCCGAGCCCGCAGATAGTGGAGCAG AGGGGTCCAGGGAGGCGCTGCACCGACGTTGGGGAGA AT |
| 217 | GPR160 | 2651852 | TTCAGGAGGAGAACTCCGTTACACGTCACGAA |
| 218 | GPR160 | 2651853 | AAAACCTCCGGCCTCGTCTTGTGATTCCACCAATGCAGC CATCGCCAAGCAAGCCTTGAAATAGCCCATCAAGGGCA AACAGGCCCCCGAAAAAAAGCTCAAGGAAAAGTCGCA AACTCACGGATTTCTACCCTGTCCCAAGGAGCTCCAGG AAGGGCAAAGCGGAGCTGCAATTTGAAGAAAGGGAAA GAATAGATGAATTGGTTGAAAGCGGAAAGGAAAGAAG GAGTGAAGACTGACCTCATCAATGACAAAGGCCGGGTG TGAACACCAGAGGGAGCTCTCCCGGGGCGCCTTTGTGG TAGAAAAGCACCGGAGCCTCACGGAGATCACCGACGCC ACGGGACCCCTCCATGGTGGATCTCCGTGGATCTCC |
| 219 | GPR160 | 2651854 | GTTGAACGTTTTGTGCTTCCCATGCATGC |
| 220 | GPR160 | 2651864 | TGCTCCACTTATCGGGCTCACCAAATACAGCTGCAGTAT GAATTCCATCTTCTACACAACAGTAAACCAGAATGTTC ATGTTCACAGCGTTCATCTCCCATCCTGTTGTCTAACGC ACATGGTTTTTTTAAACTTTTCTAAGATTGCATGAGATT CTGCAACACAACTGATTATAAAAACACTTGAAGTTTTT ACCTTTTTTTTTACTTTCCAACTCTCGTGAATGTACAGA GGACTTTCCA |
| 221 | GPR160 | 2651865 | CAGGGGAGAATAAGCTGAACGCAGCTGTTCTCTGACCT TGAGGCAGAGGGCAAGGAGTAGGTACAAGGACGTGTA GGAGAATTTATCTTAAATAGGCTTGTTCACTTGTGTTGT CCAGAAACGACTTTTGATCATCAGCGCGCATGACTGCT |

TABLE 8-continued

Subtyping Target Sequences

| SEQ ID NO. | Gene | Affy Probeset ID | Sequence |
|---|---|---|---|
| | | | CCCTGAAAGGAAGAACAATAATGTTAATTACCCGCAGACTGTGTTTGCTCCAGGCTTTCGGCATTATGTCTGTACTGAATAAAAGCAAGCAGCTCCAGCTGTTCGAGGCTGCTCTCTTCTTCAGCCATTAGTGCCGGGCAGCCC |
| 222 | GPR160 | 2651866 | AGCTTACTCACATAGCATATTGGTATATCAAAATGAAATGCAAGGAACCAAAAATAACATAATTGAAGGCAGTAAAAGTGAAATTAAATAGGAAGATCATCAGTCAA |
| 223 | GPR160 | 2651869 | GAGCTTCAGGAAAAGACTTAATCTGAAGGATCCTGCAGCTAAAAAGCTTTGAAAACTGTGTTAAGGGGCCCCATAAGCATCGCTTCTAAACTTCACTGACAAAAGGGACTGGGGTCATGCTGTCTGGAGTCA |
| 224 | GPR160 | 2651870 | TGTATTTCAGCAGGTCTTCTTGAAA |
| 225 | GPR160 | 2651871 | TCCAGTTTTCCTGACAGCTTGTATAGATTATTGCCTGAATTTCTCTAAAACAACCAAGCTTTCATTTAAGTGTCAAAAATTATTTTATTTCTTTACAGTAATTTTAATTTGGATTTCAGTCCTTGCTTATGTTTTGGGAGACCCAGCCATCTACCAAAGCCTGAAGGCACAGAATGCTTATTCTCGTCACTGTCCTTTCTATGTCAGCATTCAGAGTTACTGGCTGTCATTTTTCATGGTGATGATTTTATTTGTAGCTTTCATAACCTGTTGGGAAGAAGTTACTACTTTGGTACAGGCTATCAGGA |
| 226 | GPR160 | 2651872 | TGTTTTACTTAAAGTTCAGATTCCAGCATATATTGAGATGAATATTCCCTGGTTATACTTTGTCAATAGTTTTCTC |
| 227 | GPR160 | 2651873 | AAAGACATTGGATTACCTTTGGATCCATTTGTCAACTGGAAGTGCTGCTTCATTCCACTTACAATTCCTAATCTTGAGCAAATTGAAAAGCCTATATCAATAATGATT |
| 228 | GPR160 | 2651874 | GTTACAGCTGTCATAAGATCATAATTTTATGAACAGAAAGAACTCAGGACATATTAAAAA |
| 229 | GPR160 | 2651875 | CCCTGACTGATAGCATTTCAGAATGTGTCTTTTGAAGGGCTATGATACCAGTTATTAAATAGTGTTTTATTTTAAAAACAAAATAATTCCAAGAAGTTTTTATAGTTATTCAGGGACACTATATTACAAATATTACTTTGTTATTAACACAAAAAGTGATAAGAGTTAACATTTGGCTATACTGATGTTTGTGTTACTCAAAAAAACTACTGGATGCAAACTGTTATGTAAATCTGAGATTTCACTGACAACTTTA |
| 230 | CCNB1 | 2813417 | GTGCGGGGTTTAAATCTGAGGCTAG |
| 231 | CCNB1 | 2813418 | CTCTTCTCGGCGTGCTGCGGCGGAACGGCTGTTGGTTTCTGC |
| 232 | CCNB1 | 2813419 | GTAGGTCCTTGGCTGGTCGGGCCTCCGGTGTTCTGCTTCTCCCC |
| 233 | CCNB1 | 2813420 | AGCCGCTTCGGACTGCGAACTAACGCGGCCTTCTTAGCTGCTGCCTGCTCTCCCTGCCTCGCCTGCGGGAGCCTCCCGAGCGGGAGAGGGCCGCAGGAGCGATTTGGGGAGGAAGGTGGGAGGGGACTCACCAAGAGAGCGCCGAGGTGGG |
| 234 | CCNB1 | 2813421 | TGCTGAAAATAAGGCGAAGATCAACATGGCAGGCGCAAAGCGCGTTCCTACGGCCCCTGCTGCAACCTCCAAGCCCGGACTGAGGCCAAGAACAGCTCTTGGGGACATTGGTAACAAAGTCAGTG |
| 235 | CCNB1 | 2813422 | AAGCAAAACCTTCAGCTACTGGAAAAGTCATTGATAAAAAACT |
| 236 | CCNB1 | 2813425 | ACTGGAAACATGAGAGCCATCCTAATTGACTGGCTAGTACAGGTTCAAATGAAATTCAGGTTGTTGCAGGAGACCATGTACATGACTGTCTCCATTATTGATCGGTTC |
| 237 | CCNB1 | 2813427 | TGTGACTGACAACACTTATACTAAGCACCAAATCAGACAGATGGAAATGAAGATTCTAAGAGCTTTAAACTTTGGTCTGGGTCGGCCTCTACCTTTGCACTTCCTTCGGAGAGCATCTAAGATTGG |

TABLE 8-continued

Subtyping Target Sequences

| SEQ ID NO. | Gene | Affy Probeset ID | Sequence |
|---|---|---|---|
| 238 | CCNB1 | 2813429 | TGATGTCGAGCAACATACTTTGGCCAAATACCTGATGGAACTAACTATGTTGGACTATGACATGGTGC |
| 239 | CCNB1 | 2813432 | AACATTACCTGTCATATACTGAAGAATCTCTTCTTCCAGTTATGCAGCACCTGGCTAAGAATGTAGTCATGGTAAATCAAGGACTTACAAAGC |
| 240 | CCNB1 | 2813434 | TCAAGAACAAGTATGCCACATCGAAGCATGCTAAGATCAGCACTCTACCACAGCTGAATTCTGCACTAGTTCAAG |
| 241 | CCNB1 | 2813435 | AAACTTGAGTTGGAGTACTATATTTACAA |
| 242 | CCNB1 | 2813436 | ATTACTGTTGCATTTACTTTTAATAAAGCTTGTGG |
| 243 | CCNB1 | 2813437 | CCTGGGGATCCAATTGATGTATATGTTTATATACTGGGTTCTTGTTTTATATACCTGGCTTTTACTTTATTAATATGAGTTACTGAAGGTGATGGAGGTATTTGAAAATTTTACTTCCATAGGACATACTGCATGTAAGCCAAGTCATGGAGAATCTG |
| 244 | CXXC5 | 2831352 | CCCGGGCAGCGTTCATAGCTCCTGCCCGGGCGGGCGCGCGGCGGCGGCGGCAGAGGCGGCTGAGCCTGAGCGGGGATGTAGAGGCGGCGGCAGCAGAGGCGGCACTGGCGGCAAGAGCAGACGCCCGAGCCGAGCGAGAAGAGCGGCAGAGCCTTATCCCCTGAAGCCGGGCCCCGCGTCCCAGCCCTGCCCAGCCCGCGCCCAGCCATGCGCGCCGCCTGCTGAGTCCGGGCGCCGCACGCTGAGCCCTCCGCCCGCGAGCCGCGCTCAGCTCGGGGGTGATTAGTTGCTTT |
| 245 | CXXC5 | 2831353 | AGTTCGCTGCAAGTCGGCGGAAAGTTTGGCTGCGCGGGTTCCCCCGAAGTTCA |
| 246 | CXXC5 | 2831354 | CCTCATCCTCGCAGTAGCTGGGTCTCTCCCAGGGACGCCCCTAGTCAGCCTTGG |
| 247 | CXXC5 | 2831356 | GTAATTATGGAATTTTGCTTGGGAAATTAATTTGAAAAAGTTAATTAATTGGTGGTTCCGGAGGTGGCGGGCTCCACGCCCGGCCAGTCTTGCTGACGTCAGTGCTGACCCACTGGAGACGTGCAGCTTCCG |
| 248 | CXXC5 | 2831357 | GGGGTCTGTGACAGCTTGCCCCCAACCACGGAGAGG |
| 249 | CXXC5 | 2831359 | TTGTCCAGGGTGGTCTCAAAACTCC |
| 250 | CXXC5 | 2831360 | CTGAGCAGCGAGGCCCACCAGGCATCTCTGTTGTGGGCAGCAGGGCCAGGTCCTGGTCTGTGGACCCTCGGCAGTTGGCAGGCTCCCTCTG |
| 251 | CXXC5 | 2831361 | GCTCCCAGGATGCCGGCGGCAGTAGCAG |
| 252 | CXXC5 | 2831362 | CAGGAGCAGCAGACAAGAGTGCAGTGGTGGCTGCCGCCGCACCAG |
| 253 | CXXC5 | 2831363 | CCCGAGCGTCGGAACAAGAGCGGTATCATCAGTGAGCCCCTCAACAAGAGCCTGCGCCGCTCCCGC |
| 254 | CXXC5 | 2831364 | CCATGGCGGTGGACAAAAGCAACCCTACCTCAAAGCACAAAAGTGGTGCTGTGGCCAGCCTGCTGAGCAAGGCAGAGCGGGCCACGGAGCTGGCAGCCGAGGGACAGCTGACGCTGCAGCAGTTTGCGCAGTCCACAGAGATGCTGAAGCGCGTGGTGCAGGAGCATCTCCCGCTGATGAGCGAGGCGGGTGCTGGCCTGCCTGACATGGAGGCTGTGGCAGGTGCCGAAGCCCTCAATGGCCAGTCCGACTTCCCCTACCTGGGCGCTTTCCCCATCAACCCAGGCCTCTTCATTATGACCCCGGCAGGTGTGTTCCTGGCCGAGAGCGCGCTGCACATGGCGGGCCTGGCTGAGTACCCCATGCAGGGAGAGCTGGCCTCTGCCATCAGCTCCGGCAAGAAGA |
| 255 | CXXC5 | 2831365 | TTCAGAAAATGTGAGGAACTCAAAAAGAAGCCTTCCGCTGCTCTGGA |
| 256 | CXXC5 | 2831367 | GTGATGCTTCCGACGGGAGCCGCCTTCCGGTGGTTTCAGTGA |

TABLE 8-continued

Subtyping Target Sequences

| SEQ ID NO. | Gene | Affy Probeset ID | Sequence |
|---|---|---|---|
| 257 | CXXC5 | 2831368 | AATGTCACTGCTCGTGTGGTCTCCAGCAAGGGATTCGG GCGAAGACAAACGGATGCACCCGTCTTTAGAACCAAAA ATATTCTCTCACAGATTTCATTCCTGTTTTTATATATATA TTTTTTGTTGTCGTTTTAACATCTCCACGTCCCTAGCATA AAAAG |
| 258 | CXXC5 | 2831369 | ATCTATAAAGTACCGAGACTTCCTGGGCAAAGAATGGA CAATCAGTTTCCTTCCTGTGTCGATGTCGATGTTGTCTG TGCAGGAGATGCAGTTTTTGTGTAGAGAATGTAAATTTT CTGTAACCTTTTGAAATCTAGTTACTAATAAGCACTACT GTAATTTAGCACAGTTTAACTCCACCCTCATTTAAACTT CCTTTGATTCTTTCCGACCATGAAATAG |
| 259 | CXXC5 | 2831370 | CCTGGAGAATCCACTCACGTTCATAAAGAGAATGTTGA TGGCGCCGTGTAGAAGCCGCTCTGTATCCATCCACGCG TGCAGAGC |
| 260 | PTTG1 | 2838203 | GGCTTAGATGGCTCCGAGCCCGTTTGAGCGTGGTCTCG GACTGCTAACTGGACCAACGGCAACTGTCTGATGAGTG CCAGCCCCAAACCGCGCGCTGCTCGGGACCTTAGAGCC TCTG |
| 261 | PTTG1 | 2838204 | TGTTCCGCTGTTTAGCTCTTGTTTTTTGTGTGGACACTCC TAGGATAGAAAGTTTGGTATGTTGCTATACCTTTGCTTC |
| 262 | PTTG1 | 2838205 | GCACCCGTGTGGTTGCTAAGGATGGGC |
| 263 | PTTG1 | 2838206 | TATACAAGGCTGCAGTCGGATACACTGGTATTGTGGAC GTGGCCTGGAGCTGGACGAGACATTTAGTGTACTTTTTG GGCAATTGGAGTCGTTTGTTATTGGTCCTTTTTCATTTTT AATATCTTAATGAGATGATTTAAGGAAGTTACTGAATC TCTGCTATTAGGCCTATC |
| 264 | PTTG1 | 2838207 | GATCTCAAGTTTCAACACCACGTTTTGGCAAAACGTTCG ATGCCCCACCAGCC |
| 265 | PTTG1 | 2838208 | GTAAGTGTTGGCTATAAAGACACTGTTTAAACACTTAA GCACTTTTGACTCTTAAAATGACTATTGGCATCATCCTA CGTAGCTTTCTTC |
| 266 | PTTG1 | 2838209 | CTGCCTCAGATGATGCCTATCCAGAAATAGAAAAATTC TTTCCCTTCAATCCTCTAG |
| 267 | PTTG1 | 2838210 | ATGAGACTGTCTGAATCTGGGTTGCTTTGGACAAGTGT ACTTGTTGATGGAATTATTTGCAAGGTATCATCTTAGGT CAGGAGGGGAATAGGAACAAAGATGTAGAAGACATTG TTCCTGTCTGTAAAAGCTTATCACCTAGAGGAGGTAAG ATGTATTCATGAACATTGAATAAGTCCCATTGTGGACA GTCTTTCTCACAAGGCTT |
| 268 | PTTG1 | 2838211 | CTGAAGAGCACCAGATTGCGCACCTCCCCTTGAGTGGA GTGCCTCTCATGATCCTTGACGAGGAGAGAGA |
| 269 | PTTG1 | 2838212 | CTGTTGCAGTCTCCTTCAAGCATTCTGTCGACCCTGGAT GTTGAATTGCCACCTGTTTGCTGTGACATAGATAT |
| 270 | PTTG1 | 2838213 | TCTTAGTGCTTCAGAGTTTGTGTGTATTTGT |
| 271 | FGFR4 | 2842913 | CCGCCGTCGCGGGTACATTCCTCGCTCCCGGCCGAGGA GCGCTCGGGCTGTCTGCGGACCCTGCCGCGTGCAGGGG TCGCGG |
| 272 | FGFR4 | 2842915 | GGCAGTTGGTGGGAAGTCCAGCTTGGGTCCCTGAGAGC T |
| 273 | FGFR4 | 2842916 | CCCTGTTGGGGGTCCTGCTGAGTGTGCCTGGGCCTCCAG TCTTGTCCCTGGAGGCCTCTGAGGAAGTGGA |
| 274 | FGFR4 | 2842918 | TACAAGGAGGGCAGTCGCCTGGCACCTGCTGGCCGTGT ACGGGGCTGGAGGGGCCGCCTAGAGATTGCCAGCTTCC TACCTGAGGATGCTGGCCGCTACCTCTGCCTGGCACGA GGCTCCATGATCGTCCTGCAGA |

TABLE 8-continued

Subtyping Target Sequences

| SEQ ID NO. | Gene | Affy Probeset ID | Sequence |
|---|---|---|---|
| 275 | FGFR4 | 2842920 | TTGACCTCCAGCAACGATGATGAGGACCCCAAGTCCCA TAGGGACCCCTCGAATAGGCACAGTTACCCCCAGCAA |
| 276 | FGFR4 | 2842921 | GCTGCTCATCTGATCACTGAGAAGAGGAGGCCTGTGTG GGAACACACGGTCATTCTAGGGGCCTTCC |
| 277 | FGFR4 | 2842922 | CTGCATGCAGTACCTGCGGGGAACACCGTCAAGTTCCG CTGTCCAGCTGCAGGCAACCCCACGCCCACCATCCGCT GGCTTAAGGATGGACAGGCCTTTCATGGGGAGAACC |
| 278 | FGFR4 | 2842923 | CTGCGCCATCAGCACTGGAGTCTCGTG |
| 279 | FGFR4 | 2842924 | ACATACACCTGCCTGGTAGAGAACGCTGTGGGCAGCAT CCGCTATAACTACCTGCTAGAT |
| 280 | FGFR4 | 2842926 | CGGCCAACACCACAGCCGTGGTGGGCAGCGACGTGGA GCTGCTGTGCAAGGTGTACAGCGATGCCCAGCCCCACA TCCAGTGGCTGAAGCACATCGTCATCAACGGCAGCAGC TTCGGAGCCGACGGTTTCC |
| 281 | FGFR4 | 2842928 | AGGTCCTGTACCTGCGGAACGTGTCAGCCGAGGACGCA GGCGAGTACACCTGCCTCGCAGGCAATTCCATCGGCCT CTCCTACCAGTCTG |
| 282 | FGFR4 | 2842929 | AGGAGATGCTGCGAGATGCCCCTCTGGGCC |
| 283 | FGFR4 | 2842930 | GCCCGAGGCCAGGTATACGGACATCATCCTGTACGCGT CGGGCTCCCTGGCCTTGGCTGTGCTCCTGCTGCTGGCCG GGCTGTATCGAGGGCAGGCGCTCCACG |
| 284 | FGFR4 | 2842931 | GGCGCATCCCCCACCTCACATGTGACAGCCTGACTCCA GCAGGCAGAACCAAGTCT |
| 285 | FGFR4 | 2842932 | TTCCGGCAAGTCAAGCTCATCCCTGGTACGAGGCGTGC GTCTCTCCTCCAGCGGCCCCGCCTTGCTCGCCGGCCTCG TGAGTCTAGATCTACCTCTCGACCCACTATGGGAGTTC |
| 286 | FGFR4 | 2842933 | CCCTAGGCGAGGGCTGCTTTGGCCAGGTAGTACGTGCA GAGGCCTTTG |
| 287 | FGFR4 | 2842934 | AGGTGATGAAGCTGATCGGCCGACACAAGAACATCATC A |
| 288 | FGFR4 | 2842935 | CCCTGTACGTGATCGTGGAGTGCGCCGCCAAGGGAAAC CTGCGGGAGTTCCTGCGGGCCCGGCGCCCCCCAGGCCC CGACCTCAGCCCCGACGGTCCTCGGAGCAGTGAGGGGC |
| 289 | FGFR4 | 2842936 | CGGCGTCCACCACATTGACTACTATAAGAAAA |
| 290 | FGFR4 | 2842938 | GGCCTTGTTTGACCGGGTGTACACACACCAG |
| 291 | FGFR4 | 2842939 | TCGGGGGCTCCCCGTATCCTGGCATCCCGGTGGAGGAG CTGTTCTCGCTGCTGCGGGAGGGACATCGGATGGACCG ACCCCCACACTGC |
| 292 | FGFR4 | 2842940 | CTGAGGCTCCCTGTGACCCTCCGCCC |
| 293 | FGFR4 | 2842941 | ACGGGCTGATGCGTGAGTGCTGGCACGCAGCGCCCTCC |
| 294 | FGFR4 | 2842943 | CTCGACCTCCGCCTGACCTTCGGACCCTATTCCCCCTCT GGTGGGGACGCCAGCAGCACCTGCTCCTCCAGCGATTC TGTCTTCAGCCACGACCCCCTGCCATTGGGATC |
| 295 | FGFR4 | 2842944 | CCTGACACAGTGCTCGACCTTGATAGCATGGGGCCCCT GGCCCAGAGTTGCTGTGCCGTGTCCAAGGGCCGTGCCC TTGCCCTTGGAGCTGCCGTGCCTGTGTCCTGATGGCCCA AATGTCAGGGTTCTGCTCGGCTTCTTGGACCTTGGCGCT TAGTCCCCATCCCGGGTTTGGCTGAGCCTGGCTGGAGA GCTGCTATGCTAAACCTCCTGCC |
| 296 | FOXC1 | 2891769 | AGAAGGGCGCCTGCTTGTTCTTTCTTTTTGTCTGCTTTCC CCCGTTTGCGCCTGGAAGCTGCGCCGCGAGTTCCTGCA AGGCGGTCTGCCGCGGCCGGGCCCGGCCTTCTCCCCTC GCAGCGACCCCGCCTCGCGGCCGCGCGGGCCCCGAGGT |

TABLE 8-continued

| Subtyping Target Sequences | | | |
|---|---|---|---|
| SEQ ID NO. | Gene | Affy Probeset ID | Sequence |
| | | | AGCCCGAGGCGCCGGAGGAGCCAGCCCCAGCGAGCGC CGGGAGAGGCGGCAGCGCAGCCGGACGCACAGCGCAG C |
| 297 | FOXC1 | 2891770 | ATGCAGGCGCGCTACTCCGTGTCCAGCCCCAACTCCCT GGGAGTGGTGCCCTACCTCGGCGGCGAGCAGAGCTACT ACCGCGCGGCGGCCGCGGCGGCCGGGGGCGGCTACAC CGCCATGCCGGCC |
| 298 | FOXC1 | 2891771 | ATGAGCGTGTACTCGCACCCTGCGCACGCCGAGCAGTA CCCGGGCGGCATGGCCCGCGCCTACGGGCCCTACACGC CGCAGCCGCAGCCCAAGGACATGGTGAAGCCGCCCTAT AGCTACATCGCGCTCATCACCATGGCCATCCAGAACGC CCCGGACAAGAAGATCACCCTGAAC |
| 299 | FOXC1 | 2891772 | AGGACAGGCTGCACCTCAAGGAGCCGCCCCCG |
| 300 | FOXC1 | 2891773 | GCCGACGGCAACGCGCCCGGTCCGCA |
| 301 | FOXC1 | 2891774 | GCGCATCCAGGACATCAAGACCGAGAACG |
| 302 | FOXC1 | 2891775 | CGCCGCGGTGCCCAAGATCGAGAGCCCCGACAGCAGCA GCAGCAGCCTGTCCAGCGGGAGCAGCCCCCCGGGCAGC CTGCCGTCGGCGCGGCCGCTCAG |
| 303 | FOXC1 | 2891776 | CCGCCGCCGCACCATAGCCAGGGCTTCAGCGTGGACAA CATCATGACGTCGCTGCGGGGGTCGCCGCAGAGCGCGG CCGCGGAGCTCAGCTCCGGCCTTCTGGCCTCGGCGGCC |
| 304 | FOXC1 | 2891777 | GTCCTCGCGCGCGGGGATCGCACCCCCGCTGGCGCTCG GCGCCTACTCGCCCGGCCAGAGCTCCCTCTACAGCTCCC CCTGCAGCCAGACCTCCAGCGCGGGCAGCTCGGGCGGC GGCGGCGGCGGCGCGGGGGCCGCGGGGGGCGCGGGCG GCGCCGGGACCTACCACTGCAACCT |
| 305 | FOXC1 | 2891778 | ATGAGCCTGTACGCGGCCGGCGAGCGCGGGGGCCACTT GCAGGGCGCGCCCGGGGGCGCGGGCGGCTCGGCCGTG GACGACCCCCTGCCCGACTACTCTCTGCCTCCGGT |
| 306 | FOXC1 | 2891779 | GGCCGGCCACCACCCTGCGGCCCACCAAGGCCGCCTCA C |
| 307 | FOXC1 | 2891780 | ACCTGGGCCACTTGGCGAGCGCGGCGG |
| 308 | FOXC1 | 2891781 | CAGAACTTCCACTCGGTGCGGGAGATGTTCGAGTCACA GAGGATCGGCTTGAACAACTCTCCAGTGAACGGGAATA GTAGCTGTCAAATGGCCTTCCCTTCCAGCCAGTCTCTGT ACCGCACGTCCGGAGCTTTCGTCTACGA |
| 309 | FOXC1 | 2891782 | TGAGAATATTCACCACACCAGCGAACAGAATATCCCTC CAAAAATTCAGCTCACCAGCACCAGCACGAAGAAAACT CTATTTTCTTAACCGATTAATTCAGAGCCACCTCCACTT TGCCTTGTCTAAATAAACAAACCCGTAAACTGTTTTATA CAGAGACAGCAAAATCTTGGTTTATTAAAGGACAGTGT TACTCCAGATAACACGTAAGTTTCTTCTTGCTTTTCAGA GACCTGCTTTCCCCTCCTCCCGTCTCCCCTCTCTTGCCTT CTTCCTTGCCTCTCACCTGTAAGATATTATTTTATCCTAT GTTGAAGGGAGGGGGAAAGTCCCCGTTTATGAAAGTCG CTTTCTTTTTATTCATGGACTTGTTTTAAAATGTAAATTG CAACATAGTAATTTATTTTTAATTTGTAGTTGGATGTCG TGGACCAAACGCCAGAAAGTG |
| 310 | FOXC1 | 2891783 | GGAGAAACCCTCTGACTAGTCCATGTCAAATTTTACTA AAAGTCTTTTTGTTTAGATTTATTTTCCTGCAGCATCTTC TGCAAAATGTACTATATAGTCAGCTTGCTTTGAGGCTAG TAAAAAGATATTTTTCTAAACAGATTGGAGTTGGCATA TAAACAAATACGTTTTCTCACTAATGACAGTCCATGATT CGGAAATTTTAAGCCCATGAATCAGCCGCGGTCTTACC ACGGTGATGCCTGTGTGCCGAGAGATGGGACTGTGCGG CCAGATATGCACAGATAAATATTTGGCTTGTGTATTCCA TATAAAATTGCAGTGCATATTATACATCCCTGTGAGCCA GATGCTGAATAGATATTTTCCTATTATTTCAGTCCTTTA TAAAAGGAAAAATAAACCAGTTTTTAAATGTATGTATA TAATTCTCCCCCATTTACAATCCTTCATGTATTACATAG |

TABLE 8-continued

Subtyping Target Sequences

| SEQ ID NO. | Gene | Affy Probeset ID | Sequence |
|---|---|---|---|
| | | | AAGGATTGCTTTTTTAAAAATATACTGCGGGTTGGAAA GGGATATTTAATCTTTGAGAAACTATTTTAGAAAATATG TTTGTAGAACAATTATTTTTGAAAAAGATTTAAAGCAAT AACAAGAAGGAAGGCGAGAGGAGCAGAACATTTTGGT CTAGGGTGGTTTCTTTTTAAACCATTTTTTCTTGTTAATT TACAGTTAAACCTAGGGGACAATCCGGATTGGCCCTCC CCCTTTTGTAAATAACCCAGGAAATGTAATAAATTCATT ATCTTAGGGTGATCTGCCCTGCCAATCAGACTTTGGGG AGATGGCGATTTGATTACAGACGTTCGGGGGGGTGGGG GGCTTGCAGTTTGTTTTGGAGATAATACAGTTTCCTGCT ATCTGCCGCTCCTATCTAGAGG |
| 311 | ESR1 | 2931764 | AGAAGCTCTTTAACAGGCTCGAAAGGTCCATGCTCCTTT CTCCTGCCCATTCTATAGCATAAG |
| 312 | ESR1 | 2931765 | CAAAGATCTCTTCACATTCTCCGGGACTGCGGTACCAA ATATCAGCACAGCACTTCTTGAAAAAGGATGTAGATTT TAATCTGAACTT |
| 313 | ESR1 | 2931775 | ACGAAGTGGAGGAGTATTACATTTCAGCTGGAAACACA TCCCTAGAATGCCAAAACATTTATTCCAAAGTCTGGTTT CCTGGTGCAATCGGAGGCATGGCAATGCCTCTGTTCAG AGA |
| 314 | ESR1 | 2931776 | AAGCATAGGGTACTTTCCAGCCTCCAAGGGTAGGGGCA AAGGGGCTGGGGTTTCTCCTCCCCAGTACAGCTTTCTCT GGCTGTGCCACACTGCTCCCTGTGAGCAGACAGCAAGT CTCCCCTCACTCCCCACTGCCATTCATCCAGCGCTGTGC AGTAGCCCAGCTGCGTGTCTGCCGGGAGGGGCTGCCAA GTGCCCTGCCTACTGGCTGCTTC |
| 315 | ESR1 | 2931779 | GCAGCACATTAGAGAAAGCCGGCCCCTGGATCCGTCTT TCGCGTTTATTTTAAGCCCAGTCTTCCCTGGGCCACCTT TAGCAGATCCTCGTGCGCCCCCGCCCCCTGGCCGTGAA ACTCAGCCTCTATCCAGCAGCGACGACAAGTA |
| 316 | ESR1 | 2931780 | CCAATGTCAGGGCAAGGCAACAGTCCCTGGCCGTCCTC CAGCACCTTTGTAATGCATATGAGCTCGGGAGACCAGT ACTTAAAGTTGGAGGCCCGGGAGCCCAGGAGCTGGCGG AGGGCGTTCGTCCTGGGACTGCACTTGCTCCCGTCGGGT CGCCCGGCTTCACCGGACCCGCAGGCTCCCGGGGCAGG GCCGGGGCCAGAGCTCGCGTGTCGGCGGGACATGCGCT GCGTCGCCTCTAACCTCGGGCTGTGCT |
| 317 | ESR1 | 2931781 | GTGGCCCGCCGGTTTCTGAGCCTTCTGCCCTGCGGGGAC ACGGTCTGCACCCTGCCCGCGGCCACGGACC |
| 318 | ESR1 | 2931782 | TCTGGGATGGCCCTACTGCATCAGATCCAAGGGAACGA GCTGGAGCCC |
| 319 | ESR1 | 2931783 | CCCCTGGGCGAGGTGTACCTGGACAGCAGCAAGCCCGC CGTGTACAACTACCCCGAGGGCGCCGCCTACGAGTTCA ACGCCGCGGCCGCCGCCAACGCGCAGGTCTACGGTCAG |
| 320 | ESR1 | 2931784 | TGAGGCTGCGGCGTTCGGCTCCAACGGCCTGGGGGGTT TCCCCCCACTCAACAGCGTGTCTCCGAGCCCGCTGATGC TACTGCACCCGCCGCCGCAGCTGTCGCCTTTCCTGCAGC CCCACGGCCAGCAGGTGCCCTACTACCTGGAGAACGAG C |
| 321 | ESR1 | 2931791 | GTGCTGTCATGTGGACTGTCCTCCCGAGTGTCCCACTGG ATGTTCAGAGAATTTATGTGAAGGTCACGTCATTTAGC ATTGAGATGCTGTGGTTACCTTCTTCCATTTCTTCCATA ATATGCAGCCACATCTATGTGTGAAGAAATGTAATAGA TAAAATTTCTCTGGACGCATAATAATGTGAGAAAGATT GTCACATGTCCCAGCAA |
| 322 | ESR1 | 2931798 | CAAATTCAGATAATCGACGCCAGGGTGGCAGAGAAAG ATTGGCCAGTACCAATGACAAGGGA |
| 323 | ESR1 | 2931799 | AATCTGCCAAGGAGACTCGCTACTGTGCAGTGTGCAAT GACTATGCTTCAGGCTACCATTATGGAGTCTGGTCCTGT |

TABLE 8-continued

| Subtyping Target Sequences | | | |
|---|---|---|---|
| SEQ ID NO. | Gene | Affy Probeset ID | Sequence |
| 324 | ESR1 | 2931812 | CAGGCCTGCCGGCTCCGTAAATGCTACGAAGTGGGAATGA |
| 325 | ESR1 | 2931821 | AACCTTTGGCCAAGCCCGCTCATGATCAAACGCTCTAAGAAGAACAGCCTGGCCTTGTCCCTGACGGCCGACCAGATGGTCAGTGCCTTGTTGGATGCTGAGCCCCCGATACTCTATTCCGAGTATGATCCTACCAGACCCTTCAGTGAAGCTTCGATGATGGGCTTACTGACCAACCTGGCAGA |
| 326 | ESR1 | 2931835 | TGGATATATGTGTGATCCTGGGTGTGCCAAATGCTGTGGCTTCCTGAAGCTTAGATTTCCAGCTTGTCACCTTCAAGGTTACCTTGTGAATAGGAC |
| 327 | ESR1 | 2931836 | TGACTATGGATTTTGCCTGTTGCTTTGTTTCCACCAACTCTCCCTGAAGATGAGGCGCACAGACAGACAACTCACAGGCAAGAACAGCCTGGTCCATCTTGAAAGATTCTC |
| 328 | ESR1 | 2931839 | GCTTTGTGGATTTGACCCTCCATGATCAG |
| 329 | ESR1 | 2931840 | GTCCACCTTCTAGAATGTGCCTGGCTAGAGATCCTGATGATTGGTCTCGTCTGGCGCTCCATGGAGCACCCAGGGAAGCTACTGTTTGCTCCTA |
| 330 | ESR1 | 2931850 | TGGAGATCTTCGACATGCTGCTGGCTACATCATCTCGGTTCCGCATGATGAATCTGCAGGGAGAGGAGTTTGTGTG |
| 331 | ESR1 | 2931859 | GAGAAGGACCATATCCACCGAGTCCTGGACAAGATCACAGA |
| 332 | ESR1 | 2931861 | CATGAAGTGCAAGAACGTGGTGCCCCTCTATGACCTGCTGCTGGAGATGCTGGACGCCCACCGCCTACATGCGCCCACTAGCCGTGGAGGGGCATCCGTGGAGGAGACGGACCAAAGCCACTTGGCCACTGCGGGCTCTACTTCATCGCATTCCTTG |
| 333 | ESR1 | 2931862 | CCTGGCTCCCACACGGTTCAGATAATCCCTGCTGCATTTTACCCTCATCATGCACCACTTTAGCCAAATTCTGTCTCCTGCATACACTCCGGCATGCATCCAACACCAATGGCTTTCTAGATGAGTGGCCATTCATTTGCTTGCTCAGTTCTTAGTGGCACATCTTCTGTCTTCTGTTGGGAACAGCCAAAGGGATTCCAAGGCTAAATCTTTGTAACAGCTCTCTTTCCCCCTTGCTATGTTACTAAGCGTGAGGATTCCCGTAGCTCTTCACAGCTGAACTCAGTCTATGGGTTGGGGCTCAGATAACTCTGTGCATTTAAGCTACTTGTAGAGACCCAGGCCTGGAGAGTAGACATTTTGCCTCTGATAAGCACTTTTTAAATGGCTCTAAGAATAAGCCACAGCAAAGAATTTAAAGTGGCTCCTTTAATTGGTGACTTGGAGAAAGCTAGGTCAAGGGTTTATTATAGCACCCTCTTGTATTCCTATGGCAATGCATCCTTTTATGAAAGTGGTACACCTTAAAGCTTTTATATGACTGTAGCAGAGTATCTGGTGATTGTCAATTCATTCCCCCTATAGGAATACAAGGGGCACACAGGGAAGGCAGATCCCCTAGTTGGCAAGACTATTTTAACTTGATACACTGCAGATTCAGATGTGCTGAAAGCTCTGCCTCTGGCTTTCCGGTCATGGGTTCCAGTTAATTCATGCCTCCCATGGACCTATGGAGAGCAGCAAGTTGATCTTAGTTAAGTCTCCCTATATGAGGGATAAGTTCCTGATTTTTGTTTTTATTTTTGTGTTACAAAAGAAAGCCCTCCCTCCCTGAACTTGCAGTAAGGTCAGCTTCAGGACCTGTTCCAGTGGGCACTGTACTTGGATCTTCCCGGCGTGTGTGTGCCTTACACAGGGGTGAACTGTTCACTGTGGTGATGCATGATGAGGGTAAATGGTAGTTGAAAGGAGCAGGGGCCCTGGTGTTGCATTTAGCCCTGGGGCATGGAGCTGAACAGTACTTGTGCAGGATTGTTGTGGCTACTAGAGAACAAGAGGGAAAGTAGGGCAGAAACTGGATACAGTTCTGAGGCACAGCCAGACTTGCTCAGGGTGGCCCTGCCACAGGCTGCAGCTACCTAGGAACATTCCTTGCAGACCCCGCATTGCCCTTTGGGGGTGCCCTGGGATCCCTGGGGTAGTCCAGCTCTTCTTCATTTCCCAGCGTGGCCCTGGTTGGAAGAAGCAGCTGTCACAGCTGCTGTAGACAGCTGTGTTCCTACAATTGGCCCAGCACCCTGGGGCACGGGAGAAGGGTGGGGACCGTTGCTGTCACTACTCAGGCTGACTGGGGCCTGGTCAGATTACGTATGCCCTTGGTGGTTTAGAGATAATCCAAAATCAGGGTTTGGTTTGGGGAAGAAAATCCTCCCCCTTCCTCCCCCGCCCCGTTCCCTACCGC |

TABLE 8-continued

Subtyping Target Sequences

| SEQ ID NO. | Gene | Affy Probeset ID | Sequence |
|---|---|---|---|
| | | | CTCCACTCCTGCCAGCTCATTTCCTTCAATTTCCTTTGAC<br>CTATAGGCTAAAAAAGAAAGGCTCATTCCAGCCACAGG<br>GCAGCCTTCCCTGGGCCTTTGCTTCTCTAGCACAATTAT<br>GGGTTACTTCCTTTTTCTTAACAAAAAAGAATGTTTGAT<br>TTCCTCTGGGTGACCTTATTGTCTGTAATTGAAACCCTA<br>TTGAGAGGTGATGTCTGTGTTAGCCAATGACCCAGGTG<br>AGCTGCTCGGGCTTCTCTTGGTATGTCTTGTTTGGAAAA<br>GTGGATTTCATTCATTTCTGATTGTCCAGTTAAGTGATC<br>ACCAAAGGACTGAGAATCTGGGAGGGCAAAAAAAAAA<br>AAAAAGTTTTTATGTGCACTTAAATTTGGGGACAATTTT<br>ATGTATCTGTGTTAAGGATATGTTTAAGAACATAATTCT<br>TTTGTTGCTGTTTGTTTAAGAAGCACCTTAGTTTGTTTA<br>AGAAGCACCTTATATAGTATAATATATATTTTTTTGAAA<br>TTACATTGCTTGTTTATCAGACAATTGAATGTAGTAATT<br>CTGTTCTGGATTTAATTTGACTGGGTTAACATGCAAAAA<br>CCAAGGAAAAATATTTAGTTTTTTTTTTTTTTTTTGTATA<br>CTTTTCAAGCTACCTTGTCATGTATACAGTCATTTATGC<br>CTAAAGCCTGGTGATTATTCATTTAAATGAAGATCACAT<br>TTCATATCAACTTTTGTATCCACAGTAGACAAAATAGCA<br>CTAATCCAGATGCCTATTGTTGGATACTGAATGACAGA<br>CAATCTTATGTAGCAAAGATTATGCCTGAAAAGGAAAA<br>TTATTCAGGGCAGCTAATTTTGCTTTTACCAAAATATCA<br>GTAGTAATATTTTTGGACAGTAGCTAATGGGTCAGTGG<br>GTTCTTTTTAATGTTTATACTTAGATTTTCTTTTAAAAAA<br>ATTAAAATAAAACAAAAAAAAATTTCTAGGACTAGACG<br>ATGTAATACCAGCTAAAGCCAAACAATTATACAGTGGA<br>AGGTTTTACATTATTCATCCAATGTGTTTCTATTCATGTT<br>AAGATACTACTACATTTGAAGTGGGCAGAGAACATCAG<br>ATGATTGAAATGTTCGCCCAGGGGTCTCCAGCAACTTT<br>GGAAATCTCTTTGTATTTTTACTTGAAGTGCCACTAATG<br>GACAGCAGATATTTTCTGGCTGATGTTGGTATTGGGTGT<br>AGGAACATGATTTAAAAAAAAACTCTTGCCTCTGCTTTC<br>CCCCACTCTGAGGCAAGTTAAAATGTAAAAGATGTGAT<br>TTATCTGGGGGGCTCAGGTATGGTGGGGAAGTGGATTC<br>AGGAATCTGGGGAATGGCAAATATATTAAGAAGAGTAT<br>TGAAAGTATTTGGAGGAAAATGGTTAATTCTGGGTGTG<br>CACCAGGGTTCAGTAGAGTCCACTTCTGCCCTGGAGAC<br>CACAAATCAACTAGCTCCATTTACAGCCATTTCTAAAAT<br>GGCAGCTTCAGTTCTAGAGAAGAAAGAACAACATCAGC<br>AGTAAAGTCCATGGAATAGCTAGTGGTCTGTGTTTCTTT<br>TCGCCATTGCCTAGCTTGCCGTAATGATTCTATAATGCC<br>ATCATGCAGCAATTATGAGAGGCTAGGTCATCCAAAGA<br>GAAGACCCTATCAATGTAGGTTGCAAAATCTAACCCCT<br>AAGGAAGTGCAGTCTTTGATTTGATTTCCCTAGTAACCT<br>TGCAGATATGTTTAACCAAGCCATAGCCCATGCCTTTTG<br>AGGGCTGAACAA |
| 334 | ESR1 | 2931877 | AGAAGAGAATCCTGAACTTGCATCCTAAAATAT |
| 335 | ESR1 | 2931878 | GGCAACTTGTTGACTACCCACTGGTCATTCTCCTCTGGT<br>CTTATTACATACATGGATGCCAGTTTAGATTGTGTTTAT<br>ATAGGAAAAATTAAATGTGTGAGCCTCCTTAAGGAACA<br>TCATCAATACAGATATATCAGATAGTTCTGTCCAGCAA<br>AAAACGTGCTTATTTGCTACAAGTAAATTTTTATTTATT<br>TTTCTCACTTCCCTCACTCCTTCAAATTTCCAGGTAAAT<br>AGCTGCCCAGGAGTTGCTTCATCTCTGTCCCAAAATACC<br>TAGACAATTGCGGGATAAGGAGAATGGCAGGGAGGGA<br>GTAGTGGCTAAAATCACACCCTTCAAAAGAAAGTGTGT<br>AGGACACACAATTGTGAGAAGTCTGAATGCCATGCACA<br>TAGGGTATGACTCACTTTGAAAATTGTTTATAATCAAGG<br>AAATGAAAATGAGTTAATTTCGTGCATGCATCATTTAA<br>AGCCAAATGAGAAGAAACTTCTAATTTATTTTGTTACTT<br>TTCGGCTAACACTGGCAGTATGTAACAGATTTATTTTGC<br>AGAAACATCTAGATTGTCCGTGATCTTGATCCTGCCCTT<br>ATGTGTCTTGTCTTTGAAACCCAGTGTTTCCTGGATATA<br>TGGTTCAGGAGACAAGTTTCCAGAATCAAGTTAGGACC<br>CAGGTCTTCTTTTTTTTCCAAACCAAACATTCTTGCTAAT<br>CCTAAACTACCTGAGGCAGCCTGTGGTGGCCTCAGCTC<br>TAAAACCATTGTTTAAAGGCTTCTACCCATCAATGGCCC<br>TTCAGCAGAGTGGTACGGTTAACGGGGTAGGGTCTGGA<br>GTCAGGGGAGACCTGGGTTCAAATCCTACATCTTTACA<br>CCTCTAATCCCCAGTGTCCTTGTCTATAAATTGGGAATA<br>TAGCCATGTCATGGGATTCTTGTGAGGGTTAAATGAGG<br>TAAAACACATACAATGCTTAGCATGTATACAATTAAGC |

TABLE 8-continued

Subtyping Target Sequences

| SEQ ID NO. | Gene | Affy Probeset ID | Sequence |
|---|---|---|---|
| | | | ACTAAATAATTGAAACACATTAAGTACTAAATGAATGT CAGCAGCTTATCACTATTATCTGTATAATGATACCAAGG GTGTGCCGACTCATACCCTTAGGGGT |
| 336 | ESR1 | 2931879 | AGGAAGGCCTACCTCAAATAGCAACAGAGA |
| 337 | ESR1 | 2931880 | TCTGTGCTGAGGCTCTTTGAATGCTTTGAATAA |
| 338 | ESR1 | 2931881 | CCTCTTTCAGTGTTTCGGCCAGTCATTTGCCACTTCTCAT TCCATCTTAGTTCTCTGTAAAGAAGGTGCCAGAGACCT AAGGTGCCCAAGGCAATTTTGCATTTTACAATTCTAAGC TTTAGAATGAAGTCATCAATTTGCTACATCCGGACTACA GTGCAATTATTCCTTTGCCTTGCTGGAAATTGGAGTGAA ATCTTTCTAGCTGTCAATTTCAACTCAGTTGCAGTAGTG TTTTGAAGAATTAATGGCGATAAGGTTAGAAAATTTTA AGTCAAACGTAGGGAAAAAGTACCAGCTAGACCATCAT AAGCATTTGCTTTGAAAGCATGCTTCTAAAGTGTGTTTA ACCTCAAATAACAGTCACAAATATGGTTATTATGAATG TATGCACAGATTTTTATGTTTCTAATTTTAAGAAGTTCT AGGGAGCTCCCTGTAACGATTTAGGGAATCTCTAGATT CTGATATACTGCAAGTCTTTTAATGGTAGGAATCACATT GAATTAATTTTGTAGGCCCAGGGCCTAAATTTAGTAGG TGTTCAGTACCTATTGGCATCAATTCATATGTAGGTTTA AAATACTGTATGAAGATACAGAATCACCACCATCAAAT CAAATTGAAATATGTAACAGGCTAGTATAATATTAACA TCTGACTTTAAACAACAACAAAGAAACCAAATGAGTAA CTCCTCCCTTCAAACTAATAGTCAGTTTCTTCCAACTCA GTCTCTTTCTCCTCTCAGGAAGAATGCGTATCTAAAAAT TTCCCATTGCAGACTGCTGGAAACAACATTCTAAACTAT TTATGCTTCTGCAATAACCTTTCCAATTTGCTGGACCAG TGCAAGATTAAACACGAGATATCTCAAGTCTCAATGTA AAGGAACACCACGACAGCCTGGACTGTGGGTGAAGTTC ATTCTTCCCCAGCAGACTCTGCCTTTCATTCTCGGGGTT GGGTGTGCCCCAAACAGAGGTACCGACGGTAACGAAG CCCAAGAATGTTCAACCACAACCTGTCTGTGAAGGTGT TGGATGACGTTTGCCATTCAGGTGAAGATTATTTATGTT CCAGTCCCACCTGAGTAGCAAAGTGAACACTGTGCTGA ATGCTCAGAAAGATGTTAATGAACCGTGCTGGACAGAG CAGAGCTGAAAGGCGCCTTGCGAGTGTCGTAGTGAGAA TGTGGCTGTCCCAGCTGCAAAGCCCTGTTAGGAGGCAT GAGGAAGCACTTGCTGCCCTAAGAAACGATGCCTTCGA CATTTTCAAAAGATCTATGTGGCTGTCTGAAACAATGC GGAGAGCAGATAGACGCAATATTTGGGAACCAAAGAG TGACTGCTGTTGGCGTTGCATCATAACATAAGCGCTTTC CCCCTTCTCGTCACTATCATTTGTATCAACCAAAGAACT GATCTCTGGTATCCTCGAAGGAATGCTGTGGGGATATT CTTCATCTCTGTTCATGGTACATCAGCAATTTGTGGGGA AAAGATGGACTATATAACACAATGATCTGCCTAAAAGA AACTGTCTCTACTTATAGGGGGCTGAGCAAACCTTAGA GCATCTGCGGATGCTCGTCATTATCTTC |
| 339 | ANLN | 2997377 | GAAATTCAAATTTGAACGGCTGCAGAGGCCGAGTCCGT CACTGGAAGCCGAGAGGAGAGGACAGCTGGTTGTGGG AGAGTTCCCCCGCCTCAGA |
| 340 | ANLN | 2997378 | ACACACTGAGCTGAGACTCACTTTTCTCTTCCTGAATTT GAACCACCGTTTCCATCGTCTCGTAGTCCGACGCCTGGG |
| 341 | ANLN | 2997379 | GGAGGAAGGCTTTGAGTCTGTCCTAAAAGGCTGTTGCG AGAGGTCTTTCAGC |
| 342 | ANLN | 2997380 | TCCTGGCGCAGCAAGAGTGAGGCGCAGGCCTGCGGAAC GGGTCCTGCTGGAAGCAGCTGGAATGCCCTGCAGGGCG GGGTCCGGGGCCGGTGACTCAGTGCGGCTGCCGCCGGG AAAGGCAGTAGGATGTGTGATTTGCGGAGTTCACGCAG CCCGCAGGGGAGATGCTAATGAAA |
| 343 | ANLN | 2997381 | AACTGCTGGAGCGAACCCGTGCCAGGCGAGAGAATCTT CAGAGAA |
| 344 | ANLN | 2997382 | CAGCAGCTCCAAGGTCTATGACTCATGCTAAGCGAGCT AGACAGCCACTTTC |

TABLE 8-continued

Subtyping Target Sequences

| SEQ ID NO. | Gene | Affy Probeset ID | Sequence |
|---|---|---|---|
| 345 | ANLN | 2997384 | AGAAATCTTGTACAAAACCATCGCCATCAAAAAAACGC TGTTCTGACAACACTGAAGTAGAAGTTTCTAACTTGGA AAATAAACAACCAGTTGAGTCGACATCTGCAAAATCTT GTTCTCCAAGTCCTGTGTCTCCT |
| 346 | ANLN | 2997385 | GCCACAAGCAGCAGATACCATCAGTGATTCTGTTGCTG TCCCGGCATCACTGCTGGGCATGAGGAGAGGGCTGAAC TCAAGATTGGAAGCAACTGCAGCCTCCTCAGTTAAAAC ACGTATGCAAAAACTTGCAGAGCAACGGCGCCGTTGGG ATAATGATGATATGA |
| 347 | ANLN | 2997387 | GCTTTCAAATGCCTCGGCAACTCCAGTTGGCAGAAGGG GCCGTCTGGCCAATCTTGCTGCAACTATTTGCTCCTGGG AA |
| 348 | ANLN | 2997388 | GCCTGGTACCGCTTGTTTATCCAAATTTTCCTCTGCAAG TGGAGCATCTGCTAGGATCAATAGCAGCAGTGTTAAGC AGGAAGCTACATTCTGTTCCCAAAGGGATGGCGATGCC TCTTTGAATAAAGCCCTATCCTCAAGTGCTGATGATG |
| 349 | ANLN | 2997389 | TCCAGTGAAATCTACTACATCTATCACTGATGCTAAAA GTTGTGAGGGACAAAATCCTGAGCTACTTCCAAAAACT CCTATTAGTCCTCTGAAAACGGGGGTATCGAAACCAAT TGTGAAGTCAACTTTATCCCAGACAGTTCCATCCAAGG |
| 350 | ANLN | 2997391 | AGCCTTTCCTGGAACGCTTTGGAGAGCGTTGTCAAGAA CATAGCAAAGAAAGTCCAGCTCGTAGCACACCCCACAG AACCCCCATTATTACTCCAAATACAAAGGCCATCCAAG A |
| 351 | ANLN | 2997393 | AGAACTAGCATGTCTTCGTGGCCGATTTGACAAGGGCA ATATATGGAGTGCAGAAAAAGGCGGAAACTCAAA |
| 352 | ANLN | 2997394 | GTTTCAAAAACTCAGTCACTTCCAGTAACAGAAAAGGT GACCGAAAACCAGATACCAGCCAAAAATTCTAGTACAG |
| 353 | ANLN | 2997395 | CATCAGACCCAAAGGTTGAGCAGAA |
| 354 | ANLN | 2997396 | TCTTCAGTGATGTCCTAGAGGAAGGTGAACTAGATATG GAGAAGAGCCAAGAGGAGATGGATCAAGCATTAGCAG AAAGCAGCGAAGAACAGGAAGATGCACTGAATATCTC CTCAATGTCTTTACTTGCACCATTGGCACAAACAGTTGG |
| 355 | ANLN | 2997397 | AGTTTAGTGTCCACACCTAGACTGGAATTGAAAGACAC CAGCAG |
| 356 | ANLN | 2997399 | TTCAAAGAAACAGAACGTCCATCAATAAAGCAGGTGAT TGTTCGGAAGGAAGATGTTAC |
| 357 | ANLN | 2997400 | GAACTCAATAACGAAATAAATATGCAACAGACAGTGAT CTATCAAGCTAGCCAGGCTCTTAACTGCTGTGTTGATGA AGAACATGGAAAAGGGTCCCTAGAAGAAGCTGAAGCA GAAAGACTTCTTCTAATTGCA |
| 358 | ANLN | 2997402 | TGCCATCCAAAGGATCAGTTACTTTGTCAGAAATCCGCT TGCCTCTAAAAGCAGATTTTGTCTGCAGTACGGTTCA |
| 359 | ANLN | 2997403 | ATGGTAGCCACACCATTAGCAAGTACTTCAAACTCTCTT AACGGTGATGCTCTGACATTCACTACTACATTTACTC |
| 360 | ANLN | 2997406 | AAGAAAGATCCCTCAGGCCTTGATAAGAAG |
| 361 | ANLN | 2997408 | GGCCAGTCCAGGAGGTCTTAGTGCTGTGCGAACCAGCA ACTTCGCCCTTGTTGGATCTTACACATTATCATTGTC |
| 362 | ANLN | 2997409 | TAAGAGAGCGAGAGCTACTGGGCTATTTGTTCCAGGAA AA |
| 363 | ANLN | 2997414 | GTTTTGGTGCCTGGCATCGAAGATGGTGTGTTCTTTCTG GAAACTGTATATCTTATTGGACTTATCCAGATGATG |
| 364 | ANLN | 2997417 | TTGGCTGTTGGCTCATGTGTGCCTATATGTGTTTCTTTTC CCATTTTCAGGACCATTTGGTCTCGTGAATGTTTTCCTC |

TABLE 8-continued

Subtyping Target Sequences

| SEQ ID NO. | Gene | Affy Probeset ID | Sequence |
|---|---|---|---|
| | | | CACTTTGACTCGTATCATAGGAATTCATGGCTGCCAACA ATCCAGGGCAGTTGTCTGCCCTTATCTTTCATAGATATA TAAAGAAATATTTACACATGAAATCCAATGTCTAGGTT TCCTTTTATAGAAAGGGGAGAAGTGGGTAAGTTGTAGA TAAAAGGCACTTGAGTGTGTTTCTCATTGTTATAGCTGG TTTTGGTACCTGGGGCTCATTATACTGTTGTTTGTATTTT TTATTTGAAGTTCACCATAATAAAGAGCTTTATAGGATA GTTGGCAAGAGCTACCAGTTGATATTT |
| 365 | ANLN | 2997418 | CATAGGAAGGATAAATCTGGCTAATTGTACCAG |
| 366 | ANLN | 2997419 | GTGCAAGACGCAACACTTTTGAATTAATTACTGTCCGA CCACAAAGAGAAGATGACCGAGAGACTCTTGTCAGCCA ATGCAGGGACACACTCTGTG |
| 367 | ANLN | 2997422 | TGGCTGTCTGCAGATACTAAAGAAGAGCGGGATCTCTG GATGCAAAAACTCAATCAAGTTCTTGTTGATATTCGCCT CTGG |
| 368 | ANLN | 2997423 | TTGCTACAAACCTATTGGAAAGCCTTA |
| 369 | ANLN | 2997424 | TACGAAAGGGTTTGTGCCAATATTCACTACGTATTATGC AGTATTTATATCTTTTGTATGTAAAACTTTAACTGATTT CTGTCATTCATCAATGAGTAGAAGTAAATACATTATAG TTGATTTTGCTAAATCTTAATTTAAAAGCCTCATTTTCCT AGAAATCTAATTATTCAGTTATTCATGACAATATTTTTT TAAAAGTAAGAAATTCTGAGTTGTCTTCTTGGAGCTGTA GGTCTTGAAGCAGCAACGTCTTTCAGGGGTTGGAGACA GAAACCCATTCTCCAATCTCAGTAGTTTTTTCGAAAGGC TGTGATCATTTATTGATCGTGATATGACTTGTTACTAGG GTACTGAAAAAAATGTCTAAGGCCTTTACAGAAACATT TTTAGTAATGAGGATGAGAACTTTTTCAAATAGCAAAT ATATATTGGCTTAAAGCATGAGGCTGTCTTCAGAAAAG TGATGTGGACATAGGAGGCAATGTGTGAGACTTGGGGG TTCAATATTTTATATAGAAGAGTTAATAAGCACATGGTT TACATTTACTCAGCTACTATATATGCAGTGTGGTGCACA TTTTCACAGAATTCTGGCTTCATTAAGATCATTATTTTT GCTGCGTAGCTTACAGACTTAGCATA |
| 370 | BLVRA | 2999566 | CCGAGAGGAAGTTTGGCGTGGTGGTGGTTGGTGTTGGC CGAGCCGGCTCCGTGCGGATGAGGGACTTGCGGAATCC ACACCCTTCCTCAGCGTTCCTGAACCTGATTGGCTTCGT GTCGA |
| 371 | BLVRA | 2999568 | AGCTCGGGAGCATTGATGGAGTCCAGCAGATTTCTTTG GAGGATGCTCTTTCCAGCCAAGAGGTGGAGGTCGCCTA TATCTGCAGTGAGAGCTCCAGCCA |
| 372 | BLVRA | 2999571 | TTCCTTAATGCTGGCAAGCACGTCCTTGTGGAATACCCC ATGACACTGTCATTGGCGGCCGCTCAGGAACTGTG |
| 373 | BLVRA | 2999573 | GAAAAGTCTTGCACGAGGAGCATGTTGAACTCTTGATG GAGGAATTCGCTTTCCTGAAAAAAGAAGTGGTGGGGAA AGACCTGCTGAAAGGGTCGCTCCTCTTC |
| 374 | BLVRA | 2999576 | AGAAGAGCGGTTTGGCTTCCCTGCATTCAGCGGCATCT CTCGCCTGACCTGGCTGGTCTCCCTCTTTGGGGAGCTTT CTCTTGTGTCTGCCACTTTGGAAGAGCGAAAGGAAGAT CAGTATATG |
| 375 | BLVRA | 2999577 | CCTGGTCTAAAACGAAACAGATATTTAAGCTTCCATTTC AAGTCTGGGTCCTTGGAGAATGTGCCAAATGTAGGAGT GAATAAGAACATATTTCTGAAAGATCAAAATATATTTG TCCAGAAAC |
| 376 | BLVRA | 2999578 | GGTTCTTCTCAAGAGTTGACCATTATCTCTATTCTTAAA ATT |
| 377 | EGFR | 3002642 | GGCTGCGCTCTGCCCGGCGAGTCGGGCT |
| 378 | EGFR | 3002666 | ATGATCCTTTGCCTGGACTTTCTAAGTGCCC |
| 379 | EGFR | 3002667 | GTTGCACTTGGCCTAGCATTCCAACCTCACCTGCCTCAG CTTGTTCAACCTGAAAACCTACCAAGTGAAAGCAAGAG |

TABLE 8-continued

| SEQ ID NO. | Gene | Affy Probeset ID | Sequence |
|---|---|---|---|
| | | | CCACGTGAAGACGCCTTAGTTATATGCACCCACCCAGA CACTTG |
| 380 | EGFR | 3002717 | AACTACAGGCCTTTTGAGAGAGTGCCCTCCTAATGAAT TGAGTACCTATTTCTCCATACACAGTGTCTATCATGACC TACAAACCCTTTTCCCATGAGGTGTAACAGAGAGAGAT TACAGCCTTGGAACTGGATGTCAGACTCTCCTGGTTTAA GACAATAAGCCATGACATAGAGCCTGAAACCA |
| 381 | EGFR | 3002729 | CAAGCTCACGCAGTTGGGCACTTTTGAAGATCATTTTCT CAGCCTCCAGAGGATGTTCAATAACTGTGAGGTGGTCC TTGGGAATTTGGAAATTACCTATGTGCAGAGGAATTAT GATCTTTCC |
| 382 | EGFR | 3002731 | AGGTGGCTGGTTATGTCCTCATTGCCCTCAACACAGTGG AGCGAATTCCTTTGGAAAACCTGCAGATCATCAGAGGA AATATGTACTACGAAAATTCCTATGCCTTAGCAGTCTTA TCTA |
| 383 | EGFR | 3002733 | GGCGCCGTGCGGTTCAGCAACAACCCTGCCCTGTGCAA CGTGGAGAGCATCCAGTGGCGGGACATAGTCAGCAGTG ACTTTCTCAGCAACATGTCGATGGA |
| 384 | EGFR | 3002738 | GCCAAAAGTGTGATCCAAGCTGTCCCAATGGGAGCTGC TGG |
| 385 | EGFR | 3002741 | AAAATCATCTGTGCCCAGCAGTGCTCCGGGCGCTGCCG TGGCAAGTCCCCCAGTGACTGCTGCCACAACCAGTGTG CTGCAGGCTGCACAGGCCCCCGGGAGAGCGACT |
| 386 | EGFR | 3002743 | CGAAGCCACGTGCAAGGACACCTGCCCCCCACTCATGC TCTACAACCCCACCACGTACCAGATGGATGTGAACCCC GAGGGCAAATACAGCTTTGGTGCCACCTGCGTGAAGA |
| 387 | EGFR | 3002747 | TAATTATGTGGTGACAGATCACGGCTCGTGCGTCCGAG CCTGTGGGGCCGACAGCTATGAGATGGAGGAAGACGG CGTCCGCAAGTGTAAGAAGTG |
| 388 | EGFR | 3002750 | TGGATATTCTGAAAACCGTAAAGGA |
| 389 | EGFR | 3002751 | TGTTTTAGAGAGAGAACTTTTCGACATATTTCCTGTTCC CTTGGAATA |
| 390 | EGFR | 3002757 | TTTTCTCTTGCAGTCGTCAGCCTGAACATAACATCCTTG GGATTACGCTCCCTCAAGGAGATAAGTGATGGAGATGT GATAATTTCAGGAAACAAAAATTTGTGCTATGC |
| 391 | EGFR | 3002760 | CACAGGCCAGGTCTGCCATGCCTTGTGCTCCCCCGAGG GCTGCTGGGGCCCGGAGCCCAGGGACTGCGTCTCTTGC CGGAATGTCAGCCGAGGCAGGGAATGCGTGGACAAGT GCAACCTTCTGGAG |
| 392 | EGFR | 3002763 | TGTATCCAGTGTGCCCACTACATTGACGGCCCCCACTGC GTCAAGACCTGCCCGGCAGGAGTCATGGGAGAAAACA ACACCCTGGTCTGGAAGTACGCAGACGCCGGCCATGTG TGCCACCTG |
| 393 | EGFR | 3002769 | GCCAGGAAATGAGAGTCTCAAAGCCATGTTATTCTGCC TTTTTAAACTATCATCCTGTAATCAAAGTAATGATGGCA GCGTGTCCCACCAGAGCGGGAGCCCAGCTGCTCAGGAG TCATGCTTAGGATGGATCCCTTCTCTTCTGCCGTCAGAG TTTCAGCTG |
| 394 | EGFR | 3002770 | GCCTCATGCCTTCACGTGTCTGTTCCCCCCGCTTTTCCTT TCTGCCACCCCTGCACGTGGGCCGCCAGGTTCCCAAGA GTATCCTACCCATTTCCTTCCTTCCACTCCCTTTGCCAGT GCCTCTCACCCCAACTAGTAGCTAACCATCACCCCCAG GACTGACCTCTTCCTCCTCGCTGCCAGATGATTGTTCAA AGCACAGAATTTGTCAGAAACCTGCAGGGACTCCATGC TGCCAGCCTTCTCCGTAATTAGCATGGCCCCAGTCCATG CTTCTAGCCTTGGTTCCTTCTGCCCCTCTGTTTGAAATTC TAGAGCCAGCTGTG |
| 395 | EGFR | 3002771 | GCCAGGTCTTGAAGGCTGTCCAACG |

TABLE 8-continued

| Subtyping Target Sequences | | | |
|---|---|---|---|
| SEQ ID NO. | Gene | Affy Probeset ID | Sequence |
| 396 | EGFR | 3002774 | AAGCTACATAGTGTCTCACTTTCCA |
| 397 | EGFR | 3002775 | GCCTAAGATCCCGTCCATCGCCACTGGG |
| 398 | EGFR | 3002776 | GTGGCCCTGGGGATCGGCCTCTTCATGCGAAGGCGCCA CATCGTTCGGAAGCGCACGCTG |
| 399 | EGFR | 3002778 | GCCTCTTACACCCAGTGGAGAAGCTCCCAACCAAGCTC TCTTGAGGATCTTGAAGGAAACTGAATTCAAAAAGATC AAAGTGCTGGGCTCCGGTGCGTTCGGCACGGTGTAT |
| 400 | EGFR | 3002779 | TTAAAATTCCCGTCGCTATCAAGGAATTAAGAGAAGCA ACATCTCCGAAAGCCAACAAG |
| 401 | EGFR | 3002786 | CTACGTGATGGCCAGCGTGGACAACCCCCACGTGTGCC GCCTGCTGGGCATCTGCCTCACCTCCACCGTGCAGCTCA TCACGCAGCTCATGCCCTTCGGCTGCCTCCTGGACTATG TCCGGGAACACAAAGACAATATTGGCTCCCAGTACCTG CTCAACTG |
| 402 | EGFR | 3002798 | GGCATGAACTACTTGGAGGACCGTCGCTTGGTGCACCG CGACCTGGCAGCCAGGAACGTACTGGTGAAAACACCGC AGCATGTCAAGATCACAGATTTTGGGCTGGCCAAACTG CTGGGTGCGGAAGAGAAAGAATACC |
| 403 | EGFR | 3002800 | GTGCCTATCAAGTGGATGGCATTGGAATCAATTTTACA CAGAATCTATACCCACCAGAGTGA |
| 404 | EGFR | 3002801 | AGTTGATGACCTTTGGATCCAAGCCATATGACGGAATC CCTGCCAGCGAGATCTCCTCCATCCTGGAGAAAGGAGA ACGCCTCCCTCAGCCACCCATATGTACCATCGATGTCTA CA |
| 405 | EGFR | 3002802 | CTGGATGATAGACGCAGATAGTCGCCCAAAGTTCCGTG AGTTGATCATCGAATTCTCCAAAATGGCCCGAGA |
| 406 | EGFR | 3002803 | GCTTCCATTGGGAAGAGTCCCTCTAATGAGCATCTCATG TCACTGTGTTCTGTCACATGCCAGCCTGGCCTCCCTGTG TCCCAGATCGCATTATTAAACCCTCCAGCGCATTAGAG CAAGCCTCAGTAAGGCGCAGGCCACATCGTGAACTAAG CAGCATCCGTGAGTGGGGCCCACCCAACTCCATCTCCC CCTCCCCGTCTGAACTCTCCTCTGGTGCTCGTCCTCACT GTCCGGCTAG |
| 407 | EGFR | 3002806 | GGGGATGAAAGAATGCATTTGCCAAGTCCTACAGACTC CAACTTCTACCGTGCCCTGATGGATGAAGAAGACATGG ACGACGTGGTGGATGCCGACGAGTACCTCATCC |
| 408 | EGFR | 3002808 | GACAGCTTCTTGCAGCGATACAGCTCAGACCCCACAGG CGCCTTGACTGAGGACAGCATAGACGACACCTTCCTC |
| 409 | EGFR | 3002809 | TCCTGCTCCTCAACCTCCTCGACCCACTCAGCAG |
| 410 | EGFR | 3002810 | CCTCCAGCATCTCCAGAGGGGGAAACAGTG |
| 411 | EGFR | 3002811 | GTCAACAGCACATTCGACAGCCCTGCCCACTGGGCCCA GAAAGGCAGCCACCAAATTAGCCTGGACAACCCTGACT ACCAGCAGGACTTCTTTCCCAAGGAAGCCAAGCCAAAT GGCATCTTTAAGGGCTCCACAGCTGAAAATGCAGAATA CCTAAGGGTCGCGCCACAAAGCAGTGAAT |
| 412 | EGFR | 3002812 | CCACAGACTGGTTTTGCAACGTTTACACCGACTAGCCA GGAAGTACTTCCACCTCGGGCACATTTTGGGAAGTTGC ATTCCTTTGTCTTCAAACTGTGAAGCATTTACAGAAACG CATCCAGCAAGAATATTGTCCCTTTGAGCAGAAATTTAT CTTTCAAAGAGGTATATTTGAAAAAAAAAAAAAGTATA TGTGAGGATTTTTATTGATTGGGGATCTTGGAGTTTTTC ATTGTCGCTATTGATTTTTACTTCAATGGGCTCTTCCAA CAAGGAAGAAGCTTGCTGGTAGCACTTGCTACCCTGAG TTCATCCAGGCCCAACTGTGAGCAAGGAGCACAAGCCA CAAGTCTTCCAGAGGATGCTTGATTCCAGTGGTTCTGCT TCAAGGCTTCCACTGCAAAACACTAAAGATCCAAGAAG GCCTTCATGGCCCCAGCAGGCCGGATCGGTACTGTATC |

TABLE 8-continued

Subtyping Target Sequences

| SEQ ID NO. | Gene | Affy Probeset ID | Sequence |
|---|---|---|---|
| | | | AAGTCATGGCAGGTACAGTAGGATAAGCCACTCTGTCC CTTCCTGGGCAAAGAAGAAACGGAGGGGATGGAATTCT TCCTTAGACTTACTTTTGTAAAAATGTCCCCACGGTACT TACTCCCCACTGATGGACCAGTGGTTTCCAGTCATGAGC GTTAGACTGACTTGTTTGTCTTCCATTCCATTGTTTTGAA ACTCAGTATGCTGCCCCTGTCTTGCTGTCATGAAATCAG CAAGAGAGGATGACACATCAAATAATAACTCGGATTCC AGCCCACATTGGATTCATCAGCATTTGGACCAATAGCC CACAGCTGAGAATGTGGAATACCTAAGGATAGCACCGC TTTTGTTCTCGCAAAAACGTATCTCCTAATTTGAGGCTC AGATGAAATGCATCAGGTCCTTTGGGGCATAGATCAGA AGACTACAAAAATGAAGCTGCTCTGAAATCTCCTTTAG CCATCACCCCAACCCCCCAAAATTAGTTTGTGTTACTTA TGGAAGATAGTTTTCTCCTTTTACTTCACTTCAAAAGCT TTTTACTCAAAGAGTATATGTTCCCTCCAGGTCAGCTGC CCCCAAACCCCCTCCTTACGCTTTGTCACACAAAAAGTG TCTCTGCCTTGAGTCATCTATTCAAGCACTTACAGCTCT GGCCACAACAGGGCATTTTACAGGTGCGAATGACAGTA GCATTATGAGTAGTGTGGAATTCAGGTAGTAAATATGA AACTAGGGTTTGAAATTGATAATGCTTTCACAACATTTG CAGATGTTTTAGAAGGAAAAAAGTTCCTTCCTAAAATA ATTTCTCTACAATTGGAAGATTGGAAGATTCAGCTAGTT AGGAGCCCACCTTT |
| 413 | EGFR | 3002813 | GGCACCCTGACCGAGGAAACAGCTGCCAGAGGCCTCCA CTGCTAAAGTCCACATAAGGCTGAGGTCAGTCACCCTA AACAACCTGCTCCCTCTAAGCCAGGGGATGAGCTTGGA GCATCCCACAAGTTC |
| 414 | EGFR | 3002814 | GAAATATTTCAGTCAGAACTGGGAAACAGAAGGACCTA CATTCTGCTGTCACTTATGTGTCAAGAAGCAGATGATCG ATGAGGCA |
| 415 | EGFR | 3002815 | GTCAGTTGTAAGTGAGTCACATTGTAGCATTAAATTCTA GTATTTTTGTAGTTTGAAACAGTAACTTAATA |
| 416 | EGFR | 3002816 | CACAGTTCTGTCTGGTAGAAGCCGCAAAGCCCTTAGCC TCTTCACGGATCT |
| 417 | EGFR | 3002817 | GATAGCCTGGCCTTAATACCCTACAGAAAGCCTGTCCA TTGGCTGTTTCTTCCTCAGTCAGTTCCTGGAAGACCTTA CCCCATGACCCCAGCTTCAGATGTGGTCTTTGGAAACA GAGGTCGAAGGAA |
| 418 | EGFR | 3002818 | CTAGGCCTCTGATTGCACTTGTGTAGGATGAAGCTGGT GGGTGATGGGAACTCAGCACCTCCCCTCAGGCAGAAAA GAATCATCTGTGGAGCTTCAAAAGAAGGGGCCTGGAGT CTCTGCAGACCAATTCAACCCAAATCTCGGGGGCTCTTT CATGATTCTAATGGGCAACCAGGGTTGAAACCCTTATTT CTAGGGTCTTCAGTTGTACAAGACTGTGGGTCTGTACCA GAGCCCCCGTCAGAGTAGAATAAAAGGCTGGGTAGGGT AGAGATTCCCATGTGCAGTGGAGAGAACAATCTGCAGT CACTGATAAGCCTGAGACTTGGCTCATTTCAAAAGCGT TCAATTCATCCTCACCAGCAGTTCAGCTGGAAAGGGGC AAATACCCCCACCTGAGCTTTGAAAACGCCCTGGGACC CTCTGCATTCTCTAAGTAAGTTATAGAAACCAGTCTCTT CCCTCCTTTGTGAGTGAGCTGCTATTCCACGTAGGCAAC ACCTGTTGAAATTGCCCTCAATGTCTACTCTGCATTTCT TTCTTGTGATAAGCACACACTTTTATTGCAACATAATGA TCTGCTCACATTTCCTTGCCTGGGGGCTGTAAAACCTTA CAGAACAGAAATCCTTGCCTCTTTCACCAGCCACACCT GCCATACCAGGGGTACAGCTTTGTACTATTGAAGACAC AGACAGGATTTTTAAATGTAAATCTATTTTTGTAACTTT GTTGCGGGATATAGTTCTCTTTATGTAGCACTGAACTTT GTACAATATATTTTTAGAAACTCATTTTTCTACTAAAAC AAACACAGTTTACTTTAGAGAGACTGCAATAGAATCAA AATTTGAAACTGAAATCTTTGTTTAAAAGGGTTAAGTTG AGGCAAGAGGAAAGCCCTTTCTCTCTCTTATAAAAAGG CACAACCTCATTGGGGAGCTAAGCTAGGTCATTGTCAT GGTGAAGAAGAGAAGCATCGTTTTTATATTTAGGAAAT TTTAAAAGATGATGGAAAGCACATTTAGCTTGGTCTGA GGCAGGTTCTGTTGGGGCAGTGTTAATGGAAAGGGCTC ACTGTTGTTACTACTAGAAAAATCCAGTTGCATGCCATA CTCTCATCATCTGCCAGTGTAACCCTGTACATGTAAGAA |

TABLE 8-continued

Subtyping Target Sequences

| SEQ ID NO. | Gene | Affy Probeset ID | Sequence |
|---|---|---|---|
| | | | AAGCAATAACATAGCACTTTGTTGGTTTATATATATAAT GTGACTTCAATGCAAATTTTATTTTTATATTTACAATTG ATATGCATTTACCAGTATAAACTAGACATGTCTGGAGA GCCTAATAATGTTCAGCACACTTTGGTTAGTTCACCAAC AGTCTTACCAAGCCTGGGCCCAGCCACCCTAGAGAAGT TATTCAGCCCTGGCTGCAGTGACATCACCTGAGGAGCT TTTAAAAGCTTGAAGCCCAGCTACACCTCAGACCGATT AAACGCAAATCTCTGGGGCTGAAACCCAAGCATTCGTA GTTTTTAAAGCTCCTGAGGTCATTCCAATGTGCGGCCAA AGTTGAGAACTACTGGCCTAGGGATTAGCCACAAGGAC ATGGACTTGGAGGCAAATTCTGCAGGTGTATGTGATTC TCAGGCCTAGAGAGCTAAGACACAAAGACCTCCACATC TGTCGCTGAGAGTCAAGAACCTGAACAGAGTTTCCATG AAGGTTCTCCAAGCACTAGAAGGGAGAGTGTCTAAACA ATGGTTGAAAAGCAAAGGAAATATAAAACAGACACCT CTTTCCATTTCCTAAGGTTTCTCTCTTTATTAAGGGTGG ACTAGTAATAAAATATAATATTCTTGCTGCTTATGCAGC TGACATTGTTGCCCTCCCTAAAG |
| 419 | EGFR | 3002819 | GAAAACGCTGGCCTATCAGTTACATTACAAAA |
| 420 | EGFR | 3002820 | ACTACCTGCAGTGTGTCCTCTGAGGCTGCAAGTCTGTCC TATCTGAATTCCCAGCAGAAGCACTAAGAAGCTCCACC CTATCACCTAGCAGATAAAACTATGGGGAAAACTTAAA TCTGTGCATACATTTCTGGATGCATTTACTTATCTTTAA AAAAAAAGGAATCCTATGACCTGATTTGGCCACAAAAA TAATCTTGCTGTACAATACAATCTCTTGGAAATTAAGAG ATCCTATGGATTTGATGACTGGTATTAGAGGTGACAAT GTAACCGATTAACAACAGACAGCAATAACTTCGTTTTA GAAACATTCAAGCAATAGCTTTATAGCTTCAACATATG GTACGTTTTA |
| 421 | EGFR | 3002827 | CCAGCTGCTGCTCTTATTGGGCTAAGGGATGAAGACTA CACAGGCTGTCGAGTTCTCCTCCAGGATACTCACTGACT CCCAGGTGGCCTACTCTATCAACCCATGAGCATGGTCA GCCCTGAGACACTGTCAGGAAGTGAGAGGCCACTGTAG GAGTGTCACGCTAACAGCTAACCCAGCGGCCCCCATGA AGGCTGACGCTTGGCATCCCTGGAGAATGGGTCACACT TTTACCTCATCGCATAGCCATAGTCTCTGCCTCCACAGC CTTCATTTTCTCACTTTTTCTATCAATGCCCAAGAAAAG AATGTTTTTCCATGCAAAACCCAGCAAAGAAATAAAGT CCCCAAGCCTGTGTGCAGGGTTAAAGGAACCTCATGAG AGTGAAGCACTAGGCTGCGAAGGGGAGAAACCCACTT GGGAAAAGCCCACCACTTCGGGGAACCTGGATGACGGC CCATAGAGCATAGTGCCACAAACAGTGACTCTGAAAGT TCGTGTTCCATGGTTCCAAGATTTGAAGTAGTGTTACTC CTCAGAGGCCTTTGTTACTAATCCCCACGGTGGGCTTTT TCCACCACAGGTTTTAACCTAGCTTTGAACTATGTTCAA GTCCTATGAGGTTGCAAAGCACCACCCCAATATTCTTAT ACCTATAACGGGGCACAGAAGCTACTGAAGCATTTGGT AGGGCTGTGGCTGCCTGTGCAGTGGGCTATGTGAAAAT CAACTGGAGTCTCCTGGAGAGTGGGCTCTGGAAGTCTC CTCAGTCATCAACGCAGGCTCTTGACCTCTCGTGCACTA TATGACCAAAGTCTACGCAGGCTATGTGGGCTATTTGC GATTCAAGTCCAGCTATGTGCTGCTTCTAACCCAGGCA GTATTCCAGACTGCAGTCCAGCTGAGCGTGGAATGTGT ATCCTGGTGCCCGGATTCCACACTTCACTGCCTTGGTGA TTCAGCCGACCCTCA |
| 422 | EGFR | 3002828 | GCATTTTGCTAAGTCCCTGAGGGTCACTGGTCCTCAAAG CGGCATGGCGGCATGGCGTGGCTGGTTCTGCCACATGC CAGCTGTGTGACCTCTGAGACTCCACTTCTTCAGTGCTG AAAATAAAGAAGGAGTTTTACTAAGGACCAAACAAGA TAATGAATGTGAAACTGCTCCACGAACCCCAAAGAATT ATGCACATAGATGCGATCATTAAGATGCGAAGCCATCG AGTTACCACCTGGCATGCTTAAACTGTAAA |
| 423 | ACTR3B | 3032458 | CTGCGGCGGCTCGCGGGAGACGCTGCGCGCGGGGCTAG CGGGCGGCGGAGCGGACGGCGACGGGGCGCTCTCGGG CT |
| 424 | ACTR3B | 3032459 | TCCCTGCCTCCCTGCGTGGTGGACTGTGGCACC |
| 425 | ACTR3B | 3032468 | AACTATCTCCTTCCTGCTGTAATCAGT |

TABLE 8-continued

Subtyping Target Sequences

| SEQ ID NO. | Gene | Affy Probeset ID | Sequence |
|---|---|---|---|
| 426 | ACTR3B | 3032488 | AGGCTCCACCATGTTCAGGGATTTCGGACGCCGACTGC AGAGGGATTT |
| 427 | ACTR3B | 3032489 | GAGGTCCAGGTGGTCACGCATCACATGCAGCGCTACGC CGTGTGGTTCGGAGGCTCCATGCT |
| 428 | ACTR3B | 3032491 | AAGGACTATGAAGAGTACGGGCCCAGCATCTGCCGCCA CAACCCCGTCTTTGGAGTCATGT |
| 429 | ACTR3B | 3032492 | TTCGATGGTGTCACGTTGGGGAACAAGTGTCCTTCAGA ACCCAGAGAAGGCCGCCGTTCTGTAAATAGCGACGTCG GTGTTGCTGCCCAGCAGCGTGCTTGCATTGC |
| 430 | ACTR3B | 3032493 | CCATTTATCCGTGTGCCGACCGCTGTCTGCCAGCCTCCT CCTTCTCCCGCCCTCCTCACCCTCGCTCTCCCTCCTCCTC CTCCTCCGAGCTGCTAGCTGACAAATACAATTCTGAAG GAATCCAAATGTGACTTTGAAAATTGTTAGAGAAAACA ACATTAGAAAATGGCGCAAAATCGTTAGGTCCCAGGAG A |
| 431 | ACTR3B | 3032494 | GTACAACTGGCTGATACTAAGCACGAATAGATATTGAT GTTATGGAGTGCTGTAATCCAAAGTTTTTAATTGTGAGG CATGTTCTGATATGTTTATAGGCAAACAAATAAAACAG CAAACTTTTTTGCCACATGTTTGCTAGAAAATGATTATA CTTTATTGGAGTGACATGAAGTTTGAACACTAAACAGT AATGTATGAGAATTACTACAGATACATGTATCTTTTAGT TTTTTTTGTTTGAACTTTCTGGAGCTGTTTTATAGAAGAT GATGGTTTGTTGTCGGTGAGTGTTGGATGAAATACTTCC TTGCACCATTGTAATAAAAGC |
| 432 | NAT1 | 3087948 | ATTGACCCAGTCGACAGGATCTGAACTTCCAGT |
| 433 | NAT1 | 3087952 | GGACCTGTTCCAAGCTCTCACGTTCCACATCACACATGG GACATCTAGTGTCAGGCTCCCAGAGAGCAGGAACCAGG TGAAATATAAGAGCACAGTCCTCCCAGCCGGTGGCATG GGGATAATCGGACAATACAACTCTC |
| 434 | NAT1 | 3087956 | CCCTGAACATGGACTTGCAGAATTCCACAGAAGAGAGG AGACTGGCCTAGACAGACAGCCCCAGGAGCTGAGGGC CCAACAGGCTTTCTACCCTGGATGCTGCTCCCATGCCCT GACATGAGGCCCACTACA |
| 435 | NAT1 | 3087957 | CAGCCTGGATGTGAACTGCAACTCCAAAGTGTGTCCAG ACTCAAGGCAAGGGCACTAGGCTTTCCAGACCTCCTAC TAAGTCATTGATCCAGCACTGCCCTGCCAGGACATAAA TCCCTGGCACCTCTTGCTCTCTGCAAAGGAGGGCAAAG CAGCTTCAGGAGCCCTTGGGAGTCCTCCAAAGAGAGTC TAGGGTACAGGTC |
| 436 | NAT1 | 3087958 | ACAGAAGGGCCATGCTGTTATTACTCTTACACAAGGAG GCAGCCCTCGAGCCACAGGGTCCAGCTGTTGGCTATAA TAGCCTACCGGTCTCTGATGATCACCATGTTT |
| 437 | NAT1 | 3087960 | GCAGCAATCTGTCTTCTGGATTAAAACTGAAGATCAAC CTACTTTCAACTTACT |
| 438 | NAT1 | 3087961 | AAATATAGCCATAATTAGCCTACTCAAATCCAAGTGTA AA |
| 439 | NAT1 | 3087962 | CCATTGTGGGGATGCCATGGACTTAGGCTTAGAGGCCA TTTTTGATCAAGTTGTGAGAAGAAATCGGGGTGGATGG TGTCTCCAGGTCAATCATCTTCTGTACTGGGCTCTGACC ACTATTGGTTTTGAGACCACGATGTTGGGAGGGTATGTT TACAGCACTCCAGCCAAAAAATACAGCACTGGCATGAT TCACCTTCTCCTGCAGGTGACCATTGATGGCAGGAACT ACATTGTCGATGCTGGGTTTGGACGCTCATACCAGATGT GGCAGCCTCTGGAGTTAATTTCTGGGAAGGATCAGCCT CAGGTGCCTTGTGTCTTCCGTTTGACGGAAGAGAATGG ATTCTGGTATCTAGACCAAATCAGAAGGGAACAGTACA TTCCAAATGAAGAATTTCTTCATTCTGATCTCCTAGAAG ACAGCAAATACCGAAAAATCTACTCCTTTACTCTTAAG CCTCGAACAATTGAAGATTTTGAGTCTATGAATACATA CCTGCAGACATCTCCATCATCTGTGTTTACTAGTAAATC |

TABLE 8-continued

Subtyping Target Sequences

| SEQ ID NO. | Gene | Affy Probeset ID | Sequence |
|---|---|---|---|
| | | | ATTTTGTTCCTTGCAGACCCCAGATGGGGTTCACTGTTTGGTGGGCTTCACCCTCACCCATAGGAGATTCAATTATAAGGACAATACAGATCTAATAGAGTTCAAGACTCTGAGTGAGGAAGAAATAGAAAAAGTGCTGAAAAATATATTTAATATTTCCTTGCAGAGAAAGCTTGTGCCCAAACATGGTGATAGA |
| 440 | NAT1 | 3087963 | ATAAGGAGTAAAACAATCTTGTCTATTTGTCATCCAGCTCACCAGTTATCAACTGACGACCTATCATGTATCTTCTGTACCCTTACCTTA |
| 441 | NAT1 | 3087964 | AAAGATGGCCTGTGGTTATCTTGGAAATTGGTGATTTATGCTAGAAAGCTTTTA |
| 442 | NAT1 | 3087965 | CTTGTGTAGATCTGAGTTGAAATCCTGTGGACACTGGGCGAATTACTTTTTAGATCTGTAGCTCTGACTCCTCAGGCATAAAATGGGAATAATGCTTTTACAGTTTAGTGGCGGAAC |
| 443 | MYC | 3115511 | TAACGCGCTCTCCAAGTATACGTGGCAATGCGTTGCTGGGTTATTTTAATCATTCTAGGCATCGTTTTCCTCCTTATGCCTCTATCATTCCTCCCTATCTACACTAACATCCCACGCTCTGAACGCGCGCCCATTAATACCCTTCTTTCCTCCACTCTCCCTGGGACTCTTGATCAAAGCGC |
| 444 | MYC | 3115512 | ATGCGGTTTGTCAAACAGTACTGCTACGGAGGAGCAGCAGAGA |
| 445 | MYC | 3115513 | GTAGGCGCGCGTAGTTAATTCATGCGGCTCTCTTACTCTGTTTACATCCTAGAGCTAGAGTGCTCGGCTGCCCGGCTGAGTCTCCTCCCCACCTTCCCCACCCTCCCCACCCTCCCCATAAGCGCCCCTCCCGGGTTCCCAAAGCAGAGGGCGTGGGGGAAAAGAAAAAAGATCCTCTCTCGCTAATCTCCGCCCACCGGCCCTTTATAATGCGAGGGTCTGGACGGCTGAGGACCCCCGAGCTGTGCTGCTCGCGGCCGCCACCGCCGGGCCCCGGCCGTCCCTGGCTCCCCTCCTGCCTCGAGAAGGGCAGGGCTTCTCAGAGGCTTGGCGGGAAAAAGAACGGAGGGAGGGATCGCGCTGAGTATAAAAGCCGGTTTTC |
| 446 | MYC | 3115514 | CAACCCTTGCCGCATCCACGAAACTTTGCCCATAG |
| 447 | MYC | 3115515 | TTACAACACCCGAGCAAGGACGCGACTCTCCCGACGCGGGGAGGCTATTCTGCCCATTTGGGGACACTTCCCCGCCGCTGCCAGGACCCGCTTCTCTGAAAGGCTCTCCTTGCAGCTGCTTAGACGCTGGATTTTTT |
| 448 | MYC | 3115522 | AGCCGTATTTCTACTGCGACGAGGAGGAGAACTTCTACCAGCAGCAGCAGCAGAGCGAGCTGCAGCCCCCGGCGCCCAGCGAGGATATCTGGAAGAAATTCGAGCTGCTGCCCACCCCGCCCCTGTCCCCTAGCCGCCGCTCCGGGCTCTGCTCGCCCTCCTACGTTGCGGTCACACCCTTCTCCCTTCGGGGAGACAACGACGGCGGTGGCGGGAGCTTCTCCACGGCCGACCAGCTGGAGATGGTGACCGAGCTGCTGGGAGGAGACATGGTGAACCAGAGTTTCATCTGCGACCCGGACGACGAGACCTTCATCAAAAACATCATCATCCAGGACTGTATGTGGAGCGGCTTCTCGGCCGCCGCCAAGCTCGTCTCAGAGAAGC |
| 449 | MYC | 3115523 | GAAGGACTATCCTGCTGCCAAGAGGGTCAAGTTGGACAGTGTCAGAGTCCTGAGACAGATCAGCAACAACCGAAAATGCACCAGCCCCAGGTCCTCGGACACCGAGGAGAATGTCAAGAGGCGAACACACAACGTCTTGGAGCGCCAGAGGAGGAACGAGCTAAAACGGAGCTTTTTTGCCCTGCGTGACCAGATCCCGGAGTTGGAAAACAATGAAAAGGCCCCCAAGGTAGTTATCCTTAAAAAAGCCACAGCATACATCCTGTCCGTCCAAGCAGAGGAGC |
| 450 | MYC | 3115524 | TTCCTTCTAACAGAAATGTCCTGAGCAATCACCTATGAACTTGTTTCAAATGCATGATCAAATGCAACCTCACAACCTTGGCTGAGTCTTGAGACTGAAAGATTTAGCCATAATGTAAACTGCCTCAAATTGGACTTTG |
| 451 | MYC | 3115525 | TCCTAGTATATAGTACCTAGTATTATAGGTACTATAAA |

TABLE 8-continued

Subtyping Target Sequences

| SEQ ID NO. | Gene | Affy Probeset ID | Sequence |
|---|---|---|---|
| 452 | SFRP1 | 3132783 | TGTGCAGCTCTCTAAATGGGAATTCTCAGGTAGGAAGC AACAGCTTCAGAAAGAGCTCAAAATAAATTGGAAATGT GAATCGCAGCTGTGGGTTTTACCACCGTCTGTCTCAGAG TCCCAGGACCTTGAGTGTCATTAGTTACTTTATTGAAGG TTTTAGACCCATAGCAGCTTTGTCTCTGTCACATCAGCA ATTTCAGAACCAAAAGGGAGGCTCTCTGTAGGCACAGA GCTGCACTATCACGAGCCTTTGTTTTTCTCCACAAAGTA TCTAACAAAACCAATGTGCAGACTGATTGGCCTGGTCA TTGGTCTCCGAGAGAGGAGGTTTGCCTGTGATTTCCTAA TTATCGCTAGGGCCAAGGTGGGATTTGTAAAGCTTTAC AATAATCATTCTGGATAGAGTCCTGGGAGGTCCTTGGC AGAACTCAGTTAAATCTTTGAAGAATATTTGTAGTTATC TTAGAAGATAGCATGGGAGGTGAGGATTCCAAAAACAT TTTATTTTTAAAATATCCTGTGTAACACTTGGCTCTTGG TACCTGTGGGTTAGCATCAAGTTCTCC |
| 453 | SFRP1 | 3132784 | GCGCCTGTCAGTAGTGGACATTGTAATCCAGTCGGCTT GTTCTTGCAGCATTCCCGCTCCCTTCCCTCCATAGCCAC GCTCCAAACCCCAGGGTAGCCATGGCCGGGTAAAGCAA GGGCCATTTAGATTAGGAAGGTTTTTAAGATCCGCAAT GTGGAGCAGCAGCCACTGCACAGGAGGAGGTGACAAA CCATTTCCAACAGCAACACAGCCACTAAAACACAAAAA GGGGGATTGGGCGGAAAGTGAGAGCCAGCAGCAAAAA CTACATTTTGCAACTTGTTGGTGTGGATCTATTGGCTGA TCTATGCCTTTCAACTAGAAAATTCTAATGATTGGCAAG TCACGTTGTTTTCAGGTCCAGAGTAGTTTCTTTCTGTCT GCTTTAAATGGAAACAGACTCATACCACACTTACAATT AAGGTCAAGCCCAGAAAGTGATAAGTGCAGGGAGGAA AAGTGCAAGTCCATTATGTAATAGTGACAGCAAAGGGA CCAGGGGAGAGGCATTGCCTTCTCTGCCCACAGTCTTTC CGTGTGATTGTCTTTGAATCTGAATCAGCCAGTCTCAGA TGCCCCAAAGTTTCGGTTCCTATGAGCCCGGGGCATGA TCTGATCCCCAAGACATGTGGAGGGGCAGCCTGTGCCT GCCTTTGTGTCAGAAAAAGGAAACCACAGTGAGCCTGA GAGAGACGGCGATTTTCGGGCTGAGAAGGCAGTAGTTT TCAAAACACATAGTTAAAAAAGAAACAAATGAAAAAA ATTTTAGAACAGTCCAGCAAATTGCTAGTCAGGGTGAA TTGTGAAATTGGGTGAAGAGCTTAGGATTCTAATCTCAT GTTTTTTCCTTTTCACATTTTTAAAAGAACAATGACAAA CACCCACTTATTTTTCAAGGTTTTAAAACAGTCTACATT GAGCATTTGAAAGGTGTGCTAGAACAAGGTCTCCTGAT CCGTCCGAGGCTGCTTCCCAGAGGAGCAGCTCTCCCCA GGCATTTGCCAAGGGAGGCGGATTTCCCTGGTAGTGTA GCTGTGTGGCTTTCCTTCCTGAAGAGTCCGTGGTTGCCC TAGAACCTAACACCCCCTAGCAAAACTCACAGAGCTTT CCGTTTTTTTCTTTCCTGTAAAGAAACATTTCCTTTGAAC TTGATTGCCTATGGATCAAAGAAATTCAGAACAGCCTG CCTGTCCCCCCGCACTTTTTACATATATTTGTTTCATTTC TGCAGATGGAAAGTTGACATGGGTGGGGTGTCCCCATC CAGCGAGAGAGTTTCAAAAGCAAAACATCTCTGCAGTT TTTCCCAAGTACCCTGAGATACTTCCCAAAGCCCTTATG TTTAATCAGCGATGTATATAAGCCAGTTCACTTAGACA ACTTTACCCTTCTTGTCCAATGTACAGGAAGTAGTTCTA AAAAAAATGCATATTAATTTCTTCCCCCCAAAGCCGGAT TCTTAATTCTCTGCAACACTTTGAGGACATTTATGATTG TCCCTCTGGGCCAATGCTTATACCCAGTGAGGA |
| 454 | SFRP1 | 3132785 | AATGAAAAACCATGAGTGCCCCACCTTTCAGTCCGTGT TTAAGTGA |
| 455 | SFRP1 | 3132786 | CTTCCTCATCATGGGCCGCAAGGTGAAGAGCCAGTACT TGCTGACGGCCATCCACAA |
| 456 | SFRP1 | 3132787 | AAGTTGGGGCCCATCAAGAAGAAGGACCTGAAGAAGC TTGTGCTGTACCTGAAGAATGGGGCTGACTGTCCCTGCC |
| 457 | SFRP1 | 3132788 | AGAAAATGGCGACAAGAAGATTGTCCCCAAG |
| 458 | SFRP1 | 3132808 | TGTGTCCTCCCTGTGACAACGAGTTGAAATCTGAGGCC ATCATTGAACATCTCTGTGCCAGCGAGTTTG |
| 459 | SFRP1 | 3132810 | GCTCGGCTGCGGAAAAGGTGCTGCAGTCCACAGGGAAC ATGGGGGGATTGGACGGGTTGCCTGAAGAAGAGAGGA |

TABLE 8-continued

Subtyping Target Sequences

| SEQ ID NO. | Gene | Affy Probeset ID | Sequence |
|---|---|---|---|
| | | | AAGAATCCCTCACCCCAGCCCCCAAAAGGCTGTGATGG GATGGGGAAACCCCATAATCGCTGTCTTCCGGACACCT TTTGCCCCTTGGCTGCAGTTCCACTGGTCGGCGCCCTTC TCAGCCTGGCTTGGAACCGTCCTCACTCA |
| 460 | SFRP1 | 3132814 | TCGGCCAGCGAGTACGACTACGTGAGCTTCCAGTCGGA CATCGGCCCGTACCAGAGCGGGCGCTTCTACACCAAGC CACCTCAGTGCGTGGACATCCCCGCGGACCTGCGGCTG TGCCACAACGTGGGCTACAAGAAGATGGTGCTGCCCAA CCTGCTGGAGCACGAGACCATGGCGGAGGTGAAGCAG CAGGCCAGCAGCTGGGTGCCCCTGCTCAACAAGAACTG CCACGCCGGCACCCAGGTCTTCCTCTGCTCGCTCTTCGC GCCCGTCTGCCTGGACCGGCCCATCTACCCGTGTCGCTG GCTCTGCGAGGCCGTGCGCGACTCGTGCGAGCCGGTCA TGCAGTTCTTCGGCTTCTACTGGCCCGAGATGCTTAAGT GTGACA |
| 461 | SFRP1 | 3132815 | GTCGCGGAGAACAGGGCGCAGAGCCGGC |
| 462 | SFRP1 | 3132816 | TCCCTGGAAGTTTGCGGCAGGACGCGC |
| 463 | SFRP1 | 3132817 | TGCAGCCTCCGGAGTCAGTGCCGCGCGCCCGCCGCCCC GCGCCTTCCTGCTCGCCGCACCTCCGGGAGCCGGGGCG CACCCAGCCCGCAGCGCCGCCTCCCCGCCCGCGCCGCC TCCGACCGCAGGCCGAGGGCCGCCACTGGCCGGGGGG ACCGGGCAGCAGCTTGCGGCCGCGGAGCCGGGCAACG CTGGGGACTGCGCCTTTTGTCC |
| 464 | SFRP1 | 3132819 | AATGGATCCAACTGCTTGCCCCGTCATCCCAGATGGCT AGGCCCCCATTCATCCCCTCTCGCTCTCCTACTGGAGGA ACTGCTGTATGAATCATAAAGCTCTGGGTAGGGAAGCA GGGAGCAGGTTCCAGGCAGAGCTGACAAGTGACTTCAC TTTTGAGCATCGGTTGAACCAG |
| 465 | MELK | 3168509 | AAGCGGCCACAACCCGGCGATCGAAAAGATTCTTAGGA ACGCCGTACCAGCCGCGTCTCTCAGGACAGCAGGCCCC TGTCCTTCTGTCGGGCGCCGCTCA |
| 466 | MELK | 3168510 | CCCAGTTTGCTCCTGGCTCTCGGGAGACTGGAGGATTTC ATCGGAGCCCCGCGCTTTACCAGCCCTGTTCCCTGGATA AGATATTTGACCTTTCCGACCCGCG |
| 467 | MELK | 3168511 | TTCTAATTCCAAATAAACTTGCAAGAGGACT |
| 468 | MELK | 3168512 | TGAAAGATTATGATGAACTTCTCAAATATTATGAATTAC ATGAA |
| 469 | MELK | 3168513 | AAAGGTCAAACTTGCCTGCCATATCCTTACTGGAGAGA TGGTAGCTATAAAAATC |
| 470 | MELK | 3168514 | CCCGGATCAAAACGGAGATTGAGGCCTTGAAGAACCTG AGACATCAGCATATATGTCAACTCTACCATGTGCTAGA GACAGCCAACAAAATATTCATGGTTCTTG |
| 471 | MELK | 3168515 | TACTGCCCTGGAGGAGAGCTGTTTGACTATATAATTTCC CAG |
| 472 | MELK | 3168516 | CAGAAGAGGAGACCCGGGTTGTCTTCCGTCAGATAGTA TCTGCTGTTGCTTATGTGCACAGCCAGGGC |
| 473 | MELK | 3168518 | ACAAGGATTACCATCTACAGACATGCTGTGGGAGTCTG GCTTATGCAGCACCTGAGTTAATACAAGGCAAATCATA TC |
| 474 | MELK | 3168519 | GCAGATGTTTGGAGCATGGGCATACTGTTATATGTTCTT A |
| 475 | MELK | 3168522 | AAGTGGCTCTCTCCCAGTAGCATTCTGCTTCTTCAA |
| 476 | MELK | 3168523 | GACCCAAAGAAACGGATTTCTATGA |
| 477 | MELK | 3168524 | GCAAGATTACAACTATCCTGTTGAGTGGCAAAGCAAGA |

TABLE 8-continued

Subtyping Target Sequences

| SEQ ID NO. | Gene | Affy Probeset ID | Sequence |
|---|---|---|---|
| 478 | MELK | 3168525 | TTTATTCACCTCGATGATGATTGCGTAACAGAACTTTCT GTACATCACAGAAACAACAGGCAAACAATGGAGGATT |
| 479 | MELK | 3168526 | TGGCAGTATGATCACCTCACGGCTACCTATCTTCTGCTT CTAGCCAAGAAGGCTCGGGGAAAACCAGTTCGTTTAAG GCTTTCTTCTTTCTCCTGTGGACAAGCCAGTGCT |
| 480 | MELK | 3168528 | TGGAAGATGTGACCGCAAGTGATAAAAATTATGTGGCG GGATTAATAGACTATGATTGGTGTGAAGATGATTTATC AACAGGTGCTGCTACTCCCCGAACATCA |
| 481 | MELK | 3168529 | GGGGTGGAATCTAAATCATTAACTCCAGCCTTATGCAG AACACCTGCAAATAAATTAAAGAACAAAGAAAATGTAT ATACTCCTAAGTCTGCTGTAAAGAATGAAGAGTACTTT ATGTTTCCTGAGCCAAAGACTCCAGTTAATA |
| 482 | MELK | 3168530 | GAAACCAGTGCCTGAAAGAAACTCCAATTAAAATACCA GTAAATTCAACAGGAACAGACAAGTTAATGACAGGTGT CATTAGCCC |
| 483 | MELK | 3168531 | TGGATCTCAACCAAGCACATATGGAGGAGACTCCAAAA AGAAAGGGAGCCAAAGTGTTTGGGAGCCTTGAAAGGG GGTTGGATAAGGTTATCACTGTGCTCACCAGGAGCAAA AGGAAGGGTTCTGCCAGAGACGGGCCCAGAAGA |
| 484 | MELK | 3168533 | CTTCACTATAACGTGACTACAACTAGATTAGTGAATCC AGATCAACTGTTGA |
| 485 | MELK | 3168535 | ATACACTGAAGTGTCAAACACAGTCAGATTTTGGGAAA GTGACAATGCAATTTGAATTAGAAGTGTGCCAGCTTCA AAAA |
| 486 | MELK | 3168536 | CTTAAGGGCGATGCCTGGGTTTACAAAAGATTAGTGGA AGACATCCTATCTAGCTGCA |
| 487 | MELK | 3168537 | ATGGATTCTTCCATCCTGCCGGATGAGTGTGGGTGTGAT ACAGCCTACATAAAGACTGTTATGATCGCTTTGATTTTA AAGTTCATTGGAACTACCAACTTGTTTCTAAAGAGCTAT CTTAAGACCAATATCTCTTTGTTTTTAAACAAAAGATAT TATTTTGTGTATGAATCTAAATCAAGCCCATCTGTCATT ATGTTACTGTC |
| 488 | CDC20 | 3177818 | GAGGGGGCACCAGTGATCGACACATTTGCATCTGGAAC GTGTGCTCTGGGGCCTGTCTGAGTGCCGTGGATGCCC |
| 489 | CDC20 | 3177820 | TTATTTGGAAGTACCCAACCATGGC |
| 490 | BAG1 | 3203483 | CGGACCTATGTCCTACCTGTTCATGCAGTTGTCCATATC CAGTGGGATGTCCTAGGGGCTCAACTGTCCACAAACAT CACTGCCCCCCACAGAACTGGTACAGACCCCCAAACCA CCCATCTCAGCCCATGAAACCACTGGCCACCCAAGCCC ACAAATCAGAAACCAGTATGCTGCCTCCTTCCCCTCAG CCTTTACATACAGTCACATACCAAGCCTGTCAATTCCAC TCCCAATGTACCTCCTAACCATGAGTCTTTG |
| 491 | BAG1 | 3203484 | ACCTTCTCAGGAGCTGTAGTGTACCATTCAGGGACCTG GCACAGTCCATCCAGACATCCTGCTGAGCGTCGCCCAC ATATGCAGT |
| 492 | BAG1 | 3203486 | TCTTTCAGGTCCTCAGATGCACTGCACCCTCTCCTGCCT GGGGGTCTTTGCTCCTGCTACTACCTCTGCTTGAACAGC TCCTCACCTTCCTTCCTCCAACCCTACCCTTGTATAGGT GACTTTTGTTCATCCTTCAGAATTCAACTCACATGTCTC TTGCATGGAGAACCCTCACCTACTGTGTTGAGACCCTGT CCAGCCCCCAGGTGGGATCCTCTCTCGACTTCCCATACA TTTCTTTCACAGCATTTACATAGTCCATGATAGTTTACT TGTGGGATTATTTGGTTAATCTTTGCCTTTAACACCAGG GTTCCTTGGGTGAAGGAGCTTCTTTATC |
| 493 | BAG1 | 3203487 | AGAGTCGTTGAAGTCCCAGGAATTCAGGACTGGGCAGG TTAAGACCTCAGACAAGGTAGTAGAGGTAGACTTGTGG ACAAGGCTCGGGTCCCAGCCCACCGCACCCCAACTTTA ATCAGAGTGGTTCACTATTGATCTATTTTTGTGTGATAG |

TABLE 8-continued

Subtyping Target Sequences

| SEQ ID NO. | Gene | Affy Probeset ID | Sequence |
|---|---|---|---|
| | | | CTGTGTGGCGTGGGCCACAACATTTAATGAGAAGTTAC TGTGCACCAAACTGCCGAACACCATTCTAAACTATTCAT ATATATTAGTCATTTAATTCTTACATAACTTGAGAGGTA GACAGATATCCTTATTTTAGAGATGAGGAAACCAAGAG AACTTAGGTCATTAGCGCAAGGTTGTAGAGTAAGCGGC AAAGCCAAGACACAAAGCTGGGTGGTTTGGTTTCAGAG CCAGTGCTTTTCCCCTCTACTGTACTGCCTCTCAACCAA CACAGGGTTGCACAGGCCCATTCTCTGATTTTTTTCCTC TTGTCCTCTGCCTCTCCCTCTAGCTCCCACTTCCTCTCTG CTCTAGTTCATTTTCTTTAGAGCAGCCCGAGTGATCATG AAGTGCAAATCTTGCCATGTCAGTCCCCTGCTTAGAACC CTCCAATGGCTCACTTTCTCTTTAGGCA |
| 494 | BAG1 | 3203488 | CTTCTGTCTCTGTGGTTGTACTGTCCAGCAATCCACCTT TTCTGGAGAGGGCCACCTCTGCCCAAATTTTCCCAGCTG TTTGGACCTCTGGGTGCTTTCTTTGGGCTGGTGAGAGCT CTAATTTGCCTTGGGCCAGTTTCAGGTTTATAGGCCCCC TCAGTCTTCAGATACATGAGGGCTTCTTTGCTCTTGTGA TCGTGTAGTCCCATA |
| 495 | BAG1 | 3203489 | TTTCCTACTCTCACACTGGTTCTCAATGAAAA |
| 496 | BAG1 | 3203490 | AATGGCGCCACCAGCTCTGCCGTCTCTGGAGCGGAATT TACCTGATTTCTTCAGGGCTGCTGGGGGCAACTGGCCAT TTGCCA |
| 497 | BAG1 | 3203493 | TTCAAAGACAGTAGATTGAAAAGGAAAGGCT |
| 498 | BAG1 | 3203495 | GAAGCTCTCTGCAAACTTGATAGGAGAGTAAAAGCCAC AATAGAGCAGTTTATGA |
| 499 | BAG1 | 3203496 | AGCTCTTGCTACGTGTTGTGAAATCTGTGTCTGTAGCTC GTGGCTGTGATAAACATCCTCAGAGATCCCTGCTATCC AACTCTTGTCACCAGCTAACTGGTCATTAGGCCAAGCT GTGTGAGTGAACCATTAGACAATTTGATAAAAATAAGC ACTGCTGCCATTCTTTAGCATGCGTCTGTGCCACAAGTT AGTGACACATGTACATATATTCCCTTTACCTCACAGTAA CCATCTAGGGTGTGGGCATCATAATCTTCATTTTTAAAA TGAGGGTACTGAGGCATGAATAGGCTAAATAATTTGCT CAAGATCACAAGTTAGTAAATGGCAGTCAGTTTTCAGG CGTAGGCTTTGAAGACTCTAAACCTGTGCTTTTAACATC TGCCTCTTCTTGTGACTGGGGGCTTCACTGGAGCCAAGC CTCAGGAGGCATTTGCAGCCACAGTGGGTCATGCGAGG TAGAGCAGACTGCAACCTGATAGAATTCTTGGACTGGC CCACGGCCAGCCTTTTTAATTTTTCCAAGAGTTAAAGTT GTGGATCTGAGATGTGGCCTGGCCTGCCAGGGCTATGG TGGGCTCAGTGTGATTGCATCATTAGTATTGTGGCATGG AGTCTTCCGTCAGCCTCAGAGA |
| 500 | BAG1 | 3203497 | AGTCCACAGGAAGAGGTTGAACTAAAGAAGTTGAAAC ATTTGGAGAAGTCTGTGGAGAAGATAGCTGACCAGCTG GAAGAGTTGAATAAAGAGCTTACTGGAATCCAGCA |
| 501 | BAG1 | 3203498 | CTAAATTTCTTGCTTCAGGGTCAGGGAGAATGGTGATG GGCAACAGGCAGAACCAAAGAGTCAAGTTTGAAGAAA CTATAGGACTTTTACTTGGAGCTGACACAGAGCGTATG GAGCGAAGTGTGAACTCAAGGAAGGCACCATGGCACA TGCCTATTGTCCCAGCAAGTTGGGAGTCTGAGACAGGA GGATCACTTGAGTCCAGGGGTTTGAGGCTGCAGTGAGT TATGATCATGCCTGTAAACAGCCACTGCACTCCAACCT GGGAACCGTAGTGAGACCCTATCTCAAAAAAGAAAAA AGTCTGAACTTAAGTCTAATCTACCTCTTTTGGACTGTG TGATCTCATGTTACTTTACTACATTAAGCCTCAGTTTCA TCATCTGTAAAACAGCAGTACTTCCCTGATGGAGTTGTG GTAAGGCTTAAAAAATAGGTAAGGTGCTTAGGATAGTG TGTGGCATGTAGGAAGTGTTCAATAAAAGTATTCATCG TTGTTAACCAGCATCACATTAAACAGGAGCGCTCAATT GGAGGCTGCCATTTAGGAATTCCATTTAAAGGAATGGT AGAATTCCACCTTTCTTGCCATTCTGGACTCCTCACAAG TGTTTACTG |
| 502 | BAG1 | 3203499 | GGAAATGGAAACACCGTTGTCAGCACTTGGAATACAAG ATGGTTGCCGGGT |

TABLE 8-continued

Subtyping Target Sequences

| SEQ ID NO. | Gene | Affy Probeset ID | Sequence |
|---|---|---|---|
| 503 | BAG1 | 3203500 | GACCTGCTAGGTATTGGACACTCTCAAACACCTGGACAGGTGTCAGATTTGAAGTCTTATGATGATGGCAGAAATCTCACCATTTTCGATGAAGCTCATGGGCAGTCTTC |
| 504 | BAG1 | 3203501 | GAGAAGCACGACCTTCATGTTACCTCCCAGCAGGGCAGCAGTGAACCAGTTGTCCAAGACCTGGCCCAGGTTGTTGAAGAGGTCATAGGGGTTCCACAGTCTTTTC |
| 505 | BAG1 | 3203504 | GGCAGCTGGGCTCACCGTGACTGTCACCCAC |
| 506 | BAG1 | 3203505 | GAGGCGACCCAGGGCGAAGAGATGAATCGGAGCCAGGAGGTG |
| 507 | BAG1 | 3203506 | AGTTGACCCTGAGTGAGGAAGCGACCTGGAGTGAAGAGGCGACCCAGAGTGAG |
| 508 | BAG1 | 3203507 | ACCCGGCGCCGCTCGACCCGGAGCGAGGA |
| 509 | BAG1 | 3203508 | TGGGCGTCCACCTGCCCGGAGTACTGCCAGCGGGCATGACCGACCCACCAGGGGCGCCGC |
| 510 | BAG1 | 3203509 | CTGGGTTCCCGGCTGCGCGCCCTTCGGCCAG |
| 511 | BAG1 | 3203510 | GCGGGGTTGTGAGACGCCGCGCTCAGCTTCCATCGCTGGGCGGTCAACAAGTGCG |
| 512 | CEP55 | 3258448 | TGTGACTCGGCCGACGCGAGCGCCGCGCTTCGCTTCAGCTGCT |
| 513 | CEP55 | 3258449 | GGAGGCGACCGCGGAGGGTGGCGAGGGGCGGCCAGGACCCGCAGCCC |
| 514 | CEP55 | 3258450 | GGCAGATCGCGTCCGCGGGATTCAATCTCTGCCCGCTCTGATAACAGTCCTTTTCCCTGGCGCTCACTTCGTGCCTGGCACCCGGCTGGGCGCCTCAAGACCGTTGTCTCTTCGATCGCTTCTTTGGACTTGG |
| 515 | CEP55 | 3258451 | ATGTCTTCCAGAAGTACCAAAGATTTAATTA |
| 516 | CEP55 | 3258452 | TAAGTGGGGATCGAAGCCTAGTAACTCCAAATCCGAAACTACATTAGAAAAATTAAAGGGAGAAATTGCACACTTAAAGACATCAGTGGATGAAATCACAAGTGGGAAAGGAAAGCTGACTGATAAAGAGAGACACAGACTT |
| 517 | CEP55 | 3258453 | GCGACTGAGAGACCAACTGAAGGCCAGATATAGTACTACCACATTGCTTGAACAGCTGGAAGAGACAACGAGAGAAGGAGAAAGGAGGGAGCAGGTGTTGAAAGCCTTATCTGAAGAGAAAGACGTATTGAAACAACAGTTGTCTGCTGCAACCTCA |
| 518 | CEP55 | 3258454 | CTGTGGCTCCAAACTGCTTCAACTCATCAATAAATAAT |
| 519 | CEP55 | 3258455 | TCTGGAGAAAAATCAGCAGTGGCTCGTGTATGATCAGCAGCGGGAAGTCTATGTAAAAGGACTTTTAGCAAAGATCTTTGAGTTGGAAAAGAAAACGGAAACAGCTGCTCATTCACTCCCACAGCAGACAAAAAAGC |
| 520 | CEP55 | 3258456 | GAAGCAGAAATGTTACAACGATCTCTTGGCAAGTGCAAAAAAAGATCTTGAGGTTGAACGACAAACCATAACTCAG |
| 521 | CEP55 | 3258457 | AGCTGTTGTATTCACAAAGAAGGGCAGATGTGCAACATCTGGAAGATGATAGGCATAAAACAGAGAAGATACAAAAACTCAGGGAAGAGAATGATATTGCTAGGGGAAAACTTGAAGAAGAGAAGAAGAGATCCGAAGAGCTCTTATCTC |
| 522 | CEP55 | 3258459 | CTTTACACATCTCTGCTAAAGCAGCAAGAAGAACAAACAAGGGTAGCTCTGTTGGAACAACAG |
| 523 | CEP55 | 3258460 | ACTCATTCGGGTTGCTTCTAAATTCAATTCTGCCTGTTAGAAAATGCAGTTTTTCCTCATGTTTATGCTGTTCTATGGAGAACTGTTTGAAAGTTGTGAAAAGTGTCT |

TABLE 8-continued

Subtyping Target Sequences

| SEQ ID NO. | Gene | Affy Probeset ID | Sequence |
|---|---|---|---|
| 524 | CEP55 | 3258461 | TGAAAAACTCGACCGTCAACATGTGCAGCATCAATTGC ATGTAATTCTTAAGGAGCTCCGAAAAGCAAGAAATCAA ATAACACAGTTGGAATCCTTG |
| 525 | CEP55 | 3258462 | TCCGAACTTAGGAGGATACAGCTTAACACACAGCTAGC TGTATCTCAAATCAGTAGGTAGAGCCTCTGCCTCATTTG AAGCAACTGCCCTTTGAGCATCAATTCAGAGGACATGA AAGAGGGACATGATCACATCTGGAAACA |
| 526 | CEP55 | 3258463 | CAGAGCCATTAGTCACTTTCCAAGGAGAGACTGAAAAC AGAGAAAAAGTTGCCGCCTCACCAAAAAGTCCCACTGC TGCACTCAATGAAAGCCTGGTGGAATGTCCCAAGTGCA ATATACAGTATCCAGCCACTGAGCATCGCGATCTGCTT GTCCATG |
| 527 | CEP55 | 3258464 | TACCTTTGACACTCCAGCATGCTAGTGAATCATGTATCT TTTAGGCTGCTGTGCATTTCTCTTGGCAGTGATACCTCC CTGACATGGTTCATCATCAGGCTGCAATGACAGAATGT GGTGAGCAGCGTCTACTGAGACTACTAACATTTTGCAC TGTCAAAATACTTGGTGAGGAAAAGATAGCTCAGGTTA TTGCTAATGGGTTAATGCACCAGCAAGCAAAATATTTT ATGTTTTGGGGGTTTTGAAAAATCAAAGATAATTAACC AAGGATCTTAACTGTGTTCGCATTTTTTATCCAAGCACT TAGAAAACCTACAATCCTAATTTTGATGTCCATTGTTAA GAGGTGGTGATAGATACTATTTTTTTTTTCATATTGTAT AGCGGTTATTAGAAAAGTTGGGGATTTTCTTGATCTTTA TTGCTGCTTACCATTGAAACTTAACCCAGCTGTGTTCCC CAACTCTGTTCTGCGCACGAAACAGTATCTG |
| 528 | CEP55 | 3258465 | TCAGATCTTTGTTTGTCTGAACAGGTATTTTTATACATG CTTTTTGTAAACCAAAAACTTTTAAATTTCTTCAGGTTT TCTAACATGCTTACCACTGGGCTACTGTAAATGAGAAA |
| 529 | MKI67 | 3312496 | ACTCGTGAGCACATCTTTAGGGACCAAGAGTGACTTTC TGTAAGGAGTGACTCGTGGCTTGCCTTGGTCTCTTGGGA ATACTTTTCTAACTAGGGTTGCTCTCACCTGAGACATTC TCCACCCGCGGAATCTCAGGGTCCCAGGCTGTGGGCCA TCACGACCTCAAACTGGCTCCTAATCTCCAGCTTTCCTG TCATTGAAAGCTTCGGAAGTTTACTGGCTCTGCTCCCGC CTGTTTTCTTTCTGACTCTATCTGGCAGCCCGATGCCAC CCAGTACAGGAAGTGACACCAGTACTCTGTAAAGCATC ATCATCCTTGGAGAGACTGAGCACTCAGCACCTTCAGC CACGATTTCAGGATCGCTTCCTTGTGAGCCGCTGCCTCC GAAATCTCCTTTGAAGCCCAGACATCTTTCTCCAGCTTC AGACTTGTAGATATAACTCGTTCATCTTCATTTACTTTC CACTTTGCCCCCTGTCCTCTCTGTGTTCCCCAAATCAGA GAATAGCCCGCCATCCCCCAGGTCACCTGTCTGGATTCC TCCCCATTCACCCACCTTGCCAGGTGCAGGTGAGGATG GTGCACCAGACAGGGTAGCTGTCCCCCAAAATGTGCCC TGTGCGGGCAGTGCCCTGTCTCCACGTTTGTTTCCCCAG TGTCTGGCGGGGAGCCAGGTGACATCATAAATACTTGC TGAATGAATGCAGAAATCAGCGGTACTGACTTGTACTA TATTGGCTGCCATGATAGGGTTCTCACAGCGTCATCCAT GATCGTAAGGGAGAATGACATTCTGCTTGAGGGAGGGA ATAGAAAGGGGCAGGGAGGGGACATCTGAGGGCTTCA CAGGGCTGCAAAGGGTACAGGGATTGCACCAGGGCAG AACAGGGGAGGGTGTTCAAGGAAGAGTGGCTCTTAGCA GAGGCACTTTGGAAGGTGTGAGGCATAAATGCTTCCTT CTACGTAGGCCAACCTCAAAACTTTCAGTAGGAATGTT GCTATGATCAAGTTGTTCTAACACTTTAGACTTAGTAGT AATTATGAACCTCACATAGAAAAATTTCATCCAGCCAT ATGCCTGTGGAGTGGAATATTCTGTTTAGTAGAAAAAT CCTTTAGAGTTCAGCTCTAACCAGAAATCTTGCTGAAGT ATGTCAGCACCTTTTCTCACCCTGGTAAGTACAGTATTT CAAGAGCACGCTAAGGGTGGTTTTCATTTTACAGGGCT GTTGATGATGGGTTAAAAATGTTCATTTAAGGGCTACC CCCGTGTTTAATAGATGAACACCACTTCTACACAACCCT CCTTGGTACTGGGGGAGGGAGAGATCTGACAAATACTG CCCATTCCCCTAGGCTGACTGGATTTGAGAACA |
| 530 | MKI67 | 3312497 | ATGAGCGCACGGATGAATGGAGCTTACAAGATCTGTCT TTCCAATGGCCGGGGGCATTTGGTCCCCAAATTAAGGC TATTGGACATCTGCACAGGACAGTCCTATTTTTGATGTC |

TABLE 8-continued

| Subtyping Target Sequences | | | |
|---|---|---|---|
| SEQ ID NO. | Gene | Affy Probeset ID | Sequence |
| 531 | MKI67 | 3312498 | AGGAACAACTATCCTCGTCTGTCCCAACACTGAGCAGG CACTCGGTAAAC |
| 532 | MKI67 | 3312499 | ATTTGCTGGGTCTGAATCGGCTTCATAAACTCCACTGGG AGCACTGCTGGGCTCCTGGACTGAGAATAGTTGAACAC CGGGGGCTTTGTGAAGGAGTCTGGGCCAAGGTTTGCCC TCAGCTTTGCAGAATGAAGCCTTGAGGTCTGTCACCAC CCACAGCCACCCTACAGCAGCCTTAACTGTGACACTTG CCACACTGTGTCGTCGTTTGTTTGCCTATGTCCTCC |
| 533 | MKI67 | 3312500 | GGACAATGTGTGTGTCAAGAAAATAAGAACCAGAAGTC ATAGGGACAGTGAAGATATTTG |
| 534 | MKI67 | 3312502 | CAGAAGAGTGCGAAGGTTCTCATGCAGAATCAGAAAG GGAAAGGAGAAGCAGGAAATTCAGACTCCATGTGCCTG AGATCAAGAAAGACAAAAAGCCAGCCTGCAGCAAGCA CTTTGGAGAGCAAATCTGTGCAGAGAGTAACGCGGAGT GTCAA |
| 535 | MKI67 | 3312503 | GAGCCCGGAAACCCATACCTAGAGACAAAG |
| 536 | MKI67 | 3312504 | TATCCCTGCGCTCCAGACGCCAAAAT |
| 537 | MKI67 | 3312506 | AAGAGGCTGCGCTGCATGCCAGCACCAGAGGAAATTGT GGAGGAGCTGCCAGCCAGCAAGAAGCAGAGGGTTGCT CCCAGGGCAAGAGGCAAATCATCCGAACCCGTGGTCAT CATGAAGAGAAGTTTGAGGACTTCTGCAAAAAGAATTG AACCTGCGGAAGAGCTGAACAGCAACGACATGAAAAC CAACAAAGAGGAACACAAATTACAAGACTCGGTCCCTG |
| 538 | MKI67 | 3312507 | CCCGTGCTCTAGAAGACCTGGTTGACTTCAAAGAGCTC TTCTCAGCACCAGGTCACACTGAAGAGTCAATGACTAT TGACAAAAACACAAAAATTCCCTGCAAATCTCCCCCAC CAGAACTAACAGACACTGCCACGAGCACAAAGAGATG CCCCAAGACACGTCCCAGGAAAGAAGTAAAAGAGGAG CTCTCAGCAGTTGAGAGGCTCACGCAAACATCAGGGCA AAGCACACACACACACAAAGAACCAGCAAGCGGTGAT GAGGGCATCAAAGTATTGAAGCAACGTGCAAAGAAGA AACCAAACCCAGTAGAAGAGGAACCCAGCAGGAGAAG GCCAAGAGCACCTAAGGAAAAGGCCCAACCCCTGGAA GACCTGGCCGGCTTCACAGAGCTCTCTGAAACATCAGG TCACACTCAGGAATCACTGACTGCTGGCAAAGCCACTA AAATACCCTGCGAATCTCCCCCACTAGAAGTGGTAGAC ACCACAGCAAGCACAAAGAGGCATCTCAGGACACGTGT GCAGAAGGTACAAGTAAAAGAAGAGCCTTCAGCAGTC AAGTTCACACAAACATCAGGGGAAACCACGGATGCAG ACAAAGAACCAGCAGGTGAAGATAAAGGCATCAAAGC ATTGAAGGAATCTGCAAAACAGACACCGGCTCCAGCAG CAAGTGTAACTGGCAGCAGGAGACGGCCAAGAGCACC CAGGGAAAGTGCCCAAGCCATAGAAGACCTAGCTGGCT TCAAAGACCCAGCAGCAGGTCACACTGAAGAATCAATG ACTGATGACAAAACCACTAAAATACCCTGCAAATCATC ACCAGAACTAGAAGACACCGCAACAAGCTCAAAGAGA CGGCCCAGGACACGTGCCCAGAAAGTAGAAGTGAAGG AGGAGCTGTTAGCAGTTGGCAAGCTCACACAAACCTCA GGGGAGACCACGCACACCGACAAAGAGCCGGTAGGTG AGGGCAAAGGCACGAAAGCATTTAAGCAACCTGCAAA GCGGAAGCTGGACGCAGAAGATGTAATTGGCAGCAGG AGACAGCCAAGAGCACCTAAGGAAAAGGCCCAACCCC TGGAAGATCTGGCCAGCTTCCAAGAGCTCTCTCAAACA CCAGGCCACACTGAGGAACTGGCAAATGGTGCTGCTGA TAGCTTTACAAGCGCTCCAAAGCAAACACCTGACAGTG GAAAACCTCTAAAAATATCCAGAAGAGTTCTTCGGGCC CCTAAAGTAGAACCCGTGGGAGACGTGGTAAGCACCAG AGACCCTGTA |
| 539 | MKI67 | 3312508 | GGAGAACTCTTAGCGTGCAGGAATCTAATGCCATCAGC AGGCAAAGCCATGCACACGCCTAAACCATCAGTAGGTG AAGAGAAAGACATCATCATATTTGTGGGAACTCCAGTG CAGAAACTGGACCTGACAGAGAACTTAACCGGCAGCA AGAGACGGCCACAAACTCCTAAGGAAGAGGCCCAGGC TCTGGAAGACCTGACTGGCTTTAAAGAGCTCTTCCAGA CCCCTGGTCATACTGAAGAAGCAGTGGCTGCTGGCAAA |

TABLE 8-continued

Subtyping Target Sequences

| SEQ ID NO. | Gene | Affy Probeset ID | Sequence |
|---|---|---|---|
| | | | ACTACTAAAATGCCCTGCGAATCTTCTCCACCAGAATC |
| | | | AGCAGACACCCCAACAAGCACAAGAAGGCAGCCCAAG |
| | | | ACACCTTTGGAGAAAAGGGACGTACAGAAGGAGCTCTC |
| | | | AGCCCTGAAGAAGCTCACACAGACATCAGGGGAAACC |
| | | | ACACACACAGATAAAGTACCAGGAGGTGAGGATAAAA |
| | | | GCATCAACGCGTTTAGGGAAACTGCAAAACAGAAACTG |
| | | | GACCCAGCAGCAAGTGTAACTGGTAGCAAGAGGCACCC |
| | | | AAAAACTAAGGAAAAGGCCCAACCCCTAGAAGACCTG |
| | | | GCTGGCTTGAAAGAGCTCTTCCAGACACCAGTATGCAC |
| | | | TGACAAGCCCACGACTCACGAGAAAACTACCAAAATAG |
| | | | CCTGCAGATCACAACCAGACCCAGTGGACACACCAACA |
| | | | AGCTCCAAGCCACAGTCCAAGAGAAGTCTCAGGAAAGT |
| | | | GGACGTAGAAGAAGAATTCTTCGCACTCAGGAAACGAA |
| | | | CACCATCAGCAGGCAAAGCCATGCACACACCCAAACCA |
| | | | GCAGTAAGTGGTGAGAAAAACATCTACGCATTTATGGG |
| | | | AACTCCAGTGCAGAAACTGGACCTGACAGAGAACTTAA |
| | | | CTGGCAGCAAGAGACGGCTACAAACTCCTAAGGAAAA |
| | | | GGCCCAGGCTCTAGAAGACCTGGCTGGCTTTAAAGAGC |
| | | | TCTTCCAGACACGAGGTCACACTGAGGAATCAATGACT |
| | | | AACGATAAAACTGCCAAAGTAGCCTGCAAATCTTCACA |
| | | | ACCAGACCCAGACAAAAACCCAGCAAGCTCCAAGCGA |
| | | | CGGCTCAAGACATCCCTGGGGAAAGTGGGCGTGAAAG |
| | | | AAGAGCTCCTAGCAGTTGGCAAGCTCACACAGACATCA |
| | | | GGAGAGACTACACACACACACACAGAGCCAACAGGAG |
| | | | ATGGTAAGAGCATGAAAGCATTTATGGAGTCTCCAAAG |
| | | | CAGATCTTAGACTCAGCAGCAAGTCTAACTGGCAGCAA |
| | | | GAGGCAGCTGAGAACTCCTAAGGGAAAGTCTGAAGTCC |
| | | | CTGAAGACCTGGCCGGCTTCATCGAGCTCTTCCAGACA |
| | | | CCAAGTCACACTAAGGAATCAATGACTAACGAAAAAAC |
| | | | TACCAAAGTATCCTACAGAGCTTCACAGCCAGACCTAG |
| | | | TGGACACCCCAACAAGCTCCAAGCCACAGCCCAAGAGA |
| | | | AGTCTCAGGAAAGCAGACACTGAAGAAGAATTTTTAGC |
| | | | ATTTAGGAAACAAACGCCATCAGCAGGCAAAGCCATGC |
| | | | ACACACCCAAACCAGCAGTAGGTGAAGAGAAAGACAT |
| | | | CAACACGTTTTTGGGAACTCCAGTGCAGAAACTGGACC |
| | | | AGCCAGGAAATTTACCTGGCAGCAATAGACGGCTACAA |
| | | | ACTCGTAAGGAAAAGGCCCAGGCTCTAGAAGAACTGAC |
| | | | TGGCTTCAGAGAGCTTTTCCAGACACCATGCACTGATA |
| | | | ACCCCACGACTGATGAGAAAACTACCAAAAAAATACTC |
| | | | TGCAAATCTCCGCAATCAGACCCAGCGGACACCCCAAC |
| | | | AAACACAAAGCAACGGCCCAAGAGAAGCCTCAAGAAA |
| | | | GCAGACGTAGAGGAAGAATTTTTAGCATTCAGGAAACT |
| | | | AACACCATCAGCAGGCAAAGCCATGCACACGCCTAAAG |
| | | | CAGCAGTAGGTGAAGAGAAAGACATCAACACATTTGTG |
| | | | GGGACTCCAGTGGAGAAACTGGACCTGCTAGGAAATTT |
| | | | ACCTGGCAGCAAGAGACGGCCACAAACTCCTAAAGAA |
| | | | AAGGCCAAGGCTCTAGAAGATCTGGCTGGCTTCAAAGA |
| | | | GCTCTTCCAGACACCAGGTCACACTGAGGAATCAATGA |
| | | | CCGATGACAAAATCACAGAAGTATCCTGCAAATCTCCA |
| | | | CAACCAGACCCAGTCAAAACCCCAACAAGCTCCAAGCA |
| | | | ACGACTCAAGATATCCTTGGGGAAAGTAGGTGTGAAAG |
| | | | AAGAGGTCCTACCAGTCGGCAAGCTCACACAGACGTCA |
| | | | GGGAAGACCACACAGACACACAGAGAGACAGCAGGAG |
| | | | ATGGAAAGAGCATCAAAGCGTTTAAGGAATCTGCAAAG |
| | | | CAGATGCTGGACCCAGCAAACTATGGAACTGGGATGGA |
| | | | GAGGTGGCCAAGAACACCTAAGGAAGAGGCCCAATCA |
| | | | CTAGAAGACCTGGCCGGCTTCAAAGAGCTCTTCCAGAC |
| | | | ACCAGACCACACTGAGGAATCAACAACTGATGACAAA |
| | | | ACTACCAAAATAGCCTGCAAATCTCCACCACCAGAATC |
| | | | AATGGACACTCCAACAAGCACAAGGAGGCGGCCCAAA |
| | | | ACACCTTTGGGGAAAAGGGATATAGTGGAAGAGCTCTC |
| | | | AGCCCTGAAGCAGCTCACACAGACCACACACACAGACA |
| | | | AAGTACCAGGAGATGAGGATAAAGGCATCAACGTGTTC |
| | | | AGGGAAACTGCAAAACAGAAACTGGACCCAGCAGCAA |
| | | | GTGTAACTGGTAGCAAGAGGCAGCCAAGAACTCCTAAG |
| | | | GGAAAAGCCCAACCCCTAGAAGACTTGGCTGGCTTGAA |
| | | | AGAGCTCTTCCAGACACCAATATGCACTGACAAGCCCA |
| | | | CGACTCATGAGAAAACTACCAAAATAGCCTGCAGATCT |
| | | | CCACAACCAGACCCAGTGGGTACCCCAACAATCTTCAA |
| | | | GCCACAGTCCAAGAGAAGTCTCAGGAAAGCAGACGTA |
| | | | GAGGAAGAATCCTTAGCACTCAGGAAACGAACACCATC |
| | | | AGTAGGGAAAGCTATGGACACACCCAAACCAGCAGGA |
| | | | GGTGATGAGAAAGACATGAAAGCATTTATGGGAACTCC |
| | | | AGTGCAGAAATTGGACCTGCCAGGAAATTTACCTGGCA |

TABLE 8-continued

Subtyping Target Sequences

| SEQ ID NO. | Gene | Affy Probeset ID | Sequence |
|---|---|---|---|
| | | | GCAAAAGATGGCCACAAACTCCTAAGGAAAAGGCCCA GGCTCTAGAAGACCTGGCTGGCTTCAAAGAGCTCTTCC AGACACCAGGCACTGACAAGCCCACGACTGATGAGAA AACTACCAAAATAGCCTGCAAATCTCCACAACCAGACC CAGTGGACACCCCAGCAAGCACAAAGCAACGGCCCAA GAGAAACCTCAGGAAAGCAGACGTAGAGGAAGAATTT TTAGCACTCAGGAAACGAACACCATCAGCAGGCAAAGC CATGGACACACCAAAACCAGCAGTAAGTGATGAGAAA AATATCAACACATTTGTGGAAACTCCAGTGCAGAAACT GGACCTGCTAGGAAATTTACCTGGCAGCAAGAGACAGC CACAGACTCCTAAGGAAAAGGCTGAGGCTCTAGAGGAC CTGGTTGGCTTCAAAGAA |
| 540 | MKI67 | 3312509 | AACAACAGTTGAAGGCATCCCTGGGGAAAGTAGGTGTG AAAGAAGAGCTCCTAGCAGTCGGCAAGTTCACACGGAC GTCAGGGGAGACCACGCACACGCACAGAGAGCCAGCA GGAGATGGCAAGAGCATCAGAACGTTTAAGGAGTCTCC AAAGCAGATCCTGGACCCAGCAGCCCGTGTAACTGGAA TGAAGAAGTGGCCAAGAACGCCTAAGGAAGAGGCCCA GTCACTAGAAGACCTGGCTGGCTTCAAAGAGCTCTTCC AGACACCAGGTCCCTCTGAGGAATCAATGACTGATGAG AAAACTACCAAAATAGCCTGCAAATCTCCACCACCAGA ATCAGTGGACACTCCAACAAGCACAAAGCAATGGCCTA AGAGAAGTCTC |
| 541 | MKI67 | 3312510 | TGCAAACAGGTCAGGAAGGTCTACAGAGTTCAGGAATA TACAGAAGCTACCTGTGGAAAGTAAGAGTGAAGAAAC AAATACAGAAATTGTTGAGTGCATCCTAAAAAGAGGTC AGAAGGCAACACTACTACAACAAAGGAGAGAAGGAGA GATGAAGGAAATAGAAAGACCTTTTGAGACATATAAGG AAAATATTGAATTAAAAGAAAACGATGAAAAGATGAA AGCAATGAAGAGATCAAGAACTTGGGGGCAGAAATGT GCACCAATGTCTGACCTGACAGACCTCAAGAGCTTGCC TGATACAGAACTCATGAAAGACACGGCACGTGGC |
| 542 | MKI67 | 3312511 | CCCAGTGAAGGAGCAACCGCAGTTGACAAGCACATGTC ACATCGCTATTTCAAATTCAGAGA |
| 543 | MKI67 | 3312513 | TAAAAACGTAGTCTTAGATCTTATAAATCTTTTGACTCT ACTGTTTTTTACTGTGTTAATGTTTGTTTTGCTAACTTTG TTTATCTGCTG |
| 544 | MKI67 | 3312514 | CGCAAACTCTCCTTGTACCATAATAATAGGGAAAGCTC ATACTGAAAAAGTACATGTGCCTGCTCGACCCTACAGA GTGCTCAA |
| 545 | MKI67 | 3312515 | AGCCTGTGGGCGAAGTTCACAGTCAA |
| 546 | MKI67 | 3312516 | CATGGGCAGATGTAGTAAAACTTGGTGCAAAACAAACA CAAACTAAAGTCATAAAACATGGTCCTCAAAGGTC |
| 547 | MKI67 | 3312517 | AAGAGAGTGTCTATCAGCCGAAGTCAACATGATATTTT ACAGATGATATGTTCCAAAAGAAGAAGTGGTGCTTCGG AAGCAAAT |
| 548 | MKI67 | 3312518 | AAACAAGAGTCAGGTTCAGAAATCCATGTGGAAGTGAA GGCACAAAGCTTGGTTATAAGCCCTCCAGCTCCTAGTC CTAGGAAAACTCCAGTTGCCAGTGATCAACGCCGTAGG TC |
| 549 | MKI67 | 3312519 | CCTTTGAAAAGAAGGCGTGTGTCCTTTGGTGGGCACCT AAGACCTGAACTATTTGATGAAAACTTGCCTCCTAATA CGCCTCTCAAAAGGGGAGAAGCCCCAACCAAAAGAAA GTCTCTGGTAATGCACACTCC |
| 550 | MKI67 | 3312520 | GGACAGATGTGCTCTGGGTTACCTGGTCTTAGTTCAGTT GATATCAACAACTTTGGTGATTCCATT |
| 551 | MKI67 | 3312521 | TTGAGAGGAAGATCCAAAAGGATTCCCTCAG |
| 552 | MKI67 | 3312522 | GAAGCTTTCAACTAGAAATCGAACACCAGCTAAAGTTG AAGATGCAGCTGACTCTGCCACTAAGCCAGAAAATCTC TCTTCCAAAACCAGAGGAAGTATTCCTACAGATGTGGA AGTTCTGCCTACGGAAACTGAAATTCACAATGAGC |

TABLE 8-continued

Subtyping Target Sequences

| SEQ ID NO. | Gene | Affy Probeset ID | Sequence |
|---|---|---|---|
| 553 | MKI67 | 3312523 | CCAGCGTTAAATTAGTGAGCCGTTATGGAGAATTGAAGTCTGTTCCCACTACACAATGTCTTGACAATAGCAAAAAAAATGAATCTCCCTTTTGGAAGCTTTATGAGTCAGTGAAGAAAGAGTTGGATGTAAAATCACAAAAAGAAAATGTCCTACAGTATTGTAGAAAATCTGGATTACAAACTGATTACGCAACAGAGAAAGAAAGTGCTGATGGTTTACAGGGGGAGACCCAACTGTTGGTCTCGCGTAAGTCAAGACCAAAATCTGGTGGGAGCGGCCACGCTGTGGCAGAGCCTGCTTCACCTGAACAAGAGCTTGACCAGAACAAGGGGAAGGGAAGAGACGTGGAGTCTGTTCAGACTCCCAGCAAGGCTGTGGGCGCCAGCTTTCCTCTCTATGAGCCGGCTAAAATG |
| 554 | MKI67 | 3312524 | AGCCAGCACGTCGTGTCTCAAGATCTAGCTTCT |
| 555 | MKI67 | 3312526 | TTCAGAATGGAAGGAAGTCAACTGAATTTC |
| 556 | MKI67 | 3312527 | CCAACACAAGTAAATGGGTCTGTTATTGATGAGCCTGTACGGCTAAAACATGGAGATGTAATAACTATTATTGATCGTTCCTTCAG |
| 557 | MKI67 | 3312528 | TGTGACATCCGTATCCAGCTTCCTGTTGTGTCAAAACAACATT |
| 558 | MKI67 | 3312530 | CCTGAGCCTCAGCACCTGCTTGTTTGGAAG |
| 559 | MKI67 | 3312531 | CCCACGAGACGCCTGGTTACTATCAA |
| 560 | MKI67 | 3312532 | TTTGCTTCTGGCCTTCCCCTACGGATTATACCTGGCCTTCCCCTACGGATTATACTCAACTTACTGTTTAGA |
| 561 | MKI67 | 3312533 | GACTCGGTGGGAGCCGCTAGAGCCGGGCGCCCGGGGACGTAGCCTGTAGGGCCACCGGGTCCCCGTCAGAGGCGGCGGCGGGAGCAGCGGGGACTGCAGGCCGGGGTGCAGCGAACGCGACCCCGCGGGCTGCGGCCCGGTGTGTGCGGAGCGTGGCGGGCGCAGCTTACCGGGCGGAGGTGAGCGCGGCGCCGGCTCCTCCTGCGGCGGACTTTGGGTGCGACTTGACGAGCGGTGGTTCGACAAGTGGCCTTGCGGGCCGGAT |
| 562 | TMEM45B | 3356039 | TGCAGACGGCTGCGAGGCGCTGGGC |
| 563 | TMEM45B | 3356044 | GCAGGGCTGAGACTATCTTCTGCTCAGGAA |
| 564 | TMEM45B | 3356053 | TCTCATGTTTTTCTATAAGCAGTTAAGAGAAGCCACACAGCATCCTGAACACTTTGCTTTCT |
| 565 | TMEM45B | 3356054 | ATGGCAAATTTCAAGGGCCACGCGCTTCCAGGGAGTTTCTTCCTGATCATTGGGCTGTGTTGGTCAGTGAAGTACCCGCT |
| 566 | TMEM45B | 3356055 | GTACTTTAGCCACACGCGGAAGAACAGCCCACTACATTACTATCAG |
| 567 | TMEM45B | 3356056 | CGTCTCGAGATCGTCGAAGCCGCAATTAGGACTTTGTTTTCCGTCACTG |
| 568 | TMEM45B | 3356057 | GTCATTTGGTCTAGGGAATCTCCTCATCATACCCAGAACCTTTAATTCATTTTCTGAGCCCTGTGAAATAGATGTTCCCACTGGCAGAGATAATAGGGCAACAATTTCCTGATGGCCACTAGACTATTTTATCGTAACATCCATTGTGTACAGAGCTTTATAATACTAACGGTTGACAGCTCTCACATCATG |
| 569 | TMEM45B | 3356058 | CACCATGTACCTATTCTTTGCAGTCTCAGGAATTGTTGACATGCTCACCTATCTGGTCAGCCACGTTCCCTTGG |
| 570 | TMEM45B | 3356061 | AACCGGCCTCCGCTGGACCAGCACATCCACTCACTCCTGCTGTATGCTCTGTTCGGAGGGTGTGTTAGTATCTCCCTAGAGGTGATCTTCCGGGACCACATTGTGCTGGAACTTTTCCGAACCAGTCTCATC |

TABLE 8-continued

Subtyping Target Sequences

| SEQ ID NO. | Gene | Affy Probeset ID | Sequence |
|---|---|---|---|
| 571 | TMEM45B | 3356063 | ATTGGGTTTGTGCTGTTCCCACCTTTTGGAACACCCGAA TGGGACCAGAAGGATGATGCCAACCTCATGTTCATCAC CATGTGCTTCTGCTGGCACTACCTGGCTGCCCTCAGCAT TGTGGCCGTCAACTATTCTCTTG |
| 572 | TMEM45B | 3356065 | CCTTTTGACTCGGATGAAGAGACACGGAAGGGGAGAA ATCATTGGAATTCAGAAGCTGAATTCAGATGACACTTA CCAGACCGCCCTCTTGAGTGGCTCAGA |
| 573 | TMEM45B | 3356066 | TAAAGTCTGTGTTGGTATAGTACCCTTCATAAGGAAAA ATGAAGTAATGCCTATAAGTAGCAGGCCTTTGTGCCTC AGTGTCAAGAGAAATCAAGAGATGCTAAAAGCTTTACA ATGGAAGTGGCCTCATGGATGAATCCGGGGTATGAGCC CAGGAGAACGTGCTGCTTTTGGTAACTTATCCCTTTTTC TCTTAAGAAAGCAGGTACTTTCTTATTAGAAATATGTTA GAATGTGTAAGCAAACGACAGTGCCTTTAGAATTACAA TTCTAACTTACATATTTTTTGAAAGTAAAATAATTCACA AGCTTTGGTATTTTAAAATTATTGTTAAACATATCATAA CTAATCATACCAGGGTACTGCAATACCACTGTTTATAA GTGACAAAATTAGGCCAAAGGTGATTTTTTTTTAAATCA GGAAGCTGGTTACTGGCTCTACTGAGAGTTGGAGCCCT GATGTTCTGATTCTTCAAAGTCACCCTAAAAGAAGATCT GACAGGAAAGCTGTATAATGAGATAGAAAAACGTCAG GTATGGAAGGCTTTCAGTTTTAATATGGCTGAAAGCAA AGGATAACGAATTCAGAATTAGTAATGTAAAATCTTGA TACCCTAATCTTGCTTCTGGATCTGTTCTTTTTTTAAAAA AACTTCCTTCACCGCGCCTATAATCCTAGCACTTTGGGA GGCCGAGGCAGGCAGATCACGGGGTCAGGAGATCAAG ACCATCCTGGCTAACATGGTGAAACCCCGTCTCTACTG AAAATACAAAAAATTAGCCGGGTGTGGTGGCGGGCGCC TGTAGTTCCAGCTACTCGGGAGGCTGAGGCAAGAGAAT GGCATGAACCCGGTAGGGGAGCTTGCAGTGAGCCCAGA TCATGCCACTGTACTCCAGCCTAGGTGACAGAGCAAGA CTCTGTCTCAAAAACAAGCAAACAGACTTCCTTCAACA AATATTTATTAAATATCCACTTTGCAACAGCACTGAAAT GGCTGTAAGGACTCCTGAGATATGTGTCCAGCAAGG |
| 574 | PGR | 3388371 | AGTGTTCCCGTCTTCTCCGAGCTTAGAGTTGGATGGGGA ATAAAGACAGGTAAACAGATAGCTACAATATTGTACTG TGAATGCTTATGCTGGAGGAAGTACAGGGAACTATTGG AGCACCTAAGAGGAGCACCTACCTTGAATTTAGGGGTT AGCAGAGGCATCCTGAAAAAAGTCAAAGCTAAGCCAC AATCTATAAGCAGTTTAGGAATTAGCAGAACGTGCGTG GTGAGGAGATGCCAAAGGCAAGAAGAGAAGAGTATTC CAAACAGGAGGGATTCCAAAGAGAGAAGAGTATCCCA AACAACATTTGCACAAACCTGATGGGGAGAGAGAATGT GGGGTGGGGATGGATGATGAGACTGAAGAAGAAAGCC AGGTCTAGATAATCAGTGGCCTTGTACACCATGTTAAA GAGTGTAGACTTGATTCTGTTGTAAACAGGAAAGCAGC ACAATTCATATGAATATTTTAGAAGACTCCCACTGGAA TATGGAGAATAAAGTTGGAGATGACTAATCCTGGAAGC AGGGAGAACATTTTTGAGGAAGTTGCACTATTTTGGTG AAAATGATGATCATAAACATGAAGAATTGTAGGTGATC ATGACCTCCTCTCTAATTTTCCAGAAGGGTTTTGGAAGA TATAACATAGGAACATTGACAGGACTGACGAAAGGAG ATGAAATACACCATATAAATTGTCAAACACAAGGCCAG ATGTCTAATTATTTTGCTTATGTGTTGAAATTACAAATT TTTCATCAGGAAACCAAAAACTACAAAACTTAGTTTTC CCAAGTCCCAGAATTCTATCTGTCCAAACAATCTGTACC ACTCCACCTATATCCCTACCTTTGCATGTCTGTCCAACC TCAAAGTCCAGGTCTATACACACGGGTAAGACTAGAGC AGTTCAAGTTTCAGAAAATGAGAAAGAGGAACTGAGTT GTGCTGAACCCATACAAAATAAACACATTCTTTGTATA GATTCTTGGAACCTCGAGAGGAATTCACCTAACTCATA GGTATTTGATGGTATGAATCCATGGCTGGGCTCGGCTTT TAAAAAGCCTTATCTGGGATTCCTTCTATGGAACCAAGT TCCATCAAAGCCCATTTAAAAGCCTACATTAAAAACAA AATTCTTGCTGCATTGTATACAAATAATGATGTCATGAT CAAATAATCAGATGCCATTATCAAGTGGAATTACAAAA TGGTATACCCACTCCAAAAAAAAAAAAAAAGCTAAATT CTCAGTAGAACATTGTGACTTCATGAGCCCTCCACAGC CTTGGAGCTGAGGAGGGAGCACTGGTGAGCAGTAGGTT GAAGAGAAAACTTGGCGCTTAATAATCTATCCATGTTTT |

TABLE 8-continued

Subtyping Target Sequences

| SEQ ID NO. | Gene | Affy Probeset ID | Sequence |
|---|---|---|---|
| | | | TTCATCTAAAAGAGCCTTCTTTTTGGATTACCTTATTCA<br>ATTTCCATCAAGGAAATTGTTAGTTCCACTAACCAGAC<br>AGCAGCTGGGAAGGCAGAAGCTTACTGTATGTACATGG<br>TAGCTGTGGGAAGGAGGTTTCTTTCTCCAGGTCCTCACT<br>GGCCATACACCAGTCCCTTGTTAGTTATGCCTGGTCATA<br>GACCCCCGTTGCTATCATCTCATATTTAAGTCTTTGGCT<br>TGTGAATTTATCTATTCTTTCAGCTTCAGCACTGCAGAG<br>TGCTGGGACTTTGCTAACTTCCATTTCTTGCTGGCTTAG<br>CACATTCCTCATAGGCCCAGCTCTTTTCTCATCTGGCCC<br>TGCTGTGGAGTCACCTTGCCCCTTCAGGAGAGCCATGG<br>CTTACCACTGCCTGCTAAGCCTCCACTCAGCTGCCACCA<br>CACTAAATCCAAGCTTCTCTAAGATGTTGCAGACTTTAC<br>AGGCAAGCATAAAAGGCTTGATCTTCCTGGACTTCCCTT<br>TACTTGTCTGAATCTCACCTCCTTCAACTTTCAGTCTCA<br>GAATGTAGGCATTTGTCCTCTTTGCCCTACATCTTCCTT<br>CTTCTGAATCATGAAAGCCTCTCACTTCCTCTTGCTATG<br>TGCTGGAGGCTTCTGTCAGGTTTTAGAATGAGTTCTCAT<br>CTAGTCCTAGTAGCTTTTGATGCTTAAGTCCACCTTTTA<br>AGGATACCTTTGAGATTTAGACCATGTTTTTCGCTTGAG<br>AAAGCCCTAATCTCCAGACTTGCCTTTCTGTGGATTTCA<br>AAGACCAACTGAGGAAGTCAAAAGCTGAATGTTGACTT<br>TCTTTGAACATTTCCGCTATAACAATTCCAATTCTCCTC<br>AGAGCAATATGCCTGCCTCCAACTGACCAGGAGAAAGG<br>TCCAGTGCCAAAGAGAAAAACACAAAGATTAATTATTT<br>CAGTTGAGCACATACTTTCAAAGTGGTTTGGGTATTCAT<br>ATGAGGTTTTCTGTCAAGAGGGTGAGACTCTTCATCTAT<br>CCATG |
| 575 | PGR | 3388372 | GCCTTGTAAGTAGCCATGGAATGTCAACCTGTAACTTA<br>AATTATCCACAGATAGTCATGTGTTTGATGATGGGCACT<br>GTGGAGATAACTGACATAGGACTGTGCCCCCCTTCTCT<br>GCCACTTACTAGCTGGATGAGATTAAGCAAGTCATTTA<br>ACTGCTCTGATTAAACCTGCCTTTCCCAAGTGCTTTGTA<br>ATGAATAGAAATGGAAACCAAAAAAAACGTATACAGG<br>CCTTCAGAAATAGTAATTGCTACTATTTTGTTTTCATTA<br>AGCCATAGTTCTGGCTATAATTTTATCAAACTCACCAGC<br>TATATTCTACAGTGAAAGCAGGATTCTAGAAAGTCTCA<br>CTGTTTTATTTATGTCACCATGTGCTATGATATATTTGGT<br>TGAATTCATTTGAAATTAGGGCTGGAAGTATTCAAGTA<br>ATTTCTTCTGCTGAAAAAATACAGTGTTTTGAGTTTAGG<br>GCCTGTTTTATCAAAGTTCTAAAGAGCCTATCACTCTTC<br>CATTGTAGA |
| 576 | PGR | 3388373 | GTCCTATCTACTAATGTCTCCATTACTATTTAGTCATCA<br>TAACCATTATCTTCATTTTACATGTCGTGTTCTTTCTGGT<br>AGCTCTAAAATGACACTAAATCATAAGAAGACAGGTTA<br>CATATCAGGAAATACTTGAAGGTTACTGAAATAGATTC<br>TTGAGTTAATGAAAATATTTTCTGTAAAAAGGTTTGAA<br>AAGCCATTTGAGTCTAAAGCATTATACCTCCATTATCAG<br>TAGTTATGTGACAATTGTGTG |
| 577 | PGR | 3388374 | GCAGTAATTTGCCTTCTCCTAGAGTTTACCTGCCATTTT<br>GTGCACATTTGAGTTACAGTAGCATGTTATTTTACAATT<br>GTGACTCTCCTGGGAGTCTGGGAGCCATATAAAGTGGT<br>CAATAGTGTTTGCTGACTGAGAGTTGAATGACATTTTCT<br>CTCTGTCTTGGTATTACTGTAGATTTCGATCATTCTTTGG<br>TTACATTTCTGCATATTTCTGTACCCATGACTTTATCACT<br>TTCTTCTCCCATGCTTTATCTCCATCAATTATCTTCATTA<br>CTTTTAAATTTTCCACCTTTGCTTCCTACTTTGTGAGATC<br>TCTCCCTTTACTGACTATAACATAGAAGAATAGAAGTG<br>TATTTTATGTGTCTTAAGGACAATACTTTAGATTCCTTG<br>TTCTAAGTTTTTAAACTGAATGAATGGAATATTATTTCT<br>CTCCCTAAGCAAAATTCCACAAAACAATTATTTCTTATG<br>TTTATGTAGCCTTAAATTGTTTTGTACTGTAAACCTCAG<br>CATAAAAACTTTCTTCATTTCTAATTTCATTCAACAAAT<br>ATTGATTGAATACCTGGTATTAGCACAAGAAAAATGTG<br>CTAATAAGCCTTATGAGAATTTGGAGCTGAAGAAAGAC<br>ATATAACTCAGGAAAGTTACAGTCCAGTAGTAGGTATA<br>AATTACAGTGCCTGATAAATAGGCATTTTAATATTTGTA<br>CACTCAACGTATACTAGGTAGGTGCAAAACATTTACAT<br>ATAATTTTACTGATACCCATGCAGCACAAAGGTACTAA<br>CTTTAAATATTAAATAACACCTTTATGTGTCAGTAATTC<br>ATTTGCATTAAATCTTATTGAAAAGGCTTTCAATATATT<br>TTCCCCACAAATGTCATCCCAAGAAAAAAGTATTTTTA |

TABLE 8-continued

Subtyping Target Sequences

| SEQ ID NO. | Gene | Affy Probeset ID | Sequence |
|---|---|---|---|
| | | | ACATCTCCCAAATATAATAGTTACAGGAAATCTACCTCT GTGAGAGTGACACCTCTCAGAATGAACTGTGTGACACA AGAAAATGAATGTAGGTCTATCCAAAAAAAACCCCAAG AAACAAAAACAATATTATTAGCCCTTTATGCTTAAGTG ATGGACTC |
| 578 | PGR | 3388375 | TAGGTAACTCCCTTTGTGTCAATTATATTTCCAAAAATG AACCTTTAAAATGGTATGCAAAATTTTGTCTATATATAT TTGTGTGAGGAGGAAATTCATAACTTTCCTCAGATTTTC AAAAGTATTTTTAATGCAAAAAATGTAGAAAGAGTTTA AAACCACTAAAATAGATTGATGTTCTTCAAACTAGGCA AAACAACTCATATGTTAAGACCATTTTCCAGATTGGAA ACACAAATCTCTTAGGAAGTTAATAAGTAGATTCATAT CATTATGCAAATAGTATTGTGGGTTTTGTAGGTTTTTAA AATAACCTTTTTTGGGGAGAGAATTGTCCTCTAATGAG GTATTGCGAGTGG |
| 579 | PGR | 3388376 | CAAACAACTTCATCTGTACTGCTTGAATACATTTATCCA GTCCCGGGCACTGAGTGTTGAATTTCCAGAAATGATGT CTGAAGTTATTGCTGCACAATTACCCAAGATATTG |
| 580 | PGR | 3388377 | ATGAGGTCAAGCTACATTAGAGAGCTCATCAAGGCAAT TGGTTTGAGGCAAAAAGGAGTTGTGTCGAGCTCACAGC GTTTCTATCAACTTA |
| 581 | PGR | 3388378 | TGGAAGGGCTACGAAGTCAAACCCA |
| 582 | PGR | 3388379 | CAGGAGTTTGTCAAGCTTCAAGTTAGCCAAGAA |
| 583 | PGR | 3388382 | TATTTTGCACCTGATCTAATACTAAATGA |
| 584 | PGR | 3388383 | CTTACATATTGATGACCAGATAACTCTCATTCAGTATTC TTGGATGAGCTTAATGGTGTTTGGTCTAGGATGGA |
| 585 | PGR | 3388387 | CAGCCAGTGGGCGTTCCAAATGAAAGCCAAGCCCTAAG CCAGAGATTCACTTTTTCACCAGGTCAAGACATACAGTT GATTCCACCACTGATCAACCTGTTAATGAGCATTGAAC CAGATGTGATCTATGCAGGACATGACAACACAAAACCT GACACCTCCAGTTCTTTGCTGACAAGTCTTAATCAACTA GGCGAGAGGCAACTTCTTTCAGTAGTCAAGTGGTCTA |
| 586 | PGR | 3388388 | ATGGAGTTTATATATATTTACATGAATTTCTTTTTTTTCT TCTCTG |
| 587 | PGR | 3388389 | AGACCATTGGCGTACCACCAGTTTGTGGAGGGAACTGG AAAAACTGGAATACACATGCCCCATCCAAAAGCAACCA TTGCAACTAAACTTTAACAGATTGTTGCCACCTAAGTAA TTCACGGATGGTCTCATAATTCTGGTCAGCATTGTCTGA GCCAAACAAAATGTATCTATGGGCATGATCAGATACTA GAGCCAGCAGATTGCAACCTCTGCTTAGATAATTGCAG GTATCAGCCTTCCCTTGGCTAAACAGCTACTTCATACTG ATAAGTAGCCCTTGCCTGGCACAAAGCAGGTGGGGCTG AATCCAGCCTGATATCACATCACCACAACTTTCTCTAAT TCTCCTCAAGGCGTCTGTGAACTACCA |
| 588 | PGR | 3388393 | TGACTGCATCGTTGATAAAATCCGCAGAAAAAACTGCC CAGCATGTCGCCTTAGAAAGTGCTG |
| 589 | PGR | 3388407 | CAGGCTGTCATTATGGTGTCCTTACCTGTGGGAGCTGTA AGGTCTTCTTTAAGAGGGCAATGGAA |
| 590 | PGR | 3388408 | AGCCAGAGCCCACAATACAGCTTCGAGTCATTACCTCA GAAGATTTGTTTA |
| 591 | PGR | 3388410 | TCGGCTACCAGGCCGCCGTGCTCAAGGAGGGCCTGCCG CAGGTCTACCCGCCCTATCTCAACTACCTGA |
| 592 | PGR | 3388411 | GCCGCCCTGCAAGGCGCCGGGCGCGAGCGGCTGCCTGC TCCCGCGGGACGGCCTGCCCTCCACCTCCGCCTCTGCCG CCGCCGCCGGGGCGGCCCCCGCGCTCTACCCTGCACTC GGCCTCAACGGGCTC |
| 593 | PGR | 3388412 | GTGCCTCAGTCTCGTCTGCGTCCTCCTCGGGGTCGACCC TGGAGTGCATCCTGTACAAAGCGGAGGGCGCG |

TABLE 8-continued

Subtyping Target Sequences

| SEQ ID NO. | Gene | Affy Probeset ID | Sequence |
|---|---|---|---|
| 594 | PGR | 3388413 | CTGCCTCTCAATCACGCCTTATTGGCAGCCCGCACTCGG CAGCTGCTGGAAGACGAAAGTTACGACGGCGGGGCCG GGGCTGCCAGCGCCTTTGCCCCGCCGCGGAGTTCACCC TGTGCCTCGTCCACCCCGGTCGCTGTAGGCGACTTCCCC GACTGCGCGTACCCGCCCGACGCCGAGCCCAAGGACGA CGCGTACCCTCTCTATAGCGACTTCCAGCCGCCCGCTCT AAAGATAAAGG |
| 595 | PGR | 3388414 | TTGCCTGAAGTTTCGGCCATACCTATCTCCCTGGACGGG CTACTCTTCCCTCGGCCCTGCCAGGGACAGGACCCCTCC GACGAAAAGACGCAGGACCAGCAGTCGCTGTCGGACG TGGAGGGCGCATATTCCAGAGCTGAAGCTACAAGGGGT GCTGGAGGCAGCAGTTCTAGTCCCCCAGAAAAGGACAG CGGACTGCTGGACAGTGTCTTGGACACTCTGTTGGCGC CCTCAGGTCCCGGGCAGAGCCAACCCAGCCCTCCCGCC TGCGAGGTCACCAGCTCTTGGTGCCTGTTTGGCCCCGAA CTTCCCGAAGATCCACCGGCTGCCCCCGCCACCCAGCG GGTGTTGTCCCCGCTCATGAGCCGGTCCGGGTGCAAGG TTGGAGACAGCTCCGGGACGGCAGCTGCCCATAAAGTG CTGCCCCGGGGCCTGTCACCAGCCCGGCAGCTGCTGCT CCCGGCCTCTGAGAGCCCTCACTGGTCCGGGGCCCCAG TGAAGCCGTCTCCGCAGGCCGCTGCGGTGGAGGTTGAG GAGGAGGATGGCTCTGAGTCCGAGGAGTCTGCGGGTCC GCTTCTGAAGGGCAAACCTCGGGCTCTGGGTGGCGCGG CGGCTGGAGGAGGAGCCGCGGCTGTCCCGCCGGGGGC GGCAGCAGGAGGCGTCGCCCTGGTCCCCAAGGAAGATT CCCGCTTCTCAGCGCCCAGGGTCGCCCTGGTGGAGCAG GACGCGCCGATGGCGCCCGGGCGCTCCCCGCTGGCCAC CACGGTGATGGATTTCATCC |
| 596 | PGR | 3388415 | TGAAATCTACAACCCGAGGCGGCTAGTGCTCCCGCACT ACTGGGATCTGAGATCTTCGGAGATGACTGTCGCCCGC AGTACGGAGCCAGCAGAAGTCCGACCCTTCCTGGGAAT GGGCTGTACCGAGAGGTCCGACTAGCCCCAGGGTTTTA GTGAGGGGGCAGTGGAACTCAGCGAGGGACTGAGAGC TTCACAGCATGCACGAGTTTGATGCCAGAGAAAAAGTC GGGAGATAAAGGAGCCGCGTGTCACTAAATTGCC |
| 597 | MDM2 | 3421302 | CGCACCGAGGCACCGCGGCGAGCTTGGCTGCTTCTGGG GCCTGTGTGGCCCTGTGTGTCGGAAAGATGGAGCAAGA AGCCGAGCCCGAGGGGCGGCCGCGACCCCTCTGACCGA GATCCTGCTGCTTTCGCAGCCAGGAGCACCGTC |
| 598 | MDM2 | 3421303 | GTACGAGCGCCCAGTGCCCTGGCCCGGAGAGTGGA |
| 599 | MDM2 | 3421304 | GAGGCCCAGGGCGTCGTGCTTCCGCGCGCCCCGT |
| 600 | MDM2 | 3421305 | ACTCCAAGCGCGAAAACCCCGGATGGTGAGGAGCA |
| 601 | MDM2 | 3421306 | TTCAGTGGCGATTGGAGGGTAGACCTGTGGGCACGGAC GCACGCCACTTTTTCTCTG |
| 602 | MDM2 | 3421307 | TGTACCTACTGATGGTGCTGTAACCACCTC |
| 603 | MDM2 | 3421310 | ACCAAAGCCATTGCTTTTGAAGTTATTAAA |
| 604 | MDM2 | 3421311 | GTCTGTTGGTGCACAAAAAGACACTTATACTATGAAA |
| 605 | MDM2 | 3421312 | GACTTCTTGGGCATCCCTGGATCCCAGGTTAAGAACTTC TGCACTAGAGATACATGA |
| 606 | MDM2 | 3421313 | GTACAGTATACTGATCTTTCTGGGATAG |
| 607 | MDM2 | 3421314 | GGGCTCAAGGGATCTGCTTACCTCGGCCTCCTAA |
| 608 | MDM2 | 3421315 | TATGACTAAACGATTATATGATGAGAA |
| 609 | MDM2 | 3421316 | CTTCTAGGAGATTTGTTTGGCGTGCCAAGCTTCTCT |
| 610 | MDM2 | 3421317 | ATTGTAAAAAGCCATCTGGGCTAACATTTC |

TABLE 8-continued

Subtyping Target Sequences

| SEQ ID NO. | Gene | Affy Probeset ID | Sequence |
|---|---|---|---|
| 611 | MDM2 | 3421321 | AGGTTAAATTGCATAAGGGTTTGTGTTAGACTGATAGC ATATCTACTGAGTAGCGCCCCGCCGCCCCCCGCCCACC ACCAAGTTTCTGATCCTTTT |
| 612 | MDM2 | 3421322 | AATCATCGGACTCAGGTACATCTGTGA |
| 613 | MDM2 | 3421323 | GTGAGAACAGGTGTCACCTTGAAGGTGGGAG |
| 614 | MDM2 | 3421325 | TCACATTTGGTTTCTAGACCATCTACCTCATCTAGAAGG AGAGCAATTAGTGAGACA |
| 615 | MDM2 | 3421326 | ATATTTATTTGACGCATTCACACAGCTTTTTGATATTCTT TCTCTAATGAAATTAGTGCTTTTAGACTTAAT |
| 616 | MDM2 | 3421328 | TCAGATGAATTATCTGGTGAACGACAAAGAAAACGCCA CAAATCTGATAGT |
| 617 | MDM2 | 3421329 | AAAGCCTGGCTCTGTGTGTAATAAGGGAGATATGTTGT GAAAGAAGCAGTAGCAGTGAATCTACAGGGACGCCA |
| 618 | MDM2 | 3421334 | TTCAGTTTCAGATCAGTTTAGTGTAGAATTTGAAGTTGA ATCTCTCGACTCAGAAGATTATAGCCTTAGTGAAGA |
| 619 | MDM2 | 3421336 | TGCAATGAAATGAATCCCCCCCTTCCATCACATTGCAAC AGATGTTGGGCCCTTCGTGAGAATTGGCTTCCTGAAGA |
| 620 | MDM2 | 3421337 | CTATAGTGAATGATTCCAGAGAGTCATGTGTTGAGGAA AATGATGATAAAATTACACAAGCTTCACAAT |
| 621 | MDM2 | 3421338 | TCTCAGCCATCAACTTCTAGTAGCA |
| 622 | MDM2 | 3421339 | AAGAGAGTGTGGAATCTAGTTTGCCCCTTAATGCCATT GAA |
| 623 | MDM2 | 3421340 | TCAAGGTCGACCTAAAAATGGTTGCATTGTCC |
| 624 | MDM2 | 3421341 | ATATTTCTAACTATATAACCCTAGGA |
| 625 | MDM2 | 3421342 | ACCGCGTCCGGCCTAAATGTCACTTAGTACCTTTGATAT AAAGAGAAAATGTGTGAAAGATTTAGTTTTTTGTTTTTT TGTTTGTTTGTTTGTTTGTTTGTTTTGAGATGAGTCTCTC TGTCGCCCAGGCTGGAGTGCAGTGTCATGATCTAGCAG TCTCCGCTTCCCGGGTTCAAGCCATTCTCCTGGCTCAGC CTCTGGAGCAGCTGGGATTACAGGCATGCACCACCATG CCCAGCTAATTTTTGTATTTTTAGTAGAGATAGGGTTTC ACCATGTTGGCCAGGCTGGTCACGAACTCCTGACCTCA AGTGAGGTCACCCGCCTCGGCCTCCCGAAGTGCTGGGA TTGCAGATGTGAGCCACCATGTCCAGCCAAGAATTAGT ATTTAAATTTTAGATACTCTTTTTTTTTTTTTTTTTTTTT TTTTTGAGACAGAGTCTTGCTCCATCACCCATGCTAGAG TGCAGTGGAGTGATCTCGGCTCACTGCAACTTCCGCCTT CTGGGTTCAAGCTATTCTCCTGCCTCAGCCTTCCAAGTA ACTGGGATTACAGGCATGTACCACCATACCAGCTGATT TTTTTGTATTTTTAGTAAAGACAGGGTTTCACCATGTTA GCCAGGCTGATCTTGAACTCCTAAACTCAAGTGATCTA CTCACCTCAGCCTCCCAAAATGCTGGGATTACAGATGT GAGGCACCTGGCCTCAGATTTTTGA |
| 626 | MDM2 | 3421343 | TGGAGGCCCATCCGAGCTCAGCACTGA |
| 627 | MDM2 | 3421344 | ACAAGCCTGTCAAATATCTGCAAGAACTATGGAATAAA ACTACTGATGCAGTGAAGACAGTTGAAAAGATCAAACA AATGCCAAGCTATATTTATAATGAACAAATTCAAGAAA AAGGACTACGGAAAGTTCAGGACATCAAAGAAGTCAG GCAAAACTCATCTTGACCCCTGTTGCAGGCAAAGGAAC GCAGCTGGAAGAAAAGATGATATAACAGTTAACAGGA TGCAGACATGGCAGAGGTTTCCTAAAAATCTCATTATCT ATAACCATTTCTATATTTACATTTGAAAATCTCCTTTGG AGACTTAGAACCTCTAAATTATTGACTTATTTTTTATAT AAGGTCACTCCGATGAAAGGTGATTACA |
| 628 | MDM2 | 3421345 | TGAGAGCCGAATAAGGTTTGCCTGAAATAACTGACACT ATATAATTTCTGCTTTGGCAAATACTAAGTTCTAACTTG |

TABLE 8-continued

Subtyping Target Sequences

| SEQ ID NO. | Gene | Affy Probeset ID | Sequence |
|---|---|---|---|
| | | | TCATTCCTGGTAGAACAAGCTTTATTTTTCGAGCCTAGC AATGATCTAGAAGCAGATGTTATCTCAGTGCCTTTTG |
| 629 | MDM2 | 3421346 | CTGATGGGTGTGCTAATTACACTGATTTGATCAATACCC ATTGTATGTGAAACAGTACATACACCATATTTACAATTA TGTATTTAACATTTAAAATTTCTAATATAAGTATCTCTC AAACTGTGGATTAACTTCTTGATTTATATTTAAATATGA ATCTTAAGCAAAACAGTGAAAATAACCATCTTGATTTA GTGTTTTTCTCCCATATGTGAATTGTATATAC |
| 630 | MDM2 | 3421347 | GCTTAGAATAGGACTGAGGTAATTCTGCACAGCAACTT TACTAATGGTA |
| 631 | MDM2 | 3421348 | GTCCTCCAAGCATTATTTGGAGTTGATAATACTTCAGCT ACAACCAAGCAGAATCTCTTTTTTTTGGA |
| 632 | MDM2 | 3421349 | GATAATACTTCAGCTTCAATTTGGAGTTGATAATATTTC AGCTAGAACCTAGTAGAATC |
| 633 | MDM2 | 3421350 | CACTTGATATATGGAGGCAGTGACAGCTATTTTTACAA AATTTAAATCTGCAAATGGATTCAACATGTTTATGGGTT ATTAAAATTGTCTGATTTCTTAGGTTCTTTATAGTACAC GTGTTGA |
| 634 | MDM2 | 3421351 | TGGGAGCCTCCAATGAGAGCAACTTGAGAGAATGATGT TGCAAGTTAGTAGGAGTAAGAAATGCTGTGTTCTCCCT GTCTTCTCTTAGGTCACATGGCAGCCTGGCCTAAGTGAT CGTGAATGGTCTATAAGGGAGGTAGCTGGGACAGGGA GGGGAGTTTGGGCTAGCCACCGTACCACTTGTCAGCGT GAAAAGTAAGATTGTAATTGCCTGTTTAGTTTTCTGCCT CATCTTTGAAAGTTCCACCAAGCTGGGAACCTCTTGATT GTGAGGCACAAATGTAAGTACATCAGAAAAAAACAAA AAAACTGGCTTTAAAGCAGGAGCTTGTGGGCCCCTAAG CCAGACGGGGACTAGCTTTTGGCATTATATAATTAAGA TTTTTTAAATCCTTAATAAGGGTTTTATTTTATTTTTATT TATTTTTTGAGACGGAGTCTTGCTCTGTGGCTCAGGCTG GAGTACAGTGGTGCAATCTTGGCTCACTGCAACCTCTG CCTCCTGGCTGTGTTCAAGTGGTTCT |
| 635 | MDM2 | 3421359 | GAAACATTAAGAATACCATATGAGTAAATTAAACACTT TGGCTCTTTTCGGAAAAAAACAGATGAGCTCTTATATTT TAAAGTTTGGTTTTGACAGAAAAAAATTCCTAGATTTTT TGGTTAATAAAAACTTTATTAGATAGATTAAATTGTGAT G |
| 636 | MDM2 | 3421361 | AGGGAACTTCTGCTTAAGAGGCTTCTATGTAATGAAAT TCTCTTGAAAACAGAGAAACTATTTCCTGTTTATTTTCT AAATTGAGACGTCACTTTTTAAAAATTGGTACCTGTAAT TTAGCCATTTCCTACTCAGCAATGTCTCATTTAAACTAT TATTTGTTTAGCGTGTTTCAAAGAGCAGATGTAAGCTTG AGCCCATCCTCTGTCCTATGACTAAGTCGATATTAGCAG GGGTTAGGACTGTTAGTTTTCCAGTTCCTACTGGAGGCA AATTCTT |
| 637 | KRT5 | 3455207 | CCTTTTCTGGAGAGTAGTCTAGACCAAGCCAATTGCAG AACCACATTCTTTGGTTCCCAGGAGAGCCCCATTCCCAG CCCCTGGTCTCCCGTGCCGCAGTTCTATATTCTGCTTCA AATCAGCCTTCAGGTTTCCCACAGCATGGCCCCTGCTGA CACGAGAACCCAAAGTT |
| 638 | KRT5 | 3455208 | TCTTGCCGGAGGTAGCAGTGGAAGCTACTACTCCAGCA GCAGTGGGGGTGTCGGCCTAGGTGGTGGGCTCAGTGTG GGGGGCTCTGGCTTCAGTGCAAGCAGTGGCCGAGGGCT GGGGGTGGGCTTTGGCAGTGGCGGGGGTAGCAGCTCCA GCGTCAAATTTGTCTCCAC |
| 639 | KRT5 | 3455211 | ACTCAGTGGAGAAGGAGTTGGACCAGTCAACATCT |
| 640 | KRT5 | 3455212 | AGGTCAATCCCTCTTCATTGGAAAATCCCTCTGGAGAGT TCTCCCTTCCTTTAACTTAAGCAGCTTTTGGGTGTACAG ACTCCTGGCTTATGGAATGAACTCGAATCATGAGGATG GGAGTTAGCCACATAGACTAATGCTGTCTTTTTGGGAG CTGTTAACCCTTAATTCA |

TABLE 8-continued

| Subtyping Target Sequences | | | |
|---|---|---|---|
| SEQ ID NO. | Gene | Affy Probeset ID | Sequence |
| 641 | KRT5 | 3455214 | CAAGATGGCCTTCAGCTGATAAAGCGAAGCTGCTCTAC TGTGGGGTGTACAACACACATACATGAGATCAGTGACT TGTGCGTGATAATGACACATCATCAACACTATTTCAGTC TGACTCATGGCCATATAGCTGACCTCAACTCACTTTTCT GGTCTCTTTTCCCCCACCGGTGTTCCTGGGCACTGGCTG TCCTCCAAGCACCTGAGCAACTCAGCAATCTTCTTGACA CTTGTGCCTTTTCTGCTTTTGCTCACGTCCTTTGCTCAAC CTCAATATCCATGTCATG |
| 642 | KRT5 | 3455215 | TGCGCCAATCTGCAGAACGCCATTGCGGATGCCGAGC |
| 643 | KRT5 | 3455216 | CTTTTGCTAAACACACGCAGCTAGATCCAGTACCAGTG TTTCAGTGTCCTGCCACCCACGATGTACTGGTTTCTCTC TGGGATTCATGATAGTTTGGTTTGTCTGACCCAGAAACT CAG |
| 644 | KRT5 | 3455217 | AGCTGGCCGGCATGGCGATGACCTCCGCAACACCAAGC ATGAGATCTCTGAGATGAACCGGATGATCCAGAGGCTG AGAGCCGAGATTGACAATGTCAAGA |
| 645 | KRT5 | 3455219 | CAGATGCAGACGCATGTCTCTGACACCTCAGTGGTCCT CTCCATGGACAACAACCGCAACCTGGACCTGGATAGCA TCATCGCTGAGGTCAAGGCCCAGTATGAGGAGATTGCC AACCGCAGCCGGACAGAAGCCGAGTCCTGGTATCAGAC CAAG |
| 646 | KRT5 | 3455220 | CAGAACCAGATGACCGACTCCAAATCTCCCTG |
| 647 | KRT5 | 3455222 | GGCCAAGGTTGATGCACTGATGGATGAGATTAACT |
| 648 | KRT5 | 3455223 | GCAGCCTGCAGCTATGCTCTCTAAGCGTGGAGCTCACTT GAGTAGGGTGACGGTGTG |
| 649 | KRT5 | 3455224 | TGAAATCAACAAGCGTACCACTGCTGAGAATGAG |
| 650 | KRT5 | 3455225 | AAAAGAACACTAGAGAAATTGACTAG |
| 651 | KRT5 | 3455228 | GTGGACACGTTCTGAATTAGACTGGCAGCTGGGAAG |
| 652 | KRT5 | 3455229 | CAACCTGCAAATCGACCCCAGCATCCAGAGGGTGAGGA CCGAGGAGCGCGAGCAGATCAAGA |
| 653 | KRT5 | 3455230 | GAGGTGGTGCCGGTAGTGGATTTGGTTTCGGCGGTGGA GCTGGTGGT |
| 654 | KRT5 | 3455231 | GGCAGCTTCAGGAACCGGTTTGGTGCTGGTGC |
| 655 | KRT5 | 3455232 | GGGCTCCAAGAGGATATCCATCAGCACTAGTG |
| 656 | KRT5 | 3455233 | TGTGGAGTGGGTGGCTATGGCAGCCGGAGCCTCTACAA CCTGGG |
| 657 | KRT5 | 3455234 | TGGTGGCTTCGGCAGGGTCAGCCTTGCGG |
| 658 | KRT5 | 3455235 | TCAAGTGTGTCCTTCCGGAGCGGGGGCAGTCGTAGCTT CAGCACCGCCTCTGCCATCACCCCGTCTGTCTCCCGCAC CAG |
| 659 | KRT5 | 3455236 | ACAGCTCGACAGCTCTCTCGCCCAGCCCAGTTCTGGAA GGGATAAAAAGGGGGCATCACCGTTCCTGGGTAACAGA GCCACCTTCTGCGTCCTGCTGAGCTCTGTTCTCTCCAGC ACCTCCCAACCCACTAGTGCCT |
| 660 | KRT5 | 3455237 | CCCAGCCTCTATGGTGAAGACATACTTGCTAGCAGCGT CACCAACTTGCTGCCAAGAGATCAGTGCTGCAAGGCAA GGTTATTTCTAACTGAGCAGAGCCTG |
| 661 | FOXA1 | 3561726 | CAGGTCTGTGGCAATACTCTTAACCATAAGAATTGAAA TGGTGAAGAAACAAGTATACACTAGAGGCTCTTAAAAG TATTGAAAGACAATACTGCTGTTATATAGCAAGACATA AACAGATTATAAACATCAGAGCCATTTGCTTCTCAGTTT ACATTTCTGATACATGCAGATAGCAGATGTCTTTAAATG AAATACATGTATATTGTGTATGGACTTAATTATGCACAT GCTCAGATGTGTAGACATCCTCCGTATATTTACATAACA |

TABLE 8-continued

| SEQ ID NO. | Gene | Affy Probeset ID | Sequence |
|---|---|---|---|
| | | | TATAGAGGTAATAGATAGGTGATATACATGATACATTC TCAAGAGTTGCTTGACCGAAAGTTACAAGGACCCCAAC CCCTTTGTCCTCTCTACCCACAGATGGCCCTGGGAATCA ATTCCTCAGGAATTGCCCTCAAGAACTCTGCTTCTTGCT TTGCAGAGTGCCATGGTCATGTCATTCTGAGGTCACATA ACACATAAAATTAGTTTCTATGAGTGTATACCATTTAAA GAATTTTTTTTTCAGTAAAAGGGAATATTACAATGTTGG AGGAGAGATAAGTTATAGGGAGCTGGATTTCAAAACGT GGTCCAAGATTCAAAAATCCTATTGATAGTGGCCATTTT AATCATTGCCATCGTGTGCTTGTTTCATCCAGTGTTA |
| 662 | FOXA1 | 3561727 | GTGTGTATTCCAGACCCGTCCTAAACACTTCCTAG |
| 663 | FOXA1 | 3561728 | TCGGAGCAGCAGCATAAGCTGGACTTCAAGGCATACGA ACAGGCACTGCAATACTCGCCTTACGGCTCTACGTTGCC CGCCAGCCTGCCTCTAGGCAGCGCCTCGGTGACCACCA GGA |
| 664 | FOXA1 | 3561729 | GGGCGCCTCGGAGTTGAAGACTCCAGCCTCCTCAACTG CGCCCCCCATAA |
| 665 | FOXA1 | 3561730 | GGCGGCCCTGAGAGCCGCAAGGACCCCTCTGGCGCCTC TAACCCCAGCGCCGACTCGCCCCTCCATCGGGGTGTGC ACGGGAAGACCGGCCAGCTA |
| 666 | FOXA1 | 3561731 | AGGCGCCCAGCAAGATGCTCACGCTGAGCGAGATCTAC CAGTGGATCATGGACCTCTTCCCCTATTACCGGCAGAA CCAGCAGCGCTGGCAGAACTCCATCCGCCACTCGCTGT CCTTCAATGACTGCTTCGTCAAGGTGGCACGCTCCCCGG ACAAGCCGGGCAAGGGCTCCTACTGGACGCTGCACCCG GACTCCGGCAACATG |
| 667 | FOXA1 | 3561732 | TACGCGCCGTCCAACCTGGGCCGCAGCCGCGCGGGCGG CGGCGGCGACGCCAAGACGTTCAAGCGCAG |
| 668 | FOXA1 | 3561733 | TCCGTCCCGGTCAGCAACATGAACTCAGGCCTGGGCTC CATGAACTCCATGAACACCTACATGACCATGAACACCA TGACTACGAGCGGCAACATGACCCCGGCGTCCTTCAAC ATGTCCTATGCCAACCCGGGCCTAGGGGCCGGCCTGAG TCCCGGCGCAGTAGCCGGCATGCCGGGGGGCTCGGCGG GCGCCATGAACAGCATGACT |
| 669 | FOXA1 | 3561736 | TGGAAGGGCATGAAACCAGCGACTGGAACAGCTACTAC GCAGACACGCAGGAG |
| 670 | FOXA1 | 3561738 | CTTTGTGCGGCGGACAAATGGGGAGAG |
| 671 | FOXA1 | 3561741 | TCATAAAGATATAAACCGGTGCTGTGACTCACCTGCTCT TAGCCGCAG |
| 672 | ORC6 | 3658927 | GGGGTCGGAGCTGATCGGGCGCCTAGCCCCGCGCCTGG GCCTCGCCGAGCCCGACATGCTGAG |
| 673 | ORC6 | 3658928 | GTGAGTTCGGCCGCGCAAGACCAGGGCTGGGCTTCCGC CTCGCGGCCCTGGGC |
| 674 | ORC6 | 3658931 | CTCTCACCAGAGGATATGACCTTCATTCCCAGCCCCAG ATAAACGAGCCACAGGAGTTAGGCTTAGTGTGAAGCTA ACCAGGCTGTATT |
| 675 | ORC6 | 3658932 | AAGCAGAGGAGTACTTGCGCCTGTCCCGGGTGAAGTGT GTCGGCCTCTCCGCACGCACCACGGAGACCAGCAGTG |
| 676 | ORC6 | 3658934 | GATCTTGACTTATCCAGGCCACTTTTCAC |
| 677 | ORC6 | 3658935 | GCCAAGTGACTATATTCCCAGTTTATCCCATAATGTAGC TAACAACTTGGAACTAGTGTTGCCAGAATTCCACTAGC AAATAGCAGCTGTATATATATGCTGGGAATTCTGATTTC AGTCTGCCTTTTGTAAGAGATGATATC |
| 678 | ORC6 | 3658937 | AAGTCATGAAGCACTACAGCAAATGTCTTTTATGTGCC CCTTTTGTTATAAAATAGATCCCATGTGCATTTTAACTC TCAGTCCAATAAACAACTAAACAACTTAGCATAGATAA TAACATGTTTGGAATGAAGGAAAAAAACTAGACAGAG |

TABLE 8-continued

Subtyping Target Sequences

| SEQ ID NO. | Gene | Affy Probeset ID | Sequence |
|---|---|---|---|
| | | | GCTCTGGAAGCATGGTCAAAAAGAAAATAAGTTGATTA TCTGGTTGCCCAGAGAAGAAAACTGTACAGGTCTTGAG AAAAGC |
| 679 | ORC6 | 3658938 | GATTCTAAAGCTGAAAGTGGATAAAAACAA |
| 680 | ORC6 | 3658939 | AAAAAGCTATATTTGATCGACTGTGTAAACAACTAGAG AAGATTGGACAGCAGGTCGACA |
| 681 | ORC6 | 3658940 | TTATTTGTGATCCAAAACATGCCCAAATACTGAAATTG AG |
| 682 | ORC6 | 3658941 | ACCTGGAGATGTAGCTACTCCACCACGGAAGAGAAAGA AGATAGTGGTTGAAGCCC |
| 683 | ORC6 | 3658943 | AAGGTAGAGGAGATGCCACATAAACCACAGAAAGATG AAGATCTGACACA |
| 684 | ORC6 | 3658944 | TTGGAAAATGCTGCCAGTGCTCAAAAGGCTACAGCAGA GTG |
| 685 | ORC6 | 3658945 | TCTCCAGGAAGACTTGACGGCTTTGGGATTTTGTTTAAA CTTTTATAATAAGGATCCTAAGACTGTTGCCTTTAAATA GCAAAGCAGCCTACCTGGAGGCTAAGTCTGGGCAGTGG GCTGGCCCCTGGTGTGAGCATTAGACCAGCCACAGTGC CTGATTGGTATAGCCTTATGTGCTTTCCTACAAAATGGA ATTGGAGGCCGGGCGCAGTGGCTCACGCCTGTAATCCC AGCACTTTGGGAGGCCAAGGTGGGTGGATCACCTGAGG TCAGGAGCTCGAGACCAGCCTGGCCAACATGGTGAAAC CCCATCTCTACTAAAAATACAAAAATTAGCCAGGTGTG ATGGTGCATGCCTGTAATCCCAGCTCCTCAGTAGGCTG AGACAGGAGCATCACTTGAACGTGGGAGGCAGAGGTT GCAGTGAGCCGAGATTGCACCACCGCACTCCAGCCTGG GTGACAGAGCGAGACTTATCTCATAAATAAATAGATAG ATACTCCAGCCTGG |
| 686 | ORC6 | 3658946 | TGGAGCCATTTTGCTTTAAGTGAATGGCAGTCCCTTGTC TTATTCAGAATATAAAATTCAGTCTGAATGGCATCTTAC AGATTTTACTTCAATTTTTGTGTACGGTATTTTTTATTTG ACTAAATCAATATATTGTACAGCCTAAGTTAATAA |
| 687 | CDH3 | 3666367 | CGGAGCCTCCGTTTTCAGTCGACTTCAGATGTGTCTCCA CTTTTTTCCGCTGTAGCCGCAAGGCAAGGAAACATTTCT CTTCCCGTACTGAGGAGGCTGAGGAGTGCACTGGGTGT TCTTTTCTCCTCTAACCCAGAACTGCGAGACAGAGGCTG AGTCCCTGTA |
| 688 | CDH3 | 3666368 | ATGGGGCTCCCTCGTGGACCTCTCGCGTCTCTCCTC |
| 689 | CDH3 | 3666369 | GCTGGCTGCAGTGCGCGGCCTCCGAGCCGTGCCGGGCG GTCTTCAGGGAGGCTGAAGTGACCTTGGAGGC |
| 690 | CDH3 | 3666376 | AAGAGCCAGCTCTGTTTAGCACTGATAATGATGACTTC ACTGTGCGGAATGGCGAGACAGTCC |
| 691 | CDH3 | 3666380 | GATCTTCCCATCCAAACGTATCTTACGAAGACACA |
| 692 | CDH3 | 3666381 | TGGGTGGTTGCTCCAATATCTGTCC |
| 693 | CDH3 | 3666382 | TTTCTACAGCATCACGGGGCCGGGGGCAGACAGCCCCC CTGAGGGTGTCTTCGCTGTAGAGAAGGAGACAGGCTGG TTGTTGTTGAATAAGCCACTGGACCGGGAGGA |
| 694 | CDH3 | 3666384 | CTCAGTGGAGGACCCCATGAACATCTCCATCATCGTGA CCGACCAGAATGACCACAAGCCCAAGTTTACCCAGGAC ACCTTCCGAGGGAGTGTCTTAGAGGGAGTCCTACCA |
| 695 | CDH3 | 3666385 | TGACAGCCACGGATGAGGATGATGCCATCTACACCTAC AATGGGGTGGTTGCTTACTCCATCCATAGCCAAGAACC AAAGGACCCACACGACCTCATGTTCACCATTCACCGGA GCACAGGCACCATCAG |
| 696 | CDH3 | 3666387 | AGGCCCATGTGCCTGAGAATGCAGTGGGCCATGAGGTG CAGAGGCTGACGGTCACTGATCTGGACGCCCCCAACTC |

TABLE 8-continued

Subtyping Target Sequences

| SEQ ID NO. | Gene | Affy Probeset ID | Sequence |
|---|---|---|---|
| | | | ACCAGCGTGGCGTGCCACCTACCTTATCATGGGCGGTG ACGACGGGGACCATTTTACCATC |
| 697 | CDH3 | 3666388 | CCAGCACACCCTGTACGTTGAAGTGACCAACGAGGCCC CTTTTGTGCTGAAG |
| 698 | CDH3 | 3666389 | ACAGCCACCATAGTGGTCCACGTGGAGGATGTGAATGA GGCACCTGTGTTTGTCCCACCCTCCAAAGTCGTTGAGGT CCAGGA |
| 699 | CDH3 | 3666390 | GCTGTGGGCACCCTCGACCGTGAGGAT |
| 700 | CDH3 | 3666394 | ACGGGAACCCTTCTGCTAACACTGATTGATGTCAATGA CCATGGCCCAGTCCCTGAGCCCCGTCAGATCACCATCT GCAACCAAAGCCCTGTGCGCCAGGTGCTGAACATCACG GACAAGGACCTGTCTCCCCACACCTCCCCTTTCCAGGCC CAGCTCACAGATGACTCAGACATCTACTGGACGGC |
| 701 | CDH3 | 3666395 | GTGGTCTTGTCCCTGAAGAAGTTCCTGAAGCAGGATAC ATATGACGTGCACCTTTCTCTGTCTGACCATGGCAACAA AGAGCAGCTGACGGTGATCAGGGCCACT |
| 702 | CDH3 | 3666396 | GTGTGCGACTGCCATGGCCATGTCGAAACCTGCCCTGG |
| 703 | CDH3 | 3666397 | CTCCCAGAAGATGACACCCGTGACAACGTCTTCTACTA TGGCGAAGAGGGG |
| 704 | CDH3 | 3666398 | CACCCAGCTCCACCGAGGTCTGGAGGCCAGGCCGGAGG TGGTTCTCCGCAATGACGTGGCACCAACCATCATCCCG ACACCCATGTACCGTCCTCGGCCAGCCAACCCAGATGA AATC |
| 705 | CDH3 | 3666400 | GCAAGAGGCAGGACCCGCCGCTCCTAACTACCTGTTCT CTG |
| 706 | CDH3 | 3666401 | ACCTGAAGGCGGCTAACACAGACCCCACAGCCCCGCCC TACGACACCCTCTTGGTGTTCGACTATGAGGGCAGCGG CTCCGACGCCGCGTCCCTGAGCTCCCTCACCTCCTCCGC CTCCGACCAAGACCAAGATTACGATTATCTGAACGAGT GGGGC |
| 707 | CDH3 | 3666402 | TCTGACGTTAGAGTGGTGGCTTCCTTAGCCTTTCAGGAT GGAGGAATGTGGGCAGTTTGACTTCAGCACTGAAAACC TCTCCACCTGGGCCAGGGTTGCCTCAGAGGCCAAGTTT CCAGAAGCCTCTTACCTGCCGTAAAATGCTCAACCCTGT GTCCTGGGCCTGGGCCTGCTGTGACTGACCTACAGTGG ACTTTCTCTCTGGAATGGAACCTTCTTAGGCCTCCTGGT GCAACTTAATTTTTTTTTTTAATGCTATCTTCAAAACGTT AGAGAAAGTTCTTCAAAAGTGCAGCCCAGAGCTGCTGG GCCCACTGGCCGTCCTGCATTTCTGGTTTCCAGACCCCA ATGCCTCCCATTCGGATGGATCTCTGCGTTTTTATAC |
| 708 | CDH3 | 3666404 | AGAGAACCTACCCAAGATGTCAGTGAAATTGGAACATT CCTGACAATACCAGGGCATAAATGCAGGAATCAGGAAT AGGCAGCAGTGATAGAACAATTCTGTTTGTGCCCTTGTT AACGTGAAGTTCAA |
| 709 | ERBB2 | 3720403 | TTCCCGGATTTTTGTGGGCGCCTGCCCCGCCCCTCGTCC CCCTGCTGTGTCCATATATCGAGGCGATAGGGTTAAGG GAAGGCGGACGCCTGATGGGTTAATGAGCAAACTGAA GTGTTTTCCATGATCTTTT |
| 710 | ERBB2 | 3720404 | CGCAATTGAAGTACCACCTCCCGAGGGTGATTGCTTCC CCATGCGGGGTAGAACCTTTGC |
| 711 | ERBB2 | 3720406 | CCAGTGGTCTATACCTCCAGCAGCAAGTCGAGTGAGCA AGTGATGTCCTGAAAGGCCCAGTGGATCAGTGGAATGA AGCGGGCAGGAAGACTTAGTGCTCCTGAAACAAGGAAT CCAGAATCCAGGAGAAGGATGGCTCAGTGGGGCTTTCA AGGGACAAGTATGGGGGTTGAAGGGGTCACTGTCCCTA TACC |

TABLE 8-continued

Subtyping Target Sequences

| SEQ ID NO. | Gene | Affy Probeset ID | Sequence |
|---|---|---|---|
| 712 | ERBB2 | 3720407 | GGCAAAGCAAAGCTATATTCAAGACCACATGCAAAGCT ACTCCCTGAGCAAAGAGTCACAGATAAAACGGGGGCA CCAGTAGAATGGCCAGGACAAACGCAGTGCAGCA |
| 713 | ERBB2 | 3720408 | GATGAGAGTGACATGTACTGTTGTGGACATGC |
| 714 | ERBB2 | 3720410 | TGCCCCGGGGGTCCTGGAAGCCACA |
| 715 | ERBB2 | 3720411 | AGAATGAAGTTGTGAAGCTGAGATTCCCCTCCATTGGG ACCGGAGAAACCAGGGGAGCCCCCCGGGCAGCCGCGC GCCCCTTCCCACGGGGCCCTTTACTGCGCCGCG |
| 716 | ERBB2 | 3720412 | CAGCCGGAGCCATGGGGCCGGAGCCG |
| 717 | ERBB2 | 3720413 | GAGCTGGCGGCCTTGTGCCGCTGGGGGCTCCTCCTCG |
| 718 | ERBB2 | 3720417 | TGTGCACCGGCACAGACATGAAGCTGCGGCTCCCTGCC AGTCCCGAGACCCACCTGGACATGCTCCGCCACCTCTA CCAGGGCTGCCAGGTGGTGCAGGGAAACCTGGAACTCA CCTACCTGCCCACCAATGCCAGCCTGT |
| 719 | ERBB2 | 3720419 | TTGGGAGCAGTTGTGAAGCTCAGAAGAGAAATGTCTGT GAAAAGGTTATGAACAGGAGGGAGAGTGGAAACCAAC CTGCTGGATCGTGTCCACAGACCCTGGAATGGGGCCAC ATGCTTGGTTTGTCAAATTGCAGACGCCGGCCGGGT |
| 720 | ERBB2 | 3720420 | CAGGGCTACGTGCTCATCGCTCACAACCAAGTGAGGCA GGTCCCACTGCAGAGGCTGCGGATTGTGCGAGGCACCC AGCTCTTTGAGGACAACTATGCCCTGGCCGTGCTAGAC AATGGAGACCCGCTGAACA |
| 721 | ERBB2 | 3720421 | AGGGGAAAGGGTCCTCTGATCATTGCTCACCC |
| 722 | ERBB2 | 3720422 | GGTCTTGATCCAGCGGAACCCCCAGCTCTGCTACCAGG ACACGATTTTGTGGAAGGACATCTTCCACAAGAACAAC CAGCTGGCTCTCACACTGATAGACACCAACCGCTCTCG GGCC |
| 723 | ERBB2 | 3720425 | GCCACTGCCCACTGACTGCTGCCATGAGCAGTGTGCTG CCGGCTGCACGGGC |
| 724 | ERBB2 | 3720427 | TGGTCACCTACAACACAGACACGTTTGAGTCCATGCCC AATCCCGAGGGCCGGTATACATTCGGCGCCAGCTGT |
| 725 | ERBB2 | 3720428 | ACCTTTCTACGGACGTGGGATCCTGCACCCTCGTCTGCC CCCTGCACAACCAAGAGGTGACAGCAGAGGATGGAAC ACAGCGGTGTGAGAAGTGCAGCAAGCCCTGT |
| 726 | ERBB2 | 3720429 | TGCAGTTCCTGTCCCTCTGCGCATGCAGCCTGGCCCAGC CCACCCTGTCCTATCCTTC |
| 727 | ERBB2 | 3720430 | TACAAGTGTCCCTATATCCCCTGTCAGTGTGGGGAGGG GCCCGGACCCTGATGCTCATGTGGC |
| 728 | ERBB2 | 3720431 | GGCATGGAGCACTTGCGAGAGGTGAGGGCAGTTACCAG TGCCAATATCCAGGAGTTTGCTGGCTGCAAGAAGATCT TTGGGA |
| 729 | ERBB2 | 3720432 | AACACTGCCCCGCTCCAGCCAGAGCAGCTCCAAGTGTT TGAGACTCTGGAAGAGATC |
| 730 | ERBB2 | 3720434 | GGCGCCTACTCGCTGACCCTGCAAGGGCTGGGCATCAG CTGGCTGGGGCTGCGCTCACTGAGGGAACTGGGCAGTG GACTGGCCCTCATCCACCATAACACCCACCTCTGCTTCG TGCACACGGTGCCCTGGGACCAGCTCTTTCGGAACCCG CA |
| 731 | ERBB2 | 3720435 | AGCAGCGTTCTTGGACTTGTGCAGACTGCCCGTCTCTGT GCACCCTTCTTGACTCAGCACAGCTCTGGCTGGCTTGGC CTCTTGGCATGGCTTCTCTAGCTGGGTCCTACCTGCCTT |

TABLE 8-continued

Subtyping Target Sequences

| SEQ ID NO. | Gene | Affy Probeset ID | Sequence |
|---|---|---|---|
| | | | GGCATCCTTCCCTCCCCCTCTGTTTCTGAAATCTCAGAA CTCTTCCTCTCCCTACATCGGCCCCACCTGTCCCCACCC CTCCAGCCCACAGCCATGCCCACAGCCAGTTCCCTGGTT CACTTGGACCTG |
| 732 | ERBB2 | 3720436 | GCCACCAGCTGTGCGCCCGAGGGCACTGCTGGGGTCCA GGGCCCACCCAGTGTGTCAACTGCAGCCAGTTCCTTCG GGGCCAGGAGTGCGTGGAGGAATGCCGA |
| 733 | ERBB2 | 3720437 | TGGCTGGAGGGGTGCATGGGGCTCCTCTCAGACCCCCT CACCACTGT |
| 734 | ERBB2 | 3720438 | GCTCCCCAGGGAGTATGTGAATGCCAGGCACT |
| 735 | ERBB2 | 3720439 | ACTCGCTGTTACACCTTAGGTAATGCGTTTTCCTCTCTG GGTGCCTCCCATTTTCTGGCTCAAGTCCCTGCCCAGGAT CAAGCTTGGAGGAGGGCCCCGAGGGAGGGGCCACAGA GACTGGGTGAAGAGCAAGGGTGTTTGTCCCAGGAGCAT GGCGAAAATTGCTGCTGGGTGGCCTTGGGAAGCACAAA GGGGACCCAACTAAGGGCCTGATCCTACTGCC |
| 736 | ERBB2 | 3720440 | GTGGCCTGTGCCCACTATAAGGACCCTCCCTTCTGCGTG GCCCGCTGCCCCAGCGGTGTGAAACCTGACCTCTCCTA CATGCCCATCTGGAAGTTTCCAGATGAGGAGGGCGCAT GCCA |
| 737 | ERBB2 | 3720441 | GTGAGTCCAACGGTCTTTTCTGCAGAAAGGAGGACTTT CCTTTCAGGGGTCTTTCTGGGGCTCTTACTATAAAAG |
| 738 | ERBB2 | 3720442 | GGGCTGCCCCGCCGAGCAGAGAGCC |
| 739 | ERBB2 | 3720443 | TTCCACTGTGGAACCTCCTGTCATTTTCCACTTCACCAA GTGACAGAGGACCTGCTCAGATGCTGAGGGGAGGGGA CTGCAAGGAAAGATGGCTAGGAAACCCAGTCCCTCCAC ACCCTAGAGTAACTTGATGCCTTGTGAGGGACACAGGC AAAGTTCAATTC |
| 740 | ERBB2 | 3720444 | GTGGTCTTTGGGATCCTCATCAAGCGACGGCAGCAGAA GATCCGGAAGTACACGATGCGGAGACTGCTGCAGG |
| 741 | ERBB2 | 3720446 | AGCGATGCCCAACCAGGCGCAGATGCGGATCCTGAAAG AGACGGAGCTGAGGAAGGTGAAGGTGCTTGGATCTGGC GCTTT |
| 742 | ERBB2 | 3720447 | GCATCTGGATCCCTGATGGGGAGAATGTGAAAATTCCA GTGGCCATCAAAGTGTTGAGGGAAAACACATCCCCCAA AGCCAACAAAGAAATCTTAG |
| 743 | ERBB2 | 3720449 | TGGGCATCTGCCTGACATCCACGGTGCAGCTGGTGACA CAGCTTATGCCCTATGGCTGCCTCTTAGACCATGTCCGG GAAAACCGCGGACGCCTGGGCTCCCAGGACCTGCTGAA CTGGTGTATGCAGATTGCCA |
| 744 | ERBB2 | 3720452 | ATGTGCGGCTCGTACACAGGGACTTGGCCGCTCGGAAC GTGCTGGTCAAGAGTCCCAACCATGTCAAAATTACAGA CTTCGGGCTGGCTCGGCTGCTGGACATTGACGAGACAG AGTA |
| 745 | ERBB2 | 3720453 | CTGGGTGGAGTGGTGTCTAGCCCATGGGAGAACTCTG |
| 746 | ERBB2 | 3720454 | CTGGAGTCCATTCTCCGCCGGCGGTTCACCCACCAGAG TGA |
| 747 | ERBB2 | 3720455 | ACTGTGTGGGAGCTGATGACTTTTGGGGCCAAACCTTA CGATGGGATCCCAGCCCGGGAGATCCCTGACCTGCTG |
| 748 | ERBB2 | 3720456 | GTGCGTGGCTGAGCTGTGCTGGCTGCCTGGA |
| 749 | ERBB2 | 3720457 | GTTGGATGATTGACTCTGAATGTCGGCCAAGATTCCGG G |
| 750 | ERBB2 | 3720458 | GTTGGTGTCTGAATTCTCCCGCATGGCCAGGGACCCCC AGCGCTTTGTGGT |

TABLE 8-continued

Subtyping Target Sequences

| SEQ ID NO. | Gene | Affy Probeset ID | Sequence |
|---|---|---|---|
| 751 | ERBB2 | 3720460 | TCTACCGCTCACTGCTGGAGGACGATGACATGGGGGAC CTGGTG |
| 752 | ERBB2 | 3720462 | GTGGGGACCTGACACTAGGGCTGGAGCCCTCTGAAGAG GAGGCCCCCAGGTCTCCACTGGCACCCTCCGAAGGGGC TGGCTCCGATGTATTTGATGGTGACCTGGGAATGGGGG CAGCCAAGGGGCTGCAAAGCCTCCCCACACATGACCCC AGCCCTCTACAGCGGTACAGTGAGGACCCCACAGTACC CCTGCCCTCTGAGACTGATGGCTACGTTGCCCCCCTGA |
| 753 | ERBB2 | 3720463 | ATGTGAACCAGCCAGATGTTCGGCCCCAGCCC |
| 754 | ERBB2 | 3720464 | AGCCTTCGACAACCTCTATTACTGGGACCAGGACCCAC CAGAGCGGGGGGCTCCACCCAGCACCTTCAAAGGGACA CCTACGGCAGAGAACCCAGAGTACCTGGGTCTGGACGT GCCAGTGT |
| 755 | ERBB2 | 3720465 | AGAAGGCCAAGTCCGCAGAAGCCCT |
| 756 | ERBB2 | 3720466 | CGACCACTTCCAGGGGAACCTGCCATGCCAGGAACCTG T |
| 757 | ERBB2 | 3720467 | CTTCCTGCTTGAGTTCCCAGATGGCTGGAAGGGGTCCA GCCTCGTTGGAAGAGGAACAGCACTGGGGAGTCTTTGT GGATTCTGAGGCCCTGCCCAATGAGACTCTA |
| 758 | ERBB2 | 3720468 | GGTACTGAAAGCCTTAGGGAAGCTGGCCTGAGAGGGG AAGCGGCCCTAAGGGAGTGTCTAAGAACAAAAGCGAC CCATTCAGAGACTGTCCCTGAAACCTAGTACTGCCC |
| 759 | ERBB2 | 3720469 | AGTATCCAGGCTTTGTACAGAGTGCTTTTCT |
| 760 | GRB7 | 3720477 | CCTCCCTGAAGACGTGGTCCCAGCCGGGTGTC |
| 761 | GRB7 | 3720478 | GGAGAGGGATCCTCTAAATTGTCGAGGCTTCATCTCTCC AGATTGTATGCCCTTCTC |
| 762 | GRB7 | 3720481 | CTGGTTCCGTTAAGCCCCTCTCTTG |
| 763 | GRB7 | 3720482 | ATCTTAGCAGCTCTCCGGAAGACCTTTGCCCAGCCCCTG GGACCCCTCCTGGGACTCCCCGGCCCCCTGATACCCCTC TGCCTG |
| 764 | GRB7 | 3720483 | GTAAAGAGGTCCCAGCCTCTCCTCAT |
| 765 | GRB7 | 3720485 | GAAACTTCGAGAGGAGGAGAGGCGTGCCACCTCCCTCC |
| 766 | GRB7 | 3720486 | TCTCGGGGGCCCCTCCAGTGCAAGGGGGCTGCTCCCCC GCGATGCCAGCCGCCCCCA |
| 767 | GRB7 | 3720487 | TGGGAGATACACAGCCGCTTCCATGGAGGCAGGGGATC TTGGTTAGGAGTCCCTGAGGGTCTAGCAGGTGCGGAAA GGGAATGAATCAC |
| 768 | GRB7 | 3720488 | GCCACAGCTCGCCACGTGTGTGAAATGCTGGTGCAGCG AGCTCACGCCTTGAGCGACGAGACCTG |
| 769 | GRB7 | 3720490 | ACCACGAGTCCGTGGTGGAAGTGCAGGCTGCCTGGCCC GTGGGCGGAGATAGCCGCTTCGTCTTCCGGAAAAACTT CGCCAAGTACGAACTGTTCAAGAGCTCCC |
| 770 | GRB7 | 3720491 | TCTGGGCGCTGGGATGCCCTGATCCTCAACCTGGATGCT GGAGCCCTGATCCCTGACACTTGTCTACCCACAG |
| 771 | GRB7 | 3720492 | TCCAGCTGTCTCGATGCACACACTGGTATATCCCATGAA GACC |
| 772 | GRB7 | 3720494 | TCAGGACGGAAGCTTTGGAAACGCTTTTTCTGCTTCTTG CGCCGATCTGGCCTCTATTACTCCACCAAGGGCACCTCT A |

TABLE 8-continued

Subtyping Target Sequences

| SEQ ID NO. | Gene | Affy Probeset ID | Sequence |
|---|---|---|---|
| 773 | GRB7 | 3720495 | CAGTCCCTGGTCCTTTTAGAAGTTGCCCCTTCTCTGCTG GAACCTCTGAGCCCTTCTCCCCCTGGGCCCCCCAGGCCA GCCACCTCCAGTTTACCATCTCTCCCTACATCCTTGCCT AGCTCACCTGCCCAG |
| 774 | GRB7 | 3720496 | ATCCGAGGCACCTGCAGTACGTGGCAGATGTGAACGAG TCCAACGTGTACGTGGTGACGCAGGGCCGCAAGCTCTA CGGGATGCCCACTGACTTCGGTTTCTGTGTC |
| 775 | GRB7 | 3720498 | CAACAAGCTTCGAAATGGCCACAAGGGGCTTCGGATCT TCTGCAGTGAAGATGAGCAGAGCCGCACCTGCTGGCTG |
| 776 | GRB7 | 3720501 | TACGGGGTGCAGCTGTACAAGAATTACCAGCAGGCACA GTCTCGCCATCTGCATCCATCTTGTTTGGGCTCCCCACC |
| 777 | GRB7 | 3720502 | AGAAGTGCCTCAGATAATACCCTGGTGGCCATGGACTT CTCTGGCCATGCTGGGCGTGTCATTGAGAACCCCCGGG AGGCTCT |
| 778 | GRB7 | 3720505 | CCATCCACCGCACCCAACTCTGGTTCCACGGGCGCATTT CCCGTGAGGAGAGCCAGCGGCTTATTGGACAGCAGGGC T |
| 779 | GRB7 | 3720507 | CTGTTCCTGGTCCGGGAGAGTCAGCGGAACCCCCAGGG CTTTGTCCTCTCTTTGTGCCACCTGCAGAAAGTG |
| 780 | GRB7 | 3720510 | AGGAGGGCCGCCTGTACTTCAGCATGGATGATGGCCAG ACCCGCTTCACTGACCTGCTGCAGCTCGTGGAGTTCCAC CAGCTGAACCGCGGCATCCTGCCGTGCTTGCTGCGCCA TTGCTGCACGCGG |
| 781 | GRB7 | 3720511 | CCCATCCAGTGGACTCTGGGGCGCGGCCACAGGGGACG GGATGAGGAGCGGGAGGGTTCCGCCACTCCAGTTTTCT CCTCTGCTTCTTTGCCTCCCTCAGATAGAAAACAGCCCC CACTCCAGTCCACTCCTGACCCCTCTCCTCAAGGGAAG GCCTTGGGTGGCCCCCTCTCCTTCTCCTAGCTCTGGAGG TGCTGCTCTAGGGCAGGGAATTATGGGAGAAGTGGGGG CAGCCCAGGCGGTTTCACGCCCCACACTTTGTACAGAC CGAGAGGCCAGTTGATCTGCTCTGTTTTA |
| 782 | CDC6 | 3720897 | TGGCCTCACAGCGACTCTAAGACTTGGGGCTCTCTCATT GGCTGTAACTCTTCCACTGGATTGGTAGCAAAAAAAGA GGCGGTGCCCAAGGCGAAAGGCTCTGTGACTACAGCCA ATCAGAATCGAGGCCGGGCTTT |
| 783 | CDC6 | 3720900 | CTGTCTCGGGCATTGAACAAAGCTAAAAACTCCAGTGA TGCCAAACTAGAACCAACAAATGTCCAAACCGTAACCT GTTCTCCTCGTGTAAAAGCCCTGC |
| 784 | CDC6 | 3720901 | GCGATGACAACCTATGCAACACTCCCCATTTACCTCCTT GTTCTCCACCAAAGCAAGGCAAGAAAGAGAATGGTCCC CCTCACTCACATACACTTAAGGGACGAAGATTGGTATT TGACAATCAGCTGACAATTAAGTCTCCTAGCAAAAGAG AACTAGCCAAAGTTCACCAAAACAAAATACTTTCTTCA GTTAGAAAAAGTCAAGAGATCACAACAAATTCTGAGCA GAGATGTCCACTGAAGAAAGAATCTGCATGTGTGAGAC TATTCAAGC |
| 785 | CDC6 | 3720902 | TGCTACCAGCAAGCAAAGCTGGTCCTGAACACAGCTGT CCCAGATCGGCTGCCTGCCAGGGAAAGGGAGATGGATG TCATCAGGAATTTCTTGAGGGAACACATCTGTGGGAAA AAAGCTGGAAGCCTTTACCTTTCTGGTGCTCCTGGAACT GGAAAAACTGCCTGCTTAAGCCGGA |
| 786 | CDC6 | 3720903 | TTTAAAACTATCATGCTGAATTGCATGTCCTTGAGGACT GCCCAGGCTGTATTCCCAGCTATTGCTCAGGAGATTTGT CAGGAAGAGGTATCCAGGCCAGC |
| 787 | CDC6 | 3720904 | GACAGCAAAGGCCAGGATGTATTGTACACGCTATTTGA ATGGCCATGGCTAAGCAATTCTC |
| 788 | CDC6 | 3720905 | GTATTGCTAATACCCTGGATCTCACAGATAGAATTCTAC CTAGGCTTCAAGCTAGAGAAAAATGTAAGCCACAGCTG |

TABLE 8-continued

Subtyping Target Sequences

| SEQ ID NO. | Gene | Affy Probeset ID | Sequence |
|---|---|---|---|
| | | | TTGAACTTCCCACCTTATACCAGAAATCAGATAGTCACT ATTTTGCAAGATCGACTTA |
| 789 | CDC6 | 3720906 | GTATCTAGAGATCAGGTTCTGGACAATGCTGCAGTTCA ATTCTGTGCCCGCAAAGTCTCTGCT |
| 790 | CDC6 | 3720907 | GAGATGTTCGCAAAGCACTGGATGTTTGCA |
| 791 | CDC6 | 3720908 | GTGAGTTACGGCTCTGTTGCATTCTT |
| 792 | CDC6 | 3720910 | AGATGTCAAAAGCCAGACTATTCTCAA |
| 793 | CDC6 | 3720913 | GTAAATCACCTTCTGAGCCTCTGATTCCCAAG |
| 794 | CDC6 | 3720914 | TATCCCAAGTCATCTCAGAAGTTGATGGTAACAGGATG ACCTTGAGCCAAGAAGGAGCACAAGATTCCTTCCCTCT TCAGCAGAAGATCTTGGTTTGCTCTTTGATGCTCTTGAT CAGGCAGTTGAAAATCAAAGAGGTCACTCTG |
| 795 | CDC6 | 3720916 | TACAGTAAAGTCTGTCGCAAACAGCAGGTGGCGGCTGT GGACCAGTCAGAGTGTTTGTCACTTTCAGGGCTCTTGGA AGCCAGGGGCATTTTAGGATTAAAGA |
| 796 | CDC6 | 3720917 | GAAATAGAACATGCTCTGAAAGATA |
| 797 | CDC6 | 3720918 | CCCGAAAGTATTCAGCTGGCATTTAGAGAGCTACAGTC TTCATTTTAGTGCTTTACACATTCGGGCCTGAAAACAAA TATGACCTTTTTTACTTGAAGCCAATGAATTTTAATCTA TAGATTCTTTAATATTAGCACAGAATAATATCTTTGGGT CTTACTATTTTTACCCATAAAAGTGACCAGGTAGACCCT TTTTAATTACATTCACTACTTCTACCACTTGTGTATCTCT AGCCAATGTGCTTGCAAGTGTACAGATCTGTGTAGAGG AATGTGTGTATATTTACCTCTTCGTTTGCTCAAACATGA GTGGGTATTTTTTTGTTTGTTTTTTTTGTTGTTGTTGTTTT TGAGGCGCGTCTCACCCTGTTGCCCAGGCTGGAGTGCA ATGGCGCGTTCTCTGCTCACTACAGCACCCGCTTCCCAG GTTGAAGTGATTCTCTTGCCTCAGCCTCCCGAGTAGCTG GGATTACAGGTGCCCACCACCGCGCCCAGCTAATTTTTT AATTTTTAGTAGAGACAGGGTTTTACCATGTTGGCCAG GCTGGTCTTGAACTCCTGACCCTCAAGTGATCTGCCCAC CTTGGCCTCCCTAAGTGCTGGGATTATAGGCGTGAGCC ACCATGCTCAGCCATTAAGGTATTTTGTTAAGAACTTTA AGTTTAGGGTAAGAAGAATGAAAATGATCCAGAAAAA TGCAAGCAAGTCCACATGGAGATTTGGAGGACACTGGT TAAAGAATTTATTTCTTTGTATAGTATACTATGTTCATG GTGCAGATACTACAACATTGTGGCATTTTAGACTCGTTG AGTTTCTTGGGCACTCCCAAGGGCGTTGGGGTCATAAG GAGACTATAACTCTACAGATTGTGAATATATTTATTTTC AAGTTGCATTCTTTGTCTTTTTAAGCAATCAGATTTCAA GAGAGCTCAAGCTTTCAGAAGTCAATGTGAAAATTCCT TCCTAGGCTGTCCCACAGTCTTTGCTGCCCTTAGATGAA GCCACTTG |
| 798 | MAPT | 3723688 | GCCGGCCTCAGGAACGCGCCCTCTTCGCCGGCGCGCGC CCTCGCAGTCACCGCCACCCACCAGCTCCGGCACCAAC AGCAGCGCCGCTGCCACCGCCCACCTTCTGCCGCCGCC ACCACAGCCACCTTCTCCTCCTCCGCTGTCCTCTCCCGT CCTCGCCTCTGTCGACTATCA |
| 799 | MAPT | 3723690 | TAAGGTTACTGGTGCTTCGGCCACACCCATCTTTCTGAG CCCACTGGACTGGGCGCAGAGGGGGGATTGCCATGGAA ACCACAGGTGTCCGGAGAGGGGATCTTGGGGCTGGCCT CACCCCTTCCCTGCGGAGATTGGGGACCCTGGGGTAGG GGGAGCCGCGCCCAGTCGGCCTCCTGGAGGACACGGGA GGAAGCCCCGAACCCCCGCGCCTGAGGCTGTTTCTGAT TGGCCCCTGGAGGCCGCAGACACGCAGATAGGCGGCCC TGGGTGTATTTTTATTAATATTATGTCCGTACTGATTAA TATTATTTATCTTAAATAAATTTCACCCGTGTCCAAGTT CACCGCGCCCCCAAAACCGAGTCTGGGGCGGCAGGGG GAACTCCTGGCCAACGAATCCATGCCTCGCCCTCCTGTG ATGAACCTGGTACGCACGGTTTTCTGGTTAATTCTATCG CTGAAAACTGGTGCGGGGGGCGCACTTCTGAGACGGAA GAGCATCTAGGAGCTGAATCCTCCACGCGGGTCGCCCA GGTTGATCTGAATTTCTGGGGAATGGCTTGGCTGCCCGC |

TABLE 8-continued

Subtyping Target Sequences

| SEQ ID NO. | Gene | Affy Probeset ID | Sequence |
|---|---|---|---|
| | | | CCGGGACCAGGCCGACCCTCCTTGACGGTGGCGTAGAG GGCTGGAGCCTGGGTACTGCGAGGCTCCTCGCATGGCT GGGCCCGCCGCGAGGGGTTGCAGAGCGGCTCAGGGATC GATTCAAGCATCGTCTCTCCTCCCTCGCCCCCAGACAGA GCTGGGCGCGGGGTTCCCCTTCCAGATGGAGCGAGGGT CTCGGGGTGGCCCCGGAAAAGGGGAGCCCGCGGCCAC GGCTACGTATTGCCATCTCGCGAGCAGAGATGTCACCT CCTGCCTTTGGAGGAAAGGGAGCCCGGTGGGGATGAGC GCATTTAGCCCAATGCTGGGAACAAAGCGCACTCCGCG CTTCTGCGATTTCGCTCCATTTTGAAATGTGTTGGCGCT TTGGTGGGGCCGCTGCGGTGGGCAAGGCCGGGGGCGCT GTTAATGGAGGAACCTCAGGGGGACGGTCCTTCGTAGG AAACTCTATCCTGGCTCTGCGCGCGCTTTAAGGAAATG GC |
| 800 | MAPT | 3723691 | ACCTCGAGGGATGCAGCTTTTGCGCGGATGACGGTGGG GTGCTGAACCAGCCGGTGCGCCTCTGGAAATGTCTGGG CACGGATCCTGGGGCCATCGACGACTCCTCCCCATTCCC AGCAGGCGGGAGCTCTTACATTCCGAG |
| 801 | MAPT | 3723692 | GAAATGTCTTTCCTACCGCGGTTGATTCTGGGGTGTCAT TTTGTGTTTTGTGATGGCTGCTTATATTTACTGTATAAG CATTGTATTTACTGTATAAGCATTGTATTATAATTACTG TATAAGCTGCTTATATTTACTGTATAAGCATCTCCAAAT CCTCCCTCTACGTAAACAAATTAATGGATAAACAGATA AGTGTATCCCCTGCCCCCACCCCTGCTACGCAGGTCCGG AGTGACTCTTGAAGCTCATACATTCCTTGGCCAAGTTTG CTTCTCTAACAGATGTTTATATAGCAATAACCTGGCTTG GCTCTTGGGTTCACCTTTGGACGATTTGGGGAAGGGGC TTGTTGGCTTTGCTGGGTTTTGGATGAGTGACAGTCCAT GACTGTTCCTGCTGGAAGGGCGTGACTTTTAAGTGGTTT CTAATATCAGGCATTGCTCCTCCGACAGGAACAAAAGA AATGGATACTGCCCATAAATTGTTAGAAAACTTAGAAT CGCTTTGATTGAGGAAAGGTTAGATTTATTCCGGTTGGA AAAAGTGGCCTTTCTATTAAACGTGCCCTTTGACCCTCA TGCCCTTGGAGGTCGGTGCCAGCCTGGAGATGGGATAA GATTGTGGTTTTCCTTCTGCCTTTTTAACATCTGTTGTTA CAGTCCATTTGTTGAAAATTTAAAGAAACTGTTTTATTC CACTTTCCCTCAGCATTTATGTGTGTGGTTTCAGTAGCT CTGTGGCTATATGTACGAACACGTGTTATTTTTCCAATT GGACATGTGATAATTTTCCAACTGGACCTTGCCTTCTAT TGATGTA |
| 802 | MAPT | 3723707 | CCCGCCAGGAGTTCGAAGTGATGGAAGATCACGCTGGG ACGTACGGGTTGGGGGACAGGAAAGATCAGGGGGGCT ACACCATGCACCAAGACCAA |
| 803 | MAPT | 3723712 | TGTGACAGCACCCTTAGTGGATGAGGGAGCTCCCGGCA AGCAGGCTGCCGCGCAGCCCCACACGGAGATCCCAGAA GGAACC |
| 804 | MAPT | 3723713 | GCCAGTCCCATGTGACAGTCAAAGCTTCTAACTCCATTC AAAGTTGCAGCCATTCCCCTCGAGGGCTGGCAGGGAGG GGAGGGGTAAGAGAAACAGGAAGGTTCTTACTGAGTTG GTCCTGGTGTGAGCTGCGTCACACTCCCTGCAGAGGTTT CAAGGAGACTCTCTCTCTCTCTGTCTCCATGGGGACCTT ATTTGAATTCTTCTACTCTTACCCCAGCCTGCCATCTCC AGCTATCCTCCCCTGAAGAGCCCTTCTGCTGCGCTGGAT TCTGGTGGCCATGTCATCTCCTCGGCCCCGTGGGAGTCT GAAGATCTGGCTGCAGCCTCACCTCTGAGGTCCTGCTA GTTGCCACCTCTTAAA |
| 805 | MAPT | 3723714 | AGCCTGGAAGACGAAGCTGCTGGTCACGTGACCCAAG |
| 806 | MAPT | 3723715 | CTGGAATTGCCTGCCATGACTTGGGGGTTGGGGGGAGG GACATGGGGTGGGCTCTGCCCTGAAAAGATCATTTGGA CCTGAGCTCTAATTCACAAGTCCAGGAGATTTTAGGGA GTTGGTTCTTATCAAAGGTTGGCTACTCA |
| 807 | MAPT | 3723716 | GCGATTCTCACTGCAGGCTGCCCTGTGGCTGATCCAGG AGCAAGGCCTTAACCATGTCATCCCCAAGCGATTGCTT GTAAACTTTCTTCTGTGCAGCCTTCAACCCTTATTATGA TTTTCTTCTCAGGAACCAAACTGCTGTATTCAAGAAAGG CAGCTTTGTGTAATCATTTATCATAAATATCTTAAGAAA |

TABLE 8-continued

Subtyping Target Sequences

| SEQ ID NO. | Gene | Affy Probeset ID | Sequence |
|---|---|---|---|
| | | | AATCCTAGAGATTCCTAATTTTAGGAAATGGGAGACCT ATGGTACTGATATAATGTGGGCTGGGCTTGTTTTCTGTC ATTTGCTAGATAAATGAACTTGAGAGCCTACTGTAAAA TGTGGAAGCTTCTAGATTGCAGAAGGGCTGGAAAGACA CTGTTCTTTTCTCCCGAGTGATGGGATCTGTCCAGTATT TAGAGCTGCCTCTGAGGCCATCTGATTCTAGGAGACTCT GCCTCGTTGAGGATATTTTGAGGCCTAACTACACATTCC TGCCCCCAGAGAGGTCACAGCCTATAGCAGGCTGATGT TTCTCATGTCAC |
| 808 | MAPT | 3723717 | TAAGCTATGGGAAGGCCTGTATACGAGGGGTGGACTTT TCTTCTGTAAGTGTCCAGAGACCAGGCCTCCTGAAGAG GGCATGGGGGCTTAACTTACCTGGACTACTGTG |
| 809 | MAPT | 3723720 | GCCAATGAGATTAGCGCCCACGTCCAGCCTGGACCCTG CGGAGAGGCCTCTGGGGTCTCTGGGCCGTGCCTCGGGG AGAAAGAGCCAGAAGCTCCCGTCCCGCTGACCGCGAGC CTTCCTCAGCACCGTCCCGTTTGCCCAGCGCCTCCTCCA ACAGGAGGCCCTCAGGAGCCCTCCCTGGAGTGGGGACA AAAAGGCGGGGACTGGGCCGAGAAGGGTCCGGCCTTTC CGAAGCCCGCCACCACTGCGTATCTC |
| 810 | MAPT | 3723721 | CTCATGTCCGGCATGCCTGGGGCTCCCCTCCTGCCTGAG GGCCCCAGAGAGGCCACACGCCAACCTTCGGGGACAG GACCTGAGGACACAGAGGGCGGCCGCCACGCCCCTGA GCTGCTCAAGCACCAGCTTCTAGGAGACCTGCA |
| 811 | MAPT | 3723722 | ATGAAGACCGCGACGTCGATGAGTCCTCCCCCCAAGAC TCCCCTCCCTCCAAGGCCTCCCCAGCCCAAGATGGGCG GCCTCCCCAGACAGCCGCCAGAGAAGCCACC |
| 812 | MAPT | 3723725 | ACGGGACTGGAAGCGATGACAAAAAAGCCAA |
| 813 | MAPT | 3723731 | ACATCCACACGTTCCTCTGCTAAAACCTTGAA |
| 814 | MAPT | 3723732 | CTCAGACCCTCTGATCCAACCCTCCAG |
| 815 | MAPT | 3723733 | TCTTCTGTCACTTCCCGAACTGGCAG |
| 816 | MAPT | 3723735 | GGGCTGATGGTAAAACGAAGATCGCCACACCGCGG |
| 817 | MAPT | 3723736 | CCAGGCCAACGCCACCAGGATTCCAGCAAAAACCCCGC CCGCTCCAAAGACACCACCCA |
| 818 | MAPT | 3723737 | CCAAGTCGCCGTCTTCCGCCAAGAGCCGCCTGCAGACA GCCCCCGTGCCCATGCCAGACCTGAAGAATGTCAAGTC CAAGATCGGCTCCACTGAGAACCTGAAGCACCAGCCGG GAGGCG |
| 819 | MAPT | 3723740 | AGAAGCTGGATCTTAGCAACGTCCAGTCCAAGTGTGGC TCAAAGGATAATATCAAACACGTCCCGGGAGGC |
| 820 | MAPT | 3723743 | TAGTCTACAAACCAGTTGACCTGAGCAAGGTGACCTCC AAGTGTGGCTCATTAGGCAACATCCATCATA |
| 821 | MAPT | 3723746 | CAGAGTCCAGTCGAAGATTGGGTCCCTGGACAATATCA CCCACGTCCCTGGCGGAGGAAAT |
| 822 | MAPT | 3723747 | TCGTGTACAAGTCGCCAGTGGTGTCTGGGGACACGTCT CCACGGCATCTCAGCAATGTCTCCTCCACCGGCAGCAT CGACATGGTAGACTCGCCCCAGCTCGCCACGCTAGCTG ACGAGGTGTCTGCCTCCC |
| 823 | MAPT | 3723748 | CCCTGGGGCGGTCAATAATTGTGGAGAGGAGAGAATGA GAGAGTGTGGAAAAAAAAAGAATAATGACCCGGCCCC CGCCCTCTGCCCCCAGCTGCTCCTCGCAGTTCGGTTAAT TGGTTAATCACTTAACCTGCTTTTGTCACTCGGCTTTGG CTCGGGACTTCAAAATCAGTGATGGGAGTAAGAGCAAA TTTCATCTTTCCAAATTGATGGGTGGGCTAGTA |
| 824 | MAPT | 3723749 | ACATGGCCACATCCAACATTTCCTCAGG |
| 825 | MAPT | 3723750 | TGCTTCTGGGGGATTTCAAGGGACTGGGGGTGCCAACC ACCTCTGGCCCTGTTGTGGGGGTGTCACAGAGGCAGTG |

TABLE 8-continued

Subtyping Target Sequences

| SEQ ID NO. | Gene | Affy Probeset ID | Sequence |
|---|---|---|---|
| | | | GCAGCAACAAAGGATTTGAAACTTGGTGTGTTCGTGGA GCCACAGGCAGACGATGTCAACCTTGT |
| 826 | MAPT | 3723751 | CCTCCTTGCCGCTGGGAGAGCCAAGGCCTATGCCACCT GCAGCGTCTGAGCGGCCGCCTGTCCTTGGTGGCCGGGG GTGGGGGCCTGCTGTGGGTCAGTGTGCCACCCTCTGCA GGGCAGCCTGTGGGAGAAGGGACAGCGGGTAAAAAGA GAAGGCAAGCTGGCAGGAGGGTGGCACTTCGTGGATG ACCTCCTTAGAAAAGACTGACCTTGATGTCTTGAGAGC GCTGG |
| 827 | MAPT | 3723752 | TTGCAGACCTGGGACTTTAGGGCTAACCAGTTCTCTTTG TAAGGACTTGTGCCTCTTGGGAGACGTCCACCCGTTTCC AAGCCTGGGCCACTGGCATCTCTGGAGTGTGTGGGGGT CTGGGAGGCAGGTCCCGAGCCCCCTGTCCTTCCCACGG CCACTGCAGTCACCCCGTCTGCGCCGCTGTGCTGTTGTC TGCCGTGAGAGCCCAATCACTGCCTATACCCCTCATCAC ACGTCACAATGTCCCGAATTCCCAGCCTCACCACCCCTT CTCAGTAATGACCCTGGTTGGTTGCAGGAGGTACCTAC TCCATACTGAGGGTGAAATTAAGGGAAGGCAAAGTCCA GGCACAAGAGTGGGACCCCAGCCTCTCACTCTCAGTTC CACTCATCCAACTGGGACCCTCACCACGAATCTCATGA TCTGATTCGGTTCCCTGTC |
| 828 | MAPT | 3723753 | CCACTTGCACCCTAGCTTGTAGCTGCCAACCTCCCAGAC AGCCCAGCCCGCTGCTCAGCTCCACATGCATAGTATCA GCCCTCCACACCCGACAAAGGGGAACACACCCCCTTGG AAATGGTTCTTTTCCCCCAGTCCCAGCTGGAAGCCATGC TGTCTGTTCTGCTGGAGCAGCTGAACATATACATAGAT GTTGCCCTGCCCTCCCCATCTGCACCCTGTTGAGTTGTA GTTGGATTTGTCTGTTTATGCTTGGATTCACCA |
| 829 | MAPT | 3723754 | TTCTAGCAGCTAAGGAGGCCGTTCAGCTGTGACGAAGG CCTGAAGCACAGGATTAGGACTGAAGCGATGATGTCCC CTTCCCTACTTCCCCTTGGGGCTCCCTGTGTCAGGGCAC AGACTAGGTCTTGTGGCTGGTCTGGCTTGCGGCGCGAG GATGGTTCTCTCTGGTCATAGCCCGAAGTCTCATGGCAG TCCCAAAGGAGGCTTACAACTCCTGCATCACAAGAAAA AGGAAGCCACTGCCAGCTGGGGGGATCTGCAGCTCCCA GAAGCTCCGTGAGCCTCAGCCACCCCTCAGACTGGGTT CCTCTCCAAGCTCGCCCTCTGGAGGGGCAGCGCAGCCT CCCACCAAGGGCCCTGCGACCACAGCAGGGATTGGGAT GAATTGCCTGTCCTGGATCTGCTCTAGAGGCCCAAGCT GCCTGCCTGAGGAAGGATGACTTGACAAGTCAGGAGAC ACTGTTCCCAAAGCCTTGACCAGAGCACCTCAGCCCGC TGACCTTGCACAAACTCCATCTGCTGCCATGAGAAAAG GGAAGCCGCCTTTGCAAAACATTGC |
| 830 | MAPT | 3723756 | GTGTCTGCTGCTCCCTAGTCTGGGCC |
| 831 | MAPT | 3723757 | CCGGCCCTCATTGAATGCGGGGTTAATTTAACTCAGCCT CTGTGTGAGTGGATGATTCAGGTTGCCAGAGACAGAAC CCTCAGCTTAGCATGGGAAGTAGCTTCCCTGTTGACCCT GAGTTCATCTGAGGTTGGCTTGGAAGGTGTGGGCACCA TTTGGCCCAGTTCTTACAGCTCTGAAGAGAGCAGCAGG AATGGGGCTGAGCAGGGAAGACAACTTTCCATTGAAGG CCCCTTTCAGGGCCAGAACTGTCCCTCCCACCCTGCAGC TGCCCTGCCTCTGCCCATGAGGGGTGAGAGTCAGGCGA CCTCATGCCAAGTGTA |
| 832 | BIRC5 | 3736291 | GGGTGGACCGCCTAAGAGGGCGTGCGCTCCCGAC |
| 833 | BIRC5 | 3736292 | GCGGCGCGCCATTAACCGCCAGATTTGAATCGCGGGAC CCGTTGGCAG |
| 834 | BIRC5 | 3736293 | TGCCCCGACGTTGCCCCCTGCCTGGCA |
| 835 | BIRC5 | 3736294 | TTTCTCAAGGACCACCGCATCTCTACATTCAAGAACTGG CCCTTCTTG |
| 836 | BIRC5 | 3736295 | TGGCTTCATCCACTGCCCCACTGAGAACGAGCCAGACT TGGCCCAGTGTTTCTTCTGCTTCAAGGAGCTGGAAGGCT GGGAGCCAGATGACGACCCC |

TABLE 8-continued

| Subtyping Target Sequences | | | |
|---|---|---|---|
| SEQ ID NO. | Gene | Affy Probeset ID | Sequence |
| 837 | BIRC5 | 3736296 | CCTCGATGGGCTTTGTTTTGAACTGAGTTGTCAAAAGATTTGAGTTGCAAAGACACTTAGTATGGGAGGGTTGCTTTCCACCCTCATTGCTTCTTAAACAGCTGTTGTGAACGGATACCTCTCTATATGCTGGTGCCTTGGTGATG |
| 838 | BIRC5 | 3736298 | GCTTGGGCAAAGCACTGATGCCATCAACTTCAGACTTGACGTCTTACTCCTGAGGCAGAGCAGGGTGTGCCTGTGGAGGGCGTGGGGAGGTGGCCCGTGGGGAGTGGACTGCCGCTTTAATCCCTTCAGCTGCCTTTCCGCTGTTGTTTTGATT |
| 839 | BIRC5 | 3736299 | ACATAAAAAGCATTCGTCCGGTTGCGCTTTCCTTTCTGTCAAGAAGCAGTTTGAAGAATTAACCCTTGGTGAATTTTTGAAACTGGACAGA |
| 840 | BIRC5 | 3736301 | AAGAATTTCTGTTCGAGGAAGAGCCTGATGTTTGCCAGGGTCTGTTTAACTGGACATGAA |
| 841 | BIRC5 | 3736303 | AGAATTTGAGGAAACTGCGGAGAAAGTGCGCCGTGCCATCGAGCAGCTG |
| 842 | BIRC5 | 3736304 | GGCTGCACCACTTCCAGGGTTTATTCCCTGGTGCCACCAGCCTTCCTGTGGGCCCCTTAGCAATGTCTTAGGAAAGGAGATCAACATTTTCAAATTAGATGTTTCAACTGTGCTCTTGTTTTGTCTTGAAAGTGGCACCAGAGGTGCTTCTGCCTGTGCAGCGGGTGCTGCTGGTAACAGTGGCTGCTTCTCTCTCTCTCTCTCTTTTTTGGGGGCTCATTTTTGCTGTTTTGATTCCCGGGCTTACCAGGTGAGAAGTGAGGGAGGAAGAAGGCAGTGTCCCTTTTGCTAGAGCTGACAGCTTTGTTCGCGTGGGCAGAGCCTTCCACAGTGAATGTGTCTGGACCTCATGTTGTTGA |
| 843 | BIRC5 | 3736305 | GGTTCCTTATCTGTCACACCTGTGCCTCCTCAGAGGACAGTTTTTTTGTTGTTGTGTTTTTTTGTTTTTTTTTTTTTGGTAGATGCATGACTTGTGTGTGATGAGAGAATGGAGACAGAGTCCCTGGCTCCTCTACTGTTTAACAACATGGCTTTCTTATTTTGTTTGAATTGTTAATTCACAGAATAGCACAAACTACAATTA |
| 844 | BIRC5 | 3736306 | AACGGGGTGAACTTCAGGTGGATGAGGAGACAGAATAGAGTGATAGGAAGCGTCTGGCAGATACTCCTTTTGCCACTGCTGTGTGATTAGACAGGCCCAGTGAGCCGCGGGGCACATGCTGGCCGCTCCTCCCTCAGAAAAAGGCAGTGGCCTAAATCCTTTTTAAATGACTTGGCTCGATGCTGTGG |
| 845 | BIRC5 | 3736307 | CGTGTGTCTGTCAGCCCAACCTTCACATCTGTCACGTTCTCCACACGGGGGAGAGACGCAGTCCGCCCAGGTCCCCGCTTTCTTTGGAGGCAGCAGCTCCCGCAGGGCTGAAGTCTGGCGTAAGATGATGGATTTGATTCGCCCTCCTCCCTGTCATAGAGCTGCAGGGTGGATTGTTACAGCTTCGCTGGAAACCTCTGGAGGTCATC |
| 846 | BIRC5 | 3736308 | TGTTCCTGAGAAATAAAAAGCCTGTCATTTC |
| 847 | BIRC5 | 3736309 | GTTTTTCATCGTCGTCCCTAGCCTGCCAACAGCCATCTGCCCAGACAGCCGCAGTGAGGATGAGCGTCCTGGCAGAGACGCAGTTGTCTCTGGGCGCTTGCCAGAGCCACGAACCCCAGACCTGTTTGTATCATCCGGGCTCCTTCCGGGCAGAAACAACTGAAAATGCACTTCAGACCCACTTATTTCTGCCACATCTGAGTCGGCCTGAGATAGACTTTTCCCTCTAAACTGGGAGAATATCACAGTGGTTTTTGTTAGCAGAAAATGCACTCCAGCCTCTGTACTCATCTAAGCTGCTTA |
| 848 | BIRC5 | 3736310 | CTGTGCTGTGGGCAGGGCTGAGCTGGAGCCGCCCCTCTCAGCCCGC |
| 849 | BIRC5 | 3736311 | ATCCTTAAAACCAGACCCTCATGGCTACCAGCACCTGAAAGCTTCCTCGACATCTGTTAATAAAGCCGTAGGCCCTTGTCTAAGTGC |
| 850 | BIRC5 | 3736312 | CCGCCTAGACTTTCTTTCAGATACATGTCCACATGTCCATTTTTCAGGTTCTCTAAGTTGGAGTGGAGTCTGGGAAGGGTTGTGAATGAGGCTTCTGGGCTATGGGTGAGGTTCCAATGGCAGGTTAGAGCCCCTCGGGCCAACTGCCATCCTG |

TABLE 8-continued

| Subtyping Target Sequences | | | |
|---|---|---|---|
| SEQ ID NO. | Gene | Affy Probeset ID | Sequence |
| | | | GAAAGTAGAGACAGCAGTGCCCGCTGCCCAGAAGAGA CCAGCAAGCCAAACTGGAGCCCCCATTGCAGGCTGTCG CCATGTGGAAAGAGTA |
| 851 | KRT14 | 3757155 | TAGGAGGCCCCCCGTGTGGACACAG |
| 852 | KRT14 | 3757156 | TCCAGCCGCCAAATCCGCACCAAGGTCATGGA |
| 853 | KRT14 | 3757157 | TGAGCTCTAGTGCTGTCACCCAGTTTCCCTTGTGAACCT CCTTGGGTGGAAGAAGCTATTTTCTAAACCCTCCTTAGG GCTAGGAGAGGCAGCCCCCACCTCTTGCTTCTACGTGG TGTCTGTGGCAGATCCTATTGCTGTTGTGGTCAGCACCA TGAACAGGGCCCTACAGGGCTCTTCCCACTGAGACCAC TCCATTGGGTGAATATGGATGGAACCAGCCAGGTGTGA GCTCTTAGGAAGCTCTAATCTGAGGGCAAAGACTCTGT CTCTGACCTTTGGGAGCCCTCGTCTGAAAGAAATG |
| 854 | KRT14 | 3757160 | CTGGAGGAGACCAAAGGTCGCTACTGCATGCAGCTGGC CCAGATCCAGGAGATGATTGGCAGCGT |
| 855 | KRT14 | 3757162 | CAAGAGCGAGATCTCGGAGCTCCGGCGCACCATGCAGA AC |
| 856 | KRT14 | 3757164 | GGAGATGGACGCTGCACCTGGCGTGGACCTGAGCCGCA TTCTGAACGAGATGCGTGACCAGTAT |
| 857 | KRT14 | 3757167 | GATGGGTGTCTCATACCTTTTCTCTGGGGTCATTCCAG |
| 858 | KRT14 | 3757169 | AGCCACAGTGGACAATGCCAATGTCCTTCTGCAGATTG ACAATGCCCGTCTGGCCGCGGATGACTTCCGCACCAA |
| 859 | KRT14 | 3757172 | TGGCCTTGGTGCTGGCTTGGGTGGTGGCTTTGGTGGTGG CTTTGCTGGTG |
| 860 | KRT14 | 3757174 | ACCCGAGCACCTTCTCTTCACTCAGCCAACTGCTCGCTC GCTCA |
| 861 | KRT14 | 3757199 | GAGAAGGTGACCATGCAGAACCTCAATGACCGCCTGGC C |
| 862 | KRT17 | 3757215 | GGACTCAGCTACCCCGGCCGGCCAC |
| 863 | KRT17 | 3757218 | CCAGGAATACAAAATCCTGCTGGAT |
| 864 | KRT17 | 3757219 | AAGAGTGAGATCTCGGAGCTCCGGCGCACC |
| 865 | KRT17 | 3757221 | AGGTGGGTGGTGAGATCAATGTGGAGATGGACGCTGCC CCAGGCGTGGACCTGAGCCGCATCCTCAACGAGATGCG TGAC |
| 866 | KRT17 | 3757222 | GTGCACCGGGATTAGTCACCTTAGAGGGCTTCCCTGTCT GCAGAGCCCTGATCCTTGGGGTCCAGTGTGCAGGGCAG ACTCCTCTTTGTACCACACTGCTTCTCTGTACACAAGGA ACCTC |
| 867 | KRT17 | 3757223 | CTGGCCAGAGCCGACCTGGAGATGCAGATTGAGAACCT CAAGGAG |
| 868 | KRT17 | 3757224 | CCCTGCGCCTGAGTGTGGAGGCCGACATCAATGGCCTG |
| 869 | KRT17 | 3757227 | GTCTGGCTGCTGATGACTTCCGCAC |
| 870 | KRT17 | 3757228 | GGTACTGAGTATCGGGGGAAGAAGA |
| 871 | KRT17 | 3757230 | GGCAGCAGCTTTGGGGGTGTTGATGGGCTGCTGGCTGG AGGTGAGAAGGCCACCATGCAG |
| 872 | KRT17 | 3757231 | GTCCCGCACCTCCTGCCGGCTGTCTGGCGGCCTGGGTGC CGGCTCCTGCAGGCTGGGATCTGCTGGCGGCCTGGGCA GCACCCTCGGGGGTAGCAGCTACTCCAGCTGCTACAGC TTTGGCTCTGGTGGTG |
| 873 | KRT17 | 3757234 | ACACGCACGGCACTCAGCACGAGGATTTGGAGA |

TABLE 8-continued

| Subtyping Target Sequences | | | |
|---|---|---|---|
| SEQ ID NO. | Gene | Affy Probeset ID | Sequence |
| 874 | TYMS | 3775844 | TTGGCCTGCCTCCGTCCCGCCGCGCCAC |
| 875 | TYMS | 3775845 | CTGCCTCCGTCCCGCCGCGCCACTT |
| 876 | TYMS | 3775846 | GCCTGTGGCCGGCTCGGAGCTGCCGC |
| 877 | TYMS | 3775850 | CGCTTCGCAGCGTTTTCAAAAACTGGAGCGAAAGTGATGTGGGCGGGGCAAAGGCGGCGGGAAGAGGAGAGCACTGAAGCTGGCGCGGGAACTTGGTTTCCTGGTGGCCTCCCATCCAATCCCCACGAACCAGCTTTCCTCTTAAACCTTGAAAAGAGAAATTCGGGAGTTCGAGTATAAGTTCTTAGTCGTCCTTTCCTCTTTCCTTTCCGACAGGAGCACCCCAGGCAAAAAATGTCTCGCGGGTCATTGGCGCCAGGCTTTCAGGGGACAGTGGGGCGGGGCGGGGTGGGCACAGGACGTTAGGCAGCCGTTGGC |
| 878 | TYMS | 3775851 | CGTCCTGCCGTCCTGGATCCTGCGCCAGCTGCG |
| 879 | TYMS | 3775853 | CTCTGCTGACAACCAAACGTGTGTTCTGGAAGGGTGTT |
| 880 | TYMS | 3775855 | GCTGTCTTCCAAGGGAGTGAAAATCTGGGATGCCAATGGATCCCGAGACTTTTTGGACAGCCTGGGATTCTCCACCAGA |
| 881 | TYMS | 3775856 | AGGACAGGGAGTTGACCAACTGCAAAGAGTGATTGACACCATCAAAACCAACCCTGACGACAGAAGAATCATC |
| 882 | TYMS | 3775857 | AAGCAATCTGGTTTTGTGCAGAGGCACCTGAGGGAGGCAGGACCCTGGGAACTTCCCCCAGCCACATGGTTGATTGTGTGACGTTGG |
| 883 | TYMS | 3775861 | CTCTGCCAGTTCTATGTGGTGAACAGTGAGCTGTCCTGCCAGCTGTACCAGAGATCGGGAGACATGGGCCTCGGTGTGCCTTTCAACATCGCCAGCTACGCCCTGCTCACGTACATGATTGCGCACATCACGGGCCTGAA |
| 884 | TYMS | 3775862 | GGAGATGCACATATTTACCTGAATCACATCGAGCCACTGAAAATT |
| 885 | TYMS | 3775864 | CCAAAGCTCAGGATTCTTCGAAAAGTTGAGAAAATTGATGACTTCAAAGCTGAAGACTTTCAGATTGAAGGGTACAATCCGCATCCAACTATTAAAATGGA |
| 886 | TYMS | 3775865 | AGGAGCTCGAAGGATATTGTCAGTCTTTAGGGGTTGGGCTGGATGCCGAGGTAAAAGTTCTTTTTGCTCTAAAAGAAAAAGGAACTAGGTCAAAAATCTGTCCGTGACCTATCAGTTATTA |
| 887 | TYMS | 3775866 | CACTGAGGGTATCTGACAATGCTGAGGTTATGAACAAAGTGAGGAGAATGAAATGTATGTGCTCTTAGCAAAAACATGTATGTGCATTTCAATCCCACGTACTTATAAAGAAGGTTGGTGAATTTCACAAGCTATTTTTGGAATATTTTTAGAATATTTTAAGAATTTCACAAGCTATTCCCTCAAATCTGAGGGAGCTGAGTAACACCATCGATCATGATGTAGAGTGTGGTTA |
| 888 | TYMS | 3775867 | TTGTTCATTCTGTACTGCCACTTATCTGCTCAGTTCCTTC |
| 889 | NDC80 | 3776145 | AGCGCCGGCGGAGAATTTCAAATTCGAACGGCTTTGGCGGGCCGAGGAAGGACCTGGTGTTTTGATGACCGCTGTCCTGTCTAGCAGATACTTGCACGGTTTACAGAAATTCGGTCC |
| 890 | NDC80 | 3776147 | ATGAAGCGCAGTTCAGTTTCCAGCGGTGGTGCTGGCCGCCTCTCCATGCAGGAGTTAAGATCCCAGGATGTAAATAAACAAGGCCTCTATACCCCTCA |
| 891 | NDC80 | 3776149 | GTGGACATGGATCCCGGAATAGTCAACTTGGTATATTTTCCAGTTCTGAGAAAATCAAGGACCCGAGACCACTTAATGACAAAGCATTCATTC |

TABLE 8-continued

Subtyping Target Sequences

| SEQ ID NO. | Gene | Affy Probeset ID | Sequence |
|---|---|---|---|
| 892 | NDC80 | 3776150 | CTTACAGAAAATGGTTATGCACATAATGTGTCCATGAA ATCTCTACAAGCTCCCTCTGTTAAAGACTTCCTGAAGAT CTTCACATTTCTTTATGGCTTCCTGTGCCCCTCATACGA ACTTCCTGACACAAAGT |
| 893 | NDC80 | 3776151 | CTCCTCATACATGGCCTCACATTGTGGCAGCCTTAGTTT GGCTAATAGACTGCATCAAG |
| 894 | NDC80 | 3776152 | TGAAATGTATACATGGGAAAGGGTTTTTTTCCTCAAAA AAAATATTTTCTCTCCCAGTCTTTTGACAGTATTCTCAA AGTCTGCTTCAGAGTTTTCATTTTTCAAAGCACATTTGA TTTTAAG |
| 895 | NDC80 | 3776154 | ATGAAAGAAAGCTCACCTTTATTTGATGATGGG |
| 896 | NDC80 | 3776155 | CTACACCATAAAATGCTATGAGAGTTTTATGAGTGGTG CCGACAGCTTTGATGAGAT |
| 897 | NDC80 | 3776156 | GCTTTTAAGCTGGAATCATTAGAAGCAAAAAACAGAGC ATTGAATGAACAGATTGCAAGATTGGAACAAGA |
| 898 | NDC80 | 3776157 | AATCGTCTAGAGTCGTTGAGAAAACTGAAGGCTTCCTT ACAAGGAGATGTTCAAAAGTATCAGGCATACATGAGCA ATTTGGAGTCTCATTCAGCCATTCTTGACCAGAAATTAA ATGGTCTCAATGAGGAAATTGC |
| 899 | NDC80 | 3776159 | AACCAGAAGTACTCAGTTGCAGACATTGAGCGAATAAA TCATGAAAGAAATGAATTGCAGCAGACTATTAATAAAT TAACCAAGGACCTGGAAGCTGAACAACAGAAGTTGTGG AATGAGGAGTTA |
| 900 | NDC80 | 3776161 | CAGAGTATCACAAATTGGCTAGAAAATTAAAACTTATT CCTAAAGGTGCTGAGAATTCCAAAGGTTATGACTTTGA AATTAAGTTTAATCCCGAGGCTGGTGCCAACTGCCTTGT CAAATACA |
| 901 | NDC80 | 3776162 | GTACCTCTTAAGGAACTCCTGAATGAAACTGAAGAAGA AATTAATAAAGCCCTAAATAAAAAAATGGGTTTGGAGG ATACTTTAGAACA |
| 902 | NDC80 | 3776163 | TTGAATGCAATGATAACAGAAAGCAAGAGAAGTGTGA GAACTCTGAAAGAAGAAGTTCAAAAGCTGGATGATCTT TACCAACAAAAA |
| 903 | NDC80 | 3776165 | ACCTGCTAGAAAGTACTGTTAACCAGGGGCTCAGTGAA GCTATGAATGAATTAGATGCTGTTC |
| 904 | NDC80 | 3776166 | TAGTTGTGCAAACCACGACTGAAGAAAGACGAAAAGT GGGAAATAACTTGCAACGTCTGTTAGAGATGGTTGCTA CACATGTTG |
| 905 | NDC80 | 3776167 | CTGGGGTGAAGCAGCCGCATGCTAAGGAACACCAAGG ACTGCCAGGAGCCGCCAGCAACTGGGGAGAGACGAAG AAGGATTCTTCCCTAGAGCCTTCAGAGAGACCATGGCC CTGCTGACGTCTTGATTTCAAACTTCCGGCCTCCAGAGC TGAAAGAGTACATTTCTGTTGTTTTAAGCCACCTAGTTT GTGGCAATTTGTTACAGTATCAGTATTTGAAATCGCAA AAAAATCAACAAAAACAACAAGAAAAAATAATGTGGC ATGTTAGTTTCCCA |
| 906 | NDC80 | 3776168 | AACATCTTGAGGAGCAGATTGCTAAAGTTGATAGAGAA TATGAAGAATGCATGTCAGAAGATCTCTCGGAAAATAT TAAAGAGATTAGAGATAAGTATGAGAAGAAAGCTACTC TAATTAAGTCTTCTGAAG |
| 907 | NDC80 | 3776169 | TATATCCATAGTGAATAAAATTGTCTCAGTAAA |
| 908 | SLC39A6 | 3804200 | CAAAATGTTCGTGCGGGTATATACCAGATGAGTACAGT GAGTAGTTTTATGTATCACCAGACTGGGTTATTGCCAAG TTATATATCACCAAAAGCTGTATGACTGGATGTTCTGGT TACCTGGTTTACAAAATTATCAGAGTAGTAAAACTTTG ATATATATGAGGATATTAAAACTACACTAAGTATCATTT GATTCGATTCAGAAAGTACTTTGATATCTCTCAGTGCTT |

TABLE 8-continued

Subtyping Target Sequences

| SEQ ID NO. | Gene | Affy Probeset ID | Sequence |
|---|---|---|---|
| | | | CAGTGCTATCATTGTGAGCAATTGTCTTTTATATACGGT ACTGTAGCCATACTAGGCCTGTCTGTGGCATT |
| 909 | SLC39A6 | 3804201 | AGAACTGCTGGTGTTTAGGAATAAGAAT |
| 910 | SLC39A6 | 3804202 | AGTTTCAGTAGGTCATAGGGAGATGAGTTTGTATGCTG TACTATGCAGCGTTTAAAGTTAGTGGGTTTTGTGATTTT TGTATTGAATATTGCTGTCTGTTACAAAGTCAGTTAAAG GTACGTTTTAATATTTAAGTTATTCTATCTTGGAGATAA AATCTGTATGTGCAATTCACCGGTATTA |
| 911 | SLC39A6 | 3804203 | AGAATGCTGGGATGCTTTTGGGTTTTGGAATTATGTTAC TTATTTCCATATTTGAACATAAAATCGTGTTTCGTATAA ATTTCTAG |
| 912 | SLC39A6 | 3804204 | ATGCTGCACAATGATGCTAGTGACCATGGATGTAGCCG CTGG |
| 913 | SLC39A6 | 3804206 | GCATGACCGTTAAGCAGGCTGTCCTTTATAATGCATTGT CAGCCATGCTGGCGTATCTTGGAATGGCAACAGGAATT TTCATTGGTCATTATGCTGAAAATGTTTCTATGTGGATA TTTGCACTTACTGCTGGCTTATTCATGTATGTTGCTCTG GTTGATATG |
| 914 | SLC39A6 | 3804207 | GTTGCTGTGTTCTGTCATGAGTTGCCTCATGAATT |
| 915 | SLC39A6 | 3804208 | GAGCTGAAAGATGCCGGCGTCGCCACTCTGGCCTGGAT GGTGATAATGGGTGATGGCCTGCACAATTTCAGCGATG GCCTAGCAATTG |
| 916 | SLC39A6 | 3804209 | ACCATCATATTCTCCATCATCACCACCACCAAAACCACC ATCCTCACAGTCACAGCCAGCGCTACTCTCGGGAG |
| 917 | SLC39A6 | 3804210 | CCACAGGAAGTCTACAATGAATATGTACCCAGAGGGTG CAAGAATAAATGCCATTCACATTTCCACGATACACTCG GCCAGTCAGACGATCTCATTCACCA |
| 918 | SLC39A6 | 3804212 | TGATGTGGAGATTAAGAAGCAGTTGTCCAAGTATGAAT CTCAACTTTCAACAAATGAGGAGA |
| 919 | SLC39A6 | 3804213 | TGCCTATTTTGATTCCACGTGGAAGGGTCTAACAGCTCT AGGAGGCCTGTATTTCATGTTTCTTGTTGAACATGTCCT CACATTGATCAAACAATTTA |
| 920 | SLC39A6 | 3804214 | TCAGTCATCTGTCTTCTCAAAACATA |
| 921 | SLC39A6 | 3804217 | GTTTTATAGCCATTTCCATCATCAGTTTCCTGTCTCTGCT GGGGGTTATCTTAGTGCCTCTCATGAATCGGGTGTTTTT CAAATTTCTCCTGAGTTTCCTTGTGGCACTGGCCGTTGG GACTTTGAGTGGTGATGCTT |
| 922 | SLC39A6 | 3804218 | GAATGCAACAGAGTTCAACTATCTCTGTCCAGCCATCA TCAACCAAATTGATGCTAGATCTTGTCTGATTCATACAA GTGAAAAGAAGGCTGAAATCCCTCCAAAGACCTATTCA TTACA |
| 923 | SLC39A6 | 3804219 | GCATCAAAGCTACTGACATCTCATGGC |
| 924 | SLC39A6 | 3804221 | TGAGCCGGCTGGCTGGTAGGAAAACAAATGAATCTGTG AGTGAGCCCCGAAAAGGCTTTATGT |
| 925 | SLC39A6 | 3804222 | ACTCAGATAGTTCAGGTAAAGATCCTAGAAACAGCCAG GGGAAAGGAGCTCACCGACCAGAACATGCCAGTGGTA GAAGGAATGTCAAGGACAGTGTTAGTGCTAGTGAAGTG ACCTCAACTGTGTACAACACTGTCTCTGAAGGAACTCA CTTTCTAGAGACAATAGAGACTCCAAGACCTGGAAAAC TCTTCCCCAAAGATGTAAGCAGCTCCACTCCACCCAGT GTCACATCAAAGAGCCGG |
| 926 | SLC39A6 | 3804223 | CGCAATGGCGAGGAAGTTATCTGTAATCTTGATCCTGA CCTTTGCCCTCTCTGTCACAAATCCCCTTCATGAACTAA AAGCAGCTGCTTTCCCCCAGACCACTGAGAAAATTAGT |

TABLE 8-continued

| Subtyping Target Sequences | | | |
|---|---|---|---|
| SEQ ID NO. | Gene | Affy Probeset ID | Sequence |
| | | | CCGAATTGGGAATCTGGCATTAATGTTGACTTGGCAATT TCCACACGGCAATATCATCTACAACAGCTTTTCTACCGC TATGGAGA |
| 927 | SLC39A6 | 3804226 | TGTGGAACCAAACCTGCGCGCGTGGCCGGGCCGTGGGA CAACGAGGCCGCGGAGAC |
| 928 | SLC39A6 | 3804227 | AGATTTCTCGAAGACACCAGTGGGCCCG |
| 929 | SLC39A6 | 3804228 | CTGCGCGCGGCGGTAATTAGTGATTGTCTTCCAGCTTCG CGAAGGCTAGGGGCGCGGCTGCCGGGTGGCTGCGCGGC GCTGCCCCCGGACCGAGGGGCAGCCAACCCAATGAAAC CACCGCGTGTTCGCGCCTG |
| 930 | BCL2 | 3811353 | TGAAGAAAAATAAAGTACAGTGTGAG |
| 931 | BCL2 | 3811354 | TGTATTGAAAGCTTTTGTTATCAAGATTTTCATACTTTT ACCTTCCATGGCTCTTTTTAAGATTGATACTTTTAAGAG GTGGCTGATATTCTGCAACACTGTACACATAAAAAATA CGGTAAGGATACTTTACATGGTTAAGGTAAAGTAAGTC TCCAGTTGGCCACCATTAGCTATAATGGCACTTTGTTTG TGTTGTTGGAAAAAGTCACATTGCCATTAAACTTTCCTT GTCTGTC |
| 932 | BCL2 | 3811355 | CTGTAGTGTAGATACTGAGTAAATCCATGCACCTAAAC CTTTTGGAAAATCTGCCGTGGGCCCTCCAGATAGCTCAT TTCATTAAGTTTTTCCCTCCAAGGTAGAATTTGCA |
| 933 | BCL2 | 3811356 | GGAGGATGGAAAGGCTCGCTCAATCAAGAAAATTC |
| 934 | BCL2 | 3811357 | GACCTTGGACAATCATGAAATATGCATCTCACTGGATG CAAAGAAAATCAGATGGAGCATGAATGGTACTGTACCG GTTCATCTGGACTGCCCCAGAAAAATAACTTCAAGCAA ACATCCTATCAACAACAAGGTTGTTCTGCATACCAAGC TGAG |
| 935 | BCL2 | 3811358 | CCTGTGCTGCTATCCTGCCAAAATCATTTTAATGGAGTC AGTTTGCAGTATGCTCCACGTGGTAAGATCCTCCAAGCT GCTTTAGAAGTAACAATGAAGAACGTGGACGTTTTTAA TATAAAGCCTGTTTTGTCTTTTGTTGTTGTTCAAACGGG ATTCACAGAGTATTTGAAAAATGTATATATATTAAGAG GTCACGGGGGCTAATTGCTGGCTGGCTGCCTTTTGCTGT GGGGTTTTGTTACCTGGTTTTAATAACAGTAAATGTGCC CAGCCTCTTGGCCCCAGAACTGTACAGTATTGTGGCTGC ACTTGCTCTAAGAGTAGTTGATGTTGCATTTTCCTTATT GTTAAAAACATGTTAGAAGCAATGAATGTATATAAAAG CCTCAACTAGTCATTTTTTTCTCCTCTTCTTTTTTTTCATT ATATCTAATTATTTTGCAGTTGGGCAACAGAGAACCAT CCCTATTTTGTATTGAAGAGGGATTCACATCTGCATCTT AACTGCTCTTTATGAATGAAAAAACAGTCCTCTGTATGT ACTCCTCTTTACACTGGCCAGGGTCAGAGTTAAATAGA GTATATGCACTTTCCAAATTGGGGACAAGGGCTCTAAA AAAAGCCCCAAAAGGAGAAGAACATCTGAGAACCTCC TCGGCCCTCCCAGTCCCTCGCTGCACAAATACTCCGCAA GAGAGGCCAGAATGACAGCTGACAGGGTCTATGGCCAT CGGGTCGTCTCCGAAGATTTGGCAGGGGCAGAAAACTC TGGCAGGCTTAAGATTTGGAATAAAGTCACAGAATTAA GGAAGCACCTCAATTTAGTTCAAACAAGACGCCAACAT TCTCTCCACAGCTCACTTACCTCTCTGTGTTCAGATGTG GCCTTCCATTTATATGTGATCTTTGTTTTATTAGTAAATG CTTATCATCTAAAGATGTAGCTCTGGCCCAGTGGGAAA AATTAGGAAGTGATTATAAATCGAGAGGAGTTATAATA ATCAAGATTAAATGTAAATAATCAGGGCAATCCCAACA CATGTCTAGCTTTCACCTCCAGGATCTATTGAGTGAACA GAATTGCAAATAGTCTCTATTTGTAATTGAACTTATCCT AAAACAAATAGTTTATAAATGTGAACTTAAACTCTAAT TAATTCCAACTGTACTTTTAAGGCAGTGGCTGTTTTTAG ACTTTCTTATCACTTATAGTTAGTAATGTACACCTACTC TATCAGAGAAAAACAGGAAAGGCTCGAAATACAAGCC ATTCTAAGGAAATTAGGGAGTCAGTTGAAATTCTATTCT GATCTTATTCTGTGGTGTCTTTTGCAGCCCAGACAAATG TGGTTACACACTTTTTAAGAAATACAATTCTACATTGTC AAGCTTATGAAGGTTCCAATCAGATCTTTATTGTTATTC AATTTGGATCTTTCAGGGATTTTTTTTTTAAATTATTATG |

TABLE 8-continued

Subtyping Target Sequences

| SEQ ID NO. | Gene | Affy Probeset ID | Sequence |
|---|---|---|---|
| | | | GGACAAAGGACATTTGTTGGAGGGGTGGGAGGGAGGA AGAATTTTTAAATGTAAAACATTCCCAAGTTTGGATCA GGGAGTTGGAAGTTTTCAGAATAACCAGAACTAAGGGT ATGAAGGACCTGTATTGGGGTCGATGTGATGCCTCTGC GAAGAACCTTGTGTGACAAATGAGAAACATTTTGAAGT TTGTGGTACGACCTTTAGATTCCAGAGACATCAGCATG GCTCAAAGTGCAGCTCCGTTTGGCAGTGCAATGGTATA AATTTCAAGCTGGATATGTCTAATGGGTATTTAAACAAT AAATGTGCAGTTTTAACTAACAGGATATTTAATGACAA CCTTCTGGTTGGTAGGGACATC |
| 936 | BCL2 | 3811359 | CGTCCCTGGGCAATTCCGCATTTAATTCATGGTATTCAG GATTACATGCATGTTTGGTTAAACCCATGAGATTCATTC AGTTAAAAATCCAGATGGCAAATGACCAGCAGATTCAA ATCTATGGTGGTTTGACCTTTAGAGAGTTGCTTTACGTG GCCTGTTTCAACACAGACCCACCCAGAGCCCTCCTGCC CTCCTTCCGCGGGGGCTTTCTCATGGCTGTCCTTCAGGG TCTTCCTGAAATGCAGTGGTGCTTACGCTCCACCAAGA AAGC |
| 937 | BCL2 | 3811360 | TAGGCCCGTTTTCACGTGGAGCATGGGAGCCACGACCC TTCTTAAGACATGTATCACTGTAGAGGGAAGGAACAGA GGCCCTGGGCCCTTCCTATCAGAAGGACATGGTGAAGG CTGGGAACGTGAGGAGAGGCAATGGCCACGGCCCATTT TGGCTGTAGCACATGGCACGTTGGCTGTGTGGCCTTGG CCCACCTGTGAGTTTAAAGCAAGGCTTTAAATGACTTTG GAGAGGGTCACAAATCCTAAAAGAAGCATTGAAGTGA GGTGTCATGGATTAATTGACCCCTGTCTATGGAATTACA TGTAAAACATTATCTTGTCACTGTAGTTTGGTTTTATTT GAAAACCTGACAAAAAAAAAGTTCCAGGTGTGGAATAT GGGGGTTATCTGTACATCCTGGGGCATT |
| 938 | BCL2 | 3811361 | CAACAGGGCAGTGTGGTCTCCGAATGTCTGGAAGCTGA T |
| 939 | BCL2 | 3811362 | CACCTGGATGTTCTGTGCCTGTAAACATAGATTCGCTTT CCATGTTGTTGGCCGGATCACCATCTGAAGAGCAGACG GATGGAAAAAGGACCTGATCATTGGGGAAGCTGGCTTT CTGGCTGCTGGAGGCTGGGGAGAAGGTGTTCATTCACT TGCATTTCTTTGCCCTGGGGGCTGTGATATTAACAGAGG GAGGGTTCCTGTGGGGGGAAGTCCATGCCTCCCTGGCC TGAAGAAGAGACTCTTTGCATATGACTCACATGATGCA TACCTGGTGGGAGGAAAAGAGTTGGGAACTTCAGATGG ACCTAGTACCCACTGAGATTTCCACGCCGAAGGACAGC GATGGGAAAAATGCCCTTAAATCATAGGAAAGTATTTT TTTAAGCTACCAATTGTGCCGAGAAAAGCATTTTAGCA ATTTATACAATATCATCCAGTACCTTAAGCCCTGATTGT GTATATTCATATATTTTGGATACGCACCCCCCAACTCCC AATACTGGCTCTGTCTGAGTAAGAAACAGAATCCTCTG GAACTTGAGGAAGTGAACATTTCGGTGACTTCCGCATC AGGAAGGCTAGAGTTACCCAGAGCATCAGGCCGCCACA AGTGCCTGCTTTTAGGAGACCGAAGTC |
| 940 | BCL2 | 3811363 | GTGGGAGCTTGCATCACCCTGGGTGCCTATCTGGGCCA CAA |
| 941 | BCL2 | 3811364 | TGTGGAACTGTACGGCCCCAGCATGCGGCCTCTGTTTG ATTTCTCCTGGCTGTCTCTGAAGACTCTGCTCAGTTTGG CCCT |
| 942 | BCL2 | 3811433 | GCAATACCATTCTCATGCCAGTGTACAAATTACATGAA AGAGCATCATTTTTCTAGTGTCTGAGGATTGGCTGCTTA TGGCCAATTTTGGCAGCAAGACGATAGGATTAAAAATA GCTTGAAGATGATCTAGTCTTAAATAATATATTTCATGA TGAACTTTCCTTGGGAAAGTGCATCTTTCTGCCTACAAG AATCACATGACCCCTTTCAATAATTTATGTAGTAGAGA AAAACACACTATTTCTCATAGAGTTTTCAGTCATGTGCT GTGGTGTGATTGTTTCTGGACATTCATAAAATTTTATAG TTAACTGAATTCTCTTTTCTGTTTTGTTGCTATTTAACGT CCATTGAAAACATGGCTTTCTTTTGCGCATTCTGTTACT TTCAGCTGTACTTTCTAATAAGAATGGATTGCCCTTTTT AGCAATCTTTGATTGAACTGGTACATTTCAGATTACTTA AATGTCATCAGGCCACACAGCATACCAGG |

TABLE 8-continued

Subtyping Target Sequences

| SEQ ID NO. | Gene | Affy Probeset ID | Sequence |
|---|---|---|---|
| 943 | BCL2 | 3811441 | ACTTCGCCGAGATGTCCAGCCAGCTGCACCTGACGCCC TTCACCGCGCGGGGACGCTTTGCCACGGTGGTGGAGGA GCTCTTCAGGGACGGGGTGAACTGGGGGAGGATTGTGG CCTTCTTTGAGTTCGGTGGGGTCATGTGTGTGGAGAGCG TCAACCGGGAGATGTCGCCCCTGGTGGACAACATCGCC CTGTGGATGACTGAGTACC |
| 944 | BCL2 | 3811442 | GCCACCTGTGGTCCACCTGACCCTC |
| 945 | BCL2 | 3811443 | CCCGCACCGGGCATCTTCTCCTCCCAGCCCGGGCACAC GCCCCATCCAGCCGCATCCCGGGACCCGGTCGCCAGGA CCTCGCCGCT |
| 946 | BCL2 | 3811444 | GTACGATAACCGGGAGATAGTGATGAAGTACATCCATT ATAAGCTGTCGCAGAGGGGCTACGA |
| 947 | BCL2 | 3811445 | CACAGAGGAAGTAGACTGATATTAACAATACTTACTAA TAATAACGTGCCTCATGAAATAAAGATCCGAAAGGAAT TGGAATAAAAATTTCCTGCATCTCATGCCAAGGGGGAA ACACCAGAATCAAGTGTTCCGCGTGATTGAAGACACCC CCTCGTCCAAGAATGCAAAGCACATCCAATAAAATAGC TGGATTATAACTCCTCTTCTTT |
| 948 | BCL2 | 3811446 | TGTAACTTTCAATGGAAACCTTTGAGATTTTTTACTTAA AGTGCATTCGAGTAAATTTAATTTCCAGGCAGCTTAATA CATTCTTTTTAGCCGTGTTACTTGTAGTGTGTATGCCCT GCTTTCACTCAGTGTGTACAGGGAAACGCACCTGATT |
| 949 | BCL2 | 3811447 | GGCGCGTCCTGCCTTCATTTATCCAGCAGCTTTTCGGAA AATGCATTTGCTGTTCGGAGTTTAATCAGAAGAGGATT CCTGCCTCCGTCCCCGGCTCCTTCATCGTCCCCTCTCCC CTGTCTCTCTCCTGGGGAGGCGTGAAGCGGTCCCGTGG ATAGAGATTCATGCCTGTGCCCGCGCGTGTGTGCGCGC GTGTAAATTGCCGAGAAGGGGAAAACATCACAGGACTT CTGCGAATACCGGACTGAAAATTGTAATTCATCTGCCG CCGCCGCTGCCTTTTTTTTTTCTCGAGCTCTTGAGATCTC CGGTTGGGATTCCTGCGGATTGACATTTCTGTGAAGCA GAAGTCTGGGAATCGATCTGGAAATCCTCCTAATTTTTA CTCCCTCTCCCCGCGACTCCTGATTCATTGGGAA |
| 950 | BCL2 | 3811448 | GGAGGCGGCCGTAGCCAGCGCCGCCGC |
| 951 | BCL2 | 3811449 | TGCCGGGGCTCCGGGCCCTCCCTGCCGGCGGCCGTCAG |
| 952 | BCL2 | 3811450 | CCGCCGCTCTCCGTGGCCCCGCCGCGCTGCC |
| 953 | CCNE1 | 3828126 | TTTTAAATGTCCCGCTCTGAGCCGG |
| 954 | CCNE1 | 3828128 | GACGGCGGCGCGGAGTTCTCGGCTCGCTCCAGGAAGAG G |
| 955 | CCNE1 | 3828129 | GAAATGGCCAAAATCGACAGGACGGCGAGGGACCAGT GTGGGAGCC |
| 956 | CCNE1 | 3828130 | TCTAATGCAGCCACAGCCCATATGGCCCAGCACTGTAC CTGTCAGTGGGCACTGGCCTCTGCCAGTCCTGGGATTCC AGGAAGCTTGGTGTTCCTGACTGGCACCGTCTGAGATT ACAGATATGTGCCTAGCCTGGAAGA |
| 957 | CCNE1 | 3828131 | AGAAGATGATGACCGGGTTTACCCAAACTCAACGTGCA AGCCTCGGATTATTGCACCATCCAGAGGCT |
| 958 | CCNE1 | 3828132 | AAAGACATACTTAAGGGATCAGCACTTTCTTGAGCAAC ACCCTCTTCTGCAGCCAAAAAATGCGAGCAATTCTTCTGG ATTGGT |
| 959 | CCNE1 | 3828133 | GGGAGACCTTTTACTTGGCACAAGATTTCTTTGACCGGT ATATGGCGACACAAGAAAATGTTGTAAAAACTCTTTTA CAGCTTATTGGGATTTCATCTTTAT |
| 960 | CCNE1 | 3828134 | GAAATCTATCCTCCAAAGTTGCACCAGTTTGCGTATGTG ACAGATGGAGCTTGTTCAGGAGATGAAATTCTCACCAT GGAATT |

TABLE 8-continued

Subtyping Target Sequences

| SEQ ID NO. | Gene | Affy Probeset ID | Sequence |
|---|---|---|---|
| 961 | CCNE1 | 3828135 | TGGCGTTTAAGTCCCCTGACTATTGTGTCCTGGCTGAATGTATACATGCAGGTTGCATATCTAAATGACTTACATGAAGTGCTACTGCCGCAGTATCCC |
| 962 | CCNE1 | 3828136 | CTGGATGTTGACTGCCTTGAATTTCCTTATGGTATACTTGCTGCTTCGGCCTTGTATCATTTCTCGTCATCTGAATTGATGCAAAAGG |
| 963 | CCNE1 | 3828137 | CTGTGTCAAGTGGATGGTTCCATTTGCCATGGTTATAAGGGAGACGGGGAGCTCAAAACTGAAGCACTTCAGGGGCGTCGCTGATGAAGATGCACACAACATA |
| 964 | CCNE1 | 3828138 | GACAAAGCCCGAGCAAAGAAAGCCATGTTGTCTGAACAAAATAGGGCTTCTCCTC |
| 965 | CCNE1 | 3828139 | GTAAGAAGCAGAGCAGCGGGCCGGAAATGGCGTGA |
| 966 | CCNE1 | 3828140 | GCGTGCGTTTGCTTTTACAGATATCTGAATGGAAGAGTGTTTCTTCCACAACAGAAGTATTTCTGTGGATGGCATCAAACAGGGCAAAGTGTTTTTTATTGAATGCTTATAGGTTTTTTTTAAATAAGTGGGTCAAGTACACCAGCCACCTCCAGACACCAGTGCGTGCTCCCGATGCTGCTATGGAAGGTGCTACTTGACCTAAGGGACTCCCA |
| 967 | CCNE1 | 3828141 | TGGGCTCCGTTGTACCAAGTGGAGCAGGTGGTTGCGGGCAAGCGTTGTGCAGAGCCCATAGCCAGCTGGGCAGGGGGCTGCCCTCTCCACATTATCAGTTGACAGTGTACAATGCCTTTGATGAACTGTT |
| 968 | CCNE1 | 3828142 | GTAAGTGCTGCTATATCTATCCATTTTTTAATAAAG |
| 969 | MIA | 3833795 | TCTAGGTGGTGTGGGCGAAGTTTGGGACTGGTTTAGGGCGGGGACAAGACCAAGAACACAAGTTTCCTTGTACTACGGGAGAGAGGGA |
| 970 | MIA | 3833796 | GGTCCCTGGTGTGCCTTGGTGTCATCATCTTGCTGTCTG |
| 971 | MIA | 3833798 | TTCAGGACTACATGGCCCCCGACTGCCGATTCCTGACCATTCACCGGGGCCAAGTGGT |
| 972 | MIA | 3833799 | GCCGTGGGCGGCTCTTCTGGGGAGG |
| 973 | MIA | 3833800 | CATTTAAGCTGAGATTCATATGACAAGGATGGAGCAGTTATGTGGAGATCAGGGAGAAGGGAGAATGCAAAGGCCTTCAGCAGGCACAAGCTTGCCATCTTCCCAGACCCTAGCTTTTAACTCCTCTTCCCCAG |
| 974 | MIA | 3833801 | GTTCAGGGAGATTACTATGGAGATCTGGCTGCTCGCCTGGGCTATTTCCCCAGTAGCATTGTCCGAGAGGACCAGACCC |
| 975 | MYBL2 | 3886226 | AAAGTGCTTCAACCCGCGCCGGCGGCGACTGCAGTTCCTGCGAGCGAGGAGCGCGGGACCTGCTGACACGCTGACGCCTTCGAGCGCGGCCC |
| 976 | MYBL2 | 3886229 | GCTGCACTACCAGGACACAGATTCAGATGTGCCGGAGCAGAGGGATAGCAAGTGCAAGGTCAAATGGACCCATGAGGA |
| 977 | MYBL2 | 3886231 | CCCTGGTGAGGCAGTTTGGACAGCAGGACTGGAAGTTCCTGGCCAGCCACTTCC |
| 978 | MYBL2 | 3886232 | TCCAGACCTTGTCAAGGGGCCATGGACCAAAGAGGA |
| 979 | MYBL2 | 3886235 | TGATTGCCAAGCACCTGAAGGGCCGGCTGGGGAAGCAGTGCCGTGAACGCTGGCACAACCACCTCAACCCTGAGGTGAAGAAGTCTTGCTGGACCGAGGAGGAGGACCGCATCATCTGCGAGGCCCACAAGGTGCTGGGCAACCGCTGGGCCGAGATCGCCAAGATGTTGCCAGGG |
| 980 | MYBL2 | 3886237 | ACACAGGAGGCTTCTTGAGCGAGTCCAAAGACTGCAAGCCCC |

TABLE 8-continued

Subtyping Target Sequences

| SEQ ID NO. | Gene | Affy Probeset ID | Sequence |
|---|---|---|---|
| 981 | MYBL2 | 3886238 | GCAGCCACCACATCGAAGGAACAGGAGCCCATCGGTAC AGATCTGGACGCAGTGCGAACACCAGAGCCCTTGGAGG AATTCCCGAAGCGTGAGGACCAGGAAGGCTCCCCACCA GAAACGAGCCTGCCTTACAAGTGGGTGGTGGAGGCAGC TAACCTCCTCATCCCTGCTGTGGGTTCTAGCCTCTCTGA AGC |
| 982 | MYBL2 | 3886239 | CTGATGCTTGGTGTGACCTGAGTAAATTTGACCTCCCTG AGGA |
| 983 | MYBL2 | 3886240 | GTATCAACAACAGCCTAGTGCAGCTGCAAGCGTCACAT CAGCAGCAAGTCCT |
| 984 | MYBL2 | 3886241 | CAGTGTGACCGAGTACCGCCTGGATGGCCACACCATCT CAGACCTGAGCCGGAGCAGCCGGGGCGAGCTGATCCCC ATCTCCCCCAGCACTGAAGTCGGGGGCTCTGGCATTGG CACACCGCCCTCTGTGCTCAAGCGGCAGAGGAAGAGGC GTGTGGCTCTGTCCCCTGTCACTGAGAATAGCACCAGTC TGTCCTTCCTGGATTCCTGTAACAGCCTCACGCCCAAGA GCA |
| 985 | MYBL2 | 3886242 | TTTCTGAACTTCTGGAACAAACAGGACACATTGGAGCT GGAGAGCCCCTCGCTGACATCCACCCCAGTGTGCAGCC AGAAGGTGGTGGTCACCACACCACTGCA |
| 986 | MYBL2 | 3886245 | CTCCATGGACAACACTCCCCACACGCCAACCCCGTTCA AGAACGCCCTGGAGAAGTACGGACCCCTGAAGCC |
| 987 | MYBL2 | 3886248 | ACTTGAAGGAGGTGCTGCGTTCTGAGGCTGGCATCGAA CTCATCATCGAGGACGACATCAGGCCCGAGAAGC |
| 988 | MYBL2 | 3886250 | CCGACAACTGCCCCTTCAAACTCTTCCAG |
| 989 | MYBL2 | 3886251 | CCTCACCCTGTCAGGTATCAAAGAAGACAAC |
| 990 | MYBL2 | 3886252 | CTTGCTCAACCAGGGCTTCTTGCAGGCCAAGCCCGAGA AGGCAGCAGTGGCCCAGAAGCCCCGAAGCCACTTCACG ACACCTGCCC |
| 991 | MYBL2 | 3886254 | CAGCCACACATCTCGGACCCTCATCTTGTCCTGA |
| 992 | MYBL2 | 3886255 | GTGTCACGAGCCCATTCTCATGTTTACAGGGGTTGTGGG GGCAGAGGGGGTCTGTGAATCTGAGAGTCATTCAGGTG ACCTCCTGCAGGGAGCCTTCTGCCACCAGCCCCTCCCCA GACTCTCAGGTGGAGGCAACAGGGCCATGTGCTGCCCT GTTGCCGAGCCCAGCTGTGGGCGGCTCCTGGTGCTAAC AACAAAGTTCCACTTCCAGGTCTGCCTGGTTCCCTCCCC AAGGCCACAGGGAGCTCCGTCAGCTTCTCCCAAG |
| 993 | UBE2C | 3887050 | GTCCTGCAGTTGCAGTCGTGTTCTCCGAGTTCCTGTCTC TCTGCCAACGCCGCC |
| 994 | UBE2C | 3887051 | TGGCTTCCCAAAACCGCGACCCAGCCGCCACTAGCGTC GCCGCCGCCCGTAAAGGAGCTGAGCCGA |
| 995 | UBE2C | 3887054 | GAGCTCAGACCGCTCTTTGAGACTCTCCCGAAGGAGAA TGGGAGGGTAGGGGCGCTGCCAGACTCCTTCCCTGGTG GGCCTAGATGAAGACGCTCAAGGACCCTCGTGACTTGG CCGAGACAGGGGAAGGGAGAAGTTGAGTCGGGCAAGG AAGAGATGCTAAAGCCTGGGGAATTAAGAACATGCCA GAATCATCCCGAGGGAGTCTGGAATTAGGGAGGGTGAG GACTCGCTAGGATCGTCCTGTGGATC |
| 996 | UBE2C | 3887059 | ATGTCTGGCGATAAAGGGATTTCTGCCTTCCCTGAATCA GACAACCTTTTCA |
| 997 | UBE2C | 3887061 | CAGTTTGTCTACTGTCCGGTCCCAG |
| 998 | UBE2C | 3887062 | ACTCAAGATTCTAGCAAGCCCCTTGTGTGGGGCT |
| 999 | UBE2C | 3887063 | GGTATAAGCTCTCGCTAGAGTTCCCCAGTGGCTACCCTT ACAATGCGCCCACAGTGAAGTTCCTCACGCCCTGCTAT CACCCCAACGTGGA |

TABLE 8-continued

Subtyping Target Sequences

| SEQ ID NO. | Gene | Affy Probeset ID | Sequence |
|---|---|---|---|
| 1000 | UBE2C | 3887066 | ACACACATGCTGCCGAGCTCTGGAAAAACCCCA |
| 1001 | UBE2C | 3887067 | GTACCTGCAAGAAACCTACTCAAAGCAGGTCACCAGCC AGGAG |
| 1002 | UBE2C | 3887068 | GTGATTTCTGTATAGGACTCTTTATCTTGAGCTGTG |
| 1003 | MMP11 | 3939471 | GGCCTTTACGCGACATCCGAGCAGCGTGTCTATCCCAA AGGCCTAGGAGCATTTGCCCGGCTCGGTCAAATCTAGC GCAAGTTTGAAGCCTGCGGCCTCGCAATTTTAGCAGCTT C |
| 1004 | MMP11 | 3939472 | GTGGAGTCTTCTTGAATAAGCTGTGAAACATTTCCCCAC CCGCTTCCCTTTCTTGGCCCAGGCTTCCTGACCACAGCC TCACCTTTGAGCAGCTCAGAGCCCTGCCTGCCAGGATG CGAGCCACTGCCTGGATCGTGGCTCTGCAG |
| 1005 | MMP11 | 3939473 | GGCCCGGAGCGGCCCAGCAAGCCCAGCAGCCC |
| 1006 | MMP11 | 3939474 | GGCTCCGGCCGCCTGGCTCCGCAGCGCGGCCGCGCGCG CCCTCCTGCCCCCGA |
| 1007 | MMP11 | 3939475 | CATGCAGCCCTGCCCAGTAGCCCGGCACCTGCC |
| 1008 | MMP11 | 3939476 | GAAGCCCCCCGGCCTGCCAGCAGCCTCAG |
| 1009 | MMP11 | 3939477 | CTGTGGCGTGCCCGACCCATCTGATGGGCTGAGTGCCC GCAACCGACAGAAGAG |
| 1010 | MMP11 | 3939478 | GCGCTGGGAGAAGACGGACCTCACCTACAG |
| 1011 | MMP11 | 3939479 | CAGGGAGGTCATCTATGGGCAAACCCCCCTGAAACCCCA ACTTAGACACATACACATATGGAGACCCTCCCTCAGCA GAGGGGCAGAGCCTCCGTCATCATGCAAAGAGTCGCAG CACATGCCTGCGGACGGGTGTTCAGTCACTCAGGCAGC CTTTACAAGAGACCTGTGAGGACCAGGCTCTGGGACTC CACGGTGAATGAGGCAGACACAGCCCCATCCTCTGTGT CAGTCTGAGGTGGGTGTCAGCCATGTCATTGTCCAACTC TACCATCACAACTTGGGCTTCGAGCAGGTGGAGACAGT GGTAAGCGGGGAGAGGCAATAGTGGGCATCTCACTGG GTGACCTGGGAGGACCCTGGGCAGGTGATGGGGAAGCT GAGGCTCACACATCCTGCGGGTGGGGACCCAGCCTGAA GAATGGGCTGGTGTCACACAGCATTGGAGCTGAGACTG GGGTCTTTAGAATTTCCTAGGTGGGGGCCTGGGAACCA ACAGGGGCTCAAGGAACCAAGGTGTCCCCACAGTAAGT GGCACTGTCAGGTCTAGGATGGGGGTCTCGGGACCCCT GGTCCTGGTTCTTTCCACTGAATTC |
| 1012 | MMP11 | 3939480 | TTCGGTTCCCATGGCAGTTGGTGCAGGAGCAGGTGCGG CAGACGATGGCAGAGGCCCTAAAGGTATGGAGCGATGT GACGCCACTCACCTTTACTGAGGTGCACGAGGGCCGTG CTGACATCATGATCGACTTCGCCA |
| 1013 | MMP11 | 3939481 | GGACGACCTGCCGTTTGATGGGCCTGGGGGCATCCTGG CCCATGCCTTCTTCCCCAAGACTCACCGAGAAGGGGAT GTCCACTTCGACTATGATGA |
| 1014 | MMP11 | 3939482 | AGGTGGCAGCCCATGAATTTGGCCA |
| 1015 | MMP11 | 3939483 | TACACCTTTCGCTACCCACTGAGTCTCAGCCCAGATGAC TGCAGGGGCGTTCAACACCTATATGGCCAGCCCTGGCC CACTGTCACCTCCAGGACCCCAGCCCTGGGCCCCCAGG CTGGGATAGACACCAATGA |
| 1016 | MMP11 | 3939484 | ACTGTGACTGCAGCATATGCCCTCAGCATGTGTC |
| 1017 | MMP11 | 3939485 | CCGAGGCGAGCTCTTTTTCTTCAAAGCGGGCTTTGTGTG GCGCCTCCGTGGGGGCCAGCTGCAGCCCGGCTACCCAG CATTGGCCTCTCGCCACTGGCAGGGACTGCCCAGCCCT GTGGACGCTGCCTTCGAGGATGCCCAGGG |
| 1018 | MMP11 | 3939486 | GGAGCATTGCAGATGCCAGGGACTTCACAAATGAAGGC ACAGCATGGGAAACCTGCGTGGGTTCCAGGGCAG |

TABLE 8-continued

Subtyping Target Sequences

| SEQ ID NO. | Gene | Affy Probeset ID | Sequence |
|---|---|---|---|
| 1019 | MMP11 | 3939487 | TTTGTCACAGCCAAATGCCAGTGGAAGGAGCAGCCGCC CAGGCAGCCCTCTACTGATGAGAGTAACCTCACCCGTG CACTAGTTTACAGAGCATTCACTGCCCCAGCTTATCCCA GGCCTCCCGCTTCCCTCTGCGGGTGGGGTGCTGAGCAG GCATTATTGGCCTGCATGTTTTACTGA |
| 1020 | MMP11 | 3939488 | CTCAGTACTGGGTGTACGACGGTGAAAAGCCAGTCCTG GGCCCCGCACCCCTCACCGAGCTGGGCCTGGTGAGGTT CCCGGTCCATGCTGCCTTGGTCTGGGGTCCCGAGAAGA ACA |
| 1021 | MMP11 | 3939489 | AGCACCCGGCGTGTAGACAGTCCCGTGCCCCGCAGGGC CACTGACTGGAGAGGGGTGCCCTCTGAGATCGACGCTG CCTTCCAGGAT |
| 1022 | MMP11 | 3939491 | GCTATGCCTACTTCCTGCGCGGCCGCCTCTACTGGAAGT TTGACCCTGTGAAGGTG |
| 1023 | MMP11 | 3939492 | TCCTGACTTCTTTGGCTGTGCCGAGCCTGCCAACACTTT CC |
| 1024 | MMP11 | 3939493 | CTGCCAGGCCACGAATATCAGGCTAGAGACCCATGGCC ATCTTTGTGGCTGTGGGCACCAGGCATGGGACTGAGCC CATGTCTCCTCAGGGGGATGGGGTGGGGTACAACCACC ATGACAACTGCCGGGAGGGCCACGCAGGTCGTGGTCAC CTGCCAGCGACTGTCTCAGACTGGGCAGGGAGGCTTTG GCATGACTTAAGAGGA |
| 1025 | MMP11 | 3939494 | GAGTGTCCTTGCTGTATCCCTGTTGTGAGGTTCCTTCCA GGGGCTGGCACTGAAGCAAGGGTGCTGGGGCCCCATGG CCTTCAGCCCTGGCTGAGCAACTGGGCTGTAGGGCAGG GCC |
| 1026 | MMP11 | 3939495 | GCCTTCTGGCTGACAATCCTGGAAATCTGTTCTCCAGAA TCCAGGCCAAAAAGTTCACAGTCAAATGGGGAGGGGTA TTCTTCATGCAGGAGACCCCAGGCCCTGGAGGCTGCAA CATACCTCAATCCTGTCCCAGGCCGGATCCTCCTGAAGC CCTTTTCGCAGCACTG |
| 1027 | MDM2 | 3979479 | CTGATGGGTGTGCTAATTACACTGATTTAATCGATACCC ATTGTATGTGAAACAGTATATACACCATATTTACAATTA TGTATCAGTTTAACATTTAAAAAAACATTTCTAATATAA GTATCTCTCAAACTGTGGATTAACTTCTTGATTTATATT TAAATATGAATCTTGAGGAAAATAGTGAAAATAACCAT CTTGATTTAGTGTATTTCTCCCATATGTGAATTGTATAT AC |
| 1028 | RRM2 | 4006364 | AACGATGCCTTGTGTCAAGAAGAAGGCAGATTGGGCCT TGCGCTGGATTGGGGACAAAG |
| 1029 | RRM2 | 4006368 | AGCTGCAGCTCTCGCCGCTGAAGGGGC |

TABLE 9

| Gene Targets Gene |
|---|
| CDC20 |
| KIF2C |
| PHGDH |
| NUF2 |
| CENPF |
| EXO1 |
| UBE2T |
| RRM2 |
| MLPH |
| GPR160 |
| CCNB1 |
| CXXC5 |
| PTTG1 |

TABLE 9-continued

| Gene Targets Gene |
|---|
| FGFR4 |
| FOXC1 |
| ESR1 |
| ANLN |
| BLVRA |
| EGFR |
| ACTR3B |
| NAT1 |
| MYC |
| SFRP1 |
| MELK |
| BAG1 |
| CEP55 |

TABLE 9-continued

| Gene Targets Gene |
|---|
| MKI67 |
| TMEM45B |
| PGR |
| MDM2 |
| KRT5 |
| FOXA1 |
| ORC6 |
| CDH3 |
| ERBB2 |
| GRB7 |
| CDC6 |
| MAPT |
| BIRC5 |
| KRT14 |
| KRT17 |
| TYMS |
| NDC80 |
| SLC39A6 |
| BCL2 |
| CCNE1 |
| MIA |
| MYBL2 |
| UBE2C |
| MMP11 |

What is claimed is:

1. A method comprising:

a) providing a biological sample from a subject having prostate cancer;

b) extracting nucleic acids from the biological sample;

c) detecting the presence or expression level in the biological sample for targets CDC20, KIF2C, PHGDH, NUF2, CENPF, EXO1, UBE2T, RRM2, MLPH, GPR160, CCNB1, CXXC5, PTTG1, FGFR4, FOXC1, ESR1, ANLN, BLVRA, EGFR, ACTR3B, NAT1, MYC, SFRP1, MELK, BAG1, CEP55, MKI67, TMEM45B, PGR, MDM2, KRT5, FOXA1, ORC6, CDH3, ERBB2, GRB7, CDC6, MAPT, BIRC5, KRT14, KRT17, TYMS, NDC80, SLC39A6, BCL2, CCNE1, MIA, MYBL2, UBE2C, and MMP11;

d) subtyping the prostate cancer in the subject according to a genomic subtyping classifier based on the presence or expression levels of the plurality of targets, wherein said subtyping comprises assigning the prostate cancer to a luminal B subtype; and e) administering a treatment comprising androgen deprivation therapy to a subject who has the luminal B subtype.

2. A method comprising:

a) selecting a subject with prostate cancer having a luminal B subtype, wherein the subtype is determined according to a genomic subtyping classifier based on the presence or expression levels in a biological sample from the subject of targets CDC20, KIF2C, PHGDH, NUF2, CENPF, EXO1, UBE2T, RRM2, MLPH, GPR160, CCNB1, CXXC5, PTTG1, FGFR4, FOXC1, ESR1, ANLN, BLVRA, EGFR, ACTR3B, NAT1, MYC, SFRP1, MELK, BAG1, CEP55, MKI67, TMEM45B, PGR, MDM2, KRT5, FOXA1, ORC6, CDH3, ERBB2, GRB7, CDC6, MAPT, BIRC5, KRT14, KRT17, TYMS, NDC80, SLC39A6, BCL2, CCNE1, MIA, MYBL2, UBE2C, and MMP11; and b) treating the subject with a treatment comprising androgen deprivation therapy.

3. The method of claim 2, wherein the biological sample is a biopsy.

4. The method of claim 2, wherein the biological sample is a urine sample, a blood sample or a prostate tumor sample.

5. The method of claim 4, wherein the blood sample is plasma, serum, or whole blood.

6. The method of claim 2, wherein the subject is a human.

7. The method of claim 2, wherein the levels of expression are increased or reduced compared to a control.

8. The method of claim 2, wherein the levels of expression are obtained by a method comprising in situ hybridization, a PCR-based method, an array-based method, an immunohistochemical method, an RNA assay method, or an immunoassay method.

9. The method of claim 8, wherein the levels of expression are obtained by a method comprising using a reagent selected from the group consisting of a nucleic acid probe, one or more nucleic acid primers, and an antibody.

10. The method of claim 9, wherein the levels of expression are obtained by a method comprising measuring the level of an RNA transcript.

* * * * *

SEQUENCE LISTING

<160> NUMBER OF SEQ ID NOS: 1029

<210> SEQ ID NO 1
<211> LENGTH: 102
<212> TYPE: DNA
<213> ORGANISM: Homo sapiens

<400> SEQUENCE: 1
gggtgctagg ccggaagggg ctgcagccga gggtggccct gattttgtgg ccggccagga 60
gcgaaggggt ccctttctgt cccctgagca ccgtcgcctc ct 102

<210> SEQ ID NO 2
<211> LENGTH: 33
<212> TYPE: DNA
<213> ORGANISM: Homo sapiens

<400> SEQUENCE: 2
gcaccaactg caaggacccc tccccctgcg ggc 33

<210> SEQ ID NO 3
<211> LENGTH: 146
<212> TYPE: DNA
<213> ORGANISM: Homo sapiens

<400> SEQUENCE: 3
ttcgcgttcg agagtgacct gcactcgctg cttcagctgg atgcacccat ccccaatgca 60
ccccctgcgc gctggcagcg caaagccaag gaagccgcag gcccggcccc ctcacccatg 120
cgggccgcca accgatccca cagcgc 146

<210> SEQ ID NO 4
<211> LENGTH: 144
<212> TYPE: DNA
<213> ORGANISM: Homo sapiens

<400> SEQUENCE: 4
gcaaatccag ttccaaggtt cagaccactc ctagcaaacc tggcggtgac cgctatatcc 60
cccatcgcag tgctgcccag atggaggtgg ccagcttcct cctgagcaag gagaaccagc 120
ctgaaaacag ccagacgccc acca 144

<210> SEQ ID NO 5
<211> LENGTH: 55
<212> TYPE: DNA
<213> ORGANISM: Homo sapiens

<400> SEQUENCE: 5
gtagaggaag ccaagatcct tcggctcagt ggaaaaccac aaaatgcgcc agagg 55

<210> SEQ ID NO 6
<211> LENGTH: 25
<212> TYPE: DNA
<213> ORGANISM: Homo sapiens

<400> SEQUENCE: 6
cgaagttcct ggttcctgga gggag 25

<210> SEQ ID NO 7
<211> LENGTH: 28
<212> TYPE: DNA
<213> ORGANISM: Homo sapiens

<400> SEQUENCE: 7
cctcttccta tctaagattg agggcaag 28

<210> SEQ ID NO 8
<211> LENGTH: 30
<212> TYPE: DNA
<213> ORGANISM: Homo sapiens

<400> SEQUENCE: 8
cagaacagac tgaaagtact ctacagccaa 30

<210> SEQ ID NO 9
<211> LENGTH: 35
<212> TYPE: DNA
<213> ORGANISM: Homo sapiens

<400> SEQUENCE: 9
cctgccagac cgtatcctgg atgcgcctga aatcc 35

<210> SEQ ID NO 10
<211> LENGTH: 145
<212> TYPE: DNA
<213> ORGANISM: Homo sapiens

<400> SEQUENCE: 10
acctgaacct tgtggattgg agttctggga atgtactggc cgtggcactg gacaacagtg 60
tgtacctgtg gagtgcaagc tctggtgaca tcctgcagct tttgcaaatg gagcagcctg 120
gggaatatat atcctctgtg gcctg 145

<210> SEQ ID NO 11
<211> LENGTH: 74
<212> TYPE: DNA
<213> ORGANISM: Homo sapiens

<400> SEQUENCE: 11
cagcagcaga aacggcttcg aaatatgacc agtcactctg cccgagtggg ctccctaagc 60
tggaacagct atat 74

<210> SEQ ID NO 12
<211> LENGTH: 115
<212> TYPE: DNA
<213> ORGANISM: Homo sapiens

<400> SEQUENCE: 12
catccaccac catgatgttc gggtagcaga acaccatgtg gccacactga gtggccacag 60
ccaggaagtg tgtgggctgc gctgggcccc agatggacga catttggcca gtggt 115

<210> SEQ ID NO 13
<211> LENGTH: 94
<212> TYPE: DNA
<213> ORGANISM: Homo sapiens

<400> SEQUENCE: 13
gtaatgataa cttggtcaat gtgtggccta gtgctcctgg agagggtggc tgggttcctc 60
tgcagacatt cacccagcat caaggggctg tcaa 94

<210> SEQ ID NO 14
<211> LENGTH: 31
<212> TYPE: DNA
<213> ORGANISM: Homo sapiens

<400> SEQUENCE: 14
gtgtccctgg cagtccaatg tcctggcaac a 31

<210> SEQ ID NO 15
<211> LENGTH: 25
<212> TYPE: DNA
<213> ORGANISM: Homo sapiens

<400> SEQUENCE: 15
gcctgtctga gtgccgtgga tgccc 25

<210> SEQ ID NO 16
<211> LENGTH: 25
<212> TYPE: DNA
<213> ORGANISM: Homo sapiens

<400> SEQUENCE: 16
ttatttggaa gtacccaacc atggc 25

<210> SEQ ID NO 17
<211> LENGTH: 107
<212> TYPE: DNA
<213> ORGANISM: Homo sapiens

<400> SEQUENCE: 17
cacacatccc gggtcctgag tctgaccatg agcccagatg gggccacagt ggcatccgca 60
gcagcagatg agaccctgag gctatggcgc tgttttgagt tggaccc 107

<210> SEQ ID NO 18
<211> LENGTH: 31
<212> TYPE: DNA
<213> ORGANISM: Homo sapiens

<400> SEQUENCE: 18
agaccaaccc atcacctcag ttgtttttta t 31

<210> SEQ ID NO 19
<211> LENGTH: 75
<212> TYPE: DNA
<213> ORGANISM: Homo sapiens

<400> SEQUENCE: 19
tgcggcggtt tacgcggcgt taagacttcg tagggttagc gaaattgagg tttcttggta 60
ttgcgcgttt ctctt 75

<210> SEQ ID NO 20
<211> LENGTH: 25
<212> TYPE: DNA
<213> ORGANISM: Homo sapiens

<400> SEQUENCE: 20
gtccctaggt caaggggact cgtga 25

<210> SEQ ID NO 21
<211> LENGTH: 31
<212> TYPE: DNA
<213> ORGANISM: Homo sapiens

<400> SEQUENCE: 21
gtttaattca cagtgccaat gtaaggactg t 31

<210> SEQ ID NO 22
<211> LENGTH: 275
<212> TYPE: DNA
<213> ORGANISM: Homo sapiens

<400> SEQUENCE: 22
tcttagggtt aggtagcagc tgtcaggaac ttgcccctgc ccataagatc ctaaagggcc 60
cccatttgac tctcaccaga cagttagaac ttgtttcctc ctccgtgtca gccatcaaga 120
ggtgcttggg gggctgtgcc cagcaggacc tcactgccca gcagatcagc aggggagcca 180
agtggcctag atctgctgtg gagtacccga ctgtttgcct gcctgtctgc cctcctcttc 240
acctcattct catcactgac gtctaccatt ggctt 275

<210> SEQ ID NO 23
<211> LENGTH: 72
<212> TYPE: DNA
<213> ORGANISM: Homo sapiens

<400> SEQUENCE: 23
atgatgtggc tgcaataaac ccagaactct tacagcttct tcccttacat ccgaaggaca 60
atctgccctt gc 72

<210> SEQ ID NO 24
<211> LENGTH: 32
<212> TYPE: DNA
<213> ORGANISM: Homo sapiens

<400> SEQUENCE: 24
caaaaacgga gatccgtcaa ctccaaaatt cc 32

<210> SEQ ID NO 25
<211> LENGTH: 94
<212> TYPE: DNA
<213> ORGANISM: Homo sapiens

<400> SEQUENCE: 25
ggacctattt caccttgtac agaaacttgg aggtttgccc ctgaccaccc tcgagatcgt 60
gcagcactga ctggctactg ctctcggttc tcca 94

<210> SEQ ID NO 26
<211> LENGTH: 30
<212> TYPE: DNA
<213> ORGANISM: Homo sapiens

<400> SEQUENCE: 26
ctgcccccac taggccttcc tgccctgcag 30

<210> SEQ ID NO 27
<211> LENGTH: 64
<212> TYPE: DNA
<213> ORGANISM: Homo sapiens

<400> SEQUENCE: 27
ggctgaaata ccattgagga tggtcagcga ggagatggaa gagcaagtcc attccatccg 60
aggc 64

<210> SEQ ID NO 28
<211> LENGTH: 28
<212> TYPE: DNA
<213> ORGANISM: Homo sapiens

<400> SEQUENCE: 28
aggcccagaa ctctgaaatg agaatgaa 28

<210> SEQ ID NO 29
<211> LENGTH: 92
<212> TYPE: DNA
<213> ORGANISM: Homo sapiens

<400> SEQUENCE: 29
tatgacagta gttttccaaa ctgggaattt gcccgaatga ttaaagaatt tcgggctact 60
ttggaatgtc atccacttac tatgactgat cc 92

<210> SEQ ID NO 30
<211> LENGTH: 26
<212> TYPE: DNA
<213> ORGANISM: Homo sapiens

<400> SEQUENCE: 30
gagcaccccc tgaaatactc tccttc 26

<210> SEQ ID NO 31
<211> LENGTH: 88
<212> TYPE: DNA
<213> ORGANISM: Homo sapiens

<400> SEQUENCE: 31
acatgaaccc aagttgaaag tggacttaac aaagtatctg gagaaccaag cattctgctt 60
tgactttgca tttgatgaaa cagcttcg 88

<210> SEQ ID NO 32
<211> LENGTH: 33
<212> TYPE: DNA
<213> ORGANISM: Homo sapiens

<400> SEQUENCE: 32
aggccactgg tacagacaat ctttgaaggt gga 33

<210> SEQ ID NO 33
<211> LENGTH: 88
<212> TYPE: DNA
<213> ORGANISM: Homo sapiens

<400> SEQUENCE: 33
cgggacgtct tcctcctgaa gaatcaaccc tgctaccgga agttgggcct ggaagtctat 60
gtgacattct tcgagatcta caatggga 88

<210> SEQ ID NO 34
<211> LENGTH: 92
<212> TYPE: DNA
<213> ORGANISM: Homo sapiens

<400> SEQUENCE: 34
aggacggcaa gcaacaggtg caagtggtgg ggctgcagga gcatctggtt aactctgctg 60
atgatgtcat caagatgatc gacatgggca gc 92

<210> SEQ ID NO 35
<211> LENGTH: 155
<212> TYPE: DNA
<213> ORGANISM: Homo sapiens

<400> SEQUENCE: 35
gctcccacgc gtgcttccaa attattcttc gagctaaagg gagaatgcat ggcaagttct 60
ctttggtaga tctggcaggg aatgagcgag gcgcggacac ttccagtgct gaccggcaga 120
cccgcatgga gggcgcagaa atcaacaaga gtctc 155

<210> SEQ ID NO 36
<211> LENGTH: 26
<212> TYPE: DNA
<213> ORGANISM: Homo sapiens

<400> SEQUENCE: 36
gctgggtgag gggcttttcc agtcca 26

<210> SEQ ID NO 37
<211> LENGTH: 65
<212> TYPE: DNA
<213> ORGANISM: Homo sapiens

<400> SEQUENCE: 37
gcaaggttgc cattccatcc ccttggagcc tcaagcctcg aagcctgggc ggtgccacat 60
tcctc 65

<210> SEQ ID NO 38
<211> LENGTH: 44
<212> TYPE: DNA
<213> ORGANISM: Homo sapiens

<400> SEQUENCE: 38
agtaccaagg gggtgctgtg ggatctgaga cctccttgtt tcct 44

<210> SEQ ID NO 39
<211> LENGTH: 40
<212> TYPE: DNA
<213> ORGANISM: Homo sapiens

<400> SEQUENCE: 39
gaagagatgg aagcctgctc taacggggcg ctgattccag 40

<210> SEQ ID NO 40
<211> LENGTH: 35
<212> TYPE: DNA
<213> ORGANISM: Homo sapiens

<400> SEQUENCE: 40
ccagatgtcc agctttaacg aagccatgac tcaga 35

<210> SEQ ID NO 41
<211> LENGTH: 96
<212> TYPE: DNA
<213> ORGANISM: Homo sapiens

<400> SEQUENCE: 41
aaggaccaga ctggcttgag ctctctgaga tgaccgagca gccagactat gacctggaga 60
cctttgtgaa caaagcggaa tctgctctgg cccagc 96

<210> SEQ ID NO 42
<211> LENGTH: 27
<212> TYPE: DNA
<213> ORGANISM: Homo sapiens

<400> SEQUENCE: 42
gtcatcaagg ccttgcgcct ggccatg 27

<210> SEQ ID NO 43
<211> LENGTH: 29
<212> TYPE: DNA
<213> ORGANISM: Homo sapiens

<400> SEQUENCE: 43
cgactgcaaa taaaaatctg tttggtttg 29

<210> SEQ ID NO 44
<211> LENGTH: 29
<212> TYPE: DNA
<213> ORGANISM: Homo sapiens

<400> SEQUENCE: 44
gggacaggtt ctggtaaatg ccaagtatg 29

<210> SEQ ID NO 45
<211> LENGTH: 245
<212> TYPE: DNA
<213> ORGANISM: Homo sapiens

<400> SEQUENCE: 45
ttcctcagtt gtcgccctca cgagaggaag gagctcttag ttaccctttt gtgttgccct 60
tctttccatc aaggggaatg ttctcagcat agagctttct ccgcagcatc ctgcctgcgt 120
ggactggctg ctaatggaga gctccctggg gttgtcctgg ctctggggag agagacggag 180
cctttagtac agctatctgc tggctctaaa ccttctacgc ctttgggccg agcactgaat 240
gtctt 245

<210> SEQ ID NO 46
<211> LENGTH: 37
<212> TYPE: DNA
<213> ORGANISM: Homo sapiens

<400> SEQUENCE: 46
gtctccctag agatcctaga ggatccctac tgttttc 37

<210> SEQ ID NO 47
<211> LENGTH: 29
<212> TYPE: DNA
<213> ORGANISM: Homo sapiens

<400> SEQUENCE: 47
aggagccaca tgctctcatc aagcagaaa 29

<210> SEQ ID NO 48
<211> LENGTH: 76
<212> TYPE: DNA
<213> ORGANISM: Homo sapiens

<400> SEQUENCE: 48
gtgcccaacc agtgaggcca cgtttcgaaa agaagaaaga aacgacaaac taaaatacat 60
gactgtgtag atgagg 76

<210> SEQ ID NO 49
<211> LENGTH: 84
<212> TYPE: DNA
<213> ORGANISM: Homo sapiens

<400> SEQUENCE: 49
gctggagaat actgcccagt tactctagcg cgccaggccg aaccgcagct tcttggctta 60
ggtacttcta ctcacagcgg ccga 84

<210> SEQ ID NO 50
<211> LENGTH: 67
<212> TYPE: DNA
<213> ORGANISM: Homo sapiens

<400> SEQUENCE: 50
atggcttttg caaatctgcg gaaagtgctc atcagtgaca gcctggaccc ttgctgccgg 60
aagatct 67

<210> SEQ ID NO 51
<211> LENGTH: 67
<212> TYPE: DNA
<213> ORGANISM: Homo sapiens

<400> SEQUENCE: 51
gcagcctaag catcattcct cttctcttct tagtggagat aaaattaccc actgctctcc 60
ttacatt 67

<210> SEQ ID NO 52
<211> LENGTH: 1003
<212> TYPE: DNA
<213> ORGANISM: Homo sapiens

<400> SEQUENCE: 52
gtgtgggccc ttaccctaga agccaacttc tcatgacctt tctctatctc cagaatccat 60
gcagtgggaa tgaaggtaaa agaaggtttt catgggatcc agctgagagc tctacgggga 120
aaatggatct gaggagccat gtgctccatc tcttttattt tacaggtaga gactaggggt 180
atagagtgag gtgaattacc gcagtgaccc acacattgtt ggcagaccta ggattagaac 240
tctgtcttcc tggttcccag cttggtgctt ttgaaagcat acttgctgct ttcttaccgg 300
cctggtgtct gccactttgg gacagagtgt ggacttgctc acctgcccca tttcttaggg 360
attctcattc tgtgtttgag caagaatatt cttattctgg aaagaaccac ataccacagg 420
attctgggtg agcataagga agattgtctt ggggatctga cttagctcac gtatagtggc 480
tatgatgaat tcagtgtctt attttttgca tatgtatatt tttagtctaa tattgcctgg 540
gtgtctgagc aagtctagat gaatttaatt gctctcattt ttcccctgcc cctcttcctt 600
tggtctctct tttaggaaat gtttttcttt caacattcgt ttcattcatt atttactcat 660
tcggccaacc aacatttatt gagtgccttc cctgtatcag ggacaggggc ttacaaagta 720
gaatttgatc ccacctctgc cctcagtagc tcagtgtcta atggaggtag tgatgttcat 780
taagcgtcgc cagatactgt gctaggtgct gtgcctgttc tctctcgctt gttcctcaca 840
cacttgagaa ggccgaagct gattcatagc ttggaaggca ggggccttgg atttgaaccc 900
aggcctgacc aatggcagaa cctatcagat gtgtggacag atgacattgc ctttctttct 960
ttggatatat caaaatcagc cagcaggcag gaactcccat ttt 1003

<210> SEQ ID NO 53
<211> LENGTH: 28
<212> TYPE: DNA
<213> ORGANISM: Homo sapiens

<400> SEQUENCE: 53
tgtgtctgat ggacatccag gctgcagg 28

<210> SEQ ID NO 54
<211> LENGTH: 86
<212> TYPE: DNA
<213> ORGANISM: Homo sapiens

<400> SEQUENCE: 54
atggtgctgt ctagagagat gagccaggtg cccagagccc atgggccaat gctgcccttt 60
cttgagcatg ccaaacaaag cggttg 86

<210> SEQ ID NO 55
<211> LENGTH: 50
<212> TYPE: DNA
<213> ORGANISM: Homo sapiens

<400> SEQUENCE: 55
cagtctcctc cactctaagt aaaaatcagc atgagtccta gcccacattt 50

<210> SEQ ID NO 56
<211> LENGTH: 71
<212> TYPE: DNA
<213> ORGANISM: Homo sapiens

<400> SEQUENCE: 56
tgagtatacc aaagatatct atgaactggc agtcatcagt gacttcctaa ggttccggaa 60
atgcatctct t 71

<210> SEQ ID NO 57
<211> LENGTH: 40
<212> TYPE: DNA
<213> ORGANISM: Homo sapiens

<400> SEQUENCE: 57
atgtgcctgc ggctttacga gttctcacag aatgactttc 40

<210> SEQ ID NO 58
<211> LENGTH: 72
<212> TYPE: DNA
<213> ORGANISM: Homo sapiens

<400> SEQUENCE: 58
actgtgaagg ccttattgtt cgctctgcca ccaaggtgac cgctgatgtc atcaacgcag 60
ctgagaaact cc 72

<210> SEQ ID NO 59
<211> LENGTH: 31
<212> TYPE: DNA
<213> ORGANISM: Homo sapiens

<400> SEQUENCE: 59
atctggaggc cgcaacaagg aagggcatct t 31

<210> SEQ ID NO 60
<211> LENGTH: 113
<212> TYPE: DNA
<213> ORGANISM: Homo sapiens

<400> SEQUENCE: 60
tgagtgcgga gactgaccac acctagggag aaaaaactca cttgagagaa agctgagtcc 60
attggaaggg cttccaggag gatgcctggt ctagggcctg catggtcaac aca 113

<210> SEQ ID NO 61
<211> LENGTH: 122
<212> TYPE: DNA
<213> ORGANISM: Homo sapiens

<400> SEQUENCE: 61
attacttttc ccatggcgag acctgctttc cctcctgctg gaggaggatc tgggggaatt 60
tacctctgct ctaactcctc cctgcagttt ccatctgagc tctctggtat tcactgatat 120
tc 122

<210> SEQ ID NO 62
<211> LENGTH: 45
<212> TYPE: DNA
<213> ORGANISM: Homo sapiens

<400> SEQUENCE: 62
gcagattccc caggcgacgg cttcgatgaa ggacggcaaa tggga 45

<210> SEQ ID NO 63
<211> LENGTH: 33
<212> TYPE: DNA
<213> ORGANISM: Homo sapiens

<400> SEQUENCE: 63
gagaggtagc tacccggatg cagtcctttg gga 33

<210> SEQ ID NO 64
<211> LENGTH: 88
<212> TYPE: DNA
<213> ORGANISM: Homo sapiens

<400> SEQUENCE: 64
ttccttctcc gtggcaccac tacacatcaa tattcctggc aatattcttc atcatggaga 60
cttcggcagc gacttcaacc agatgaaa 88

<210> SEQ ID NO 65
<211> LENGTH: 84
<212> TYPE: DNA
<213> ORGANISM: Homo sapiens

<400> SEQUENCE: 65
gaaacatggc ttggatcatt ccgtctccca cctcagcccc tccggagctg cctggacctc 60
atcattccgg agagtctaag tggc 84

<210> SEQ ID NO 66
<211> LENGTH: 125
<212> TYPE: DNA
<213> ORGANISM: Homo sapiens

<400> SEQUENCE: 66
cagtcccagc atcattgtgt ggtcatgaga attaattaag ctgatcatgg tacttagtat 60
atggtaaata gtacttagta tgtggaacat ggtacttagt gtatggtaaa ttaactggag 120
aatta 125

<210> SEQ ID NO 67
<211> LENGTH: 52
<212> TYPE: DNA
<213> ORGANISM: Homo sapiens

<400> SEQUENCE: 67
ggtatgaccc catcatttcc ccagaggtct cggcctcctt tggtgttcag ca 52

<210> SEQ ID NO 68
<211> LENGTH: 78
<212> TYPE: DNA
<213> ORGANISM: Homo sapiens

<400> SEQUENCE: 68
cctttgccca gtgcaagaag ggggtgcgtg tggtgaactg tgcccgtgga gggatcgtgg 60
acgaaggcgc cctgctcc 78

<210> SEQ ID NO 69
<211> LENGTH: 78
<212> TYPE: DNA
<213> ORGANISM: Homo sapiens

<400> SEQUENCE: 69
gccttggtgg accatgagaa tgtcatcagc tgtccccacc tgggtgccag caccaaggag 60
gctcagagcc gctgtggg 78

<210> SEQ ID NO 70
<211> LENGTH: 54
<212> TYPE: DNA
<213> ORGANISM: Homo sapiens

<400> SEQUENCE: 70
atggttgact ttacaagtta tctcaataaa agtggccaga tgcctaactc agaa 54

<210> SEQ ID NO 71
<211> LENGTH: 438
<212> TYPE: DNA
<213> ORGANISM: Homo sapiens

<400> SEQUENCE: 71
tggacttcgc atgcgttgat atttgaagca cgatcatcaa aactttgtga taattgatcg 60
tagtgtttag taacaatgta aacacttaaa aaaattcaag atagaaaata aaaatgaagg 120
caagttggga ctgccagaga agacccgtca ctcctcatcc aagttatctg cgactcccat 180
atgttttgtg tcaaagactc acctttattg tgctgtccaa tcccttcccc agtgcagaaa 240
caagtctccc atggaggggg ctggggcaga cacagtttgc tgaaaggagc aattttgagt 300
ggttgtggca ttctgtgtcc atttctggct ccacagcttt cttcatttgt aggaacaagt 360
ccttgtcctg ttgttagtgg ctgatggaag ttgtcaccca ccaggcacca aggcaggagt 420
gaccctatac tgtctttc 438

<210> SEQ ID NO 72
<211> LENGTH: 60
<212> TYPE: DNA
<213> ORGANISM: Homo sapiens

<400> SEQUENCE: 72
ccaagccttg gattggtctg gcagaagctc tggggacact gatgcgagcc tgggctgggt 60

<210> SEQ ID NO 73
<211> LENGTH: 96
<212> TYPE: DNA
<213> ORGANISM: Homo sapiens

<400> SEQUENCE: 73
aatgctggga actgcctaag ccccgcagtc attgtcggcc tcctgaaaga ggcttccaag 60
caggcggatg tgaacttggt gaacgctaag ctgctg 96

<210> SEQ ID NO 74
<211> LENGTH: 47
<212> TYPE: DNA
<213> ORGANISM: Homo sapiens

<400> SEQUENCE: 74
tgggcttggt ccaaggcact acgcctgtac tgcaggggct caatgga 47

<210> SEQ ID NO 75
<211> LENGTH: 75
<212> TYPE: DNA
<213> ORGANISM: Homo sapiens

<400> SEQUENCE: 75
caggcgtgcg gctgctgtcc taccagactt cactggtgtc agatggggag acctggcacg 60
tcatgggcat ctcct 75

<210> SEQ ID NO 76
<211> LENGTH: 71
<212> TYPE: DNA
<213> ORGANISM: Homo sapiens

<400> SEQUENCE: 76
ccactgtgat caatagggag agaaaatcca cattcttggg ctgaacgcgg gcctctgaca 60
ctgcttacac t 71

<210> SEQ ID NO 77
<211> LENGTH: 114
<212> TYPE: DNA
<213> ORGANISM: Homo sapiens

<400> SEQUENCE: 77
tccagtagga ggcggcaagt ttgaaaagtg atgacggttg acgtttgctg atttttgact 60
ttgcttgtag ctgctccccg aactcgccgt cttcctgtcg gcggccggca ctgt 114

<210> SEQ ID NO 78
<211> LENGTH: 118
<212> TYPE: DNA
<213> ORGANISM: Homo sapiens

<400> SEQUENCE: 78
tgagcgcgag aggacggagg aaggaagcct gcagacagac gccttctcca tcccaaggcg 60
cgggcaggtg ccgggacgct gggcctggcg gtgttttcgt cgtgctcagc ggtgggag 118

<210> SEQ ID NO 79
<211> LENGTH: 205
<212> TYPE: DNA
<213> ORGANISM: Homo sapiens

<400> SEQUENCE: 79
tcaaactatg tagttggaaa gtgtcttcat ctctcgttaa tgaataaatt gtaactgaaa 60
ttgtacttcg aaagaatgat agaatttgga tattggagga ggttccaaaa ggaaatactg 120
gaagtttggg aaagttagga gactaacttg gagcagaaat ttcattcaat tattaaaggg 180
tttagaagcc tagcagaaaa atttg 205

<210> SEQ ID NO 80
<211> LENGTH: 91
<212> TYPE: DNA
<213> ORGANISM: Homo sapiens

<400> SEQUENCE: 80
aatgtagctg agattgtgat tcatattcgc aataagatct taacaggagc tgatggtaaa 60
aacctcacca agaatgatct ttatccaaat c 91

<210> SEQ ID NO 81
<211> LENGTH: 55
<212> TYPE: DNA
<213> ORGANISM: Homo sapiens

<400> SEQUENCE: 81
catgatctac atgagagcct tacaaatagt atatggaatt cgactggaac atttt 55

<210> SEQ ID NO 82
<211> LENGTH: 70
<212> TYPE: DNA
<213> ORGANISM: Homo sapiens

<400> SEQUENCE: 82
tgaactctga agtcatgtat ccacatttaa tggaaggctt cttaccattc agcaatttag 60
ttactcatct 70

<210> SEQ ID NO 83
<211> LENGTH: 31
<212> TYPE: DNA
<213> ORGANISM: Homo sapiens

<400> SEQUENCE: 83
tttaagtggc attatcaact ttattcactt c 31

<210> SEQ ID NO 84
<211> LENGTH: 61
<212> TYPE: DNA
<213> ORGANISM: Homo sapiens

<400> SEQUENCE: 84
tcctctgcgg acaaaatgca acagttaaac gccgcacacc aggaggcatt aatgaaactg 60
g 61

<210> SEQ ID NO 85

<211> LENGTH: 27
<212> TYPE: DNA
<213> ORGANISM: Homo sapiens

<400> SEQUENCE: 85
tgaggacagg tatttcattt tagcctt 27

<210> SEQ ID NO 86
<211> LENGTH: 26
<212> TYPE: DNA
<213> ORGANISM: Homo sapiens

<400> SEQUENCE: 86
attcaggagc tacaacaatc actaaa 26

<210> SEQ ID NO 87
<211> LENGTH: 30
<212> TYPE: DNA
<213> ORGANISM: Homo sapiens

<400> SEQUENCE: 87
aaaatgaaag atacggtcca gaagcttaaa 30

<210> SEQ ID NO 88
<211> LENGTH: 117
<212> TYPE: DNA
<213> ORGANISM: Homo sapiens

<400> SEQUENCE: 88
atctatggag actcagttga ctgcctgcct tcatgtcagt tggaagtgca gttatatcaa 60
aagaaaatac aggacctttc agataatagg gaaaaattag ccagtatctt aaaggag 117

<210> SEQ ID NO 89
<211> LENGTH: 105
<212> TYPE: DNA
<213> ORGANISM: Homo sapiens

<400> SEQUENCE: 89
cgttcaaaag actgatgatt gtgaagaagg aaaaacttgc cacagcacaa ttcaaaataa 60
ataagaagca tgaagatgtt aagcaataca aacgcacagt aattg 105

<210> SEQ ID NO 90
<211> LENGTH: 45
<212> TYPE: DNA
<213> ORGANISM: Homo sapiens

<400> SEQUENCE: 90
aaaaagaggt gctgtctatg aacgagtaac cacaattaat caaga 45

<210> SEQ ID NO 91
<211> LENGTH: 87
<212> TYPE: DNA
<213> ORGANISM: Homo sapiens

<400> SEQUENCE: 91
aaaactgctt tggagaaata ccacgacggt attgaaaagg cagcagagga ctcctatgct 60
aagatagatg agaagacagc tgaactg 87

<210> SEQ ID NO 92
<211> LENGTH: 148
<212> TYPE: DNA
<213> ORGANISM: Homo sapiens

<400> SEQUENCE: 92
aaaagttgaa gcgaatggaa gtatcagaag taccaaataa tgttggcttc atcagttttt 60
atacactctc ataagtagtt aataagatga atttaatgta ggcttttatt aatttataat 120
taaaataact tgtgcagcta ttcatgtc 148

<210> SEQ ID NO 93
<211> LENGTH: 32
<212> TYPE: DNA
<213> ORGANISM: Homo sapiens

<400> SEQUENCE: 93
gctgcgggca gtttgaatta gactctgggc tc 32

<210> SEQ ID NO 94
<211> LENGTH: 36
<212> TYPE: DNA
<213> ORGANISM: Homo sapiens

<400> SEQUENCE: 94
cgcgccagaa ctgtactctc cgagaggtcg ttttcc 36

<210> SEQ ID NO 95
<211> LENGTH: 79
<212> TYPE: DNA
<213> ORGANISM: Homo sapiens

<400> SEQUENCE: 95
tgtcccagac cctactcggt cacggactca cactttaggg gatcattttc ttcctccgta 60
aaagaattgg agatgacta 79

<210> SEQ ID NO 96
<211> LENGTH: 34
<212> TYPE: DNA
<213> ORGANISM: Homo sapiens

<400> SEQUENCE: 96
tttacaaatg ttggagtaat aaagaaggca gaac 34

<210> SEQ ID NO 97
<211> LENGTH: 133
<212> TYPE: DNA
<213> ORGANISM: Homo sapiens

<400> SEQUENCE: 97
gaaagaaggg ctgcctacaa gagctcttca gaaaattcaa gagcttgaag gacagcttga 60
caaactgaag aaggaaaagc agcaaaggca gtttcagctt gacagtctcg aggctgcgct 120
gcagaagcaa aaa 133

<210> SEQ ID NO 98
<211> LENGTH: 78
<212> TYPE: DNA
<213> ORGANISM: Homo sapiens

<400> SEQUENCE: 98
gaagatttct catgaacttc aagtcaagga gtcacaagtg aatttccagg aaggacaact 60
gaattcaggc aaaaaaaca 78

<210> SEQ ID NO 99

<211> LENGTH: 137
<212> TYPE: DNA
<213> ORGANISM: Homo sapiens

<400> SEQUENCE: 99
tattttggga tggtatttat agggatgata tttgtatgta ttaatcagat gcgtttgtct 60
tttcctttaa caatataatt attatacttt gcaatttttt ttcctggtag aataagtaat 120
gattcggtct ctgtacc 137

<210> SEQ ID NO 100
<211> LENGTH: 30
<212> TYPE: DNA
<213> ORGANISM: Homo sapiens

<400> SEQUENCE: 100
gaagccaaca agctgcgcag tctgcagatg 30

<210> SEQ ID NO 101
<211> LENGTH: 64
<212> TYPE: DNA
<213> ORGANISM: Homo sapiens

<400> SEQUENCE: 101
agactcttcc acaagccacc atgaatcacc gcgacattgc ccggcatcag gcttcatcat 60
ctgt 64

<210> SEQ ID NO 102
<211> LENGTH: 152
<212> TYPE: DNA
<213> ORGANISM: Homo sapiens

<400> SEQUENCE: 102
taggagagat ttctctgcat cttacttttc tggggaacaa gaggtgactc caagtcgatc 60
aactttgcaa atagggaaaa gagatgctaa tagcagtttc tttgacaatt ctagcagtcc 120
tcatcttttg gatcaattaa aagcgcagaa tc 152

<210> SEQ ID NO 103
<211> LENGTH: 49
<212> TYPE: DNA
<213> ORGANISM: Homo sapiens

<400> SEQUENCE: 103
actgaaaaaa ttgacggaag atttgagttg tcagcgacaa aatgcagaa 49

<210> SEQ ID NO 104
<211> LENGTH: 118
<212> TYPE: DNA
<213> ORGANISM: Homo sapiens

<400> SEQUENCE: 104
gagctctccc gtcaacagcg ttctttccaa acactggacc aggagtgcat ccagatgaag 60
gccagactca cccaggagtt acagcaagcc aagaatatgc acaacgtcct gcaggctg 118

<210> SEQ ID NO 105
<211> LENGTH: 60
<212> TYPE: DNA
<213> ORGANISM: Homo sapiens

<400> SEQUENCE: 105
agagtttaag caaaagttgt gcagagctga acaggcgttc caggcgagtc agatcaagga 60

<210> SEQ ID NO 106
<211> LENGTH: 84
<212> TYPE: DNA
<213> ORGANISM: Homo sapiens

<400> SEQUENCE: 106
aaaggccaga gaagtctgcc acctggaggc agaactcaag aacatcaaac agtgtttaaa 60
tcagagccag aattttgcag aaga 84

<210> SEQ ID NO 107
<211> LENGTH: 501
<212> TYPE: DNA
<213> ORGANISM: Homo sapiens

<400> SEQUENCE: 107
gccttgctga gtgctttaga gttaaaaaag aaagaatatg aagaattgaa agaagagaaa 60
actctgtttt cttgttggaa aagtgaaaac gaaaaacttt taactcagat ggaatcagaa 120
aaggaaaact tgcagagtaa aattaatcac ttggaaactt gtctgaagac acagcaaata 180
aaaagtcatg aatacaacga gagagtaaga acgctggaga tggacagaga aaacctaagt 240
gtcgagatca gaaaccttca caacgtgtta gacagtaagt cagtggaggt agagacccag 300
aaactagctt atatggagct acagcagaaa gctgagttct cagatcagaa acatcagaag 360
gaaatagaaa atatgtgttt gaagacttct cagcttactg ggcaagttga agatctagaa 420
cacaagcttc agttactgtc aaatgaaata atggacaaag accggtgtta ccaagacttg 480
catgccgaat atgagagcct c 501

<210> SEQ ID NO 108
<211> LENGTH: 767
<212> TYPE: DNA
<213> ORGANISM: Homo sapiens

<400> SEQUENCE: 108
tttggctttt gatcagcagc ctgccatgca tcattccttt gcaaatataa ttggagaaca 60
aggaagcatg ccttcagaga ggagtgaatg tcgtttagaa gcagaccaaa gtccgaaaaa 120
ttctgccatc ctacaaaata gagttgattc acttgaattt tcattagagt ctcaaaaaca 180
gatgaactca gacctgcaaa agcagtgtga agagttggtg caaatcaaag gagaaataga 240
agaaaatctc atgaaagcag aacagatgca tcaaagtttt gtggctgaaa caagtcagcg 300
cattagtaag ttacaggaag acacttctgc tcaccagaat gttgttgctg aaaccttaag 360
tgcccttgag aacaaggaaa aagagctgca acttttaaat gataaggtag aaactgagca 420
ggcagagatt caagaattaa aaaagagcaa ccatctactt gaagactctc taaaggagct 480
acaactttta tccgaaaccc taagcttgga gaagaaagaa atgagttcca tcatttctct 540
aaataaaagg gaaattgaag agctgaccca agagaatggg actcttaagg aaattaatgc 600
atccttaaat caagagaaga tgaacttaat ccagaaaagt gagagttttg caaactatat 660
agatgaaagg gagaaaagca tttcagagtt atctgatcag tacaagcaag aaaaacttat 720
tttactacaa agatgtgaag aaaccggaaa tgcatatgag gatctta 767

<210> SEQ ID NO 109
<211> LENGTH: 83
<212> TYPE: DNA
<213> ORGANISM: Homo sapiens

<400> SEQUENCE: 109
actgtgaaat agatgcggaa gaaaagtata tttcagggcc tcatgagttg tcaacaagtc 60
aaaacgacaa tgcacacctt cag 83

<210> SEQ ID NO 110
<211> LENGTH: 135
<212> TYPE: DNA
<213> ORGANISM: Homo sapiens

<400> SEQUENCE: 110
tctgcaaaca acaatgaaca agctgaatga gctagagaaa atatgtgaaa tactgcaggc 60
tgaaaagtat gaactcgtaa ctgagctgaa tgattcaagg tcagaatgta tcacagcaac 120
taggaaaatg gcaga 135

<210> SEQ ID NO 111
<211> LENGTH: 321
<212> TYPE: DNA
<213> ORGANISM: Homo sapiens

<400> SEQUENCE: 111
tggctccatt ggacgagagt aattcctacg agcacttgac attgtcagac aaagaagttc 60
aaatgcactt tgccgaattg caagagaaat tcttatcttt acaaagtgaa cacaaaattt 120
tacatgatca gcactgtcag atgagctcta aaatgtcaga gctgcagacc tatgttgact 180
cattaaaggc cgaaaatttg gtcttgtcaa cgaatctgag aaactttcaa ggtgacttgg 240
tgaaggagat gcagctgggc ttggaggagg ggctcgttcc atccctgtca tcctcttgtg 300
tgcctgacag ctctagtctt a 321

<210> SEQ ID NO 112
<211> LENGTH: 143
<212> TYPE: DNA
<213> ORGANISM: Homo sapiens

<400> SEQUENCE: 112
gctgacaagc gtgactctgg agatggagtc caagttggcg gcagaaaaga aacagacgga 60
acaactgtca cttgagctgg aagtagcacg actccagcta caaggtctgg acttaagttc 120
tcggtctttg cttggcatcg aca 143

<210> SEQ ID NO 113
<211> LENGTH: 392
<212> TYPE: DNA
<213> ORGANISM: Homo sapiens

<400> SEQUENCE: 113
agataccaat tatgagcctc caggggaaga taaaacccag ggctcttcag aatgcatttc 60
tgaattgtca ttttctggtc ctaatgcttt ggtacctatg gatttcctgg ggaatcagga 120
agatatccat aatcttcaac tgcgggtaaa agagacatca aatgagaatt tgagattact 180
tcatgtgata gaggaccgtg acagaaaagt tgaaagtttg ctaaatgaaa tgaaagaatt 240
agactcaaaa ctccatttac aggaggtaca actaatgacc aaaattgaag catgcataga 300
attggaaaaa atagttgggg aacttaagaa agaaaactca gatttaagtg aaaaattgga 360
atatttttct tgtgatcacc aggagttact cc 392

<210> SEQ ID NO 114
<211> LENGTH: 792

<212> TYPE: DNA
<213> ORGANISM: Homo sapiens

<400> SEQUENCE: 114
attgagcatg aagccctcta cctggaggct gacttagagg tagttcaaac agagaagcta 60
tgtttagaaa aagacaatga aaataagcag aaggttattg tctgccttga agaagaactc 120
tcagtggtca caagtgagag aaaccagctt cgtggagaat tagatactat gtcaaaaaaa 180
accacggcac tggatcagtt gtctgaaaaa atgaaggaga aaacacaaga gcttgagtct 240
catcaaagtg agtgtctcca ttgcattcag gtggcagagg cagaggtgaa ggaaaagacg 300
gaactccttc agactttgtc ctctgatgtg agtgagctgt taaaagacaa aactcatctc 360
caggaaaagc tgcagagttt ggaaaaggac tcacaggcac tgtctttgac aaaatgtgag 420
ctggaaaacc aaattgcaca actgaataaa gagaaagaat tgcttgtcaa ggaatctgaa 480
agcctgcagg ccagactgag tgaatcagat tatgaaaagc tgaatgtctc caaggccttg 540
gaggccgcac tggtggagaa aggtgagttc gcattgaggc tgagctcaac acaggaggaa 600
gtgcatcagc tgagaagagg catcgagaaa ctgagagttc gcattgaggc cgatgaaaag 660
aagcagctgc acatcgcaga gaaactgaaa gaacgcgagc gggagaatga ttcacttaag 720
gataaagttg agaaccttga aagggaattg cagatgtcag aagaaaacca ggagctagtg 780
attcttgatg cc 792

<210> SEQ ID NO 115
<211> LENGTH: 296
<212> TYPE: DNA
<213> ORGANISM: Homo sapiens

<400> SEQUENCE: 115
agagtctaga cccaccaata gaggaagagc atcagctgag aaatagcatt gaaaagctga 60
gagcccgcct agaagctgat gaaaagaagc agctctgtgt cttacaacaa ctgaaggaaa 120
gtgagcatca tgcagattta cttaagggta gagtggagaa ccttgaaaga gagctagaga 180
tagccaggac aaaccaagag catgcagctc ttgaggcaga gaattccaaa ggagaggtag 240
agaccctaaa agcaaaaata gaagggatga cccaaagtct gagaggtctg gaatta 296

<210> SEQ ID NO 116
<211> LENGTH: 286
<212> TYPE: DNA
<213> ORGANISM: Homo sapiens

<400> SEQUENCE: 116
gctcaatgag agagtggcag ccctgcataa tgaccaagaa gcctgtaagg ccaaagagca 60
gaatcttagt agtcaagtag agtgtcttga acttgagaag gctcagttgc tacaaggcct 120
tgatgaggcc aaaaataatt atattgtttt gcaatcttca gtgaatggcc tcattcaaga 180
agtagaagat ggcaagcaga aactggagaa gaaggatgaa gaaatcagta gactgaaaaa 240
tcaaattcaa gaccaagagc agcttgtctc taaactgtcc caggtg 286

<210> SEQ ID NO 117
<211> LENGTH: 29
<212> TYPE: DNA
<213> ORGANISM: Homo sapiens

<400> SEQUENCE: 117
agagaaaaat aggctagctg gagagttgc 29

<210> SEQ ID NO 118
<211> LENGTH: 108
<212> TYPE: DNA
<213> ORGANISM: Homo sapiens

<400> SEQUENCE: 118
atagtgaatt gaagaagagc ctagattgca tgcacaaaga ccaggtggaa aaggaaggga 60
aagtgagaga ggaaatagct gaatatcagc tacggcttca tgaagctg 108

<210> SEQ ID NO 119
<211> LENGTH: 123
<212> TYPE: DNA
<213> ORGANISM: Homo sapiens

<400> SEQUENCE: 119
aatccagaca taccgagaga aattgacttc taaagaagaa tgtctcagtt cacagaagct 60
ggagatagac cttttaaagt ctagtaaaga agagctcaat aattcattga aagctactac 120
tca 123

<210> SEQ ID NO 120
<211> LENGTH: 175
<212> TYPE: DNA
<213> ORGANISM: Homo sapiens

<400> SEQUENCE: 120
tcttcctttg gaaattcatg atgccatatc agatggtttt agaattctgc actttaataa 60
tgtaatgcat atgccatata taatatccca gagggatctg ctataatatt gcataatcga 120
attcatattt ctgcagcaaa atgtgtggat actctcacaa ggcaggataa ataga 175

<210> SEQ ID NO 121
<211> LENGTH: 30
<212> TYPE: DNA
<213> ORGANISM: Homo sapiens

<400> SEQUENCE: 121
tttttccata tgcttataaa aagaaattca 30

<210> SEQ ID NO 122
<211> LENGTH: 25
<212> TYPE: DNA
<213> ORGANISM: Homo sapiens

<400> SEQUENCE: 122
atggacaatc taaaatatgt aaatc 25

<210> SEQ ID NO 123
<211> LENGTH: 93
<212> TYPE: DNA
<213> ORGANISM: Homo sapiens

<400> SEQUENCE: 123
gaagttgttg atcaaatcct gtaaacagct ggaagaggaa aaggagatac tgcagaaaga 60
actctctcaa cttcaagctg cacaggagaa gca 93

<210> SEQ ID NO 124
<211> LENGTH: 226
<212> TYPE: DNA
<213> ORGANISM: Homo sapiens

<400> SEQUENCE: 124
tctaaacaag attcccgagg gtctcctttg ctaggtccag ttgttccagg accatctcca 60
atcccttctg ttactgaaaa gaggttatca tctggccaaa ataaagcttc aggcaagagg 120
caaagatcca gtggaatatg ggagaatggt agaggaccaa cacctgctac cccagagagc 180
ttttctaaaa aaagcaagaa agcagtcatg agtggtattc accctg 226

<210> SEQ ID NO 125
<211> LENGTH: 137
<212> TYPE: DNA
<213> ORGANISM: Homo sapiens

<400> SEQUENCE: 125
gactagccca tatatcctgc gaagaacaac catggcaact cggaccagcc cccgcctggc 60
tgcacagaag ttagcgctat ccccactgag tctcggcaaa gaaaatcttg cagagtcctc 120
caaaccaaca gctggtg 137

<210> SEQ ID NO 126
<211> LENGTH: 179
<212> TYPE: DNA
<213> ORGANISM: Homo sapiens

<400> SEQUENCE: 126
ctcagcggag cccagtagat tcaggcacca tcctccgaga acccaccacg aaatccgtcc 60
cagtcaataa tcttcctgag agaagtccga ctgacagccc cagagagggc ctgagggtca 120
agcgaggccg acttgtcccc agccccaaag ctggactgga gtccaacggc agtgagaac 179

<210> SEQ ID NO 127
<211> LENGTH: 149
<212> TYPE: DNA
<213> ORGANISM: Homo sapiens

<400> SEQUENCE: 127
ttctctttag tcagggcatg ctttattagt gaggagaaaa caattcctta gaagtcttaa 60
atatattgta ctctttagat ctcccatgtg taggtattga aaaagtttgg aagcactgat 120
cacctgttag cattgccatt cctctactg 149

<210> SEQ ID NO 128
<211> LENGTH: 118
<212> TYPE: DNA
<213> ORGANISM: Homo sapiens

<400> SEQUENCE: 128
cttcctagag gtgtgctata ccatgcgtct gtcgttgtgc ttttttctgt ttttagacca 60
attttttaca gttctttggt aagcattgtc gtatctggtg atggattaac atatagcc 118

<210> SEQ ID NO 129
<211> LENGTH: 34
<212> TYPE: DNA
<213> ORGANISM: Homo sapiens

<400> SEQUENCE: 129
ggccatcagc gccagtgcca ctcgcgccct caag 34

<210> SEQ ID NO 130
<211> LENGTH: 47
<212> TYPE: DNA
<213> ORGANISM: Homo sapiens

<400> SEQUENCE: 130
tcggagcggg tttctccaac cgcaatcggc tccgctcaag gggagga 47

<210> SEQ ID NO 131
<211> LENGTH: 204
<212> TYPE: DNA
<213> ORGANISM: Homo sapiens

<400> SEQUENCE: 131
aaacgtgtcg tctggaatgg gcttgggggc cacgcctgca catctccgcg agacagaggg 60
ataaagtgaa gatggtgctg ttattgttac ctcgagtgcc acatgcgacc tctgagatat 120
gtacacagtc attcttacta tcgcactcag ccattcttac tacgctaaag aagaaataat 180
tattcgagga tatttgcctg gccc 204

<210> SEQ ID NO 132
<211> LENGTH: 96
<212> TYPE: DNA
<213> ORGANISM: Homo sapiens

<400> SEQUENCE: 132
tagtgaatcc cagtcactga gtggagttga gagtctaaga acctctgaaa tttgagaact 60
gctggaccag agcctttaga gctctgataa ggtgtc 96

<210> SEQ ID NO 133
<211> LENGTH: 159
<212> TYPE: DNA
<213> ORGANISM: Homo sapiens

<400> SEQUENCE: 133
tggggataca gggattgcta caatttatca aagaagcttc agaacccatc catgtgagga 60
agtataaagg gcaggtagta gctgtggata catattgctg gcttcacaaa ggagctattg 120
cttgtgctga aaaactagcc aaaggtgaac ctactgata 159

<210> SEQ ID NO 134
<211> LENGTH: 58
<212> TYPE: DNA
<213> ORGANISM: Homo sapiens

<400> SEQUENCE: 134
ctatctcatg ggatcaagcc tattctcgta tttgatggat gtactttacc ttctaaaa 58

<210> SEQ ID NO 135
<211> LENGTH: 83
<212> TYPE: DNA
<213> ORGANISM: Homo sapiens

<400> SEQUENCE: 135
agacgacaag ccaatcttct taagggaaag caacttcttc gtgaggggaa agtctcggaa 60
gctcgagagt gtttcacccg gtc 83

<210> SEQ ID NO 136
<211> LENGTH: 106
<212> TYPE: DNA
<213> ORGANISM: Homo sapiens

<400> SEQUENCE: 136
ctcgtggctc cctatgaagc tgatgcgcag ttggcctatc ttaacaaagc gggaattgtg 60
caagccataa ttacagagga ctcggatctc ctagcttttg gctgta 106

<210> SEQ ID NO 137
<211> LENGTH: 124
<212> TYPE: DNA
<213> ORGANISM: Homo sapiens

<400> SEQUENCE: 137
tgaaattgat caagctcggc taggaatgtg cagacagctt ggggatgtat tcacggaaga 60
gaagtttcgt tacatgtgta ttctttcagg ttgtgactac ctgtcatcac tgcgtgggat 120
tgga 124

<210> SEQ ID NO 138
<211> LENGTH: 151
<212> TYPE: DNA
<213> ORGANISM: Homo sapiens

<400> SEQUENCE: 138
tatcacggta ccagaggatt acatcaacgg gtttattcgg gccaacaata ccttcctcta 60
tcagctagtt tttgatccca tcaaaaggaa acttattcct ctgaacgcct atgaagatga 120
tgttgatcct gaaacactaa gctacgctgg g 151

<210> SEQ ID NO 139
<211> LENGTH: 87
<212> TYPE: DNA
<213> ORGANISM: Homo sapiens

<400> SEQUENCE: 139
tgatgattcc atagctcttc aaatagcact tggaaataaa gatataaata cttttgaaca 60
gatcgatgac tacaatccag acactgc 87

<210> SEQ ID NO 140
<211> LENGTH: 144
<212> TYPE: DNA
<213> ORGANISM: Homo sapiens

<400> SEQUENCE: 140
catagttggg atgacaaaac atgtcaaaag tcagctaatg ttagcagcat ttggcatagg 60
aattactctc ccagaccaga gtcgggtact gtttcagatg ccccacaatt gaaggaaaat 120
ccaagtactg tgggagtgga acga 144

<210> SEQ ID NO 141
<211> LENGTH: 153
<212> TYPE: DNA
<213> ORGANISM: Homo sapiens

<400> SEQUENCE: 141
acctgttgag tcagtattct ctttcattta cgaagaagac caagaaaaat agctctgaag 60
gcaataaatc attgagcttt tctgaagtgt ttgtgcctga cctggtaaat ggacctacta 120
acaaaaagag tgtaagcact ccacctagga cga 153

<210> SEQ ID NO 142
<211> LENGTH: 26
<212> TYPE: DNA
<213> ORGANISM: Homo sapiens

<400> SEQUENCE: 142
gtggtgcagt tgtggttcca gggacc 26

<210> SEQ ID NO 143
<211> LENGTH: 466
<212> TYPE: DNA
<213> ORGANISM: Homo sapiens

<400> SEQUENCE: 143
gcctctggat gaaactgctg tcacagataa agagaacaat ctgcatgaat cagagtatgg 60
agaccaagaa ggcaagagac tggttgacac agatgtagca cgtaattcaa gtgatgacat 120
tccgaataat catattccag gtgatcatat tccagacaag gcaacagtgt ttacagatga 180
agagtcctac tcttttgaga gcagcaaatt tacaaggacc atttcaccac ccactttggg 240
aacactaaga agttgtttta gttggtctgg aggtcttgga gatttttcaa gaacgccgag 300
cccctctcca agcacagcat tgcagcagtt ccgaagaaag agcgattccc ccacctcttt 360
gcctgagaat aatatgtctg atgtgtcgca gttaaagagc gaggagtcca gtgacgatga 420
gtctcatccc ttacgagaag aggcatgttc ttcacagtcc caggaa 466

<210> SEQ ID NO 144
<211> LENGTH: 69
<212> TYPE: DNA
<213> ORGANISM: Homo sapiens

<400> SEQUENCE: 144
tctgattgca atattaagtt acttgacagt caaagtgacc agacctccaa gctacgttta 60
tctcatttc 69

<210> SEQ ID NO 145
<211> LENGTH: 140
<212> TYPE: DNA
<213> ORGANISM: Homo sapiens

<400> SEQUENCE: 145
ggctatataa gtccagttct gcagactctc tttctacaac caagatcaaa cctctaggac 60
ctgccagagc cagtgggctg agcaagaagc cggcaagcat ccagaagaga aagcatcata 120
atgccgagaa caagccgggg 140

<210> SEQ ID NO 146
<211> LENGTH: 86
<212> TYPE: DNA
<213> ORGANISM: Homo sapiens

<400> SEQUENCE: 146
agagataaca tccaactaac tccagaagcg gaagaggata tatttaacaa acctgaatgt 60
ggccgtgttc aaagagcaat attcca 86

<210> SEQ ID NO 147
<211> LENGTH: 28
<212> TYPE: DNA
<213> ORGANISM: Homo sapiens

<400> SEQUENCE: 147
tctcgctgtg tcacaatctc agctcact 28

<210> SEQ ID NO 148
<211> LENGTH: 124
<212> TYPE: DNA
<213> ORGANISM: Homo sapiens

<400> SEQUENCE: 148
ttcctccatc ctaggcagaa ataaagtccc aaatctttgt tttttaacgg gtcatagagg 60
acccatcatc accctttatt cattccttga tcatctcagg ctagagaagt ctagggatac 120
agct 124

<210> SEQ ID NO 149
<211> LENGTH: 65
<212> TYPE: DNA
<213> ORGANISM: Homo sapiens

<400> SEQUENCE: 149
tgtcctggtt catcttagtt aatgtgttct ttgccaaggt gatctaagtt gcctaccttg 60
aattt 65

<210> SEQ ID NO 150
<211> LENGTH: 75
<212> TYPE: DNA
<213> ORGANISM: Homo sapiens

<400> SEQUENCE: 150
accagaggct ggtgactcca gagtacacaa ctcaacacag aaaaggaagg ccagtcagct 60
agtaggcata gaaaa 75

<210> SEQ ID NO 151
<211> LENGTH: 34
<212> TYPE: DNA
<213> ORGANISM: Homo sapiens

<400> SEQUENCE: 151
atttaaatat aataagccag ccttcctcaa gaat 34

<210> SEQ ID NO 152
<211> LENGTH: 29
<212> TYPE: DNA
<213> ORGANISM: Homo sapiens

<400> SEQUENCE: 152
gctctaacca ctgcaaatca tgtttttct 29

<210> SEQ ID NO 153
<211> LENGTH: 42
<212> TYPE: DNA
<213> ORGANISM: Homo sapiens

<400> SEQUENCE: 153
ctctgcaaca catatcctac cttgtctata ccgctaactc tc 42

<210> SEQ ID NO 154
<211> LENGTH: 86
<212> TYPE: DNA
<213> ORGANISM: Homo sapiens

<400> SEQUENCE: 154
catccctcaa catcgcaact gtgttgacct ctattcagct gctcatgtca gaacccaacc 60
ctgatgaccc gctcatggct gacata 86

<210> SEQ ID NO 155
<211> LENGTH: 90
<212> TYPE: DNA
<213> ORGANISM: Homo sapiens

<400> SEQUENCE: 155
tgaacctcct cagatccgat ttctcactcc aatttatcat ccaaacattg attctgctgg 60
aaggatttgt ctggatgttc tcaaattgcc 90

<210> SEQ ID NO 156
<211> LENGTH: 58
<212> TYPE: DNA
<213> ORGANISM: Homo sapiens

<400> SEQUENCE: 156
tggagccaac acaccttatg agaaaggtgt ttttaagcta gaagttatca ttcctgag 58

<210> SEQ ID NO 157
<211> LENGTH: 103
<212> TYPE: DNA
<213> ORGANISM: Homo sapiens

<400> SEQUENCE: 157
agagcttcac gtctgaagag agagctgcac atgttagcca cagagccacc cccaggcatc 60
acatgttggc aagataaaga ccaaatggat gacctgcgag ctc 103

<210> SEQ ID NO 158
<211> LENGTH: 27
<212> TYPE: DNA
<213> ORGANISM: Homo sapiens

<400> SEQUENCE: 158
gtgtgtggtt ccttctactt ggggatc 27

<210> SEQ ID NO 159
<211> LENGTH: 247
<212> TYPE: DNA
<213> ORGANISM: Homo sapiens

<400> SEQUENCE: 159
tcccgcgctg cgcttgaaaa tcgcgcgcgg ccccgcggcc agcctgggta ggggcaaggc 60
gcagccaatg ggaagggtcg gaggcatggc acagccaatg ggaagggccg gggcaccaaa 120
gccaatggga agggccggga gcgcgcggcg cgggagattt aaaggctgct ggagtgaggg 180
gtcgcccgtg caccctgtcc cagccgtcct gtcctggctg ctcgctctgc ttcgctgcgc 240
ctccact 247

<210> SEQ ID NO 160
<211> LENGTH: 27
<212> TYPE: DNA
<213> ORGANISM: Homo sapiens

<400> SEQUENCE: 160
agctgcagct ctcgccgctg aaggggc 27

<210> SEQ ID NO 161
<211> LENGTH: 44
<212> TYPE: DNA
<213> ORGANISM: Homo sapiens

<400> SEQUENCE: 161
gacccgcgtc ctggccagca agaccgcgag gaggatcttc cagg 44

<210> SEQ ID NO 162
<211> LENGTH: 125

<212> TYPE: DNA
<213> ORGANISM: Homo sapiens

<400> SEQUENCE: 162
tctgctgcga cccacggagt gcgacgggac agccacgttt tcacatcggg ccccgtgaaa 60
ttgccgccaa tggaaaggac ttggtccaga aaaacgttag tttcatatgg ttcgcccggt 120
actta 125

<210> SEQ ID NO 163
<211> LENGTH: 33
<212> TYPE: DNA
<213> ORGANISM: Homo sapiens

<400> SEQUENCE: 163
gctgcccccg gcgtggagga tgagccgctg ctg 33

<210> SEQ ID NO 164
<211> LENGTH: 86
<212> TYPE: DNA
<213> ORGANISM: Homo sapiens

<400> SEQUENCE: 164
cccgccgctt tgtcatcttc cccatcgagt accatgatat ctggcagatg tataagaagg 60
cagaggcttc cttttggacc gccgag 86

<210> SEQ ID NO 165
<211> LENGTH: 30
<212> TYPE: DNA
<213> ORGANISM: Homo sapiens

<400> SEQUENCE: 165
atcggaggac cccagaagac ccctgcaggg 30

<210> SEQ ID NO 166
<211> LENGTH: 26
<212> TYPE: DNA
<213> ORGANISM: Homo sapiens

<400> SEQUENCE: 166
cccgaggaga gatattttat atccca 26

<210> SEQ ID NO 167
<211> LENGTH: 204
<212> TYPE: DNA
<213> ORGANISM: Homo sapiens

<400> SEQUENCE: 167
tgacgatctg aggtcgaact agttcgcttt cctcgtcttg tatgtttttc catgctgagt 60
gcatctgtgt gtgtaagctg ggttttatat tacatggcat ttcctgtttt gtaacacttt 120
gcagttcttt cttatggtat tttcccgact ctagagaagc tgagacaata ttaagtggta 180
gcaatgtgat gactctttgt ggcc 204

<210> SEQ ID NO 168
<211> LENGTH: 41
<212> TYPE: DNA
<213> ORGANISM: Homo sapiens

<400> SEQUENCE: 168
agtcttctta ttgacactta cataaaagat cccaaagaaa g 41

<210> SEQ ID NO 169
<211> LENGTH: 282
<212> TYPE: DNA
<213> ORGANISM: Homo sapiens

<400> SEQUENCE: 169
ccctgctgta ctggactatg ttttactgtc tgtagaccct gaagctcaat atgaactaca 60
gaatacccaa acttgtatta atgtaaatca agtgttgagg tttttaaaag aacactggag 120
ggaaaaactg accagtaaaa ataaaacatt tcggtgtgag ttcttccttt aggaagagga 180
ttggcaaata cttgaatttg gcctttgtcc cagagctctt atctagcagt tggtaatcgg 240
aggtctttta ctgtaatgct tcaattgctg ataccgtatg tg 282

<210> SEQ ID NO 170
<211> LENGTH: 59
<212> TYPE: DNA
<213> ORGANISM: Homo sapiens

<400> SEQUENCE: 170
aacgatgcct tgtgtcaaga agaaggcaga ctgggccttg cgctggattg gggacaaag 59

<210> SEQ ID NO 171
<211> LENGTH: 28
<212> TYPE: DNA
<213> ORGANISM: Homo sapiens

<400> SEQUENCE: 171
tcgatattct ggctcaagaa acgaggac 28

<210> SEQ ID NO 172
<211> LENGTH: 68
<212> TYPE: DNA
<213> ORGANISM: Homo sapiens

<400> SEQUENCE: 172
caactcgggc atgctcttgt gttcactgac ggggacctga gatgctagat ggcatatatc 60
cacattta 68

<210> SEQ ID NO 173
<211> LENGTH: 28
<212> TYPE: DNA
<213> ORGANISM: Homo sapiens

<400> SEQUENCE: 173
acacctggta cacaaaccat cggaggag 28

<210> SEQ ID NO 174
<211> LENGTH: 81
<212> TYPE: DNA
<213> ORGANISM: Homo sapiens

<400> SEQUENCE: 174
gctcattggg atgaattgca ctctaatgaa gcaatacatt gagtttgtgg cagacagact 60
tatgctggaa ctgggtttta g 81

<210> SEQ ID NO 175
<211> LENGTH: 135
<212> TYPE: DNA
<213> ORGANISM: Homo sapiens

<400> SEQUENCE: 175
agtagagaac ccatttgact ttatggagaa tatttcactg gaaggaaaga ctaacttctt 60
tgagaagaga gtaggcgagt atcagaggat gggagtgatg tcaagtccaa cagagaattc 120
ttttaccttg gatgc 135

<210> SEQ ID NO 176
<211> LENGTH: 168
<212> TYPE: DNA
<213> ORGANISM: Homo sapiens

<400> SEQUENCE: 176
tgaagatgtg cccttacttg gctgattttt tttttccatc tcataagaaa aatcagctga 60
agtgttacca actagccaca ccatgaattg tccgtaatgt tcattaacag catctttaaa 120
actgtgtagc tacctcacaa ccagtcctgt ctgtttatag tgctggta 168

<210> SEQ ID NO 177
<211> LENGTH: 89
<212> TYPE: DNA
<213> ORGANISM: Homo sapiens

<400> SEQUENCE: 177
ctttagtgag cttagcacag cgggattaaa cagtccttta accagcacag ccagttaaaa 60
gatgcagcct cactgcttca acgcagatt 89

<210> SEQ ID NO 178
<211> LENGTH: 1311
<212> TYPE: DNA
<213> ORGANISM: Homo sapiens

<400> SEQUENCE: 178
agtcagtcct gtgtatacct agatattagt cagttggtgc cagatagaag acaggttgtg 60
tttttatcct gtggcttgtg tagtgtcctg ggattctctg ccccctctga gtagagtgtt 120
gtgggataaa ggaatctctc agggcaagga gcttcttaag ttaaatcact agaaatttag 180
gggtgatctg ggccttcata tgtgtgagaa gccgtttcat tttatttctc actgtatttt 240
cctcaacgtc tggttgatga gaaaaaattc ttgaagagtt ttcatatgtg ggagctaagg 300
tagtattgta aaatttcaag tcatccttaa acaaaatgat ccacctaaga tcttgcccct 360
gttaagtggt gaaatcaact agaggtggtt cctacaagtt gttcattcta gttttgtttg 420
gtgtaagtag gttgtgtgag ttaattcatt tatatttact atgtctgtta aatcagaaat 480
tttttattat ctatgttctt ctagatttta cctgtagttc atacttcagt cacccagtgt 540
cttattctgg cattgtctaa atctgagcat tgtctagggg gatcttaaac tttagtagga 600
aaccatgagc tgttaataca gtttccattc aaatattaat ttcagaatga aacataattt 660 ttttttttt ttttgagatg gagtctcgct ctgttgccca ggctggagtg cagtggcgcg 720
attttggctc actgtaacct ccatctcctg ggttcaagca attctcctgt ctcagcctcc 780
ctagtagctg ggactgcagg tatgtgctac cacacctggc taattttgt atttttagta 840 gagatggagt ttcaccatat tggtcaggct ggtcttgaac tcctgacctc aggtgatcca 900
cccacctcgg cctcccaaag tgctgggatt gcaggcgtga taaacaaata ttcttaatag 960
ggctactttg aattaatctg cctttatgtt tgggagaaga aagctgagac attgcatgaa 1020
agatgatgag agataaatgt tgatcttttg gccccatttg ttaattgtat tcagtatttg 1080
aacgtcgtcc tgtttattgt tagttttctt catcatttat tgtatagaca atttttaaat 1140
ctctgtaata tgatacattt tcctatcttt taagttattg ttacctaaag ttaatccaga 1200
ttatatggtc cttatatgtg tacaacatta aaatgaaagg ctttgtcttg cattgtgagg 1260
tacaggcgga agttggaatc aggttttagg attctgtctc tcattagctg a 1311

<210> SEQ ID NO 179
<211> LENGTH: 43
<212> TYPE: DNA
<213> ORGANISM: Homo sapiens

<400> SEQUENCE: 179
gtctcaaaat tgaataatgc acaagtctta agtgattaaa ata 43

<210> SEQ ID NO 180
<211> LENGTH: 171
<212> TYPE: DNA
<213> ORGANISM: Homo sapiens

<400> SEQUENCE: 180
tgagcaccca aaggccggcc ctagagtcca ggagaagagc gcagcggcgc ggagctccca 60
ggcgttcccc gcagcgcgtc ctcggtcctg gaaccaccgc gccgcgcgtc ctggcttcca 120
catctgcccc atttgcccgc ggatcttgac tttttcttgg cgggcaaggc c 171

<210> SEQ ID NO 181
<211> LENGTH: 119
<212> TYPE: DNA
<213> ORGANISM: Homo sapiens

<400> SEQUENCE: 181
gagagccagg cgctaaccag ccgctctgcg ccccgcgccc tgcttgcccc cattatccag 60
ccttgccccg gcgccctgac ctgacgccct ggcctgacgc cctgcttcgt cgcctcctt 119

<210> SEQ ID NO 182
<211> LENGTH: 34
<212> TYPE: DNA
<213> ORGANISM: Homo sapiens

<400> SEQUENCE: 182
tgctggacca gggactgagc gtcccccgga gagg 34

<210> SEQ ID NO 183
<211> LENGTH: 36
<212> TYPE: DNA
<213> ORGANISM: Homo sapiens

<400> SEQUENCE: 183
ttggaagttg ttcaacgaga ttttgacctc cgaagg 36

<210> SEQ ID NO 184
<211> LENGTH: 308
<212> TYPE: DNA
<213> ORGANISM: Homo sapiens

<400> SEQUENCE: 184
caaacctggg gcgttagctc aactcttgcc cccctgctga aggagaccaa aacaatgctt 60
gatcaggaaa caccatctgg ctttgccccc aggattctgt gactgccctg gggagggcgc 120
agtgacctgc caaccaaaat tggtacaatt gtaaacagcc acagaaatgc ttaaatgcaa 180
tatcatttct atgaaattaa cgtgtttcca ttccattcca gccaccaaaa ttgcccgttt 240
gagctcagcc ctcaaaacaa agatgcctgt gtggctttgc ccaacgttgg gtcactgttt 300

```
tctgcata                                                                     308

<210> SEQ ID NO 185
<211> LENGTH: 30
<212> TYPE: DNA
<213> ORGANISM: Homo sapiens

<400> SEQUENCE: 185

atgcccaata tatttcttgt ttctgatatt                                              30

<210> SEQ ID NO 186
<211> LENGTH: 32
<212> TYPE: DNA
<213> ORGANISM: Homo sapiens

<400> SEQUENCE: 186

cgttgaaggg caagattaag aaggaaagct cc                                           32

<210> SEQ ID NO 187
<211> LENGTH: 148
<212> TYPE: DNA
<213> ORGANISM: Homo sapiens

<400> SEQUENCE: 187

aagagggagc tgctttccga cactgcccat ctgaacgaga cccactgcgc ccgctgcctg             60

cagccctacc agctgcttgt gaatagcaaa aggcagtgcc tggaatgtgg cctcttcacc           120

tgcaaaagct gtggccgcgt ccacccgg                                              148

<210> SEQ ID NO 188
<211> LENGTH: 90
<212> TYPE: DNA
<213> ORGANISM: Homo sapiens

<400> SEQUENCE: 188

agtcgtgaag atcggctcac tggagtggta ctatgagcat gtgaaagccc gcttcaagag             60

gttcggaagt gccaaggtca tccggtccct                                              90

<210> SEQ ID NO 189
<211> LENGTH: 50
<212> TYPE: DNA
<213> ORGANISM: Homo sapiens

<400> SEQUENCE: 189

agtggagagt aagaacggct ttttgttccc aggcatttta ggaatattaa                        50

<210> SEQ ID NO 190
<211> LENGTH: 272
<212> TYPE: DNA
<213> ORGANISM: Homo sapiens

<400> SEQUENCE: 190

atgggtgggt aggtgaatac atggatggat gagccactga ttgagtgggt ggatgggtgg             60

atgaatagat gggtggagga tagataggtg ggtgtatggg tgggtggatg gattgatgca            120

tggatggatg ggctgcccat tgagtaggtg gatgagtgga taaatgggtg ggtgggtagg            180

tgaatagatg aatagattga taaatagggg gatgggtgga ttggtagatg ggtagatgga            240

gggatacatt gctgtgtgga taggtgggtg aa                                          272

<210> SEQ ID NO 191
```

<211> LENGTH: 27
<212> TYPE: DNA
<213> ORGANISM: Homo sapiens

<400> SEQUENCE: 191
ggatgggtgg atgggctgac aaatggc 27

<210> SEQ ID NO 192
<211> LENGTH: 82
<212> TYPE: DNA
<213> ORGANISM: Homo sapiens

<400> SEQUENCE: 192
ctgggcctga actgatatct gaagagagaa gtggagacag cgaccagaca gatgaggatg 60
gagaacctgg ctcagaggcc ca 82

<210> SEQ ID NO 193
<211> LENGTH: 61
<212> TYPE: DNA
<213> ORGANISM: Homo sapiens

<400> SEQUENCE: 193
aaaaagcgcc tcctctccgt ccacgacttc gacttcgagg gagactcaga tgactccact 60
c 61

<210> SEQ ID NO 194
<211> LENGTH: 69
<212> TYPE: DNA
<213> ORGANISM: Homo sapiens

<400> SEQUENCE: 194
tctgggtgcc actcccatcc ggaagagcag ccgaccagca tctcaccttc cagacacggc 60
gccctggct 69

<210> SEQ ID NO 195
<211> LENGTH: 34
<212> TYPE: DNA
<213> ORGANISM: Homo sapiens

<400> SEQUENCE: 195
ggtcgaatgt catcaggaat gagcagctgc ccct 34

<210> SEQ ID NO 196
<211> LENGTH: 69
<212> TYPE: DNA
<213> ORGANISM: Homo sapiens

<400> SEQUENCE: 196
ccgatgtgga cacctctgat gaggaaagca tccgggctca cgtgatggcc tcccaccatt 60
ccaagcgga 69

<210> SEQ ID NO 197
<211> LENGTH: 80
<212> TYPE: DNA
<213> ORGANISM: Homo sapiens

<400> SEQUENCE: 197
atctttgagc tgaataagca tatttcagct gtggaatgcc tgctgaccta cctggagaac 60
acagttgtgc ctcccttggc 80

<210> SEQ ID NO 198
<211> LENGTH: 186
<212> TYPE: DNA
<213> ORGANISM: Homo sapiens

<400> SEQUENCE: 198
gtcattcccg atctttccac cgagggcctc tgtgatttgg gggctttgtc aggaaagtgg 60
agcctcacgg aaaagcatac tggctaaaac acgcggcttc ttcatcgact caatctaatc 120
atccccttgg tgttcgtctg tgagacccca ggcagccagc cctgtcgatc tgtctcaata 180
ggcttc 186

<210> SEQ ID NO 199
<211> LENGTH: 30
<212> TYPE: DNA
<213> ORGANISM: Homo sapiens

<400> SEQUENCE: 199
gtgctggagt gcgcacggag gccgatgtag 30

<210> SEQ ID NO 200
<211> LENGTH: 48
<212> TYPE: DNA
<213> ORGANISM: Homo sapiens

<400> SEQUENCE: 200
aggaggaggc cctgaggagg aagctggagg agctgaccag caacgtca 48

<210> SEQ ID NO 201
<211> LENGTH: 78
<212> TYPE: DNA
<213> ORGANISM: Homo sapiens

<400> SEQUENCE: 201
caggagacct cgtccgagga ggaggaagcc aaggacgaaa aggcagagcc caacagggac 60
aaatcagttg ggcctctc 78

<210> SEQ ID NO 202
<211> LENGTH: 30
<212> TYPE: DNA
<213> ORGANISM: Homo sapiens

<400> SEQUENCE: 202
ggcacggctg cccatcaaac caacagacag 30

<210> SEQ ID NO 203
<211> LENGTH: 88
<212> TYPE: DNA
<213> ORGANISM: Homo sapiens

<400> SEQUENCE: 203
ctggggaccc cgtccagtac aacaggacca cagatgagga gctgtcagag ctggaggaca 60
gagtggcagt gacggcctca gaagtcca 88

<210> SEQ ID NO 204
<211> LENGTH: 62
<212> TYPE: DNA
<213> ORGANISM: Homo sapiens

<400> SEQUENCE: 204
attgaatcca ggattgcagc cctgagggcc gcagggctca cggtgaagcc ctcgggaaag 60
cc 62

<210> SEQ ID NO 205
<211> LENGTH: 129
<212> TYPE: DNA
<213> ORGANISM: Homo sapiens

<400> SEQUENCE: 205
tctttatgag gggactctga gcctctgctc tgaggatctg aaacacacac accctgacag 60
tgtaaaatcc aaaaggagcc gcctgaatca tgttgcctca tgtggaaatc cttagtccgc 120
cgccacgtg 129

<210> SEQ ID NO 206
<211> LENGTH: 288
<212> TYPE: DNA
<213> ORGANISM: Homo sapiens

<400> SEQUENCE: 206
aagaccacac accagtgcag tgtgatgggc ctttctgctg cttcattagt gtgaggattt 60
ccagggccac agtgaggaag aatgttaatg ccagtgccag agcaaaggag aaagaagttg 120
gcaaaactgt tgatttgcat gacagctgaa atgtaaatac tttttaaaaa atatgtgatg 180
tggaagcttc ttaaaagggg atatgtccat ttttttctac cttttaaatt tctgaggagg 240
ccaaggcact tgtttgggct aagtatgtga ttgataaagc accatccc 288

<210> SEQ ID NO 207
<211> LENGTH: 58
<212> TYPE: DNA
<213> ORGANISM: Homo sapiens

<400> SEQUENCE: 207
atgatgattc ttttgatcgg aaatcagtgt accgaggctc gctgacacag agaaaccc 58

<210> SEQ ID NO 208
<211> LENGTH: 99
<212> TYPE: DNA
<213> ORGANISM: Homo sapiens

<400> SEQUENCE: 208
aggagtggcc ccaaccaatg tgatcagtcg caggaggcaa ccaatcagag gctgaaggga 60
agttacaaag ttacacatga agacttggcc gatgaccag 99

<210> SEQ ID NO 209
<211> LENGTH: 25
<212> TYPE: DNA
<213> ORGANISM: Homo sapiens

<400> SEQUENCE: 209
aaacctgtgg tggcccacca gtcct 25

<210> SEQ ID NO 210
<211> LENGTH: 77
<212> TYPE: DNA
<213> ORGANISM: Homo sapiens

<400> SEQUENCE: 210
acagagcagc cctgcactgt tttccctcca ccacagccat cctgtccctc attggctctg 60
tgctttccac tatacac 77

-continued

<210> SEQ ID NO 211
<211> LENGTH: 1156
<212> TYPE: DNA
<213> ORGANISM: Homo sapiens

<400> SEQUENCE: 211
cacctgcaag tggacagcga cattcagtcc tgcactgctc acctgggttt actgatgact 60
cctggctgcc ccaccatcct ctctgatctg tgagaaacag ctaagctgct gtgacttccc 120
tttaggacaa tgttgtgtaa atctttgaag gacacaccga agacctttat actgtgatct 180
tttacccctt tcactcttgg ctttcttatg ttgctttcat gaatggaatg gaaaaaagat 240
gactcagtta aggcaccagc catatgtgta ttcttgatgg tctatatcgg ggtgtgagca 300
gatgtttgcg tatttcttgt gggtgtgact ggatattaga catccggaca agtgactgaa 360
ctaatgatct gctgaataat gaaggaggaa tagacacccc agtccccacc ctacgtgcac 420
ccgctctgca agttcccatg tgatctgtag accaggggaa attacactgc ggtcaagggc 480
agagcctgca catgacagca agtgagcatt tgatagatgc tcagatgcta gtgcagagag 540
cctgctggga gacgaagaga cagcaggcag agctccagat gggcaaggaa gaggcttggt 600
tctagcctgg ctctgcccct cactgcagtg gatccagtgg ggcagaggac agagggtcac 660
aaccaatgag ggatgtctgc caaggatggg ggtgcagagg ccacaggagt cagcttgcca 720
ctcgcccatt ggttacatag atgatctctc agacaggctg ggactcagag ttatttccta 780
gtatcggtgt gccccatcca gttttaagtg gagccctcca agactctcca gagctgcctt 840
tgaacatcct aacagtaatc acatctcacc ctccctgagg ttcactttag acaggaccca 900
atggctgcac tgcctttgtc agagggggtg ctgagaggag tggcttcttt tagaatcaaa 960
cagtagagac aagagtcaag ccttgtgtct tcaagcattg accaagttaa gtgtttcctt 1020
ccctctctca ataagacact tccaggagct ttccaatctc tcacttaaaa ctaaggtttg 1080
aatctcaaag tgttgctggg aggctgatac tcctgcaact tcaggagacc tgtgagcaca 1140
cattagcagc tgtttc 1156

<210> SEQ ID NO 212
<211> LENGTH: 71
<212> TYPE: DNA
<213> ORGANISM: Homo sapiens

<400> SEQUENCE: 212
ccaggagtgg agcccggacg cccgagcctt cctgcttcgg gatggggatt accgcggagc 60
cttagcaact g 71

<210> SEQ ID NO 213
<211> LENGTH: 71
<212> TYPE: DNA
<213> ORGANISM: Homo sapiens

<400> SEQUENCE: 213
atcctggctg gctcaaaatt ccctctagat tacctgcgac cacccccagg aacccggaga 60
ctgaaactcc t 71

<210> SEQ ID NO 214
<211> LENGTH: 98
<212> TYPE: DNA
<213> ORGANISM: Homo sapiens

<400> SEQUENCE: 214
cctgcagtcc ggagacgaac gcacggaccg ggcctccgga ggcaggttcg gctggaagga 60
accgctctcg cttcgtccta cacttgcgca aatgtctc 98

<210> SEQ ID NO 215
<211> LENGTH: 112
<212> TYPE: DNA
<213> ORGANISM: Homo sapiens

<400> SEQUENCE: 215
gctttgtgca gtggccattt catagccagt gaagtttatc tgaggcactt gctaattgaa 60
aacttttctc aataccctgc catgatgaaa tatggttggc actggcaatt tt 112

<210> SEQ ID NO 216
<211> LENGTH: 114
<212> TYPE: DNA
<213> ORGANISM: Homo sapiens

<400> SEQUENCE: 216
atgtccaagt cccgtgcggc ggaggcagca gcgggggtga cagcgacggc cccgagcccg 60
cagatagtgg agcagagggg tccagggagg cgctgcaccg acgttgggga gaat 114

<210> SEQ ID NO 217
<211> LENGTH: 32
<212> TYPE: DNA
<213> ORGANISM: Homo sapiens

<400> SEQUENCE: 217
ttcaggagga gaactccgtt acacgtcacg aa 32

<210> SEQ ID NO 218
<211> LENGTH: 376
<212> TYPE: DNA
<213> ORGANISM: Homo sapiens

<400> SEQUENCE: 218
aaaacctccg gcctcgtctt gtgattccac caatgcagcc atcgccaagc aagccttgaa 60
atagcccatc aagggcaaac aggcccccga aaaaaagctc aaggaaaagt cgcaaactca 120
cggatttcta ccctgtccca aggagctcca ggaagggcaa agcggagctg caatttgaag 180
aaagggaaag aatagatgaa ttggttgaaa gcggaaagga aagaaggagt gaagactgac 240
ctcatcaatg acaaaggccg ggtgtgaaca ccagagggag ctctcccggg gcgcctttgt 300
ggtagaaaag caccggagcc tcacggagat caccgacgcc acgggacccc tccatggtgg 360
atctccgtgg atctcc 376

<210> SEQ ID NO 219
<211> LENGTH: 29
<212> TYPE: DNA
<213> ORGANISM: Homo sapiens

<400> SEQUENCE: 219
gttgaacgtt ttgtgcttcc catgcatgc 29

<210> SEQ ID NO 220
<211> LENGTH: 242
<212> TYPE: DNA
<213> ORGANISM: Homo sapiens

<400> SEQUENCE: 220
tgctccactt atcgggctca ccaaatacag ctgcagtatg aattccatct tctacacaac 60
agtaaaccag aatgttcatg ttcacagcgt tcatctccca tcctgttgtc taacgcacat 120
ggttttttta aacttttcta agattgcatg agattctgca acacaactga ttataaaaac 180
acttgaagtt tttacctttt tttttacttt ccaactctcg tgaatgtaca gaggactttc 240
ca 242

<210> SEQ ID NO 221
<211> LENGTH: 296
<212> TYPE: DNA
<213> ORGANISM: Homo sapiens

<400> SEQUENCE: 221
caggggagaa taagctgaac gcagctgttc tctgaccttg aggcagaggg caaggagtag 60
gtacaaggac gtgtaggaga atttatctta aataggcttg ttcacttgtg ttgtccagaa 120
acgacttttg atcatcagcg cgcatgactg ctccctgaaa ggaagaacaa taatgttaat 180
tacccgcaga ctgtgtttgc tccaggcttt cggcattatg tctgtactga ataaaagcaa 240
gcagctccag ctgttcgagg ctgctctctt cttcagccat tagtgccggg cagccc 296

<210> SEQ ID NO 222
<211> LENGTH: 107
<212> TYPE: DNA
<213> ORGANISM: Homo sapiens

<400> SEQUENCE: 222
agcttactca catagcatat tggtatatca aaatgaaatg caaggaacca aaaataacat 60
aattgaaggc agtaaaagtg aaattaaata ggaagatcat cagtcaa 107

<210> SEQ ID NO 223
<211> LENGTH: 132
<212> TYPE: DNA
<213> ORGANISM: Homo sapiens

<400> SEQUENCE: 223
gagcttcagg aaaagactta atctgaagga tcctgcagct aaaaagcttt gaaaactgtg 60
ttaaggggcc ccataagcat cgcttctaaa cttcactgac aaaagggact ggggtcatgc 120
tgtctggagt ca 132

<210> SEQ ID NO 224
<211> LENGTH: 25
<212> TYPE: DNA
<213> ORGANISM: Homo sapiens

<400> SEQUENCE: 224
tgtatttcag caggtcttct tgaaa 25

<210> SEQ ID NO 225
<211> LENGTH: 308
<212> TYPE: DNA
<213> ORGANISM: Homo sapiens

<400> SEQUENCE: 225
tccagttttc ctgacagctt gtatagatta ttgcctgaat ttctctaaaa caaccaagct 60
ttcatttaag tgtcaaaaat tattttattt ctttacagta attttaattt ggatttcagt 120
ccttgcttat gttttgggag acccagccat ctaccaaagc ctgaaggcac agaatgctta 180
ttctcgtcac tgtcctttct atgtcagcat tcagagttac tggctgtcat tttcatggt 240 gatgatttta tttgtagctt tcataacctg ttgggaagaa gttactactt tggtacaggc 300
tatcagga 308

<210> SEQ ID NO 226
<211> LENGTH: 76
<212> TYPE: DNA
<213> ORGANISM: Homo sapiens

<400> SEQUENCE: 226
tgttttactt aaagttcaga ttccagcata tattgagatg aatattccct ggttatactt 60
tgtcaatagt tttctc 76

<210> SEQ ID NO 227
<211> LENGTH: 108
<212> TYPE: DNA
<213> ORGANISM: Homo sapiens

<400> SEQUENCE: 227
aaagacattg gattaccttt ggatccattt gtcaactgga agtgctgctt cattccactt 60
acaattccta atcttgagca aattgaaaag cctatatcaa taatgatt 108

<210> SEQ ID NO 228
<211> LENGTH: 60
<212> TYPE: DNA
<213> ORGANISM: Homo sapiens

<400> SEQUENCE: 228
gttacagctg tcataagatc ataattttat gaacagaaag aactcaggac atattaaaaa 60

<210> SEQ ID NO 229
<211> LENGTH: 256
<212> TYPE: DNA
<213> ORGANISM: Homo sapiens

<400> SEQUENCE: 229
ccctgactga tagcatttca gaatgtgtct tttgaagggc tatgatacca gttattaaat 60
agtgttttat tttaaaaaca aaataattcc aagaagtttt tatagttatt cagggacact 120
atattacaaa tattactttg ttattaacac aaaaagtgat aagagttaac atttggctat 180
actgatgttt gtgttactca aaaaaactac tggatgcaaa ctgttatgta aatctgagat 240
ttcactgaca acttta 256

<210> SEQ ID NO 230
<211> LENGTH: 25
<212> TYPE: DNA
<213> ORGANISM: Homo sapiens

<400> SEQUENCE: 230
gtgcggggtt taaatctgag gctag 25

<210> SEQ ID NO 231
<211> LENGTH: 42
<212> TYPE: DNA
<213> ORGANISM: Homo sapiens

<400> SEQUENCE: 231
ctcttctcgg cgtgctgcgg cggaacggct gttggtttct gc 42

<210> SEQ ID NO 232
<211> LENGTH: 44

<212> TYPE: DNA
<213> ORGANISM: Homo sapiens

<400> SEQUENCE: 232
gtaggtcctt ggctggtcgg gcctccggtg ttctgcttct cccc 44

<210> SEQ ID NO 233
<211> LENGTH: 151
<212> TYPE: DNA
<213> ORGANISM: Homo sapiens

<400> SEQUENCE: 233
agccgcttcg gactgcgaac taacgcggcc ttcttagctg ctgcctgctc tccctgcctc 60
gcctgcggga gcctcccgag cgggagaggg ccgcaggagc gatttgggga ggaaggtggg 120
aggggactca ccaagagagc gccgaggtgg g 151

<210> SEQ ID NO 234
<211> LENGTH: 125
<212> TYPE: DNA
<213> ORGANISM: Homo sapiens

<400> SEQUENCE: 234
tgctgaaaat aaggcgaaga tcaacatggc aggcgcaaag cgcgttccta cggcccctgc 60
tgcaacctcc aagcccggac tgaggccaag aacagctctt ggggacattg gtaacaaagt 120
cagtg 125

<210> SEQ ID NO 235
<211> LENGTH: 43
<212> TYPE: DNA
<213> ORGANISM: Homo sapiens

<400> SEQUENCE: 235
aagcaaaacc ttcagctact ggaaaagtca ttgataaaaa act 43

<210> SEQ ID NO 236
<211> LENGTH: 108
<212> TYPE: DNA
<213> ORGANISM: Homo sapiens

<400> SEQUENCE: 236
actggaaaca tgagagccat cctaattgac tggctagtac aggttcaaat gaaattcagg 60
ttgttgcagg agaccatgta catgactgtc tccattattg atcggttc 108

<210> SEQ ID NO 237
<211> LENGTH: 126
<212> TYPE: DNA
<213> ORGANISM: Homo sapiens

<400> SEQUENCE: 237
tgtgactgac aacacttata ctaagcacca aatcagacag atggaaatga agattctaag 60
agctttaaac tttggtctgg gtcggcctct acctttgcac ttccttcgga gagcatctaa 120
gattgg 126

<210> SEQ ID NO 238
<211> LENGTH: 68
<212> TYPE: DNA
<213> ORGANISM: Homo sapiens

<400> SEQUENCE: 238

-continued tgatgtcgag caacatactt tggccaaata cctgatggaa ctaactatgt tggactatga 60
catggtgc 68

<210> SEQ ID NO 239
<211> LENGTH: 93
<212> TYPE: DNA
<213> ORGANISM: Homo sapiens

<400> SEQUENCE: 239
aacattacct gtcatatact gaagaatctc ttcttccagt tatgcagcac ctggctaaga 60
atgtagtcat ggtaaatcaa ggacttacaa agc 93

<210> SEQ ID NO 240
<211> LENGTH: 75
<212> TYPE: DNA
<213> ORGANISM: Homo sapiens

<400> SEQUENCE: 240
tcaagaacaa gtatgccaca tcgaagcatg ctaagatcag cactctacca cagctgaatt 60
ctgcactagt tcaag 75

<210> SEQ ID NO 241
<211> LENGTH: 29
<212> TYPE: DNA
<213> ORGANISM: Homo sapiens

<400> SEQUENCE: 241
aaacttgagt tggagtacta tatttacaa 29

<210> SEQ ID NO 242
<211> LENGTH: 35
<212> TYPE: DNA
<213> ORGANISM: Homo sapiens

<400> SEQUENCE: 242
attactgttg catttacttt taataaagct tgtgg 35

<210> SEQ ID NO 243
<211> LENGTH: 158
<212> TYPE: DNA
<213> ORGANISM: Homo sapiens

<400> SEQUENCE: 243
cctggggatc caattgatgt atatgtttat atactgggtt cttgttttat atacctggct 60
tttactttat taatatgagt tactgaaggt gatggaggta tttgaaaatt ttacttccat 120
aggacatact gcatgtaagc caagtcatgg agaatctg 158

<210> SEQ ID NO 244
<211> LENGTH: 293
<212> TYPE: DNA
<213> ORGANISM: Homo sapiens

<400> SEQUENCE: 244
cccgggcagc gttcatagct cctgcccggg cgggcgcgcg gcggcggcgg cagaggcggc 60
tgagcctgag cggggatgta gaggcggcgg cagcagaggc ggcactggcg gcaagagcag 120
acgcccgagc cgagcgagaa gagcggcaga gccttatccc ctgaagccgg gccccgcgtc 180
ccagccctgc ccagcccgcg cccagccatg cgcgccgcct gctgagtccg ggcgccgcac 240
gctgagccct ccgcccgcga gccgcgctca gctcgggggt gattagttgc ttt 293

<210> SEQ ID NO 245
<211> LENGTH: 53
<212> TYPE: DNA
<213> ORGANISM: Homo sapiens

<400> SEQUENCE: 245
agttcgctgc aagtcggcgg aaagtttggc tgcgcgggtt cccccgaagt tca 53

<210> SEQ ID NO 246
<211> LENGTH: 54
<212> TYPE: DNA
<213> ORGANISM: Homo sapiens

<400> SEQUENCE: 246
cctcatcctc gcagtagctg ggtctctccc agggacgccc ctagtcagcc ttgg 54

<210> SEQ ID NO 247
<211> LENGTH: 132
<212> TYPE: DNA
<213> ORGANISM: Homo sapiens

<400> SEQUENCE: 247
gtaattatgg aattttgctt gggaaattaa tttgaaaaag ttaattaatt ggtggttccg 60
gaggtggcgg gctccacgcc cggccagtct tgctgacgtc agtgctgacc cactggagac 120
gtgcagcttc cg 132

<210> SEQ ID NO 248
<211> LENGTH: 36
<212> TYPE: DNA
<213> ORGANISM: Homo sapiens

<400> SEQUENCE: 248
ggggtctgtg acagcttgcc cccaaccacg gagagg 36

<210> SEQ ID NO 249
<211> LENGTH: 25
<212> TYPE: DNA
<213> ORGANISM: Homo sapiens

<400> SEQUENCE: 249
ttgtccaggg tggtctcaaa actcc 25

<210> SEQ ID NO 250
<211> LENGTH: 91
<212> TYPE: DNA
<213> ORGANISM: Homo sapiens

<400> SEQUENCE: 250
ctgagcagcg aggcccacca ggcatctctg ttgtgggcag cagggccagg tcctggtctg 60
tggaccctcg gcagttggca ggctccctct g 91

<210> SEQ ID NO 251
<211> LENGTH: 28
<212> TYPE: DNA
<213> ORGANISM: Homo sapiens

<400> SEQUENCE: 251
gctcccagga tgccggcggc agtagcag 28

<210> SEQ ID NO 252

<211> LENGTH: 45
<212> TYPE: DNA
<213> ORGANISM: Homo sapiens

<400> SEQUENCE: 252
caggagcagc agacaagagt gcagtggtgg ctgccgccgc accag 45

<210> SEQ ID NO 253
<211> LENGTH: 66
<212> TYPE: DNA
<213> ORGANISM: Homo sapiens

<400> SEQUENCE: 253
cccgagcgtc ggaacaagag cggtatcatc agtgagcccc tcaacaagag cctgcgccgc 60
tcccgc 66

<210> SEQ ID NO 254
<211> LENGTH: 405
<212> TYPE: DNA
<213> ORGANISM: Homo sapiens

<400> SEQUENCE: 254
ccatggcggt ggacaaaagc aaccctacct caaagcacaa aagtggtgct gtggccagcc 60
tgctgagcaa ggcagagcgg gccacggagc tggcagccga gggacagctg acgctgcagc 120
agtttgcgca gtccacagag atgctgaagc gcgtggtgca ggagcatctc ccgctgatga 180
gcgaggcggg tgctggcctg cctgacatgg aggctgtggc aggtgccgaa gccctcaatg 240
gccagtccga cttcccctac ctgggcgctt tccccatcaa cccaggcctc ttcattatga 300
ccccggcagg tgtgttcctg gccgagagcg cgctgcacat ggcgggcctg gctgagtacc 360
ccatgcaggg agagctggcc tctgccatca gctccggcaa gaaga 405

<210> SEQ ID NO 255
<211> LENGTH: 47
<212> TYPE: DNA
<213> ORGANISM: Homo sapiens

<400> SEQUENCE: 255
ttcagaaaat gtgaggaact caaaaagaag ccttccgctg ctctgga 47

<210> SEQ ID NO 256
<211> LENGTH: 42
<212> TYPE: DNA
<213> ORGANISM: Homo sapiens

<400> SEQUENCE: 256
gtgatgcttc cgacgggagc cgccttccgg tggtttcagt ga 42

<210> SEQ ID NO 257
<211> LENGTH: 161
<212> TYPE: DNA
<213> ORGANISM: Homo sapiens

<400> SEQUENCE: 257
aatgtcactg ctcgtgtggt ctccagcaag ggattcgggc gaagacaaac ggatgcaccc 60
gtctttagaa ccaaaaatat tctctcacag atttcattcc tgtttttata tatatatttt 120
ttgttgtcgt tttaacatct ccacgtccct agcataaaaa g 161

<210> SEQ ID NO 258
<211> LENGTH: 222

<212> TYPE: DNA
<213> ORGANISM: Homo sapiens

<400> SEQUENCE: 258
atctataaag taccgagact tcctgggcaa agaatggaca atcagtttcc ttcctgtgtc 60
gatgtcgatg ttgtctgtgc aggagatgca gtttttgtgt agagaatgta aattttctgt 120 aacctttga aatctagtta ctaataagca ctactgtaat ttagcacagt ttaactccac 180
cctcatttaa acttcctttg attctttccg accatgaaat ag 222

<210> SEQ ID NO 259
<211> LENGTH: 84
<212> TYPE: DNA
<213> ORGANISM: Homo sapiens

<400> SEQUENCE: 259
cctggagaat ccactcacgt tcataaagag aatgttgatg gcgccgtgta gaagccgctc 60
tgtatccatc cacgcgtgca gagc 84

<210> SEQ ID NO 260
<211> LENGTH: 118
<212> TYPE: DNA
<213> ORGANISM: Homo sapiens

<400> SEQUENCE: 260
ggcttagatg gctccgagcc cgtttgagcg tggtctcgga ctgctaactg gaccaacggc 60
aactgtctga tgagtgccag ccccaaaccg cgcgctgctc gggaccttag agcctctg 118

<210> SEQ ID NO 261
<211> LENGTH: 79
<212> TYPE: DNA
<213> ORGANISM: Homo sapiens

<400> SEQUENCE: 261
tgttccgctg tttagctctt gttttttgtg tggacactcc taggatagaa agtttggtat 60
gttgctatac ctttgcttc 79

<210> SEQ ID NO 262
<211> LENGTH: 27
<212> TYPE: DNA
<213> ORGANISM: Homo sapiens

<400> SEQUENCE: 262
gcacccgtgt ggttgctaag gatgggc 27

<210> SEQ ID NO 263
<211> LENGTH: 173
<212> TYPE: DNA
<213> ORGANISM: Homo sapiens

<400> SEQUENCE: 263
tatacaaggc tgcagtcgga tacactggta ttgtggacgt ggcctggagc tggacgagac 60
atttagtgta ctttttgggc aattggagtc gtttgttatt ggtccttttt catttttaat 120
atcttaatga gatgatttaa ggaagttact gaatctctgc tattaggcct atc 173

<210> SEQ ID NO 264
<211> LENGTH: 53
<212> TYPE: DNA
<213> ORGANISM: Homo sapiens

<400> SEQUENCE: 264
gatctcaagt ttcaacacca cgttttggca aaacgttcga tgccccacca gcc 53

<210> SEQ ID NO 265
<211> LENGTH: 90
<212> TYPE: DNA
<213> ORGANISM: Homo sapiens

<400> SEQUENCE: 265
gtaagtgttg gctataaaga cactgtttaa acacttaagc acttttgact cttaaaatga 60
ctattggcat catcctacgt agctttcttc 90

<210> SEQ ID NO 266
<211> LENGTH: 57
<212> TYPE: DNA
<213> ORGANISM: Homo sapiens

<400> SEQUENCE: 266
ctgcctcaga tgatgcctat ccagaaatag aaaaattctt tcccttcaat cctctag 57

<210> SEQ ID NO 267
<211> LENGTH: 208
<212> TYPE: DNA
<213> ORGANISM: Homo sapiens

<400> SEQUENCE: 267
atgagactgt ctgaatctgg gttgctttgg acaagtgtac ttgttgatgg aattatttgc 60
aaggtatcat cttaggtcag gaggggaata ggaacaaaga tgtagaagac attgttcctg 120
tctgtaaaag cttatcacct agaggaggta agatgtattc atgaacattg aataagtccc 180
attgtggaca gtctttctca caaggctt 208

<210> SEQ ID NO 268
<211> LENGTH: 70
<212> TYPE: DNA
<213> ORGANISM: Homo sapiens

<400> SEQUENCE: 268
ctgaagagca ccagattgcg cacctcccct tgagtggagt gcctctcatg atccttgacg 60
aggagagaga 70

<210> SEQ ID NO 269
<211> LENGTH: 74
<212> TYPE: DNA
<213> ORGANISM: Homo sapiens

<400> SEQUENCE: 269
ctgttgcagt ctccttcaag cattctgtcg accctggatg ttgaattgcc acctgtttgc 60
tgtgacatag atat 74

<210> SEQ ID NO 270
<211> LENGTH: 31
<212> TYPE: DNA
<213> ORGANISM: Homo sapiens

<400> SEQUENCE: 270
tcttagtgct tcagagtttg tgtgtatttg t 31

<210> SEQ ID NO 271
<211> LENGTH: 82

<212> TYPE: DNA
<213> ORGANISM: Homo sapiens

<400> SEQUENCE: 271
ccgccgtcgc gggtacattc ctcgctcccg gccgaggagc gctcgggctg tctgcggacc 60
ctgccgcgtg caggggtcgc gg 82

<210> SEQ ID NO 272
<211> LENGTH: 39
<212> TYPE: DNA
<213> ORGANISM: Homo sapiens

<400> SEQUENCE: 272
ggcagttggt gggaagtcca gcttgggtcc ctgagagct 39

<210> SEQ ID NO 273
<211> LENGTH: 70
<212> TYPE: DNA
<213> ORGANISM: Homo sapiens

<400> SEQUENCE: 273
ccctgttggg ggtcctgctg agtgtgcctg ggcctccagt cttgtccctg gaggcctctg 60
aggaagtgga 70

<210> SEQ ID NO 274
<211> LENGTH: 136
<212> TYPE: DNA
<213> ORGANISM: Homo sapiens

<400> SEQUENCE: 274
tacaaggagg gcagtcgcct ggcacctgct ggccgtgtac ggggctggag gggccgccta 60
gagattgcca gcttcctacc tgaggatgct ggccgctacc tctgcctggc acgaggctcc 120
atgatcgtcc tgcaga 136

<210> SEQ ID NO 275
<211> LENGTH: 75
<212> TYPE: DNA
<213> ORGANISM: Homo sapiens

<400> SEQUENCE: 275
ttgacctcca gcaacgatga tgaggacccc aagtcccata gggacccctc gaataggcac 60
agttaccccc agcaa 75

<210> SEQ ID NO 276
<211> LENGTH: 67
<212> TYPE: DNA
<213> ORGANISM: Homo sapiens

<400> SEQUENCE: 276
gctgctcatc tgatcactga gaagaggagg cctgtgtggg aacacacggt cattctaggg 60
gccttcc 67

<210> SEQ ID NO 277
<211> LENGTH: 112
<212> TYPE: DNA
<213> ORGANISM: Homo sapiens

<400> SEQUENCE: 277
ctgcatgcag tacctgcggg gaacaccgtc aagttccgct gtccagctgc aggcaacccc 60
acgcccacca tccgctggct taaggatgga caggcctttc atggggagaa cc 112

<210> SEQ ID NO 278
<211> LENGTH: 27
<212> TYPE: DNA
<213> ORGANISM: Homo sapiens

<400> SEQUENCE: 278
ctgcgccatc agcactggag tctcgtg 27

<210> SEQ ID NO 279
<211> LENGTH: 60
<212> TYPE: DNA
<213> ORGANISM: Homo sapiens

<400> SEQUENCE: 279
acatacacct gcctggtaga gaacgctgtg ggcagcatcc gctataacta cctgctagat 60

<210> SEQ ID NO 280
<211> LENGTH: 132
<212> TYPE: DNA
<213> ORGANISM: Homo sapiens

<400> SEQUENCE: 280
cggccaacac cacagccgtg gtgggcagcg acgtggagct gctgtgcaag gtgtacagcg 60
atgcccagcc ccacatccag tggctgaagc acatcgtcat caacggcagc agcttcggag 120
ccgacggttt cc 132

<210> SEQ ID NO 281
<211> LENGTH: 90
<212> TYPE: DNA
<213> ORGANISM: Homo sapiens

<400> SEQUENCE: 281
aggtcctgta cctgcggaac gtgtcagccg aggacgcagg cgagtacacc tgcctcgcag 60
gcaattccat cggcctctcc taccagtctg 90

<210> SEQ ID NO 282
<211> LENGTH: 30
<212> TYPE: DNA
<213> ORGANISM: Homo sapiens

<400> SEQUENCE: 282
aggagatgct gcgagatgcc cctctgggcc 30

<210> SEQ ID NO 283
<211> LENGTH: 104
<212> TYPE: DNA
<213> ORGANISM: Homo sapiens

<400> SEQUENCE: 283
gcccgaggcc aggtatacgg acatcatcct gtacgcgtcg ggctccctgg ccttggctgt 60
gctcctgctg ctggccgggc tgtatcgagg gcaggcgctc cacg 104

<210> SEQ ID NO 284
<211> LENGTH: 56
<212> TYPE: DNA
<213> ORGANISM: Homo sapiens

<400> SEQUENCE: 284
ggcgcatccc ccacctcaca tgtgacagcc tgactccagc aggcagaacc aagtct 56

<210> SEQ ID NO 285
<211> LENGTH: 115
<212> TYPE: DNA
<213> ORGANISM: Homo sapiens

<400> SEQUENCE: 285
ttccggcaag tcaagctcat ccctggtacg aggcgtgcgt ctctcctcca gcggccccgc 60
cttgctcgcc ggcctcgtga gtctagatct acctctcgac ccactatggg agttc 115

<210> SEQ ID NO 286
<211> LENGTH: 48
<212> TYPE: DNA
<213> ORGANISM: Homo sapiens

<400> SEQUENCE: 286
ccctaggcga gggctgcttt ggccaggtag tacgtgcaga ggcctttg 48

<210> SEQ ID NO 287
<211> LENGTH: 39
<212> TYPE: DNA
<213> ORGANISM: Homo sapiens

<400> SEQUENCE: 287
aggtgatgaa gctgatcggc cgacacaaga acatcatca 39

<210> SEQ ID NO 288
<211> LENGTH: 114
<212> TYPE: DNA
<213> ORGANISM: Homo sapiens

<400> SEQUENCE: 288
ccctgtacgt gatcgtggag tgcgccgcca agggaaacct gcgggagttc ctgcgggccc 60
ggcgcccccc aggccccgac ctcagccccg acggtcctcg gagcagtgag gggc 114

<210> SEQ ID NO 289
<211> LENGTH: 32
<212> TYPE: DNA
<213> ORGANISM: Homo sapiens

<400> SEQUENCE: 289
cggcgtccac cacattgact actataagaa aa 32

<210> SEQ ID NO 290
<211> LENGTH: 31
<212> TYPE: DNA
<213> ORGANISM: Homo sapiens

<400> SEQUENCE: 290
ggccttgttt gaccgggtgt acacacacca g 31

<210> SEQ ID NO 291
<211> LENGTH: 89
<212> TYPE: DNA
<213> ORGANISM: Homo sapiens

<400> SEQUENCE: 291
tcgggggctc cccgtatcct ggcatcccgg tggaggagct gttctcgctg ctgcgggagg 60
gacatcggat ggaccgaccc ccacactgc 89

<210> SEQ ID NO 292

<211> LENGTH: 26
<212> TYPE: DNA
<213> ORGANISM: Homo sapiens

<400> SEQUENCE: 292
ctgaggctcc ctgtgaccct ccgccc 26

<210> SEQ ID NO 293
<211> LENGTH: 38
<212> TYPE: DNA
<213> ORGANISM: Homo sapiens

<400> SEQUENCE: 293
acgggctgat gcgtgagtgc tggcacgcag cgccctcc 38

<210> SEQ ID NO 294
<211> LENGTH: 110
<212> TYPE: DNA
<213> ORGANISM: Homo sapiens

<400> SEQUENCE: 294
ctcgacctcc gcctgacctt cggaccctat tccccctctg gtggggacgc cagcagcacc 60
tgctcctcca gcgattctgt cttcagccac gaccccctgc cattgggatc 110

<210> SEQ ID NO 295
<211> LENGTH: 215
<212> TYPE: DNA
<213> ORGANISM: Homo sapiens

<400> SEQUENCE: 295
cctgacacag tgctcgacct tgatagcatg gggcccctgg cccagagttg ctgtgccgtg 60
tccaagggcc gtgcccttgc ccttggagct gccgtgcctg tgtcctgatg gcccaaatgt 120
cagggttctg ctcggcttct tggaccttgg cgcttagtcc ccatcccggg tttggctgag 180
cctggctgga gagctgctat gctaaacctc ctgcc 215

<210> SEQ ID NO 296
<211> LENGTH: 229
<212> TYPE: DNA
<213> ORGANISM: Homo sapiens

<400> SEQUENCE: 296
agaagggcgc ctgcttgttc tttctttttg tctgctttcc cccgtttgcg cctggaagct 60
gcgccgcgag ttcctgcaag gcggtctgcc gcggccgggc ccggccttct cccctcgcag 120
cgaccccgcc tcgcggccgc gcgggccccg aggtagcccg aggcgccgga ggagccagcc 180
ccagcgagcg ccgggagagg cggcagcgca gccggacgca cagcgcagc 229

<210> SEQ ID NO 297
<211> LENGTH: 126
<212> TYPE: DNA
<213> ORGANISM: Homo sapiens

<400> SEQUENCE: 297
atgcaggcgc gctactccgt gtccagcccc aactccctgg gagtggtgcc ctacctcggc 60
ggcgagcaga gctactaccg cgcggcggcc gcggcggccg gggcggcta caccgccatg 120 ccggcc 126

<210> SEQ ID NO 298
<211> LENGTH: 177

<212> TYPE: DNA
<213> ORGANISM: Homo sapiens

<400> SEQUENCE: 298
atgagcgtgt actcgcaccc tgcgcacgcc gagcagtacc cgggcggcat ggcccgcgcc 60
tacgggccct acacgccgca gccgcagccc aaggacatgg tgaagccgcc ctatagctac 120
atcgcgctca tcaccatggc catccagaac gccccggaca agaagatcac cctgaac 177

<210> SEQ ID NO 299
<211> LENGTH: 32
<212> TYPE: DNA
<213> ORGANISM: Homo sapiens

<400> SEQUENCE: 299
aggacaggct gcacctcaag gagccgcccc cg 32

<210> SEQ ID NO 300
<211> LENGTH: 26
<212> TYPE: DNA
<213> ORGANISM: Homo sapiens

<400> SEQUENCE: 300
gccgacggca acgcgcccgg tccgca 26

<210> SEQ ID NO 301
<211> LENGTH: 29
<212> TYPE: DNA
<213> ORGANISM: Homo sapiens

<400> SEQUENCE: 301
gcgcatccag gacatcaaga ccgagaacg 29

<210> SEQ ID NO 302
<211> LENGTH: 99
<212> TYPE: DNA
<213> ORGANISM: Homo sapiens

<400> SEQUENCE: 302
cgccgcggtg cccaagatcg agagccccga cagcagcagc agcagcctgt ccagcgggag 60
cagccccccg ggcagcctgc cgtcggcgcg gccgctcag 99

<210> SEQ ID NO 303
<211> LENGTH: 114
<212> TYPE: DNA
<213> ORGANISM: Homo sapiens

<400> SEQUENCE: 303
ccgccgccgc accatagcca gggcttcagc gtggacaaca tcatgacgtc gctgcggggg 60
tcgccgcaga gcgcggccgc ggagctcagc tccggccttc tggcctcggc ggcc 114

<210> SEQ ID NO 304
<211> LENGTH: 177
<212> TYPE: DNA
<213> ORGANISM: Homo sapiens

<400> SEQUENCE: 304
gtcctcgcgc gcggggatcg caccccccgct ggcgctcggc gcctactcgc ccggccagag 60
ctccctctac agctcccccct gcagccagac ctccagcgcg ggcagctcgg gcggcggcgg 120
cggcggcgcg ggggccgcgg ggggcgcggg cggcgccggg acctaccact gcaacct 177

<210> SEQ ID NO 305
<211> LENGTH: 110
<212> TYPE: DNA
<213> ORGANISM: Homo sapiens

<400> SEQUENCE: 305
atgagcctgt acgcggccgg cgagcgcggg ggccacttgc agggcgcgcc cgggggcgcg 60
ggcggctcgg ccgtggacga ccccctgccc gactactctc tgcctccggt 110

<210> SEQ ID NO 306
<211> LENGTH: 39
<212> TYPE: DNA
<213> ORGANISM: Homo sapiens

<400> SEQUENCE: 306
ggccggccac caccctgcgg cccaccaagg ccgcctcac 39

<210> SEQ ID NO 307
<211> LENGTH: 27
<212> TYPE: DNA
<213> ORGANISM: Homo sapiens

<400> SEQUENCE: 307
acctgggcca cttggcgagc gcggcgg 27

<210> SEQ ID NO 308
<211> LENGTH: 143
<212> TYPE: DNA
<213> ORGANISM: Homo sapiens

<400> SEQUENCE: 308
cagaacttcc actcggtgcg ggagatgttc gagtcacaga ggatcggctt gaacaactct 60
ccagtgaacg ggaatagtag ctgtcaaatg gccttccctt ccagccagtc tctgtaccgc 120
acgtccggag ctttcgtcta cga 143

<210> SEQ ID NO 309
<211> LENGTH: 449
<212> TYPE: DNA
<213> ORGANISM: Homo sapiens

<400> SEQUENCE: 309
tgagaatatt caccacacca gcgaacagaa tatccctcca aaaattcagc tcaccagcac 60
cagcacgaag aaaactctat tttcttaacc gattaattca gagccacctc cactttgcct 120
tgtctaaata aacaaacccg taaactgttt tatacagaga cagcaaaatc ttggtttatt 180
aaaggacagt gttactccag ataacacgta agtttcttct tgcttttcag agacctgctt 240
tcccctcctc ccgtctcccc tctcttgcct tcttccttgc ctctcacctg taagatatta 300
ttttatccta tgttgaaggg agggggaaag tccccgttta tgaaagtcgc tttcttttta 360
ttcatggact tgttttaaaa tgtaaattgc aacatagtaa tttattttta atttgtagtt 420
ggatgtcgtg gaccaaacgc cagaaagtg 449

<210> SEQ ID NO 310
<211> LENGTH: 871
<212> TYPE: DNA
<213> ORGANISM: Homo sapiens

<400> SEQUENCE: 310
ggagaaaccc tctgactagt ccatgtcaaa ttttactaaa agtctttttg tttagattta 60
ttttcctgca gcatcttctg caaaatgtac tatatagtca gcttgctttg aggctagtaa 120
aaagatattt ttctaaacag attggagttg gcatataaac aaatacgttt tctcactaat 180
gacagtccat gattcggaaa ttttaagccc atgaatcagc cgcggtctta ccacggtgat 240
gcctgtgtgc cgagagatgg gactgtgcgg ccagatatgc acagataaat atttggcttg 300
tgtattccat ataaaattgc agtgcatatt atacatccct gtgagccaga tgctgaatag 360
atattttcct attatttcag tcctttataa aaggaaaaat aaaccagttt ttaaatgtat 420
gtatataatt ctcccccatt tacaatcctt catgtattac atagaaggat tgcttttta 480 aaaatatact gcgggttgga aagggatatt taatctttga gaaactattt tagaaaatat 540
gtttgtagaa caattatttt tgaaaaagat ttaaagcaat aacaagaagg aaggcgagag 600
gagcagaaca ttttggtcta gggtggtttc tttttaaacc attttttctt gttaatttac 660
agttaaacct aggggacaat ccggattggc cctcccccctt ttgtaaataa cccaggaaat 720
gtaataaatt cattatctta gggtgatctg ccctgccaat cagactttgg ggagatggcg 780
atttgattac agacgttcgg gggggtgggg ggcttgcagt ttgttttgga gataatacag 840
tttcctgcta tctgccgctc ctatctagag g 871

<210> SEQ ID NO 311
<211> LENGTH: 63
<212> TYPE: DNA
<213> ORGANISM: Homo sapiens

<400> SEQUENCE: 311
agaagctctt taacaggctc gaaaggtcca tgctcctttc tcctgcccat tctatagcat 60
aag 63

<210> SEQ ID NO 312
<211> LENGTH: 88
<212> TYPE: DNA
<213> ORGANISM: Homo sapiens

<400> SEQUENCE: 312
caaagatctc ttcacattct ccgggactgc ggtaccaaat atcagcacag cacttcttga 60
aaaaggatgt agattttaat ctgaactt 88

<210> SEQ ID NO 313
<211> LENGTH: 118
<212> TYPE: DNA
<213> ORGANISM: Homo sapiens

<400> SEQUENCE: 313
acgaagtgga ggagtattac atttcagctg gaaacacatc cctagaatgc caaaacattt 60
attccaaagt ctggtttcct ggtgcaatcg gaggcatggc aatgcctctg ttcagaga 118

<210> SEQ ID NO 314
<211> LENGTH: 215
<212> TYPE: DNA
<213> ORGANISM: Homo sapiens

<400> SEQUENCE: 314
aagcataggg tactttccag cctccaaggg taggggcaaa ggggctgggg tttctcctcc 60
ccagtacagc tttctctggc tgtgccacac tgctccctgt gagcagacag caagtctccc 120
ctcactcccc actgccattc atccagcgct gtgcagtagc ccagctgcgt gtctgccggg 180
aggggctgcc aagtgccctg cctactggct gcttc 215

<210> SEQ ID NO 315
<211> LENGTH: 147
<212> TYPE: DNA
<213> ORGANISM: Homo sapiens

<400> SEQUENCE: 315
gcagcacatt agagaaagcc ggcccctgga tccgtctttc gcgtttattt taagcccagt 60
cttccctggg ccacctttag cagatcctcg tgcgcccccg ccccctggcc gtgaaactca 120
gcctctatcc agcagcgacg acaagta 147

<210> SEQ ID NO 316
<211> LENGTH: 256
<212> TYPE: DNA
<213> ORGANISM: Homo sapiens

<400> SEQUENCE: 316
ccaatgtcag ggcaaggcaa cagtccctgg ccgtcctcca gcacctttgt aatgcatatg 60
agctcgggag accagtactt aaagttggag gcccgggagc ccaggagctg gcggagggcg 120
ttcgtcctgg gactgcactt gctcccgtcg ggtcgcccgg cttcaccgga cccgcaggct 180
cccggggcag ggccggggcc agagctcgcg tgtcggcggg acatgcgctg cgtcgcctct 240
aacctcgggc tgtgct 256

<210> SEQ ID NO 317
<211> LENGTH: 70
<212> TYPE: DNA
<213> ORGANISM: Homo sapiens

<400> SEQUENCE: 317
gtggcccgcc ggtttctgag ccttctgccc tgcggggaca cggtctgcac cctgcccgcg 60
gccacggacc 70

<210> SEQ ID NO 318
<211> LENGTH: 48
<212> TYPE: DNA
<213> ORGANISM: Homo sapiens

<400> SEQUENCE: 318
tctgggatgg ccctactgca tcagatccaa gggaacgagc tggagccc 48

<210> SEQ ID NO 319
<211> LENGTH: 114
<212> TYPE: DNA
<213> ORGANISM: Homo sapiens

<400> SEQUENCE: 319
cccctgggcg aggtgtacct ggacagcagc aagcccgccg tgtacaacta ccccgagggc 60
gccgcctacg agttcaacgc cgcggccgcc gccaacgcgc aggtctacgg tcag 114

<210> SEQ ID NO 320
<211> LENGTH: 155
<212> TYPE: DNA
<213> ORGANISM: Homo sapiens

<400> SEQUENCE: 320
tgaggctgcg gcgttcggct ccaacggcct ggggggtttc cccccactca acagcgtgtc 60
tccgagcccg ctgatgctac tgcacccgcc gccgcagctg tcgcctttcc tgcagcccca 120
cggccagcag gtgccctact acctggagaa cgagc 155

<210> SEQ ID NO 321
<211> LENGTH: 209
<212> TYPE: DNA
<213> ORGANISM: Homo sapiens

<400> SEQUENCE: 321
gtgctgtcat gtggactgtc ctcccgagtg tcccactgga tgttcagaga atttatgtga 60
aggtcacgtc atttagcatt gagatgctgt ggttaccttc ttccatttct tccataatat 120
gcagccacat ctatgtgtga agaaatgtaa tagataaaat ttctctggac gcataataat 180
gtgagaaaga ttgtcacatg tcccagcaa 209

<210> SEQ ID NO 322
<211> LENGTH: 62
<212> TYPE: DNA
<213> ORGANISM: Homo sapiens

<400> SEQUENCE: 322
caaattcaga taatcgacgc cagggtggca gagaaagatt ggccagtacc aatgacaagg 60
ga 62

<210> SEQ ID NO 323
<211> LENGTH: 77
<212> TYPE: DNA
<213> ORGANISM: Homo sapiens

<400> SEQUENCE: 323
aatctgccaa ggagactcgc tactgtgcag tgtgcaatga ctatgcttca ggctaccatt 60
atggagtctg gtcctgt 77

<210> SEQ ID NO 324
<211> LENGTH: 40
<212> TYPE: DNA
<213> ORGANISM: Homo sapiens

<400> SEQUENCE: 324
caggcctgcc ggctccgtaa atgctacgaa gtgggaatga 40

<210> SEQ ID NO 325
<211> LENGTH: 185
<212> TYPE: DNA
<213> ORGANISM: Homo sapiens

<400> SEQUENCE: 325
aacctttggc caagcccgct catgatcaaa cgctctaaga agaacagcct ggccttgtcc 60
ctgacggccg accagatggt cagtgccttg ttggatgctg agccccccgat actctattcc 120 gagtatgatc ctaccagacc cttcagtgaa gcttcgatga tgggcttact gaccaacctg 180
gcaga 185

<210> SEQ ID NO 326
<211> LENGTH: 96
<212> TYPE: DNA
<213> ORGANISM: Homo sapiens

<400> SEQUENCE: 326
tggatatatg tgtgatcctg ggtgtgccaa atgctgtggc ttcctgaagc ttagatttcc 60
agcttgtcac cttcaaggtt accttgtgaa taggac 96

<210> SEQ ID NO 327
<211> LENGTH: 111
<212> TYPE: DNA
<213> ORGANISM: Homo sapiens

<400> SEQUENCE: 327
tgactatgga ttttgcctgt tgctttgttt ccaccaactc tccctgaaga tgaggcgcac 60
agacagacaa ctcacaggca agaacagcct ggtccatctt gaaagattct c 111

<210> SEQ ID NO 328
<211> LENGTH: 29
<212> TYPE: DNA
<213> ORGANISM: Homo sapiens

<400> SEQUENCE: 328
gctttgtgga tttgaccctc catgatcag 29

<210> SEQ ID NO 329
<211> LENGTH: 94
<212> TYPE: DNA
<213> ORGANISM: Homo sapiens

<400> SEQUENCE: 329
gtccaccttc tagaatgtgc ctggctagag atcctgatga ttggtctcgt ctggcgctcc 60
atggagcacc cagggaagct actgtttgct ccta 94

<210> SEQ ID NO 330
<211> LENGTH: 76
<212> TYPE: DNA
<213> ORGANISM: Homo sapiens

<400> SEQUENCE: 330
tggagatctt cgacatgctg ctggctacat catctcggtt ccgcatgatg aatctgcagg 60
gagaggagtt tgtgtg 76

<210> SEQ ID NO 331
<211> LENGTH: 41
<212> TYPE: DNA
<213> ORGANISM: Homo sapiens

<400> SEQUENCE: 331
gagaaggacc atatccaccg agtcctggac aagatcacag a 41

<210> SEQ ID NO 332
<211> LENGTH: 157
<212> TYPE: DNA
<213> ORGANISM: Homo sapiens

<400> SEQUENCE: 332
catgaagtgc aagaacgtgg tgcccctcta tgacctgctg ctggagatgc tggacgccca 60
ccgcctacat gcgcccacta gccgtggagg ggcatccgtg gaggagacgg accaaagcca 120
cttggccact gcgggctcta cttcatcgca ttccttg 157

<210> SEQ ID NO 333
<211> LENGTH: 3214
<212> TYPE: DNA
<213> ORGANISM: Homo sapiens

<400> SEQUENCE: 333

-continued

```
cctggctccc acacggttca gataatccct gctgcatttt accctcatca tgcaccactt     60
tagccaaatt ctgtctcctg catacactcc ggcatgcatc caacaccaat ggctttctag    120
atgagtggcc attcatttgc ttgctcagtt cttagtggca catcttctgt cttctgttgg    180
gaacagccaa agggattcca aggctaaatc tttgtaacag ctctctttcc cccttgctat    240
gttactaagc gtgaggattc ccgtagctct tcacagctga actcagtcta tgggttgggg    300
ctcagataac tctgtgcatt taagctactt gtagagaccc aggcctggag agtagacatt    360
ttgcctctga taagcacttt ttaaatggct ctaagaataa gccacagcaa agaatttaaa    420
gtggctcctt taattggtga cttggagaaa gctaggtcaa gggtttatta tagcaccctc    480
ttgtattcct atggcaatgc atccttttat gaaagtggta caccttaaag cttttatatg    540
actgtagcag agtatctggt gattgtcaat tcattccccc tataggaata caaggggcac    600
acagggaagg cagatcccct agttggcaag actattttaa cttgatacac tgcagattca    660
gatgtgctga aagctctgcc tctggctttc cggtcatggg ttccagttaa ttcatgcctc    720
ccatggacct atggagagca gcaagttgat cttagttaag tctccctata tgagggataa    780
gttcctgatt tttgttttta tttttgtgtt acaaaagaaa gccctccctc cctgaacttg    840
cagtaaggtc agcttcagga cctgttccag tgggcactgt acttggatct tcccggcgtg    900
tgtgtgcctt acacaggggt gaactgttca ctgtggtgat gcatgatgag ggtaaatggt    960
agttgaaagg agcaggggcc ctggtgttgc atttagccct ggggcatgga gctgaacagt   1020
acttgtgcag gattgttgtg gctactagag aacaagaggg aaagtagggc agaaactgga   1080
tacagttctg aggcacagcc agacttgctc agggtggccc tgccacaggc tgcagctacc   1140
taggaacatt ccttgcagac cccgcattgc cctttggggg tgccctggga tccctggggt   1200
agtccagctc ttcttcattt cccagcgtgg ccctggttgg aagaagcagc tgtcacagct   1260
gctgtagaca gctgtgttcc tacaattggc ccagcaccct ggggcacggg agaagggtgg   1320
ggaccgttgc tgtcactact caggctgact ggggcctggt cagattacgt atgcccttgg   1380
tggtttagag ataatccaaa atcagggttt ggtttgggga agaaaatcct ccccccttcct   1440
cccccgcccc gttccctacc gcctccactc ctgccagctc atttccttca atttcctttg   1500
acctataggc taaaaaagaa aggctcattc cagccacagg gcagccttcc ctgggccttt   1560
gcttctctag cacaattatg ggttacttcc tttttcttaa caaaaaagaa tgtttgattt   1620
cctctgggtg accttattgt ctgtaattga aaccctattg agaggtgatg tctgtgttag   1680
ccaatgaccc aggtgagctg ctcgggcttc tcttggtatg tcttgtttgg aaaagtggat   1740
ttcattcatt tctgattgtc cagttaagtg atcaccaaag gactgagaat ctgggagggc   1800
aaaaaaaaaa aaaaagtttt tatgtgcact taaatttggg gacaatttta tgtatctgtg   1860
ttaaggatat gtttaagaac ataattcttt tgttgctgtt tgtttaagaa gcaccttagt   1920
ttgtttaaga agcaccttat atagtataat atatattttt ttgaaattac attgcttgtt   1980
tatcagacaa ttgaatgtag taattctgtt ctggatttaa tttgactggg ttaacatgca   2040
aaaaccaagg aaaaatattt agtttttttt tttttttttg tatacttttc aagctacctt   2100
gtcatgtata cagtcattta tgcctaaagc ctggtgatta ttcatttaaa tgaagatcac   2160
atttcatatc aacttttgta tccacagtag acaaaatagc actaatccag atgcctattg   2220
ttggatactg aatgacagac aatcttatgt agcaaagatt atgcctgaaa aggaaaatta   2280
ttcagggcag ctaattttgc ttttaccaaa atatcagtag taatattttt ggacagtagc   2340
```

```
taatgggtca gtgggttctt tttaatgttt atacttagat tttcttttaa aaaaattaaa   2400

ataaaacaaa aaaaaatttc taggactaga cgatgtaata ccagctaaag ccaaacaatt   2460

atacagtgga aggttttaca ttattcatcc aatgtgtttc tattcatgtt aagatactac   2520

tacatttgaa gtgggcagag aacatcagat gattgaaatg ttcgcccagg ggtctccagc   2580

aactttggaa atctctttgt atttttactt gaagtgccac taatggacag cagatatttt   2640

ctggctgatg ttggtattgg gtgtaggaac atgatttaaa aaaaaactct tgcctctgct   2700

ttcccccact ctgaggcaag ttaaaatgta aaagatgtga tttatctggg gggctcaggt   2760

atggtgggga agtggattca ggaatctggg gaatggcaaa tatattaaga agagtattga   2820

aagtatttgg aggaaaatgg ttaattctgg gtgtgcacca gggttcagta gagtccactt   2880

ctgccctgga gaccacaaat caactagctc catttacagc catttctaaa atggcagctt   2940

cagttctaga gaagaaagaa caacatcagc agtaaagtcc atggaatagc tagtggtctg   3000

tgtttctttt cgccattgcc tagcttgccg taatgattct ataatgccat catgcagcaa   3060

ttatgagagg ctaggtcatc caaagagaag accctatcaa tgtaggttgc aaaatctaac   3120

ccctaaggaa gtgcagtctt tgatttgatt tccctagtaa ccttgcagat atgtttaacc   3180

aagccatagc ccatgccttt tgagggctga acaa                               3214


<210> SEQ ID NO 334
<211> LENGTH: 33
<212> TYPE: DNA
<213> ORGANISM: Homo sapiens

<400> SEQUENCE: 334

agaagagaat cctgaacttg catcctaaaa tat                                  33


<210> SEQ ID NO 335
<211> LENGTH: 1065
<212> TYPE: DNA
<213> ORGANISM: Homo sapiens

<400> SEQUENCE: 335

ggcaacttgt tgactaccca ctggtcattc tcctctggtc ttattacata catggatgcc     60

agtttagatt gtgtttatat aggaaaaatt aaatgtgtga gcctccttaa ggaacatcat    120

caatacagat atatcagata gttctgtcca gcaaaaaacg tgcttatttg ctacaagtaa    180

atttttattt atttttctca cttccctcac tccttcaaat ttccaggtaa atagctgccc    240

aggagttgct tcatctctgt cccaaaatac ctagacaatt gcgggataag gagaatggca    300

gggagggagt agtggctaaa atcacaccct tcaaaagaaa gtgtgtagga cacacaattg    360

tgagaagtct gaatgccatg cacatagggt atgactcact ttgaaaattg tttataatca    420

aggaaatgaa aatgagttaa tttcgtgcat gcatcattta aagccaaatg agaagaaact    480

tctaatttat tttgttactt ttcggctaac actggcagta tgtaacagat ttattttgca    540

gaaacatcta gattgtccgt gatcttgatc ctgcccttat gtgtcttgtc tttgaaaccc    600

agtgtttcct ggatatatgg ttcaggagac aagtttccag aatcaagtta ggacccaggt    660

cttctttttt tccaaaccaa acattcttgc taatcctaaa ctacctgagg cagcctgtgg    720

tggcctcagc tctaaaacca ttgtttaaag gcttctaccc atcaatggcc cttcagcaga    780

gtggtacggt taacggggta gggtctggag tcaggggaga cctgggttca aatcctacat    840

ctttacacct ctaatcccca gtgtccttgt ctataaattg ggaatatagc catgtcatgg    900

gattcttgtg agggttaaat gaggtaaaac acatacaatg cttagcatgt atacaattaa    960
```

gcactaaata attgaaacac attaagtact aaatgaatgt cagcagctta tcactattat 1020
ctgtataatg ataccaaggg tgtgccgact cataccctta ggggt 1065

<210> SEQ ID NO 336
<211> LENGTH: 30
<212> TYPE: DNA
<213> ORGANISM: Homo sapiens

<400> SEQUENCE: 336
aggaaggcct acctcaaata gcaacagaga 30

<210> SEQ ID NO 337
<211> LENGTH: 33
<212> TYPE: DNA
<213> ORGANISM: Homo sapiens

<400> SEQUENCE: 337
tctgtgctga ggctctttga atgctttgaa taa 33

<210> SEQ ID NO 338
<211> LENGTH: 1603
<212> TYPE: DNA
<213> ORGANISM: Homo sapiens

<400> SEQUENCE: 338
cctctttcag tgtttcggcc agtcatttgc cacttctcat tccatcttag ttctctgtaa 60
agaaggtgcc agagacctaa ggtgcccaag gcaattttgc attttacaat tctaagcttt 120
agaatgaagt catcaatttg ctacatccgg actacagtgc aattattcct ttgccttgct 180
ggaaattgga gtgaaatctt tctagctgtc aatttcaact cagttgcagt agtgttttga 240
agaattaatg gcgataaggt tagaaaattt taagtcaaac gtagggaaaa agtaccagct 300
agaccatcat aagcatttgc tttgaaagca tgcttctaaa gtgtgtttaa cctcaaataa 360
cagtcacaaa tatggttatt atgaatgtat gcacagattt ttatgtttct aattttaaga 420
agttctaggg agctccctgt aacgatttag ggaatctcta gattctgata tactgcaagt 480
cttttaatgg taggaatcac attgaattaa ttttgtaggc ccagggccta aatttagtag 540
gtgttcagta cctattggca tcaattcata tgtaggttta aaatactgta tgaagataca 600
gaatcaccac catcaaatca aattgaaata tgtaacaggc tagtataata ttaacatctg 660
actttaaaca acaacaaaga aaccaaatga gtaactcctc ccttcaaact aatagtcagt 720
ttcttccaac tcagtctctt tctcctctca ggaagaatgc gtatctaaaa atttcccatt 780
gcagactgct ggaaacaaca ttctaaacta tttatgcttc tgcaataacc tttccaattt 840
gctggaccag tgcaagatta aacacgagat atctcaagtc tcaatgtaaa ggaacaccac 900
gacagcctgg actgtgggtg aagttcattc ttccccagca gactctgcct ttcattctcg 960
gggttgggtg tgccccaaac agaggtaccg acggtaacga agcccaagaa tgttcaacca 1020
caacctgtct gtgaaggtgt tggatgacgt ttgccattca ggtgaagatt atttatgttc 1080
cagtcccacc tgagtagcaa agtgaacact gtgctgaatg ctcagaaaga tgttaatgaa 1140
ccgtgctgga cagagcagag ctgaaaggcg ccttgcgagt gtcgtagtga gaatgtggct 1200
gtcccagctg caaagccctg ttaggaggca tgaggaagca cttgctgccc taagaaacga 1260
tgccttcgac attttcaaaa gatctatgtg gctgtctgaa acaatgcgga gagcagatag 1320
acgcaatatt tgggaaccaa agagtgactg ctgttggcgt tgcatcataa cataagcgct 1380

|  |  |
|---|---|
| ttcccccttc tcgtcactat catttgtatc aaccaaagaa ctgatctctg gtatcctcga | 1440 |
| aggaatgctg tggggatatt cttcatctct gttcatggta catcagcaat ttgtggggaa | 1500 |
| aagatggact atataacaca atgatctgcc taaaagaaac tgtctctact tatagggggc | 1560 |
| tgagcaaacc ttagagcatc tgcggatgct cgtcattatc ttc | 1603 |

```
<210> SEQ ID NO 339
<211> LENGTH: 94
<212> TYPE: DNA
<213> ORGANISM: Homo sapiens

<400> SEQUENCE: 339
```

|  |  |
|---|---|
| gaaattcaaa tttgaacggc tgcagaggcc gagtccgtca ctggaagccg agaggagagg | 60 |
| acagctggtt gtgggagagt tcccccgcct caga | 94 |

```
<210> SEQ ID NO 340
<211> LENGTH: 78
<212> TYPE: DNA
<213> ORGANISM: Homo sapiens

<400> SEQUENCE: 340
```

|  |  |
|---|---|
| acacactgag ctgagactca cttttctctt cctgaatttg aaccaccgtt tccatcgtct | 60 |
| cgtagtccga cgcctggg | 78 |

```
<210> SEQ ID NO 341
<211> LENGTH: 52
<212> TYPE: DNA
<213> ORGANISM: Homo sapiens

<400> SEQUENCE: 341
```

|  |  |
|---|---|
| ggaggaaggc tttgagtctg tcctaaaagg ctgttgcgag aggtctttca gc | 52 |

```
<210> SEQ ID NO 342
<211> LENGTH: 176
<212> TYPE: DNA
<213> ORGANISM: Homo sapiens

<400> SEQUENCE: 342
```

|  |  |
|---|---|
| tcctggcgca gcaagagtga ggcgcaggcc tgcggaacgg gtcctgctgg aagcagctgg | 60 |
| aatgccctgc agggcggggt ccggggccgg tgactcagtg cggctgccgc cgggaaaggc | 120 |
| agtaggatgt gtgatttgcg gagttcacgc agcccgcagg ggagatgcta atgaaa | 176 |

```
<210> SEQ ID NO 343
<211> LENGTH: 45
<212> TYPE: DNA
<213> ORGANISM: Homo sapiens

<400> SEQUENCE: 343
```

|  |  |
|---|---|
| aactgctgga gcgaacccgt gccaggcgag agaatcttca gagaa | 45 |

```
<210> SEQ ID NO 344
<211> LENGTH: 52
<212> TYPE: DNA
<213> ORGANISM: Homo sapiens

<400> SEQUENCE: 344
```

|  |  |
|---|---|
| cagcagctcc aaggtctatg actcatgcta agcgagctag acagccactt tc | 52 |

```
<210> SEQ ID NO 345
<211> LENGTH: 137
```

<212> TYPE: DNA
<213> ORGANISM: Homo sapiens

<400> SEQUENCE: 345
agaaatcttg tacaaaacca tcgccatcaa aaaaacgctg ttctgacaac actgaagtag 60
aagtttctaa cttggaaaat aaacaaccag ttgagtcgac atctgcaaaa tcttgttctc 120
caagtcctgt gtctcct 137

<210> SEQ ID NO 346
<211> LENGTH: 167
<212> TYPE: DNA
<213> ORGANISM: Homo sapiens

<400> SEQUENCE: 346
gccacaagca gcagatacca tcagtgattc tgttgctgtc ccggcatcac tgctgggcat 60
gaggagaggg ctgaactcaa gattggaagc aactgcagcc tcctcagtta aaacacgtat 120
gcaaaaactt gcagagcaac ggcgccgttg ggataatgat gatatga 167

<210> SEQ ID NO 347
<211> LENGTH: 79
<212> TYPE: DNA
<213> ORGANISM: Homo sapiens

<400> SEQUENCE: 347
gctttcaaat gcctcggcaa ctccagttgg cagaaggggc cgtctggcca atcttgctgc 60
aactatttgc tcctgggaa 79

<210> SEQ ID NO 348
<211> LENGTH: 152
<212> TYPE: DNA
<213> ORGANISM: Homo sapiens

<400> SEQUENCE: 348
gcctggtacc gcttgtttat ccaaattttc ctctgcaagt ggagcatctg ctaggatcaa 60
tagcagcagt gttaagcagg aagctacatt ctgttcccaa agggatggcg atgcctcttt 120
gaataaagcc ctatcctcaa gtgctgatga tg 152

<210> SEQ ID NO 349
<211> LENGTH: 152
<212> TYPE: DNA
<213> ORGANISM: Homo sapiens

<400> SEQUENCE: 349
tccagtgaaa tctactacat ctatcactga tgctaaaagt tgtgagggac aaaatcctga 60
gctacttcca aaaactccta ttagtcctct gaaaacgggg gtatcgaaac caattgtgaa 120
gtcaacttta tcccagacag ttccatccaa gg 152

<210> SEQ ID NO 350
<211> LENGTH: 115
<212> TYPE: DNA
<213> ORGANISM: Homo sapiens

<400> SEQUENCE: 350
agcctttcct ggaacgcttt ggagagcgtt gtcaagaaca tagcaaagaa agtccagctc 60
gtagcacacc ccacagaacc cccattatta ctccaaatac aaaggccatc caaga 115

<210> SEQ ID NO 351

<211> LENGTH: 72
<212> TYPE: DNA
<213> ORGANISM: Homo sapiens

<400> SEQUENCE: 351
agaactagca tgtcttcgtg gccgatttga caagggcaat atatggagtg cagaaaaagg 60
cggaaactca aa 72

<210> SEQ ID NO 352
<211> LENGTH: 76
<212> TYPE: DNA
<213> ORGANISM: Homo sapiens

<400> SEQUENCE: 352
gtttcaaaaa ctcagtcact tccagtaaca gaaaaggtga ccgaaaacca gataccagcc 60
aaaaattcta gtacag 76

<210> SEQ ID NO 353
<211> LENGTH: 25
<212> TYPE: DNA
<213> ORGANISM: Homo sapiens

<400> SEQUENCE: 353
catcagaccc aaaggttgag cagaa 25

<210> SEQ ID NO 354
<211> LENGTH: 151
<212> TYPE: DNA
<213> ORGANISM: Homo sapiens

<400> SEQUENCE: 354
tcttcagtga tgtcctagag gaaggtgaac tagatatgga gaagagccaa gaggagatgg 60
atcaagcatt agcagaaagc agcgaagaac aggaagatgc actgaatatc tcctcaatgt 120
ctttacttgc accattggca caaacagttg g 151

<210> SEQ ID NO 355
<211> LENGTH: 44
<212> TYPE: DNA
<213> ORGANISM: Homo sapiens

<400> SEQUENCE: 355
agtttagtgt ccacacctag actggaattg aaagacacca gcag 44

<210> SEQ ID NO 356
<211> LENGTH: 59
<212> TYPE: DNA
<213> ORGANISM: Homo sapiens

<400> SEQUENCE: 356
ttcaaagaaa cagaacgtcc atcaataaag caggtgattg ttcggaagga agatgttac 59

<210> SEQ ID NO 357
<211> LENGTH: 135
<212> TYPE: DNA
<213> ORGANISM: Homo sapiens

<400> SEQUENCE: 357
gaactcaata acgaaataaa tatgcaacag acagtgatct atcaagctag ccaggctctt 60
aactgctgtg ttgatgaaga acatggaaaa gggtccctag aagaagctga agcagaaaga 120
cttcttctaa ttgca 135

<210> SEQ ID NO 358
<211> LENGTH: 76
<212> TYPE: DNA
<213> ORGANISM: Homo sapiens

<400> SEQUENCE: 358
tgccatccaa aggatcagtt actttgtcag aaatccgctt gcctctaaaa gcagattttg 60
tctgcagtac ggttca 76

<210> SEQ ID NO 359
<211> LENGTH: 76
<212> TYPE: DNA
<213> ORGANISM: Homo sapiens

<400> SEQUENCE: 359
atggtagcca caccattagc aagtacttca aactctctta acggtgatgc tctgacattc 60
actactacat ttactc 76

<210> SEQ ID NO 360
<211> LENGTH: 30
<212> TYPE: DNA
<213> ORGANISM: Homo sapiens

<400> SEQUENCE: 360
aagaaagatc cctcaggcct tgataagaag 30

<210> SEQ ID NO 361
<211> LENGTH: 75
<212> TYPE: DNA
<213> ORGANISM: Homo sapiens

<400> SEQUENCE: 361
ggccagtcca ggaggtctta gtgctgtgcg aaccagcaac ttcgcccttg ttggatctta 60
cacattatca ttgtc 75

<210> SEQ ID NO 362
<211> LENGTH: 40
<212> TYPE: DNA
<213> ORGANISM: Homo sapiens

<400> SEQUENCE: 362
taagagagcg agagctactg ggctatttgt tccaggaaaa 40

<210> SEQ ID NO 363
<211> LENGTH: 75
<212> TYPE: DNA
<213> ORGANISM: Homo sapiens

<400> SEQUENCE: 363
gttttggtgc ctggcatcga agatggtgtg ttctttctgg aaactgtata tcttattgga 60
cttatccaga tgatg 75

<210> SEQ ID NO 364
<211> LENGTH: 378
<212> TYPE: DNA
<213> ORGANISM: Homo sapiens

<400> SEQUENCE: 364
ttggctgttg gctcatgtgt gcctatatgt gtttcttttc ccattttcag gaccatttgg 60

| | |
|---|---|
| tctcgtgaat gttttcctcc actttgactc gtatcatagg aattcatggc tgccaacaat | 120 |
| ccagggcagt tgtctgccct tatctttcat agatatataa agaaatattt acacatgaaa | 180 |
| tccaatgtct aggtttcctt ttatagaaag gggagaagtg ggtaagttgt agataaaagg | 240 |
| cacttgagtg tgtttctcat tgttatagct ggttttggta cctggggctc attatactgt | 300 |
| tgtttgtatt ttttatttga agttcaccat aataaagagc tttataggat agttggcaag | 360 |
| agctaccagt tgatattt | 378 |

<210> SEQ ID NO 365
<211> LENGTH: 33
<212> TYPE: DNA
<213> ORGANISM: Homo sapiens

<400> SEQUENCE: 365

| | |
|---|---|
| cataggaagg ataaatctgg ctaattgtac cag | 33 |

<210> SEQ ID NO 366
<211> LENGTH: 96
<212> TYPE: DNA
<213> ORGANISM: Homo sapiens

<400> SEQUENCE: 366

| | |
|---|---|
| gtgcaagacg caacactttt gaattaatta ctgtccgacc acaaagagaa gatgaccgag | 60 |
| agactcttgt cagccaatgc agggacacac tctgtg | 96 |

<210> SEQ ID NO 367
<211> LENGTH: 81
<212> TYPE: DNA
<213> ORGANISM: Homo sapiens

<400> SEQUENCE: 367

| | |
|---|---|
| tggctgtctg cagatactaa agaagagcgg gatctctgga tgcaaaaact caatcaagtt | 60 |
| cttgttgata ttcgcctctg g | 81 |

<210> SEQ ID NO 368
<211> LENGTH: 27
<212> TYPE: DNA
<213> ORGANISM: Homo sapiens

<400> SEQUENCE: 368

| | |
|---|---|
| ttgctacaaa cctattggaa agcctta | 27 |

<210> SEQ ID NO 369
<211> LENGTH: 645
<212> TYPE: DNA
<213> ORGANISM: Homo sapiens

<400> SEQUENCE: 369

| | |
|---|---|
| tacgaaaggg tttgtgccaa tattcactac gtattatgca gtatttatat cttttgtatg | 60 |
| taaaacttta actgatttct gtcattcatc aatgagtaga agtaaataca ttatagttga | 120 |
| ttttgctaaa tcttaattta aaagcctcat tttcctagaa atctaattat tcagttattc | 180 |
| atgacaatat ttttttaaaa gtaagaaatt ctgagttgtc ttcttggagc tgtaggtctt | 240 |
| gaagcagcaa cgtctttcag gggttggaga cagaaaccca ttctccaatc tcagtagttt | 300 |
| tttcgaaagg ctgtgatcat ttattgatcg tgatatgact tgttactagg gtactgaaaa | 360 |
| aaatgtctaa ggcctttaca gaaacatttt tagtaatgag gatgagaact ttttcaaata | 420 |
| gcaaatatat attggcttaa agcatgaggc tgtcttcaga aaagtgatgt ggacatagga | 480 |

ggcaatgtgt gagacttggg ggttcaatat tttatataga agagttaata agcacatggt 540
ttacatttac tcagctacta tatatgcagt gtggtgcaca ttttcacaga attctggctt 600
cattaagatc attatttttg ctgcgtagct tacagactta gcata 645

<210> SEQ ID NO 370
<211> LENGTH: 120
<212> TYPE: DNA
<213> ORGANISM: Homo sapiens

<400> SEQUENCE: 370
ccgagaggaa gtttggcgtg gtggtggttg gtgttggccg agccggctcc gtgcggatga 60
gggacttgcg gaatccacac ccttcctcag cgttcctgaa cctgattggc ttcgtgtcga 120

<210> SEQ ID NO 371
<211> LENGTH: 100
<212> TYPE: DNA
<213> ORGANISM: Homo sapiens

<400> SEQUENCE: 371
agctcgggag cattgatgga gtccagcaga tttctttgga ggatgctctt tccagccaag 60
aggtggaggt cgcctatatc tgcagtgaga gctccagcca 100

<210> SEQ ID NO 372
<211> LENGTH: 74
<212> TYPE: DNA
<213> ORGANISM: Homo sapiens

<400> SEQUENCE: 372
ttccttaatg ctggcaagca cgtccttgtg gaataccccca tgacactgtc attggcggcc 60
gctcaggaac tgtg 74

<210> SEQ ID NO 373
<211> LENGTH: 104
<212> TYPE: DNA
<213> ORGANISM: Homo sapiens

<400> SEQUENCE: 373
gaaaagtctt gcacgaggag catgttgaac tcttgatgga ggaattcgct ttcctgaaaa 60
aagaagtggt ggggaaagac ctgctgaaag ggtcgctcct cttc 104

<210> SEQ ID NO 374
<211> LENGTH: 124
<212> TYPE: DNA
<213> ORGANISM: Homo sapiens

<400> SEQUENCE: 374
agaagagcgg tttggcttcc ctgcattcag cggcatctct cgcctgacct ggctggtctc 60
cctctttggg gagctttctc ttgtgtctgc cactttggaa gagcgaaagg aagatcagta 120
tatg 124

<210> SEQ ID NO 375
<211> LENGTH: 124
<212> TYPE: DNA
<213> ORGANISM: Homo sapiens

<400> SEQUENCE: 375
cctggtctaa aacgaaacag atatttaagc ttccatttca agtctgggtc cttggagaat 60
gtgccaaatg taggagtgaa taagaacata tttctgaaag atcaaaatat atttgtccag 120
aaac 124

<210> SEQ ID NO 376
<211> LENGTH: 42
<212> TYPE: DNA
<213> ORGANISM: Homo sapiens

<400> SEQUENCE: 376
ggttcttctc aagagttgac cattatctct attcttaaaa tt 42

<210> SEQ ID NO 377
<211> LENGTH: 28
<212> TYPE: DNA
<213> ORGANISM: Homo sapiens

<400> SEQUENCE: 377
ggctgcgctc tgcccggcga gtcgggct 28

<210> SEQ ID NO 378
<211> LENGTH: 31
<212> TYPE: DNA
<213> ORGANISM: Homo sapiens

<400> SEQUENCE: 378
atgatccttt gcctggactt tctaagtgcc c 31

<210> SEQ ID NO 379
<211> LENGTH: 121
<212> TYPE: DNA
<213> ORGANISM: Homo sapiens

<400> SEQUENCE: 379
gttgcacttg gcctagcatt ccaacctcac ctgcctcagc ttgttcaacc tgaaaaccta 60
ccaagtgaaa gcaagagcca cgtgaagacg ccttagttat atgcacccac ccagacactt 120
g 121

<210> SEQ ID NO 380
<211> LENGTH: 186
<212> TYPE: DNA
<213> ORGANISM: Homo sapiens

<400> SEQUENCE: 380
aactacaggc cttttgagag agtgccctcc taatgaattg agtacctatt tctccataca 60
cagtgtctat catgacctac aaaccctttt cccatgaggt gtaacagaga gagattacag 120
ccttggaact ggatgtcaga ctctcctggt ttaagacaat aagccatgac atagagcctg 180
aaacca 186

<210> SEQ ID NO 381
<211> LENGTH: 124
<212> TYPE: DNA
<213> ORGANISM: Homo sapiens

<400> SEQUENCE: 381
caagctcacg cagttgggca cttttgaaga tcattttctc agcctccaga ggatgttcaa 60
taactgtgag gtggtccttg ggaatttgga aattacctat gtgcagagga attatgatct 120
ttcc 124

<210> SEQ ID NO 382
<211> LENGTH: 120
<212> TYPE: DNA
<213> ORGANISM: Homo sapiens

<400> SEQUENCE: 382
aggtggctgg ttatgtcctc attgccctca acacagtgga gcgaattcct ttggaaaacc 60
tgcagatcat cagaggaaat atgtactacg aaaattccta tgccttagca gtcttatcta 120

<210> SEQ ID NO 383
<211> LENGTH: 101
<212> TYPE: DNA
<213> ORGANISM: Homo sapiens

<400> SEQUENCE: 383
ggcgccgtgc ggttcagcaa caaccctgcc ctgtgcaacg tggagagcat ccagtggcgg 60
gacatagtca gcagtgactt tctcagcaac atgtcgatgg a 101

<210> SEQ ID NO 384
<211> LENGTH: 41
<212> TYPE: DNA
<213> ORGANISM: Homo sapiens

<400> SEQUENCE: 384
gccaaaagtg tgatccaagc tgtcccaatg ggagctgctg g 41

<210> SEQ ID NO 385
<211> LENGTH: 109
<212> TYPE: DNA
<213> ORGANISM: Homo sapiens

<400> SEQUENCE: 385
aaaatcatct gtgcccagca gtgctccggg cgctgccgtg gcaagtcccc cagtgactgc 60
tgccacaacc agtgtgctgc aggctgcaca ggcccccggg agagcgact 109

<210> SEQ ID NO 386
<211> LENGTH: 113
<212> TYPE: DNA
<213> ORGANISM: Homo sapiens

<400> SEQUENCE: 386
cgaagccacg tgcaaggaca cctgcccccc actcatgctc tacaacccca ccacgtacca 60
gatggatgtg aaccccgagg gcaaatacag ctttggtgcc acctgcgtga aga 113

<210> SEQ ID NO 387
<211> LENGTH: 96
<212> TYPE: DNA
<213> ORGANISM: Homo sapiens

<400> SEQUENCE: 387
taattatgtg gtgacagatc acggctcgtg cgtccgagcc tgtggggccg acagctatga 60
gatggaggaa gacggcgtcc gcaagtgtaa gaagtg 96

<210> SEQ ID NO 388
<211> LENGTH: 25
<212> TYPE: DNA
<213> ORGANISM: Homo sapiens

<400> SEQUENCE: 388
tggatattct gaaaaccgta aagga 25

<210> SEQ ID NO 389
<211> LENGTH: 48
<212> TYPE: DNA
<213> ORGANISM: Homo sapiens

<400> SEQUENCE: 389
tgttttagag agagaacttt tcgacatatt tcctgttccc ttggaata 48

<210> SEQ ID NO 390
<211> LENGTH: 110
<212> TYPE: DNA
<213> ORGANISM: Homo sapiens

<400> SEQUENCE: 390
ttttctcttg cagtcgtcag cctgaacata acatccttgg gattacgctc cctcaaggag 60
ataagtgatg gagatgtgat aatttcagga aacaaaaatt tgtgctatgc 110

<210> SEQ ID NO 391
<211> LENGTH: 127
<212> TYPE: DNA
<213> ORGANISM: Homo sapiens

<400> SEQUENCE: 391
cacaggccag gtctgccatg ccttgtgctc ccccgagggc tgctggggcc cggagcccag 60
ggactgcgtc tcttgccgga atgtcagccg aggcagggaa tgcgtggaca agtgcaacct 120
tctggag 127

<210> SEQ ID NO 392
<211> LENGTH: 123
<212> TYPE: DNA
<213> ORGANISM: Homo sapiens

<400> SEQUENCE: 392
tgtatccagt gtgcccacta cattgacggc ccccactgcg tcaagacctg cccggcagga 60
gtcatgggag aaaacaacac cctggtctgg aagtacgcag acgccggcca tgtgtgccac 120
ctg 123

<210> SEQ ID NO 393
<211> LENGTH: 163
<212> TYPE: DNA
<213> ORGANISM: Homo sapiens

<400> SEQUENCE: 393
gccaggaaat gagagtctca aagccatgtt attctgcctt tttaaactat catcctgtaa 60
tcaaagtaat gatggcagcg tgtcccacca gagcgggagc ccagctgctc aggagtcatg 120
cttaggatgg atcccttctc ttctgccgtc agagtttcag ctg 163

<210> SEQ ID NO 394
<211> LENGTH: 326
<212> TYPE: DNA
<213> ORGANISM: Homo sapiens

<400> SEQUENCE: 394
gcctcatgcc ttcacgtgtc tgttcccccc gcttttcctt tctgccaccc ctgcacgtgg 60
gccgccaggt tcccaagagt atcctaccca tttccttcct tccactccct ttgccagtgc 120
ctctcacccc aactagtagc taaccatcac ccccaggact gacctcttcc tcctcgctgc 180
cagatgattg ttcaaagcac agaatttgtc agaaacctgc agggactcca tgctgccagc 240
cttctccgta attagcatgg ccccagtcca tgcttctagc cttggttcct tctgcccctc 300
tgtttgaaat tctagagcca gctgtg 326

<210> SEQ ID NO 395
<211> LENGTH: 25
<212> TYPE: DNA
<213> ORGANISM: Homo sapiens

<400> SEQUENCE: 395
gccaggtctt gaaggctgtc caacg 25

<210> SEQ ID NO 396
<211> LENGTH: 25
<212> TYPE: DNA
<213> ORGANISM: Homo sapiens

<400> SEQUENCE: 396
aagctacata gtgtctcact ttcca 25

<210> SEQ ID NO 397
<211> LENGTH: 28
<212> TYPE: DNA
<213> ORGANISM: Homo sapiens

<400> SEQUENCE: 397
gcctaagatc ccgtccatcg ccactggg 28

<210> SEQ ID NO 398
<211> LENGTH: 60
<212> TYPE: DNA
<213> ORGANISM: Homo sapiens

<400> SEQUENCE: 398
gtggccctgg ggatcggcct cttcatgcga aggcgccaca tcgttcggaa gcgcacgctg 60

<210> SEQ ID NO 399
<211> LENGTH: 112
<212> TYPE: DNA
<213> ORGANISM: Homo sapiens

<400> SEQUENCE: 399
gcctcttaca cccagtggag aagctcccaa ccaagctctc ttgaggatct tgaaggaaac 60
tgaattcaaa aagatcaaag tgctgggctc cggtgcgttc ggcacggtgt at 112

<210> SEQ ID NO 400
<211> LENGTH: 59
<212> TYPE: DNA
<213> ORGANISM: Homo sapiens

<400> SEQUENCE: 400
ttaaaattcc cgtcgctatc aaggaattaa gagaagcaac atctccgaaa gccaacaag 59

<210> SEQ ID NO 401
<211> LENGTH: 162
<212> TYPE: DNA
<213> ORGANISM: Homo sapiens

<400> SEQUENCE: 401
ctacgtgatg gccagcgtgg acaaccccca cgtgtgccgc ctgctgggca tctgcctcac 60
ctccaccgtg cagctcatca cgcagctcat gcccttcggc tgcctcctgg actatgtccg 120

-continued ggaacacaaa gacaatattg gctcccagta cctgctcaac tg 162

<210> SEQ ID NO 402
<211> LENGTH: 139
<212> TYPE: DNA
<213> ORGANISM: Homo sapiens

<400> SEQUENCE: 402
ggcatgaact acttggagga ccgtcgcttg gtgcaccgcg acctggcagc caggaacgta 60
ctggtgaaaa caccgcagca tgtcaagatc acagattttg ggctggccaa actgctgggt 120
gcggaagaga aagaatacc 139

<210> SEQ ID NO 403
<211> LENGTH: 62
<212> TYPE: DNA
<213> ORGANISM: Homo sapiens

<400> SEQUENCE: 403
gtgcctatca agtggatggc attggaatca attttacaca gaatctatac ccaccagagt 60
ga 62

<210> SEQ ID NO 404
<211> LENGTH: 117
<212> TYPE: DNA
<213> ORGANISM: Homo sapiens

<400> SEQUENCE: 404
agttgatgac ctttggatcc aagccatatg acggaatccc tgccagcgag atctcctcca 60
tcctggagaa aggagaacgc ctccctcagc cacccatatg taccatcgat gtctaca 117

<210> SEQ ID NO 405
<211> LENGTH: 72
<212> TYPE: DNA
<213> ORGANISM: Homo sapiens

<400> SEQUENCE: 405
ctggatgata gacgcagata gtcgcccaaa gttccgtgag ttgatcatcg aattctccaa 60
aatggcccga ga 72

<210> SEQ ID NO 406
<211> LENGTH: 241
<212> TYPE: DNA
<213> ORGANISM: Homo sapiens

<400> SEQUENCE: 406
gcttccattg ggaagagtcc ctctaatgag catctcatgt cactgtgttc tgtcacatgc 60
cagcctggcc tccctgtgtc ccagatcgca ttattaaacc ctccagcgca ttagagcaag 120
cctcagtaag gcgcaggcca catcgtgaac taagcagcat ccgtgagtgg ggcccaccca 180
actccatctc cccctccccg tctgaactct cctctggtgc tcgtcctcac tgtccggcta 240
g 241

<210> SEQ ID NO 407
<211> LENGTH: 109
<212> TYPE: DNA
<213> ORGANISM: Homo sapiens

<400> SEQUENCE: 407
ggggatgaaa gaatgcattt gccaagtcct acagactcca acttctaccg tgccctgatg 60
gatgaagaag acatggacga cgtggtggat gccgacgagt acctcatcc 109

<210> SEQ ID NO 408
<211> LENGTH: 75
<212> TYPE: DNA
<213> ORGANISM: Homo sapiens

<400> SEQUENCE: 408
gacagcttct tgcagcgata cagctcagac cccacaggcg ccttgactga ggacagcata 60
gacgacacct tcctc 75

<210> SEQ ID NO 409
<211> LENGTH: 34
<212> TYPE: DNA
<213> ORGANISM: Homo sapiens

<400> SEQUENCE: 409
tcctgctcct caacctcctc gacccactca gcag 34

<210> SEQ ID NO 410
<211> LENGTH: 30
<212> TYPE: DNA
<213> ORGANISM: Homo sapiens

<400> SEQUENCE: 410
cctccagcat ctccagaggg ggaaacagtg 30

<210> SEQ ID NO 411
<211> LENGTH: 181
<212> TYPE: DNA
<213> ORGANISM: Homo sapiens

<400> SEQUENCE: 411
gtcaacagca cattcgacag ccctgcccac tgggcccaga aaggcagcca ccaaattagc 60
ctggacaacc ctgactacca gcaggacttc tttcccaagg aagccaagcc aaatggcatc 120
tttaagggct ccacagctga aaatgcagaa tacctaaggg tcgcgccaca aagcagtgaa 180
t 181

<210> SEQ ID NO 412
<211> LENGTH: 1324
<212> TYPE: DNA
<213> ORGANISM: Homo sapiens

<400> SEQUENCE: 412
ccacagactg gttttgcaac gtttacaccg actagccagg aagtacttcc acctcgggca 60
cattttggga agttgcattc ctttgtcttc aaactgtgaa gcatttacag aaacgcatcc 120
agcaagaata ttgtcccttt gagcagaaat ttatctttca aagaggtata tttgaaaaaa 180
aaaaaaagta tatgtgagga tttttattga ttggggatct tggagttttt cattgtcgct 240
attgattttt acttcaatgg gctcttccaa caaggaagaa gcttgctggt agcacttgct 300
accctgagtt catccaggcc caactgtgag caaggagcac aagccacaag tcttccagag 360
gatgcttgat tccagtggtt ctgcttcaag gcttccactg caaaacacta aagatccaag 420
aaggccttca tggccccagc aggccggatc ggtactgtat caagtcatgg caggtacagt 480
aggataagcc actctgtccc ttcctgggca aagaagaaac ggaggggatg gaattcttcc 540
ttagacttac ttttgtaaaa atgtccccac ggtacttact ccccactgat ggaccagtgg 600

-continued

```
tttccagtca tgagcgttag actgacttgt ttgtcttcca ttccattgtt ttgaaactca    660

gtatgctgcc cctgtcttgc tgtcatgaaa tcagcaagag aggatgacac atcaaataat    720

aactcggatt ccagcccaca ttggattcat cagcatttgg accaatagcc cacagctgag    780

aatgtggaat acctaaggat agcaccgctt ttgttctcgc aaaaacgtat ctcctaattt    840

gaggctcaga tgaaatgcat caggtccttt ggggcataga tcagaagact acaaaaatga    900

agctgctctg aaatctcctt tagccatcac cccaaccccc caaaattagt ttgtgttact    960

tatggaagat agttttctcc ttttacttca cttcaaaagc tttttactca aagagtatat   1020

gttccctcca ggtcagctgc ccccaaaccc cctccttacg ctttgtcaca caaaaagtgt   1080

ctctgccttg agtcatctat tcaagcactt acagctctgg ccacaacagg gcattttaca   1140

ggtgcgaatg acagtagcat tatgagtagt gtggaattca ggtagtaaat atgaaactag   1200

ggtttgaaat tgataatgct ttcacaacat ttgcagatgt tttagaagga aaaaagttcc   1260

ttcctaaaat aatttctcta caattggaag attggaagat tcagctagtt aggagcccac   1320

cttt                                                                1324
```

<210> SEQ ID NO 413
<211> LENGTH: 129
<212> TYPE: DNA
<213> ORGANISM: Homo sapiens

<400> SEQUENCE: 413

```
ggcaccctga ccgaggaaac agctgccaga ggcctccact gctaaagtcc acataaggct     60

gaggtcagtc accctaaaca acctgctccc tctaagccag gggatgagct tggagcatcc    120

cacaagttc                                                            129
```

<210> SEQ ID NO 414
<211> LENGTH: 85
<212> TYPE: DNA
<213> ORGANISM: Homo sapiens

<400> SEQUENCE: 414

```
gaaatatttc agtcagaact gggaaacaga aggacctaca ttctgctgtc acttatgtgt     60

caagaagcag atgatcgatg aggca                                           85
```

<210> SEQ ID NO 415
<211> LENGTH: 71
<212> TYPE: DNA
<213> ORGANISM: Homo sapiens

<400> SEQUENCE: 415

```
gtcagttgta agtgagtcac attgtagcat taaattctag tatttttgta gtttgaaaca     60

gtaacttaat a                                                          71
```

<210> SEQ ID NO 416
<211> LENGTH: 51
<212> TYPE: DNA
<213> ORGANISM: Homo sapiens

<400> SEQUENCE: 416

```
cacagttctg tctggtagaa gccgcaaagc ccttagcctc ttcacggatc t              51
```

<210> SEQ ID NO 417
<211> LENGTH: 128
<212> TYPE: DNA
<213> ORGANISM: Homo sapiens

<400> SEQUENCE: 417
gatagcctgg ccttaatacc ctacagaaag cctgtccatt ggctgtttct tcctcagtca 60
gttcctggaa gaccttaccc catgacccca gcttcagatg tggtctttgg aaacagaggt 120
cgaaggaa 128

<210> SEQ ID NO 418
<211> LENGTH: 1828
<212> TYPE: DNA
<213> ORGANISM: Homo sapiens

<400> SEQUENCE: 418
ctaggcctct gattgcactt gtgtaggatg aagctggtgg gtgatgggaa ctcagcacct 60
cccctcaggc agaaaagaat catctgtgga gcttcaaaag aaggggcctg gagtctctgc 120
agaccaattc aacccaaatc tcgggggctc tttcatgatt ctaatgggca accagggttg 180
aaacccttat ttctagggtc ttcagttgta caagactgtg ggtctgtacc agagcccccg 240
tcagagtaga ataaaaggct gggtagggta gagattccca tgtgcagtgg agagaacaat 300
ctgcagtcac tgataagcct gagacttggc tcatttcaaa agcgttcaat tcatcctcac 360
cagcagttca gctggaaagg ggcaaatacc cccacctgag ctttgaaaac gccctgggac 420
cctctgcatt ctctaagtaa gttatagaaa ccagtctctt ccctcctttg tgagtgagct 480
gctattccac gtaggcaaca cctgttgaaa ttgccctcaa tgtctactct gcatttcttt 540
cttgtgataa gcacacactt ttattgcaac ataatgatct gctcacattt ccttgcctgg 600
gggctgtaaa accttacaga acagaaatcc ttgcctcttt caccagccac acctgccata 660
ccaggggtac agctttgtac tattgaagac acagacagga tttttaaatg taaatctatt 720
tttgtaactt tgttgcggga tatagttctc tttatgtagc actgaacttt gtacaatata 780
tttttagaaa ctcatttttc tactaaaaca aacacagttt actttagaga gactgcaata 840
gaatcaaaat ttgaaactga aatctttgtt taaaagggtt aagttgaggc aagaggaaag 900
ccctttctct ctcttataaa aaggcacaac ctcattgggg agctaagcta ggtcattgtc 960
atggtgaaga agagaagcat cgtttttata tttaggaaat tttaaaagat gatggaaagc 1020
acatttagct tggtctgagg caggttctgt tggggcagtg ttaatggaaa gggctcactg 1080
ttgttactac tagaaaaatc cagttgcatg ccatactctc atcatctgcc agtgtaaccc 1140
tgtacatgta agaaaagcaa taacatagca ctttgttggt ttatatatat aatgtgactt 1200
caatgcaaat tttattttta tatttacaat tgatatgcat ttaccagtat aaactagaca 1260
tgtctggaga gcctaataat gttcagcaca ctttggttag ttcaccaaca gtcttaccaa 1320
gcctgggccc agccacccta gagaagttat tcagccctgg ctgcagtgac atcacctgag 1380
gagcttttaa aagcttgaag cccagctaca cctcagaccg attaaacgca aatctctggg 1440
gctgaaaccc aagcattcgt agtttttaaa gctcctgagg tcattccaat gtgcggccaa 1500
agttgagaac tactggccta gggattagcc acaaggacat ggacttggag gcaaattctg 1560
caggtgtatg tgattctcag gcctagagag ctaagacaca aagacctcca catctgtcgc 1620
tgagagtcaa gaacctgaac agagtttcca tgaaggttct ccaagcacta gaagggagag 1680
tgtctaaaca atggttgaaa agcaaaggaa atataaaaca gacacctctt tccatttcct 1740
aaggtttctc tctttattaa gggtggacta gtaataaaat ataatattct tgctgcttat 1800
gcagctgaca ttgttgccct ccctaaag 1828

<210> SEQ ID NO 419
<211> LENGTH: 32
<212> TYPE: DNA
<213> ORGANISM: Homo sapiens

<400> SEQUENCE: 419
gaaaacgctg gcctatcagt tacattacaa aa 32

<210> SEQ ID NO 420
<211> LENGTH: 355
<212> TYPE: DNA
<213> ORGANISM: Homo sapiens

<400> SEQUENCE: 420
actacctgca gtgtgtcctc tgaggctgca agtctgtcct atctgaattc ccagcagaag 60
cactaagaag ctccacccta tcacctagca gataaaacta tggggaaaac ttaaatctgt 120
gcatacattt ctggatgcat ttacttatct ttaaaaaaaa aggaatccta tgacctgatt 180
tggccacaaa aataatcttg ctgtacaata caatctcttg gaaattaaga gatcctatgg 240
atttgatgac tggtattaga ggtgacaatg taaccgatta acaacagaca gcaataactt 300
cgttttagaa acattcaagc aatagcttta tagcttcaac atatggtacg tttta 355

<210> SEQ ID NO 421
<211> LENGTH: 973
<212> TYPE: DNA
<213> ORGANISM: Homo sapiens

<400> SEQUENCE: 421
ccagctgctg ctcttattgg gctaagggat gaagactaca caggctgtcg agttctcctc 60
caggatactc actgactccc aggtggccta ctctatcaac ccatgagcat ggtcagccct 120
gagacactgt caggaagtga gaggccactg taggagtgtc acgctaacag ctaacccagc 180
ggcccccatg aaggctgacg cttggcatcc ctggagaatg ggtcacactt ttacctcatc 240
gcatagccat agtctctgcc tccacagcct tcattttctc actttttcta tcaatgccca 300
agaaaagaat gtttttccat gcaaaaccca gcaaagaaat aaagtcccca agcctgtgtg 360
cagggttaaa ggaacctcat gagagtgaag cactaggctg cgaaggggag aaacccactt 420
gggaaaagcc caccacttcg gggaacctgg atgacggccc atagagcata gtgccacaaa 480
cagtgactct gaaagttcgt gttccatggt tccaagattt gaagtagtgt tactcctcag 540
aggcctttgt tactaatccc cacggtgggc tttttccacc acaggtttta acctagcttt 600
gaactatgtt caagtcctat gaggttgcaa agcaccaccc caatattctt atacctataa 660
cggggcacag aagctactga agcatttggt agggctgtgg ctgcctgtgc agtgggctat 720
gtgaaaatca actggagtct cctggagagt gggctctgga agtctcctca gtcatcaacg 780
caggctcttg acctctcgtg cactatatga ccaaagtcta cgcaggctat gtgggctatt 840
tgcgattcaa gtccagctat gtgctgcttc taacccaggc agtattccag actgcagtcc 900
agctgagcgt ggaatgtgta tcctggtgcc cggattccac acttcactgc cttggtgatt 960
cagccgaccc tca 973

<210> SEQ ID NO 422
<211> LENGTH: 259
<212> TYPE: DNA
<213> ORGANISM: Homo sapiens

<400> SEQUENCE: 422
gcattttgct aagtccctga gggtcactgg tcctcaaagc ggcatggcgg catggcgtgg 60
ctggttctgc cacatgccag ctgtgtgacc tctgagactc cacttcttca gtgctgaaaa 120
taaagaagga gttttactaa ggaccaaaca agataatgaa tgtgaaactg ctccacgaac 180
cccaaagaat tatgcacata gatgcgatca ttaagatgcg aagccatcga gttaccacct 240
ggcatgctta aactgtaaa 259

<210> SEQ ID NO 423
<211> LENGTH: 77
<212> TYPE: DNA
<213> ORGANISM: Homo sapiens

<400> SEQUENCE: 423
ctgcggcggc tcgcgggaga cgctgcgcgc ggggctagcg ggcggcggag cggacggcga 60
cggggcgctc tcgggct 77

<210> SEQ ID NO 424
<211> LENGTH: 33
<212> TYPE: DNA
<213> ORGANISM: Homo sapiens

<400> SEQUENCE: 424
tccctgcctc cctgcgtggt ggactgtggc acc 33

<210> SEQ ID NO 425
<211> LENGTH: 27
<212> TYPE: DNA
<213> ORGANISM: Homo sapiens

<400> SEQUENCE: 425
aactatctcc ttcctgctgt aatcagt 27

<210> SEQ ID NO 426
<211> LENGTH: 48
<212> TYPE: DNA
<213> ORGANISM: Homo sapiens

<400> SEQUENCE: 426
aggctccacc atgttcaggg atttcggacg ccgactgcag agggattt 48

<210> SEQ ID NO 427
<211> LENGTH: 62
<212> TYPE: DNA
<213> ORGANISM: Homo sapiens

<400> SEQUENCE: 427
gaggtccagg tggtcacgca tcacatgcag cgctacgccg tgtggttcgg aggctccatg 60
ct 62

<210> SEQ ID NO 428
<211> LENGTH: 61
<212> TYPE: DNA
<213> ORGANISM: Homo sapiens

<400> SEQUENCE: 428
aaggactatg aagagtacgg gcccagcatc tgccgccaca accccgtctt tggagtcatg 60
t 61

<210> SEQ ID NO 429

<211> LENGTH: 107
<212> TYPE: DNA
<213> ORGANISM: Homo sapiens

<400> SEQUENCE: 429
ttcgatggtg tcacgttggg gaacaagtgt ccttcagaac ccagagaagg ccgccgttct 60
gtaaatagcg acgtcggtgt tgctgcccag cagcgtgctt gcattgc 107

<210> SEQ ID NO 430
<211> LENGTH: 194
<212> TYPE: DNA
<213> ORGANISM: Homo sapiens

<400> SEQUENCE: 430
ccatttatcc gtgtgccgac cgctgtctgc cagcctcctc cttctcccgc cctcctcacc 60
ctcgctctcc ctcctcctcc tcctccgagc tgctagctga caaatacaat tctgaaggaa 120
tccaaatgtg actttgaaaa ttgttagaga aaacaacatt agaaaatggc gcaaaatcgt 180
taggtcccag gaga 194

<210> SEQ ID NO 431
<211> LENGTH: 331
<212> TYPE: DNA
<213> ORGANISM: Homo sapiens

<400> SEQUENCE: 431
gtacaactgg ctgatactaa gcacgaatag atattgatgt tatggagtgc tgtaatccaa 60
agtttttaat tgtgaggcat gttctgatat gtttataggc aaacaaataa aacagcaaac 120
ttttttgcca catgtttgct agaaaatgat tatactttat tggagtgaca tgaagtttga 180
acactaaaca gtaatgtatg agaattacta cagatacatg tatcttttag tttttttttgt 240 ttgaactttc tggagctgtt ttatagaaga tgatggtttg ttgtcggtga gtgttggatg 300
aaatacttcc ttgcaccatt gtaataaaag c 331

<210> SEQ ID NO 432
<211> LENGTH: 33
<212> TYPE: DNA
<213> ORGANISM: Homo sapiens

<400> SEQUENCE: 432
attgacccag tcgacaggat ctgaacttcc agt 33

<210> SEQ ID NO 433
<211> LENGTH: 140
<212> TYPE: DNA
<213> ORGANISM: Homo sapiens

<400> SEQUENCE: 433
ggacctgttc caagctctca cgttccacat cacacatggg acatctagtg tcaggctccc 60
agagagcagg aaccaggtga aatataagag cacagtcctc ccagccggtg gcatggggat 120
aatcggacaa tacaactctc 140

<210> SEQ ID NO 434
<211> LENGTH: 132
<212> TYPE: DNA
<213> ORGANISM: Homo sapiens

<400> SEQUENCE: 434
ccctgaacat ggacttgcag aattccacag aagagaggag actggcctag acagacagcc 60
ccaggagctg agggcccaac aggctttcta ccctggatgc tgctcccatg ccctgacatg 120
aggcccacta ca 132

<210> SEQ ID NO 435
<211> LENGTH: 203
<212> TYPE: DNA
<213> ORGANISM: Homo sapiens

<400> SEQUENCE: 435
cagcctggat gtgaactgca actccaaagt gtgtccagac tcaaggcaag ggcactaggc 60
tttccagacc tcctactaag tcattgatcc agcactgccc tgccaggaca taaatccctg 120
gcacctcttg ctctctgcaa aggagggcaa agcagcttca ggagcccttg ggagtcctcc 180
aaagagagtc tagggtacag gtc 203

<210> SEQ ID NO 436
<211> LENGTH: 108
<212> TYPE: DNA
<213> ORGANISM: Homo sapiens

<400> SEQUENCE: 436
acagaagggc catgctgtta ttactcttac acaaggaggc agccctcgag ccacagggtc 60
cagctgttgg ctataatagc ctaccggtct ctgatgatca ccatgttt 108

<210> SEQ ID NO 437
<211> LENGTH: 54
<212> TYPE: DNA
<213> ORGANISM: Homo sapiens

<400> SEQUENCE: 437
gcagcaatct gtcttctgga ttaaaactga agatcaacct actttcaact tact 54

<210> SEQ ID NO 438
<211> LENGTH: 40
<212> TYPE: DNA
<213> ORGANISM: Homo sapiens

<400> SEQUENCE: 438
aaatatagcc ataattagcc tactcaaatc caagtgtaaa 40

<210> SEQ ID NO 439
<211> LENGTH: 733
<212> TYPE: DNA
<213> ORGANISM: Homo sapiens

<400> SEQUENCE: 439
ccattgtggg gatgccatgg acttaggctt agaggccatt tttgatcaag ttgtgagaag 60
aaatcggggt ggatggtgtc tccaggtcaa tcatcttctg tactgggctc tgaccactat 120
tggttttgag accacgatgt tgggagggta tgtttacagc actccagcca aaaaatacag 180
cactggcatg attcaccttc tcctgcaggt gaccattgat ggcaggaact acattgtcga 240
tgctgggttt ggacgctcat accagatgtg gcagcctctg gagttaattt ctgggaagga 300
tcagcctcag gtgccttgtg tcttccgttt gacggaagag aatggattct ggtatctaga 360
ccaaatcaga agggaacagt acattccaaa tgaagaattt cttcattctg atctcctaga 420
agacagcaaa taccgaaaaa tctactcctt tactcttaag cctcgaacaa ttgaagattt 480
tgagtctatg aatacatacc tgcagacatc tccatcatct gtgtttacta gtaaatcatt 540

-continued

```
ttgttccttg cagaccccag atggggttca ctgtttggtg ggcttcaccc tcacccatag    600

gagattcaat tataaggaca atacagatct aatagagttc aagactctga gtgaggaaga    660

aatagaaaaa gtgctgaaaa atatatttaa tatttccttg cagagaaagc ttgtgcccaa    720

acatggtgat aga                                                       733
```

<210> SEQ ID NO 440
<211> LENGTH: 90
<212> TYPE: DNA
<213> ORGANISM: Homo sapiens

<400> SEQUENCE: 440

```
ataaggagta aaacaatctt gtctatttgt catccagctc accagttatc aactgacgac     60

ctatcatgta tcttctgtac ccttacctta                                      90
```

<210> SEQ ID NO 441
<211> LENGTH: 54
<212> TYPE: DNA
<213> ORGANISM: Homo sapiens

<400> SEQUENCE: 441

```
aaagatggcc tgtggttatc ttggaaattg gtgatttatg ctagaaagct ttta           54
```

<210> SEQ ID NO 442
<211> LENGTH: 117
<212> TYPE: DNA
<213> ORGANISM: Homo sapiens

<400> SEQUENCE: 442

```
cttgtgtaga tctgagttga aatcctgtgg acactgggcg aattactttt tagatctgta     60

gctctgactc ctcaggcata aaatgggaat aatgctttta cagtttagtg gcggaac       117
```

<210> SEQ ID NO 443
<211> LENGTH: 182
<212> TYPE: DNA
<213> ORGANISM: Homo sapiens

<400> SEQUENCE: 443

```
taacgcgctc tccaagtata cgtggcaatg cgttgctggg ttattttaat cattctaggc     60

atcgttttcc tccttatgcc tctatcattc ctccctatct acactaacat cccacgctct    120

gaacgcgcgc ccattaatac ccttctttcc tccactctcc ctgggactct tgatcaaagc    180

gc                                                                   182
```

<210> SEQ ID NO 444
<211> LENGTH: 43
<212> TYPE: DNA
<213> ORGANISM: Homo sapiens

<400> SEQUENCE: 444

```
atgcggtttg tcaaacagta ctgctacgga ggagcagcag aga                      43
```

<210> SEQ ID NO 445
<211> LENGTH: 382
<212> TYPE: DNA
<213> ORGANISM: Homo sapiens

<400> SEQUENCE: 445

```
gtaggcgcgc gtagttaatt catgcggctc tcttactctg tttacatcct agagctagag     60

tgctcggctg cccggctgag tctcctcccc accttcccca ccctccccac cctccccata    120
```

agcgcccctc ccgggttccc aaagcagagg gcgtggggga aaagaaaaaa gatcctctct 180
cgctaatctc cgcccaccgg ccctttataa tgcgagggtc tggacggctg aggacccccg 240
agctgtgctg ctcgcggccg ccaccgccgg gccccggccg tccctggctc ccctcctgcc 300
tcgagaaggg cagggcttct cagaggcttg gcgggaaaaa gaacggaggg agggatcgcg 360
ctgagtataa aagccggttt tc 382

<210> SEQ ID NO 446
<211> LENGTH: 35
<212> TYPE: DNA
<213> ORGANISM: Homo sapiens

<400> SEQUENCE: 446
caacccttgc cgcatccacg aaactttgcc catag 35

<210> SEQ ID NO 447
<211> LENGTH: 137
<212> TYPE: DNA
<213> ORGANISM: Homo sapiens

<400> SEQUENCE: 447
ttacaacacc cgagcaagga cgcgactctc ccgacgcggg gaggctattc tgcccatttg 60
gggacacttc cccgccgctg ccaggacccg cttctctgaa aggctctcct tgcagctgct 120
tagacgctgg atttttt 137

<210> SEQ ID NO 448
<211> LENGTH: 387
<212> TYPE: DNA
<213> ORGANISM: Homo sapiens

<400> SEQUENCE: 448
agccgtattt ctactgcgac gaggaggaga acttctacca gcagcagcag cagagcgagc 60
tgcagccccc ggcgcccagc gaggatatct ggaagaaatt cgagctgctg cccaccccgc 120
ccctgtcccc tagccgccgc tccgggctct gctcgccctc ctacgttgcg gtcacaccct 180
tctcccttcg gggagacaac gacggcggtg gcgggagctt ctccacggcc gaccagctgg 240
agatggtgac cgagctgctg ggaggagaca tggtgaacca gagtttcatc tgcgacccgg 300
acgacgagac cttcatcaaa aacatcatca tccaggactg tatgtggagc ggcttctcgg 360
ccgccgccaa gctcgtctca gagaagc 387

<210> SEQ ID NO 449
<211> LENGTH: 284
<212> TYPE: DNA
<213> ORGANISM: Homo sapiens

<400> SEQUENCE: 449
gaaggactat cctgctgcca agagggtcaa gttggacagt gtcagagtcc tgagacagat 60
cagcaacaac cgaaaatgca ccagccccag gtcctcggac accgaggaga atgtcaagag 120
gcgaacacac aacgtcttgg agcgccagag gaggaacgag ctaaaacgga gctttttgc 180 cctgcgtgac cagatcccgg agttggaaaa caatgaaaag gcccccaagg tagttatcct 240
taaaaaagcc acagcataca tcctgtccgt ccaagcagag gagc 284

<210> SEQ ID NO 450
<211> LENGTH: 139
<212> TYPE: DNA

<213> ORGANISM: Homo sapiens

<400> SEQUENCE: 450
ttccttctaa cagaaatgtc ctgagcaatc acctatgaac ttgtttcaaa tgcatgatca 60
aatgcaacct cacaaccttg gctgagtctt gagactgaaa gatttagcca taatgtaaac 120
tgcctcaaat tggactttg 139

<210> SEQ ID NO 451
<211> LENGTH: 38
<212> TYPE: DNA
<213> ORGANISM: Homo sapiens

<400> SEQUENCE: 451
tcctagtata tagtacctag tattataggt actataaa 38

<210> SEQ ID NO 452
<211> LENGTH: 566
<212> TYPE: DNA
<213> ORGANISM: Homo sapiens

<400> SEQUENCE: 452
tgtgcagctc tctaaatggg aattctcagg taggaagcaa cagcttcaga aagagctcaa 60
aataaattgg aaatgtgaat cgcagctgtg ggttttacca ccgtctgtct cagagtccca 120
ggaccttgag tgtcattagt tactttattg aaggttttag acccatagca gctttgtctc 180
tgtcacatca gcaatttcag aaccaaaagg gaggctctct gtaggcacag agctgcacta 240
tcacgagcct ttgtttttct ccacaaagta tctaacaaaa ccaatgtgca gactgattgg 300
cctggtcatt ggtctccgag agaggaggtt tgcctgtgat ttcctaatta tcgctagggc 360
caaggtggga tttgtaaagc tttacaataa tcattctgga tagagtcctg ggaggtcctt 420
ggcagaactc agttaaatct ttgaagaata tttgtagtta tcttagaaga tagcatggga 480
ggtgaggatt ccaaaaacat tttattttta aaatatcctg tgtaacactt ggctcttggt 540
acctgtgggt tagcatcaag ttctcc 566

<210> SEQ ID NO 453
<211> LENGTH: 1528
<212> TYPE: DNA
<213> ORGANISM: Homo sapiens

<400> SEQUENCE: 453
gcgcctgtca gtagtggaca ttgtaatcca gtcggcttgt tcttgcagca ttcccgctcc 60
cttccctcca tagccacgct ccaaacccca gggtagccat ggccgggtaa agcaagggcc 120
atttagatta ggaaggtttt taagatccgc aatgtggagc agcagccact gcacaggagg 180
aggtgacaaa ccatttccaa cagcaacaca gccactaaaa cacaaaaagg gggattgggc 240
ggaaagtgag agccagcagc aaaaactaca ttttgcaact tgttggtgtg gatctattgg 300
ctgatctatg cctttcaact agaaaattct aatgattggc aagtcacgtt gttttcaggt 360
ccagagtagt ttctttctgt ctgctttaaa tggaaacaga ctcataccac acttacaatt 420
aaggtcaagc ccagaaagtg ataagtgcag ggaggaaaag tgcaagtcca ttatgtaata 480
gtgacagcaa agggaccagg ggagaggcat tgccttctct gcccacagtc tttccgtgtg 540
attgtctttg aatctgaatc agccagtctc agatgcccca aagtttcggt tcctatgagc 600
ccggggcatg atctgatccc caagacatgt ggaggggcag cctgtgcctg cctttgtgtc 660
agaaaaagga aaccacagtg agcctgagag agacggcgat tttcgggctg agaaggcagt 720
agttttcaaa acacatagtt aaaaaagaaa caaatgaaaa aaattttaga acagtccagc 780
aaattgctag tcagggtgaa ttgtgaaatt gggtgaagag cttaggattc taatctcatg 840
ttttttcctt ttcacatttt taaaagaaca atgacaaaca cccacttatt tttcaaggtt 900
ttaaaacagt ctacattgag catttgaaag gtgtgctaga acaaggtctc ctgatccgtc 960
cgaggctgct tcccagagga gcagctctcc ccaggcattt gccaagggag gcggatttcc 1020
ctggtagtgt agctgtgtgg ctttccttcc tgaagagtcc gtggttgccc tagaacctaa 1080 cacccccctag caaaactcac agagctttcc gtttttttct ttcctgtaaa gaaacatttc 1140
ctttgaactt gattgcctat ggatcaaaga aattcagaac agcctgcctg tccccccgca 1200
ctttttacat atatttgttt catttctgca gatggaaagt tgacatgggt ggggtgtccc 1260
catccagcga gagagtttca aaagcaaaac atctctgcag tttttcccaa gtaccctgag 1320
atacttccca aagcccttat gtttaatcag cgatgtatat aagccagttc acttagacaa 1380
ctttaccctt cttgtccaat gtacaggaag tagttctaaa aaaaatgcat attaatttct 1440
tcccccaaag ccggattctt aattctctgc aacactttga ggacatttat gattgtccct 1500
ctgggccaat gcttataccc agtgagga 1528

<210> SEQ ID NO 454
<211> LENGTH: 46
<212> TYPE: DNA
<213> ORGANISM: Homo sapiens

<400> SEQUENCE: 454
aatgaaaaac catgagtgcc ccacctttca gtccgtgttt aagtga 46

<210> SEQ ID NO 455
<211> LENGTH: 57
<212> TYPE: DNA
<213> ORGANISM: Homo sapiens

<400> SEQUENCE: 455
cttcctcatc atgggccgca aggtgaagag ccagtacttg ctgacggcca tccacaa 57

<210> SEQ ID NO 456
<211> LENGTH: 76
<212> TYPE: DNA
<213> ORGANISM: Homo sapiens

<400> SEQUENCE: 456
aagttggggc ccatcaagaa gaaggacctg aagaagcttg tgctgtacct gaagaatggg 60
gctgactgtc cctgcc 76

<210> SEQ ID NO 457
<211> LENGTH: 31
<212> TYPE: DNA
<213> ORGANISM: Homo sapiens

<400> SEQUENCE: 457
agaaaatggc gacaagaaga ttgtccccaa g 31

<210> SEQ ID NO 458
<211> LENGTH: 69
<212> TYPE: DNA
<213> ORGANISM: Homo sapiens

<400> SEQUENCE: 458
tgtgtcctcc ctgtgacaac gagttgaaat ctgaggccat cattgaacat ctctgtgcca 60
gcgagtttg 69

<210> SEQ ID NO 459
<211> LENGTH: 219
<212> TYPE: DNA
<213> ORGANISM: Homo sapiens

<400> SEQUENCE: 459
gctcggctgc ggaaaaggtg ctgcagtcca cagggaacat ggggggattg gacgggttgc 60
ctgaagaaga gaggaaagaa tccctcaccc cagccccccaa aaggctgtga tgggatgggg 120
aaaccccata atcgctgtct tccggacacc ttttgcccct tggctgcagt tccactggtc 180
ggcgcccttc tcagcctggc ttggaaccgt cctcactca 219

<210> SEQ ID NO 460
<211> LENGTH: 388
<212> TYPE: DNA
<213> ORGANISM: Homo sapiens

<400> SEQUENCE: 460
tcggccagcg agtacgacta cgtgagcttc cagtcggaca tcggcccgta ccagagcggg 60
cgcttctaca ccaagccacc tcagtgcgtg gacatccccg cggacctgcg gctgtgccac 120
aacgtgggct acaagaagat ggtgctgccc aacctgctgg agcacgagac catggcggag 180
gtgaagcagc aggccagcag ctgggtgccc ctgctcaaca agaactgcca cgccggcacc 240
caggtcttcc tctgctcgct cttcgcgccc gtctgcctgg accggcccat ctacccgtgt 300
cgctggctct gcgaggccgt gcgcgactcg tgcgagccgg tcatgcagtt cttcggcttc 360
tactggcccg agatgcttaa gtgtgaca 388

<210> SEQ ID NO 461
<211> LENGTH: 28
<212> TYPE: DNA
<213> ORGANISM: Homo sapiens

<400> SEQUENCE: 461
gtcgcggaga acagggcgca gagccggc 28

<210> SEQ ID NO 462
<211> LENGTH: 27
<212> TYPE: DNA
<213> ORGANISM: Homo sapiens

<400> SEQUENCE: 462
tccctggaag tttgcggcag gacgcgc 27

<210> SEQ ID NO 463
<211> LENGTH: 210
<212> TYPE: DNA
<213> ORGANISM: Homo sapiens

<400> SEQUENCE: 463
tgcagcctcc ggagtcagtg ccgcgcgccc gccgccccgc gccttcctgc tcgccgcacc 60
tccgggagcc ggggcgcacc cagcccgcag cgccgcctcc ccgcccgcgc cgcctccgac 120
cgcaggccga gggccgccac tggccggggg gaccgggcag cagcttgcgg ccgcggagcc 180
gggcaacgct ggggactgcg ccttttgtcc 210

<210> SEQ ID NO 464
<211> LENGTH: 175
<212> TYPE: DNA
<213> ORGANISM: Homo sapiens

<400> SEQUENCE: 464
aatggatcca actgcttgcc ccgtcatccc agatggctag gcccccattc atcccctctc 60
gctctcctac tggaggaact gctgtatgaa tcataaagct ctgggtaggg aagcagggag 120
caggttccag gcagagctga caagtgactt cacttttgag catcggttga accag 175

<210> SEQ ID NO 465
<211> LENGTH: 100
<212> TYPE: DNA
<213> ORGANISM: Homo sapiens

<400> SEQUENCE: 465
aagcggccac aacccggcga tcgaaaagat tcttaggaac gccgtaccag ccgcgtctct 60
caggacagca ggcccctgtc cttctgtcgg gcgccgctca 100

<210> SEQ ID NO 466
<211> LENGTH: 103
<212> TYPE: DNA
<213> ORGANISM: Homo sapiens

<400> SEQUENCE: 466
cccagtttgc tcctggctct cgggagactg gaggatttca tcggagcccc gcgctttacc 60
agccctgttc cctggataag atatttgacc tttccgaccc gcg 103

<210> SEQ ID NO 467
<211> LENGTH: 31
<212> TYPE: DNA
<213> ORGANISM: Homo sapiens

<400> SEQUENCE: 467
ttctaattcc aaataaactt gcaagaggac t 31

<210> SEQ ID NO 468
<211> LENGTH: 44
<212> TYPE: DNA
<213> ORGANISM: Homo sapiens

<400> SEQUENCE: 468
tgaaagatta tgatgaactt ctcaaatatt atgaattaca tgaa 44

<210> SEQ ID NO 469
<211> LENGTH: 55
<212> TYPE: DNA
<213> ORGANISM: Homo sapiens

<400> SEQUENCE: 469
aaaggtcaaa cttgcctgcc atatccttac tggagagatg gtagctataa aaatc 55

<210> SEQ ID NO 470
<211> LENGTH: 105
<212> TYPE: DNA
<213> ORGANISM: Homo sapiens

<400> SEQUENCE: 470
cccggatcaa aacggagatt gaggccttga agaacctgag acatcagcat atatgtcaac 60
tctaccatgt gctagagaca gccaacaaaa tattcatggt tcttg 105

<210> SEQ ID NO 471
<211> LENGTH: 42
<212> TYPE: DNA
<213> ORGANISM: Homo sapiens

<400> SEQUENCE: 471
tactgccctg gaggagagct gtttgactat ataatttccc ag 42

<210> SEQ ID NO 472
<211> LENGTH: 68
<212> TYPE: DNA
<213> ORGANISM: Homo sapiens

<400> SEQUENCE: 472
cagaagagga gacccgggtt gtcttccgtc agatagtatc tgctgttgct tatgtgcaca 60
gccagggc 68

<210> SEQ ID NO 473
<211> LENGTH: 78
<212> TYPE: DNA
<213> ORGANISM: Homo sapiens

<400> SEQUENCE: 473
acaaggatta ccatctacag acatgctgtg ggagtctggc ttatgcagca cctgagttaa 60
tacaaggcaa atcatatc 78

<210> SEQ ID NO 474
<211> LENGTH: 40
<212> TYPE: DNA
<213> ORGANISM: Homo sapiens

<400> SEQUENCE: 474
gcagatgttt ggagcatggg catactgtta tatgttctta 40

<210> SEQ ID NO 475
<211> LENGTH: 36
<212> TYPE: DNA
<213> ORGANISM: Homo sapiens

<400> SEQUENCE: 475
aagtggctct ctcccagtag cattctgctt cttcaa 36

<210> SEQ ID NO 476
<211> LENGTH: 25
<212> TYPE: DNA
<213> ORGANISM: Homo sapiens

<400> SEQUENCE: 476
gacccaaaga aacggatttc tatga 25

<210> SEQ ID NO 477
<211> LENGTH: 38
<212> TYPE: DNA
<213> ORGANISM: Homo sapiens

<400> SEQUENCE: 477
gcaagattac aactatcctg ttgagtggca aagcaaga 38

<210> SEQ ID NO 478
<211> LENGTH: 76
<212> TYPE: DNA
<213> ORGANISM: Homo sapiens

<400> SEQUENCE: 478
tttattcacc tcgatgatga ttgcgtaaca gaactttctg tacatcacag aaacaacagg 60
caaacaatgg aggatt 76

<210> SEQ ID NO 479
<211> LENGTH: 111
<212> TYPE: DNA
<213> ORGANISM: Homo sapiens

<400> SEQUENCE: 479
tggcagtatg atcacctcac ggctacctat cttctgcttc tagccaagaa ggctcgggga 60
aaaccagttc gtttaaggct ttcttctttc tcctgtggac aagccagtgc t 111

<210> SEQ ID NO 480
<211> LENGTH: 104
<212> TYPE: DNA
<213> ORGANISM: Homo sapiens

<400> SEQUENCE: 480
tggaagatgt gaccgcaagt gataaaaatt atgtggcggg attaatagac tatgattggt 60
gtgaagatga tttatcaaca ggtgctgcta ctcccccgaac atca 104

<210> SEQ ID NO 481
<211> LENGTH: 145
<212> TYPE: DNA
<213> ORGANISM: Homo sapiens

<400> SEQUENCE: 481
ggggtggaat ctaaatcatt aactccagcc ttatgcagaa cacctgcaaa taaattaaag 60
aacaaagaaa atgtatatac tcctaagtct gctgtaaaga atgaagagta ctttatgttt 120
cctgagccaa agactccagt taata 145

<210> SEQ ID NO 482
<211> LENGTH: 85
<212> TYPE: DNA
<213> ORGANISM: Homo sapiens

<400> SEQUENCE: 482
gaaaccagtg cctgaaagaa actccaatta aaataccagt aaattcaaca ggaacagaca 60
agttaatgac aggtgtcatt agccc 85

<210> SEQ ID NO 483
<211> LENGTH: 146
<212> TYPE: DNA
<213> ORGANISM: Homo sapiens

<400> SEQUENCE: 483
tggatctcaa ccaagcacat atggaggaga ctccaaaaag aaagggagcc aaagtgtttg 60
ggagccttga aagggggttg gataaggtta tcactgtgct caccaggagc aaaaggaagg 120
gttctgccag agacgggccc agaaga 146

<210> SEQ ID NO 484
<211> LENGTH: 52
<212> TYPE: DNA
<213> ORGANISM: Homo sapiens

<400> SEQUENCE: 484
cttcactata acgtgactac aactagatta gtgaatccag atcaactgtt ga 52

<210> SEQ ID NO 485
<211> LENGTH: 80
<212> TYPE: DNA
<213> ORGANISM: Homo sapiens

<400> SEQUENCE: 485
atacactgaa gtgtcaaaca cagtcagatt ttgggaaagt gacaatgcaa tttgaattag 60
aagtgtgcca gcttcaaaaa 80

<210> SEQ ID NO 486
<211> LENGTH: 58
<212> TYPE: DNA
<213> ORGANISM: Homo sapiens

<400> SEQUENCE: 486
cttaagggcg atgcctgggt ttacaaaaga ttagtggaag acatcctatc tagctgca 58

<210> SEQ ID NO 487
<211> LENGTH: 206
<212> TYPE: DNA
<213> ORGANISM: Homo sapiens

<400> SEQUENCE: 487
atggattctt ccatcctgcc ggatgagtgt gggtgtgata cagcctacat aaagactgtt 60
atgatcgctt tgattttaaa gttcattgga actaccaact tgtttctaaa gagctatctt 120
aagaccaata tctctttgtt tttaaacaaa agatattatt ttgtgtatga atctaaatca 180
agcccatctg tcattatgtt actgtc 206

<210> SEQ ID NO 488
<211> LENGTH: 75
<212> TYPE: DNA
<213> ORGANISM: Homo sapiens

<400> SEQUENCE: 488
gagggggcac cagtgatcga cacatttgca tctggaacgt gtgctctggg gcctgtctga 60
gtgccgtgga tgccc 75

<210> SEQ ID NO 489
<211> LENGTH: 25
<212> TYPE: DNA
<213> ORGANISM: Homo sapiens

<400> SEQUENCE: 489
ttatttggaa gtacccaacc atggc 25

<210> SEQ ID NO 490
<211> LENGTH: 261
<212> TYPE: DNA
<213> ORGANISM: Homo sapiens

<400> SEQUENCE: 490
cggacctatg tcctacctgt tcatgcagtt gtccatatcc agtgggatgt cctaggggct 60
caactgtcca caaacatcac tgccccccac agaactggta cagaccccca aaccacccat 120
ctcagcccat gaaaccactg gccacccaag cccacaaatc agaaaccagt atgctgcctc 180
cttcccctca gcctttacat acagtcacat accaagcctg tcaattccac tcccaatgta 240
cctcctaacc atgagtcttt g 261

<210> SEQ ID NO 491
<211> LENGTH: 85
<212> TYPE: DNA
<213> ORGANISM: Homo sapiens

<400> SEQUENCE: 491
accttctcag gagctgtagt gtaccattca gggacctggc acagtccatc cagacatcct 60
gctgagcgtc gcccacatat gcagt 85

<210> SEQ ID NO 492
<211> LENGTH: 340
<212> TYPE: DNA
<213> ORGANISM: Homo sapiens

<400> SEQUENCE: 492
tctttcaggt cctcagatgc actgcaccct ctcctgcctg gggtctttg ctcctgctac 60 tacctctgct tgaacagctc ctcaccttcc ttcctccaac cctacccttg tataggtgac 120
ttttgttcat ccttcagaat tcaactcaca tgtctcttgc atggagaacc ctcacctact 180
gtgttgagac cctgtccagc ccccaggtgg gatcctctct cgacttccca tacatttctt 240
tcacagcatt tacatagtcc atgatagttt acttgtggga ttatttggtt aatctttgcc 300
tttaacacca gggttccttg ggtgaaggag cttctttatc 340

<210> SEQ ID NO 493
<211> LENGTH: 607
<212> TYPE: DNA
<213> ORGANISM: Homo sapiens

<400> SEQUENCE: 493
agagtcgttg aagtcccagg aattcaggac tgggcaggtt aagacctcag acaaggtagt 60
agaggtagac ttgtggacaa ggctcgggtc ccagcccacc gcaccccaac tttaatcaga 120
gtggttcact attgatctat ttttgtgtga tagctgtgtg gcgtgggcca caacatttaa 180
tgagaagtta ctgtgcacca aactgccgaa caccattcta aactattcat atatattagt 240
catttaattc ttacataact tgagaggtag acagatatcc ttattttaga gatgaggaaa 300
ccaagagaac ttaggtcatt agcgcaaggt tgtagagtaa gcggcaaagc caagacacaa 360
agctgggtgg tttggtttca gagccagtgc ttttcccctc tactgtactg cctctcaacc 420
aacacagggt tgcacaggcc cattctctga ttttttttcct cttgtcctct gcctctccct 480
ctagctccca cttcctctct gctctagttc attttcttta gagcagcccg agtgatcatg 540
aagtgcaaat cttgccatgt cagtcccctg cttagaaccc tccaatggct cactttctct 600
ttaggca 607

<210> SEQ ID NO 494
<211> LENGTH: 210
<212> TYPE: DNA
<213> ORGANISM: Homo sapiens

<400> SEQUENCE: 494
cttctgtctc tgtggttgta ctgtccagca atccaccttt tctggagagg gccacctctg 60
cccaaatttt cccagctgtt tggacctctg ggtgctttct ttgggctggt gagagctcta 120
atttgccttg ggccagtttc aggtttatag gccccctcag tcttcagata catgagggct 180
tctttgctct tgtgatcgtg tagtcccata 210

<210> SEQ ID NO 495
<211> LENGTH: 32
<212> TYPE: DNA
<213> ORGANISM: Homo sapiens

<400> SEQUENCE: 495
tttcctactc tcacactggt tctcaatgaa aa 32

<210> SEQ ID NO 496
<211> LENGTH: 83
<212> TYPE: DNA
<213> ORGANISM: Homo sapiens

<400> SEQUENCE: 496
aatggcgcca ccagctctgc cgtctctgga gcggaattta cctgatttct tcagggctgc 60
tgggggcaac tggccatttg cca 83

<210> SEQ ID NO 497
<211> LENGTH: 31
<212> TYPE: DNA
<213> ORGANISM: Homo sapiens

<400> SEQUENCE: 497
ttcaaagaca gtagattgaa aaggaaaggc t 31

<210> SEQ ID NO 498
<211> LENGTH: 55
<212> TYPE: DNA
<213> ORGANISM: Homo sapiens

<400> SEQUENCE: 498
gaagctctct gcaaacttga taggagagta aaagccacaa tagagcagtt tatga 55

<210> SEQ ID NO 499
<211> LENGTH: 638
<212> TYPE: DNA
<213> ORGANISM: Homo sapiens

<400> SEQUENCE: 499
agctcttgct acgtgttgtg aaatctgtgt ctgtagctcg tggctgtgat aaacatcctc 60
agagatccct gctatccaac tcttgtcacc agctaactgg tcattaggcc aagctgtgtg 120
agtgaaccat tagacaattt gataaaaata agcactgctg ccattcttta gcatgcgtct 180
gtgccacaag ttagtgacac atgtacatat attcccttta cctcacagta accatctagg 240
gtgtgggcat cataatcttc atttttaaaa tgagggtact gaggcatgaa taggctaaat 300
aatttgctca agatcacaag ttagtaaatg gcagtcagtt ttcaggcgta ggctttgaag 360
actctaaacc tgtgctttta acatctgcct cttcttgtga ctgggggctt cactggagcc 420
aagcctcagg aggcatttgc agccacagtg ggtcatgcga ggtagagcag actgcaacct 480
gatagaattc ttggactggc ccacggccag cctttttaat ttttccaaga gttaaagttg 540
tggatctgag atgtggcctg gcctgccagg gctatggtgg gctcagtgtg attgcatcat 600
tagtattgtg gcatggagtc ttccgtcagc ctcagaga 638

<210> SEQ ID NO 500
<211> LENGTH: 110
<212> TYPE: DNA
<213> ORGANISM: Homo sapiens

<400> SEQUENCE: 500
agtccacagg aagaggttga actaaagaag ttgaaacatt tggagaagtc tgtggagaag 60
atagctgacc agctggaaga gttgaataaa gagcttactg gaatccagca 110

<210> SEQ ID NO 501
<211> LENGTH: 618
<212> TYPE: DNA
<213> ORGANISM: Homo sapiens

<400> SEQUENCE: 501
ctaaatttct tgcttcaggg tcagggagaa tggtgatggg caacaggcag aaccaaagag 60
tcaagtttga agaaactata ggacttttac ttggagctga cacagagcgt atggagcgaa 120
gtgtgaactc aaggaaggca ccatggcaca tgcctattgt cccagcaagt tgggagtctg 180
agacaggagg atcacttgag tccaggggtt tgaggctgca gtgagttatg atcatgcctg 240
taaacagcca ctgcactcca acctgggaac cgtagtgaga ccctatctca aaaaagaaaa 300
aagtctgaac ttaagtctaa tctacctctt ttggactgtg tgatctcatg ttactttact 360
acattaagcc tcagtttcat catctgtaaa acagcagtac ttccctgatg gagttgtggt 420
aaggcttaaa aaataggtaa ggtgcttagg atagtgtgtg gcatgtagga agtgttcaat 480
aaaagtattc atcgttgtta accagcatca cattaaacag gagcgctcaa ttggaggctg 540
ccatttagga attccattta aaggaatggt agaattccac ctttcttgcc attctggact 600
cctcacaagt gtttactg 618

<210> SEQ ID NO 502
<211> LENGTH: 51
<212> TYPE: DNA
<213> ORGANISM: Homo sapiens

<400> SEQUENCE: 502
ggaaatggaa acaccgttgt cagcacttgg aatacaagat ggttgccggg t 51

<210> SEQ ID NO 503
<211> LENGTH: 110
<212> TYPE: DNA
<213> ORGANISM: Homo sapiens

<400> SEQUENCE: 503
gacctgctag gtattggaca ctctcaaaca cctggacagg tgtcagattt gaagtcttat 60
gatgatggca gaaatctcac cattttcgat gaagctcatg ggcagtcttc 110

<210> SEQ ID NO 504
<211> LENGTH: 106
<212> TYPE: DNA
<213> ORGANISM: Homo sapiens

<400> SEQUENCE: 504
gagaagcacg accttcatgt tacctcccag cagggcagca gtgaaccagt tgtccaagac 60
ctggcccagg ttgttgaaga ggtcataggg gttccacagt cttttc 106

<210> SEQ ID NO 505
<211> LENGTH: 31
<212> TYPE: DNA
<213> ORGANISM: Homo sapiens

<400> SEQUENCE: 505
ggcagctggg ctcaccgtga ctgtcaccca c 31

<210> SEQ ID NO 506
<211> LENGTH: 42
<212> TYPE: DNA
<213> ORGANISM: Homo sapiens

<400> SEQUENCE: 506
gaggcgaccc agggcgaaga gatgaatcgg agccaggagg tg 42

<210> SEQ ID NO 507
<211> LENGTH: 53
<212> TYPE: DNA
<213> ORGANISM: Homo sapiens

<400> SEQUENCE: 507
agttgaccct gagtgaggaa gcgacctgga gtgaagaggc gacccagagt gag 53

<210> SEQ ID NO 508
<211> LENGTH: 29
<212> TYPE: DNA
<213> ORGANISM: Homo sapiens

<400> SEQUENCE: 508
acccggcgcc gctcgacccg gagcgagga 29

<210> SEQ ID NO 509
<211> LENGTH: 60
<212> TYPE: DNA
<213> ORGANISM: Homo sapiens

<400> SEQUENCE: 509
tgggcgtcca cctgcccgga gtactgccag cgggcatgac cgacccacca ggggcgccgc 60

<210> SEQ ID NO 510
<211> LENGTH: 31
<212> TYPE: DNA
<213> ORGANISM: Homo sapiens

<400> SEQUENCE: 510
ctgggttccc ggctgcgcgc ccttcggcca g 31

<210> SEQ ID NO 511
<211> LENGTH: 55
<212> TYPE: DNA
<213> ORGANISM: Homo sapiens

<400> SEQUENCE: 511
gcggggttgt gagacgccgc gctcagcttc catcgctggg cggtcaacaa gtgcg 55

<210> SEQ ID NO 512
<211> LENGTH: 43
<212> TYPE: DNA
<213> ORGANISM: Homo sapiens

<400> SEQUENCE: 512
tgtgactcgg ccgacgcgag cgccgcgctt cgcttcagct gct 43

<210> SEQ ID NO 513
<211> LENGTH: 47
<212> TYPE: DNA
<213> ORGANISM: Homo sapiens

<400> SEQUENCE: 513
ggaggcgacc gcggagggtg gcgaggggcg gccaggaccc gcagccc 47

<210> SEQ ID NO 514
<211> LENGTH: 133
<212> TYPE: DNA
<213> ORGANISM: Homo sapiens

<400> SEQUENCE: 514
ggcagatcgc gtccgcggga ttcaatctct gcccgctctg ataacagtcc ttttccctgg 60
cgctcacttc gtgcctggca cccggctggg cgcctcaaga ccgttgtctc ttcgatcgct 120
tctttggact tgg 133

<210> SEQ ID NO 515
<211> LENGTH: 31
<212> TYPE: DNA
<213> ORGANISM: Homo sapiens

<400> SEQUENCE: 515
atgtcttcca gaagtaccaa agatttaatt a 31

<210> SEQ ID NO 516
<211> LENGTH: 142
<212> TYPE: DNA
<213> ORGANISM: Homo sapiens

<400> SEQUENCE: 516
taagtgggga tcgaagccta gtaactccaa atccgaaact acattagaaa aattaaaggg 60
agaaattgca cacttaaaga catcagtgga tgaaatcaca agtgggaaag gaaagctgac 120
tgataaagag agacacagac tt 142

<210> SEQ ID NO 517
<211> LENGTH: 157
<212> TYPE: DNA
<213> ORGANISM: Homo sapiens

<400> SEQUENCE: 517
gcgactgaga gaccaactga aggccagata tagtactacc acattgcttg aacagctgga 60
agagacaacg agagaaggag aaaggaggga gcaggtgttg aaagccttat ctgaagagaa 120
agacgtattg aaacaacagt tgtctgctgc aacctca 157

<210> SEQ ID NO 518
<211> LENGTH: 38
<212> TYPE: DNA
<213> ORGANISM: Homo sapiens

<400> SEQUENCE: 518
ctgtggctcc aaactgcttc aactcatcaa taaataat 38

<210> SEQ ID NO 519
<211> LENGTH: 137
<212> TYPE: DNA
<213> ORGANISM: Homo sapiens

<400> SEQUENCE: 519
tctggagaaa aatcagcagt ggctcgtgta tgatcagcag cgggaagtct atgtaaaagg 60
acttttagca aagatctttg agttggaaaa gaaaacggaa acagctgctc attcactccc 120
acagcagaca aaaaagc 137

<210> SEQ ID NO 520

<211> LENGTH: 76
<212> TYPE: DNA
<213> ORGANISM: Homo sapiens

<400> SEQUENCE: 520
gaagcagaaa tgttacaacg atctcttggc aagtgcaaaa aaagatcttg aggttgaacg 60
acaaaccata actcag 76

<210> SEQ ID NO 521
<211> LENGTH: 150
<212> TYPE: DNA
<213> ORGANISM: Homo sapiens

<400> SEQUENCE: 521
agctgttgta ttcacaaaga agggcagatg tgcaacatct ggaagatgat aggcataaaa 60
cagagaagat acaaaaactc agggaagaga atgatattgc taggggaaaa cttgaagaag 120
agaagaagag atccgaagag ctcttatctc 150

<210> SEQ ID NO 522
<211> LENGTH: 63
<212> TYPE: DNA
<213> ORGANISM: Homo sapiens

<400> SEQUENCE: 522
ctttacacat ctctgctaaa gcagcaagaa gaacaaacaa gggtagctct gttggaacaa 60
cag 63

<210> SEQ ID NO 523
<211> LENGTH: 108
<212> TYPE: DNA
<213> ORGANISM: Homo sapiens

<400> SEQUENCE: 523
actcattcgg gttgcttcta aattcaattc tgcctgttag aaaatgcagt ttttcctcat 60
gtttatgctg ttctatggag aactgtttga aagttgtgaa aagtgtct 108

<210> SEQ ID NO 524
<211> LENGTH: 97
<212> TYPE: DNA
<213> ORGANISM: Homo sapiens

<400> SEQUENCE: 524
tgaaaaactc gaccgtcaac atgtgcagca tcaattgcat gtaattctta aggagctccg 60
aaaagcaaga aatcaaataa cacagttgga atccttg 97

<210> SEQ ID NO 525
<211> LENGTH: 143
<212> TYPE: DNA
<213> ORGANISM: Homo sapiens

<400> SEQUENCE: 525
tccgaactta ggaggataca gcttaacaca cagctagctg tatctcaaat cagtaggtag 60
agcctctgcc tcatttgaag caactgccct ttgagcatca attcagagga catgaaagag 120
ggacatgatc acatctggaa aca 143

<210> SEQ ID NO 526
<211> LENGTH: 159
<212> TYPE: DNA
<213> ORGANISM: Homo sapiens

<400> SEQUENCE: 526
cagagccatt agtcactttc caaggagaga ctgaaaacag agaaaaagtt gccgcctcac 60
caaaaagtcc cactgctgca ctcaatgaaa gcctggtgga atgtcccaag tgcaatatac 120
agtatccagc cactgagcat cgcgatctgc ttgtccatg 159

<210> SEQ ID NO 527
<211> LENGTH: 494
<212> TYPE: DNA
<213> ORGANISM: Homo sapiens

<400> SEQUENCE: 527
tacctttgac actccagcat gctagtgaat catgtatctt ttaggctgct gtgcatttct 60
cttggcagtg atacctccct gacatggttc atcatcaggc tgcaatgaca gaatgtggtg 120
agcagcgtct actgagacta ctaacatttt gcactgtcaa aatacttggt gaggaaaaga 180
tagctcaggt tattgctaat gggttaatgc accagcaagc aaaatatttt atgttttggg 240
ggttttgaaa aatcaaagat aattaaccaa ggatcttaac tgtgttcgca tttttttatcc 300 aagcacttag aaaacctaca atcctaattt tgatgtccat tgttaagagg tggtgataga 360
tactattttt tttttcatat tgtatagcgg ttattagaaa agttggggat tttcttgatc 420
tttattgctg cttaccattg aaacttaacc cagctgtgtt ccccaactct gttctgcgca 480
cgaaacagta tctg 494

<210> SEQ ID NO 528
<211> LENGTH: 116
<212> TYPE: DNA
<213> ORGANISM: Homo sapiens

<400> SEQUENCE: 528
tcagatcttt gtttgtctga acaggtattt ttatacatgc tttttgtaaa ccaaaaactt 60
ttaaatttct tcaggttttc taacatgctt accactgggc tactgtaaat gagaaa 116

<210> SEQ ID NO 529
<211> LENGTH: 1377
<212> TYPE: DNA
<213> ORGANISM: Homo sapiens

<400> SEQUENCE: 529
actcgtgagc acatctttag ggaccaagag tgactttctg taaggagtga ctcgtggctt 60
gccttggtct cttgggaata cttttctaac tagggttgct ctcacctgag acattctcca 120
cccgcggaat ctcagggtcc caggctgtgg gccatcacga cctcaaactg gctcctaatc 180
tccagctttc ctgtcattga aagcttcgga agtttactgg ctctgctccc gcctgttttc 240
tttctgactc tatctggcag cccgatgcca cccagtacag gaagtgacac cagtactctg 300
taaagcatca tcatccttgg agagactgag cactcagcac cttcagccac gatttcagga 360
tcgcttcctt gtgagccgct gcctccgaaa tctcctttga agcccagaca tctttctcca 420
gcttcagact tgtagatata actcgttcat cttcatttac tttccacttt gccccctgtc 480
ctctctgtgt tccccaaatc agagaatagc ccgccatccc ccaggtcacc tgtctggatt 540
cctccccatt cacccacctt gccaggtgca ggtgaggatg gtgcaccaga cagggtagct 600
gtcccccaaa atgtgccctg tgcgggcagt gccctgtctc cacgtttgtt tccccagtgt 660
ctggcgggga gccaggtgac atcataaata cttgctgaat gaatgcagaa atcagcggta 720
ctgacttgta ctatattggc tgccatgata gggttctcac agcgtcatcc atgatcgtaa 780
gggagaatga cattctgctt gagggaggga atagaaaggg gcagggaggg gacatctgag 840
ggcttcacag ggctgcaaag ggtacaggga ttgcaccagg gcagaacagg ggagggtgtt 900
caaggaagag tggctcttag cagaggcact ttggaaggtg tgaggcataa atgcttcctt 960
ctacgtaggc caacctcaaa actttcagta ggaatgttgc tatgatcaag ttgttctaac 1020
actttagact tagtagtaat tatgaacctc acatagaaaa atttcatcca gccatatgcc 1080
tgtggagtgg aatattctgt ttagtagaaa aatcctttag agttcagctc taaccagaaa 1140
tcttgctgaa gtatgtcagc accttttctc accctggtaa gtacagtatt tcaagagcac 1200
gctaagggtg gttttcattt tacagggctg ttgatgatgg gttaaaaatg ttcatttaag 1260
ggctaccccc gtgtttaata gatgaacacc acttctacac aaccctcctt ggtactgggg 1320
gagggagaga tctgacaaat actgcccatt cccctaggct gactggattt gagaaca 1377

<210> SEQ ID NO 530
<211> LENGTH: 115
<212> TYPE: DNA
<213> ORGANISM: Homo sapiens

<400> SEQUENCE: 530
atgagcgcac ggatgaatgg agcttacaag atctgtcttt ccaatggccg ggggcatttg 60
gtccccaaat taaggctatt ggacatctgc acaggacagt cctatttttg atgtc 115

<210> SEQ ID NO 531
<211> LENGTH: 50
<212> TYPE: DNA
<213> ORGANISM: Homo sapiens

<400> SEQUENCE: 531
aggaacaact atcctcgtct gtcccaacac tgagcaggca ctcggtaaac 50

<210> SEQ ID NO 532
<211> LENGTH: 227
<212> TYPE: DNA
<213> ORGANISM: Homo sapiens

<400> SEQUENCE: 532
atttgctggg tctgaatcgg cttcataaac tccactggga gcactgctgg gctcctggac 60
tgagaatagt tgaacaccgg gggctttgtg aaggagtctg ggccaaggtt tgccctcagc 120
tttgcagaat gaagccttga ggtctgtcac cacccacagc caccctacag cagccttaac 180
tgtgacactt gccacactgt gtcgtcgttt gtttgcctat gtcctcc 227

<210> SEQ ID NO 533
<211> LENGTH: 60
<212> TYPE: DNA
<213> ORGANISM: Homo sapiens

<400> SEQUENCE: 533
ggacaatgtg tgtgtcaaga aaataagaac cagaagtcat agggacagtg aagatatttg 60

<210> SEQ ID NO 534
<211> LENGTH: 155
<212> TYPE: DNA
<213> ORGANISM: Homo sapiens

<400> SEQUENCE: 534
cagaagagtg cgaaggttct catgcagaat cagaaaggga aaggagaagc aggaaattca 60
gactccatgt gcctgagatc aagaaagaca aaaagccagc ctgcagcaag cactttggag 120
agcaaatctg tgcagagagt aacgcggagt gtcaa 155

<210> SEQ ID NO 535
<211> LENGTH: 30
<212> TYPE: DNA
<213> ORGANISM: Homo sapiens

<400> SEQUENCE: 535
gagcccggaa acccatacct agagacaaag 30

<210> SEQ ID NO 536
<211> LENGTH: 26
<212> TYPE: DNA
<213> ORGANISM: Homo sapiens

<400> SEQUENCE: 536
tatccctgcg ctccagacgc caaaat 26

<210> SEQ ID NO 537
<211> LENGTH: 226
<212> TYPE: DNA
<213> ORGANISM: Homo sapiens

<400> SEQUENCE: 537
aagaggctgc gctgcatgcc agcaccagag gaaattgtgg aggagctgcc agccagcaag 60
aagcagaggg ttgctcccag ggcaagaggc aaatcatccg aacccgtggt catcatgaag 120
agaagtttga ggacttctgc aaaaagaatt gaacctgcgg aagagctgaa cagcaacgac 180
atgaaaacca acaaagagga acacaaatta caagactcgg tccctg 226

<210> SEQ ID NO 538
<211> LENGTH: 1286
<212> TYPE: DNA
<213> ORGANISM: Homo sapiens

<400> SEQUENCE: 538
cccgtgctct agaagacctg gttgacttca aagagctctt ctcagcacca ggtcacactg 60
aagagtcaat gactattgac aaaaacacaa aaattccctg caaatctccc ccaccagaac 120
taacagacac tgccacgagc acaaagagat gccccaagac acgtcccagg aaagaagtaa 180
aagaggagct ctcagcagtt gagaggctca cgcaaacatc agggcaaagc acacacacac 240
acaaagaacc agcaagcggt gatgagggca tcaaagtatt gaagcaacgt gcaaagaaga 300
aaccaaaccc agtagaagag gaacccagca ggagaaggcc aagagcacct aaggaaaagg 360
cccaacccct ggaagacctg gccggcttca cagagctctc tgaaacatca ggtcacactc 420
aggaatcact gactgctggc aaagccacta aaataccctg cgaatctccc ccactagaag 480
tggtagacac cacagcaagc acaaagaggc atctcaggac acgtgtgcag aaggtacaag 540
taaaagaaga gccttcagca gtcaagttca cacaaacatc aggggaaacc acggatgcag 600
acaaagaacc agcaggtgaa gataaaggca tcaaagcatt gaaggaatct gcaaaacaga 660
caccggctcc agcagcaagt gtaactggca gcaggagacg gccaagagca cccagggaaa 720
gtgcccaagc catagaagac ctagctggct tcaaagaccc agcagcaggt cacactgaag 780
aatcaatgac tgatgacaaa accactaaaa taccctgcaa atcatcacca gaactagaag 840
acaccgcaac aagctcaaag agacggccca ggacacgtgc ccagaaagta gaagtgaagg 900

-continued aggagctgtt agcagttggc aagctcacac aaacctcagg ggagaccacg cacaccgaca 960
aagagccggt aggtgagggc aaaggcacga aagcatttaa gcaacctgca aagcggaagc 1020
tggacgcaga agatgtaatt ggcagcagga gacagccaag agcacctaag gaaaaggccc 1080
aacccctgga agatctggcc agcttccaag agctctctca aacaccaggc cacactgagg 1140
aactggcaaa tggtgctgct gatagcttta caagcgctcc aaagcaaaca cctgacagtg 1200
gaaaacctct aaaaatatcc agaagagttc ttcgggcccc taaagtagaa cccgtgggag 1260
acgtggtaag caccagagac cctgta 1286

<210> SEQ ID NO 539
<211> LENGTH: 3489
<212> TYPE: DNA
<213> ORGANISM: Homo sapiens

<400> SEQUENCE: 539
ggagaactct tagcgtgcag gaatctaatg ccatcagcag gcaaagccat gcacacgcct 60
aaaccatcag taggtgaaga gaaagacatc atcatatttg tgggaactcc agtgcagaaa 120
ctggacctga cagagaactt aaccggcagc aagagacggc cacaaactcc taaggaagag 180
gcccaggctc tggaagacct gactggcttt aaagagctct tccagacccc tggtcatact 240
gaagaagcag tggctgctgg caaaactact aaaatgccct gcgaatcttc tccaccagaa 300
tcagcagaca ccccaacaag cacaagaagg cagcccaaga cacctttgga gaaaagggac 360
gtacagaagg agctctcagc cctgaagaag ctcacacaga catcagggga aaccacacac 420
acagataaag taccaggagg tgaggataaa agcatcaacg cgtttaggga aactgcaaaa 480
cagaaactgg acccagcagc aagtgtaact ggtagcaaga ggcacccaaa aactaaggaa 540
aaggcccaac ccctagaaga cctggctggc ttgaaagagc tcttccagac accagtatgc 600
actgacaagc ccacgactca cgagaaaact accaaaatag cctgcagatc acaaccagac 660
ccagtggaca caccaacaag ctccaagcca cagtccaaga gaagtctcag gaaagtggac 720
gtagaagaag aattcttcgc actcaggaaa cgaacaccat cagcaggcaa agccatgcac 780
acacccaaac cagcagtaag tggtgagaaa aacatctacg catttatggg aactccagtg 840
cagaaactgg acctgacaga gaacttaact ggcagcaaga gacggctaca aactcctaag 900
gaaaaggccc aggctctaga agacctggct ggctttaaag agctcttcca gacacgaggt 960
cacactgagg aatcaatgac taacgataaa actgccaaag tagcctgcaa atcttcacaa 1020
ccagacccag acaaaaaccc agcaagctcc aagcgacggc tcaagacatc cctggggaaa 1080
gtgggcgtga aagaagagct cctagcagtt ggcaagctca cacagacatc aggagagact 1140
acacacacac acacagagcc aacaggagat ggtaagagca tgaaagcatt tatggagtct 1200
ccaaagcaga tcttagactc agcagcaagt ctaactggca gcaagaggca gctgagaact 1260
cctaagggaa agtctgaagt ccctgaagac ctggccggct tcatcgagct cttccagaca 1320
ccaagtcaca ctaaggaatc aatgactaac gaaaaaacta ccaaagtatc ctacagagct 1380
tcacagccag acctagtgga caccccaaca agctccaagc cacagcccaa gagaagtctc 1440
aggaaagcag acactgaaga agaattttta gcatttagga aacaaacgcc atcagcaggc 1500
aaagccatgc acacacccaa accagcagta ggtgaagaga aagacatcaa cacgtttttg 1560
ggaactccag tgcagaaact ggaccagcca ggaaatttac ctggcagcaa tagacggcta 1620
caaactcgta aggaaaaggc ccaggctcta gaagaactga ctggcttcag agagcttttc 1680
cagacaccat gcactgataa ccccacgact gatgagaaaa ctaccaaaaa aatactctgc 1740
aaatctccgc aatcagaccc agcggacacc ccaacaaaca caaagcaacg gcccaagaga 1800
agcctcaaga aagcagacgt agaggaagaa tttttagcat tcaggaaact aacaccatca 1860
gcaggcaaag ccatgcacac gcctaaagca gcagtaggtg aagagaaaga catcaacaca 1920
tttgtgggga ctccagtgga gaaactggac ctgctaggaa atttacctgg cagcaagaga 1980
cggccacaaa ctcctaaaga aaaggccaag gctctagaag atctggctgg cttcaaagag 2040
ctcttccaga caccaggtca cactgaggaa tcaatgaccg atgacaaaat cacagaagta 2100
tcctgcaaat ctccacaacc agacccagtc aaaaccccaa caagctccaa gcaacgactc 2160
aagatatcct tggggaaagt aggtgtgaaa gaagaggtcc taccagtcgg caagctcaca 2220
cagacgtcag ggaagaccac acagacacac agagagacag caggagatgg aaagagcatc 2280
aaagcgttta aggaatctgc aaagcagatg ctggacccag caaactatgg aactgggatg 2340
gagaggtggc caagaacacc taaggaagag gcccaatcac tagaagacct ggccggcttc 2400
aaagagctct tccagacacc agaccacact gaggaatcaa caactgatga caaaactacc 2460
aaaatagcct gcaaatctcc accaccagaa tcaatggaca ctccaacaag cacaaggagg 2520
cggcccaaaa cacctttggg gaaaagggat atagtggaag agctctcagc cctgaagcag 2580
ctcacacaga ccacacacac agacaaagta ccaggagatg aggataaagg catcaacgtg 2640
ttcagggaaa ctgcaaaaca gaaactggac ccagcagcaa gtgtaactgg tagcaagagg 2700
cagccaagaa ctcctaaggg aaaagcccaa cccctagaag acttggctgg cttgaaagag 2760
ctcttccaga caccaatatg cactgacaag cccacgactc atgagaaaac taccaaaata 2820
gcctgcagat ctccacaacc agacccagtg ggtaccccaa caatcttcaa gccacagtcc 2880
aagagaagtc tcaggaaagc agacgtagag gaagaatcct tagcactcag gaaacgaaca 2940
ccatcagtag ggaaagctat ggacacaccc aaaccagcag gaggtgatga gaaagacatg 3000
aaagcattta tgggaactcc agtgcagaaa ttggacctgc caggaaattt acctggcagc 3060
aaaagatggc cacaaactcc taaggaaaag gcccaggctc tagaagacct ggctggcttc 3120
aaagagctct tccagacacc aggcactgac aagcccacga ctgatgagaa aactaccaaa 3180
atagcctgca aatctccaca accagaccca gtggacaccc cagcaagcac aaagcaacgg 3240
cccaagagaa acctcaggaa agcagacgta gaggaagaat tttagcact caggaaacga 3300 acaccatcag caggcaaagc catggacaca ccaaaaccag cagtaagtga tgagaaaaat 3360
atcaacacat ttgtggaaac tccagtgcag aaactggacc tgctaggaaa tttacctggc 3420
agcaagagac agccacagac tcctaaggaa aaggctgagg ctctagagga cctggttggc 3480
ttcaaagaa 3489

<210> SEQ ID NO 540
<211> LENGTH: 389
<212> TYPE: DNA
<213> ORGANISM: Homo sapiens

<400> SEQUENCE: 540
aacaacagtt gaaggcatcc ctggggaaag taggtgtgaa agaagagctc ctagcagtcg 60
gcaagttcac acggacgtca ggggagacca cgcacacgca cagagagcca gcaggagatg 120
gcaagagcat cagaacgttt aaggagtctc caaagcagat cctggaccca gcagcccgtg 180
taactggaat gaagaagtgg ccaagaacgc ctaaggaaga ggcccagtca ctagaagacc 240
tggctggctt caaagagctc ttccagacac caggtccctc tgaggaatca atgactgatg 300
agaaaactac caaaatagcc tgcaaatctc caccaccaga atcagtggac actccaacaa 360
gcacaaagca atggcctaag agaagtctc 389

<210> SEQ ID NO 541
<211> LENGTH: 334
<212> TYPE: DNA
<213> ORGANISM: Homo sapiens

<400> SEQUENCE: 541
tgcaaacagg tcaggaaggt ctacagagtt caggaatata cagaagctac ctgtggaaag 60
taagagtgaa gaaacaaata cagaaattgt tgagtgcatc ctaaaaagag gtcagaaggc 120
aacactacta caacaaagga gagaaggaga gatgaaggaa atagaaagac cttttgagac 180
atataaggaa aatattgaat taaaagaaaa cgatgaaaag atgaaagcaa tgaagagatc 240
aagaacttgg gggcagaaat gtgcaccaat gtctgacctg acagacctca agagcttgcc 300
tgatacagaa ctcatgaaag acacggcacg tggc 334

<210> SEQ ID NO 542
<211> LENGTH: 62
<212> TYPE: DNA
<213> ORGANISM: Homo sapiens

<400> SEQUENCE: 542
cccagtgaag gagcaaccgc agttgacaag cacatgtcac atcgctattt caaattcaga 60
ga 62

<210> SEQ ID NO 543
<211> LENGTH: 90
<212> TYPE: DNA
<213> ORGANISM: Homo sapiens

<400> SEQUENCE: 543
taaaaacgta gtcttagatc ttataaatct tttgactcta ctgtttttta ctgtgttaat 60
gtttgttttg ctaactttgt ttatctgctg 90

<210> SEQ ID NO 544
<211> LENGTH: 84
<212> TYPE: DNA
<213> ORGANISM: Homo sapiens

<400> SEQUENCE: 544
cgcaaactct ccttgtacca taataatagg gaaagctcat actgaaaaag tacatgtgcc 60
tgctcgaccc tacagagtgc tcaa 84

<210> SEQ ID NO 545
<211> LENGTH: 26
<212> TYPE: DNA
<213> ORGANISM: Homo sapiens

<400> SEQUENCE: 545
agcctgtggg cgaagttcac agtcaa 26

<210> SEQ ID NO 546
<211> LENGTH: 73
<212> TYPE: DNA
<213> ORGANISM: Homo sapiens

<400> SEQUENCE: 546
catgggcaga tgtagtaaaa cttggtgcaa aacaaacaca aactaaagtc ataaaacatg 60
gtcctcaaag gtc 73

<210> SEQ ID NO 547
<211> LENGTH: 84
<212> TYPE: DNA
<213> ORGANISM: Homo sapiens

<400> SEQUENCE: 547
aagagagtgt ctatcagccg aagtcaacat gatattttac agatgatatg ttccaaaaga 60
agaagtggtg cttcggaagc aaat 84

<210> SEQ ID NO 548
<211> LENGTH: 116
<212> TYPE: DNA
<213> ORGANISM: Homo sapiens

<400> SEQUENCE: 548
aaacaagagt caggttcaga aatccatgtg gaagtgaagg cacaaagctt ggttataagc 60
cctccagctc ctagtcctag gaaaactcca gttgccagtg atcaacgccg taggtc 116

<210> SEQ ID NO 549
<211> LENGTH: 134
<212> TYPE: DNA
<213> ORGANISM: Homo sapiens

<400> SEQUENCE: 549
cctttgaaaa gaaggcgtgt gtcctttggt gggcacctaa gacctgaact atttgatgaa 60
aacttgcctc ctaatacgcc tctcaaaagg ggagaagccc caaccaaaag aaagtctctg 120
gtaatgcaca ctcc 134

<210> SEQ ID NO 550
<211> LENGTH: 66
<212> TYPE: DNA
<213> ORGANISM: Homo sapiens

<400> SEQUENCE: 550
ggacagatgt gctctgggtt acctggtctt agttcagttg atatcaacaa ctttggtgat 60
tccatt 66

<210> SEQ ID NO 551
<211> LENGTH: 31
<212> TYPE: DNA
<213> ORGANISM: Homo sapiens

<400> SEQUENCE: 551
ttgagaggaa gatccaaaag gattccctca g 31

<210> SEQ ID NO 552
<211> LENGTH: 149
<212> TYPE: DNA
<213> ORGANISM: Homo sapiens

<400> SEQUENCE: 552
gaagctttca actagaaatc gaacaccagc taaagttgaa gatgcagctg actctgccac 60
taagccagaa aatctctctt ccaaaaccag aggaagtatt cctacagatg tggaagttct 120
gcctacggaa actgaaattc acaatgagc 149

<210> SEQ ID NO 553

<211> LENGTH: 416
<212> TYPE: DNA
<213> ORGANISM: Homo sapiens

<400> SEQUENCE: 553
ccagcgttaa attagtgagc cgttatggag aattgaagtc tgttcccact acacaatgtc 60
ttgacaatag caaaaaaaat gaatctccct tttggaagct ttatgagtca gtgaagaaag 120
agttggatgt aaaatcacaa aaagaaaatg tcctacagta ttgtagaaaa tctggattac 180
aaactgatta cgcaacagag aaagaaagtg ctgatggttt acagggggag acccaactgt 240
tggtctcgcg taagtcaaga ccaaaatctg gtgggagcgg ccacgctgtg gcagagcctg 300
cttcacctga acaagagctt gaccagaaca aggggaaggg aagagacgtg gagtctgttc 360
agactcccag caaggctgtg ggcgccagct ttcctctcta tgagccggct aaaatg 416

<210> SEQ ID NO 554
<211> LENGTH: 33
<212> TYPE: DNA
<213> ORGANISM: Homo sapiens

<400> SEQUENCE: 554
agccagcacg tcgtgtctca agatctagct tct 33

<210> SEQ ID NO 555
<211> LENGTH: 30
<212> TYPE: DNA
<213> ORGANISM: Homo sapiens

<400> SEQUENCE: 555
ttcagaatgg aaggaagtca actgaatttc 30

<210> SEQ ID NO 556
<211> LENGTH: 86
<212> TYPE: DNA
<213> ORGANISM: Homo sapiens

<400> SEQUENCE: 556
ccaacacaag taaatgggtc tgttattgat gagcctgtac ggctaaaaca tggagatgta 60
ataactatta ttgatcgttc cttcag 86

<210> SEQ ID NO 557
<211> LENGTH: 43
<212> TYPE: DNA
<213> ORGANISM: Homo sapiens

<400> SEQUENCE: 557
tgtgacatcc gtatccagct tcctgttgtg tcaaaacaac att 43

<210> SEQ ID NO 558
<211> LENGTH: 30
<212> TYPE: DNA
<213> ORGANISM: Homo sapiens

<400> SEQUENCE: 558
cctgagcctc agcacctgct tgtttggaag 30

<210> SEQ ID NO 559
<211> LENGTH: 26
<212> TYPE: DNA
<213> ORGANISM: Homo sapiens

<400> SEQUENCE: 559
cccacgagac gcctggttac tatcaa 26

<210> SEQ ID NO 560
<211> LENGTH: 72
<212> TYPE: DNA
<213> ORGANISM: Homo sapiens

<400> SEQUENCE: 560
tttgcttctg gccttcccct acggattata cctggccttc ccctacggat tatactcaac 60
ttactgttta ga 72

<210> SEQ ID NO 561
<211> LENGTH: 265
<212> TYPE: DNA
<213> ORGANISM: Homo sapiens

<400> SEQUENCE: 561
gactcggtgg gagccgctag agccgggcgc ccggggacgt agcctgtagg gccaccgggt 60
ccccgtcaga ggcggcggcg ggagcagcgg ggactgcagg ccggggtgca gcgaacgcga 120
ccccgcgggc tgcggcccgg tgtgtgcgga gcgtggcggg cgcagcttac cgggcggagg 180
tgagcgcggc gccggctcct cctgcggcgg actttgggtg cgacttgacg agcggtggtt 240
cgacaagtgg ccttgcgggc cggat 265

<210> SEQ ID NO 562
<211> LENGTH: 25
<212> TYPE: DNA
<213> ORGANISM: Homo sapiens

<400> SEQUENCE: 562
tgcagacggc tgcgaggcgc tgggc 25

<210> SEQ ID NO 563
<211> LENGTH: 30
<212> TYPE: DNA
<213> ORGANISM: Homo sapiens

<400> SEQUENCE: 563
gcagggctga gactatcttc tgctcaggaa 30

<210> SEQ ID NO 564
<211> LENGTH: 62
<212> TYPE: DNA
<213> ORGANISM: Homo sapiens

<400> SEQUENCE: 564
tctcatgttt ttctataagc agttaagaga agccacacag catcctgaac actttgcttt 60
ct 62

<210> SEQ ID NO 565
<211> LENGTH: 80
<212> TYPE: DNA
<213> ORGANISM: Homo sapiens

<400> SEQUENCE: 565
atggcaaatt tcaagggcca cgcgcttcca gggagtttct tcctgatcat tgggctgtgt 60
tggtcagtga agtacccgct 80

<210> SEQ ID NO 566

<211> LENGTH: 46
<212> TYPE: DNA
<213> ORGANISM: Homo sapiens

<400> SEQUENCE: 566
gtactttagc cacacgcgga agaacagccc actacattac tatcag 46

<210> SEQ ID NO 567
<211> LENGTH: 49
<212> TYPE: DNA
<213> ORGANISM: Homo sapiens

<400> SEQUENCE: 567
cgtctcgaga tcgtcgaagc cgcaattagg actttgtttt ccgtcactg 49

<210> SEQ ID NO 568
<211> LENGTH: 192
<212> TYPE: DNA
<213> ORGANISM: Homo sapiens

<400> SEQUENCE: 568
gtcatttggt ctagggaatc tcctcatcat acccagaacc tttaattcat tttctgagcc 60
ctgtgaaata gatgttccca ctggcagaga taatagggca acaatttcct gatggccact 120
agactatttt atcgtaacat ccattgtgta cagagcttta taatactaac ggttgacagc 180
tctcacatca tg 192

<210> SEQ ID NO 569
<211> LENGTH: 74
<212> TYPE: DNA
<213> ORGANISM: Homo sapiens

<400> SEQUENCE: 569
caccatgtac ctattctttg cagtctcagg aattgttgac atgctcacct atctggtcag 60
ccacgttccc ttgg 74

<210> SEQ ID NO 570
<211> LENGTH: 132
<212> TYPE: DNA
<213> ORGANISM: Homo sapiens

<400> SEQUENCE: 570
aaccggcctc cgctggacca gcacatccac tcactcctgc tgtatgctct gttcggaggg 60
tgtgttagta tctccctaga ggtgatcttc cgggaccaca ttgtgctgga acttttccga 120
accagtctca tc 132

<210> SEQ ID NO 571
<211> LENGTH: 139
<212> TYPE: DNA
<213> ORGANISM: Homo sapiens

<400> SEQUENCE: 571
attgggtttg tgctgttccc accttttgga acacccgaat gggaccagaa ggatgatgcc 60
aacctcatgt tcatcaccat gtgcttctgc tggcactacc tggctgccct cagcattgtg 120
gccgtcaact attctcttg 139

<210> SEQ ID NO 572
<211> LENGTH: 102
<212> TYPE: DNA
<213> ORGANISM: Homo sapiens

<400> SEQUENCE: 572 cctttgact cggatgaaga gacacggaag gggagaaatc attggaattc agaagctgaa 60
ttcagatgac acttaccaga ccgccctctt gagtggctca ga 102

<210> SEQ ID NO 573
<211> LENGTH: 1032
<212> TYPE: DNA
<213> ORGANISM: Homo sapiens

<400> SEQUENCE: 573
taaagtctgt gttggtatag tacccttcat aaggaaaaat gaagtaatgc ctataagtag 60
caggcctttg tgcctcagtg tcaagagaaa tcaagagatg ctaaaagctt tacaatggaa 120
gtggcctcat ggatgaatcc ggggtatgag cccaggagaa cgtgctgctt ttggtaactt 180
atcccttttt ctcttaagaa agcaggtact ttcttattag aaatatgtta gaatgtgtaa 240
gcaaacgaca gtgcctttag aattacaatt ctaacttaca tatttttga aagtaaaata 300 attcacaagc tttggtattt taaaattatt gttaaacata tcataactaa tcataccagg 360
gtactgcaat accactgttt ataagtgaca aaattaggcc aaaggtgatt tttttttaaa 420
tcaggaagct ggttactggc tctactgaga gttggagccc tgatgttctg attcttcaaa 480
gtcaccctaa aagaagatct gacaggaaag ctgtataatg agatagaaaa acgtcaggta 540
tggaaggctt tcagttttaa tatggctgaa agcaaaggat aacgaattca gaattagtaa 600
tgtaaaatct tgatacccta atcttgcttc tggatctgtt ctttttttaa aaaaacttcc 660
ttcaccgcgc ctataatcct agcactttgg gaggccgagg caggcagatc acggggtcag 720
gagatcaaga ccatcctggc taacatggtg aaaccccgtc tctactgaaa atacaaaaaa 780
ttagccgggt gtggtggcgg gcgcctgtag ttccagctac tcgggaggct gaggcaagag 840
aatggcatga acccggtagg ggagcttgca gtgagcccag atcatgccac tgtactccag 900
cctaggtgac agagcaagac tctgtctcaa aaacaagcaa acagacttcc ttcaacaaat 960
atttattaaa tatccacttt gcaacagcac tgaaatggct gtaaggactc ctgagatatg 1020
tgtccagcaa gg 1032

<210> SEQ ID NO 574
<211> LENGTH: 2385
<212> TYPE: DNA
<213> ORGANISM: Homo sapiens

<400> SEQUENCE: 574
agtgttcccg tcttctccga gcttagagtt ggatggggaa taaagacagg taaacagata 60
gctacaatat tgtactgtga atgcttatgc tggaggaagt acagggaact attggagcac 120
ctaagaggag cacctacctt gaatttaggg gttagcagag gcatcctgaa aaaagtcaaa 180
gctaagccac aatctataag cagtttagga attagcagaa cgtgcgtggt gaggagatgc 240
caaaggcaag aagagaagag tattccaaac aggagggatt ccaaagagag aagagtatcc 300
caaacaacat ttgcacaaac ctgatgggga gagagaatgt ggggtgggga tggatgatga 360
gactgaagaa gaaagccagg tctagataat cagtggcctt gtacaccatg ttaaagagtg 420
tagacttgat tctgttgtaa acaggaaagc agcacaattc atatgaatat tttagaagac 480
tcccactgga atatggagaa taaagttgga gatgactaat cctggaagca gggagaacat 540
ttttgaggaa gttgcactat tttggtgaaa atgatgatca taaacatgaa gaattgtagg 600

```
tgatcatgac ctcctctcta attttccaga agggttttgg aagatataac ataggaacat    660
tgacaggact gacgaaagga gatgaaatac accatataaa ttgtcaaaca caaggccaga    720
tgtctaatta ttttgcttat gtgttgaaat tacaaatttt tcatcaggaa accaaaaact    780
acaaaactta gttttcccaa gtcccagaat tctatctgtc caaacaatct gtaccactcc    840
acctatatcc ctacctttgc atgtctgtcc aacctcaaag tccaggtcta tacacacggg    900
taagactaga gcagttcaag tttcagaaaa tgagaaagag gaactgagtt gtgctgaacc    960
catacaaaat aaacacattc tttgtataga ttcttggaac ctcgagagga attcacctaa   1020
ctcataggta tttgatggta tgaatccatg gctgggctcg gcttttaaaa agccttatct   1080
gggattcctt ctatggaacc aagttccatc aaagcccatt taaaagccta cattaaaaac   1140
aaaattcttg ctgcattgta tacaaataat gatgtcatga tcaaataatc agatgccatt   1200
atcaagtgga attacaaaat ggtataccca ctccaaaaaa aaaaaaaaag ctaaattctc   1260
agtagaacat tgtgacttca tgagccctcc acagccttgg agctgaggag ggagcactgg   1320
tgagcagtag gttgaagaga aaacttggcg cttaataatc tatccatgtt ttttcatcta   1380
aaagagcctt ctttttggat taccttattc aatttccatc aaggaaattg ttagttccac   1440
taaccagaca gcagctggga aggcagaagc ttactgtatg tacatggtag ctgtgggaag   1500
gaggtttctt tctccaggtc ctcactggcc atacaccagt cccttgttag ttatgcctgg   1560
tcatagaccc ccgttgctat catctcatat ttaagtcttt ggcttgtgaa tttatctatt   1620
ctttcagctt cagcactgca gagtgctggg actttgctaa cttccatttc ttgctggctt   1680
agcacattcc tcataggccc agctcttttc tcatctggcc ctgctgtgga gtcaccttgc   1740
cccttcagga gagccatggc ttaccactgc ctgctaagcc tccactcagc tgccaccaca   1800
ctaaatccaa gcttctctaa gatgttgcag actttacagg caagcataaa aggcttgatc   1860
ttcctggact tccctttact tgtctgaatc tcacctcctt caactttcag tctcagaatg   1920
taggcatttg tcctctttgc cctacatctt ccttcttctg aatcatgaaa gcctctcact   1980
tcctcttgct atgtgctgga ggcttctgtc aggttttaga atgagttctc atctagtcct   2040
agtagctttt gatgcttaag tccacctttt aaggatacct ttgagattta gaccatgttt   2100
ttcgcttgag aaagccctaa tctccagact tgcctttctg tggatttcaa agaccaactg   2160
aggaagtcaa aagctgaatg ttgactttct ttgaacattt ccgctataac aattccaatt   2220
ctcctcagag caatatgcct gcctccaact gaccaggaga aaggtccagt gccaaagaga   2280
aaaacacaaa gattaattat ttcagttgag cacatacttt caaagtggtt tgggtattca   2340
tatgaggttt tctgtcaaga gggtgagact cttcatctat ccatg                   2385
```

<210> SEQ ID NO 575
<211> LENGTH: 510
<212> TYPE: DNA
<213> ORGANISM: Homo sapiens

<400> SEQUENCE: 575

```
gccttgtaag tagccatgga atgtcaacct gtaacttaaa ttatccacag atagtcatgt     60
gtttgatgat gggcactgtg gagataactg acataggact gtgcccccct tctctgccac    120
ttactagctg gatgagatta agcaagtcat ttaactgctc tgattaaacc tgcctttccc    180
aagtgctttg taatgaatag aaatggaaac caaaaaaaac gtatacaggc cttcagaaat    240
agtaattgct actattttgt tttcattaag ccatagttct ggctataatt ttatcaaact    300
caccagctat attctacagt gaaagcagga ttctagaaag tctcactgtt ttatttatgt    360
```

caccatgtgc tatgatatat ttggttgaat tcatttgaaa ttagggctgg aagtattcaa 420
gtaatttctt ctgctgaaaa aatacagtgt tttgagttta gggcctgttt tatcaaagtt 480
ctaaagagcc tatcactctt ccattgtaga 510

<210> SEQ ID NO 576
<211> LENGTH: 253
<212> TYPE: DNA
<213> ORGANISM: Homo sapiens

<400> SEQUENCE: 576
gtcctatcta ctaatgtctc cattactatt tagtcatcat aaccattatc ttcattttac 60
atgtcgtgtt ctttctggta gctctaaaat gacactaaat cataagaaga caggttacat 120
atcaggaaat acttgaaggt tactgaaata gattcttgag ttaatgaaaa tattttctgt 180
aaaaaggttt gaaaagccat ttgagtctaa agcattatac ctccattatc agtagttatg 240
tgacaattgt gtg 253

<210> SEQ ID NO 577
<211> LENGTH: 1054
<212> TYPE: DNA
<213> ORGANISM: Homo sapiens

<400> SEQUENCE: 577
gcagtaattt gccttctcct agagtttacc tgccattttg tgcacatttg agttacagta 60
gcatgttatt ttacaattgt gactctcctg ggagtctggg agccatataa agtggtcaat 120
agtgtttgct gactgagagt tgaatgacat tttctctctg tcttggtatt actgtagatt 180
tcgatcattc tttggttaca tttctgcata tttctgtacc catgacttta tcactttctt 240
ctcccatgct ttatctccat caattatctt cattactttt aaattttcca cctttgcttc 300
ctactttgtg agatctctcc ctttactgac tataacatag aagaatagaa gtgtatttta 360
tgtgtcttaa ggacaatact ttagattcct tgttctaagt ttttaaactg aatgaatgga 420
atattatttc tctccctaag caaaattcca caaaacaatt atttcttatg tttatgtagc 480
cttaaattgt tttgtactgt aaacctcagc ataaaaactt tcttcatttc taatttcatt 540
caacaaatat tgattgaata cctggtatta gcacaagaaa aatgtgctaa taagccttat 600
gagaatttgg agctgaagaa agacatataa ctcaggaaag ttacagtcca gtagtaggta 660
taaattacag tgcctgataa ataggcattt taatatttgt acactcaacg tatactaggt 720
aggtgcaaaa catttacata taattttact gatacccatg cagcacaaag gtactaactt 780
taaatattaa ataacacctt tatgtgtcag taattcattt gcattaaatc ttattgaaaa 840
ggctttcaat atattttccc cacaaatgtc atcccaagaa aaaagtattt ttaacatctc 900
ccaaatataa tagttacagg aaatctacct ctgtgagagt gacacctctc agaatgaact 960
gtgtgacaca agaaaatgaa tgtaggtcta tccaaaaaaa accccaagaa acaaaaacaa 1020
tattattagc cctttatgct taagtgatgg actc 1054

<210> SEQ ID NO 578
<211> LENGTH: 359
<212> TYPE: DNA
<213> ORGANISM: Homo sapiens

<400> SEQUENCE: 578
taggtaactc cctttgtgtc aattatattt ccaaaaatga acctttaaaa tggtatgcaa 60
aattttgtct atatatattt gtgtgaggag gaaattcata actttcctca gattttcaaa 120
agtattttta atgcaaaaaa tgtagaaaga gtttaaaacc actaaaatag attgatgttc 180
ttcaaactag gcaaaacaac tcatatgtta agaccatttt ccagattgga aacacaaatc 240
tcttaggaag ttaataagta gattcatatc attatgcaaa tagtattgtg ggttttgtag 300
gtttttaaaa taacctttttt tggggagaga attgtcctct aatgaggtat tgcgagtgg 359

<210> SEQ ID NO 579
<211> LENGTH: 112
<212> TYPE: DNA
<213> ORGANISM: Homo sapiens

<400> SEQUENCE: 579
caaacaactt catctgtact gcttgaatac atttatccag tcccgggcac tgagtgttga 60
atttccagaa atgatgtctg aagttattgc tgcacaatta cccaagatat tg 112

<210> SEQ ID NO 580
<211> LENGTH: 91
<212> TYPE: DNA
<213> ORGANISM: Homo sapiens

<400> SEQUENCE: 580
atgaggtcaa gctacattag agagctcatc aaggcaattg gtttgaggca aaaaggagtt 60
gtgtcgagct cacagcgttt ctatcaactt a 91

<210> SEQ ID NO 581
<211> LENGTH: 25
<212> TYPE: DNA
<213> ORGANISM: Homo sapiens

<400> SEQUENCE: 581
tggaagggct acgaagtcaa accca 25

<210> SEQ ID NO 582
<211> LENGTH: 33
<212> TYPE: DNA
<213> ORGANISM: Homo sapiens

<400> SEQUENCE: 582
caggagtttg tcaagcttca agttagccaa gaa 33

<210> SEQ ID NO 583
<211> LENGTH: 29
<212> TYPE: DNA
<213> ORGANISM: Homo sapiens

<400> SEQUENCE: 583
tattttgcac ctgatctaat actaaatga 29

<210> SEQ ID NO 584
<211> LENGTH: 74
<212> TYPE: DNA
<213> ORGANISM: Homo sapiens

<400> SEQUENCE: 584
cttacatatt gatgaccaga taactctcat tcagtattct tggatgagct taatggtgtt 60
tggtctagga tgga 74

<210> SEQ ID NO 585
<211> LENGTH: 229

<212> TYPE: DNA
<213> ORGANISM: Homo sapiens

<400> SEQUENCE: 585
cagccagtgg gcgttccaaa tgaaagccaa gccctaagcc agagattcac tttttcacca 60
ggtcaagaca tacagttgat tccaccactg atcaacctgt taatgagcat tgaaccagat 120
gtgatctatg caggacatga caacacaaaa cctgacacct ccagttcttt gctgacaagt 180
cttaatcaac taggcgagag gcaacttctt tcagtagtca agtggtcta 229

<210> SEQ ID NO 586
<211> LENGTH: 46
<212> TYPE: DNA
<213> ORGANISM: Homo sapiens

<400> SEQUENCE: 586
atggagttta tatatattta catgaatttc tttttttct tctctg 46

<210> SEQ ID NO 587
<211> LENGTH: 373
<212> TYPE: DNA
<213> ORGANISM: Homo sapiens

<400> SEQUENCE: 587
agaccattgg cgtaccacca gtttgtggag ggaactggaa aaactggaat acacatgccc 60
catccaaaag caaccattgc aactaaactt taacagattg ttgccaccta agtaattcac 120
ggatggtctc ataattctgg tcagcattgt ctgagccaaa caaaatgtat ctatgggcat 180
gatcagatac tagagccagc agattgcaac ctctgcttag ataattgcag gtatcagcct 240
tcccttggct aaacagctac ttcatactga taagtagccc ttgcctggca caaagcaggt 300
ggggctgaat ccagcctgat atcacatcac cacaactttc tctaattctc ctcaaggcgt 360
ctgtgaacta cca 373

<210> SEQ ID NO 588
<211> LENGTH: 63
<212> TYPE: DNA
<213> ORGANISM: Homo sapiens

<400> SEQUENCE: 588
tgactgcatc gttgataaaa tccgcagaaa aaactgccca gcatgtcgcc ttagaaagtg 60
ctg 63

<210> SEQ ID NO 589
<211> LENGTH: 65
<212> TYPE: DNA
<213> ORGANISM: Homo sapiens

<400> SEQUENCE: 589
caggctgtca ttatggtgtc cttacctgtg ggagctgtaa ggtcttcttt aagagggcaa 60
tggaa 65

<210> SEQ ID NO 590
<211> LENGTH: 51
<212> TYPE: DNA
<213> ORGANISM: Homo sapiens

<400> SEQUENCE: 590
agccagagcc cacaatacag cttcgagtca ttacctcaga agatttgttt a 51

<210> SEQ ID NO 591
<211> LENGTH: 69
<212> TYPE: DNA
<213> ORGANISM: Homo sapiens

<400> SEQUENCE: 591
tcggctacca ggccgccgtg ctcaaggagg gcctgccgca ggtctacccg ccctatctca 60
actacctga 69

<210> SEQ ID NO 592
<211> LENGTH: 130
<212> TYPE: DNA
<213> ORGANISM: Homo sapiens

<400> SEQUENCE: 592
gccgccctgc aaggcgccgg gcgcgagcgg ctgcctgctc ccgcgggacg gcctgccctc 60
cacctccgcc tctgccgccg ccgccggggc ggcccccgcg ctctaccctg cactcggcct 120
caacgggctc 130

<210> SEQ ID NO 593
<211> LENGTH: 71
<212> TYPE: DNA
<213> ORGANISM: Homo sapiens

<400> SEQUENCE: 593
gtgcctcagt ctcgtctgcg tcctcctcgg ggtcgaccct ggagtgcatc ctgtacaaag 60
cggagggcgc g 71

<210> SEQ ID NO 594
<211> LENGTH: 241
<212> TYPE: DNA
<213> ORGANISM: Homo sapiens

<400> SEQUENCE: 594
ctgcctctca atcacgcctt attggcagcc cgcactcggc agctgctgga agacgaaagt 60
tacgacggcg gggccggggc tgccagcgcc tttgccccgc cgcggagttc accctgtgcc 120
tcgtccaccc cggtcgctgt aggcgacttc cccgactgcg cgtacccgcc cgacgccgag 180
cccaaggacg acgcgtaccc tctctatagc gacttccagc cgcccgctct aaagataaag 240
g 241

<210> SEQ ID NO 595
<211> LENGTH: 781
<212> TYPE: DNA
<213> ORGANISM: Homo sapiens

<400> SEQUENCE: 595
ttgcctgaag tttcggccat acctatctcc ctggacgggc tactcttccc tcggccctgc 60
cagggacagg acccctccga cgaaaagacg caggaccagc agtcgctgtc ggacgtggag 120
ggcgcatatt ccagagctga agctacaagg ggtgctggag gcagcagttc tagtccccca 180
gaaaaggaca gcggactgct ggacagtgtc ttggacactc tgttggcgcc ctcaggtccc 240
gggcagagcc aacccagccc tcccgcctgc gaggtcacca gctcttggtg cctgtttggc 300
cccgaacttc ccgaagatcc accggctgcc cccgccaccc agcgggtgtt gtccccgctc 360
atgagccggt ccgggtgcaa ggttggagac agctccggga cggcagctgc ccataaagtg 420
ctgccccggg gcctgtcacc agcccggcag ctgctgctcc cggcctctga gagccctcac 480
tggtccgggg ccccagtgaa gccgtctccg caggccgctg cggtggaggt tgaggaggag 540
gatggctctg agtccgagga gtctgcgggt ccgcttctga agggcaaacc tcgggctctg 600
ggtggcgcgg cggctggagg aggagccgcg gctgtcccgc cgggggcggc agcaggaggc 660
gtcgccctgg tccccaagga agattcccgc ttctcagcgc ccagggtcgc cctggtggag 720
caggacgcgc cgatggcgcc cgggcgctcc ccgctggcca ccacggtgat ggatttcatc 780
c 781

<210> SEQ ID NO 596
<211> LENGTH: 261
<212> TYPE: DNA
<213> ORGANISM: Homo sapiens

<400> SEQUENCE: 596
tgaaatctac aacccgaggc ggctagtgct cccgcactac tgggatctga gatcttcgga 60
gatgactgtc gcccgcagta cggagccagc agaagtccga cccttcctgg gaatgggctg 120
taccgagagg tccgactagc cccagggttt tagtgagggg gcagtggaac tcagcgaggg 180
actgagagct tcacagcatg cacgagtttg atgccagaga aaaagtcggg agataaagga 240
gccgcgtgtc actaaattgc c 261

<210> SEQ ID NO 597
<211> LENGTH: 147
<212> TYPE: DNA
<213> ORGANISM: Homo sapiens

<400> SEQUENCE: 597
cgcaccgagg caccgcggcg agcttggctg cttctggggc ctgtgtggcc ctgtgtgtcg 60
gaaagatgga gcaagaagcc gagcccgagg ggcggccgcg acccctctga ccgagatcct 120
gctgctttcg cagccaggag caccgtc 147

<210> SEQ ID NO 598
<211> LENGTH: 35
<212> TYPE: DNA
<213> ORGANISM: Homo sapiens

<400> SEQUENCE: 598
gtacgagcgc ccagtgccct ggcccggaga gtgga 35

<210> SEQ ID NO 599
<211> LENGTH: 34
<212> TYPE: DNA
<213> ORGANISM: Homo sapiens

<400> SEQUENCE: 599
gaggcccagg gcgtcgtgct tccgcgcgcc ccgt 34

<210> SEQ ID NO 600
<211> LENGTH: 35
<212> TYPE: DNA
<213> ORGANISM: Homo sapiens

<400> SEQUENCE: 600
actccaagcg cgaaaacccc ggatggtgag gagca 35

<210> SEQ ID NO 601
<211> LENGTH: 57
<212> TYPE: DNA

<213> ORGANISM: Homo sapiens

<400> SEQUENCE: 601
ttcagtggcg attggagggt agacctgtgg gcacggacgc acgccacttt ttctctg 57

<210> SEQ ID NO 602
<211> LENGTH: 30
<212> TYPE: DNA
<213> ORGANISM: Homo sapiens

<400> SEQUENCE: 602
tgtacctact gatggtgctg taaccacctc 30

<210> SEQ ID NO 603
<211> LENGTH: 30
<212> TYPE: DNA
<213> ORGANISM: Homo sapiens

<400> SEQUENCE: 603
accaaagcca ttgcttttga agttattaaa 30

<210> SEQ ID NO 604
<211> LENGTH: 37
<212> TYPE: DNA
<213> ORGANISM: Homo sapiens

<400> SEQUENCE: 604
gtctgttggt gcacaaaaag acacttatac tatgaaa 37

<210> SEQ ID NO 605
<211> LENGTH: 57
<212> TYPE: DNA
<213> ORGANISM: Homo sapiens

<400> SEQUENCE: 605
gacttcttgg gcatccctgg atcccaggtt aagaacttct gcactagaga tacatga 57

<210> SEQ ID NO 606
<211> LENGTH: 28
<212> TYPE: DNA
<213> ORGANISM: Homo sapiens

<400> SEQUENCE: 606
gtacagtata ctgatctttc tgggatag 28

<210> SEQ ID NO 607
<211> LENGTH: 34
<212> TYPE: DNA
<213> ORGANISM: Homo sapiens

<400> SEQUENCE: 607
gggctcaagg gatctgctta cctcggcctc ctaa 34

<210> SEQ ID NO 608
<211> LENGTH: 27
<212> TYPE: DNA
<213> ORGANISM: Homo sapiens

<400> SEQUENCE: 608
tatgactaaa cgattatatg atgagaa 27

<210> SEQ ID NO 609
<211> LENGTH: 36

<212> TYPE: DNA
<213> ORGANISM: Homo sapiens

<400> SEQUENCE: 609
cttctaggag atttgtttgg cgtgccaagc ttctct 36

<210> SEQ ID NO 610
<211> LENGTH: 30
<212> TYPE: DNA
<213> ORGANISM: Homo sapiens

<400> SEQUENCE: 610
attgtaaaaa gccatctggg ctaacatttc 30

<210> SEQ ID NO 611
<211> LENGTH: 96
<212> TYPE: DNA
<213> ORGANISM: Homo sapiens

<400> SEQUENCE: 611
aggttaaatt gcataagggt ttgtgttaga ctgatagcat atctactgag tagcgccccg 60
ccgccccccg cccaccacca agtttctgat cctttt 96

<210> SEQ ID NO 612
<211> LENGTH: 27
<212> TYPE: DNA
<213> ORGANISM: Homo sapiens

<400> SEQUENCE: 612
aatcatcgga ctcaggtaca tctgtga 27

<210> SEQ ID NO 613
<211> LENGTH: 31
<212> TYPE: DNA
<213> ORGANISM: Homo sapiens

<400> SEQUENCE: 613
gtgagaacag gtgtcacctt gaaggtggga g 31

<210> SEQ ID NO 614
<211> LENGTH: 57
<212> TYPE: DNA
<213> ORGANISM: Homo sapiens

<400> SEQUENCE: 614
tcacatttgg tttctagacc atctacctca tctagaagga gagcaattag tgagaca 57

<210> SEQ ID NO 615
<211> LENGTH: 72
<212> TYPE: DNA
<213> ORGANISM: Homo sapiens

<400> SEQUENCE: 615
atatttattt gacgcattca cacagctttt tgatattctt tctctaatga aattagtgct 60
tttagactta at 72

<210> SEQ ID NO 616
<211> LENGTH: 51
<212> TYPE: DNA
<213> ORGANISM: Homo sapiens

<400> SEQUENCE: 616
tcagatgaat tatctggtga acgacaaaga aaacgccaca aatctgatag t 51

<210> SEQ ID NO 617
<211> LENGTH: 74
<212> TYPE: DNA
<213> ORGANISM: Homo sapiens

<400> SEQUENCE: 617
aaagcctggc tctgtgtgta ataagggaga tatgttgtga aagaagcagt agcagtgaat 60
ctacagggac gcca 74

<210> SEQ ID NO 618
<211> LENGTH: 75
<212> TYPE: DNA
<213> ORGANISM: Homo sapiens

<400> SEQUENCE: 618
ttcagtttca gatcagttta gtgtagaatt tgaagttgaa tctctcgact cagaagatta 60
tagccttagt gaaga 75

<210> SEQ ID NO 619
<211> LENGTH: 77
<212> TYPE: DNA
<213> ORGANISM: Homo sapiens

<400> SEQUENCE: 619
tgcaatgaaa tgaatccccc ccttccatca cattgcaaca gatgttgggc ccttcgtgag 60
aattggcttc ctgaaga 77

<210> SEQ ID NO 620
<211> LENGTH: 69
<212> TYPE: DNA
<213> ORGANISM: Homo sapiens

<400> SEQUENCE: 620
ctatagtgaa tgattccaga gagtcatgtg ttgaggaaaa tgatgataaa attacacaag 60
cttcacaat 69

<210> SEQ ID NO 621
<211> LENGTH: 25
<212> TYPE: DNA
<213> ORGANISM: Homo sapiens

<400> SEQUENCE: 621
tctcagccat caacttctag tagca 25

<210> SEQ ID NO 622
<211> LENGTH: 41
<212> TYPE: DNA
<213> ORGANISM: Homo sapiens

<400> SEQUENCE: 622
aagagagtgt ggaatctagt ttgcccctta atgccattga a 41

<210> SEQ ID NO 623
<211> LENGTH: 32
<212> TYPE: DNA
<213> ORGANISM: Homo sapiens

<400> SEQUENCE: 623
tcaaggtcga cctaaaaatg gttgcattgt cc 32

<210> SEQ ID NO 624
<211> LENGTH: 26
<212> TYPE: DNA
<213> ORGANISM: Homo sapiens

<400> SEQUENCE: 624
atatttctaa ctatataacc ctagga 26

<210> SEQ ID NO 625
<211> LENGTH: 722
<212> TYPE: DNA
<213> ORGANISM: Homo sapiens

<400> SEQUENCE: 625
accgcgtccg gcctaaatgt cacttagtac ctttgatata aagagaaaat gtgtgaaaga 60
tttagttttt tgtttttttg tttgtttgtt tgtttgtttg ttttgagatg agtctctctg 120
tcgcccaggc tggagtgcag tgtcatgatc tagcagtctc cgcttcccgg gttcaagcca 180
ttctcctggc tcagcctctg gagcagctgg gattacaggc atgcaccacc atgcccagct 240
aatttttgta tttttagtag agatagggtt tcaccatgtt ggccaggctg gtcacgaact 300
cctgacctca agtgaggtca cccgcctcgg cctcccgaag tgctgggatt gcagatgtga 360
gccaccatgt ccagccaaga attagtattt aaattttaga tactcttttt tttttttttt 420
tttttttttt ttgagacaga gtcttgctcc atcacccatg ctagagtgca gtggagtgat 480
ctcggctcac tgcaacttcc gccttctggg ttcaagctat tctcctgcct cagccttcca 540
agtaactggg attacaggca tgtaccacca taccagctga ttttttgta tttttagtaa 600 agacagggtt tcaccatgtt agccaggctg atcttgaact cctaaactca agtgatctac 660
tcacctcagc ctcccaaaat gctgggatta cagatgtgag gcacctggcc tcagattttt 720
ga 722

<210> SEQ ID NO 626
<211> LENGTH: 27
<212> TYPE: DNA
<213> ORGANISM: Homo sapiens

<400> SEQUENCE: 626
tggaggccca tccgagctca gcactga 27

<210> SEQ ID NO 627
<211> LENGTH: 371
<212> TYPE: DNA
<213> ORGANISM: Homo sapiens

<400> SEQUENCE: 627
acaagcctgt caaatatctg caagaactat ggaataaaac tactgatgca gtgaagacag 60
ttgaaaagat caaacaaatg ccaagctata tttataatga acaaattcaa gaaaaaggac 120
tacggaaagt tcaggacatc aaagaagtca ggcaaaactc atcttgaccc ctgttgcagg 180
caaaggaacg cagctggaag aaaagatgat ataacagtta acaggatgca gacatggcag 240
aggtttccta aaaatctcat tatctataac catttctata tttacatttg aaaatctcct 300
ttggagactt agaacctcta aattattgac ttattttttta tataaggtca ctccgatgaa 360
aggtgattac a 371

<210> SEQ ID NO 628

<211> LENGTH: 153
<212> TYPE: DNA
<213> ORGANISM: Homo sapiens

<400> SEQUENCE: 628
tgagagccga ataaggtttg cctgaaataa ctgacactat ataatttctg ctttggcaaa 60
tactaagttc taacttgtca ttcctggtag aacaagcttt atttttcgag cctagcaatg 120
atctagaagc agatgttatc tcagtgcctt ttg 153

<210> SEQ ID NO 629
<211> LENGTH: 226
<212> TYPE: DNA
<213> ORGANISM: Homo sapiens

<400> SEQUENCE: 629
ctgatgggtg tgctaattac actgatttga tcaataccca ttgtatgtga aacagtacat 60
acaccatatt tacaattatg tatttaacat ttaaaatttc taatataagt atctctcaaa 120
ctgtggatta acttcttgat ttatatttaa atatgaatct taagcaaaac agtgaaaata 180
accatcttga tttagtgttt ttctcccata tgtgaattgt atatac 226

<210> SEQ ID NO 630
<211> LENGTH: 49
<212> TYPE: DNA
<213> ORGANISM: Homo sapiens

<400> SEQUENCE: 630
gcttagaata ggactgaggt aattctgcac agcaacttta ctaatggta 49

<210> SEQ ID NO 631
<211> LENGTH: 68
<212> TYPE: DNA
<213> ORGANISM: Homo sapiens

<400> SEQUENCE: 631
gtcctccaag cattatttgg agttgataat acttcagcta caaccaagca gaatctcttt 60
tttttgga 68

<210> SEQ ID NO 632
<211> LENGTH: 59
<212> TYPE: DNA
<213> ORGANISM: Homo sapiens

<400> SEQUENCE: 632
gataatactt cagcttcaat ttggagttga taatatttca gctagaacct agtagaatc 59

<210> SEQ ID NO 633
<211> LENGTH: 123
<212> TYPE: DNA
<213> ORGANISM: Homo sapiens

<400> SEQUENCE: 633
cacttgatat atggaggcag tgacagctat ttttacaaaa tttaaatctg caaatggatt 60
caacatgttt atgggttatt aaaattgtct gatttcttag gttctttata gtacacgtgt 120
tga 123

<210> SEQ ID NO 634
<211> LENGTH: 524
<212> TYPE: DNA
<213> ORGANISM: Homo sapiens

<400> SEQUENCE: 634
tgggagcctc caatgagagc aacttgagag aatgatgttg caagttagta ggagtaagaa 60
atgctgtgtt ctccctgtct tctcttaggt cacatggcag cctggcctaa gtgatcgtga 120
atggtctata agggaggtag ctgggacagg gaggggagtt tgggctagcc accgtaccac 180
ttgtcagcgt gaaaagtaag attgtaattg cctgtttagt tttctgcctc atctttgaaa 240
gttccaccaa gctgggaacc tcttgattgt gaggcacaaa tgtaagtaca tcagaaaaaa 300
acaaaaaaac tggctttaaa gcaggagctt gtgggcccct aagccagacg gggactagct 360
tttggcatta tataattaag attttttaaa tccttaataa gggttttatt ttatttttat 420 ttatttttg agacggagtc ttgctctgtg gctcaggctg gagtacagtg gtgcaatctt 480
ggctcactgc aacctctgcc tcctggctgt gttcaagtgg ttct 524

<210> SEQ ID NO 635
<211> LENGTH: 156
<212> TYPE: DNA
<213> ORGANISM: Homo sapiens

<400> SEQUENCE: 635
gaaacattaa gaataccata tgagtaaatt aaacactttg gctcttttcg gaaaaaaaca 60
gatgagctct tatattttaa agtttggttt tgacagaaaa aaattcctag attttttggt 120
taataaaaac tttattagat agattaaatt gtgatg 156

<210> SEQ ID NO 636
<211> LENGTH: 279
<212> TYPE: DNA
<213> ORGANISM: Homo sapiens

<400> SEQUENCE: 636
agggaacttc tgcttaagag gcttctatgt aatgaaattc tcttgaaaac agagaaacta 60
tttcctgttt attttctaaa ttgagacgtc actttttaaa aattggtacc tgtaatttag 120
ccatttccta ctcagcaatg tctcatttaa actattattt gtttagcgtg tttcaaagag 180
cagatgtaag cttgagccca tcctctgtcc tatgactaag tcgatattag caggggttag 240
gactgttagt tttccagttc ctactggagg caaattctt 279

<210> SEQ ID NO 637
<211> LENGTH: 172
<212> TYPE: DNA
<213> ORGANISM: Homo sapiens

<400> SEQUENCE: 637
ccttttctgg agagtagtct agaccaagcc aattgcagaa ccacattctt tggttcccag 60
gagagcccca ttcccagccc ctggtctccc gtgccgcagt tctatattct gcttcaaatc 120
agccttcagg tttcccacag catggcccct gctgacacga gaacccaaag tt 172

<210> SEQ ID NO 638
<211> LENGTH: 171
<212> TYPE: DNA
<213> ORGANISM: Homo sapiens

<400> SEQUENCE: 638
tcttgccgga ggtagcagtg gaagctacta ctccagcagc agtgggggtg tcggcctagg 60
tggtgggctc agtgtggggg gctctggctt cagtgcaagc agtggccgag ggctgggggt 120
gggctttggc agtggcgggg gtagcagctc cagcgtcaaa tttgtctcca c 171

<210> SEQ ID NO 639
<211> LENGTH: 35
<212> TYPE: DNA
<213> ORGANISM: Homo sapiens

<400> SEQUENCE: 639
actcagtgga gaaggagttg gaccagtcaa catct 35

<210> SEQ ID NO 640
<211> LENGTH: 172
<212> TYPE: DNA
<213> ORGANISM: Homo sapiens

<400> SEQUENCE: 640
aggtcaatcc ctcttcattg gaaaatccct ctggagagtt ctcccttcct ttaacttaag 60
cagcttttgg gtgtacagac tcctggctta tggaatgaac tcgaatcatg aggatgggag 120
ttagccacat agactaatgc tgtctttttg ggagctgtta acccttaatt ca 172

<210> SEQ ID NO 641
<211> LENGTH: 290
<212> TYPE: DNA
<213> ORGANISM: Homo sapiens

<400> SEQUENCE: 641
caagatggcc ttcagctgat aaagcgaagc tgctctactg tggggtgtac aacacacata 60
catgagatca gtgacttgtg cgtgataatg acacatcatc aacactattt cagtctgact 120
catggccata tagctgacct caactcactt ttctggtctc ttttccccca ccggtgttcc 180
tgggcactgg ctgtcctcca agcacctgag caactcagca atcttcttga cacttgtgcc 240
ttttctgctt ttgctcacgt cctttgctca acctcaatat ccatgtcatg 290

<210> SEQ ID NO 642
<211> LENGTH: 37
<212> TYPE: DNA
<213> ORGANISM: Homo sapiens

<400> SEQUENCE: 642
tgcgccaatc tgcagaacgc cattgcggat gccgagc 37

<210> SEQ ID NO 643
<211> LENGTH: 119
<212> TYPE: DNA
<213> ORGANISM: Homo sapiens

<400> SEQUENCE: 643
cttttgctaa acacacgcag ctagatccag taccagtgtt tcagtgtcct gccacccacg 60
atgtactggt ttctctctgg gattcatgat agtttggttt gtctgaccca gaaactcag 119

<210> SEQ ID NO 644
<211> LENGTH: 101
<212> TYPE: DNA
<213> ORGANISM: Homo sapiens

<400> SEQUENCE: 644
agctggccgg catggcgatg acctccgcaa caccaagcat gagatctctg agatgaaccg 60
gatgatccag aggctgagag ccgagattga caatgtcaag a 101

<210> SEQ ID NO 645
<211> LENGTH: 156
<212> TYPE: DNA
<213> ORGANISM: Homo sapiens

<400> SEQUENCE: 645
cagatgcaga cgcatgtctc tgacacctca gtggtcctct ccatggacaa caaccgcaac 60
ctggacctgg atagcatcat cgctgaggtc aaggcccagt atgaggagat tgccaaccgc 120
agccggacag aagccgagtc ctggtatcag accaag 156

<210> SEQ ID NO 646
<211> LENGTH: 32
<212> TYPE: DNA
<213> ORGANISM: Homo sapiens

<400> SEQUENCE: 646
cagaaccaga tgaccgactc caaatctccc tg 32

<210> SEQ ID NO 647
<211> LENGTH: 35
<212> TYPE: DNA
<213> ORGANISM: Homo sapiens

<400> SEQUENCE: 647
ggccaaggtt gatgcactga tggatgagat taact 35

<210> SEQ ID NO 648
<211> LENGTH: 57
<212> TYPE: DNA
<213> ORGANISM: Homo sapiens

<400> SEQUENCE: 648
gcagcctgca gctatgctct ctaagcgtgg agctcacttg agtagggtga cggtgtg 57

<210> SEQ ID NO 649
<211> LENGTH: 34
<212> TYPE: DNA
<213> ORGANISM: Homo sapiens

<400> SEQUENCE: 649
tgaaatcaac aagcgtacca ctgctgagaa tgag 34

<210> SEQ ID NO 650
<211> LENGTH: 26
<212> TYPE: DNA
<213> ORGANISM: Homo sapiens

<400> SEQUENCE: 650
aaaagaacac tagagaaatt gactag 26

<210> SEQ ID NO 651
<211> LENGTH: 36
<212> TYPE: DNA
<213> ORGANISM: Homo sapiens

<400> SEQUENCE: 651
gtggacacgt tctgaattag actggcagct gggaag 36

<210> SEQ ID NO 652
<211> LENGTH: 62
<212> TYPE: DNA
<213> ORGANISM: Homo sapiens

<400> SEQUENCE: 652
caacctgcaa atcgacccca gcatccagag ggtgaggacc gaggagcgcg agcagatcaa 60
ga 62

<210> SEQ ID NO 653
<211> LENGTH: 47
<212> TYPE: DNA
<213> ORGANISM: Homo sapiens

<400> SEQUENCE: 653
gaggtggtgc cggtagtgga tttggtttcg gcggtggagc tggtggt 47

<210> SEQ ID NO 654
<211> LENGTH: 32
<212> TYPE: DNA
<213> ORGANISM: Homo sapiens

<400> SEQUENCE: 654
ggcagcttca ggaaccggtt tggtgctggt gc 32

<210> SEQ ID NO 655
<211> LENGTH: 32
<212> TYPE: DNA
<213> ORGANISM: Homo sapiens

<400> SEQUENCE: 655
gggctccaag aggatatcca tcagcactag tg 32

<210> SEQ ID NO 656
<211> LENGTH: 44
<212> TYPE: DNA
<213> ORGANISM: Homo sapiens

<400> SEQUENCE: 656
tgtggagtgg gtggctatgg cagccggagc ctctacaacc tggg 44

<210> SEQ ID NO 657
<211> LENGTH: 29
<212> TYPE: DNA
<213> ORGANISM: Homo sapiens

<400> SEQUENCE: 657
tggtggcttc ggcagggtca gccttgcgg 29

<210> SEQ ID NO 658
<211> LENGTH: 80
<212> TYPE: DNA
<213> ORGANISM: Homo sapiens

<400> SEQUENCE: 658
tcaagtgtgt ccttccggag cgggggcagt cgtagcttca gcaccgcctc tgccatcacc 60
ccgtctgtct cccgcaccag 80

<210> SEQ ID NO 659
<211> LENGTH: 137
<212> TYPE: DNA
<213> ORGANISM: Homo sapiens

<400> SEQUENCE: 659
acagctcgac agctctctcg cccagcccag ttctggaagg gataaaaagg gggcatcacc 60
gttcctgggt aacagagcca ccttctgcgt cctgctgagc tctgttctct ccagcacctc 120
ccaacccact agtgcct 137

<210> SEQ ID NO 660
<211> LENGTH: 102
<212> TYPE: DNA
<213> ORGANISM: Homo sapiens

<400> SEQUENCE: 660
cccagcctct atggtgaaga catacttgct agcagcgtca ccaacttgct gccaagagat 60
cagtgctgca aggcaaggtt atttctaact gagcagagcc tg 102

<210> SEQ ID NO 661
<211> LENGTH: 655
<212> TYPE: DNA
<213> ORGANISM: Homo sapiens

<400> SEQUENCE: 661
caggtctgtg gcaatactct taaccataag aattgaaatg gtgaagaaac aagtatacac 60
tagaggctct taaaagtatt gaaagacaat actgctgtta tatagcaaga cataaacaga 120
ttataaacat cagagccatt tgcttctcag tttacatttc tgatacatgc agatagcaga 180
tgtctttaaa tgaaatacat gtatattgtg tatggactta attatgcaca tgctcagatg 240
tgtagacatc ctccgtatat ttacataaca tatagaggta atagataggt gatatacatg 300
atacattctc aagagttgct tgaccgaaag ttacaaggac cccaacccct ttgtcctctc 360
tacccacaga tggccctggg aatcaattcc tcaggaattg ccctcaagaa ctctgcttct 420
tgctttgcag agtgccatgg tcatgtcatt ctgaggtcac ataacacata aaattagttt 480
ctatgagtgt ataccattta aagaattttt ttttcagtaa aagggaatat tacaatgttg 540
gaggagagat aagttatagg gagctggatt tcaaaacgtg gtccaagatt caaaaatcct 600
attgatagtg gccattttaa tcattgccat cgtgtgcttg tttcatccag tgtta 655

<210> SEQ ID NO 662
<211> LENGTH: 35
<212> TYPE: DNA
<213> ORGANISM: Homo sapiens

<400> SEQUENCE: 662
gtgtgtattc cagacccgtc ctaaacactt cctag 35

<210> SEQ ID NO 663
<211> LENGTH: 118
<212> TYPE: DNA
<213> ORGANISM: Homo sapiens

<400> SEQUENCE: 663
tcggagcagc agcataagct ggacttcaag gcatacgaac aggcactgca atactcgcct 60
tacggctcta cgttgcccgc cagcctgcct ctaggcagcg cctcggtgac caccagga 118

<210> SEQ ID NO 664
<211> LENGTH: 50
<212> TYPE: DNA
<213> ORGANISM: Homo sapiens

<400> SEQUENCE: 664
gggcgcctcg gagttgaaga ctccagcctc ctcaactgcg ccccccataa 50

<210> SEQ ID NO 665

<211> LENGTH: 96
<212> TYPE: DNA
<213> ORGANISM: Homo sapiens

<400> SEQUENCE: 665
ggcggccctg agagccgcaa ggacccctct ggcgcctcta accccagcgc cgactcgccc 60
ctccatcggg gtgtgcacgg gaagaccggc cagcta 96

<210> SEQ ID NO 666
<211> LENGTH: 206
<212> TYPE: DNA
<213> ORGANISM: Homo sapiens

<400> SEQUENCE: 666
aggcgcccag caagatgctc acgctgagcg agatctacca gtggatcatg gacctcttcc 60
cctattaccg gcagaaccag cagcgctggc agaactccat ccgccactcg ctgtccttca 120
atgactgctt cgtcaaggtg gcacgctccc cggacaagcc gggcaagggc tcctactgga 180
cgctgcaccc ggactccggc aacatg 206

<210> SEQ ID NO 667
<211> LENGTH: 68
<212> TYPE: DNA
<213> ORGANISM: Homo sapiens

<400> SEQUENCE: 667
tacgcgccgt ccaacctggg ccgcagccgc gcgggcggcg gcggcgacgc caagacgttc 60
aagcgcag 68

<210> SEQ ID NO 668
<211> LENGTH: 210
<212> TYPE: DNA
<213> ORGANISM: Homo sapiens

<400> SEQUENCE: 668
tccgtcccgg tcagcaacat gaactcaggc ctgggctcca tgaactccat gaacacctac 60
atgaccatga acaccatgac tacgagcggc aacatgaccc cggcgtcctt caacatgtcc 120
tatgccaacc cgggcctagg ggccggcctg agtcccggcg cagtagccgg catgccgggg 180
ggctcggcgg gcgccatgaa cagcatgact 210

<210> SEQ ID NO 669
<211> LENGTH: 53
<212> TYPE: DNA
<213> ORGANISM: Homo sapiens

<400> SEQUENCE: 669
tggaagggca tgaaaccagc gactggaaca gctactacgc agacacgcag gag 53

<210> SEQ ID NO 670
<211> LENGTH: 27
<212> TYPE: DNA
<213> ORGANISM: Homo sapiens

<400> SEQUENCE: 670
ctttgtgcgg cggacaaatg gggagag 27

<210> SEQ ID NO 671
<211> LENGTH: 48
<212> TYPE: DNA
<213> ORGANISM: Homo sapiens

<400> SEQUENCE: 671
tcataaagat ataaaccggt gctgtgactc acctgctctt agccgcag 48

<210> SEQ ID NO 672
<211> LENGTH: 63
<212> TYPE: DNA
<213> ORGANISM: Homo sapiens

<400> SEQUENCE: 672
ggggtcggag ctgatcgggc gcctagcccc gcgcctgggc ctcgccgagc ccgacatgct 60
gag 63

<210> SEQ ID NO 673
<211> LENGTH: 53
<212> TYPE: DNA
<213> ORGANISM: Homo sapiens

<400> SEQUENCE: 673
gtgagttcgg ccgcgcaaga ccagggctgg gcttccgcct cgcggccctg ggc 53

<210> SEQ ID NO 674
<211> LENGTH: 89
<212> TYPE: DNA
<213> ORGANISM: Homo sapiens

<400> SEQUENCE: 674
ctctcaccag aggatatgac cttcattccc agccccagat aaacgagcca caggagttag 60
gcttagtgtg aagctaacca ggctgtatt 89

<210> SEQ ID NO 675
<211> LENGTH: 75
<212> TYPE: DNA
<213> ORGANISM: Homo sapiens

<400> SEQUENCE: 675
aagcagagga gtacttgcgc ctgtcccggg tgaagtgtgt cggcctctcc gcacgcacca 60
cggagaccag cagtg 75

<210> SEQ ID NO 676
<211> LENGTH: 29
<212> TYPE: DNA
<213> ORGANISM: Homo sapiens

<400> SEQUENCE: 676
gatcttgact tatccaggcc acttttcac 29

<210> SEQ ID NO 677
<211> LENGTH: 143
<212> TYPE: DNA
<213> ORGANISM: Homo sapiens

<400> SEQUENCE: 677
gccaagtgac tatattccca gtttatccca taatgtagct aacaacttgg aactagtgtt 60
gccagaattc cactagcaaa tagcagctgt atatatatgc tgggaattct gatttcagtc 120
tgccttttgt aagagatgat atc 143

<210> SEQ ID NO 678
<211> LENGTH: 234
<212> TYPE: DNA

<213> ORGANISM: Homo sapiens

<400> SEQUENCE: 678
aagtcatgaa gcactacagc aaatgtcttt tatgtgcccc ttttgttata aaatagatcc 60
catgtgcatt ttaactctca gtccaataaa caactaaaca acttagcata gataataaca 120
tgtttggaat gaaggaaaaa aactagacag aggctctgga agcatggtca aaaagaaaat 180
aagttgatta tctggttgcc cagagaagaa aactgtacag gtcttgagaa aagc 234

<210> SEQ ID NO 679
<211> LENGTH: 30
<212> TYPE: DNA
<213> ORGANISM: Homo sapiens

<400> SEQUENCE: 679
gattctaaag ctgaaagtgg ataaaaacaa 30

<210> SEQ ID NO 680
<211> LENGTH: 60
<212> TYPE: DNA
<213> ORGANISM: Homo sapiens

<400> SEQUENCE: 680
aaaaagctat atttgatcga ctgtgtaaac aactagagaa gattggacag caggtcgaca 60

<210> SEQ ID NO 681
<211> LENGTH: 40
<212> TYPE: DNA
<213> ORGANISM: Homo sapiens

<400> SEQUENCE: 681
ttatttgtga tccaaaacat gcccaaatac tgaaattgag 40

<210> SEQ ID NO 682
<211> LENGTH: 56
<212> TYPE: DNA
<213> ORGANISM: Homo sapiens

<400> SEQUENCE: 682
acctggagat gtagctactc caccacggaa gagaaagaag atagtggttg aagccc 56

<210> SEQ ID NO 683
<211> LENGTH: 50
<212> TYPE: DNA
<213> ORGANISM: Homo sapiens

<400> SEQUENCE: 683
aaggtagagg agatgccaca taaaccacag aaagatgaag atctgacaca 50

<210> SEQ ID NO 684
<211> LENGTH: 41
<212> TYPE: DNA
<213> ORGANISM: Homo sapiens

<400> SEQUENCE: 684
ttggaaaatg ctgccagtgc tcaaaaggct acagcagagt g 41

<210> SEQ ID NO 685
<211> LENGTH: 510
<212> TYPE: DNA
<213> ORGANISM: Homo sapiens

<400> SEQUENCE: 685
tctccaggaa gacttgacgg ctttgggatt ttgtttaaac ttttataata aggatcctaa 60
gactgttgcc tttaaatagc aaagcagcct acctggaggc taagtctggg cagtgggctg 120
gcccctggtg tgagcattag accagccaca gtgcctgatt ggtatagcct tatgtgcttt 180
cctacaaaat ggaattggag gccgggcgca gtggctcacg cctgtaatcc cagcactttg 240
ggaggccaag gtgggtggat cacctgaggt caggagctcg agaccagcct ggccaacatg 300
gtgaaacccc atctctacta aaaatacaaa aattagccag gtgtgatggt gcatgcctgt 360
aatcccagct cctcagtagg ctgagacagg agcatcactt gaacgtggga ggcagaggtt 420
gcagtgagcc gagattgcac caccgcactc cagcctgggt gacagagcga gacttatctc 480
ataaataaat agatagatac tccagcctgg 510

<210> SEQ ID NO 686
<211> LENGTH: 153
<212> TYPE: DNA
<213> ORGANISM: Homo sapiens

<400> SEQUENCE: 686
tggagccatt ttgctttaag tgaatggcag tcccttgtct tattcagaat ataaaattca 60
gtctgaatgg catcttacag attttacttc aatttttgtg tacggtattt tttatttgac 120
taaatcaata tattgtacag cctaagttaa taa 153

<210> SEQ ID NO 687
<211> LENGTH: 165
<212> TYPE: DNA
<213> ORGANISM: Homo sapiens

<400> SEQUENCE: 687
cggagcctcc gttttcagtc gacttcagat gtgtctccac ttttttccgc tgtagccgca 60
aggcaaggaa acatttctct tcccgtactg aggaggctga ggagtgcact gggtgttctt 120
ttctcctcta acccagaact gcgagacaga ggctgagtcc ctgta 165

<210> SEQ ID NO 688
<211> LENGTH: 36
<212> TYPE: DNA
<213> ORGANISM: Homo sapiens

<400> SEQUENCE: 688
atggggctcc ctcgtggacc tctcgcgtct ctcctc 36

<210> SEQ ID NO 689
<211> LENGTH: 70
<212> TYPE: DNA
<213> ORGANISM: Homo sapiens

<400> SEQUENCE: 689
gctggctgca gtgcgcggcc tccgagccgt gccgggcggt cttcagggag gctgaagtga 60
ccttggaggc 70

<210> SEQ ID NO 690
<211> LENGTH: 63
<212> TYPE: DNA
<213> ORGANISM: Homo sapiens

<400> SEQUENCE: 690
aagagccagc tctgtttagc actgataatg atgacttcac tgtgcggaat ggcgagacag 60
tcc 63

<210> SEQ ID NO 691
<211> LENGTH: 35
<212> TYPE: DNA
<213> ORGANISM: Homo sapiens

<400> SEQUENCE: 691
gatcttccca tccaaacgta tcttacgaag acaca 35

<210> SEQ ID NO 692
<211> LENGTH: 25
<212> TYPE: DNA
<213> ORGANISM: Homo sapiens

<400> SEQUENCE: 692
tgggtggttg ctccaatatc tgtcc 25

<210> SEQ ID NO 693
<211> LENGTH: 108
<212> TYPE: DNA
<213> ORGANISM: Homo sapiens

<400> SEQUENCE: 693
tttctacagc atcacggggc cgggggcaga cagcccccct gagggtgtct tcgctgtaga 60
gaaggagaca ggctggttgt tgttgaataa gccactggac cgggagga 108

<210> SEQ ID NO 694
<211> LENGTH: 112
<212> TYPE: DNA
<213> ORGANISM: Homo sapiens

<400> SEQUENCE: 694
ctcagtggag gaccccatga acatctccat catcgtgacc gaccagaatg accacaagcc 60
caagtttacc caggacacct tccgagggag tgtcttagag ggagtcctac ca 112

<210> SEQ ID NO 695
<211> LENGTH: 130
<212> TYPE: DNA
<213> ORGANISM: Homo sapiens

<400> SEQUENCE: 695
tgacagccac ggatgaggat gatgccatct acacctacaa tggggtggtt gcttactcca 60
tccatagcca agaaccaaag gacccacacg acctcatgtt caccattcac cggagcacag 120
gcaccatcag 130

<210> SEQ ID NO 696
<211> LENGTH: 137
<212> TYPE: DNA
<213> ORGANISM: Homo sapiens

<400> SEQUENCE: 696
aggcccatgt gcctgagaat gcagtgggcc atgaggtgca gaggctgacg gtcactgatc 60
tggacgcccc caactcacca gcgtggcgtg ccacctacct tatcatgggc ggtgacgacg 120
gggaccattt taccatc 137

<210> SEQ ID NO 697
<211> LENGTH: 52
<212> TYPE: DNA
<213> ORGANISM: Homo sapiens

<400> SEQUENCE: 697
ccagcacacc ctgtacgttg aagtgaccaa cgaggcccct tttgtgctga ag 52

<210> SEQ ID NO 698
<211> LENGTH: 83
<212> TYPE: DNA
<213> ORGANISM: Homo sapiens

<400> SEQUENCE: 698
acagccacca tagtggtcca cgtggaggat gtgaatgagg cacctgtgtt tgtcccaccc 60
tccaaagtcg ttgaggtcca gga 83

<210> SEQ ID NO 699
<211> LENGTH: 27
<212> TYPE: DNA
<213> ORGANISM: Homo sapiens

<400> SEQUENCE: 699
gctgtgggca ccctcgaccg tgaggat 27

<210> SEQ ID NO 700
<211> LENGTH: 188
<212> TYPE: DNA
<213> ORGANISM: Homo sapiens

<400> SEQUENCE: 700
acgggaaccc ttctgctaac actgattgat gtcaatgacc atggcccagt ccctgagccc 60
cgtcagatca ccatctgcaa ccaaagccct gtgcgccagg tgctgaacat cacggacaag 120
gacctgtctc cccacacctc ccctttccag gcccagctca cagatgactc agacatctac 180
tggacggc 188

<210> SEQ ID NO 701
<211> LENGTH: 105
<212> TYPE: DNA
<213> ORGANISM: Homo sapiens

<400> SEQUENCE: 701
gtggtcttgt ccctgaagaa gttcctgaag caggatacat atgacgtgca cctttctctg 60
tctgaccatg gcaacaaaga gcagctgacg gtgatcaggg ccact 105

<210> SEQ ID NO 702
<211> LENGTH: 38
<212> TYPE: DNA
<213> ORGANISM: Homo sapiens

<400> SEQUENCE: 702
gtgtgcgact gccatggcca tgtcgaaacc tgccctgg 38

<210> SEQ ID NO 703
<211> LENGTH: 51
<212> TYPE: DNA
<213> ORGANISM: Homo sapiens

<400> SEQUENCE: 703
ctcccagaag atgacacccg tgacaacgtc ttctactatg gcgaagaggg g 51

<210> SEQ ID NO 704
<211> LENGTH: 118
<212> TYPE: DNA

<213> ORGANISM: Homo sapiens

<400> SEQUENCE: 704
cacccagctc caccgaggtc tggaggccag gccggaggtg gttctccgca atgacgtggc 60
accaaccatc atcccgacac ccatgtaccg tcctcggcca gccaacccag atgaaatc 118

<210> SEQ ID NO 705
<211> LENGTH: 41
<212> TYPE: DNA
<213> ORGANISM: Homo sapiens

<400> SEQUENCE: 705
gcaagaggca ggacccgccg ctcctaacta cctgttctct g 41

<210> SEQ ID NO 706
<211> LENGTH: 158
<212> TYPE: DNA
<213> ORGANISM: Homo sapiens

<400> SEQUENCE: 706
acctgaaggc ggctaacaca gaccccacag ccccgcccta cgacaccctc ttggtgttcg 60
actatgaggg cagcggctcc gacgccgcgt ccctgagctc cctcacctcc tccgcctccg 120
accaagacca agattacgat tatctgaacg agtggggc 158

<210> SEQ ID NO 707
<211> LENGTH: 385
<212> TYPE: DNA
<213> ORGANISM: Homo sapiens

<400> SEQUENCE: 707
tctgacgtta gagtggtggc ttccttagcc tttcaggatg gaggaatgtg ggcagtttga 60
cttcagcact gaaaacctct ccacctgggc cagggttgcc tcagaggcca agtttccaga 120
agcctcttac ctgccgtaaa atgctcaacc ctgtgtcctg ggcctgggcc tgctgtgact 180
gacctacagt ggactttctc tctggaatgg aaccttctta ggcctcctgg tgcaacttaa 240 ttttttttt taatgctatc ttcaaaacgt tagagaaagt tcttcaaaag tgcagcccag 300
agctgctggg cccactggcc gtcctgcatt tctggtttcc agaccccaat gcctcccatt 360
cggatggatc tctgcgtttt tatac 385

<210> SEQ ID NO 708
<211> LENGTH: 129
<212> TYPE: DNA
<213> ORGANISM: Homo sapiens

<400> SEQUENCE: 708
agagaaccta cccaagatgt cagtgaaatt ggaacattcc tgacaatacc agggcataaa 60
tgcaggaatc aggaataggc agcagtgata gaacaattct gtttgtgccc ttgttaacgt 120
gaagttcaa 129

<210> SEQ ID NO 709
<211> LENGTH: 133
<212> TYPE: DNA
<213> ORGANISM: Homo sapiens

<400> SEQUENCE: 709
ttcccggatt tttgtgggcg cctgccccgc ccctcgtccc cctgctgtgt ccatatatcg 60
aggcgatagg gttaagggaa ggcggacgcc tgatgggtta atgagcaaac tgaagtgttt 120
tccatgatct ttt 133

<210> SEQ ID NO 710
<211> LENGTH: 60
<212> TYPE: DNA
<213> ORGANISM: Homo sapiens

<400> SEQUENCE: 710
cgcaattgaa gtaccacctc ccgagggtga ttgcttcccc atgcggggta gaacctttgc 60

<210> SEQ ID NO 711
<211> LENGTH: 194
<212> TYPE: DNA
<213> ORGANISM: Homo sapiens

<400> SEQUENCE: 711
ccagtggtct atacctccag cagcaagtcg agtgagcaag tgatgtcctg aaaggcccag 60
tggatcagtg gaatgaagcg ggcaggaaga cttagtgctc ctgaaacaag gaatccagaa 120
tccaggagaa ggatggctca gtggggcttt caagggacaa gtatgggggt tgaaggggtc 180
actgtcccta tacc 194

<210> SEQ ID NO 712
<211> LENGTH: 109
<212> TYPE: DNA
<213> ORGANISM: Homo sapiens

<400> SEQUENCE: 712
ggcaaagcaa agctatattc aagaccacat gcaaagctac tccctgagca aagagtcaca 60
gataaaacgg gggcaccagt agaatggcca ggacaaacgc agtgcagca 109

<210> SEQ ID NO 713
<211> LENGTH: 32
<212> TYPE: DNA
<213> ORGANISM: Homo sapiens

<400> SEQUENCE: 713
gatgagagtg acatgtactg ttgtggacat gc 32

<210> SEQ ID NO 714
<211> LENGTH: 25
<212> TYPE: DNA
<213> ORGANISM: Homo sapiens

<400> SEQUENCE: 714
tgccccgggg gtcctggaag ccaca 25

<210> SEQ ID NO 715
<211> LENGTH: 108
<212> TYPE: DNA
<213> ORGANISM: Homo sapiens

<400> SEQUENCE: 715
agaatgaagt tgtgaagctg agattcccct ccattgggac cggagaaacc aggggagccc 60
cccgggcagc cgcgcgcccc ttcccacggg gccctttact gcgccgcg 108

<210> SEQ ID NO 716
<211> LENGTH: 26
<212> TYPE: DNA
<213> ORGANISM: Homo sapiens

<400> SEQUENCE: 716
cagccggagc catggggccg gagccg 26

<210> SEQ ID NO 717
<211> LENGTH: 37
<212> TYPE: DNA
<213> ORGANISM: Homo sapiens

<400> SEQUENCE: 717
gagctggcgg ccttgtgccg ctgggggctc ctcctcg 37

<210> SEQ ID NO 718
<211> LENGTH: 141
<212> TYPE: DNA
<213> ORGANISM: Homo sapiens

<400> SEQUENCE: 718
tgtgcaccgg cacagacatg aagctgcggc tccctgccag tcccgagacc cacctggaca 60
tgctccgcca cctctaccag ggctgccagg tggtgcaggg aaacctggaa ctcacctacc 120
tgcccaccaa tgccagcctg t 141

<210> SEQ ID NO 719
<211> LENGTH: 149
<212> TYPE: DNA
<213> ORGANISM: Homo sapiens

<400> SEQUENCE: 719
ttgggagcag ttgtgaagct cagaagagaa atgtctgtga aaaggttatg aacaggaggg 60
agagtggaaa ccaacctgct ggatcgtgtc cacagaccct ggaatggggc cacatgcttg 120
gtttgtcaaa ttgcagacgc cggccgggt 149

<210> SEQ ID NO 720
<211> LENGTH: 133
<212> TYPE: DNA
<213> ORGANISM: Homo sapiens

<400> SEQUENCE: 720
cagggctacg tgctcatcgc tcacaaccaa gtgaggcagg tcccactgca gaggctgcgg 60
attgtgcgag gcacccagct ctttgaggac aactatgccc tggccgtgct agacaatgga 120
gacccgctga aca 133

<210> SEQ ID NO 721
<211> LENGTH: 32
<212> TYPE: DNA
<213> ORGANISM: Homo sapiens

<400> SEQUENCE: 721
aggggaaagg gtcctctgat cattgctcac cc 32

<210> SEQ ID NO 722
<211> LENGTH: 118
<212> TYPE: DNA
<213> ORGANISM: Homo sapiens

<400> SEQUENCE: 722
ggtcttgatc cagcggaacc cccagctctg ctaccaggac acgattttgt ggaaggacat 60
cttccacaag aacaaccagc tggctctcac actgatagac accaaccgct ctcgggcc 118

<210> SEQ ID NO 723
<211> LENGTH: 52
<212> TYPE: DNA
<213> ORGANISM: Homo sapiens

<400> SEQUENCE: 723
gccactgccc actgactgct gccatgagca gtgtgctgcc ggctgcacgg gc 52

<210> SEQ ID NO 724
<211> LENGTH: 74
<212> TYPE: DNA
<213> ORGANISM: Homo sapiens

<400> SEQUENCE: 724
tggtcaccta caacacagac acgtttgagt ccatgcccaa tcccgagggc cggtatacat 60
tcggcgccag ctgt 74

<210> SEQ ID NO 725
<211> LENGTH: 107
<212> TYPE: DNA
<213> ORGANISM: Homo sapiens

<400> SEQUENCE: 725
acctttctac ggacgtggga tcctgcaccc tcgtctgccc cctgcacaac caagaggtga 60
cagcagagga tggaacacag cggtgtgaga agtgcagcaa gccctgt 107

<210> SEQ ID NO 726
<211> LENGTH: 58
<212> TYPE: DNA
<213> ORGANISM: Homo sapiens

<400> SEQUENCE: 726
tgcagttcct gtccctctgc gcatgcagcc tggcccagcc caccctgtcc tatccttc 58

<210> SEQ ID NO 727
<211> LENGTH: 63
<212> TYPE: DNA
<213> ORGANISM: Homo sapiens

<400> SEQUENCE: 727
tacaagtgtc cctatatccc ctgtcagtgt ggggaggggc ccggaccctg atgctcatgt 60
ggc 63

<210> SEQ ID NO 728
<211> LENGTH: 82
<212> TYPE: DNA
<213> ORGANISM: Homo sapiens

<400> SEQUENCE: 728
ggcatggagc acttgcgaga ggtgagggca gttaccagtg ccaatatcca ggagtttgct 60
ggctgcaaga agatctttgg ga 82

<210> SEQ ID NO 729
<211> LENGTH: 57
<212> TYPE: DNA
<213> ORGANISM: Homo sapiens

<400> SEQUENCE: 729
aacactgccc cgctccagcc agagcagctc caagtgtttg agactctgga agagatc 57

<210> SEQ ID NO 730

<211> LENGTH: 155
<212> TYPE: DNA
<213> ORGANISM: Homo sapiens

<400> SEQUENCE: 730
ggcgcctact cgctgaccct gcaagggctg ggcatcagct ggctggggct gcgctcactg 60
agggaactgg gcagtggact ggccctcatc caccataaca cccacctctg cttcgtgcac 120
acggtgccct gggaccagct ctttcggaac ccgca 155

<210> SEQ ID NO 731
<211> LENGTH: 246
<212> TYPE: DNA
<213> ORGANISM: Homo sapiens

<400> SEQUENCE: 731
agcagcgttc ttggacttgt gcagactgcc cgtctctgtg caccccttctt gactcagcac 60 agctctggct ggcttggcct cttggcatgg cttctctagc tgggtcctac ctgccttggc 120
atccttccct ccccctctgt ttctgaaatc tcagaactct tcctctccct acatcggccc 180
cacctgtccc cacccctcca gcccacagcc atgcccacag ccagttccct ggttcacttg 240
gacctg 246

<210> SEQ ID NO 732
<211> LENGTH: 104
<212> TYPE: DNA
<213> ORGANISM: Homo sapiens

<400> SEQUENCE: 732
gccaccagct gtgcgcccga gggcactgct ggggtccagg gcccacccag tgtgtcaact 60
gcagccagtt ccttcggggc caggagtgcg tggaggaatg ccga 104

<210> SEQ ID NO 733
<211> LENGTH: 47
<212> TYPE: DNA
<213> ORGANISM: Homo sapiens

<400> SEQUENCE: 733
tggctggagg ggtgcatggg gctcctctca gaccccctca ccactgt 47

<210> SEQ ID NO 734
<211> LENGTH: 32
<212> TYPE: DNA
<213> ORGANISM: Homo sapiens

<400> SEQUENCE: 734
gctccccagg gagtatgtga atgccaggca ct 32

<210> SEQ ID NO 735
<211> LENGTH: 223
<212> TYPE: DNA
<213> ORGANISM: Homo sapiens

<400> SEQUENCE: 735
actcgctgtt acaccttagg taatgcgttt tcctctctgg gtgcctccca ttttctggct 60
caagtccctg cccaggatca agcttggagg agggccccga gggaggggcc acagagactg 120
ggtgaagagc aagggtgttt gtcccaggag catggcgaaa attgctgctg ggtggccttg 180
ggaagcacaa aggggaccca actaagggcc tgatcctact gcc 223

<210> SEQ ID NO 736
<211> LENGTH: 119
<212> TYPE: DNA
<213> ORGANISM: Homo sapiens

<400> SEQUENCE: 736
gtggcctgtg cccactataa ggaccctccc ttctgcgtgg cccgctgccc cagcggtgtg 60
aaacctgacc tctcctacat gcccatctgg aagtttccag atgaggaggg cgcatgcca 119

<210> SEQ ID NO 737
<211> LENGTH: 75
<212> TYPE: DNA
<213> ORGANISM: Homo sapiens

<400> SEQUENCE: 737
gtgagtccaa cggtcttttc tgcagaaagg aggactttcc tttcaggggt ctttctgggg 60
ctcttactat aaaag 75

<210> SEQ ID NO 738
<211> LENGTH: 25
<212> TYPE: DNA
<213> ORGANISM: Homo sapiens

<400> SEQUENCE: 738
gggctgcccc gccgagcaga gagcc 25

<210> SEQ ID NO 739
<211> LENGTH: 164
<212> TYPE: DNA
<213> ORGANISM: Homo sapiens

<400> SEQUENCE: 739
ttccactgtg gaacctcctg tcattttcca cttcaccaag tgacagagga cctgctcaga 60
tgctgagggg aggggactgc aaggaaagat ggctaggaaa cccagtccct ccacacccta 120
gagtaacttg atgccttgtg agggacacag gcaaagttca attc 164

<210> SEQ ID NO 740
<211> LENGTH: 73
<212> TYPE: DNA
<213> ORGANISM: Homo sapiens

<400> SEQUENCE: 740
gtggtctttg ggatcctcat caagcgacgg cagcagaaga tccggaagta cacgatgcgg 60
agactgctgc agg 73

<210> SEQ ID NO 741
<211> LENGTH: 81
<212> TYPE: DNA
<213> ORGANISM: Homo sapiens

<400> SEQUENCE: 741
agcgatgccc aaccaggcgc agatgcggat cctgaaagag acggagctga ggaaggtgaa 60
ggtgcttgga tctggcgctt t 81

<210> SEQ ID NO 742
<211> LENGTH: 96
<212> TYPE: DNA
<213> ORGANISM: Homo sapiens

<400> SEQUENCE: 742
gcatctggat ccctgatggg gagaatgtga aaattccagt ggccatcaaa gtgttgaggg 60
aaaacacatc ccccaaagcc aacaaagaaa tcttag 96

<210> SEQ ID NO 743
<211> LENGTH: 135
<212> TYPE: DNA
<213> ORGANISM: Homo sapiens

<400> SEQUENCE: 743
tgggcatctg cctgacatcc acggtgcagc tggtgacaca gcttatgccc tatggctgcc 60
tcttagacca tgtccgggaa aaccgcggac gcctgggctc ccaggacctg ctgaactggt 120
gtatgcagat tgcca 135

<210> SEQ ID NO 744
<211> LENGTH: 118
<212> TYPE: DNA
<213> ORGANISM: Homo sapiens

<400> SEQUENCE: 744
atgtgcggct cgtacacagg gacttggccg ctcggaacgt gctggtcaag agtcccaacc 60
atgtcaaaat tacagacttc gggctggctc ggctgctgga cattgacgag acagagta 118

<210> SEQ ID NO 745
<211> LENGTH: 37
<212> TYPE: DNA
<213> ORGANISM: Homo sapiens

<400> SEQUENCE: 745
ctgggtggag tggtgtctag cccatgggag aactctg 37

<210> SEQ ID NO 746
<211> LENGTH: 41
<212> TYPE: DNA
<213> ORGANISM: Homo sapiens

<400> SEQUENCE: 746
ctggagtcca ttctccgccg gcggttcacc caccagagtg a 41

<210> SEQ ID NO 747
<211> LENGTH: 75
<212> TYPE: DNA
<213> ORGANISM: Homo sapiens

<400> SEQUENCE: 747
actgtgtggg agctgatgac ttttggggcc aaaccttacg atgggatccc agcccgggag 60
atccctgacc tgctg 75

<210> SEQ ID NO 748
<211> LENGTH: 31
<212> TYPE: DNA
<213> ORGANISM: Homo sapiens

<400> SEQUENCE: 748
gtgcgtggct gagctgtgct ggctgcctgg a 31

<210> SEQ ID NO 749
<211> LENGTH: 39
<212> TYPE: DNA
<213> ORGANISM: Homo sapiens

<400> SEQUENCE: 749
gttggatgat tgactctgaa tgtcggccaa gattccggg 39

<210> SEQ ID NO 750
<211> LENGTH: 51
<212> TYPE: DNA
<213> ORGANISM: Homo sapiens

<400> SEQUENCE: 750
gttggtgtct gaattctccc gcatggccag ggacccccag cgctttgtgg t 51

<210> SEQ ID NO 751
<211> LENGTH: 44
<212> TYPE: DNA
<213> ORGANISM: Homo sapiens

<400> SEQUENCE: 751
tctaccgctc actgctggag gacgatgaca tgggggacct ggtg 44

<210> SEQ ID NO 752
<211> LENGTH: 228
<212> TYPE: DNA
<213> ORGANISM: Homo sapiens

<400> SEQUENCE: 752
gtggggacct gacactaggg ctggagccct ctgaagagga ggcccccagg tctccactgg 60
caccctccga aggggctggc tccgatgtat ttgatggtga cctgggaatg gggcagcca 120 aggggctgca aagcctcccc acacatgacc ccagccctct acagcggtac agtgaggacc 180
ccacagtacc cctgccctct gagactgatg gctacgttgc ccccctga 228

<210> SEQ ID NO 753
<211> LENGTH: 32
<212> TYPE: DNA
<213> ORGANISM: Homo sapiens

<400> SEQUENCE: 753
atgtgaacca gccagatgtt cggccccagc cc 32

<210> SEQ ID NO 754
<211> LENGTH: 122
<212> TYPE: DNA
<213> ORGANISM: Homo sapiens

<400> SEQUENCE: 754
agccttcgac aacctctatt actgggacca ggacccacca gagcgggggg ctccacccag 60
caccttcaaa gggacaccta cggcagagaa cccagagtac ctgggtctgg acgtgccagt 120
gt 122

<210> SEQ ID NO 755
<211> LENGTH: 25
<212> TYPE: DNA
<213> ORGANISM: Homo sapiens

<400> SEQUENCE: 755
agaaggccaa gtccgcagaa gccct 25

<210> SEQ ID NO 756
<211> LENGTH: 39
<212> TYPE: DNA
<213> ORGANISM: Homo sapiens

<400> SEQUENCE: 756
cgaccacttc caggggaacc tgccatgcca ggaacctgt 39

<210> SEQ ID NO 757
<211> LENGTH: 107
<212> TYPE: DNA
<213> ORGANISM: Homo sapiens

<400> SEQUENCE: 757
cttcctgctt gagttcccag atggctggaa ggggtccagc ctcgttggaa gaggaacagc 60
actggggagt ctttgtggat tctgaggccc tgcccaatga gactcta 107

<210> SEQ ID NO 758
<211> LENGTH: 110
<212> TYPE: DNA
<213> ORGANISM: Homo sapiens

<400> SEQUENCE: 758
ggtactgaaa gccttaggga agctggcctg agaggggaag cggccctaag ggagtgtcta 60
agaacaaaag cgacccattc agagactgtc cctgaaacct agtactgccc 110

<210> SEQ ID NO 759
<211> LENGTH: 31
<212> TYPE: DNA
<213> ORGANISM: Homo sapiens

<400> SEQUENCE: 759
agtatccagg ctttgtacag agtgcttttc t 31

<210> SEQ ID NO 760
<211> LENGTH: 32
<212> TYPE: DNA
<213> ORGANISM: Homo sapiens

<400> SEQUENCE: 760
cctccctgaa gacgtggtcc cagccgggtg tc 32

<210> SEQ ID NO 761
<211> LENGTH: 57
<212> TYPE: DNA
<213> ORGANISM: Homo sapiens

<400> SEQUENCE: 761
ggagagggat cctctaaatt gtcgaggctt catctctcca gattgtatgc ccttctc 57

<210> SEQ ID NO 762
<211> LENGTH: 25
<212> TYPE: DNA
<213> ORGANISM: Homo sapiens

<400> SEQUENCE: 762
ctggttccgt taagcccctc tcttg 25

<210> SEQ ID NO 763
<211> LENGTH: 84
<212> TYPE: DNA
<213> ORGANISM: Homo sapiens

<400> SEQUENCE: 763
atcttagcag ctctccggaa gacctttgcc cagcccctgg gacccctcct gggactcccc 60
ggccccctga tacccctctg cctg 84

<210> SEQ ID NO 764
<211> LENGTH: 26
<212> TYPE: DNA
<213> ORGANISM: Homo sapiens

<400> SEQUENCE: 764
gtaaagaggt cccagcctct cctcat 26

<210> SEQ ID NO 765
<211> LENGTH: 38
<212> TYPE: DNA
<213> ORGANISM: Homo sapiens

<400> SEQUENCE: 765
gaaacttcga gaggaggaga ggcgtgccac ctccctcc 38

<210> SEQ ID NO 766
<211> LENGTH: 57
<212> TYPE: DNA
<213> ORGANISM: Homo sapiens

<400> SEQUENCE: 766
tctcgggggc ccctccagtg caagggggct gctcccccgc gatgccagcc gcccccca 57

<210> SEQ ID NO 767
<211> LENGTH: 89
<212> TYPE: DNA
<213> ORGANISM: Homo sapiens

<400> SEQUENCE: 767
tgggagatac acagccgctt ccatggaggc aggggatctt ggttaggagt ccctgagggt 60
ctagcaggtg cggaaaggga atgaatcac 89

<210> SEQ ID NO 768
<211> LENGTH: 65
<212> TYPE: DNA
<213> ORGANISM: Homo sapiens

<400> SEQUENCE: 768
gccacagctc gccacgtgtg tgaaatgctg gtgcagcgag ctcacgcctt gagcgacgag 60
acctg 65

<210> SEQ ID NO 769
<211> LENGTH: 105
<212> TYPE: DNA
<213> ORGANISM: Homo sapiens

<400> SEQUENCE: 769
accacgagtc cgtggtggaa gtgcaggctg cctggcccgt gggcggagat agccgcttcg 60
tcttccggaa aaacttcgcc aagtacgaac tgttcaagag ctccc 105

<210> SEQ ID NO 770
<211> LENGTH: 73
<212> TYPE: DNA
<213> ORGANISM: Homo sapiens

<400> SEQUENCE: 770
tctgggcgct gggatgccct gatcctcaac ctggatgctg gagccctgat ccctgacact 60
tgtctaccca cag 73

<210> SEQ ID NO 771
<211> LENGTH: 43
<212> TYPE: DNA
<213> ORGANISM: Homo sapiens

<400> SEQUENCE: 771
tccagctgtc tcgatgcaca cactggtata tcccatgaag acc 43

<210> SEQ ID NO 772
<211> LENGTH: 79
<212> TYPE: DNA
<213> ORGANISM: Homo sapiens

<400> SEQUENCE: 772
tcaggacgga agctttggaa acgctttttc tgcttcttgc gccgatctgg cctctattac 60
tccaccaagg gcacctcta 79

<210> SEQ ID NO 773
<211> LENGTH: 132
<212> TYPE: DNA
<213> ORGANISM: Homo sapiens

<400> SEQUENCE: 773
cagtccctgg tccttttaga agttgcccct tctctgctgg aacctctgag cccttctccc 60
cctgggcccc ccaggccagc cacctccagt ttaccatctc tccctacatc cttgcctagc 120
tcacctgccc ag 132

<210> SEQ ID NO 774
<211> LENGTH: 107
<212> TYPE: DNA
<213> ORGANISM: Homo sapiens

<400> SEQUENCE: 774
atccgaggca cctgcagtac gtggcagatg tgaacgagtc caacgtgtac gtggtgacgc 60
agggccgcaa gctctacggg atgcccactg acttcggttt ctgtgtc 107

<210> SEQ ID NO 775
<211> LENGTH: 76
<212> TYPE: DNA
<213> ORGANISM: Homo sapiens

<400> SEQUENCE: 775
caacaagctt cgaaatggcc acaaggggct tcggatcttc tgcagtgaag atgagcagag 60
ccgcacctgc tggctg 76

<210> SEQ ID NO 776
<211> LENGTH: 77
<212> TYPE: DNA
<213> ORGANISM: Homo sapiens

<400> SEQUENCE: 776
tacggggtgc agctgtacaa gaattaccag caggcacagt ctcgccatct gcatccatct 60
tgtttgggct ccccacc 77

<210> SEQ ID NO 777
<211> LENGTH: 83
<212> TYPE: DNA
<213> ORGANISM: Homo sapiens

<400> SEQUENCE: 777
agaagtgcct cagataatac cctggtggcc atggacttct ctggccatgc tgggcgtgtc 60
attgagaacc cccgggaggc tct 83

<210> SEQ ID NO 778
<211> LENGTH: 78
<212> TYPE: DNA
<213> ORGANISM: Homo sapiens

<400> SEQUENCE: 778
ccatccaccg cacccaactc tggttccacg ggcgcatttc ccgtgaggag agccagcggc 60
ttattggaca gcagggct 78

<210> SEQ ID NO 779
<211> LENGTH: 72
<212> TYPE: DNA
<213> ORGANISM: Homo sapiens

<400> SEQUENCE: 779
ctgttcctgg tccgggagag tcagcggaac ccccagggct ttgtcctctc tttgtgccac 60
ctgcagaaag tg 72

<210> SEQ ID NO 780
<211> LENGTH: 128
<212> TYPE: DNA
<213> ORGANISM: Homo sapiens

<400> SEQUENCE: 780
aggagggccg cctgtacttc agcatggatg atggccagac ccgcttcact gacctgctgc 60
agctcgtgga gttccaccag ctgaaccgcg gcatcctgcc gtgcttgctg cgccattgct 120
gcacgcgg 128

<210> SEQ ID NO 781
<211> LENGTH: 297
<212> TYPE: DNA
<213> ORGANISM: Homo sapiens

<400> SEQUENCE: 781
cccatccagt ggactctggg gcgcggccac aggggacggg atgaggagcg ggagggttcc 60
gccactccag ttttctcctc tgcttctttg cctccctcag atagaaaaca gcccccactc 120
cagtccactc ctgacccctc tcctcaaggg aaggccttgg gtggccccct ctccttctcc 180
tagctctgga ggtgctgctc tagggcaggg aattatggga gaagtggggg cagcccaggc 240
ggtttcacgc cccacacttt gtacagaccg agaggccagt tgatctgctc tgtttta 297

<210> SEQ ID NO 782
<211> LENGTH: 137
<212> TYPE: DNA
<213> ORGANISM: Homo sapiens

<400> SEQUENCE: 782
tggcctcaca gcgactctaa gacttggggc tctctcattg gctgtaactc ttccactgga 60
ttggtagcaa aaaaagaggc ggtgcccaag gcgaaaggct ctgtgactac agccaatcag 120
aatcgaggcc gggcttt 137

<210> SEQ ID NO 783
<211> LENGTH: 100
<212> TYPE: DNA

<213> ORGANISM: Homo sapiens

<400> SEQUENCE: 783
ctgtctcggg cattgaacaa agctaaaaac tccagtgatg ccaaactaga accaacaaat 60
gtccaaaccg taacctgttc tcctcgtgta aaagccctgc 100

<210> SEQ ID NO 784
<211> LENGTH: 276
<212> TYPE: DNA
<213> ORGANISM: Homo sapiens

<400> SEQUENCE: 784
gcgatgacaa cctatgcaac actccccatt tacctccttg ttctccacca aagcaaggca 60
agaaagagaa tggtccccct cactcacata cacttaaggg acgaagattg gtatttgaca 120
atcagctgac aattaagtct cctagcaaaa gagaactagc caaagttcac caaaacaaaa 180
tactttcttc agttagaaaa agtcaagaga tcacaacaaa ttctgagcag agatgtccac 240
tgaagaaaga atctgcatgt gtgagactat tcaagc 276

<210> SEQ ID NO 785
<211> LENGTH: 178
<212> TYPE: DNA
<213> ORGANISM: Homo sapiens

<400> SEQUENCE: 785
tgctaccagc aagcaaagct ggtcctgaac acagctgtcc cagatcggct gcctgccagg 60
gaaagggaga tggatgtcat caggaatttc ttgagggaac acatctgtgg gaaaaaagct 120
ggaagccttt acctttctgg tgctcctgga actggaaaaa ctgcctgctt aagccgga 178

<210> SEQ ID NO 786
<211> LENGTH: 101
<212> TYPE: DNA
<213> ORGANISM: Homo sapiens

<400> SEQUENCE: 786
tttaaaacta tcatgctgaa ttgcatgtcc ttgaggactg cccaggctgt attcccagct 60
attgctcagg agatttgtca ggaagaggta tccaggccag c 101

<210> SEQ ID NO 787
<211> LENGTH: 61
<212> TYPE: DNA
<213> ORGANISM: Homo sapiens

<400> SEQUENCE: 787
gacagcaaag gccaggatgt attgtacacg ctatttgaat ggccatggct aagcaattct 60
c 61

<210> SEQ ID NO 788
<211> LENGTH: 135
<212> TYPE: DNA
<213> ORGANISM: Homo sapiens

<400> SEQUENCE: 788
gtattgctaa taccctggat ctcacagata gaattctacc taggcttcaa gctagagaaa 60
aatgtaagcc acagctgttg aacttcccac cttataccag aaatcagata gtcactattt 120
tgcaagatcg actta 135

<210> SEQ ID NO 789
<211> LENGTH: 63
<212> TYPE: DNA
<213> ORGANISM: Homo sapiens

<400> SEQUENCE: 789
gtatctagag atcaggttct ggacaatgct gcagttcaat tctgtgcccg caaagtctct 60
gct 63

<210> SEQ ID NO 790
<211> LENGTH: 30
<212> TYPE: DNA
<213> ORGANISM: Homo sapiens

<400> SEQUENCE: 790
gagatgttcg caaagcactg gatgtttgca 30

<210> SEQ ID NO 791
<211> LENGTH: 26
<212> TYPE: DNA
<213> ORGANISM: Homo sapiens

<400> SEQUENCE: 791
gtgagttacg gctctgttgc attctt 26

<210> SEQ ID NO 792
<211> LENGTH: 27
<212> TYPE: DNA
<213> ORGANISM: Homo sapiens

<400> SEQUENCE: 792
agatgtcaaa agccagacta ttctcaa 27

<210> SEQ ID NO 793
<211> LENGTH: 32
<212> TYPE: DNA
<213> ORGANISM: Homo sapiens

<400> SEQUENCE: 793
gtaaatcacc ttctgagcct ctgattccca ag 32

<210> SEQ ID NO 794
<211> LENGTH: 146
<212> TYPE: DNA
<213> ORGANISM: Homo sapiens

<400> SEQUENCE: 794
tatcccaagt catctcagaa gttgatggta acaggatgac cttgagccaa gaaggagcac 60
aagattcctt ccctcttcag cagaagatct tggtttgctc tttgatgctc ttgatcaggc 120
agttgaaaat caaagaggtc actctg 146

<210> SEQ ID NO 795
<211> LENGTH: 103
<212> TYPE: DNA
<213> ORGANISM: Homo sapiens

<400> SEQUENCE: 795
tacagtaaag tctgtcgcaa acagcaggtg gcggctgtgg accagtcaga gtgtttgtca 60
ctttcagggc tcttggaagc caggggcatt ttaggattaa aga 103

<210> SEQ ID NO 796

<211> LENGTH: 25
<212> TYPE: DNA
<213> ORGANISM: Homo sapiens

<400> SEQUENCE: 796
gaaatagaac atgctctgaa agata 25

<210> SEQ ID NO 797
<211> LENGTH: 1015
<212> TYPE: DNA
<213> ORGANISM: Homo sapiens

<400> SEQUENCE: 797
cccgaaagta ttcagctggc atttagagag ctacagtctt cattttagtg ctttacacat 60
tcgggcctga aaacaaatat gaccttttt acttgaagcc aatgaatttt aatctataga 120
ttctttaata ttagcacaga ataatatctt tgggtcttac tatttttacc cataaaagtg 180
accaggtaga cccttttaa ttacattcac tacttctacc acttgtgtat ctctagccaa 240
tgtgcttgca agtgtacaga tctgtgtaga ggaatgtgtg tatatttacc tcttcgtttg 300
ctcaaacatg agtgggtatt tttttgtttg ttttttttgt tgttgttgtt tttgaggcgc 360
gtctcaccct gttgcccagg ctggagtgca atggcgcgtt ctctgctcac tacagcaccc 420
gcttcccagg ttgaagtgat tctcttgcct cagcctcccg agtagctggg attacaggtg 480
cccaccaccg cgcccagcta atttttttaat ttttagtaga gacagggttt taccatgttg 540
gccaggctgg tcttgaactc ctgaccctca agtgatctgc ccaccttggc ctccctaagt 600
gctgggatta taggcgtgag ccaccatgct cagccattaa ggtattttgt taagaacttt 660
aagtttaggg taagaagaat gaaaatgatc cagaaaaatg caagcaagtc cacatggaga 720
tttggaggac actggttaaa gaatttattt ctttgtatag tatactatgt tcatggtgca 780
gatactacaa cattgtggca ttttagactc gttgagtttc ttgggcactc ccaagggcgt 840
tggggtcata aggagactat aactctacag attgtgaata tatttatttt caagttgcat 900
tctttgtctt tttaagcaat cagatttcaa gagagctcaa gctttcagaa gtcaatgtga 960
aaattccttc ctaggctgtc ccacagtctt tgctgccctt agatgaagcc acttg 1015

<210> SEQ ID NO 798
<211> LENGTH: 174
<212> TYPE: DNA
<213> ORGANISM: Homo sapiens

<400> SEQUENCE: 798
gccggcctca ggaacgcgcc ctcttcgccg gcgcgcgccc tcgcagtcac cgccacccac 60
cagctccggc accaacagca gcgccgctgc caccgcccac cttctgccgc cgccaccaca 120
gccaccttct cctcctccgc tgtcctctcc cgtcctcgcc tctgtcgact atca 174

<210> SEQ ID NO 799
<211> LENGTH: 1072
<212> TYPE: DNA
<213> ORGANISM: Homo sapiens

<400> SEQUENCE: 799
taaggttact ggtgcttcgg ccacacccat ctttctgagc ccactggact gggcgcagag 60
gggggattgc catggaaacc acaggtgtcc ggagagggga tcttggggct ggcctcaccc 120
cttccctgcg gagattgggg accctggggt agggggagcc gcgcccagtc ggcctcctgg 180
aggacacggg aggaagcccc gaacccccgc gcctgaggct gtttctgatt ggcccctgga 240
ggccgcagac acgcagatag gcggccctgg gtgtattttt attaatatta tgtccgtact 300
gattaatatt atttatctta aataaatttc acccgtgtcc aagttcaccg cgcccccaaa 360
accgagtctg gggcggcagg gggaactcct ggccaacgaa tccatgcctc gccctcctgt 420
gatgaacctg gtacgcacgg ttttctggtt aattctatcg ctgaaaactg gtgcgggggg 480
cgcacttctg agacggaaga gcatctagga gctgaatcct ccacgcgggt cgcccaggtt 540
gatctgaatt tctggggaat ggcttggctg cccgcccggg accaggccga ccctccttga 600
cggtggcgta gagggctgga gcctgggtac tgcgaggctc ctcgcatggc tgggcccgcc 660
gcgaggggtt gcagagcggc tcagggatcg attcaagcat cgtctctcct ccctcgcccc 720
cagacagagc tgggcgcggg gttccccttc cagatggagc gagggtctcg gggtggcccc 780
ggaaaagggg agcccgcggc cacggctacg tattgccatc tcgcgagcag agatgtcacc 840
tcctgccttt ggaggaaagg gagcccggtg gggatgagcg catttagccc aatgctggga 900
acaaagcgca ctccgcgctt ctgcgatttc gctccatttt gaaatgtgtt ggcgctttgg 960
tggggccgct gcggtgggca aggccggggg cgctgttaat ggaggaacct caggggggacg 1020 gtccttcgta ggaaactcta tcctggctct gcgcgcgctt taaggaaatg gc 1072

<210> SEQ ID NO 800
<211> LENGTH: 142
<212> TYPE: DNA
<213> ORGANISM: Homo sapiens

<400> SEQUENCE: 800
acctcgaggg atgcagcttt tgcgcggatg acggtggggt gctgaaccag ccggtgcgcc 60
tctggaaatg tctgggcacg gatcctgggg ccatcgacga ctcctcccca ttcccagcag 120
gcgggagctc ttacattccg ag 142

<210> SEQ ID NO 801
<211> LENGTH: 822
<212> TYPE: DNA
<213> ORGANISM: Homo sapiens

<400> SEQUENCE: 801
gaaatgtctt tcctaccgcg gttgattctg gggtgtcatt ttgtgttttg tgatggctgc 60
ttatatttac tgtataagca ttgtatttac tgtataagca ttgtattata attactgtat 120
aagctgctta tatttactgt ataagcatct ccaaatcctc cctctacgta aacaaattaa 180
tggataaaca gataagtgta tcccctgccc ccacccctgc tacgcaggtc cggagtgact 240
cttgaagctc atacattcct tggccaagtt tgcttctcta acagatgttt atatagcaat 300
aacctggctt ggctcttggg ttcacctttg gacgatttgg ggaaggggct tgttggcttt 360
gctgggtttt ggatgagtga cagtccatga ctgttcctgc tggaagggcg tgacttttaa 420
gtggtttcta atatcaggca ttgctcctcc gacaggaaca aaagaaatgg atactgccca 480
taaattgtta gaaaacttag aatcgctttg attgaggaaa ggttagattt attccggttg 540
gaaaaagtgg cctttctatt aaacgtgccc tttgaccctc atgcccttgg aggtcggtgc 600
cagcctggag atgggataag attgtggttt tccttctgcc tttttaacat ctgttgttac 660
agtccatttg ttgaaaattt aaagaaactg ttttattcca ctttccctca gcatttatgt 720
gtgtggtttc agtagctctg tggctatatg tacgaacacg tgttattttt ccaattggac 780
atgtgataat tttccaactg gaccttgcct tctattgatg ta 822

<210> SEQ ID NO 802
<211> LENGTH: 95
<212> TYPE: DNA
<213> ORGANISM: Homo sapiens

<400> SEQUENCE: 802
cccgccagga gttcgaagtg atggaagatc acgctgggac gtacgggttg gggacagga 60 aagatcaggg gggctacacc atgcaccaag accaa 95

<210> SEQ ID NO 803
<211> LENGTH: 82
<212> TYPE: DNA
<213> ORGANISM: Homo sapiens

<400> SEQUENCE: 803
tgtgacagca cccttagtgg atgagggagc tcccggcaag caggctgccg cgcagcccca 60
cacggagatc ccagaaggaa cc 82

<210> SEQ ID NO 804
<211> LENGTH: 364
<212> TYPE: DNA
<213> ORGANISM: Homo sapiens

<400> SEQUENCE: 804
gccagtccca tgtgacagtc aaagcttcta actccattca aagttgcagc cattcccctc 60
gagggctggc agggagggga ggggtaagag aaacaggaag gttcttactg agttggtcct 120
ggtgtgagct gcgtcacact ccctgcagag gtttcaagga gactctctct ctctctgtct 180
ccatggggac cttatttgaa ttcttctact cttaccccag cctgccatct ccagctatcc 240
tcccctgaag agcccttctg ctgcgctgga ttctggtggc catgtcatct cctcggcccc 300
gtgggagtct gaagatctgg ctgcagcctc acctctgagg tcctgctagt tgccacctct 360
taaa 364

<210> SEQ ID NO 805
<211> LENGTH: 37
<212> TYPE: DNA
<213> ORGANISM: Homo sapiens

<400> SEQUENCE: 805
agcctggaag acgaagctgc tggtcacgtg acccaag 37

<210> SEQ ID NO 806
<211> LENGTH: 143
<212> TYPE: DNA
<213> ORGANISM: Homo sapiens

<400> SEQUENCE: 806
ctggaattgc ctgccatgac ttgggggttg gggggaggga catggggtgg gctctgccct 60
gaaaagatca tttggacctg agctctaatt cacaagtcca ggagatttta gggagttggt 120
tcttatcaaa ggttggctac tca 143

<210> SEQ ID NO 807
<211> LENGTH: 513
<212> TYPE: DNA
<213> ORGANISM: Homo sapiens

<400> SEQUENCE: 807
gcgattctca ctgcaggctg ccctgtggct gatccaggag caaggcctta accatgtcat 60
ccccaagcga ttgcttgtaa actttcttct gtgcagcctt caacccttat tatgattttc 120
ttctcaggaa ccaaactgct gtattcaaga aaggcagctt tgtgtaatca tttatcataa 180
atatcttaag aaaaatccta gagattccta attttaggaa atgggagacc tatggtactg 240
atataatgtg ggctgggctt gttttctgtc atttgctaga taaatgaact tgagagccta 300
ctgtaaaatg tggaagcttc tagattgcag aagggctgga aagacactgt tcttttctcc 360
cgagtgatgg gatctgtcca gtatttagag ctgcctctga ggccatctga ttctaggaga 420
ctctgcctcg ttgaggatat tttgaggcct aactacacat tcctgccccc agagaggtca 480
cagcctatag caggctgatg tttctcatgt cac 513

<210> SEQ ID NO 808
<211> LENGTH: 109
<212> TYPE: DNA
<213> ORGANISM: Homo sapiens

<400> SEQUENCE: 808
taagctatgg gaaggcctgt atacgagggg tggacttttc ttctgtaagt gtccagagac 60
caggcctcct gaagagggca tgggggctta acttacctgg actactgtg 109

<210> SEQ ID NO 809
<211> LENGTH: 255
<212> TYPE: DNA
<213> ORGANISM: Homo sapiens

<400> SEQUENCE: 809
gccaatgaga ttagcgccca cgtccagcct ggaccctgcg gagaggcctc tggggtctct 60
gggccgtgcc tcggggagaa agagccagaa gctcccgtcc cgctgaccgc gagccttcct 120
cagcaccgtc ccgtttgccc agcgcctcct ccaacaggag gccctcagga gccctccctg 180
gagtggggac aaaaaggcgg ggactgggcc gagaagggtc cggcctttcc gaagcccgcc 240
accactgcgt atctc 255

<210> SEQ ID NO 810
<211> LENGTH: 146
<212> TYPE: DNA
<213> ORGANISM: Homo sapiens

<400> SEQUENCE: 810
ctcatgtccg gcatgcctgg ggctcccctc ctgcctgagg gccccagaga ggccacacgc 60
caaccttcgg ggacaggacc tgaggacaca gagggcggcc gccacgcccc tgagctgctc 120
aagcaccagc ttctaggaga cctgca 146

<210> SEQ ID NO 811
<211> LENGTH: 107
<212> TYPE: DNA
<213> ORGANISM: Homo sapiens

<400> SEQUENCE: 811
atgaagaccg cgacgtcgat gagtcctccc cccaagactc ccctccctcc aaggcctccc 60
cagcccaaga tgggcggcct ccccagacag ccgccagaga agccacc 107

<210> SEQ ID NO 812
<211> LENGTH: 31
<212> TYPE: DNA
<213> ORGANISM: Homo sapiens

<400> SEQUENCE: 812
acgggactgg aagcgatgac aaaaaagcca a 31

<210> SEQ ID NO 813
<211> LENGTH: 32
<212> TYPE: DNA
<213> ORGANISM: Homo sapiens

<400> SEQUENCE: 813
acatccacac gttcctctgc taaaaccttg aa 32

<210> SEQ ID NO 814
<211> LENGTH: 27
<212> TYPE: DNA
<213> ORGANISM: Homo sapiens

<400> SEQUENCE: 814
ctcagaccct ctgatccaac cctccag 27

<210> SEQ ID NO 815
<211> LENGTH: 26
<212> TYPE: DNA
<213> ORGANISM: Homo sapiens

<400> SEQUENCE: 815
tcttctgtca cttcccgaac tggcag 26

<210> SEQ ID NO 816
<211> LENGTH: 35
<212> TYPE: DNA
<213> ORGANISM: Homo sapiens

<400> SEQUENCE: 816
gggctgatgg taaaacgaag atcgccacac cgcgg 35

<210> SEQ ID NO 817
<211> LENGTH: 59
<212> TYPE: DNA
<213> ORGANISM: Homo sapiens

<400> SEQUENCE: 817
ccaggccaac gccaccagga ttccagcaaa aaccccgccc gctccaaaga caccaccca 59

<210> SEQ ID NO 818
<211> LENGTH: 120
<212> TYPE: DNA
<213> ORGANISM: Homo sapiens

<400> SEQUENCE: 818
ccaagtcgcc gtcttccgcc aagagccgcc tgcagacagc ccccgtgccc atgccagacc 60
tgaagaatgt caagtccaag atcggctcca ctgagaacct gaagcaccag ccgggaggcg 120

<210> SEQ ID NO 819
<211> LENGTH: 71
<212> TYPE: DNA
<213> ORGANISM: Homo sapiens

<400> SEQUENCE: 819
agaagctgga tcttagcaac gtccagtcca agtgtggctc aaaggataat atcaaacacg 60
tcccgggagg c 71

<210> SEQ ID NO 820
<211> LENGTH: 69
<212> TYPE: DNA
<213> ORGANISM: Homo sapiens

<400> SEQUENCE: 820
tagtctacaa accagttgac ctgagcaagg tgacctccaa gtgtggctca ttaggcaaca 60
tccatcata 69

<210> SEQ ID NO 821
<211> LENGTH: 61
<212> TYPE: DNA
<213> ORGANISM: Homo sapiens

<400> SEQUENCE: 821
cagagtccag tcgaagattg ggtccctgga caatatcacc cacgtccctg gcggaggaaa 60
t 61

<210> SEQ ID NO 822
<211> LENGTH: 132
<212> TYPE: DNA
<213> ORGANISM: Homo sapiens

<400> SEQUENCE: 822
tcgtgtacaa gtcgccagtg gtgtctgggg acacgtctcc acggcatctc agcaatgtct 60
cctccaccgg cagcatcgac atggtagact cgccccagct cgccacgcta gctgacgagg 120
tgtctgcctc cc 132

<210> SEQ ID NO 823
<211> LENGTH: 224
<212> TYPE: DNA
<213> ORGANISM: Homo sapiens

<400> SEQUENCE: 823
ccctggggcg gtcaataatt gtggagagga gagaatgaga gagtgtggaa aaaaaaagaa 60
taatgacccg gcccccgccc tctgccccca gctgctcctc gcagttcggt taattggtta 120
atcacttaac ctgcttttgt cactcggctt tggctcggga cttcaaaatc agtgatggga 180
gtaagagcaa atttcatctt tccaaattga tgggtgggct agta 224

<210> SEQ ID NO 824
<211> LENGTH: 28
<212> TYPE: DNA
<213> ORGANISM: Homo sapiens

<400> SEQUENCE: 824
acatggccac atccaacatt tcctcagg 28

<210> SEQ ID NO 825
<211> LENGTH: 141
<212> TYPE: DNA
<213> ORGANISM: Homo sapiens

<400> SEQUENCE: 825
tgcttctggg ggatttcaag ggactggggg tgccaaccac ctctggccct gttgtggggg 60
tgtcacagag gcagtggcag caacaaagga tttgaaactt ggtgtgttcg tggagccaca 120
ggcagacgat gtcaaccttg t 141

<210> SEQ ID NO 826

<211> LENGTH: 231
<212> TYPE: DNA
<213> ORGANISM: Homo sapiens

<400> SEQUENCE: 826
cctccttgcc gctgggagag ccaaggccta tgccacctgc agcgtctgag cggccgcctg 60
tccttggtgg ccgggggtgg gggcctgctg tgggtcagtg tgccaccctc tgcagggcag 120
cctgtgggag aagggacagc gggtaaaaag agaaggcaag ctggcaggag ggtggcactt 180
cgtggatgac ctccttagaa aagactgacc ttgatgtctt gagagcgctg g 231

<210> SEQ ID NO 827
<211> LENGTH: 442
<212> TYPE: DNA
<213> ORGANISM: Homo sapiens

<400> SEQUENCE: 827
ttgcagacct gggactttag ggctaaccag ttctctttgt aaggacttgt gcctcttggg 60
agacgtccac ccgtttccaa gcctgggcca ctggcatctc tggagtgtgt gggggtctgg 120
gaggcaggtc ccgagccccc tgtccttccc acggccactg cagtcacccc gtctgcgccg 180
ctgtgctgtt gtctgccgtg agagcccaat cactgcctat acccctcatc acacgtcaca 240
atgtcccgaa ttcccagcct caccacccct tctcagtaat gaccctggtt ggttgcagga 300
ggtacctact ccatactgag ggtgaaatta agggaaggca aagtccaggc acaagagtgg 360
gaccccagcc tctcactctc agttccactc atccaactgg gaccctcacc acgaatctca 420
tgatctgatt cggttccctg tc 442

<210> SEQ ID NO 828
<211> LENGTH: 264
<212> TYPE: DNA
<213> ORGANISM: Homo sapiens

<400> SEQUENCE: 828
ccacttgcac cctagcttgt agctgccaac ctcccagaca gcccagcccg ctgctcagct 60
ccacatgcat agtatcagcc ctccacaccc gacaaagggg aacacacccc cttggaaatg 120
gttcttttcc cccagtccca gctggaagcc atgctgtctg ttctgctgga gcagctgaac 180
atatacatag atgttgccct gccctcccca tctgcaccct gttgagttgt agttggattt 240
gtctgtttat gcttggattc acca 264

<210> SEQ ID NO 829
<211> LENGTH: 559
<212> TYPE: DNA
<213> ORGANISM: Homo sapiens

<400> SEQUENCE: 829
ttctagcagc taaggaggcc gttcagctgt gacgaaggcc tgaagcacag gattaggact 60
gaagcgatga tgtccccttc cctacttccc cttggggctc cctgtgtcag ggcacagact 120
aggtcttgtg gctggtctgg cttgcggcgc gaggatggtt ctctctggtc atagcccgaa 180
gtctcatggc agtcccaaag gaggcttaca actcctgcat cacaagaaaa aggaagccac 240
tgccagctgg ggggatctgc agctcccaga agctccgtga gcctcagcca cccctcagac 300
tgggttcctc tccaagctcg ccctctggag gggcagcgca gcctcccacc aagggccctg 360
cgaccacagc agggattggg atgaattgcc tgtcctggat ctgctctaga ggcccaagct 420
gcctgcctga ggaaggatga cttgacaagt caggagacac tgttcccaaa gccttgacca 480
gagcacctca gcccgctgac cttgcacaaa ctccatctgc tgccatgaga aaagggaagc 540
cgcctttgca aaacattgc 559

<210> SEQ ID NO 830
<211> LENGTH: 26
<212> TYPE: DNA
<213> ORGANISM: Homo sapiens

<400> SEQUENCE: 830
gtgtctgctg ctccctagtc tgggcc 26

<210> SEQ ID NO 831
<211> LENGTH: 323
<212> TYPE: DNA
<213> ORGANISM: Homo sapiens

<400> SEQUENCE: 831
ccggccctca ttgaatgcgg ggttaattta actcagcctc tgtgtgagtg gatgattcag 60
gttgccagag acagaaccct cagcttagca tgggaagtag cttccctgtt gaccctgagt 120
tcatctgagg ttggcttgga aggtgtgggc accatttggc ccagttctta cagctctgaa 180
gagagcagca ggaatggggc tgagcaggga agacaacttt ccattgaagg ccccttttcag 240 ggccagaact gtccctccca ccctgcagct gccctgcctc tgcccatgag ggtgagagt 300 caggcgacct catgccaagt gta 323

<210> SEQ ID NO 832
<211> LENGTH: 34
<212> TYPE: DNA
<213> ORGANISM: Homo sapiens

<400> SEQUENCE: 832
gggtggaccg cctaagaggg cgtgcgctcc cgac 34

<210> SEQ ID NO 833
<211> LENGTH: 48
<212> TYPE: DNA
<213> ORGANISM: Homo sapiens

<400> SEQUENCE: 833
gcggcgcgcc attaaccgcc agatttgaat cgcgggaccc gttggcag 48

<210> SEQ ID NO 834
<211> LENGTH: 27
<212> TYPE: DNA
<213> ORGANISM: Homo sapiens

<400> SEQUENCE: 834
tgccccgacg ttgccccctg cctggca 27

<210> SEQ ID NO 835
<211> LENGTH: 48
<212> TYPE: DNA
<213> ORGANISM: Homo sapiens

<400> SEQUENCE: 835
tttctcaagg accaccgcat ctctacattc aagaactggc ccttcttg 48

<210> SEQ ID NO 836
<211> LENGTH: 97
<212> TYPE: DNA

<213> ORGANISM: Homo sapiens

<400> SEQUENCE: 836
tggcttcatc cactgcccca ctgagaacga gccagacttg gcccagtgtt tcttctgctt 60
caaggagctg gaaggctggg agccagatga cgacccc 97

<210> SEQ ID NO 837
<211> LENGTH: 146
<212> TYPE: DNA
<213> ORGANISM: Homo sapiens

<400> SEQUENCE: 837
cctcgatggg ctttgttttg aactgagttg tcaaaagatt tgagttgcaa agacacttag 60
tatgggaggg ttgctttcca ccctcattgc ttcttaaaca gctgttgtga acggatacct 120
ctctatatgc tggtgccttg gtgatg 146

<210> SEQ ID NO 838
<211> LENGTH: 154
<212> TYPE: DNA
<213> ORGANISM: Homo sapiens

<400> SEQUENCE: 838
gcttgggcaa agcactgatg ccatcaactt cagacttgac gtcttactcc tgaggcagag 60
cagggtgtgc ctgtggaggg cgtggggagg tggcccgtgg ggagtggact gccgctttaa 120
tcccttcagc tgcctttccg ctgttgtttt gatt 154

<210> SEQ ID NO 839
<211> LENGTH: 91
<212> TYPE: DNA
<213> ORGANISM: Homo sapiens

<400> SEQUENCE: 839
acataaaaag cattcgtccg gttgcgcttt cctttctgtc aagaagcagt ttgaagaatt 60
aacccttggt gaatttttga aactggacag a 91

<210> SEQ ID NO 840
<211> LENGTH: 60
<212> TYPE: DNA
<213> ORGANISM: Homo sapiens

<400> SEQUENCE: 840
aagaatttct gttcgaggaa gagcctgatg tttgccaggg tctgtttaac tggacatgaa 60

<210> SEQ ID NO 841
<211> LENGTH: 49
<212> TYPE: DNA
<213> ORGANISM: Homo sapiens

<400> SEQUENCE: 841
agaatttgag gaaactgcgg agaaagtgcg ccgtgccatc gagcagctg 49

<210> SEQ ID NO 842
<211> LENGTH: 359
<212> TYPE: DNA
<213> ORGANISM: Homo sapiens

<400> SEQUENCE: 842
ggctgcacca cttccagggt ttattccctg gtgccaccag ccttcctgtg ggcccttag 60 caatgtctta ggaaaggaga tcaacatttt caaattagat gtttcaactg tgctcttgtt 120
ttgtcttgaa agtggcacca gaggtgcttc tgcctgtgca gcgggtgctg ctggtaacag 180
tggctgcttc tctctctctc tctctttttt gggggctcat ttttgctgtt ttgattcccg 240
ggcttaccag gtgagaagtg agggaggaag aaggcagtgt ccctttttgct agagctgaca 300 gctttgttcg cgtgggcaga gccttccaca gtgaatgtgt ctggacctca tgttgttga 359

<210> SEQ ID NO 843
<211> LENGTH: 204
<212> TYPE: DNA
<213> ORGANISM: Homo sapiens

<400> SEQUENCE: 843
ggttccttat ctgtcacacc tgtgcctcct cagaggacag tttttttgtt gttgtgtttt 60
tttgtttttt tttttttggt agatgcatga cttgtgtgtg atgagagaat ggagacagag 120
tccctggctc ctctactgtt taacaacatg gctttcttat tttgtttgaa ttgttaattc 180
acagaatagc acaaactaca atta 204

<210> SEQ ID NO 844
<211> LENGTH: 188
<212> TYPE: DNA
<213> ORGANISM: Homo sapiens

<400> SEQUENCE: 844
aacggggtga acttcaggtg gatgaggaga cagaatagag tgataggaag cgtctggcag 60
atactccttt tgccactgct gtgtgattag acaggcccag tgagccgcgg ggcacatgct 120
ggccgctcct ccctcagaaa aaggcagtgg cctaaatcct ttttaaatga cttggctcga 180
tgctgtgg 188

<210> SEQ ID NO 845
<211> LENGTH: 209
<212> TYPE: DNA
<213> ORGANISM: Homo sapiens

<400> SEQUENCE: 845
cgtgtgtctg tcagcccaac cttcacatct gtcacgttct ccacacgggg gagagacgca 60
gtccgcccag gtccccgctt tctttggagg cagcagctcc cgcagggctg aagtctggcg 120
taagatgatg gatttgattc gccctcctcc ctgtcataga gctgcagggt ggattgttac 180
agcttcgctg gaaacctctg gaggtcatc 209

<210> SEQ ID NO 846
<211> LENGTH: 31
<212> TYPE: DNA
<213> ORGANISM: Homo sapiens

<400> SEQUENCE: 846
tgttcctgag aaataaaaag cctgtcattt c 31

<210> SEQ ID NO 847
<211> LENGTH: 303
<212> TYPE: DNA
<213> ORGANISM: Homo sapiens

<400> SEQUENCE: 847
gtttttcatc gtcgtcccta gcctgccaac agccatctgc ccagacagcc gcagtgagga 60
tgagcgtcct ggcagagacg cagttgtctc tgggcgcttg ccagagccac gaaccccaga 120
cctgtttgta tcatccgggc tccttccggg cagaaacaac tgaaaatgca cttcagaccc 180
acttatttct gccacatctg agtcggcctg agatagactt ttccctctaa actgggagaa 240
tatcacagtg gtttttgtta gcagaaaatg cactccagcc tctgtactca tctaagctgc 300
tta 303

<210> SEQ ID NO 848
<211> LENGTH: 46
<212> TYPE: DNA
<213> ORGANISM: Homo sapiens

<400> SEQUENCE: 848
ctgtgctgtg ggcagggctg agctggagcc gcccctctca gcccgc 46

<210> SEQ ID NO 849
<211> LENGTH: 87
<212> TYPE: DNA
<213> ORGANISM: Homo sapiens

<400> SEQUENCE: 849
atccttaaaa ccagaccctc atggctacca gcacctgaaa gcttcctcga catctgttaa 60
taaagccgta ggcccttgtc taagtgc 87

<210> SEQ ID NO 850
<211> LENGTH: 245
<212> TYPE: DNA
<213> ORGANISM: Homo sapiens

<400> SEQUENCE: 850
ccgcctagac tttctttcag atacatgtcc acatgtccat ttttcaggtt ctctaagttg 60
gagtggagtc tgggaagggt tgtgaatgag gcttctgggc tatgggtgag gttccaatgg 120
caggttagag cccctcgggc caactgccat cctggaaagt agagacagca gtgcccgctg 180
cccagaagag accagcaagc caaactggag cccccattgc aggctgtcgc catgtggaaa 240
gagta 245

<210> SEQ ID NO 851
<211> LENGTH: 25
<212> TYPE: DNA
<213> ORGANISM: Homo sapiens

<400> SEQUENCE: 851
taggaggccc cccgtgtgga cacag 25

<210> SEQ ID NO 852
<211> LENGTH: 32
<212> TYPE: DNA
<213> ORGANISM: Homo sapiens

<400> SEQUENCE: 852
tccagccgcc aaatccgcac caaggtcatg ga 32

<210> SEQ ID NO 853
<211> LENGTH: 304
<212> TYPE: DNA
<213> ORGANISM: Homo sapiens

<400> SEQUENCE: 853
tgagctctag tgctgtcacc cagtttccct tgtgaacctc cttgggtgga agaagctatt 60
ttctaaaccc tccttagggc taggagaggc agcccccacc tcttgcttct acgtggtgtc 120
tgtggcagat cctattgctg ttgtggtcag caccatgaac agggccctac agggctcttc 180
ccactgagac cactccattg ggtgaatatg gatggaacca gccaggtgtg agctcttagg 240
aagctctaat ctgagggcaa agactctgtc tctgaccttt gggagccctc gtctgaaaga 300
aatg 304

<210> SEQ ID NO 854
<211> LENGTH: 65
<212> TYPE: DNA
<213> ORGANISM: Homo sapiens

<400> SEQUENCE: 854
ctggaggaga ccaaaggtcg ctactgcatg cagctggccc agatccagga gatgattggc 60
agcgt 65

<210> SEQ ID NO 855
<211> LENGTH: 40
<212> TYPE: DNA
<213> ORGANISM: Homo sapiens

<400> SEQUENCE: 855
caagagcgag atctcggagc tccggcgcac catgcagaac 40

<210> SEQ ID NO 856
<211> LENGTH: 64
<212> TYPE: DNA
<213> ORGANISM: Homo sapiens

<400> SEQUENCE: 856
ggagatggac gctgcacctg gcgtggacct gagccgcatt ctgaacgaga tgcgtgacca 60
gtat 64

<210> SEQ ID NO 857
<211> LENGTH: 38
<212> TYPE: DNA
<213> ORGANISM: Homo sapiens

<400> SEQUENCE: 857
gatgggtgtc tcataccttt tctctggggt cattccag 38

<210> SEQ ID NO 858
<211> LENGTH: 75
<212> TYPE: DNA
<213> ORGANISM: Homo sapiens

<400> SEQUENCE: 858
agccacagtg gacaatgcca atgtccttct gcagattgac aatgcccgtc tggccgcgga 60
tgacttccgc accaa 75

<210> SEQ ID NO 859
<211> LENGTH: 50
<212> TYPE: DNA
<213> ORGANISM: Homo sapiens

<400> SEQUENCE: 859
tggccttggt gctggcttgg gtggtggctt tggtggtggc tttgctggtg 50

<210> SEQ ID NO 860
<211> LENGTH: 44
<212> TYPE: DNA

<213> ORGANISM: Homo sapiens

<400> SEQUENCE: 860
acccgagcac cttctcttca ctcagccaac tgctcgctcg ctca 44

<210> SEQ ID NO 861
<211> LENGTH: 39
<212> TYPE: DNA
<213> ORGANISM: Homo sapiens

<400> SEQUENCE: 861
gagaaggtga ccatgcagaa cctcaatgac cgcctggcc 39

<210> SEQ ID NO 862
<211> LENGTH: 25
<212> TYPE: DNA
<213> ORGANISM: Homo sapiens

<400> SEQUENCE: 862
ggactcagct accccggccg gccac 25

<210> SEQ ID NO 863
<211> LENGTH: 25
<212> TYPE: DNA
<213> ORGANISM: Homo sapiens

<400> SEQUENCE: 863
ccaggaatac aaaatcctgc tggat 25

<210> SEQ ID NO 864
<211> LENGTH: 30
<212> TYPE: DNA
<213> ORGANISM: Homo sapiens

<400> SEQUENCE: 864
aagagtgaga tctcggagct ccggcgcacc 30

<210> SEQ ID NO 865
<211> LENGTH: 80
<212> TYPE: DNA
<213> ORGANISM: Homo sapiens

<400> SEQUENCE: 865
aggtgggtgg tgagatcaat gtggagatgg acgctgcccc aggcgtggac ctgagccgca 60
tcctcaacga gatgcgtgac 80

<210> SEQ ID NO 866
<211> LENGTH: 121
<212> TYPE: DNA
<213> ORGANISM: Homo sapiens

<400> SEQUENCE: 866
gtgcaccggg attagtcacc ttagagggct tccctgtctg cagagccctg atccttgggg 60
tccagtgtgc agggcagact cctctttgta ccacactgct tctctgtaca caaggaacct 120
c 121

<210> SEQ ID NO 867
<211> LENGTH: 45
<212> TYPE: DNA
<213> ORGANISM: Homo sapiens

<400> SEQUENCE: 867
ctggccagag ccgacctgga gatgcagatt gagaacctca aggag 45

<210> SEQ ID NO 868
<211> LENGTH: 38
<212> TYPE: DNA
<213> ORGANISM: Homo sapiens

<400> SEQUENCE: 868
ccctgcgcct gagtgtggag gccgacatca atggcctg 38

<210> SEQ ID NO 869
<211> LENGTH: 25
<212> TYPE: DNA
<213> ORGANISM: Homo sapiens

<400> SEQUENCE: 869
gtctggctgc tgatgacttc cgcac 25

<210> SEQ ID NO 870
<211> LENGTH: 25
<212> TYPE: DNA
<213> ORGANISM: Homo sapiens

<400> SEQUENCE: 870
ggtactgagt atcgggggaa gaaga 25

<210> SEQ ID NO 871
<211> LENGTH: 60
<212> TYPE: DNA
<213> ORGANISM: Homo sapiens

<400> SEQUENCE: 871
ggcagcagct ttgggggtgt tgatgggctg ctggctggag gtgagaaggc caccatgcag 60

<210> SEQ ID NO 872
<211> LENGTH: 131
<212> TYPE: DNA
<213> ORGANISM: Homo sapiens

<400> SEQUENCE: 872
gtcccgcacc tcctgccggc tgtctggcgg cctgggtgcc ggctcctgca ggctgggatc 60
tgctggcggc ctgggcagca ccctcggggg tagcagctac tccagctgct acagctttgg 120
ctctggtggt g 131

<210> SEQ ID NO 873
<211> LENGTH: 33
<212> TYPE: DNA
<213> ORGANISM: Homo sapiens

<400> SEQUENCE: 873
acacgcacgg cactcagcac gaggatttgg aga 33

<210> SEQ ID NO 874
<211> LENGTH: 28
<212> TYPE: DNA
<213> ORGANISM: Homo sapiens

<400> SEQUENCE: 874
ttggcctgcc tccgtcccgc cgcgccac 28

<210> SEQ ID NO 875

<211> LENGTH: 25
<212> TYPE: DNA
<213> ORGANISM: Homo sapiens

<400> SEQUENCE: 875
ctgcctccgt cccgccgcgc cactt 25

<210> SEQ ID NO 876
<211> LENGTH: 26
<212> TYPE: DNA
<213> ORGANISM: Homo sapiens

<400> SEQUENCE: 876
gcctgtggcc ggctcggagc tgccgc 26

<210> SEQ ID NO 877
<211> LENGTH: 318
<212> TYPE: DNA
<213> ORGANISM: Homo sapiens

<400> SEQUENCE: 877
cgcttcgcag cgttttcaaa aactggagcg aaagtgatgt gggcggggca aaggcggcgg 60
gaagaggaga gcactgaagc tggcgcggga acttggtttc ctggtggcct cccatccaat 120
ccccacgaac cagctttcct cttaaacctt gaaaagagaa attcgggagt tcgagtataa 180
gttcttagtc gtcctttcct ctttcctttc cgacaggagc accccaggca aaaaatgtct 240
cgcgggtcat tggcgccagg ctttcagggg acagtggggc ggggcggggt gggcacagga 300
cgttaggcag ccgttggc 318

<210> SEQ ID NO 878
<211> LENGTH: 33
<212> TYPE: DNA
<213> ORGANISM: Homo sapiens

<400> SEQUENCE: 878
cgtcctgccg tcctggatcc tgcgccagct gcg 33

<210> SEQ ID NO 879
<211> LENGTH: 38
<212> TYPE: DNA
<213> ORGANISM: Homo sapiens

<400> SEQUENCE: 879
ctctgctgac aaccaaacgt gtgttctgga agggtgtt 38

<210> SEQ ID NO 880
<211> LENGTH: 79
<212> TYPE: DNA
<213> ORGANISM: Homo sapiens

<400> SEQUENCE: 880
gctgtcttcc aagggagtga aaatctggga tgccaatgga tcccgagact ttttggacag 60
cctgggattc tccaccaga 79

<210> SEQ ID NO 881
<211> LENGTH: 73
<212> TYPE: DNA
<213> ORGANISM: Homo sapiens

<400> SEQUENCE: 881
aggacaggga gttgaccaac tgcaaagagt gattgacacc atcaaaacca accctgacga 60
cagaagaatc atc 73

<210> SEQ ID NO 882
<211> LENGTH: 87
<212> TYPE: DNA
<213> ORGANISM: Homo sapiens

<400> SEQUENCE: 882
aagcaatctg gttttgtgca gaggcacctg agggaggcag gaccctggga acttcccccca 60 gccacatggt tgattgtgtg acgttgg 87

<210> SEQ ID NO 883
<211> LENGTH: 140
<212> TYPE: DNA
<213> ORGANISM: Homo sapiens

<400> SEQUENCE: 883
ctctgccagt tctatgtggt gaacagtgag ctgtcctgcc agctgtacca gagatcggga 60
gacatgggcc tcggtgtgcc tttcaacatc gccagctacg ccctgctcac gtacatgatt 120
gcgcacatca cgggcctgaa 140

<210> SEQ ID NO 884
<211> LENGTH: 45
<212> TYPE: DNA
<213> ORGANISM: Homo sapiens

<400> SEQUENCE: 884
ggagatgcac atatttacct gaatcacatc gagccactga aaatt 45

<210> SEQ ID NO 885
<211> LENGTH: 101
<212> TYPE: DNA
<213> ORGANISM: Homo sapiens

<400> SEQUENCE: 885
ccaaagctca ggattcttcg aaaagttgag aaaattgatg acttcaaagc tgaagacttt 60
cagattgaag ggtacaatcc gcatccaact attaaaatgg a 101

<210> SEQ ID NO 886
<211> LENGTH: 121
<212> TYPE: DNA
<213> ORGANISM: Homo sapiens

<400> SEQUENCE: 886
aggagctcga aggatattgt cagtctttag gggttgggct ggatgccgag gtaaaagttc 60
tttttgctct aaaagaaaaa ggaactaggt caaaaatctg tccgtgacct atcagttatt 120
a 121

<210> SEQ ID NO 887
<211> LENGTH: 235
<212> TYPE: DNA
<213> ORGANISM: Homo sapiens

<400> SEQUENCE: 887
cactgagggt atctgacaat gctgaggtta tgaacaaagt gaggagaatg aaatgtatgt 60
gctcttagca aaaacatgta tgtgcatttc aatcccacgt acttataaag aaggttggtg 120
aatttcacaa gctatttttg gaatattttt agaatatttt aagaatttca caagctattc 180
cctcaaatct gagggagctg agtaacacca tcgatcatga tgtagagtgt ggtta 235

<210> SEQ ID NO 888
<211> LENGTH: 40
<212> TYPE: DNA
<213> ORGANISM: Homo sapiens

<400> SEQUENCE: 888
ttgttcattc tgtactgcca cttatctgct cagttccttc 40

<210> SEQ ID NO 889
<211> LENGTH: 117
<212> TYPE: DNA
<213> ORGANISM: Homo sapiens

<400> SEQUENCE: 889
agcgccggcg gagaatttca aattcgaacg gctttggcgg gccgaggaag gacctggtgt 60
tttgatgacc gctgtcctgt ctagcagata cttgcacggt ttacagaaat tcggtcc 117

<210> SEQ ID NO 890
<211> LENGTH: 98
<212> TYPE: DNA
<213> ORGANISM: Homo sapiens

<400> SEQUENCE: 890
atgaagcgca gttcagtttc cagcggtggt gctggccgcc tctccatgca ggagttaaga 60
tcccaggatg taaataaaca aggcctctat acccctca 98

<210> SEQ ID NO 891
<211> LENGTH: 93
<212> TYPE: DNA
<213> ORGANISM: Homo sapiens

<400> SEQUENCE: 891
gtggacatgg atcccggaat agtcaacttg gtatattttc cagttctgag aaaatcaagg 60
acccgagacc acttaatgac aaagcattca ttc 93

<210> SEQ ID NO 892
<211> LENGTH: 133
<212> TYPE: DNA
<213> ORGANISM: Homo sapiens

<400> SEQUENCE: 892
cttacagaaa atggttatgc acataatgtg tccatgaaat ctctacaagc tccctctgtt 60
aaagacttcc tgaagatctt cacatttctt tatggcttcc tgtgcccctc atacgaactt 120
cctgacacaa agt 133

<210> SEQ ID NO 893
<211> LENGTH: 59
<212> TYPE: DNA
<213> ORGANISM: Homo sapiens

<400> SEQUENCE: 893
ctcctcatac atggcctcac attgtggcag ccttagtttg gctaatagac tgcatcaag 59

<210> SEQ ID NO 894
<211> LENGTH: 123
<212> TYPE: DNA
<213> ORGANISM: Homo sapiens

<400> SEQUENCE: 894
tgaaatgtat acatgggaaa gggttttttt cctcaaaaaa aatattttct ctcccagtct 60
tttgacagta ttctcaaagt ctgcttcaga gttttcattt ttcaaagcac atttgatttt 120
aag 123

<210> SEQ ID NO 895
<211> LENGTH: 33
<212> TYPE: DNA
<213> ORGANISM: Homo sapiens

<400> SEQUENCE: 895
atgaaagaaa gctcaccttt atttgatgat ggg 33

<210> SEQ ID NO 896
<211> LENGTH: 57
<212> TYPE: DNA
<213> ORGANISM: Homo sapiens

<400> SEQUENCE: 896
ctacaccata aaatgctatg agagttttat gagtggtgcc gacagctttg atgagat 57

<210> SEQ ID NO 897
<211> LENGTH: 71
<212> TYPE: DNA
<213> ORGANISM: Homo sapiens

<400> SEQUENCE: 897
gcttttaagc tggaatcatt agaagcaaaa aacagagcat tgaatgaaca gattgcaaga 60
ttggaacaag a 71

<210> SEQ ID NO 898
<211> LENGTH: 137
<212> TYPE: DNA
<213> ORGANISM: Homo sapiens

<400> SEQUENCE: 898
aatcgtctag agtcgttgag aaaactgaag gcttccttac aaggagatgt tcaaaagtat 60
caggcataca tgagcaattt ggagtctcat tcagccattc ttgaccagaa attaaatggt 120
ctcaatgagg aaattgc 137

<210> SEQ ID NO 899
<211> LENGTH: 126
<212> TYPE: DNA
<213> ORGANISM: Homo sapiens

<400> SEQUENCE: 899
aaccagaagt actcagttgc agacattgag cgaataaatc atgaaagaaa tgaattgcag 60
cagactatta ataaattaac caaggacctg gaagctgaac aacagaagtt gtggaatgag 120
gagtta 126

<210> SEQ ID NO 900
<211> LENGTH: 123
<212> TYPE: DNA
<213> ORGANISM: Homo sapiens

<400> SEQUENCE: 900
cagagtatca caaattggct agaaaattaa aacttattcc taaaggtgct gagaattcca 60
aaggttatga ctttgaaatt aagtttaatc ccgaggctgg tgccaactgc cttgtcaaat 120
aca 123

<210> SEQ ID NO 901
<211> LENGTH: 89
<212> TYPE: DNA
<213> ORGANISM: Homo sapiens

<400> SEQUENCE: 901
gtacctctta aggaactcct gaatgaaact gaagaagaaa ttaataaagc cctaaataaa 60
aaaatgggtt tggaggatac tttagaaca 89

<210> SEQ ID NO 902
<211> LENGTH: 87
<212> TYPE: DNA
<213> ORGANISM: Homo sapiens

<400> SEQUENCE: 902
ttgaatgcaa tgataacaga aagcaagaga agtgtgagaa ctctgaaaga agaagttcaa 60
aagctggatg atctttacca acaaaaa 87

<210> SEQ ID NO 903
<211> LENGTH: 63
<212> TYPE: DNA
<213> ORGANISM: Homo sapiens

<400> SEQUENCE: 903
acctgctaga aagtactgtt aaccaggggc tcagtgaagc tatgaatgaa ttagatgctg 60
ttc 63

<210> SEQ ID NO 904
<211> LENGTH: 84
<212> TYPE: DNA
<213> ORGANISM: Homo sapiens

<400> SEQUENCE: 904
tagttgtgca aaccacgact gaagaaagac gaaaagtggg aaataacttg caacgtctgt 60
tagagatggt tgctacacat gttg 84

<210> SEQ ID NO 905
<211> LENGTH: 279
<212> TYPE: DNA
<213> ORGANISM: Homo sapiens

<400> SEQUENCE: 905
ctggggtgaa gcagccgcat gctaaggaac accaaggact gccaggagcc gccagcaact 60
ggggagagac gaagaaggat tcttccctag agccttcaga gagaccatgg ccctgctgac 120
gtcttgattt caaacttccg gcctccagag ctgaaagagt acatttctgt tgttttaagc 180
cacctagttt gtggcaattt gttacagtat cagtatttga aatcgcaaaa aaatcaacaa 240
aaacaacaag aaaaaataat gtggcatgtt agtttccca 279

<210> SEQ ID NO 906
<211> LENGTH: 132
<212> TYPE: DNA
<213> ORGANISM: Homo sapiens

<400> SEQUENCE: 906
aacatcttga ggagcagatt gctaaagttg atagagaata tgaagaatgc atgtcagaag 60
atctctcgga aaatattaaa gagattagag ataagtatga gaagaaagct actctaatta 120
agtcttctga ag 132

<210> SEQ ID NO 907
<211> LENGTH: 33
<212> TYPE: DNA
<213> ORGANISM: Homo sapiens

<400> SEQUENCE: 907
tatatccata gtgaataaaa ttgtctcagt aaa 33

<210> SEQ ID NO 908
<211> LENGTH: 303
<212> TYPE: DNA
<213> ORGANISM: Homo sapiens

<400> SEQUENCE: 908
caaaatgttc gtgcgggtat ataccagatg agtacagtga gtagttttat gtatcaccag 60
actgggttat tgccaagtta tatatcacca aaagctgtat gactggatgt tctggttacc 120
tggtttacaa aattatcaga gtagtaaaac tttgatatat atgaggatat taaaactaca 180
ctaagtatca tttgattcga ttcagaaagt actttgatat ctctcagtgc ttcagtgcta 240
tcattgtgag caattgtctt ttatatacgg tactgtagcc atactaggcc tgtctgtggc 300
att 303

<210> SEQ ID NO 909
<211> LENGTH: 28
<212> TYPE: DNA
<213> ORGANISM: Homo sapiens

<400> SEQUENCE: 909
agaactgctg gtgtttagga ataagaat 28

<210> SEQ ID NO 910
<211> LENGTH: 183
<212> TYPE: DNA
<213> ORGANISM: Homo sapiens

<400> SEQUENCE: 910
agtttcagta ggtcataggg agatgagttt gtatgctgta ctatgcagcg tttaaagtta 60
gtgggttttg tgatttttgt attgaatatt gctgtctgtt acaaagtcag ttaaaggtac 120
gttttaatat ttaagttatt ctatcttgga gataaaatct gtatgtgcaa ttcaccggta 180
tta 183

<210> SEQ ID NO 911
<211> LENGTH: 86
<212> TYPE: DNA
<213> ORGANISM: Homo sapiens

<400> SEQUENCE: 911
agaatgctgg gatgcttttg ggttttggaa ttatgttact tatttccata tttgaacata 60
aaatcgtgtt tcgtataaat ttctag 86

<210> SEQ ID NO 912
<211> LENGTH: 42
<212> TYPE: DNA
<213> ORGANISM: Homo sapiens

<400> SEQUENCE: 912
atgctgcaca atgatgctag tgaccatgga tgtagccgct gg 42

<210> SEQ ID NO 913
<211> LENGTH: 164
<212> TYPE: DNA
<213> ORGANISM: Homo sapiens

<400> SEQUENCE: 913
gcatgaccgt taagcaggct gtcctttata atgcattgtc agccatgctg gcgtatcttg 60
gaatggcaac aggaattttc attggtcatt atgctgaaaa tgtttctatg tggatatttg 120
cacttactgc tggcttattc atgtatgttg ctctggttga tatg 164

<210> SEQ ID NO 914
<211> LENGTH: 35
<212> TYPE: DNA
<213> ORGANISM: Homo sapiens

<400> SEQUENCE: 914
gttgctgtgt tctgtcatga gttgcctcat gaatt 35

<210> SEQ ID NO 915
<211> LENGTH: 88
<212> TYPE: DNA
<213> ORGANISM: Homo sapiens

<400> SEQUENCE: 915
gagctgaaag atgccggcgt cgccactctg gcctggatgg tgataatggg tgatggcctg 60
cacaatttca gcgatggcct agcaattg 88

<210> SEQ ID NO 916
<211> LENGTH: 74
<212> TYPE: DNA
<213> ORGANISM: Homo sapiens

<400> SEQUENCE: 916
accatcatat tctccatcat caccaccacc aaaaccacca tcctcacagt cacagccagc 60
gctactctcg ggag 74

<210> SEQ ID NO 917
<211> LENGTH: 101
<212> TYPE: DNA
<213> ORGANISM: Homo sapiens

<400> SEQUENCE: 917
ccacaggaag tctacaatga atatgtaccc agagggtgca agaataaatg ccattcacat 60
ttccacgata cactcggcca gtcagacgat ctcattcacc a 101

<210> SEQ ID NO 918
<211> LENGTH: 62
<212> TYPE: DNA
<213> ORGANISM: Homo sapiens

<400> SEQUENCE: 918
tgatgtggag attaagaagc agttgtccaa gtatgaatct caactttcaa caaatgagga 60
ga 62

<210> SEQ ID NO 919
<211> LENGTH: 98
<212> TYPE: DNA
<213> ORGANISM: Homo sapiens

<400> SEQUENCE: 919
tgcctatttt gattccacgt ggaagggtct aacagctcta ggaggcctgt atttcatgtt 60
tcttgttgaa catgtcctca cattgatcaa acaattta 98

<210> SEQ ID NO 920
<211> LENGTH: 26
<212> TYPE: DNA
<213> ORGANISM: Homo sapiens

<400> SEQUENCE: 920
tcagtcatct gtcttctcaa aacata 26

<210> SEQ ID NO 921
<211> LENGTH: 138
<212> TYPE: DNA
<213> ORGANISM: Homo sapiens

<400> SEQUENCE: 921
gttttatagc catttccatc atcagtttcc tgtctctgct gggggttatc ttagtgcctc 60
tcatgaatcg ggtgtttttc aaatttctcc tgagtttcct tgtggcactg gccgttggga 120
ctttgagtgg tgatgctt 138

<210> SEQ ID NO 922
<211> LENGTH: 120
<212> TYPE: DNA
<213> ORGANISM: Homo sapiens

<400> SEQUENCE: 922
gaatgcaaca gagttcaact atctctgtcc agccatcatc aaccaaattg atgctagatc 60
ttgtctgatt catacaagtg aaaagaaggc tgaaatccct ccaaagacct attcattaca 120

<210> SEQ ID NO 923
<211> LENGTH: 27
<212> TYPE: DNA
<213> ORGANISM: Homo sapiens

<400> SEQUENCE: 923
gcatcaaagc tactgacatc tcatggc 27

<210> SEQ ID NO 924
<211> LENGTH: 63
<212> TYPE: DNA
<213> ORGANISM: Homo sapiens

<400> SEQUENCE: 924
tgagccggct ggctggtagg aaaacaaatg aatctgtgag tgagccccga aaaggcttta 60
tgt 63

<210> SEQ ID NO 925
<211> LENGTH: 245
<212> TYPE: DNA
<213> ORGANISM: Homo sapiens

<400> SEQUENCE: 925
actcagatag ttcaggtaaa gatcctagaa acagccaggg gaaaggagct caccgaccag 60
aacatgccag tggtagaagg aatgtcaagg acagtgttag tgctagtgaa gtgacctcaa 120
ctgtgtacaa cactgtctct gaaggaactc actttctaga gacaatagag actccaagac 180

-continued ctggaaaact cttccccaaa gatgtaagca gctccactcc acccagtgtc acatcaaaga 240
gccgg 245

<210> SEQ ID NO 926
<211> LENGTH: 201
<212> TYPE: DNA
<213> ORGANISM: Homo sapiens

<400> SEQUENCE: 926
cgcaatggcg aggaagttat ctgtaatctt gatcctgacc tttgccctct ctgtcacaaa 60 tcccctcat gaactaaaag cagctgcttt cccccagacc actgagaaaa ttagtccgaa 120
ttgggaatct ggcattaatg ttgacttggc aatttccaca cggcaatatc atctacaaca 180
gcttttctac cgctatggag a 201

<210> SEQ ID NO 927
<211> LENGTH: 56
<212> TYPE: DNA
<213> ORGANISM: Homo sapiens

<400> SEQUENCE: 927
tgtggaacca aacctgcgcg cgtggccggg ccgtgggaca acgaggccgc ggagac 56

<210> SEQ ID NO 928
<211> LENGTH: 28
<212> TYPE: DNA
<213> ORGANISM: Homo sapiens

<400> SEQUENCE: 928
agatttctcg aagacaccag tgggcccg 28

<210> SEQ ID NO 929
<211> LENGTH: 134
<212> TYPE: DNA
<213> ORGANISM: Homo sapiens

<400> SEQUENCE: 929
ctgcgcgcgg cggtaattag tgattgtctt ccagcttcgc gaaggctagg ggcgcggctg 60
ccgggtggct gcgcggcgct gcccccggac cgaggggcag ccaacccaat gaaaccaccg 120
cgtgttcgcg cctg 134

<210> SEQ ID NO 930
<211> LENGTH: 26
<212> TYPE: DNA
<213> ORGANISM: Homo sapiens

<400> SEQUENCE: 930
tgaagaaaaa taaagtacag tgtgag 26

<210> SEQ ID NO 931
<211> LENGTH: 239
<212> TYPE: DNA
<213> ORGANISM: Homo sapiens

<400> SEQUENCE: 931
tgtattgaaa gcttttgtta tcaagatttt catactttta ccttccatgg ctctttttaa 60
gattgatact tttaagaggt ggctgatatt ctgcaacact gtacacataa aaaatacggt 120
aaggatactt tacatggtta aggtaaagta agtctccagt tggccaccat tagctataat 180
ggcactttgt ttgtgttgtt ggaaaaagtc acattgccat taaactttcc ttgtctgtc 239

<210> SEQ ID NO 932
<211> LENGTH: 112
<212> TYPE: DNA
<213> ORGANISM: Homo sapiens

<400> SEQUENCE: 932
ctgtagtgta gatactgagt aaatccatgc acctaaacct tttggaaaat ctgccgtggg 60
ccctccagat agctcatttc attaagtttt tccctccaag gtagaatttg ca 112

<210> SEQ ID NO 933
<211> LENGTH: 35
<212> TYPE: DNA
<213> ORGANISM: Homo sapiens

<400> SEQUENCE: 933
ggaggatgga aaggctcgct caatcaagaa aattc 35

<210> SEQ ID NO 934
<211> LENGTH: 156
<212> TYPE: DNA
<213> ORGANISM: Homo sapiens

<400> SEQUENCE: 934
gaccttggac aatcatgaaa tatgcatctc actggatgca aagaaaatca gatggagcat 60
gaatggtact gtaccggttc atctggactg ccccagaaaa ataacttcaa gcaaacatcc 120
tatcaacaac aaggttgttc tgcataccaa gctgag 156

<210> SEQ ID NO 935
<211> LENGTH: 1832
<212> TYPE: DNA
<213> ORGANISM: Homo sapiens

<400> SEQUENCE: 935
cctgtgctgc tatcctgcca aaatcatttt aatggagtca gtttgcagta tgctccacgt 60
ggtaagatcc tccaagctgc tttagaagta acaatgaaga acgtggacgt ttttaatata 120
aagcctgttt tgtcttttgt tgttgttcaa acgggattca cagagtattt gaaaaatgta 180
tatatattaa gaggtcacgg gggctaattg ctggctggct gccttttgct gtggggtttt 240
gttacctggt tttaataaca gtaaatgtgc ccagcctctt ggccccagaa ctgtacagta 300
ttgtggctgc acttgctcta agagtagttg atgttgcatt ttccttattg ttaaaaacat 360
gttagaagca atgaatgtat ataaaagcct caactagtca tttttttctc ctcttctttt 420
ttttcattat atctaattat tttgcagttg ggcaacagag aaccatccct attttgtatt 480
gaagagggat tcacatctgc atcttaactg ctctttatga atgaaaaaac agtcctctgt 540
atgtactcct ctttacactg gccagggtca gagttaaata gagtatatgc actttccaaa 600
ttggggacaa gggctctaaa aaaagcccca aaaggagaag aacatctgag aacctcctcg 660
gccctcccag tccctcgctg cacaaatact ccgcaagaga ggccagaatg acagctgaca 720
gggtctatgg ccatcgggtc gtctccgaag atttggcagg ggcagaaaac tctggcaggc 780
ttaagatttg gaataaagtc acagaattaa ggaagcacct caatttagtt caaacaagac 840
gccaacattc tctccacagc tcacttacct ctctgtgttc agatgtggcc ttccatttat 900
atgtgatctt tgttttatta gtaaatgctt atcatctaaa gatgtagctc tggcccagtg 960
ggaaaaatta ggaagtgatt ataaatcgag aggagttata ataatcaaga ttaaatgtaa 1020
ataatcaggg caatcccaac acatgtctag ctttcacctc caggatctat tgagtgaaca 1080
gaattgcaaa tagtctctat ttgtaattga acttatccta aaacaaatag tttataaatg 1140
tgaacttaaa ctctaattaa ttccaactgt acttttaagg cagtggctgt ttttagactt 1200
tcttatcact tatagttagt aatgtacacc tactctatca gagaaaaaca ggaaaggctc 1260
gaaatacaag ccattctaag gaaattaggg agtcagttga aattctattc tgatcttatt 1320
ctgtggtgtc ttttgcagcc cagacaaatg tggttacaca ctttttaaga aatacaattc 1380
tacattgtca agcttatgaa ggttccaatc agatctttat tgttattcaa tttggatctt 1440
tcagggattt ttttttaaa ttattatggg acaaaggaca tttgttggag gggtgggagg 1500
gaggaagaat ttttaaatgt aaaacattcc caagtttgga tcagggagtt ggaagttttc 1560
agaataacca gaactaaggg tatgaaggac ctgtattggg gtcgatgtga tgcctctgcg 1620
aagaaccttg tgtgacaaat gagaaacatt ttgaagtttg tggtacgacc tttagattcc 1680
agagacatca gcatggctca aagtgcagct ccgtttggca gtgcaatggt ataaatttca 1740
agctggatat gtctaatggg tatttaaaca ataaatgtgc agttttaact aacaggatat 1800
ttaatgacaa ccttctggtt ggtagggaca tc 1832

<210> SEQ ID NO 936
<211> LENGTH: 274
<212> TYPE: DNA
<213> ORGANISM: Homo sapiens

<400> SEQUENCE: 936
cgtccctggg caattccgca tttaattcat ggtattcagg attacatgca tgtttggtta 60
aacccatgag attcattcag ttaaaaatcc agatggcaaa tgaccagcag attcaaatct 120
atggtggttt gacctttaga gagttgcttt acgtggcctg tttcaacaca gacccaccca 180
gagccctcct gccctccttc cgcgggggct ttctcatggc tgtccttcag ggtcttcctg 240
aaatgcagtg gtgcttacgc tccaccaaga aagc 274

<210> SEQ ID NO 937
<211> LENGTH: 410
<212> TYPE: DNA
<213> ORGANISM: Homo sapiens

<400> SEQUENCE: 937
taggcccgtt ttcacgtgga gcatgggagc cacgaccctt cttaagacat gtatcactgt 60
agagggaagg aacagaggcc ctgggccctt cctatcagaa ggacatggtg aaggctggga 120
acgtgaggag aggcaatggc cacggcccat tttggctgta gcacatggca cgttggctgt 180
gtggccttgg cccacctgtg agtttaaagc aaggctttaa atgactttgg agagggtcac 240
aaatcctaaa agaagcattg aagtgaggtg tcatggatta attgacccct gtctatggaa 300
ttacatgtaa aacattatct tgtcactgta gtttggtttt atttgaaaac ctgacaaaaa 360
aaaagttcca ggtgtggaat atgggggtta tctgtacatc ctggggcatt 410

<210> SEQ ID NO 938
<211> LENGTH: 39
<212> TYPE: DNA
<213> ORGANISM: Homo sapiens

<400> SEQUENCE: 938
caacagggca gtgtggtctc cgaatgtctg gaagctgat 39

<210> SEQ ID NO 939
<211> LENGTH: 639
<212> TYPE: DNA
<213> ORGANISM: Homo sapiens

<400> SEQUENCE: 939
cacctggatg ttctgtgcct gtaaacatag attcgctttc catgttgttg gccggatcac 60
catctgaaga gcagacggat ggaaaaagga cctgatcatt ggggaagctg gctttctggc 120
tgctggaggc tggggagaag gtgttcattc acttgcattt ctttgccctg ggggctgtga 180
tattaacaga gggagggttc ctgtgggggg aagtccatgc ctccctggcc tgaagaagag 240
actctttgca tatgactcac atgatgcata cctggtggga ggaaaagagt tgggaacttc 300
agatggacct agtacccact gagatttcca cgccgaagga cagcgatggg aaaaatgccc 360
ttaaatcata ggaaagtatt tttttaagct accaattgtg ccgagaaaag cattttagca 420
atttatacaa tatcatccag taccttaagc cctgattgtg tatattcata tattttggat 480
acgcaccccc caactcccaa tactggctct gtctgagtaa gaaacagaat cctctggaac 540
ttgaggaagt gaacatttcg gtgacttccg catcaggaag gctagagtta cccagagcat 600
caggccgcca caagtgcctg cttttaggag accgaagtc 639

<210> SEQ ID NO 940
<211> LENGTH: 41
<212> TYPE: DNA
<213> ORGANISM: Homo sapiens

<400> SEQUENCE: 940
gtgggagctt gcatcaccct gggtgcctat ctgggccaca a 41

<210> SEQ ID NO 941
<211> LENGTH: 81
<212> TYPE: DNA
<213> ORGANISM: Homo sapiens

<400> SEQUENCE: 941
tgtggaactg tacggcccca gcatgcggcc tctgtttgat ttctcctggc tgtctctgaa 60
gactctgctc agtttggccc t 81

<210> SEQ ID NO 942
<211> LENGTH: 495
<212> TYPE: DNA
<213> ORGANISM: Homo sapiens

<400> SEQUENCE: 942
gcaataccat tctcatgcca gtgtacaaat tacatgaaag agcatcattt ttctagtgtc 60
tgaggattgg ctgcttatgg ccaattttgg cagcaagacg ataggattaa aaatagcttg 120
aagatgatct agtcttaaat aatatatttc atgatgaact ttccttggga aagtgcatct 180
ttctgcctac aagaatcaca tgaccccttt caataattta tgtagtagag aaaaacacac 240
tatttctcat agagttttca gtcatgtgct gtggtgtgat tgtttctgga cattcataaa 300
attttatagt taactgaatt ctcttttctg ttttgttgct atttaacgtc cattgaaaac 360
atggctttct tttgcgcatt ctgttacttt cagctgtact ttctaataag aatggattgc 420 ccttttttagc aatctttgat tgaactggta catttcagat tacttaaatg tcatcaggcc 480
acacagcata ccagg 495

<210> SEQ ID NO 943

<211> LENGTH: 210
<212> TYPE: DNA
<213> ORGANISM: Homo sapiens

<400> SEQUENCE: 943
acttcgccga gatgtccagc cagctgcacc tgacgccctt caccgcgcgg ggacgctttg 60
ccacggtggt ggaggagctc ttcagggacg gggtgaactg ggggaggatt gtggccttct 120
ttgagttcgg tggggtcatg tgtgtggaga gcgtcaaccg ggagatgtcg cccctggtgg 180
acaacatcgc cctgtggatg actgagtacc 210

<210> SEQ ID NO 944
<211> LENGTH: 25
<212> TYPE: DNA
<213> ORGANISM: Homo sapiens

<400> SEQUENCE: 944
gccacctgtg gtccacctga ccctc 25

<210> SEQ ID NO 945
<211> LENGTH: 86
<212> TYPE: DNA
<213> ORGANISM: Homo sapiens

<400> SEQUENCE: 945
cccgcaccgg gcatcttctc ctcccagccc gggcacacgc cccatccagc cgcatcccgg 60
gacccggtcg ccaggacctc gccgct 86

<210> SEQ ID NO 946
<211> LENGTH: 63
<212> TYPE: DNA
<213> ORGANISM: Homo sapiens

<400> SEQUENCE: 946
gtacgataac cgggagatag tgatgaagta catccattat aagctgtcgc agaggggcta 60
cga 63

<210> SEQ ID NO 947
<211> LENGTH: 212
<212> TYPE: DNA
<213> ORGANISM: Homo sapiens

<400> SEQUENCE: 947
cacagaggaa gtagactgat attaacaata cttactaata ataacgtgcc tcatgaaata 60
aagatccgaa aggaattgga ataaaaattt cctgcatctc atgccaaggg ggaaacacca 120
gaatcaagtg ttccgcgtga ttgaagacac cccctcgtcc aagaatgcaa agcacatcca 180
ataaaatagc tggattataa ctcctcttct tt 212

<210> SEQ ID NO 948
<211> LENGTH: 154
<212> TYPE: DNA
<213> ORGANISM: Homo sapiens

<400> SEQUENCE: 948
tgtaactttc aatggaaacc tttgagattt tttacttaaa gtgcattcga gtaaatttaa 60
tttccaggca gcttaataca ttctttttag ccgtgttact tgtagtgtgt atgccctgct 120
ttcactcagt gtgtacaggg aaacgcacct gatt 154

<210> SEQ ID NO 949
<211> LENGTH: 419
<212> TYPE: DNA
<213> ORGANISM: Homo sapiens

<400> SEQUENCE: 949

```
ggcgcgtcct gccttcattt atccagcagc ttttcggaaa atgcatttgc tgttcggagt      60
ttaatcagaa gaggattcct gcctccgtcc ccggctcctt catcgtcccc tctcccctgt     120
ctctctcctg gggaggcgtg aagcggtccc gtggatagag attcatgcct gtgcccgcgc     180
gtgtgtgcgc gcgtgtaaat tgccgagaag gggaaaacat cacaggactt ctgcgaatac     240
cggactgaaa attgtaattc atctgccgcc gccgctgcct ttttttttc tcgagctctt     300
gagatctccg gttgggattc ctgcggattg acatttctgt gaagcagaag tctgggaatc     360
gatctggaaa tcctcctaat ttttactccc tctccccgcg actcctgatt cattgggaa     419
```

<210> SEQ ID NO 950
<211> LENGTH: 27
<212> TYPE: DNA
<213> ORGANISM: Homo sapiens

<400> SEQUENCE: 950

```
ggaggcggcc gtagccagcg ccgccgc                                          27
```

<210> SEQ ID NO 951
<211> LENGTH: 38
<212> TYPE: DNA
<213> ORGANISM: Homo sapiens

<400> SEQUENCE: 951

```
tgccggggct ccgggccctc cctgccggcg gccgtcag                              38
```

<210> SEQ ID NO 952
<211> LENGTH: 31
<212> TYPE: DNA
<213> ORGANISM: Homo sapiens

<400> SEQUENCE: 952

```
ccgccgctct ccgtggcccc gccgcgctgc c                                     31
```

<210> SEQ ID NO 953
<211> LENGTH: 25
<212> TYPE: DNA
<213> ORGANISM: Homo sapiens

<400> SEQUENCE: 953

```
ttttaaatgt cccgctctga gccgg                                            25
```

<210> SEQ ID NO 954
<211> LENGTH: 39
<212> TYPE: DNA
<213> ORGANISM: Homo sapiens

<400> SEQUENCE: 954

```
gacggcggcg cggagttctc ggctcgctcc aggaagagg                             39
```

<210> SEQ ID NO 955
<211> LENGTH: 46
<212> TYPE: DNA
<213> ORGANISM: Homo sapiens

<400> SEQUENCE: 955
gaaatggcca aaatcgacag gacggcgagg gaccagtgtg ggagcc 46

<210> SEQ ID NO 956
<211> LENGTH: 140
<212> TYPE: DNA
<213> ORGANISM: Homo sapiens

<400> SEQUENCE: 956
tctaatgcag ccacagccca tatggcccag cactgtacct gtcagtgggc actggcctct 60
gccagtcctg ggattccagg aagcttggtg ttcctgactg gcaccgtctg agattacaga 120
tatgtgccta gcctggaaga 140

<210> SEQ ID NO 957
<211> LENGTH: 68
<212> TYPE: DNA
<213> ORGANISM: Homo sapiens

<400> SEQUENCE: 957
agaagatgat gaccgggttt acccaaactc aacgtgcaag cctcggatta ttgcaccatc 60
cagaggct 68

<210> SEQ ID NO 958
<211> LENGTH: 83
<212> TYPE: DNA
<213> ORGANISM: Homo sapiens

<400> SEQUENCE: 958
aaagacatac ttaagggatc agcactttct tgagcaacac cctcttctgc agccaaaaat 60
gcgagcaatt cttctggatt ggt 83

<210> SEQ ID NO 959
<211> LENGTH: 102
<212> TYPE: DNA
<213> ORGANISM: Homo sapiens

<400> SEQUENCE: 959
gggagacctt ttacttggca caagatttct ttgaccggta tatggcgaca caagaaaatg 60
ttgtaaaaac tcttttacag cttattggga tttcatcttt at 102

<210> SEQ ID NO 960
<211> LENGTH: 83
<212> TYPE: DNA
<213> ORGANISM: Homo sapiens

<400> SEQUENCE: 960
gaaatctatc ctccaaagtt gcaccagttt gcgtatgtga cagatggagc ttgttcagga 60
gatgaaattc tcaccatgga att 83

<210> SEQ ID NO 961
<211> LENGTH: 99
<212> TYPE: DNA
<213> ORGANISM: Homo sapiens

<400> SEQUENCE: 961
tggcgtttaa gtcccctgac tattgtgtcc tggctgaatg tatacatgca ggttgcatat 60
ctaaatgact tacatgaagt gctactgccg cagtatccc 99

<210> SEQ ID NO 962
<211> LENGTH: 88

<212> TYPE: DNA
<213> ORGANISM: Homo sapiens

<400> SEQUENCE: 962
ctggatgttg actgccttga atttccttat ggtatacttg ctgcttcggc cttgtatcat 60
ttctcgtcat ctgaattgat gcaaaagg 88

<210> SEQ ID NO 963
<211> LENGTH: 103
<212> TYPE: DNA
<213> ORGANISM: Homo sapiens

<400> SEQUENCE: 963
ctgtgtcaag tggatggttc catttgccat ggttataagg gagacgggga gctcaaaact 60
gaagcacttc aggggcgtcg ctgatgaaga tgcacacaac ata 103

<210> SEQ ID NO 964
<211> LENGTH: 55
<212> TYPE: DNA
<213> ORGANISM: Homo sapiens

<400> SEQUENCE: 964
gacaaagccc gagcaaagaa agccatgttg tctgaacaaa atagggcttc tcctc 55

<210> SEQ ID NO 965
<211> LENGTH: 35
<212> TYPE: DNA
<213> ORGANISM: Homo sapiens

<400> SEQUENCE: 965
gtaagaagca gagcagcggg ccggaaatgg cgtga 35

<210> SEQ ID NO 966
<211> LENGTH: 215
<212> TYPE: DNA
<213> ORGANISM: Homo sapiens

<400> SEQUENCE: 966
gcgtgcgttt gcttttacag atatctgaat ggaagagtgt ttcttccaca acagaagtat 60
ttctgtggat ggcatcaaac agggcaaagt gttttttatt gaatgcttat aggttttttt 120
taaataagtg ggtcaagtac accagccacc tccagacacc agtgcgtgct cccgatgctg 180
ctatggaagg tgctacttga cctaagggac tccca 215

<210> SEQ ID NO 967
<211> LENGTH: 130
<212> TYPE: DNA
<213> ORGANISM: Homo sapiens

<400> SEQUENCE: 967
tgggctccgt tgtaccaagt ggagcaggtg gttgcgggca agcgttgtgc agagcccata 60
gccagctggg caggggctg ccctctccac attatcagtt gacagtgtac aatgcctttg 120
atgaactgtt 130

<210> SEQ ID NO 968
<211> LENGTH: 36
<212> TYPE: DNA
<213> ORGANISM: Homo sapiens

<400> SEQUENCE: 968
gtaagtgctg ctatatctat ccatttttta ataaag 36

<210> SEQ ID NO 969
<211> LENGTH: 88
<212> TYPE: DNA
<213> ORGANISM: Homo sapiens

<400> SEQUENCE: 969
tctaggtggt gtgggcgaag tttgggactg gtttagggcg gggacaagac caagaacaca 60
agtttccttg tactacggga gagaggga 88

<210> SEQ ID NO 970
<211> LENGTH: 39
<212> TYPE: DNA
<213> ORGANISM: Homo sapiens

<400> SEQUENCE: 970
ggtccctggt gtgccttggt gtcatcatct tgctgtctg 39

<210> SEQ ID NO 971
<211> LENGTH: 58
<212> TYPE: DNA
<213> ORGANISM: Homo sapiens

<400> SEQUENCE: 971
ttcaggacta catggccccc gactgccgat tcctgaccat tcaccggggc caagtggt 58

<210> SEQ ID NO 972
<211> LENGTH: 25
<212> TYPE: DNA
<213> ORGANISM: Homo sapiens

<400> SEQUENCE: 972
gccgtgggcg gctcttctgg ggagg 25

<210> SEQ ID NO 973
<211> LENGTH: 134
<212> TYPE: DNA
<213> ORGANISM: Homo sapiens

<400> SEQUENCE: 973
catttaagct gagattcata tgacaaggat ggagcagtta tgtggagatc agggagaagg 60
gagaatgcaa aggccttcag caggcacaag cttgccatct tcccagaccc tagcttttaa 120
ctcctcttcc ccag 134

<210> SEQ ID NO 974
<211> LENGTH: 79
<212> TYPE: DNA
<213> ORGANISM: Homo sapiens

<400> SEQUENCE: 974
gttcagggag attactatgg agatctggct gctcgcctgg gctatttccc cagtagcatt 60
gtccgagagg accagaccc 79

<210> SEQ ID NO 975
<211> LENGTH: 92
<212> TYPE: DNA
<213> ORGANISM: Homo sapiens

<400> SEQUENCE: 975
aaagtgcttc aacccgcgcc ggcggcgact gcagttcctg cgagcgagga gcgcgggacc 60
tgctgacacg ctgacgcctt cgagcgcggc cc 92

<210> SEQ ID NO 976
<211> LENGTH: 78
<212> TYPE: DNA
<213> ORGANISM: Homo sapiens

<400> SEQUENCE: 976
gctgcactac caggacacag attcagatgt gccggagcag agggatagca agtgcaaggt 60
caaatggacc catgagga 78

<210> SEQ ID NO 977
<211> LENGTH: 54
<212> TYPE: DNA
<213> ORGANISM: Homo sapiens

<400> SEQUENCE: 977
ccctggtgag gcagtttgga cagcaggact ggaagttcct ggccagccac ttcc 54

<210> SEQ ID NO 978
<211> LENGTH: 36
<212> TYPE: DNA
<213> ORGANISM: Homo sapiens

<400> SEQUENCE: 978
tccagacctt gtcaaggggc catggaccaa agagga 36

<210> SEQ ID NO 979
<211> LENGTH: 176
<212> TYPE: DNA
<213> ORGANISM: Homo sapiens

<400> SEQUENCE: 979
tgattgccaa gcacctgaag ggccggctgg ggaagcagtg ccgtgaacgc tggcacaacc 60
acctcaaccc tgaggtgaag aagtcttgct ggaccgagga ggaggaccgc atcatctgcg 120
aggcccacaa ggtgctgggc aaccgctggg ccgagatcgc caagatgttg ccaggg 176

<210> SEQ ID NO 980
<211> LENGTH: 42
<212> TYPE: DNA
<213> ORGANISM: Homo sapiens

<400> SEQUENCE: 980
acacaggagg cttcttgagc gagtccaaag actgcaagcc cc 42

<210> SEQ ID NO 981
<211> LENGTH: 194
<212> TYPE: DNA
<213> ORGANISM: Homo sapiens

<400> SEQUENCE: 981
gcagccacca catcgaagga acaggagccc atcggtacag atctggacgc agtgcgaaca 60
ccagagccct tggaggaatt cccgaagcgt gaggaccagg aaggctcccc accagaaacg 120
agcctgcctt acaagtgggt ggtggaggca gctaacctcc tcatccctgc tgtgggttct 180
agcctctctg aagc 194

<210> SEQ ID NO 982
<211> LENGTH: 43
<212> TYPE: DNA

<213> ORGANISM: Homo sapiens

<400> SEQUENCE: 982
ctgatgcttg gtgtgacctg agtaaatttg acctccctga gga 43

<210> SEQ ID NO 983
<211> LENGTH: 52
<212> TYPE: DNA
<213> ORGANISM: Homo sapiens

<400> SEQUENCE: 983
gtatcaacaa cagcctagtg cagctgcaag cgtcacatca gcagcaagtc ct 52

<210> SEQ ID NO 984
<211> LENGTH: 233
<212> TYPE: DNA
<213> ORGANISM: Homo sapiens

<400> SEQUENCE: 984
cagtgtgacc gagtaccgcc tggatggcca caccatctca gacctgagcc ggagcagccg 60
gggcgagctg atccccatct cccccagcac tgaagtcggg ggctctggca ttggcacacc 120
gccctctgtg ctcaagcggc agaggaagag gcgtgtggct ctgtcccctg tcactgagaa 180
tagcaccagt ctgtccttcc tggattcctg taacagcctc acgcccaaga gca 233

<210> SEQ ID NO 985
<211> LENGTH: 104
<212> TYPE: DNA
<213> ORGANISM: Homo sapiens

<400> SEQUENCE: 985
tttctgaact tctggaacaa acaggacaca ttggagctgg agagcccctc gctgacatcc 60
accccagtgt gcagccagaa ggtggtggtc accacaccac tgca 104

<210> SEQ ID NO 986
<211> LENGTH: 72
<212> TYPE: DNA
<213> ORGANISM: Homo sapiens

<400> SEQUENCE: 986
ctccatggac aacactcccc acacgccaac cccgttcaag aacgccctgg agaagtacgg 60
acccctgaag cc 72

<210> SEQ ID NO 987
<211> LENGTH: 72
<212> TYPE: DNA
<213> ORGANISM: Homo sapiens

<400> SEQUENCE: 987
acttgaagga ggtgctgcgt tctgaggctg gcatcgaact catcatcgag gacgacatca 60
ggcccgagaa gc 72

<210> SEQ ID NO 988
<211> LENGTH: 29
<212> TYPE: DNA
<213> ORGANISM: Homo sapiens

<400> SEQUENCE: 988
ccgacaactg ccccttcaaa ctcttccag 29

<210> SEQ ID NO 989
<211> LENGTH: 31
<212> TYPE: DNA
<213> ORGANISM: Homo sapiens

<400> SEQUENCE: 989
cctcaccctg tcaggtatca aagaagacaa c 31

<210> SEQ ID NO 990
<211> LENGTH: 86
<212> TYPE: DNA
<213> ORGANISM: Homo sapiens

<400> SEQUENCE: 990
cttgctcaac cagggcttct tgcaggccaa gcccgagaag gcagcagtgg cccagaagcc 60
ccgaagccac ttcacgacac ctgccc 86

<210> SEQ ID NO 991
<211> LENGTH: 34
<212> TYPE: DNA
<213> ORGANISM: Homo sapiens

<400> SEQUENCE: 991
cagccacaca tctcggaccc tcatcttgtc ctga 34

<210> SEQ ID NO 992
<211> LENGTH: 265
<212> TYPE: DNA
<213> ORGANISM: Homo sapiens

<400> SEQUENCE: 992
gtgtcacgag cccattctca tgtttacagg ggttgtgggg gcagaggggg tctgtgaatc 60
tgagagtcat tcaggtgacc tcctgcaggg agccttctgc caccagcccc tccccagact 120
ctcaggtgga ggcaacaggg ccatgtgctg ccctgttgcc gagcccagct gtgggcggct 180
cctggtgcta acaacaaagt tccacttcca ggtctgcctg gttccctccc caaggccaca 240
gggagctccg tcagcttctc ccaag 265

<210> SEQ ID NO 993
<211> LENGTH: 54
<212> TYPE: DNA
<213> ORGANISM: Homo sapiens

<400> SEQUENCE: 993
gtcctgcagt tgcagtcgtg ttctccgagt tcctgtctct ctgccaacgc cgcc 54

<210> SEQ ID NO 994
<211> LENGTH: 66
<212> TYPE: DNA
<213> ORGANISM: Homo sapiens

<400> SEQUENCE: 994
tggcttccca aaaccgcgac ccagccgcca ctagcgtcgc cgccgcccgt aaaggagctg 60
agccga 66

<210> SEQ ID NO 995
<211> LENGTH: 252
<212> TYPE: DNA
<213> ORGANISM: Homo sapiens

<400> SEQUENCE: 995
gagctcagac cgctctttga gactctcccg aaggagaatg ggagggtagg ggcgctgcca 60
gactccttcc ctggtgggcc tagatgaaga cgctcaagga ccctcgtgac ttggccgaga 120
caggggaagg gagaagttga gtcgggcaag gaagagatgc taaagcctgg ggaattaaga 180
acatgccaga atcatcccga gggagtctgg aattagggag ggtgaggact cgctaggatc 240
gtcctgtgga tc 252

<210> SEQ ID NO 996
<211> LENGTH: 52
<212> TYPE: DNA
<213> ORGANISM: Homo sapiens

<400> SEQUENCE: 996
atgtctggcg ataaagggat ttctgccttc cctgaatcag acaacctttt ca 52

<210> SEQ ID NO 997
<211> LENGTH: 25
<212> TYPE: DNA
<213> ORGANISM: Homo sapiens

<400> SEQUENCE: 997
cagtttgtct actgtccggt cccag 25

<210> SEQ ID NO 998
<211> LENGTH: 34
<212> TYPE: DNA
<213> ORGANISM: Homo sapiens

<400> SEQUENCE: 998
actcaagatt ctagcaagcc ccttgtgtgg ggct 34

<210> SEQ ID NO 999
<211> LENGTH: 91
<212> TYPE: DNA
<213> ORGANISM: Homo sapiens

<400> SEQUENCE: 999
ggtataagct ctcgctagag ttccccagtg gctaccctta caatgcgccc acagtgaagt 60
tcctcacgcc ctgctatcac cccaacgtgg a 91

<210> SEQ ID NO 1000
<211> LENGTH: 33
<212> TYPE: DNA
<213> ORGANISM: Homo sapiens

<400> SEQUENCE: 1000
acacacatgc tgccgagctc tggaaaaacc cca 33

<210> SEQ ID NO 1001
<211> LENGTH: 43
<212> TYPE: DNA
<213> ORGANISM: Homo sapiens

<400> SEQUENCE: 1001
gtacctgcaa gaaacctact caaagcaggt caccagccag gag 43

<210> SEQ ID NO 1002
<211> LENGTH: 36
<212> TYPE: DNA
<213> ORGANISM: Homo sapiens

<400> SEQUENCE: 1002
gtgatttctg tataggactc tttatcttga gctgtg 36

<210> SEQ ID NO 1003
<211> LENGTH: 116
<212> TYPE: DNA
<213> ORGANISM: Homo sapiens

<400> SEQUENCE: 1003
ggcctttacg cgacatccga gcagcgtgtc tatcccaaag gcctaggagc atttgcccgg 60
ctcggtcaaa tctagcgcaa gtttgaagcc tgcggcctcg caattttagc agcttc 116

<210> SEQ ID NO 1004
<211> LENGTH: 146
<212> TYPE: DNA
<213> ORGANISM: Homo sapiens

<400> SEQUENCE: 1004
gtggagtctt cttgaataag ctgtgaaaca tttccccacc cgcttccctt tcttggccca 60
ggcttcctga ccacagcctc acctttgagc agctcagagc cctgcctgcc aggatgcgag 120
ccactgcctg gatcgtggct ctgcag 146

<210> SEQ ID NO 1005
<211> LENGTH: 32
<212> TYPE: DNA
<213> ORGANISM: Homo sapiens

<400> SEQUENCE: 1005
ggcccggagc ggcccagcaa gcccagcagc cc 32

<210> SEQ ID NO 1006
<211> LENGTH: 53
<212> TYPE: DNA
<213> ORGANISM: Homo sapiens

<400> SEQUENCE: 1006
ggctccggcc gcctggctcc gcagcgcggc cgcgcgcgcc ctcctgcccc cga 53

<210> SEQ ID NO 1007
<211> LENGTH: 33
<212> TYPE: DNA
<213> ORGANISM: Homo sapiens

<400> SEQUENCE: 1007
catgcagccc tgcccagtag cccggcacct gcc 33

<210> SEQ ID NO 1008
<211> LENGTH: 29
<212> TYPE: DNA
<213> ORGANISM: Homo sapiens

<400> SEQUENCE: 1008
gaagcccccc ggcctgccag cagcctcag 29

<210> SEQ ID NO 1009
<211> LENGTH: 54
<212> TYPE: DNA
<213> ORGANISM: Homo sapiens

<400> SEQUENCE: 1009
ctgtggcgtg cccgacccat ctgatgggct gagtgcccgc aaccgacaga agag 54

<210> SEQ ID NO 1010
<211> LENGTH: 30
<212> TYPE: DNA
<213> ORGANISM: Homo sapiens

<400> SEQUENCE: 1010
gcgctgggag aagacggacc tcacctacag 30

<210> SEQ ID NO 1011
<211> LENGTH: 595
<212> TYPE: DNA
<213> ORGANISM: Homo sapiens

<400> SEQUENCE: 1011
cagggaggtc atctatgggc aaaccccctg aaaccccaac ttagacacat acacatatgg 60
agaccctccc tcagcagagg ggcagagcct ccgtcatcat gcaaagagtc gcagcacatg 120
cctgcggacg ggtgttcagt cactcaggca gcctttacaa gagacctgtg aggaccaggc 180
tctgggactc cacggtgaat gaggcagaca cagccccatc ctctgtgtca gtctgaggtg 240
ggtgtcagcc atgtcattgt ccaactctac catcacaact tgggcttcga gcaggtggag 300
acagtggtaa gcggggagag gcaatagtgg gcatctcact gggtgacctg ggaggaccct 360
gggcaggtga tggggaagct gaggctcaca catcctgcgg gtggggaccc agcctgaaga 420
atgggctggt gtcacacagc attggagctg agactggggt ctttagaatt tcctaggtgg 480
gggcctggga accaacaggg gctcaaggaa ccaaggtgtc cccacagtaa gtggcactgt 540
caggtctagg atgggggtct cgggacccct ggtcctggtt ctttccactg aattc 595

<210> SEQ ID NO 1012
<211> LENGTH: 138
<212> TYPE: DNA
<213> ORGANISM: Homo sapiens

<400> SEQUENCE: 1012
ttcggttccc atggcagttg gtgcaggagc aggtgcggca gacgatggca gaggccctaa 60
aggtatggag cgatgtgacg ccactcacct ttactgaggt gcacgagggc cgtgctgaca 120
tcatgatcga cttcgcca 138

<210> SEQ ID NO 1013
<211> LENGTH: 96
<212> TYPE: DNA
<213> ORGANISM: Homo sapiens

<400> SEQUENCE: 1013
ggacgacctg ccgtttgatg ggcctggggg catcctggcc catgccttct tccccaagac 60
tcaccgagaa ggggatgtcc acttcgacta tgatga 96

<210> SEQ ID NO 1014
<211> LENGTH: 25
<212> TYPE: DNA
<213> ORGANISM: Homo sapiens

<400> SEQUENCE: 1014
aggtggcagc ccatgaattt ggcca 25

<210> SEQ ID NO 1015
<211> LENGTH: 134
<212> TYPE: DNA
<213> ORGANISM: Homo sapiens

<400> SEQUENCE: 1015
tacacctttc gctacccact gagtctcagc ccagatgact gcaggggcgt tcaacaccta 60
tatggccagc cctggcccac tgtcacctcc aggaccccag ccctgggccc ccaggctggg 120
atagacacca atga 134

<210> SEQ ID NO 1016
<211> LENGTH: 34
<212> TYPE: DNA
<213> ORGANISM: Homo sapiens

<400> SEQUENCE: 1016
actgtgactg cagcatatgc cctcagcatg tgtc 34

<210> SEQ ID NO 1017
<211> LENGTH: 144
<212> TYPE: DNA
<213> ORGANISM: Homo sapiens

<400> SEQUENCE: 1017
ccgaggcgag ctctttttct tcaaagcggg ctttgtgtgg cgcctccgtg ggggccagct 60
gcagcccggc tacccagcat tggcctctcg ccactggcag ggactgccca gccctgtgga 120
cgctgccttc gaggatgccc aggg 144

<210> SEQ ID NO 1018
<211> LENGTH: 72
<212> TYPE: DNA
<213> ORGANISM: Homo sapiens

<400> SEQUENCE: 1018
ggagcattgc agatgccagg gacttcacaa atgaaggcac agcatgggaa acctgcgtgg 60
gttccagggc ag 72

<210> SEQ ID NO 1019
<211> LENGTH: 180
<212> TYPE: DNA
<213> ORGANISM: Homo sapiens

<400> SEQUENCE: 1019
tttgtcacag ccaaatgcca gtggaaggag cagccgccca ggcagccctc tactgatgag 60
agtaacctca cccgtgcact agtttacaga gcattcactg ccccagctta tcccaggcct 120
cccgcttccc tctgcgggtg gggtgctgag caggcattat tggcctgcat gttttactga 180

<210> SEQ ID NO 1020
<211> LENGTH: 117
<212> TYPE: DNA
<213> ORGANISM: Homo sapiens

<400> SEQUENCE: 1020
ctcagtactg ggtgtacgac ggtgaaaagc cagtcctggg ccccgcaccc ctcaccgagc 60
tgggcctggt gaggttcccg gtccatgctg ccttggtctg gggtcccgag aagaaca 117

<210> SEQ ID NO 1021
<211> LENGTH: 87
<212> TYPE: DNA
<213> ORGANISM: Homo sapiens

<400> SEQUENCE: 1021

-continued agcacccggc gtgtagacag tcccgtgccc cgcagggcca ctgactggag aggggtgccc 60
tctgagatcg acgctgcctt ccaggat 87

<210> SEQ ID NO 1022
<211> LENGTH: 56
<212> TYPE: DNA
<213> ORGANISM: Homo sapiens

<400> SEQUENCE: 1022
gctatgccta cttcctgcgc ggccgcctct actggaagtt tgaccctgtg aaggtg 56

<210> SEQ ID NO 1023
<211> LENGTH: 41
<212> TYPE: DNA
<213> ORGANISM: Homo sapiens

<400> SEQUENCE: 1023
tcctgacttc tttggctgtg ccgagcctgc caacactttc c 41

<210> SEQ ID NO 1024
<211> LENGTH: 206
<212> TYPE: DNA
<213> ORGANISM: Homo sapiens

<400> SEQUENCE: 1024
ctgccaggcc acgaatatca ggctagagac ccatggccat ctttgtggct gtgggcacca 60
ggcatgggac tgagcccatg tctcctcagg gggatggggt ggggtacaac caccatgaca 120
actgccggga gggccacgca ggtcgtggtc acctgccagc gactgtctca gactgggcag 180
ggaggctttg gcatgactta agagga 206

<210> SEQ ID NO 1025
<211> LENGTH: 118
<212> TYPE: DNA
<213> ORGANISM: Homo sapiens

<400> SEQUENCE: 1025
gagtgtcctt gctgtatccc tgttgtgagg ttccttccag ggctggcac tgaagcaagg 60 gtgctggggc cccatggcct tcagccctgg ctgagcaact gggctgtagg gcagggcc 118

<210> SEQ ID NO 1026
<211> LENGTH: 170
<212> TYPE: DNA
<213> ORGANISM: Homo sapiens

<400> SEQUENCE: 1026
gccttctggc tgacaatcct ggaaatctgt tctccagaat ccaggccaaa aagttcacag 60
tcaaatgggg aggggtattc ttcatgcagg agaccccagg ccctggaggc tgcaacatac 120
ctcaatcctg tcccaggccg gatcctcctg aagccctttt cgcagcactg 170

<210> SEQ ID NO 1027
<211> LENGTH: 235
<212> TYPE: DNA
<213> ORGANISM: Homo sapiens

<400> SEQUENCE: 1027
ctgatgggtg tgctaattac actgatttaa tcgataccca ttgtatgtga aacagtatat 60
acaccatatt tacaattatg tatcagttta acatttaaaa aaacatttct aatataagta 120
tctctcaaac tgtggattaa cttcttgatt tatatttaaa tatgaatctt gaggaaaata 180

-continued

```
gtgaaaataa ccatcttgat ttagtgtatt tctcccatat gtgaattgta tatac        235


<210> SEQ ID NO 1028
<211> LENGTH: 59
<212> TYPE: DNA
<213> ORGANISM: Homo sapiens

<400> SEQUENCE: 1028

aacgatgcct tgtgtcaaga agaaggcaga ttgggccttg cgctggattg gggacaaag      59


<210> SEQ ID NO 1029
<211> LENGTH: 27
<212> TYPE: DNA
<213> ORGANISM: Homo sapiens

<400> SEQUENCE: 1029

agctgcagct ctcgccgctg aaggggc                                         27
```